United States Patent
Babiss et al.

(10) Patent No.: US 10,233,182 B2
(45) Date of Patent: Mar. 19, 2019

(54) SUBSTITUTED SPIROCYCLIC INHIBITORS OF AUTOTAXIN

(71) Applicant: X-Rx, Inc., Waltham, MA (US)

(72) Inventors: Lee Babiss, Waltham, MA (US); Matthew Clark, Waltham, MA (US); Anthony D. Keefe, Waltham, MA (US); Mark J. Mulvihill, Waltham, MA (US); Haihong Ni, Beijing (CN); Louis Renzetti, Waltham, MA (US); Frank Ruebsam, Beijing (CN); Ce Wang, Beijing (CN); Zhifeng Xie, Beijing (CN); Ying Zhang, Waltham, MA (US)

(73) Assignee: X-Rx, Inc., Waltham, MA (US)

( * ) Notice: Subject to any disclaimer, the term of this patent is extended or adjusted under 35 U.S.C. 154(b) by 0 days.

(21) Appl. No.: 15/896,905

(22) Filed: Feb. 14, 2018

(65) Prior Publication Data

US 2018/0282332 A1 Oct. 4, 2018

Related U.S. Application Data

(63) Continuation of application No. 15/300,762, filed as application No. PCT/US2015/024338 on Apr. 3, 2015, now Pat. No. 10,011,601.

(60) Provisional application No. 61/975,123, filed on Apr. 4, 2014.

(51) Int. Cl.
| | |
|---|---|
| *C07D 221/00* | (2006.01) |
| *C07D 233/00* | (2006.01) |
| *A61K 31/4545* | (2006.01) |
| *A61K 31/415* | (2006.01) |
| *A61K 31/454* | (2006.01) |
| *C07D 471/10* | (2006.01) |
| *A61K 45/06* | (2006.01) |
| *A61K 31/435* | (2006.01) |
| *A61K 31/437* | (2006.01) |
| *A61K 31/444* | (2006.01) |
| *A61K 31/498* | (2006.01) |
| *A61K 31/517* | (2006.01) |
| *A61K 31/538* | (2006.01) |
| *A61K 31/69* | (2006.01) |
| *C07D 519/00* | (2006.01) |
| *C07F 5/02* | (2006.01) |

(52) U.S. Cl.
CPC .......... *C07D 471/10* (2013.01); *A61K 31/435* (2013.01); *A61K 31/437* (2013.01); *A61K 31/444* (2013.01); *A61K 31/498* (2013.01); *A61K 31/517* (2013.01); *A61K 31/538* (2013.01); *A61K 31/69* (2013.01); *A61K 45/06* (2013.01); *C07D 519/00* (2013.01); *C07F 5/025* (2013.01)

(58) Field of Classification Search
CPC .......... C07D 221/00; C07D 233/00; A61K 31/4545; A61K 31/415; A61K 31/445; A61K 31/454
USPC .......... 546/20, 184, 192; 514/323, 278
See application file for complete search history.

(56) References Cited

U.S. PATENT DOCUMENTS

| | | | |
|---|---|---|---|
| 5,877,182 A | 3/1999 | Nargund et al. | |
| 6,369,077 B1 | 4/2002 | Marquis et al. | |
| 7,078,420 B2* | 7/2006 | Dhar | C07D 233/96 514/341 |
| 8,263,608 B2 | 9/2012 | Shi et al. | |
| 8,754,107 B2 | 6/2014 | George et al. | |
| 2004/0192674 A1 | 9/2004 | Marquis | |
| 2004/0242656 A1 | 12/2004 | Liebeschuetz et al. | |
| 2006/0058351 A1 | 3/2006 | Diaz et al. | |
| 2007/0208056 A1 | 9/2007 | Carter et al. | |
| 2008/0176883 A1 | 7/2008 | George et al. | |
| 2010/0016258 A1 | 1/2010 | Lynch et al. | |
| 2011/0212882 A1 | 9/2011 | Schteingart et al. | |
| 2011/0230462 A1 | 9/2011 | Hendricks et al. | |
| 2012/0100592 A1 | 4/2012 | Parrill-Baker et al. | |

(Continued)

FOREIGN PATENT DOCUMENTS

| | | |
|---|---|---|
| DE | 102009033392 A1 | 1/2011 |
| JP | 2011219368 A | 11/2011 |
| KR | 2011-0023190 A | 3/2011 |

(Continued)

OTHER PUBLICATIONS

Examination Report for Australian Application No. 2015240519, dated Aug. 27, 208 (4 pages).

(Continued)

*Primary Examiner* — Niloofar Rahmani
(74) *Attorney, Agent, or Firm* — Clark & Elbing LLP

(57) ABSTRACT

The present invention relates to compounds according to Formula I and pharmaceutically acceptable salts, synthesis, intermediates, formulations, and methods of disease treatment therewith, including cancer, lymphocyte homing, chronic inflammation, neuropathic pain, fibrotic diseases, thrombosis, and cholestatic pruritus, mediated at least in part by ATX.

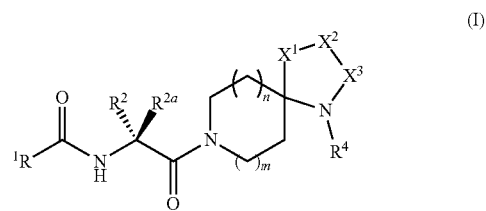

(I)

30 Claims, No Drawings

(56) References Cited

U.S. PATENT DOCUMENTS

2012/0302540 A1    11/2012    Ambarkhane et al.

FOREIGN PATENT DOCUMENTS

| WO | WO-02/069905 A2 | 9/2002 |
|---|---|---|
| WO | WO-02/070511 A1 | 9/2002 |
| WO | WO-02/079146 A2 | 10/2002 |
| WO | WO-2005/122379 A2 | 12/2005 |
| WO | WO-2006/137465 A1 | 12/2006 |
| WO | WO-2008/021927 A2 | 2/2008 |
| WO | WO-2009/117676 A2 | 9/2009 |
| WO | WO-2009/151644 A2 | 12/2009 |
| WO | WO-2010/037081 A1 | 4/2010 |
| WO | WO-2010/063352 A1 | 6/2010 |
| WO | WO-2010/112116 A1 | 10/2010 |
| WO | WO-2010/112124 A1 | 10/2010 |
| WO | WO-2010/115491 A2 | 10/2010 |
| WO | WO-2010/144646 A2 | 12/2010 |
| WO | WO-2011/006569 A1 | 1/2011 |
| WO | WO-2011/017350 A2 | 2/2011 |
| WO | WO-2011/116867 A1 | 9/2011 |
| WO | WO-2012/024620 A2 | 2/2012 |
| WO | WO-2012/166415 A1 | 12/2012 |
| WO | WO-2013/061297 A1 | 5/2013 |
| WO | WO-2013/186159 A1 | 12/2013 |
| WO | WO-2014/139978 A1 | 9/2014 |
| WO | WO-2014/168824 A1 | 10/2014 |
| WO | WO-2015/008229 A1 | 1/2015 |
| WO | WO-2015/008230 A1 | 1/2015 |
| WO | WO-2015/042052 A1 | 3/2015 |
| WO | WO-2015/042053 A1 | 3/2015 |
| WO | WO-2015/048301 A1 | 4/2015 |
| WO | WO-2015/154023 A1 | 10/2015 |
| WO | WO-2015/175171 A1 | 11/2015 |

OTHER PUBLICATIONS

Pubchem CID No. 56755867. Mar. 8, 2012. Retrieved from URL <http://pubchem.ncbi.nlm.nih.gov/summary/summary.cgi?from=compound&cid=56755867> on Jul. 13, 2015 (2 pages).
Pubchem CID No. 55023722. Jan. 24, 2012. Retrieved from URL <http://pubchem.ncbi.nlm.nih.gov/compound/55023722#section=Top> on Jul. 13, 2015 (10 pages).
International Search Report and Written Opinion for International Patent Application No. PCT/US2015/024338, dated Jun. 25, 2015 (18 pages).
Liu et al., "A novel peptide-based encoding system for "one-bead one-compound" peptidomimetic and small molecule combinatorial libraries," J Am Chem Soc. 124(26):7678-80 (2002).
Database Registry RN 302907-89-7, Nov. 15, 2000 (1 page).
Extended European Search Report for European Application No. 15773254.6, dated Aug. 2, 2017 (10 pages).
Thomsen et al., "Novel and convenient methods for the preparation of substituted thiophenes, thiazoles and 1,3,4-thiadiazole-2(3H)-thiones from bifuctional substrates," Chem. Lett. 12(6): 809-10 (1983).
Franciskovich et al., "Investigation of the terminal P4 domain in a series of D-phenylglycinamide-based factor Xa inhibitors," Bioorg Med Chem Lett. 17(24):6910-3 (2007).
Gardner et al., "The discovery of BMS-457, a potent and selective CCR1 antagonist," Bioorg Med Chem Lett. 23(13):3833-40 (2013).
Bedos et al., "A rational approach to the design and synthesis of a new Bradykinin B1 receptor antagonist," J Med Chem. 43(12):2387-94 (2000).
Pubchem CID No. 47836440. Nov. 26, 2010. Retrieved from URL <https://pubchem.ncbi.nlm.nih.gov/compound/47836440#section=Top> on Feb. 22, 2018 (11 pages).
Chemical Structures of Kaneko et al. (prepared Nov. 2017) (11 pages).
Non-Final Office Action for U.S. Appl. No. 15/303,848, dated Nov. 24, 2017 (8 pages).
English Translation of Official Action for Chilean Application No. 201602516, dated Feb. 5, 2018 (10 pages).
English Translation of Office Action for Colombian Application No. NC2016/0002679, dated Apr. 26, 2018 (7 pages).
Office Action for Chilean Patent Application No. 201602516, received Aug. 23, 2018 (16 pages).
Official Action for Cuban Application No. 2016-0150, dated May 9, 2018 (4 pages).
Official Action for Japanese Application No. 2017-503794, dated Nov. 28, 2018 (10 pages).
Pubchem CID No. 56755867. Mar. 8, 2012. Retrieved from URL <https://pubchem.ncbi.nlm.nih.gov/compound/56755867#section=Top> on Jan. 7, 2019 (10 pages).
Venkatraman et al., "Lysophosphatidate signaling stabilizes Nrf2 and increases the expression of genes involved in drug resistance and oxidative stress responses: implications for cancer treatment," FASEB J. 29(3):772-85 (2015).

* cited by examiner

SUBSTITUTED SPIROCYCLIC INHIBITORS OF AUTOTAXIN

CROSS-REFERENCE TO RELATED APPLICATIONS

This application claims the benefit under 35 U.S.C. 119(e) of U.S. Provisional Patent Application No. 61/975,123, filed on Apr. 4, 2014 and entitled "Substituted Spirocyclic Inhibitors Of Autotaxin And Their Preparation And Use In The Treatment Of LPA-Dependent Or LPA-Mediated Diseases." The entire contents of the above-referenced application is incorporated herein by reference.

FIELD AND BACKGROUND

Autotaxin (ATX) is a secreted enzyme of the ectonucleotide pyrophosphatase/phosphodiesterase family, and is also known as Ectonucleotide Pyrophosphatase/Phosphodiesterase 2 (ENPP-2 or NPP2). ATX plays a role in driving pathological conditions, including fibrosis, arthritic inflammation, neurodegeneration, neuropathic pain, and cancer. ATX is the fundamental regulator of the conversion of Lysophosphatidylcholine (LPC) to Lysophosphatidic Acid (LPA). LPA is a bioactive lipid that affects migration, proliferation, and survival of various cell types.

Inhibition of ATX has been shown to reduce LPA levels in pathological settings. Reduction of LPA may provide therapeutic benefits in diseases with unmet medical need, including cancer, lymphocyte homing, chronic inflammation, neuropathic pain, fibrotic diseases such as Idiopathic Pulmonary Fibrosis (IPF), thrombosis, and cholestatic pruritus which are caused, mediated and/or propagated by increased LPA levels and/or activation of ATX.

Fibrotic diseases are chronic, debilitating and often lethal pathologies driven by a dysregulated response to tissue or organ injury. Fibrosis can develop in the liver, kidney, lung, dermis, vasculature, gut and other sites. Fibrosis develops due to action of pathways including growth factors, cytokines, integrin and lipids.

ATX, LPA, and LPA Receptor (LPAR) pathways have been implicated in fibrotic disease. For example, profiling studies show increased levels of ATX, LPA and LPARs in various rodent models of fibrosis and in human patient fluids and biopsy tissue. LPA can induce proliferative, survival, and chemotactic responses in transformed cell lines, indicating that LPA may exert pro-inflammatory and pro-fibrotic responses in cells known to be critical in fibrotic disease, including: fibroblasts, smooth muscle cells, macrophages, epithelial and endothelial cells, and leukocytes. Gene-targeted mouse models have implicated LPARs in fibrosis pathogenesis. Inhibitors of LPARs indicate that antagonism of receptors within this pathway blocked or reversed fibrosis in the lung, liver, kidney and skin in rodents. Cell type-specific gene targeting studies have showed that ATX plays a role in the development of lung fibrosis and inflammatory arthritis.

ATX and LPA have also been implicated in tumor progression and metastasis. ATX may be responsible for increased LPA levels in ascites and plasma of ovarian cancer patients since ATX converts LPC to LPA. Increased levels of LPA, altered receptor expression and altered responses to LPA may contribute to initiation, progression or outcome of ovarian cancer. LPA has also been linked to prostate, breast, melanoma, head and neck, bowel, brain and thyroid cancers. LPA has been shown to promote tumor cell survival, proliferation, invasion and migration into neighboring tissues, which can result in the formation of metastases. Additionally, LPA promotes cytoskeletal remodeling that may enhance migratory and invasive properties of cells, which may contribute to cancer metastasis. These biological and pathobiological processes of LPA are initiated through the activation of G-protein coupled receptors.

Transcriptome analyses of more than 350 normal tissues and more than 1700 malignant tissues demonstrate that ATX is expressed in a variety of carcinomas and sarcomas, underscoring the potential contribution of LPA to metastatic disease.

Accordingly, when treating patients with diseases, such as cancer, lymphocyte homing, chronic inflammation, neuropathic pain, fibrotic diseases, thrombosis, and cholestatic pruritus it is desirable to lower LPA levels. This can be accomplished through inhibition of enzymes involved in LPA biosynthesis, such as ATX.

Since ATX is expressed in tumors and affects tumor cell proliferation and invasion into neighboring tissues both of which can lead to the formation of metastases, ATX is a target for anti-tumor therapy. Moreover, in angiogenesis, ATX, taken with other anti-angiogenetic factors, brings about blood vessel formation. Angiogenesis supplies tumors with nutrients during tumor growth. Therefore, inhibition of angiogenesis is a target for anti-tumor therapy, leading to starvation of a tumor.

ATX has also been implicated in nerve injury-induced neuropathic pain. LPA biosynthesis, through ATX, is the source of LPA for LPA1 receptor-mediated neuropathic pain. Therefore, targeted inhibition of ATX-mediated LPA biosynthesis may represent a novel treatment to prevent nerve injury-induced neuropathic pain.

Various publications refer to compounds that are capable of inhibiting ATX, including: WO2013061297, WO2012166415, US20120100592, WO2012024620, WO2011116867, WO2011017350, WO2011006569, WO2010115491, WO2010115491, WO2010112124, WO2010112116, WO2010063352, US20100016258, and WO2009151644.

Accordingly, there remains a need for ATX inhibitors having the potential to reach the clinic and obtain regulatory approval for use in the treatment and/or prophylaxis of physiological and/or pathophysiological conditions, such as cancer, lymphocyte homing, chronic inflammation, neuropathic pain, fibrotic diseases, thrombosis, and cholestatic pruritus which are caused, mediated and/or propagated by increased LPA levels and/or the activation of ATX.

SUMMARY

The present invention includes certain substituted compounds described herein, their salts, preparations thereof, pharmaceutical compositions and formulations thereof, and methods of treating disease such as cancers therewith.

The present invention includes compounds of Formula I and pharmaceutically acceptable salts thereof:

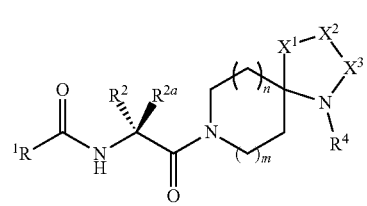

I wherein $X^1$ is selected from $C_{1-2alkyl}$, C=O, $NR^3$, or O; $X^2$ is selected from $C_{1-2alkyl}$, C=O, $NR^3$, or O; $X^3$ is selected from $C_{1-2alkyl}$, C=O, $NR^3$, O or $CR^{10}R^{11}$; $R^1$, $R^2$, $R^{2a}$, $R^4$, $R^{10}$ and $R^{11}$ are each independently optionally substituted; and m and n are each independently selected from 0, 1 or 2. Any of the above can be further substituted. Compounds of Formula I inhibit ATX.

In some embodiments, compounds of the present invention are inhibitors of ATX. In some embodiments, compounds of the present invention are selective inhibitors of ATX.

In some embodiments, the present invention includes a method for the treatment of at least one of cancer, lymphocyte homing, chronic inflammation, neuropathic pain, fibrotic diseases, thrombosis, and cholestatic pruritus comprising administering to a subject in need thereof a therapeutically effective amount of a compound or salt of the compound of Formula I that binds to and inhibits ATX providing a reduction in LPA levels.

Embodiments of the present invention include the compounds herein, pharmaceutically acceptable salts thereof, any physical forms thereof including solvates and hydrates, preparation of the compounds, intermediates, and pharmaceutical compositions and formulations thereof.

DETAILED DESCRIPTION

In some embodiments, the present invention concerns compounds and salts thereof of Formula I, as shown below and defined herein.

A compound according to Formula I:

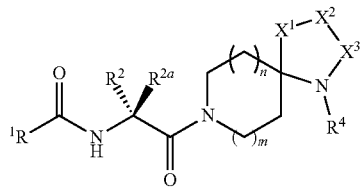

I or a pharmaceutically acceptable salt thereof, wherein:

$X^1$ and $X^2$ are each independently selected from one or more of $C_{1-2alkyl}$, C=O, $NR^3$, or O;

$X^3$ is independently selected from one or more of $C_{1-2alkyl}$, C=O, $NR^3$, O, or $CR^{10}R^{11}$;

m and n are each independently selected from 0, 1 or 2;

$R^1$ is selected from $C_{0-12}$alkyl-, $C_{3-12}$cycloalkyl-$C_{0-12}$alkyl-, $C_{3-12}$heterocycloalkyl-$C_{0-12}$alkyl-, aryl-$C_{0-12}$alkyl-, aryl-$C_{3-12}$cycloalkyl-, aryl-$C_{3-12}$heterocycloalkyl-, heteroaryl-$C_{0-12}$alkyl-, heteroaryl-$C_{3-12}$cycloalkyl-, or heteroaryl-$C_{3-12}$heterocycloalkyl-, any of which is optionally substituted with one or more independent $G^1$ substituents;

$R^2$ is selected from $C_{0-12}$alkyl-, $C_{3-12}$cycloalkyl-$C_{0-12}$alkyl-, $C_{3-12}$heterocycloalkyl-$C_{0-12}$alkyl-, aryl-$C_{0-12}$alkyl-, aryl-$C_{3-12}$cycloalkyl-, aryl-$C_{3-12}$heterocycloalkyl-, heteroaryl-$C_{0-12}$alkyl-, heteroaryl-$C_{3-12}$cycloalkyl-, or heteroaryl-$C_{3-12}$heterocycloalkyl-, any of which is optionally substituted with one or more independent $G^2$ substituents;

$R^{2a}$ is selected from $C_{0-12}$alkyl-, $C_{3-12}$cycloalkyl-$C_{0-12}$alkyl-, $C_{3-12}$heterocycloalkyl-$C_{0-12}$alkyl-, aryl-$C_{0-12}$alkyl-, aryl-$C_{3-12}$cycloalkyl-, aryl-$C_{3-12}$heterocycloalkyl-, heteroaryl-$C_{0-12}$alkyl-, heteroaryl-$C_{3-12}$cycloalkyl-, or heteroaryl-$C_{3-12}$heterocycloalkyl-, any of which is optionally substituted with one or more independent $G^{2a}$ substituents;

$R^2$ and $R^{2a}$ are each independently a linear structure, or, $R^2$ and $R^{2a}$ are taken together with the carbon atom to which they are attached to form a 3-12 membered saturated or unsaturated ring, wherein said ring optionally includes one or more additional heteroatoms selected from O, N, or $S(O)_{m1}$;

$R^3$ is selected from $C_{0-12}$alkyl-, $C_{3-12}$cycloalkyl-$C_{0-12}$alkyl-, $C_{3-12}$heterocycloalkyl-$C_{0-12}$alkyl-, aryl-$C_{0-12}$alkyl-, aryl-$C_{3-12}$cycloalkyl-, aryl-$C_{3-12}$heterocycloalkyl-, heteroaryl-$C_{0-12}$alkyl-, heteroaryl-$C_{3-12}$cycloalkyl-, or heteroaryl-$C_{3-12}$heterocycloalkyl-, any of which is optionally substituted with one or more independent $G^3$ substituents;

$R^4$ is selected from $C_{0-12}$alkyl-, $C_{3-12}$cycloalkyl-$C_{0-12}$alkyl-, $C_{3-12}$heterocycloalkyl-$C_{0-12}$alkyl-, aryl-$C_{0-12}$alkyl-, aryl-$C_{3-12}$cycloalkyl-, aryl-$C_{3-12}$heterocycloalkyl-, heteroaryl-$C_{0-12}$alkyl-, heteroaryl-$C_{3-12}$cycloalkyl-, heteroaryl-$C_{3-12}$heterocycloalkyl-, or pyridine-N-oxide, any of which is optionally substituted with one or more independent $G^4$ substituents;

$G^1$, $G^2$, $G^{2a}$, $G^3$, and $G^4$ are each independently selected from one or more of H, D, halo, —CN, —$CD_3$, —$OCD_3$, -oxo-, —$CF_3$, —$OCF_3$, —$OCHF_2$, —$NR^5R^6$, —$NO_2$, —$B(OH)_2$, —$PO(OR^{12})_2$, —$PO(OR^{12})R^{13}$, —$CONR^{12}OH$, —$C_{0-12}$alkyl, —$C_{2-12}$alkenyl, —$C_{2-12}$alkynyl, $C_{3-12}$cycloalkyl-$C_{0-12}$alkyl-, $C_{3-12}$heterocycloalkyl-$C_{0-12}$alkyl-, aryl-$C_{0-12}$alkyl-, heteroaryl-$C_{0-12}$alkyl-, —$OC_{0-12}$alkyl, —$S(O)_{n1}R^{12}$, —$C(O)R^{12}$, —$C(O)NR^{12}R^{13}$, —C(O)—C(O)$NR^{12}R^{13}$, —$C(O)OR^{12}$, —C(O)—C(O)$OR^{12}$, —$OC(O)R^{12}$, —$NR^{12}C(O)R^{13}$, —$NR^{12}C(O)OR^{13}$, —$NR^{12}S(O)_2R^{13}$, —$(CR^{14}R^{15})C(O)R^{13}$, —$(CR^{14}R^{15})C(O)OR^{12}$, —$(CR^{14}R^{15})C(O)NR^{12}R^{13}$, —$(CR^{14}R^{15})_{n1}S(O)_2NR^{12}R^{13}$, —$(CR^{14}R^{15})_{n1}NR^{12}R^{13}$, —$(CR^{14}R^{15})_{n1}OR^{12}$, —$(CR^{14}R^{15})_{n1}S(O)_{n2}R^{12}$, —$NR^{16}C(O)NR^{12}R^{13}$, —$NR^{16}S(O)_2NR^{12}R^{13}$ or —$NR^{16}S(O)NR^{12}R^{13}$, any of which is optionally substituted with one or more independent Q substituents;

$Q^1$ is selected from H, D, halo, —CN, —$CD_3$, —$OCD_3$, -oxo-, —$CF_3$, —$OCF_3$, —$OCHF_2$, —$NO_2$, —$B(OH)_2$, —$PO(OR^{17})_2$, —$PO(OR^{17})R^{18}$, $NR^{17}R^{18}$, —$CONR^{17}OH$, $C_{0-12}$alkyl-, —$C_{2-12}$ alkenyl, —$C_{2-12}$alkynyl, aryl-$C_{0-12}$alkyl-, heteroaryl-$C_{0-12}$alkyl-, $C_{3-12}$cycloalkyl-$C_{0-12}$alkyl-, $C_{3-12}$heterocycloalkyl-$C_{0-12}$alkyl-, aryl-$C_{0-12}$cycloalkyl-, heteroaryl-$C_{3-12}$cycloalkyl-, $C_{3-12}$heterocycloalkyl-$C_{3-12}$cycloalkyl-, $C_{3-12}$cycloalkyl-$C_{3-12}$cycloalkyl-, $C_{1-12}$alkyl-$C_{3-12}$heterocycloalkyl-, $C_{3-12}$heterocycloalkyl-$C_{3-12}$heterocycloalkyl-, aryl-$C_{3-12}$heterocycloalkyl-, heteroaryl-$C_{3-12}$heterocycloalkyl-, —$OC_{0-12}$alkyl, —C(O)—C(O)$NR^{17}R^{18}$, —C(O)—C(O)$OR^{17}$, —$OC(O)R^{17}$, —$NR^{17}C(O)R^{18}$, —$NR^{17}S(O)_2R^{18}$, —$(CR^{19}R^{20})_{n3}C(O)R^{17}$, —$(CR^{19}R^{20})_{n3}C(O)OR^{17}$, —$(CR^{19}R^{20})_{n3}C(O)NR^{17}R^{18}$, —$(CR^{19}R^{20})_{n3}S(O)_2NR^{17}R^{18}$, —$(CR^{19}R^{20})_{n3}NR^{17}R^{18}$, —$(CR^{19}R^{20})_{n3}OR^{17}$, —$(CR^{19}R^{20})_{n3}S(O)_{n4}R^{17}$, —$NR^{21}C(O)NR^{17}R^{18}$, —$NR^{21}S(O)_2NR^{17}R^{18}$ or —$NR^{21}S(O)NR^{17}R^{18}$, any of which is optionally substituted with one or more independent $Q^2$ substituents;

$Q^2$ is selected from one or more of H, D, halo, —CN, -oxo-, —$CD_3$, —$OCD_3$, —$CF_3$, —$OCF_3$, —$OCHF_2$, —$NO_2$, —$B(OH)_2$, —$PO(OR^{27})_2$, —$PO(OR^{27})R^{28}$, —$CONR^{27}OH$, —$CONR^{27}R^{28}C_{0-12}$alkyl-, —$C_{2-12}$ alkenyl, —$C_{2-12}$ alkynyl, —$OC_{0-12}$alkyl, aryl-$C_{0-12}$alkyl-, heteroaryl-$C_{0-12}$alkyl-, $C_{3-12}$cycloalkyl-$C_{0-12}$alkyl-, $C_{3-12}$heterocycloalkyl-$C_{0-12}$alkyl-, aryl-$C_{0-12}$cycloalkyl-, heteroaryl-$C_{3-12}$cycloalkyl-, $C_{3-12}$heterocycloalkyl-$C_{3-12}$cycloalkyl-, $C_{3-12}$cycloalkyl-$C_{3-12}$cycloalkyl-, $C_{1-12}$alkyl-$C_{3-12}$heterocycloalkyl-, $C_{3-12}$heterocycloalkyl-$C_{3-12}$heterocycloalkyl-, aryl-$C_{3-12}$heterocycloalkyl-, heteroaryl-$C_{3-12}$heterocycloalkyl-, —C(O)—C(O)$NR^{27}R^{28}$, —$C_{0-12}$alkylC(O)$OR^{27}$, —C(O)—C(O)OR$^{27}$, —OC(O)R$^{27}$, —NR$^{27}$C(O)R$^{28}$, —NR$^{27}$C(O)OR$^{28}$, —NR$^{27}$S(O)$_2$R$^{28}$, —(CR$^{29}$R$^{30}$)$_{n5}$C(O)R$^{27}$, —(CR$^{29}$R$^{30}$)$_{n5}$C(O)OR$^{27}$, —(CR$^{29}$R$^{30}$)$_{n5}$C(O)NR$^{27}$R$^{28}$, —(CR$^{29}$R$^{30}$)$_{n5}$S(O)$_2$NR$^{27}$R$^{28}$, —(CR$^{29}$R$^{30}$)$_{n5}$NR$^{27}$R$^{28}$, —(CR$^{29}$R$^{30}$)$_{n5}$OR$^{27}$, —(CR$^{29}$R$^{30}$)$_{n5}$S(O)$_{n6}$R$^{27}$, —NR$^{30}$C(O)NR$^{27}$R$^{28}$, —NR$^{30}$S(O)$_2$NR$^{27}$R$^{28}$ or —NR$^{30}$S(O)NR$^{27}$R$^{28}$ substituents, any of which may be optionally substituted;

$R^5$, $R^6$, $R^{10}$, $R^{11}$, $R^{12}$, $R^{13}$, $R^{14}$, $R^{15}$, and $R^{16}$ are each independently selected from one or more of H, $C_{1-6}$alkyl-, $C_{3-8}$cycloalkyl-$C_{0-6}$alkyl-, $C_{3-8}$heterocycloalkyl-$C_{0-6}$alkyl-, aryl-$C_{0-6}$alkyl-, aryl-$C_{3-8}$cycloalkyl-, aryl-$C_{3-8}$heterocycloalkyl-, heteroaryl-$C_{1-6}$alkyl-, heteroaryl-$C_{3-8}$cycloalkyl- or heteroaryl-$C_{3-8}$heterocycloalkyl-, any of which may be optionally substituted;

$R^{17}$, $R^{18}$, $R^{19}$, $R^{20}$, $R^{21}$, $R^{27}$, $R^{28}$, $R^{29}$, and $R^{30}$ are each independently selected from H, $C_{1-6}$alkyl-, $C_{3-8}$cycloalkyl-$C_{0-6}$alkyl-, $C_{3-8}$heterocycloalkyl-$C_{0-6}$alkyl-, aryl-$C_{0-6}$alkyl-, aryl-$C_{3-8}$cycloalkyl-, aryl-$C_{3-8}$heterocycloalkyl-, heteroaryl-$C_{1-6}$alkyl-, heteroaryl-$C_{3-8}$cycloalkyl- or heteroaryl-$C_{3-8}$heterocycloalkyl-, any of which may be optionally substituted;

—NR$^5$R$^6$ and —NR$^{12}$R$^{13}$ are each independently a linear structure, or, $R^5$ and $R^6$, or $R^{12}$ and $R^{13}$ respectively, are taken together with the nitrogen atom to which they are attached to form a 3-12 membered saturated or unsaturated ring, wherein said ring optionally includes one or more additional heteroatoms selected from O, N, or S(O)$_{m2}$;

—CR$^{10}$R$^{11}$ and —CR$^{14}$R$^{15}$ are each independently a linear structure, or, $R^{10}$ and $R^{11}$, or $R^{14}$ and $R^{15}$ respectively, are taken together with the carbon atom to which they are attached to form a 3-12 membered saturated or unsaturated ring, wherein said ring optionally includes one or more heteroatoms selected from O, N, or S(O)$_{m3}$;

—CR$^{19}$R$^{20}$ is a linear structure, or, $R^{19}$ and $R^{20}$ are taken together with the carbon atom to which they are attached to form a 3-12 membered saturated or unsaturated ring, wherein said ring optionally includes one or more additional heteroatoms selected from O, N, or S(O)$_{m4}$;

—NR$^{17}$R$^{18}$ is a linear structure, or, $R^{17}$ and $R^{18}$ are taken together with the nitrogen atom to which they are attached to form a 3-12 membered saturated or unsaturated ring, wherein said ring optionally includes one or more additional heteroatoms selected from O, N, or S(O)$_{m5}$;

—CR$^{29}$R$^{30}$ is a linear structure, or, $R^{29}$ and $R^{30}$ are taken together with the carbon atom to which they are attached to form a 3-12 membered saturated or unsaturated ring, wherein said ring optionally includes one or more additional heteroatoms selected from O, N, or S(O)$_{m6}$;

—NR$^{27}$R$^{28}$ is a linear structure, or, $R^{27}$ and $R^{28}$ are taken together with the nitrogen atom to which they are attached to form a 3-12 membered saturated or unsaturated ring, wherein said ring optionally includes one or more additional heteroatoms selected from O, N, or S(O)$_{m7}$;

wherein m1, m2, m3, m4, m5, m6, m7, n1, n2, n3, n4, n5 and n6 are each independently selected from 0, 1 or 2;

or a pharmaceutically acceptable salt, solvate or a prodrug thereof.

In some embodiments of Formula I:
$R^1$ is selected from one of $C_{3-8}$cycloalkyl-$C_{0-8}$-alkyl-, $C_{3-8}$heterocycloalkyl-$C_{0-8}$-alkyl-, aryl-$C_{0-8}$alkyl-, or heteroaryl-$C_{0-8}$alkyl-;

$G^1$ is selected from one of H, halo, —CN, -oxo-, —CF$_3$, —OCF$_3$, —OCHF$_2$, —NR$^5$R$^6$, —NO$_2$, —OC$_{0-8}$alkyl, —S(O)$_{n1}$R$^{12}$, —B(OH)$_2$, —C$_{0-8}$alkyl, —C$_{2-8}$alkenyl, —C$_{2-8}$alkynyl, $C_{3-8}$cycloalkyl-$C_{0-8}$-alkyl-, $C_{3-8}$heterocycloalkyl-$C_{0-8}$alkyl-, aryl-$C_{0-8}$alkyl-, or heteroaryl-$C_{0-8}$alkyl-.

In some embodiments of Formula I:
$G^1$ is selected from 0 to 3 of H, halo, —CN, -oxo-, —CF$_3$, —OCF$_3$, —OCHF$_2$, —NR$^5$R$^6$, —NO$_2$, —OC$_{0-8}$alkyl, —S(O)$_{n1}$R$^{12}$, —B(OH)$_2$, —C$_{0-8}$alkyl, —C$_{2-8}$alkenyl, —C$_{2-8}$alkynyl, $C_{3-8}$cycloalkyl-$C_{0-8}$-alkyl-, $C_{3-8}$heterocycloalkyl-$C_{0-8}$alkyl-, aryl-$C_{0-8}$alkyl-, or heteroaryl-$C_{0-8}$alkyl-.

In some embodiments of Formula I:
$R^2$ is selected from $C_{0-8}$alkyl-, $C_{3-8}$cycloalkyl-$C_{0-8}$alkyl-, or $C_{3-8}$heterocycloalkyl-$C_{0-8}$alkyl-;

$R^{2a}$ is $C_{0-8}$alkyl-;

$G^2$ is selected from one or more of H, halo, —CN, —CD$_3$, —OCD$_3$, —CF$_3$, —OCF$_3$, —OCHF$_2$, or —OC$_{0-8}$alkyl;

$R^2$ and $R^{2a}$ are each independently a linear structure, or, $R^2$ and $R^{2a}$ are taken together with the carbon atom to which they are attached to form a 3-12 membered saturated or unsaturated ring, wherein said ring optionally includes one or more additional heteroatoms selected from O, or N.

In some embodiments of Formula I:
$G^2$ is selected from 0 to 3 of H, halo, —CN, —CD$_3$, —OCD$_3$, —CF$_3$, —OCF$_3$, —OCHF$_2$, or —OC$_{0-8}$alkyl.

In some embodiments of Formula I:
$R^3$ is selected from $C_{0-8}$alkyl-, $C_{3-8}$cycloalkyl-$C_{0-8}$alkyl-, or $C_{3-8}$heterocycloalkyl-$C_{0-8}$alkyl-;

$G^3$ is selected from one or more of H, D, halo, —CN, —CD$_3$, —OCD$_3$, -oxo-, —CF$_3$, —OCF$_3$, —OCHF$_2$, —NR$^5$R$^6$, —C$_{0-8}$alkyl, —C$_{2-8}$alkenyl, —C$_{2-8}$alkynyl, —OC$_{0-8}$alkyl, —S(O)$_{n1}$R$^{12}$, —C(O)R$^{12}$, —C(O)NR$^{12}$R$^{13}$, or —C(O)OR$^{12}$.

In some embodiments of Formula I:
$G^3$ is selected from 0 to 3 of H, D, halo, —CN, —CD$_3$, —OCD$_3$, -oxo-, —CF$_3$, —OCF$_3$, —OCHF$_2$, —NR$^5$R$^6$, —C$_{0-8}$alkyl, —C$_{2-8}$alkenyl, —C$_{2-8}$alkynyl, —OC$_{0-8}$alkyl, —S(O)$_{n1}$R$^{12}$, —C(O)R$^{12}$, —C(O)NR$^{12}$R$^{13}$, or —C(O)OR$^{12}$.

In some embodiments of Formula I:
$R^4$ is selected from $C_{0-8}$alkyl-, $C_{3-8}$cycloalkyl-$C_{3-8}$alkyl-, $C_{3-8}$heterocycloalkyl-$C_{0-8}$alkyl-, aryl-$C_{0-8}$alkyl-, heteroaryl-$C_{0-8}$alkyl-, heteroaryl-$C_{3-8}$cycloalkyl-, heteroaryl-$C_{3-8}$heterocycloalkyl-, or pyridine-N-oxide;

$G^4$ is selected from one or more of H, D, halo, —CN, —CD$_3$, —OCD$_3$, -oxo-, —CF$_3$, —OCF$_3$, —OCHF$_2$, —NR$^5$R$^6$, —NO$_2$, —B(OH)$_2$, —CONR$^{12}$OH, —C$_{0-8}$alkyl, $C_{3-8}$cycloalkyl-$C_{0-8}$alkyl-, $C_{3-8}$heterocycloalkyl-$C_{0-8}$alkyl-, aryl-$C_{0-8}$alkyl-, heteroaryl-$C_{0-8}$alkyl-, —OC$_{0-8}$alkyl, —S(O)$_{n1}$R$^{12}$, —C(O)R$^{12}$, —C(O)NR$^{12}$R$^{13}$, —C(O)—C(O)NR$^{12}$R$^{13}$, —C(O)OR$^{12}$, —C(O)—C(O)OR$^{12}$, —OC(O)R$^{12}$, —NR$^{12}$C(O)R$^{13}$, —NR$^{12}$C(O)OR$^{13}$, —(CR$^{14}$R$^{15}$)C(O)R$^{13}$, —(CR$^{14}$R$^{15}$)$_{n1}$S(O)$_2$NR$^{12}$R$^{13}$, —(CR$^{14}$R$^{15}$)$_{n1}$NR$^{12}$R$^{13}$, —(CR$^{14}$R$^{15}$)$_{n1}$OR$^{12}$, —(CR$^{14}$R$^{15}$)$_{n1}$S(O)$_{n2}$R$^{12}$, or —NR$^{16}$C(O)NR$^{12}$R$^{13}$.

In some embodiments of Formula I:
$G^4$ is selected from 0 to 3 of H, D, halo, —CN, —CD$_3$, —OCD$_3$, -oxo-, —CF$_3$, —OCF$_3$, —OCHF$_2$, —NR$^5$R$^6$, —NO$_2$, —B(OH)$_2$, —CONR$^{12}$OH, —C$_{0-8}$alkyl, $C_{3-8}$cycloalkyl-$C_{0-8}$alkyl-, $C_{3-8}$heterocycloalkyl-$C_{0-8}$alkyl-, aryl-$C_{0-8}$alkyl-, heteroaryl-$C_{0-8}$alkyl-, —OC$_{0-8}$alkyl, —S(O)$_{n1}$R$^{12}$, —C(O)R$^{12}$, —C(O)NR$^{12}$R$^{13}$, —C(O)—C(O)NR$^{12}$R$^{13}$, —C(O)OR$^{12}$, —C(O)—C(O)OR$^{12}$, —OC(O)R$^{12}$, —NR$^{12}$C(O)R$^{13}$, —NR$^{12}$C(O)OR$^{13}$, —(CR$^{14}$R$^{15}$)C(O)R$^{13}$, —(CR$^{14}$R$^{15}$)$_{n1}$S(O)$_2$NR$^{12}$R$^{13}$, —(CR$^{14}$R$^{15}$)$_{n1}$NR$^{12}$R$^{13}$, —(CR$^{14}$R$^{15}$)$_{n1}$OR$^{12}$, —(CR$^{14}$R$^{15}$)$_{n1}$S(O)$_{n2}$R$^{12}$, or —NR$^{16}$C(O)NR$^{12}$R$^{13}$.

In some embodiments of Formula I:
$Q^1$ is selected from H, D, halo, —CN, —CD$_3$, —OCD$_3$, -oxo-, —CF$_3$, —OCF$_3$, —OCHF$_2$, NR$^{17}$R$^{18}$, $C_{0-8}$alkyl-, aryl-$C_{0-8}$alkyl-, heteroaryl-$C_{0-8}$alkyl-, $C_{3-8}$cycloalkyl- $C_{0-8}$alkyl-, $C_{3-8}$heterocycloalkyl-$C_{0-8}$alkyl-, aryl-$C_{0-8}$cycloalkyl-, heteroaryl-$C_{3-8}$cycloalkyl-, $C_{3-8}$heterocycloalkyl-$C_{3-8}$cycloalkyl-, $C_{3-8}$cycloalkyl-$C_{3-8}$heterocycloalkyl-, $C_{1-8}$alkyl-$C_{3-8}$heterocycloalkyl-, $C_{3-8}$heterocycloalkyl-$C_{3-8}$heterocycloalkyl-, aryl-$C_{3-8}$heterocycloalkyl-, heteroaryl-$C_{3-8}$heterocycloalkyl-, —$OC_{0-8}$alkyl, —C(O)—C(O)$NR^{17}R^{18}$, —C(O)—C(O)$OR^{17}$, —OC(O)$R^{17}$, —$NR^{17}$C(O)$R^{18}$, —$NR^{17}$S(O)$_2R^{18}$, —(C$R^{19}R^{20}$)$_{n3}$C(O)$R^{17}$, —(C$R^{19}R^{20}$)$_{n3}$C(O)$OR^{17}$, —(C$R^{19}R^{20}$)$_{n3}$C(O)$NR^{17}R^{18}$, —(C$R^{19}R^{20}$)$_{n3}$S(O)$_2NR^{17}R^{18}$, —(C$R^{19}R^{20}$)$_{n3}NR^{17}R^{18}$, —(C$R^{19}R^{20}$)$_{n3}OR^{17}$, —(C$R^{19}R^{20}$)$_{n3}$S(O)$_{n4}R^{17}$, —$NR^{21}$C(O)$NR^{17}R^{18}$, —$NR^{21}$S(O)$_2NR^{17}R^{18}$, or —$NR^{21}$S(O)$NR^{17}R^{18}$.

In some embodiments of Formula I:
$R^1$ is selected from one of $C_{3-6}$cycloalkyl-$C_{0-6}$alkyl-, $C_{3-6}$heterocycloalkyl-$C_{0-6}$alkyl-, aryl-$C_{0-6}$alkyl-, or heteroaryl-$C_{0-6}$alkyl-;

$G^1$ is selected from one of H, halo, —CN, -oxo-, —$CF_3$, —$OCF_3$, —$OCHF_2$, —$NR^5R^6$, —$NO_2$, —$OC_{0-6}$alkyl, —S(O)$_{n1}R^{12}$, —B(OH)$_2$, —$C_{0-6}$alkyl, —$C_{2-6}$alkenyl, —$C_{2-6}$alkynyl, $C_{3-6}$cycloalkyl-$C_{0-6}$alkyl-, $C_{3-6}$heterocycloalkyl-$C_{0-6}$alkyl-, aryl-$C_{0-6}$alkyl-, or heteroaryl-$C_{0-6}$alkyl-.

In some embodiments of Formula I:
$G^1$ is selected from 0 to 2 of H, halo, —CN, -oxo-, —$CF_3$, —$OCF_3$, —$OCHF_2$, —$NR^5R^6$, —$NO_2$, —$OC_{0-6}$alkyl, —S(O)$_{n1}R^{12}$, —B(OH)$_2$, —$C_{0-6}$alkyl, —$C_{2-6}$alkenyl, —$C_{2-6}$alkynyl, $C_{3-6}$cycloalkyl-$C_{0-6}$alkyl-, $C_{3-6}$heterocycloalkyl-$C_{0-6}$alkyl-, aryl-$C_{0-6}$alkyl-, or heteroaryl-$C_{0-6}$alkyl-.

In some embodiments of Formula I:
$R^2$ is selected from $C_{0-6}$alkyl-, $C_{3-6}$cycloalkyl-$C_{0-6}$alkyl-, or $C_{3-6}$heterocycloalkyl-$C_{0-6}$alkyl-;
$R^{2a}$ is $C_{0-6}$alkyl-;
$G^2$ is selected from one or more of H, halo, —CN, —$CD_3$, —$OCD_3$, —$CF_3$, —$OCF_3$, —$OCHF_2$, or —$OC_{0-6}$alkyl;
$R^2$ and $R^{2a}$ are each independently a linear structure, or, $R^2$ and $R^{2a}$ are taken together with the carbon atom to which they are attached to form a 3-12 membered saturated or unsaturated ring, wherein said ring optionally includes one or more additional heteroatoms selected from O, or N.

In some embodiments of Formula I:
$R^2$ and $R^{2a}$ are each independently a linear structure, or, $R^2$ and $R^{2a}$ are taken together with the carbon atom to which they are attached to form a 4-6 membered saturated or unsaturated ring, wherein said ring optionally includes one or more additional heteroatoms selected from O, or N.

In some embodiments of Formula I:
$G^2$ is selected from 0 to 2 of H, halo, —CN, —$CD_3$, —$OCD_3$, —$CF_3$, —$OCF_3$, —$OCHF_2$, or —$OC_{0-6}$alkyl.

In some embodiments of Formula I:
$R^3$ is selected from $C_{0-6}$alkyl-, $C_{3-6}$cycloalkyl-$C_{0-6}$alkyl-, or $C_{3-6}$heterocycloalkyl-$C_{0-6}$alkyl-;
$G^3$ is selected from one or more of H, D, halo, —CN, —$CD_3$, —$OCD_3$, -oxo-, —$CF_3$, —$OCF_3$, —$OCHF_2$, —$NR^5R^6$, —$C_{0-6}$alkyl, —$C_{2-6}$alkenyl, —$C_{2-6}$alkynyl, —$OC_{0-6}$alkyl, —S(O)$_{n1}R^{12}$, —C(O)$R^{12}$, —C(O)$NR^{12}R^{13}$, or —C(O)$OR^{12}$.

In some embodiments of Formula I:
$G^3$ is selected from 0 to 2 of H, D, halo, —CN, —$CD_3$, —$OCD_3$, -oxo-, —$CF_3$, —$OCF_3$, —$OCHF_2$, —$NR^5R^6$, —$C_{0-6}$alkyl, —$C_{2-6}$alkenyl, —$C_{2-6}$alkynyl, —$OC_{0-6}$alkyl, —S(O)$_{n1}R^{12}$, —C(O)$R^{12}$, —C(O)$NR^{12}R^{13}$, or —C(O)$OR^{12}$.

In some embodiments of Formula I:
$R^4$ is selected from $C_{0-6}$alkyl-, $C_{3-6}$cycloalkyl-$C_{0-6}$alkyl-, $C_{3-6}$heterocycloalkyl-$C_{0-6}$alkyl-, aryl-$C_{0-6}$alkyl-, heteroaryl-$C_{0-6}$alkyl-, heteroaryl-$C_{3-6}$cycloalkyl-, heteroaryl-$C_{3-6}$heterocycloalkyl-, or pyridine-N-oxide;

$G^4$ is selected from one or more of H, D, halo, —CN, —$CD_3$, —$OCD_3$, -oxo-, —$CF_3$, —$OCF_3$, —$OCHF_2$, —$NR^5R^6$, —$NO_2$, —B(OH)$_2$, —CON$R^{12}$OH, —$C_{0-6}$alkyl, $C_{3-6}$cycloalkyl-$C_{0-6}$alkyl-, $C_{3-6}$heterocycloalkyl-$C_{0-6}$alkyl-, aryl-$C_{0-6}$alkyl-, heteroaryl-$C_{0-6}$alkyl-, —$OC_{0-6}$alkyl, —S(O)$_{n1}R^{12}$, —C(O)$R^{12}$, —C(O)$NR^{12}R^{13}$, —C(O)—C(O)$NR^{12}R^{13}$, —C(O)$OR^{12}$, —C(O)—C(O)$OR^{12}$, —OC(O)$R^{12}$, —$NR^{12}$C(O)$R^{13}$, —$NR^{12}$C(O)$OR^{13}$, (C$R^{14}R^{15}$)C(O)$R^{13}$, —(C$R^{14}R^{15}$)$_{n1}$S(O)$_2NR^{12}R^{13}$, —(C$R^{14}R^{15}$)$_{n1}$ $NR^{12}R^{13}$, —(C$R^{14}R^{15}$)$_{n1}OR^{12}$, —(C$R^{14}R^{15}$)$_{n1}$S(O)$_{n2}R^{12}$, or —$NR^{16}$C(O)$NR^{12}R^{13}$.

In some embodiments of Formula I:
$G^4$ is selected from 0 to 2 of H, D, halo, —CN, —$CD_3$, —$OCD_3$, -oxo-, —$CF_3$, —$OCF_3$, —$OCHF_2$, —$NR^5R^6$, —$NO_2$, —B(OH)$_2$, —CON$R^{12}$OH, —$C_{0-6}$alkyl, $C_{3-6}$cycloalkyl-$C_{0-6}$alkyl-, $C_{3-6}$heterocycloalkyl-$C_{0-6}$alkyl-, aryl-$C_{0-6}$alkyl-, heteroaryl-$C_{0-6}$alkyl-, —$OC_{0-6}$alkyl, —S(O)$_{n1}R^{12}$, —C(O)$R^{12}$, —C(O)$NR^{12}R^{13}$, —C(O)—C(O)$NR^{12}R^{13}$, —C(O)$OR^{12}$, —C(O)—C(O)$OR^{12}$, —OC(O)$R^{12}$, —$NR^{12}$C(O)$R^{13}$, —$NR^{12}$C(O)$OR^{13}$, —(C$R^{14}R^{15}$)C(O)$R^{13}$, —(C$R^{14}R^{15}$)$_{n1}$S(O)$_2NR^{12}R^{13}$, —(C$R^{14}R^{15}$)$_{n1}NR^{12}R^{13}$, —(C$R^{14}R^{15}$)$_{n1}OR^{12}$, —(C$R^{14}R^{15}$)$_{n1}$S(O)$_{n2}R^{12}$, or —$NR^{16}$C(O)$NR^{12}R^{13}$.

In some embodiments of Formula I:
$Q^1$ is selected from H, D, halo, —CN, —$CD_3$, —$OCD_3$, -oxo-, —$CF_3$, —$OCF_3$, —$OCHF_2$, $NR^{17}R^{18}$, $C_{0-6}$alkyl-, aryl-$C_{0-6}$alkyl-, heteroaryl-$C_{0-6}$alkyl-, $C_{3-6}$cycloalkyl-$C_{0-6}$alkyl-, $C_{3-6}$heterocycloalkyl-$C_{0-6}$alkyl-, aryl-$C_{0-6}$cycloalkyl-, heteroaryl-$C_{3-6}$cycloalkyl-, $C_{3-6}$heterocycloalkyl-$C_{3-6}$cycloalkyl-, $C_{3-6}$cycloalkyl-$C_{3-6}$cycloalkyl-, $C_{1-6}$alkyl-$C_{3-6}$heterocycloalkyl-, $C_{3-6}$heterocycloalkyl-$C_{3-6}$heterocycloalkyl-, aryl-$C_{3-6}$heterocycloalkyl-, heteroaryl-$C_{3-6}$heterocycloalkyl-, —$OC_{0-6}$alkyl, —C(O)—C(O)$NR^{17}R^{18}$, —C(O)—C(O)$OR^{17}$, —OC(O)$R^{17}$, —$NR^{17}$C(O)$R^{18}$, —$NR^{17}$S(O)$_2R^{18}$, —(C$R^{19}R^{20}$)$_{n3}$C(O)$R^{17}$, —(C$R^{19}R^{20}$)$_{n3}$C(O)$OR^{17}$, —(C$R^{19}R^{20}$)$_{n3}$C(O)$NR^{17}R^{18}$, —(C$R^{19}R^{20}$)$_{n3}$S(O)$_2NR^{17}R^{18}$, —(C$R^{19}R^{20}$)$_{n3}NR^{17}R^{18}$, —(C$R^{19}R^{20}$)$_{n30}R^{17}$, —(C$R^{19}R^{20}$)$_{n3}$S(O)$_{n4}R^{17}$, —$NR^{21}$C(O)$NR^{17}R^{18}$, —$NR^{21}$S(O)$_2NR^{17}R^{18}$, or —$NR^{21}$S(O)$NR^{17}R^{18}$.

In some embodiments of Formula I:
$R^2$ is selected from methyl, ethyl, propyl, isopropyl, or one of the following groups:

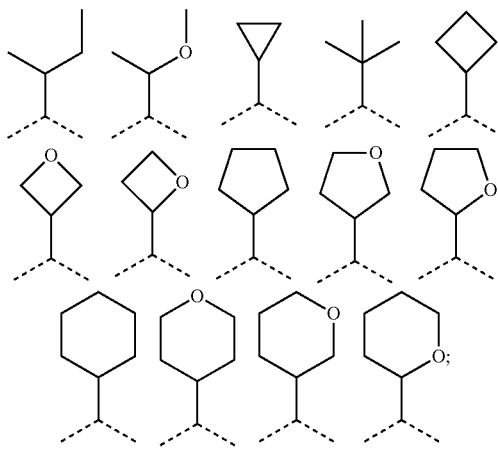

and $R^{2a}$ is selected H, methyl, ethyl, propyl, isopropyl; or $R^2$ and $R^{2a}$ are taken together with the carbon atom to which they are attached to form one of the following groups:

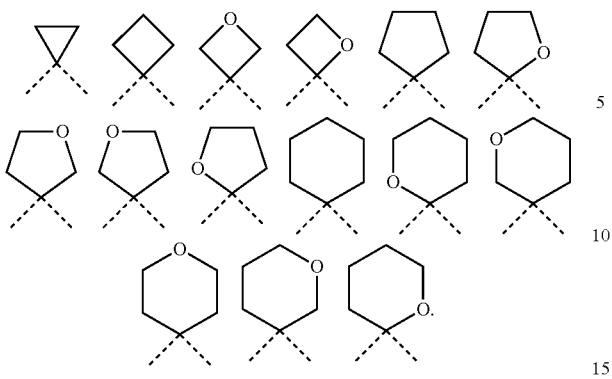

In some embodiments of Formula I:

R¹ is selected from one of $C_6$cycloalkyl-$C_{0-6}$alkyl-, $C_6$heterocycloalkyl-$C_{0-6}$alkyl-, 6-membered-aryl-$C_{0-6}$alkyl-, or 6-membered-heteroaryl-$C_{0-6}$alkyl-, wherein the 4-position of R¹ is hydrogen, and wherein R¹ is optionally substituted by one or more G¹ substituents at the 2, 3, 5 and 6 positions.

In some embodiments of Formula I:

—NR⁵R⁶ and —NR¹²R¹³ are each independently a linear structure, or, R⁵ and R⁶, or R¹² and R¹³, respectively, are taken together with the nitrogen atom to which they are attached to form a 4-8 membered saturated or unsaturated ring, wherein said ring optionally includes one or more additional heteroatoms selected from O, N, or $S(O)_{m2}$;

—CR¹⁰R¹¹ and —CR¹⁴R¹⁵ are each independently a linear structure, or, R¹⁰ and R¹¹, or R¹⁴ and R¹⁵ respectively, are taken together with the carbon atom to which they are attached to form a 4-8 membered saturated or unsaturated ring, wherein said ring optionally includes one or more heteroatoms selected from O, N, or $S(O)_{m3}$;

—CR¹⁹R²⁰ is a linear structure, or, R¹⁹ and R²⁰ are taken together with the carbon atom to which they are attached to form a 4-8 membered saturated or unsaturated ring, wherein said ring optionally includes one or more additional heteroatoms selected from O, N, or $S(O)_{m4}$;

—NR¹⁷R¹⁸ is a linear structure, or, R¹⁷ and R¹⁸ are taken together with the nitrogen atom to which they are attached to form a 4-8 membered saturated or unsaturated ring, wherein said ring optionally includes one or more additional heteroatoms selected from O, N, or $S(O)_{m5}$;

—CR²⁹R³⁰ is a linear structure, or, R²⁹ and R³⁰ are taken together with the carbon atom to which they are attached to form a 4-8 membered saturated or unsaturated ring, wherein said ring optionally includes one or more additional heteroatoms selected from O, N, or $S(O)_{m6}$;

—NR²⁷R²⁸ is a linear structure, or, R²⁷ and R²⁸ are taken together with the nitrogen atom to which they are attached to form a 4-8 membered saturated or unsaturated ring, wherein said ring optionally includes one or more additional heteroatoms selected from O, N, or $S(O)_{m7}$;

wherein m2, m3, m4, m5, m6, and m7 are each independently selected from 0, 1 or 2.

In some embodiments of Formula I, compounds of the present invention are a subgenus of Formula I, having the Formula Ia:

Ia wherein X³ is selected from C═O, or CR¹⁰R¹¹.

In some embodiments of Formula Ia, R²ᵃ is hydrogen. In other embodiments of Formula Ia, R² is $C_{1-12}$alkyl-, $C_{3-12}$cycloalkyl-, or $C_{1-12}$heteroalkyl any of which is optionally substituted with one or more independent G² substituents (e.g., methyl, ethyl, iso-propyl, sec-butyl, cyclopropyl, cyclobutyl, cyclopentyl, or cyclohexyl). In certain embodiments of Formula Ia, R¹ is aryl or heteroaryl, any of which is optionally substituted with one or more independent G¹ substituents. In other embodiments, of Formula Ia, R¹ is aryl. In certain embodiments of Formula Ia, the 4-position of said aryl is H, and wherein the 2, 3, 5 and 6 positions of said aryl are optionally substituted by one or more G¹ substituents. In some embodiments of Formula Ia, said 2, 3, 5, and 6 positions are optionally substituted with halo (e.g., fluoro, chloro, bromo), $C_{1-6}$alkyl (e.g., methyl, ethyl, CF₃), $C_{1-6}$heteroalkyl (e.g., methoxy, trifluoromethoxy), or $C_{3-8}$cycloalkyl (e.g., cyclopropyl). In some embodiments, R¹ is 3-methyl-phenyl, 3-methyl-4-fluoro-phenyl, 2-fluoro-5-ethyl-phenyl, 2-fluoro-5-trifluoromethyl-phenyl, 3-fluoro-5-methyl-phenyl, 2-fluoro-5-cyclopropyl-phenyl, 2-fluoro-5-chloro-phenyl, 3,5-dichloro-phenyl, 2-fluoro-5-methyl-phenyl, 3-chloro-5-trifluoromethyl-phenyl, 2-fluoro-5-trifluoromethoxy-phenyl, 2-fluoro-5-difluoromethoxy-phenyl, 3-fluoro-5-ethyl-phenyl, 3-cyclopropyl, 3-ethyl-phenyl, 2-fluoro-3-methyl-phenyl, or 2-fluoro-5-methoxy-phenyl.

In other embodiments of Formula Ia, R³ is $C_{1-12}$alkyl or $C_{1-12}$heteroalkyl. In certain embodiments of Formula Ia, R³ is $C_{1-12}$alkyl (e.g., methyl,

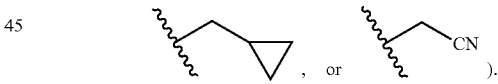

In other embodiments of Formula Ia, R³ is $C_{1-12}$heteroalkyl (e.g.

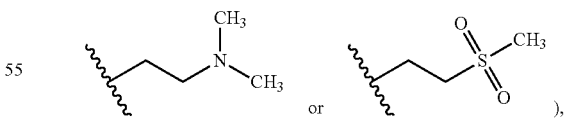

In some embodiments of Formula Ia, R⁴ is $C_{1-12}$alkyl (e.g., iso-butyl), $C_{3-8}$cycloalkyl (e.g., cyclopentyl or cyclohexyl), aryl (e.g., phenyl, 4-methoxy-phenyl, 3-fluoro-4-methoxy-phenyl, 4-cyano-phenyl, 3-cyano-phenyl, 3-methoxy-phenyl, 4-trifluoromethoxy-phenyl, 3-chloro-phenyl, 3-bromo-phenyl, 4-deutero-phenyl, 4-trifluoromethyl-phenyl, 4-carboxy-phenyl, 4-chloro-phenyl, 4-fluoro-phenyl, 4-methyl-phenyl, 3,4-dichloro-phenyl, 4-ethoxy-phenyl, 4-trideuteromethoxy-phenyl, 4-carboxymethylphenyl, 4-(oxetan-3-ylmethoxy)-phenyl, 4-(2-hydroxyethoxy)-phenyl, 4-boronic acid-phenyl, 3-methoxy-4-carboxy-phenyl, 3-chloro-4-carboxy-phenyl, 4-carboxamide-phenyl, 4-oxyacetic acid-phenyl, 4-oxyacetamide-phenyl, 4-cyanomethyl-phenyl, 4-(2-dimethylamino-ethoxy)-phenyl, 4-acetamido-phenyl, 4-methyl-sulfonamido-phenyl, 4-methylcarbamate-phenyl, benzo[d][1,3]-dioxol-5-yl, 2-chloro-phenyl, 4-methylsulfonyl-phenyl, 3-methyl-1-(3-methyl-2-oxo-2,3-dihydrobenzo[d]oxazol-5-yl, 4-(oxetan-3-ylamino)-phenyl, 4-(1H-1,2,4-triazol-3-yl)-phenyl, 4-(2H-tetrazol-5-yl)-phenyl) heteroaryl (e.g. 4-pyridyl, 1-methyl-1H-indazol-5-yl, 2-methyl-2H-indazoyl-5-yl, 1-imidazo[1,2a]pyridine-6-yl, 3-methylimidazo[1,5a]pyridine-6-yl, 1H-pyrrolo[2,3b]pyridine-5-yl, 3,4-dihydro-2H-benzo[b][1,4]oxazin-7-yl, 1-methyl-6-oxo-1,6-dihydropyridin-3-yl, 5-benzofuranyl, 2-oxo-2,3-dihydrobenzo[d]oxazol-6-yl, 1H-benzo[d][1,2,3]triazol-5-yl, 1H-indazoyl-5-yl, 1H-indol-5-yl, 3-pyridyl) aryl-$C_{1-6}$alkyl (e.g., 4-cyanobenzyl, benzyl, 4-fluorobenzyl, 4-methoxybenzyl, 4-chlorobenzyl, 3-cyano-benzyl, 3-chloro-benzyl, 2-fluoro-5-methoxy-benzyl, 2-fluoro-4-methoxy-benzyl, 2-chloro-4-methoxy-benzyl), heteroaryl-$C_{1-6}$alkyl (e.g., (2,3-dihydrobenzo[b][1,4]dioxin-6-yl)-methyl, (6-methoxypyridin-3-yl)-methyl, (quinoxalin-6-yl)-methyl, (3-methyl-2-oxo-2,3-dihydrobenzo[d]oxazol-5-yl)-methyl, (pyrimidin-2-yl)-methyl, (2-methylbenzo[d]oxazol-5-yl)-methyl), or $C_3$-12heterocycloalkyl (e.g., 1-methyl-6-oxo-1,6-dihydropyridin-3-yl) any of which is optionally substituted with one or more independent $Q^1$ substituents.

In some embodiments of Formula Ia, $X^3$ is C=O. In other embodiments of Formula Ia, $X^3$ is $CR^{10}R^{11}$ wherein $R^{10}$ is hydrogen and $R^1$ is hydrogen or methyl.

In some embodiments of Formula I, compounds of the present invention are a subgenus of Formula I, having the Formula Ih:

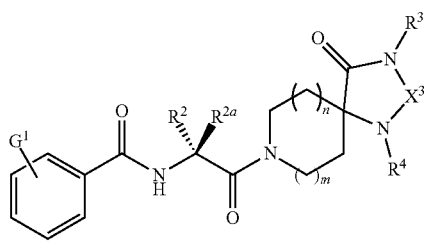

Ih wherein $X^3$ is selected from C=O, or $CR^{10}R^{11}$.

In some embodiments of Formula I:
the 4-position of the phenyl ring in Formula Ih is H, and wherein the 2, 3, 5 and 6 positions of the phenyl ring in Formula Ih are optionally substituted by one or more $G^1$ substituents.

In some embodiments of Formula I:
$R^3$ is selected from methyl, ethyl, propyl, isopropyl, —$(CH_2)_{1-3}$cyclopropyl, $C_{3-8}$cycloalkyl, —$(CH_2)_{1-3}$CN, —$(CH_2)_{1-3}$C(O)OH, or —$(CH_2)_{1-3}$S(O)$_2$Me.

In some embodiments of Formula I:
$X^1$ is selected from $C_{1-2}$alkyl or C=O;
$X^2$ is selected from $C_{1-2}$alkyl, $NR^3$, or O;
$X^3$ is selected from C=O or $CR^{10}R^{11}$;
$R^{10}$ and $R^{11}$ are each independently equal to H or $C_{1-6}$alkyl;
m and n are each equal to 1.

In some embodiments, the compounds of Formula I are inhibitors of ATX.

In some embodiments, the compound of Formula I is any one of the compounds described herein (e.g., any one of the compounds described in Examples 1 to 246)

In some embodiments, the present invention includes a pharmaceutical composition comprising the compound or salt of any one of the compounds of Formula I, formulated with or without one or more pharmaceutical carriers.

In some embodiments, the present invention includes a method for the treatment of at least one of cancer, lymphocyte homing, chronic inflammation, neuropathic pain, fibrotic diseases, thrombosis, and cholestatic pruritus mediated at least in part by ATX comprising administering to a subject in need thereof a therapeutically effective amount of a compound or salt of the compound of Formula I.

In some embodiments, the present invention includes a method for the treatment of at least one of cancer, lymphocyte homing, chronic inflammation, neuropathic pain, fibrotic diseases, thrombosis, and cholestatic pruritus comprising administering to a subject in need thereof a therapeutically effective amount of a compound or salt of the compound of Formula I that binds to and inhibits ATX providing a reduction in LPA levels.

In some embodiments, the present invention includes a method of treating fibrosis, inflammation, cancer, angiogenesis, or pain in a mammal comprising administering a therapeutically effective amount of a compound according to Formula I, or a pharmaceutically acceptable salt thereof, to the mammal in need thereof.

In some embodiments, the present invention includes a method of treating lung fibrosis, asthma, chronic obstructive pulmonary disease (COPD), renal fibrosis, acute kidney injury, chronic kidney disease, liver fibrosis, skin fibrosis, fibrosis of the gut, breast cancer, pancreatic cancer, ovarian cancer, prostate cancer, glioblastoma, bone cancer, colon cancer, bowel cancer, head and neck cancer, melanoma, multiple myeloma, chronic lymphocytic leukemia, B cell lymphoma, T cell lymphoma, cancer pain, tumor metastasis, transplant organ rejection, scleroderma, ocular fibrosis, age related macular degeneration (AMD), diabetic retinopathy, collagen vascular disease, atherosclerosis, Raynaud's phenomenon, rheumatoid arthritis, osteoarthritis or neuropathic pain in a mammal comprising administering a therapeutically effective amount of a compound according Formula I, or a pharmaceutically acceptable salt thereof, to the mammal in need thereof.

In some embodiments, the present invention further includes administering to the mammal one or more additional therapeutically active agents selected from: corticosteroids, immunosuppressants, analgesics, anti-cancer agents, anti-inflammatories, non-steroidal anti-inflammatories, dual cyclooxygenase-1 and -2 inhibitors, cyclooxygenase-2 selective inhibitors, TNFα blockers, kinase inhibitors, chemokine receptor antagonists, bronchodilators, leukotriene receptor antagonists, leukotriene formation inhibitors, prostaglandin receptor antagonists, prostaglandin formation inhibitors, monoacylglycerol kinase inhibitors, phospholipase A1 inhibitors, phospholipase A2 inhibitors, lysophospholipase D (lysoPLD) inhibitors, autotaxin inhibitors, and LPA receptor antagonists.

In some embodiments of Formula I, compounds are present as a material in substantially pure form.

In some embodiments of Formula I, compounds are selected from any one of the Examples herein or a pharmaceutically acceptable salt thereof.

Each variable definition above includes any subset thereof and the compounds of Formula I include any combination of such variables or variable subsets.

The present invention includes the compounds and salts thereof, their physical forms, preparation of the compounds, useful intermediates, and pharmaceutical compositions and formulations thereof.

The compounds of the present invention and the term "compound" in the claims include any pharmaceutically acceptable salts or solvates, and any amorphous or crystal forms, or tautomers, whether or not specifically recited in context.

The present invention includes all isomers of the compounds. Compounds may have one or more asymmetric carbon atoms can exist as two or more stereoisomers. Where a compound of the invention contains an alkenyl or alkenylene group, geometric cis/trans (or Z/E) isomers are possible. Where the compound contains, for example, a keto or oxime group or an aromatic moiety, tautomeric isomerism ('tautomerism') can occur. A single compound may exhibit more than one type of isomerism.

The present invention includes any stereoisomers, even if not specifically shown, individually as well as mixtures, geometric isomers, and pharmaceutically acceptable salts thereof. Where a compound or stereocenter is described or shown without definitive stereochemistry, it is to be taken to embrace all possible individual isomers, configurations, and mixtures thereof. Thus, a material sample containing a mixture of stereoisomers would be embraced by a recitation of either of the stereoisomers or a recitation without definitive stereochemistry. Also contemplated are any cis/trans isomers or tautomers of the compounds described.

The present invention includes all stereoisomers, geometric isomers and tautomeric forms of the inventive compounds, including compounds exhibiting more than one type of isomerism, and mixtures of one or more thereof. When a tautomer of the compound of Formula I exists, the compound of Formula I of the present invention includes any possible tautomers and pharmaceutically acceptable salts thereof, and mixtures thereof, except where specifically stated otherwise.

In an embodiment, a compound according to Formula I and above embodiments is provided, wherein the compound of Formula I is represented by the compound of Formula Ia:

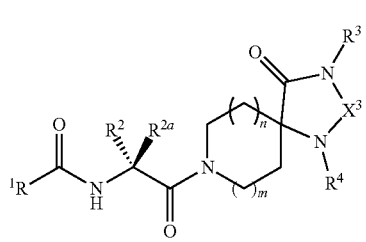

Ia wherein $R^1$, $R^2$, $R^{2a}$, $R^3$, $R^4$, $X^3$, m and n are as previously described for a compound of Formula I.

In an embodiment, a compound according to Formula I and above embodiments is provided, wherein the compound of Formula I is represented by the compound of Formula Ib:

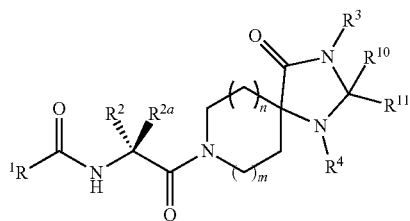

Ib wherein $R^1$, $R^2$, $R^{2a}$, $R^3$, $R^4$, $R^{10}$, $R^{11}$, m and n are as previously described for a compound of Formula I.

In an embodiment, a compound according to Formula I and above embodiments is provided, wherein the compound of Formula I is represented by the compound of Formula Ic:

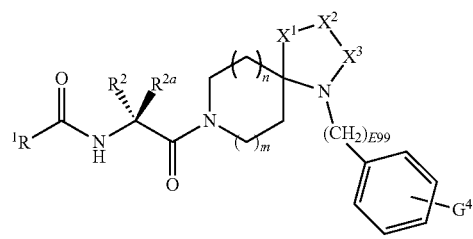

Ic wherein $R^1$, $R^2$, $R^{2a}$, $X^1$-$X^3$, $G^4$, m and n are as previously described for a compound of Formula I and wherein E99 is equal to 0, 1, 2, or 3.

In an embodiment, a compound according to Formula I and above embodiments is provided, wherein the compound of Formula I is represented by the compound of Formula Id:

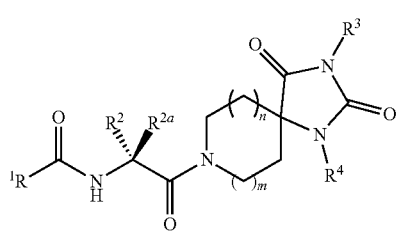

Id wherein $R^1$, $R^2$, $R^{2a}$, $R^3$, $R^4$, m and n are as previously described for a compound of Formula I.

In an embodiment, a compound according to Formula I and above embodiments is provided, wherein the compound of Formula I is represented by the compound of Formula Ie:

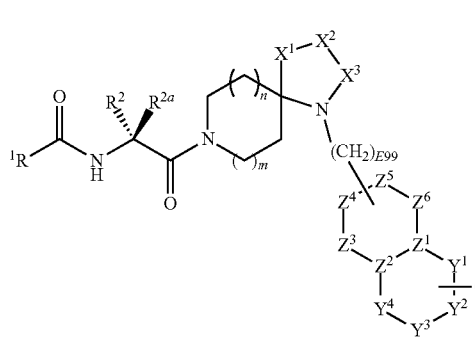

Ie wherein $R^1$, $R^2$, $R^{2a}$, $X^1$-$X^3$, $G^4$, m and n are as previously described for a compound of Formula I, wherein $Y^1$-$Y^4$ and $Z^1$-$Z^6$ are each independently selected from one or more of $C_{0-2}$alkyl, O, N or S and wherein E99 is equal to 0, 1, 2, or 3.

In an embodiment, a compound according to Formula I and above embodiments is provided, wherein the compound of Formula I is represented by the compound of Formula If:

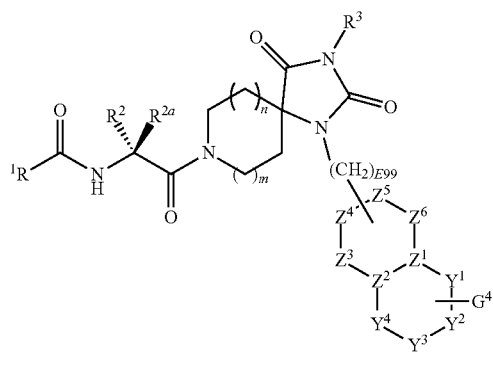

If wherein $R^1$, $R^2$, $R^{2a}$, $R^3$, $G^4$, m and n are as previously described for a compound of Formula I, wherein $Y^1$-$Y^4$ and $Z^1$-$Z^6$ are each independently selected from one or more of $C_{0-2}$alkyl, O, N or S and wherein E99 is equal to 0, 1, 2, or 3.

In an embodiment, a compound according to Formula I and above embodiments is provided, wherein the compound of Formula I is represented by the compound of Formula Ig:

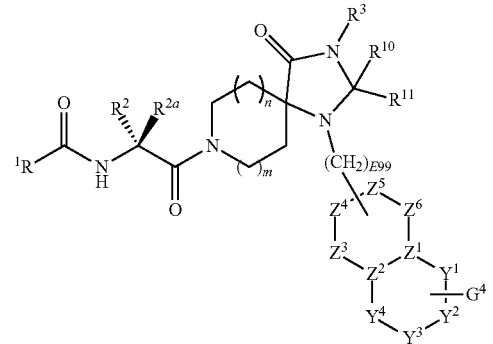

Ig wherein $R^1$, $R^2$, $R^{2a}$, $R^3$, $R^{10}$, $R^{11}$, $G^4$, m and n are as previously described for a compound of Formula I, wherein $Y^1$-$Y^4$ and $Z^1$-$Z^6$ are each independently selected from one or more of $C_{0-2}$alkyl, O, N or S and wherein E99 is equal to 0, 1, 2, or 3.

In an embodiment, a compound according to Formula I and above embodiments is provided, wherein the compound of Formula I is represented by the compound of Formula Ih:

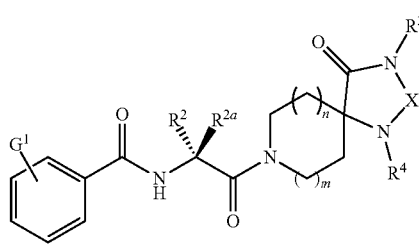

Ih wherein $R^2$, $R^{2a}$, $R^3$, $R^4$, $X^3$, G, m and n are as previously described for a compound of Formula I.

In an embodiment, a compound according to Formula I and above embodiments is provided, wherein the compound of Formula I is represented by the compound of Formula Ii:

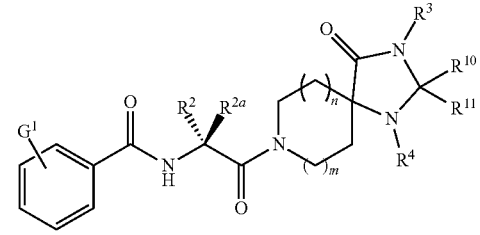

Ii wherein $R^2$, $R^{2a}$, $R^3$, $R^4$, $R^{10}$, $R^{11}$, G, m and n are as previously described for a compound of Formula I.

In an embodiment, a compound according to Formula I and above embodiments is provided, wherein the compound of Formula I is represented by the compound of Formula Ij:

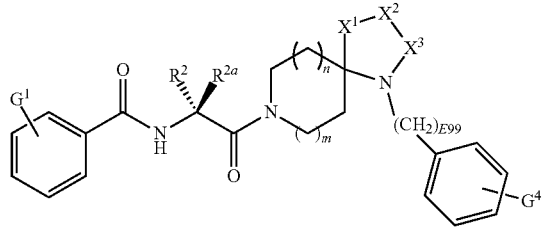

Ij wherein $R^2$, $R^{2a}$, $X^1$-$X^3$, $G^1$, $G^4$, m and n are as previously described for a compound of Formula I and wherein E99 is equal to 0, 1, 2, or 3.

In an embodiment, a compound according to Formula I and above embodiments is provided, wherein the compound of Formula I is represented by the compound of Formula Ik:

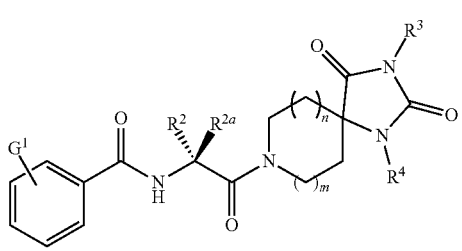

Ik wherein $R^2$, $R^{2a}$, $R^3$, $R^4$, $G^1$, m and n are as previously described for a compound of Formula I.

In an embodiment, a compound according to Formula I and above embodiments is provided, wherein the compound of Formula I is represented by the compound of Formula II:

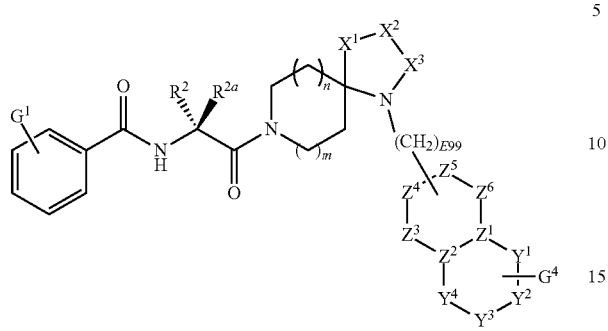

II wherein $R^2$, $R^{2a}$, $X^1$-$X^3$, G, $G^4$, m and n are as previously described for a compound of Formula I, wherein $Y^1$-$Y^4$ and $Z^1$-$Z^6$ are each independently selected from one or more of $C_{0-2}$alkyl, O, N or S and wherein E99 is equal to 0, 1, 2, or 3.

In an embodiment, a compound according to Formula I and above embodiments is provided, wherein the compound of Formula I is represented by the compound of Formula Im:

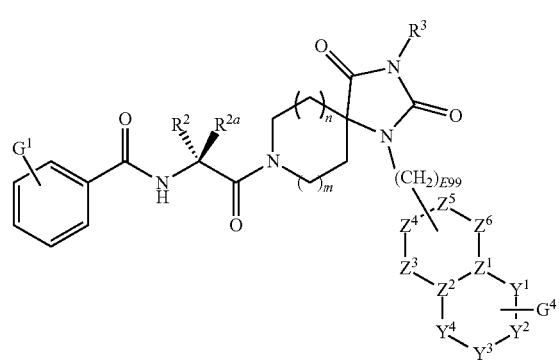

Im wherein $R^2$, $R^{2a}$, $R^3$, G, $G^4$, m and n are as previously described for a compound of Formula I, wherein $Y^1$-$Y^4$ and $Z^1$-$Z^6$ are each independently selected from one or more of $C_{0-2}$alkyl, O, N or S and wherein E99 is equal to 0, 1, 2, or 3.

In an embodiment, a compound according to Formula I and above embodiments is provided, wherein the compound of Formula I is represented by the compound of Formula In:

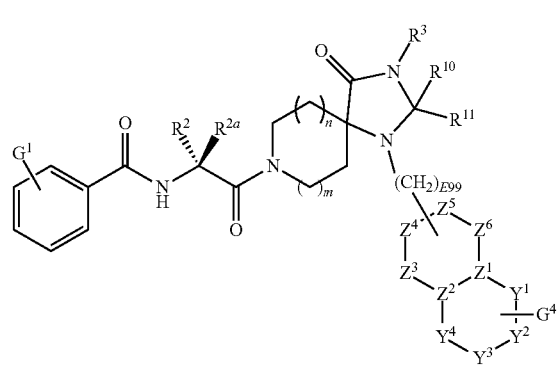

In wherein $R^2$, $R^{2a}$, $R^3$, $R^{10}$, $R^{11}$, $G^1$, $G^4$, m and n are as previously described for a compound of Formula I, wherein $Y^1$-$Y^4$ and $Z^1$-$Z^6$ are each independently selected from one or more of $C_{0-2}$alkyl, O, N or S and E99 is equal to 0, 1, 2, or 3.

In an embodiment, a compound according to Formula I and above embodiments is provided, wherein the compound of Formula I is represented by the compound of Formula Io:

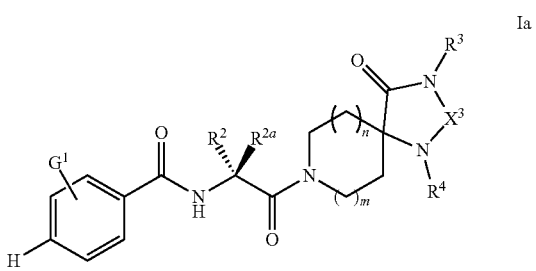

Ia wherein $R^2$, $R^{2a}$, $R^3$, $R^4$, $X^3$, $G^1$, m and n are as previously described for a compound of Formula I.

The present invention includes the compounds, intermediates, examples and synthetic methods described herein. Compounds of Formula I are prepared according to reaction schemes described herein. Unless otherwise indicated, following substituents in the schemes are defined as above.

Synthetic Methods

Compounds of the present invention include the intermediates, examples, and synthetic methods described herein.

The compounds of Formula I may be prepared by the methods described below, together with synthetic methods known in the art of organic chemistry, or modifications and derivatizations that are familiar to those of ordinary skill in the art. The starting materials used herein are commercially available or may be prepared by routine methods known in the art [such as those methods disclosed in standard reference books such as the Compendium of Organic Synthetic Methods, Vol. I-VI (Wiley-Interscience); or the Comprehensive Organic Transformations, by R. C. Larock (Wiley-Interscience)]. Preferred methods include, but are not limited to, those described below.

During any of the following synthetic sequences it may be necessary and/or desirable to protect sensitive or reactive groups on any of the molecules concerned. This can be achieved by means of conventional protecting groups, such as those described in T. W. Greene, Protective Groups in Organic Chemistry, John Wiley & Sons, 1981; T. W. Greene and P. G. M. Wuts, Protective Groups in Organic Chemistry, John Wiley & Sons, 1991, and T. W. Greene and P. G. M. Wuts, Protective Groups in Organic Chemistry, John Wiley & Sons, 1999, which are hereby incorporated by reference.

Compounds of Formula I, or their pharmaceutically acceptable salts, can be prepared according to the reaction Schemes discussed hereinbelow and the general skill in the art. Unless otherwise indicated, the substituents in the Schemes are defined as above. Isolation and purification of the products is accomplished by standard procedures, which are known to a chemist of ordinary skill.

When a general or exemplary synthetic procedure is referred to, one skilled in the art can readily determine the appropriate reagents, if not indicated, extrapolating from the general or exemplary procedures. Some of the general procedures are given as examples for preparing specific compounds. One skilled in the art can readily adapt such procedures to the synthesis of other compounds. Representation of an unsubstituted position in structures shown or referred to in the general procedures is for convenience and does not preclude substitution as described elsewhere herein. For specific groups that can be present, either as groups in the general procedures or as optional substituents not shown, refer to the descriptions in the remainder of this document, including the claims, summary and detailed description.

A general procedure for the synthesis of compounds of Formula I is shown in Scheme 1.

Scheme 1:

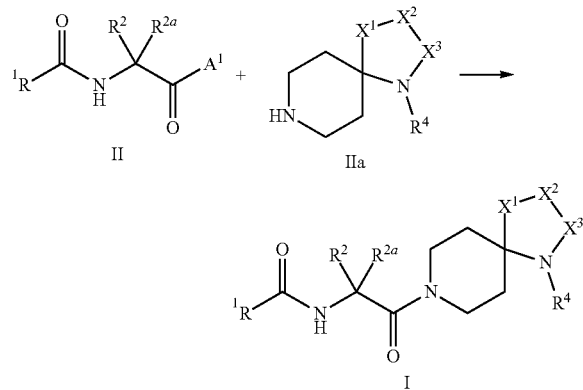

where $R^1$, $R^2$, $R^{2a}$, $R^4$, $X^1$, $X^2$, and $X^3$ are as defined previously for compound of Formula I and $A^1$=OH, alkoxy, or a suitable leaving group such as imidazole.

In a typical preparation, of a compound of Formula I, a compound of Formula II and IIa were reacted under suitable amide coupling conditions. Suitable conditions include but are not limited to treating compounds of Formula II (when $A^1$=OH) and IIa with coupling reagents such as DCC or EDC in conjunction with DMAP, HOBt, HOAt, and the like. Moreover, HATU in the presence of diisopropylethyl amine (DIPEA) can be used. Suitable solvents for use in the above process included, but were not limited to, ethers such as THF, glyme, and the like; DMF; DMSO; MeCN; halogenated solvents such as chloroform or DCM. If desired, mixtures of these solvents were used, however the preferred solvents were DCM and DMF. The above process was carried out at temperatures between about 0° C. and about 100° C. Preferably, the reaction was carried out at about rt. The above process was preferably carried out at or about atmospheric pressure although higher or lower pressures may be used if desired. Substantially equimolar amounts of reactants were preferably used although higher or lower amounts may be used if desired. Additionally, other suitable reaction conditions for the conversion of a carboxylic acid derived compound such as compound of Formula II to an amide such as compound of Formula I can be found in Larock, R. C. Comprehensive Organic Transformations, 2nd ed.; Wiley and Sons: New York, 1999, pp 1941-1949. Compounds of Formula IIa are either commercially available, are synthesized by known chemical procedures or are described in detail within.

A general procedure for the synthesis of compounds of Formula II is shown in Scheme 2.

Scheme 2:

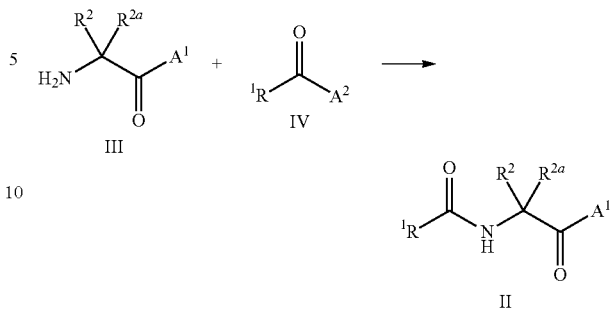

where $R^1$, $R^2$, and $R^{2a}$ are as defined previously for compound of Formula I, $A^1$=OH, and $A^2$=OH, alkoxy, or a suitable leaving group such as Cl or imidazole.

In a typical preparation, of a compound of Formula II, a compound of Formula III and IV were reacted under suitable amide coupling conditions. Suitable conditions include but are not limited to treating compounds of Formula IV (when $A^1$=OH) and compounds of Formula III with coupling reagents such as DCC or EDC in conjunction with DMAP, HOBt, HOAt, and the like. Moreover, HATU in the presence of DIPEA may be used. Suitable solvents for use in the above process include, but are not limited to, ethers such as THF, glyme, and the like; DMF; DMSO; MeCN; halogenated solvents such as chloroform or DCM. If desired, mixtures of these solvents may be used, however the preferred solvents were DCM and DMF. The above process was carried out at temperatures between about 0° C. and about 100° C. Preferably, the reaction was carried out at or about rt. The above process was preferably carried out at about atmospheric pressure although higher or lower pressures may be used if desired. Substantially equimolar amounts of reactants were preferably used although higher or lower amounts may be used if desired. Alternatively, compounds of Formula III and IV (where $A^2$=suitable leaving group such as Cl) were reacted with bases such as NaOH, TEA or DIPEA and the like in conjunction with DMAP and the like. Suitable solvents for use in this process included, but were not limited to, ethers such as THF, glyme, and the like; DMF; DMSO; MeCN; halogenated solvents such as chloroform or DCM; or alcohols or water. If desired, mixtures of these solvents may be used, however the preferred solvent was DCM. The above process was carried out at temperatures between about −20° C. and about 40° C. Preferably, the reaction was carried out between 0° C. and 25° C. The above process to produce was preferably carried out at about atmospheric pressure although higher or lower pressures were used if desired. Substantially equimolar amounts of compounds of Formula III and IV and base and sub-stoichiometric amounts of DMAP were preferably used although higher or lower amounts may be used if desired. Additionally, other suitable reaction conditions for the conversion of a carboxylic acid derived compound such as compound of Formula II to an amide such as compound of Formula I can be found in Larock, R. C. Comprehensive Organic Transformations, 2nd ed.; Wiley and Sons: New York, 1999, pp 1941-1949. Compounds of Formula III and IV as well as IIa are either commercially available, are synthesized by known chemical procedures or are described in detail within.

A typical preparation of IIa is shown in Scheme 3 wherein, PG=suitable protecting group.

Scheme 3:
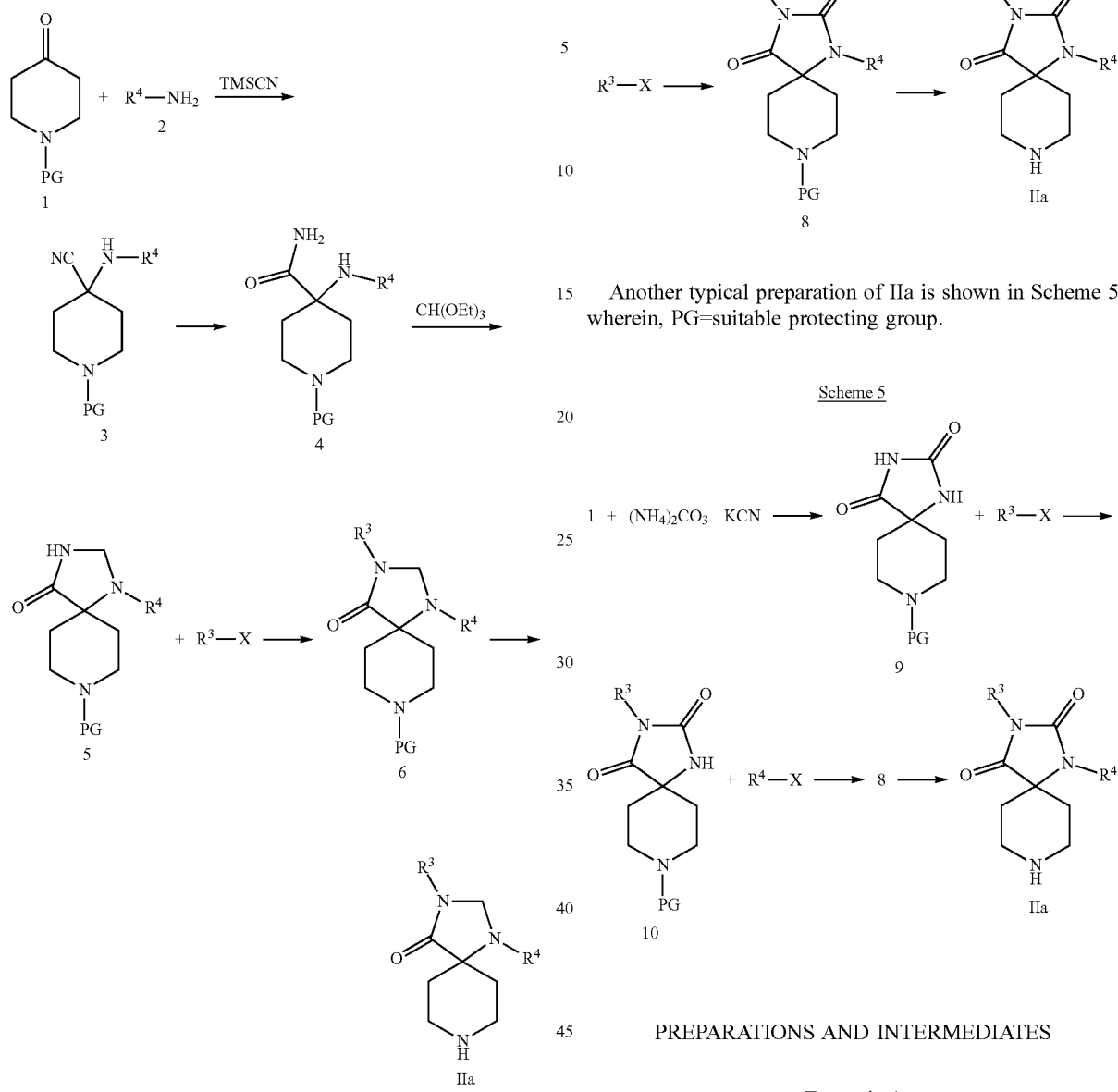
Another typical preparation of IIa is shown in Scheme 4 wherein, PG=suitable protecting group.
Another typical preparation of IIa is shown in Scheme 5 wherein, PG=suitable protecting group.
PREPARATIONS AND INTERMEDIATES
Example 1
(R)—N-(1-Cyclohexyl-2-(3-methyl-2,4-dioxo-1-phenyl-1,3,8-triazaspiro[4.5]decan-8-yl)-2-oxo-ethyl)-3-methylbenzamide
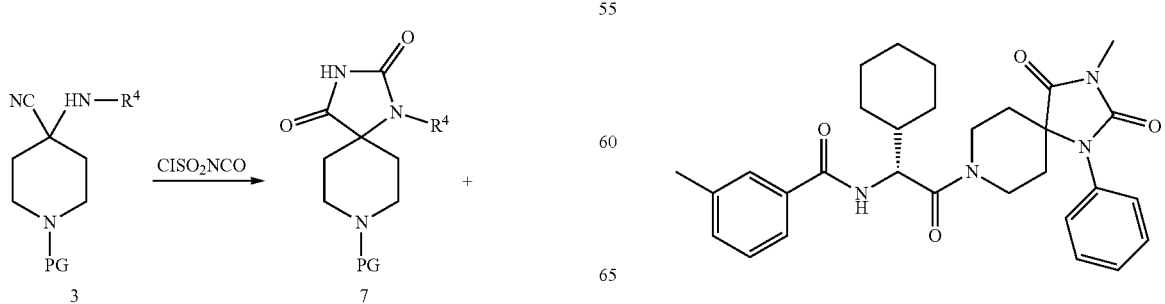

Representative Scheme:

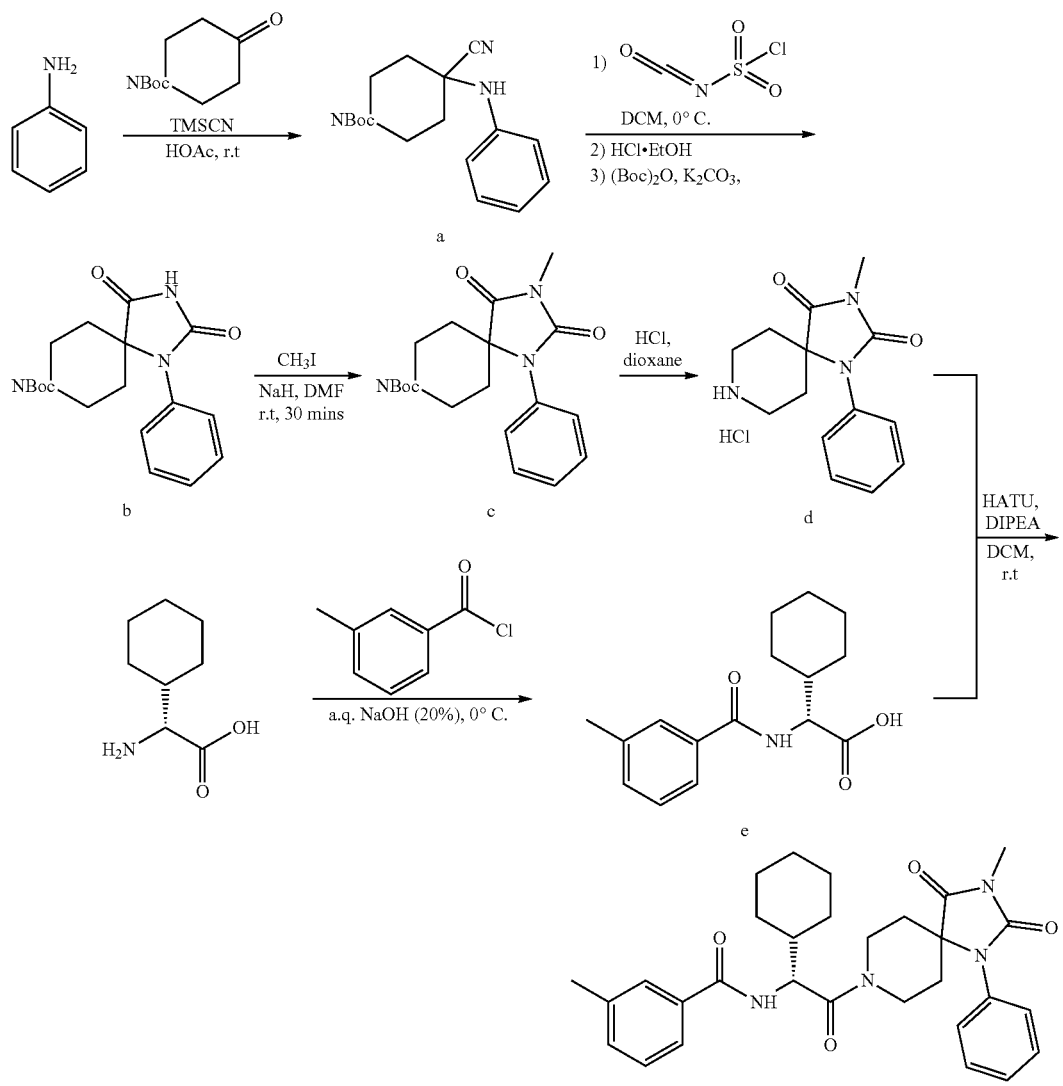

tert-Butyl-4-cyano-4-(phenylamino)piperidine-1-carboxylate

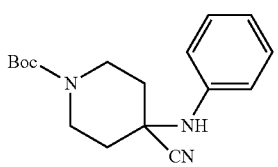 [SMILES: CC(C)(C)OC(=O)N1CCC(C#N)(Nc2ccccc2)CC1]

To a solution of aniline (0.5 g, 0.005 mol) in acetic acid (20 mL) was added tert-butyl-4-oxopiperidine-1-carboxylate (1.0 g, 0.005 mol). The resulting mixture was cooled to 0° C. and trimethylsilyl cyanide (0.49 g, 0.005 mol) was added. The resulting solution was stirred overnight at room temperature. Saturated aqueous ammonium chloride solution was added (50 mL). The mixture was extracted with ethyl acetate (3×50 mL) and the combined organic layers were dried over anhydrous sodium sulfate and concentrated under reduced pressure. The residue was purified by silica gel column chromatography eluting with dichloromethane: petroleum ether=1:1 to afford tert-butyl-4-cyano-4-(phenylamino)piperidine-1-carboxylate as a white solid (1.3 g, 86%).

LCMS (ESI): m/z=302.2 [M+H]$^+$.

tert-Butyl-2,4-dioxo-1-phenyl-1,3,8-triazaspiro[4.5]decane-8-carboxylate

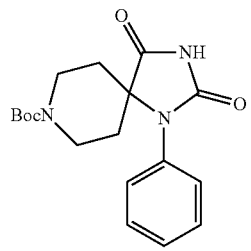 [SMILES: CC(C)(C)OC(=O)N1CCC2(CC1)C(=O)NC(=O)N2c1ccccc1]

To a solution of tert-butyl-4-cyano-4-(phenylamino)piperidine-1-carboxylate (0.45 g, 0.0015 mol) in dichloromethane was added chlorosulfonyl isocyanate (0.32 g, 0.00224 mol) at 0° C. After stirring for 30 minutes at 0° C., the reaction was quenched with a 5% aqueous hydrochloric acid solution (2 mL). The solvent was removed under reduced pressure and ethanol (10 mL) was added. The mixture was stirred for 30 minutes at 80° C. The solvent was removed under reduced pressure and the residue was dissolved in tetrahydrofuran (20 mL) and the pH of the mixture was adjusted to pH 8 by addition of a 10% aqueous potassium carbonate solution. Then di-tert-butyl-dicarbonate (0.5 g, 0.00229 mol) in tetrahydrofuran (20 mL) was added. After stirring overnight, the solvent was removed under reduced pressure and the residue was purified by silica gel column chromatography eluting with ethyl acetate:petroleum ether=10:1 to afford tert-butyl-2,4-dioxo-1-phenyl-1,3,8-triazaspiro[4.5]decane-8-carboxylate as a white solid (300 mg, 41%).

LCMS (ESI): m/z=346.2 [M+H]$^+$.

$^1$H-NMR (300 MHz, DMSO-d$_6$): δ=1.25 (s, 9H), 1.34-1.51 (m, 2H), 1.95-2.04 (m, 2H), 3.21-3.25 (m, 2H), 3.67-3.78 (m, 2H), 7.19-7.33 (m, 2H), 7.40-7.53 (m, 3H), 10.99-11.2 (s, br, 1H).

tert-Butyl-3-methyl-2,4-dioxo-1-phenyl-1,3,8-triazaspiro[4.5]decane-8-carboxylate

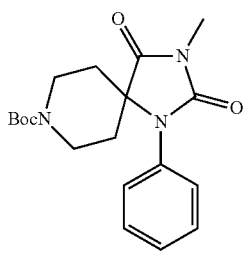 [SMILES: CN1C(=O)N(c2ccccc2)C2(CCN(C(=O)OC(C)(C)C)CC2)C1=O]

To a solution of tert-butyl-2,4-dioxo-1-phenyl-1,3,8-triazaspiro[4.5]decane-8-carboxylate (200 mg, 0.000579 mol) in N,N-dimethylformamide (5 mL) was added sodium hydride (23 mg, 60% in oil, 0.0006 mol) at 0° C. After stirring for 15 minutes, iodomethane (83 mg, 0.00057 mol) was added. The resulting mixture was stirred for 15 minutes. The reaction was quenched with ice-water (10 mL). The mixture was extracted with ethyl acetate (3×50 mL) and the combined organic layers were dried over anhydrous sodium sulfate and concentrated under reduced pressure. The residue was purified by silica gel column chromatography eluting with ethyl acetate:petroleum ether=1:3 to afford tert-butyl-3-methyl-2,4-dioxo-1-phenyl-1,3,8-triazaspiro[4.5]decane-8-carboxylate as a white solid (140 mg, 67%).

LCMS (ESI): m/z=360.2 [M+H]$^+$.

$^1$H-NMR (300 MHz, DMSO-d$_6$): δ=1.30 (s, 9H), 1.38-1.58 (m, 2H), 1.97-2.04 (m, 2H), 2.89 (s, 3H), 3.21-3.25 (m, 2H), 3.78-3.82 (m, 2H), 7.26-7.29 (m, 2H), 7.45-7.51 (m, 3H).

3-Methyl-1-phenyl-1,3,8-triazaspiro[4.5]decane-2,4-dione hydrochloride

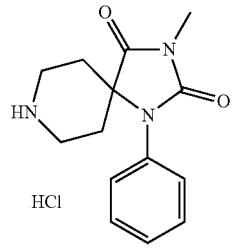

A solution of tert-butyl-3-methyl-2,4-dioxo-1-phenyl-1,3,8-triazaspiro[4.5]decane-8-carboxylate (140 mg, 0.000389 mol) in hydrochloric acid in dioxane (6.0 M, 10 mL) was stirred for 30 minutes. The precipitate was collected by filtration and dried under reduced pressure to afford 3-methyl-1-phenyl-1,3,8-triazaspiro[4.5]decane-2,4-dione hydrochloride as a white solid (92 mg, 80%).

LCMS (ESI): m/z=260.1 [M+H]$^+$.

(R)-2-Cyclohexyl-2-(3-methylbenzamido)acetic Acid

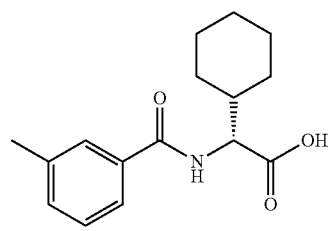 [SMILES: Cc1cccc(C(=O)N[C@@H](C(=O)O)C2CCCCC2)c1]

To a solution of (R)-2-amino-2-cyclohexylacetic acid (100 mg, 0.636 mmol) in a 20% aqueous sodium hydroxide solution (2 mL) was added dropwise 3-methylbenzoyl chloride (110 mg, 0.709 mmol) at 0° C. The mixture was stirred for 10 minutes before the reaction was quenched with ice-water (10 mL). The pH of the mixture was adjusted to 1 by addition of a 37% aqueous hydrochloric acid solution. The mixture was extracted with ethyl acetate (3×100 mL). The combined organic layers were dried over anhydrous sodium sulfate and the solvent was removed under reduced pressure. The residue was purified by silica gel column chromatography eluting with dichloromethane:methanol=20:1 to afford (R)-2-cyclohexyl-2-(3-methylbenzamido)acetic acid as a colorless oil (87 mg, 50%).

LCMS (ESI): m/z=276.2 [M+H]$^+$.

(R)—N-(1-Cyclohexyl-2-(3-methyl-2,4-dioxo-1-phenyl-1,3,8-triazaspiro[4.5]decan-8-yl)-2-oxoethyl)-3-methylbenzamide

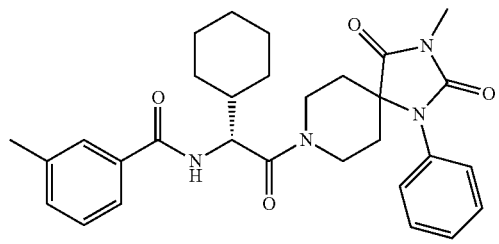 [SMILES: Cc1cccc(C(=O)N[C@@H](C(=O)N2CCC3(CC2)C(=O)N(C)C(=O)N3c2ccccc2)C2CCCCC2)c1]

To a mixture of 3-methyl-1-phenyl-1,3,8-triazaspiro[4.5]decane-2,4-dione hydrochloride (20 mg, 0.000068 mol) and (R)-2-cyclohexyl-2-(3-methylbenzamido) acetic acid (35 mg, 0.000119 mol) in dichloromethane (5 mL) was added 1-[bis(dimethylamino)methylene]-1H-1,2,3-triazolo[4,5-b]pyridinium-3-oxide hexafluorophosphate (HATU) (146 mg, 0.00038 mol) and N,N-diisopropylethylamine (83 mg, 0.00064 mol). The resulting mixture was stirred for 2 hours at room temperature before the reaction was quenched with ice-water (10 mL). The mixture was extracted with ethyl acetate (3×10 mL) and the combined organic layers were dried over anhydrous sodium sulfate and concentrated under reduced pressure. The residue was purified by prep-TLC with dichloromethane:methanol=15:1 to afford (R)—N-(1-cyclohexyl-2-(3-methyl-2,4-dioxo-1-phenyl-1,3,8-triazaspiro[4.5]decan-8-yl)-2-oxoethyl)-3-methylbenzamide as a white solid (8.4 mg, 23%).

LCMS (ESI): m/z=517.2 [M+H]$^+$.

$^1$H-NMR (400 MHz, CD$_3$OD): δ=1.04-1.88 (m, 15H), 2.40 (s, 3H), 3.09 (s, 3H), 3.46-3.47 (m, 1H), 3.92-4.51 (m, 3H), 4.83-4.85 (m, 1H), 7.15-7.52 (m, 9H).

The following 24 compounds were synthesized following the general procedure described above:

Example 2

(R)-3-Fluoro-N-(3-methyl-1-(3-methyl-2,4-dioxo-1-phenyl-1,3,8-triazaspiro[4.5]decan-8-yl)-1-oxobutan-2-yl)benzamide

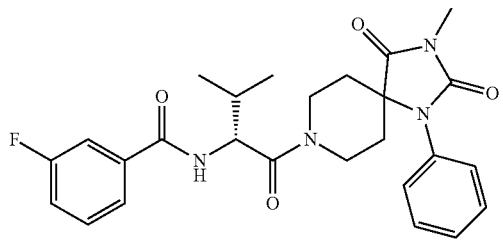 [SMILES: CC(C)[C@@H](NC(=O)c1cccc(F)c1)C(=O)N1CCC2(CC1)C(=O)N(C)C(=O)N2c1ccccc1]

3.5 mg, yield: 9%, white solid.

LCMS (ESI): m/z=481.2 [M+H]$^+$.

$^1$H-NMR (400 MHz, CD$_3$OD): δ=0.72-0.97 (m, 6H), 1.70-2.25 (m, 5H), 3.09 (s, 3H), 3.46-3.47 (m, 1H), 4.51-3.92 (m, 3H), 4.85-4.83 (m, 1H), 7.52-7.15 (m, 9H).

Example 3

(R)-2-Fluoro-3-methyl-N-(3-methyl-1-(3-methyl-2,4-dioxo-1-phenyl-1,3,8-triazaspiro[4.5]decan-8-yl)-1-oxobutan-2-yl)benzamide

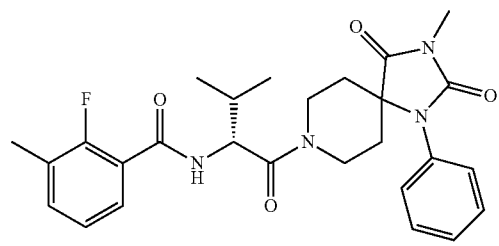 [SMILES: Cc1cccc(C(=O)N[C@@H](C(=O)N2CCC3(CC2)C(=O)N(C)C(=O)N3c2ccccc2)C(C)C)c1F]

27 mg, yield: 29%, white solid.

LCMS (ESI): m/z=495.2 [M+H]$^+$.

$^1$H-NMR (400 MHz, CD$_3$OD): δ=0.9-1.05 (m, 6H), 1.69-2.11 (m, 5H), 2.39 (s, 3H), 3.09 (s, 3H), 3.58-4.51 (m, 4H), 4.89-4.91 (m, 1H), 7.05-7.65 (m, 8H).

Example 4

2-Fluoro-3-methyl-N-((2R,3R)-3-methyl-1-(3-methyl-2,4-dioxo-1-phenyl-1,3,8-triazaspiro[4.5]decan-8-yl)-1-oxopentan-2-yl)benzamide

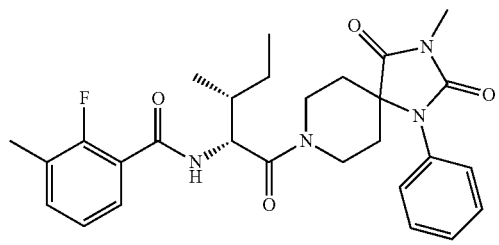 [SMILES: CC[C@@H](C)[C@@H](NC(=O)c1cccc(C)c1F)C(=O)N1CCC2(CC1)C(=O)N(C)C(=O)N2c1ccccc1]

12 mg, yield: 13%, white solid.

LCMS (ESI): m/z=509.2 [M+H]$^+$.

$^1$H-NMR (400 MHz, CD$_3$OD): δ=0.81-0.98 (m, 6H), 1.23-1.92 (m, 7H), 2.32 (s, 3H), 3.09 (s, 3H), 3.33-3.47 (m, 1H), 3.92-3.95 (m, 1H), 4.32-4.40 (m, 1H), 4.47-4.50 (m, 1H), 4.97-5.01 (m, 1H), 7.05-7.65 (m, 8H).

Example 5

(R)—N-(1-(3-(Cyanomethyl)-1-(4-methoxyphenyl)-2,4-dioxo-1,3,8-triazaspiro[4.5]decan-8-yl)-3-methyl-1-oxobutan-2-yl)-5-ethyl-2-fluorobenzamide

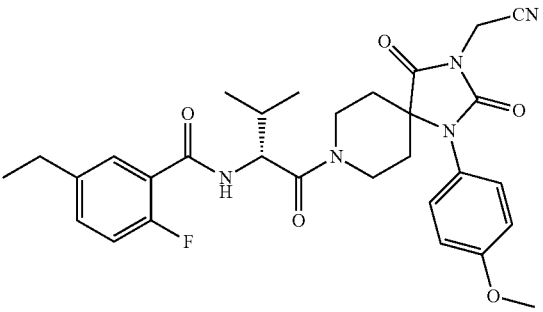 [SMILES: CCc1ccc(F)c(C(=O)N[C@@H](C(=O)N2CCC3(CC2)C(=O)N(CC#N)C(=O)N3c2ccc(OC)cc2)C(C)C)c1]

44.3 mg, yield: 47%, white solid.

LCMS (ESI): m/z=564.2 [M+H]$^+$.

$^1$H-NMR (400 MHz, CD$_3$OD): δ=0.79-1.01 (m, 6H), 1.24-1.27 (m, 3H), 1.66-1.74 (m, 1H), 1.82-2.24 (m, 4H), 2.67-2.73 (m, 2H), 3.41-3.46 (m, 1H), 3.77 (s, 2H), 3.85-3.93 (m, 2H), 4.2-4.32 (m, 1H), 4.42-4.56 (m, 1H), 4.62 (s, 2H), 4.84-4.86 (m, 1H), 6.60-7.57 (m, 7H).

Example 6

(R)-2-Fluoro-N-(1-(1-(3-fluoro-4-methoxyphenyl)-3-methyl-2,4-dioxo-1,3,8-triazaspiro[4.5]decan-8-yl)-3-methyl-1-oxobutan-2-yl)-5-(trifluoromethyl)benzamide

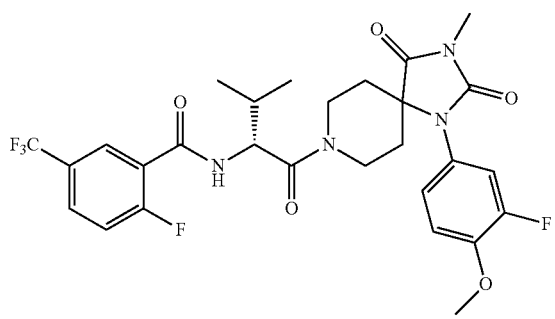 [SMILES: COc1ccc(N2C(=O)N(C)C(=O)C23CCN(C(=O)[C@H](NC(=O)c2cc(C(F)(F)F)ccc2F)C(C)C)CC3)cc1F]

58.0 mg, yield: 29%, white solid.

LCMS (ESI): m/z=596.9 [M+H]⁺.

¹H-NMR (400 MHz, CD₃OD): δ=0.82-1.02 (m, 6H), 1.67-2.20 (m, 5H), 3.07 (s, 3H), 3.45-3.51 (m, 1H), 3.84 (s, 2H), 3.92-3.97 (m, 2H), 4.19-4.29 (m, 1H), 4.41-4.53 (m, 1H), 4.84-4.88 (m, 1H), 6.99-8.50 (m, 7H).

Example 7

(R)—N-(1-(1-(4-Cyanophenyl)-3-methyl-2,4-dioxo-1,3,8-triazaspiro[4.5]decan-8-yl)-3-methyl-1-oxobutan-2-yl)-2-fluoro-5-(trifluoromethyl)benzamide

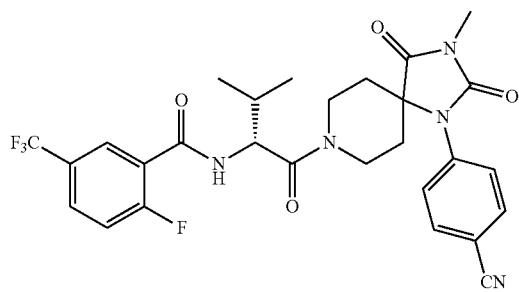 [SMILES: CC(C)[C@@H](NC(=O)c1cc(C(F)(F)F)ccc1F)C(=O)N1CCC2(CC1)C(=O)N(C)C(=O)N2c1ccc(C#N)cc1]

75.8 mg, yield: 44.9%, white solid.

LCMS (ESI): m/z=573.9 [M+H]⁺.

¹H-NMR (400 MHz, CDCl₃): δ=0.89-1.05 (m, 6H), 1.74-1.81 (m, 1H), 1.92-2.14 (m, 4H), 3.16 (s, 3H), 3.48-3.53 (m, 1H), 4.00-4.13 (m, 2H), 4.43-4.67 (m, 1H), 4.97-5.03 (m, 1H), 7.27-7.40 (m, 3H), 7.26-7.73 (m, 1H), 7.70-7.81 (m, 3H), 8.25-8.34 (m, 1H).

Example 8

(R)—N-(1-(1-(3-Cyanophenyl)-3-methyl-2,4-dioxo-1,3,8-triazaspiro[4.5]decan-8-yl)-3-methyl-1-oxobutan-2-yl)-2-fluoro-5-(trifluoromethyl)benzamide

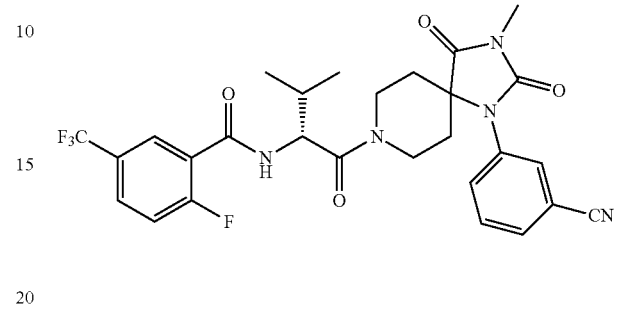

64.7 mg, yield: 31%, white solid.

LCMS (ESI): m/z=573.9 [M+H]⁺.

¹H-NMR (400 MHz, CDCl₃): δ=0.89-1.05 (m, 6H), 1.72-1.78 (m, 1H), 1.96-2.12 (m, 4H), 3.16 (s, 3H), 3.48-3.55 (m, 1H), 3.99-4.12 (m, 2H), 4.65-4.68 (m, 1H), 4.92-5.05 (m, 1H), 7.25-7.30 (m, 1H), 7.39-7.71 (m, 6H), 8.15-8.34 (m, 1H).

Example 9

(R)-2-Fluoro-N-(3-methyl-1-(3-methyl-1-(4-(methylsulfonyl)phenyl)-2,4-dioxo-1,3,8-triazaspiro[4.5]decan-8-yl)-1-oxobutan-2-yl)-5-(trifluoromethyl)benzamide

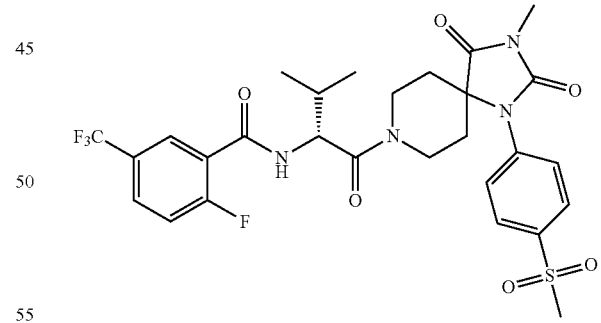

51.0 mg, yield: 30%, white solid.

LCMS (ESI): m/z=627 [M+H]⁺.

¹H-NMR (400 MHz, CD₃OD): δ=0.80-1.03 (m, 6H), 1.71-2.28 (m, 5H), 3.09-3.19 (m, 6H), 3.48-3.54 (m, 1H), 3.95-4.02 (m, 1H), 4.21-4.55 (m, 2H), 4.84-4.89 (m, 1H), 7.42-8.55 (m, 8H).

Example 10

(R)-2-Fluoro-N-(1-(1-(3-methoxyphenyl)-3-methyl-2,4-dioxo-1,3,8-triazaspiro[4.5]decan-8-yl)-3-methyl-1-oxobutan-2-yl)-5-(trifluoromethyl)benzamide

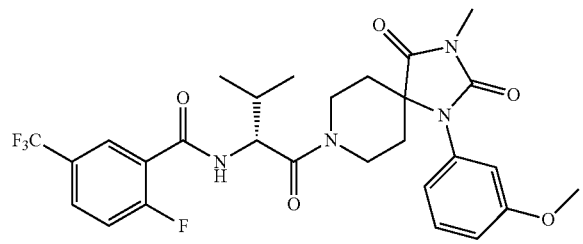 [SMILES: COc1cccc(N2C(=O)N(C)C(=O)C23CCN(C(=O)[C@H](NC(=O)c2cc(C(F)(F)F)ccc2F)C(C)C)CC3)c1]

44.0 mg, yield: 29%, white solid.

LCMS (ESI): m/z=579 [M+H]$^+$.

$^1$H-NMR (400 MHz, CD$_3$OD): δ=0.80-1.03 (m, 6H), 1.71-2.28 (m, 5H), 3.09 (s, 3H), 3.46-3.53 (m, 1H), 3.75-3.84 (m, 3H), 3.75-3.99 (m, 1H), 4.18-4.52 (m, 2H), 4.84-4.88 (m, 1H), 6.79-8.53 (m, 8H).

Example 11

(R)-2-Fluoro-N-(3-methyl-1-(3-methyl-1-(3-methyl-2-oxo-2,3-dihydrobenzo[d]oxazol-5-yl)-2,4-dioxo-1,3,8-triazaspiro[4.5]decan-8-yl)-1-oxobutan-2-yl)-5-(trifluoromethyl)benzamide

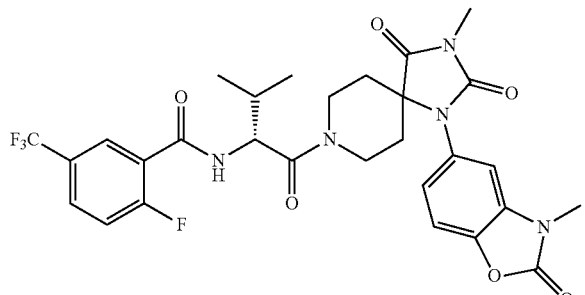

13.9 mg, yield: 20%, white solid.

LCMS (ESI): m/z=619.7 [M+H]$^+$.

$^1$H-NMR (400 MHz, CD$_3$OD): δ=0.80-1.06 (m, 6H), 1.36 (m, 1H), 1.69-1.95 (m, 1H), 2.00-2.23 (m, 3H), 3.08 (s, 3H), 3.29 (s, 2H), 3.43 (s, 1H), 3.49 (m, 1H), 3.92-3.99 (m, 1H), 4.17-4.31 (m, 1H), 4.39-4.53 (m, 1H), 4.84 (m, 1H), 7.00-7.44 (m, 4H), 7.78-8.01 (m, 2H).

Example 12

(R)-2-Fluoro-N-(3-methyl-1-(3-methyl-1-(1-methyl-1H-indazol-5-yl)-2,4-dioxo-1,3,8-triazaspiro[4.5]decan-8-yl)-1-oxobutan-2-yl)-5-(trifluoromethyl)benzamide

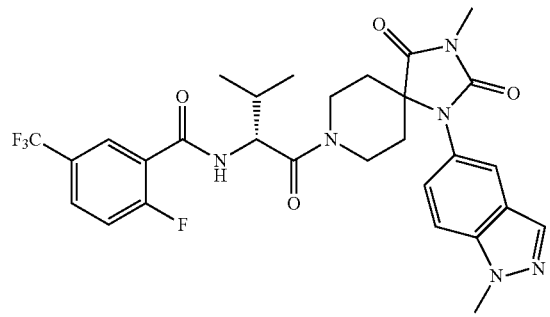 [SMILES: CC(C)[C@@H](NC(=O)c1cc(C(F)(F)F)ccc1F)C(=O)N1CCC2(CC1)C(=O)N(C)C(=O)N2c1ccc2c(cnn2C)c1]

35.8 mg, yield: 26%, white solid.

LCMS (ESI): m/z=603.2 [M+H]$^+$.

$^1$H-NMR (400 MHz, CDCl$_3$): δ=0.79-1.04 (m, 6H), 1.79-2.12 (m, 5H), 3.16 (s, 3H), 3.49-3.59 (m, 1H), 4.02-4.15 (m, 5H), 4.60-4.63 (m, 1H), 4.99-5.03 (m, 1H), 7.12-7.23 (m, 2H), 7.43-7.59 (m, 3H), 7.71-7.76 (m, 1H), 8.01-8.07 (m, 1H), 8.16-8.31 (m, 1H).

Example 13

(R)-2-Fluoro-N-(3-methyl-1-(3-methyl-1-(2-methyl-2H-indazol-5-yl)-2,4-dioxo-1,3,8-triazaspiro[4.5]decan-8-yl)-1-oxobutan-2-yl)-5-(trifluoromethyl)benzamide

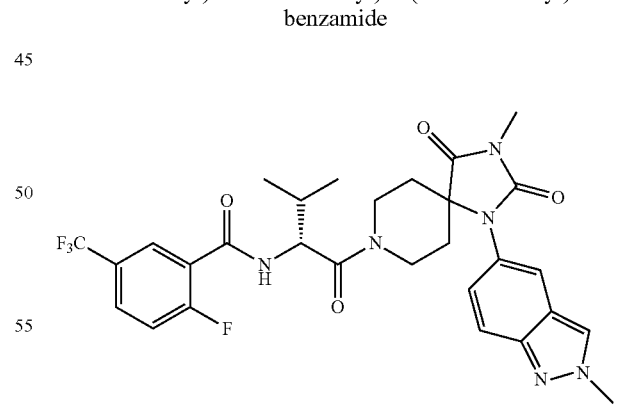

17.4 mg, yield: 33%, white solid.

LCMS (ESI): m/z=603.2 [M+H]$^+$.

$^1$H-NMR (400 MHz, CDCl$_3$): δ=0.80-1.04 (m, 6H), 1.83-2.13 (m, 5H), 3.16 (s, 3H), 3.49-3.55 (m, 1H), 4.03-4.08 (m, 2H), 4.26-4.31 (m, 3H), 4.60-4.63 (m, 1H), 4.99-5.02 (m, 1H), 7.00-7.23 (m, 2H), 7.42-7.54 (m, 2H), 7.72-7.84 (m, 2H), 7.96-8.02 (m, 1H), 8.18-8.34 (m, 1H).

Example 14

(R)-2-Fluoro-N-(1-(1-(imidazo[1,2-a]pyridin-6-yl)-3-methyl-2,4-dioxo-1,3,8-triazaspiro[4.5]decan-8-yl)-3-methyl-1-oxobutan-2-yl)-5-(trifluoromethyl)benzamide trifluoroacetic Acid Salt

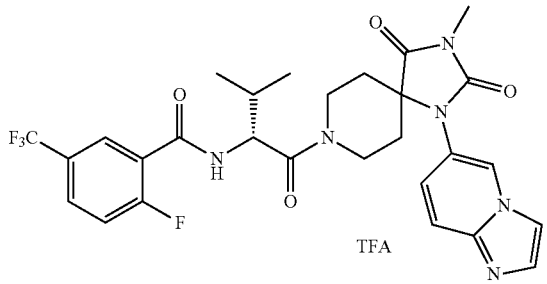 [SMILES: CC(C)[C@@H](NC(=O)c1cc(C(F)(F)F)ccc1F)C(=O)N1CCC2(CC1)C(=O)N(C)C(=O)N2c1ccc2nccn2c1]

45.6 mg, yield: 26%, white solid.

LCMS (ESI): m/z=589.2 [M+H]$^+$.

$^1$H-NMR (400 MHz, CD$_3$OD): δ=0.85-1.04 (m, 6H), 1.77-2.33 (m, 5H), 3.14 (s, 3H), 3.46-3.55 (m, 1H), 3.93-4.01 (m, 1H), 4.18-4.31 (m, 1H), 4.46-4.59 (m, 1H), 4.70-4.72 (m, 1H), 7.33-7.48 (m, 1H), 7.70-8.54 (m, 6H), 9.00 (s, 1H).

Example 15

(R)-2-Fluoro-N-(3-methyl-1-(3-methyl-1-(3-(methylsulfonyl)phenyl)-2,4-dioxo-1,3,8-triazaspiro[4.5]decan-8-yl)-1-oxobutan-2-yl)-5-(trifluoromethyl)benzamide

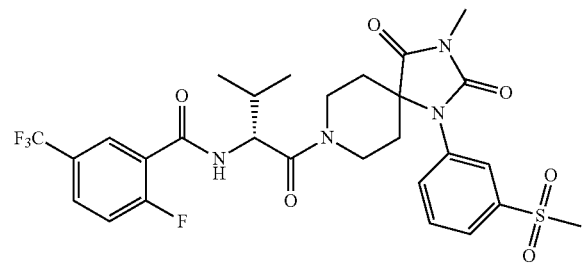 [SMILES: CC(C)[C@@H](NC(=O)c1cc(C(F)(F)F)ccc1F)C(=O)N1CCC2(CC1)C(=O)N(C)C(=O)N2c1cccc(S(C)(=O)=O)c1]

73.4 mg, yield: 43%, white solid.

LCMS (ESI): m/z=626.9 [M+H]$^+$.

$^1$H-NMR (400 MHz, CD$_3$OD): δ=0.79-1.02 (m, 6H), 1.65-1.86 (m, 1H), 2.01-2.28 (m, 4H), 3.09 (s, 2H), 3.11 (s, 3H), 3.20 (s, 1H), 3.46-3.53 (m, 1H), 3.93-3.99 (m, 1H), 4.21-4.30 (m, 1H), 4.43-4.55 (m, 1H), 4.80-4.84 (m, 1H), 7.39-7.47 (m, 1H), 7.62-8.10 (m, 6H), 8.42-8.53 (m, 1H).

Example 16

(R)-2-Fluoro-N-(3-methyl-1-(3-methyl-1-(1-methyl-1H-pyrazol-3-yl)-2,4-dioxo-1,3,8-triazaspiro[4.5]decan-8-yl)-1-oxobutan-2-yl)-5-(trifluoromethyl)benzamide

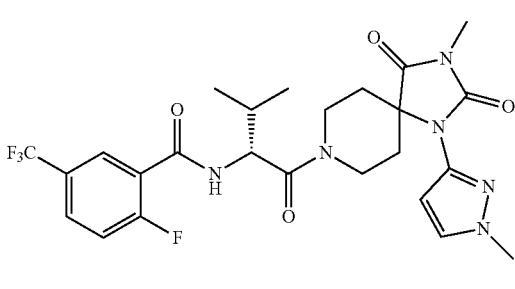 [SMILES: CC(C)[C@@H](NC(=O)c1cc(C(F)(F)F)ccc1F)C(=O)N1CCC2(CC1)C(=O)N(C)C(=O)N2c1ccn(C)n1]

128.0 mg, yield: 70%, white solid.

LCMS (ESI): m/z=553.0 [M+H]$^+$.

$^1$H-NMR (400 MHz, CD$_3$OD): δ=1.02-1.06 (m, 6H), 1.89-2.73 (m, 5H), 3.07 (s, 3H), 3.45-3.52 (m, 1H), 3.82-3.94 (m, 3H), 3.82-4.00 (m, 1H), 4.27-4.30 (m, 1H), 4.89-4.52 (m, 1H), 4.85-4.97 (m, 1H), 6.35-6.47 (m, 1H), 7.43-7.55 (m, 2H), 7.87-7.89 (m, 1H), 7.99-8.05 (m, 1H).

Example 17

(R)-2-Fluoro-N-(3-methyl-1-(3-methyl-1-(1-methyl-1H-pyrazol-4-yl)-2,4-dioxo-1,3,8-triazaspiro[4.5]decan-8-yl)-1-oxobutan-2-yl)-5-(trifluoromethyl)benzamide

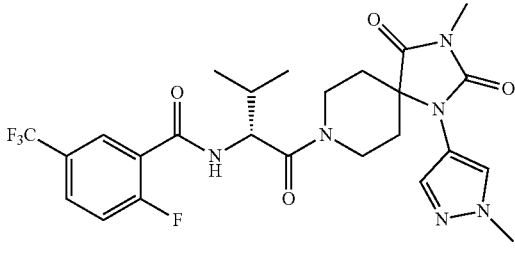 [SMILES: CC(C)[C@@H](NC(=O)c1cc(C(F)(F)F)ccc1F)C(=O)N1CCC2(CC1)C(=O)N(C)C(=O)N2c1cnn(C)c1]

159.5 mg, yield: 81%, white solid.

LCMS (ESI): m/z=553.0 [M+H]$^+$.

$^1$H-NMR (400 MHz, CD$_3$OD): δ=0.89-1.04 (m, 6H), 1.76-2.15 (m, 5H), 3.06 (s, 3H), 3.32-3.48 (m, 1H), 3.82-4.00 (m, 4H), 4.27-4.31 (m, 1H), 4.52-4.56 (m, 1H), 4.85-4.90 (m, 1H), 7.42-7.51 (m, 2H), 7.75-7.80 (m, 1H), 7.87-7.90 (m, 1H), 7.99-8.03 (m, 1H).

Example 18

(R)-5-Ethyl-2-fluoro-N-(3-methyl-1-(3-methyl-1-(3-methylimidazo[1,5-a]pyridin-6-yl)-2,4-dioxo-1,3,8-triazaspiro[4.5]decan-8-yl)-1-oxobutan-2-yl)benzamide

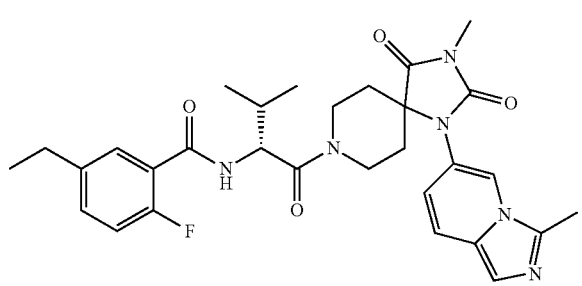 [SMILES: CCc1ccc(F)c(C(=O)N[C@@H](C(=O)N2CCC3(CC2)C(=O)N(C)C(=O)N3c2ccc3cnc(C)n3c2)C(C)C)c1]

16.0 mg, yield: 30%, white solid.
LCMS (ESI): m/z=563.1 [M+H]$^+$.
$^1$H-NMR (400 MHz, CD$_3$OD): δ=0.86-1.03 (m, 6H), 1.20-1.31 (m, 3H), 1.75-1.78 (m, 1H), 2.07-2.24 (m, 3H), 2.31-2.33 (m, 1H), 2.61-2.66 (m, 2H), 2.59 (s, 2H), 2.87 (s, 1H), 3.13 (s, 3H), 3.47-3.51 (m, 1H), 3.97-4.02 (m, 1H), 4.23-4.31 (m, 1H), 4.47-4.56 (m, 1H), 4.75-4.78 (m, 1H), 6.99-7.05 (m, 2H), 7.21-7.34 (m, 2H), 7.55-7.99 (m, 2H), 8.50 (m, 1H).

Example 19

(R)-2-Fluoro-N-(3-methyl-1-(3-methyl-1-(2-methyl-1H-benzo[d]imidazol-6-yl)-2,4-dioxo-1,3,8-triazaspiro[4.5]decan-8-yl)-1-oxobutan-2-yl)-5-(trifluoromethyl)benzamide trifluoroacetic Acid Salt

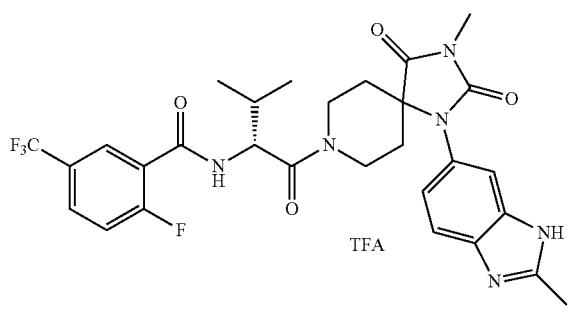 [SMILES: Cc1nc2ccc(N3C(=O)N(C)C(=O)C34CCN(C(=O)[C@H](NC(=O)c3cc(C(F)(F)F)ccc3F)C(C)C)CC4)cc2[nH]1]

12.7 mg, yield: 9%, white solid.
LCMS (ESI): m/z=603.2 [M+H]$^+$.
$^1$H-NMR (400 MHz, CD$_3$OD): δ=0.76-1.01 (m, 6H), 1.72-2.30 (m, 5H), 2.84-2.90 (m, 3H), 3.12 (s, 3H), 3.49-3.55 (t, 1H), 3.93-4.01 (t, 1H), 4.16-4.54 (m, 2H), 4.80-4.82 (m, 1H), 7.34-7.51 (m, 2H), 7.70-8.08 (m, 4H).

Example 20

(R)-2-Fluoro-N-(3-methyl-1-(3-methyl-2,4-dioxo-1-(1H-pyrrolo[2,3-b]pyridin-5-yl)-1,3,8-triazaspiro[4.5]decan-8-yl)-1-oxobutan-2-yl)-5-(trifluoromethyl)benzamide

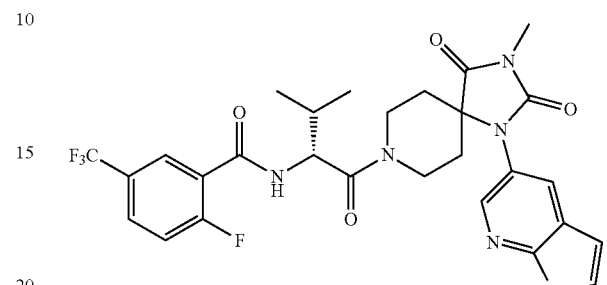

56.3 mg, yield: 32%, white solid.
LCMS (ESI): m/z=589.2 [M+H]$^+$.
$^1$H-NMR (400 MHz, CDCl$_3$): δ=0.79-1.04 (m, 6H), 1.75-2.18 (m, 5H), 3.18 (s, 3H), 3.47-3.53 (t, 1H), 3.98-4.04 (m, 2H), 4.63-4.66 (m, 1H), 4.97-5.02 (m, 1H), 6.55-6.61 (m, 1H), 7.17-7.22 (m, 1H), 7.42-7.49 (m, 2H), 7.68-7.77 (m, 1H), 7.82-7.85 (m, 1H), 8.05-8.10 (m, 1H), 8.14-8.34 (m, 1H).

Example 21

(R)—N-(1-(1-(3,4-Dihydro-2H-benzo[b][1,4]oxazin-7-yl)-3-methyl-2,4-dioxo-1,3,8-triazaspiro[4.5]decan-8-yl)-3-methyl-1-oxobutan-2-yl)-2-fluoro-5-(trifluoromethyl)benzamide

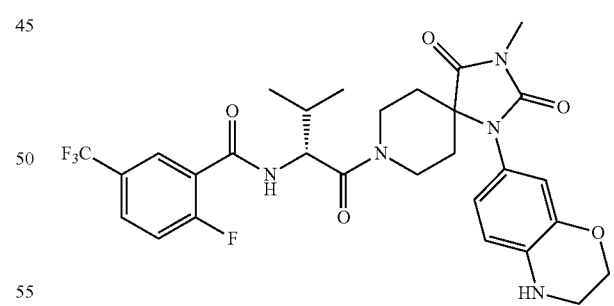

59.9 mg, yield: 27%, white solid.
LCMS (ESI): m/z=606.2 [M+H]$^+$.
$^1$H-NMR (400 MHz, CD$_3$OD): δ=0.84-1.00 (m, 6H), 1.69-2.15 (m, 5H), 3.05 (s, 3H), 3.23-3.40 (m, 3H), 3.89-3.93 (m, 1H), 4.19-4.23 (m, 3H), 4.43-4.56 (m, 1H), 4.88-4.94 (m, 1H), 6.54-6.65 (m, 3H), 7.40-7.42 (m, 1H), 7.86-8.03 (m, 2H).

Example 22

(R)-2-Fluoro-N-(3-methyl-1-(3-methyl-2,4-dioxo-1-(6-oxo-1,6-dihydropyridin-3-yl)-1,3,8-triazaspiro[4.5]decan-8-yl)-1-oxobutan-2-yl)-5-(trifluoromethyl)benzamide

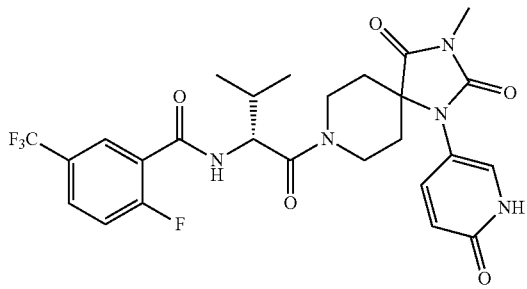 [SMILES: CC(C)[C@@H](NC(=O)c1cc(C(F)(F)F)ccc1F)C(=O)N1CCC2(CC1)C(=O)N(C)C(=O)N2c1ccc(=O)[nH]c1]

22.8 mg, yield: 14%, white solid.
LCMS (ESI): m/z=566.2.2 [M+H]+.
1H-NMR (400 MHz, CD3OD): δ=0.89-1.00 (m, 6H), 1.69-2.13 (m, 5H), 3.04 (m, 3H), 3.31-3.48 (m, 1H), 3.88-3.94 (m, 2H), 4.26-4.28 (m, 2H), 4.52-4.55 (m, 2H), 6.50-6.70 (m, 1H), 7.35-7.42 (m, 3H), 7.94-8.03 (m, 2H).

Example 23

(R)-2-Fluoro-N-(3-methyl-1-(3-methyl-1-(1-methyl-6-oxo-1,6-dihydropyridin-3-yl)-2,4-dioxo-1,3,8-triazaspiro[4.5]decan-8-yl)-1-oxobutan-2-yl)-5-(trifluoromethyl)benzamide

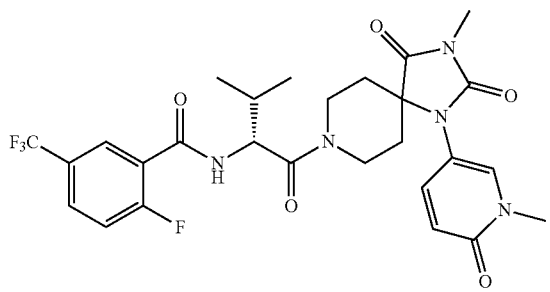 [SMILES: CC(C)[C@@H](NC(=O)c1cc(C(F)(F)F)ccc1F)C(=O)N1CCC2(CC1)C(=O)N(C)C(=O)N2c1ccc(=O)n(C)c1]

34.8 mg, yield: 45%, white solid.
LCMS (ESI): m/z=580.2 [M+H]+.
1H-NMR (400 MHz, CD3OD): δ=0.90-1.04 (m, 6H), 1.70-1.87 (m, 1H), 1.99-2.18 (m, 4H), 3.07 (s, 3H), 3.44-3.60 (m, 4H), 3.90-3.96 (m, 1H), 4.22-4.32 (m, 1H), 4.46-4.58 (m, 1H), 4.84-4.88 (m, 1H), 6.49-6.62 (m, 1H), 7.36-7.48 (m, 2H), 7.74-8.02 (m, 3H).

Example 24

(R)—N-(1-Cyclopentyl-2-(3-methyl-1-(1-methyl-6-oxo-1,6-dihydropyridin-3-yl)-2,4-dioxo-1,3,8-triazaspiro[4.5]decan-8-yl)-2-oxoethyl)-2-fluoro-5-(trifluoromethyl)benzamide

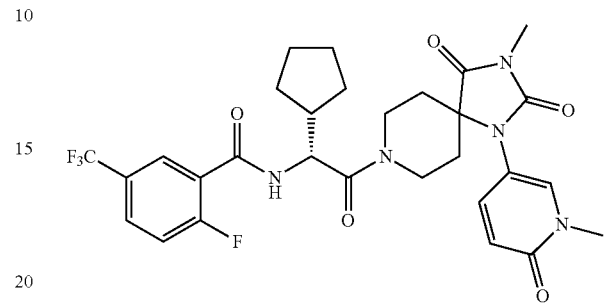

66.1 mg, yield: 30%, white solid.
LCMS (ESI): m/z=606.2 [M+H]+.
1H-NMR (400 MHz, CD3OD): δ=1.14-1.83 (m, 9H), 1.99-2.16 (m, 3H), 2.36-2.40 (m, 1H), 3.07 (s, 3H), 3.44-3.61 (m, 4H), 3.91-3.94 (m, 1H), 4.29-4.38 (m, 1H), 4.47-4.57 (m, 1H), 4.79-4.88 (m, 1H), 6.47-6.62 (m, 1H), 7.36-7.47 (m, 2H), 7.74-7.98 (m, 3H).

Example 25

(R)-2-Fluoro-N-(1-(1-(6-methoxypyridin-3-yl)-3-methyl-2,4-dioxo-1,3,8-triazaspiro[4.5]decan-8-yl)-3-methyl-1-oxobutan-2-yl)-5-(trifluoromethyl)benzamide

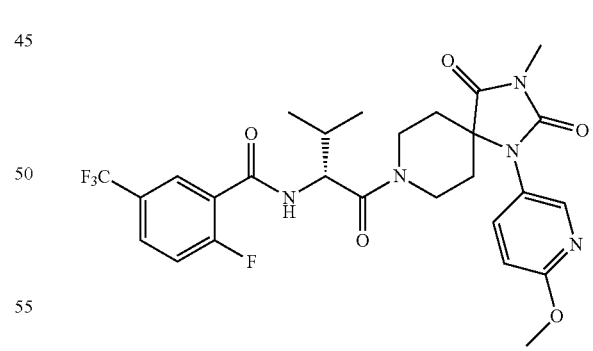

50.0 mg, yield: 40%, white solid.
LCMS (ESI): m/z=580.2 [M+H]+.
1H-NMR (400 MHz, CDCl3): δ=0.95-1.05 (m, 6H), 1.69-1.73 (m, 1H), 1.82-2.00 (m, 3H), 2.03-2.16 (m, 1H), 3.15 (s, 3H), 3.45-3.52 (m, 1H), 3.87-4.12 (m, 5H), 4.52-4.64 (m, 1H), 4.98-5.09 (m, 1H), 6.78-6.87 (m, 1H), 7.29-7.36 (m, 1H), 7.36-7.50 (m, 1H), 7.70-7.81 (m, 1H), 7.99-8.10 (m, 1H), 8.25-8.39 (m, 1H).

Example 26

(R)-2-Fluoro-N-(3-methyl-1-(3-methyl-2,4-dioxo-1-(4-(trifluoromethoxy)phenyl)-1,3,8-triazaspiro[4.5]decan-8-yl)-1-oxobutan-2-yl)-5-(trifluoromethyl)benzamide

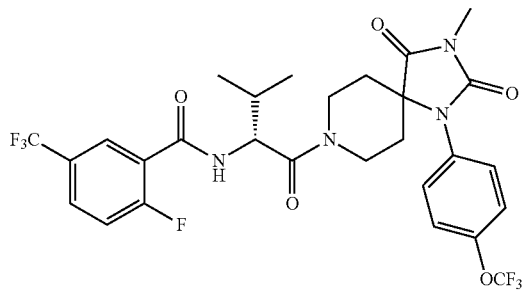 [SMILES: CC(C)[C@@H](NC(=O)c1cc(C(F)(F)F)ccc1F)C(=O)N1CCC2(CC1)C(=O)N(C)C(=O)N2c1ccc(OC(F)(F)F)cc1]

12.8 mg, 16% yield, yellow solid.
LRMS: m/z=616 [M+H]$^+$.
$^1$H-NMR (400 MHz, CD$_3$OD): δ=7.94-7.84 (m, 2H), 7.51-7.26 (m, 5H), 4.88-4.80 (m, 1H), 4.58-4.42 (m, 1H), 4.34-4.19 (m, 1H), 4.02-3.89 (m, 1H), 3.55-3.44 (m, 1H), 3.10 (s, 3H), 2.28-1.94 (m, 4H), 1.76-1.64 (m, 1H), 1.01 (dd, J=11.8, 6.7 Hz, 4H), 0.92 (d, J=6.7 Hz, 1H), 0.79 (d, J=6.7 Hz, 1H).

Example 27

(R)-2-Fluoro-N-(3-methyl-1-(3-methyl-2,4-dioxo-1-(5-benzofuran)-1,3,8-triazaspiro[4.5]decan-8-yl)-1-oxobutan-2-yl)-5-(trifluoromethyl)benzamide

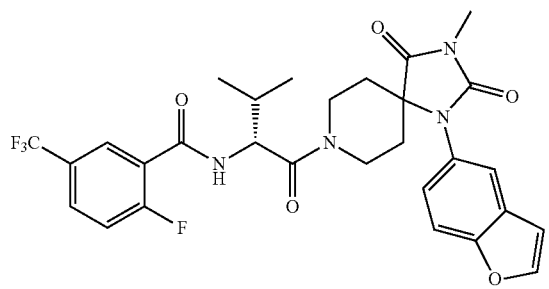 [SMILES: CC(C)[C@@H](NC(=O)c1cc(C(F)(F)F)ccc1F)C(=O)N1CCC2(CC1)C(=O)N(C)C(=O)N2c1ccc2occc2c1]

30 mg, 28% yield, yellow solid.
LRMS: m/z=588 [M+H]$^+$.
$^1$H-NMR (400 MHz, DMSO-d$_6$): δ=8.72 (dd, J=30.5, 8.8 Hz, 1H), 8.08 (d, J=30.8, 1H), 7.94 (s, 1H), 7.86-7.61 (m, 2H), 7.56-7.34 (m, 2H), 7.18 (dd, J=49.9, 8.6 Hz, 1H), 6.98 (d, J=49.5 Hz, 1H), 4.67 (t, J=8.4 Hz, 1H), 4.44-3.62 (m, 4H), 3.29 (m, 1H), 3.00 (s, 3H), 2.25-2.09 (m, 2H), 1.70-1.48 (m, 2H), 0.89-0.56 (m, 6H).

Example 28

(R)-2-Fluoro-N-(3-methyl-1-(3-methyl-2,4-dioxo-1-(2-oxo-2,3-dihydrobenzo[d]oxazol-6-yl)-1,3,8-triazaspiro[4.5]decan-8-yl)-1-oxobutan-2-yl)-5-(trifluoromethyl)benzamide

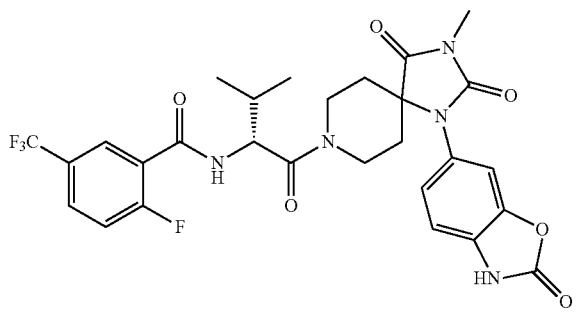 [SMILES: CC(C)[C@@H](NC(=O)c1cc(C(F)(F)F)ccc1F)C(=O)N1CCC2(CC1)C(=O)N(C)C(=O)N2c1ccc2[nH]c(=O)oc2c1]

Representative Scheme:

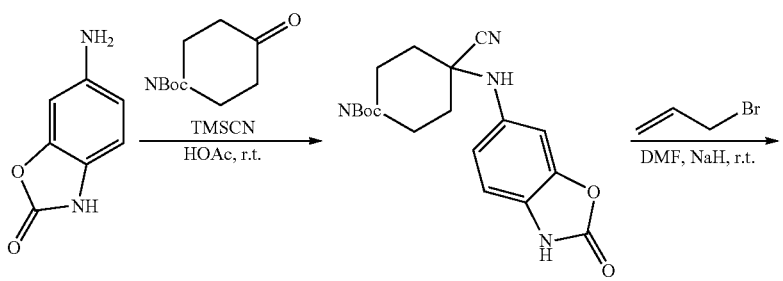

a

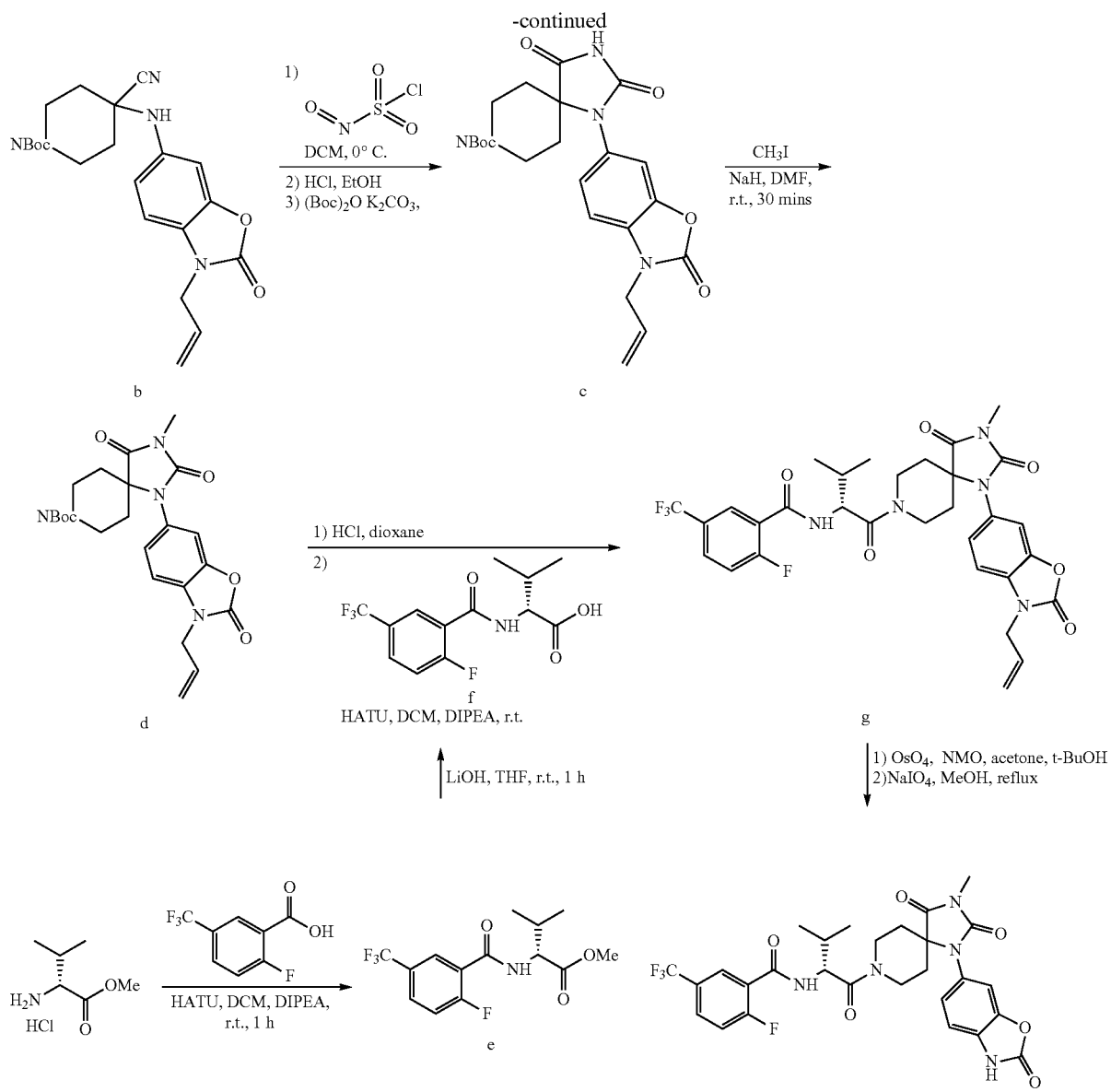

Representative General Procedure:

tert-Butyl-4-cyano-4-(2-oxo-2,3-di hydrobenzo[d]oxazol-6-ylamino) piperidine-1-carboxylate

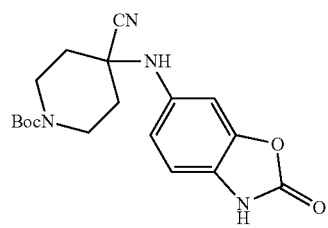 [SMILES: CC(C)(C)OC(=O)N1CCC(C#N)(Nc2ccc3[nH]c(=O)oc3c2)CC1]

To a solution of 6-aminobenzo[d]oxazol-2(3H)-one (6 g, 0.04 mol) in acetic acid (100 mL) was added tert-butyl-4-oxopiperidine-1-carboxylate (8.83 g, 0.04 mol). The resulting mixture was cooled to 0° C. and trimethylsilyl cyanide (5.99 g, 0.06 mol) was added. The resulting solution was stirred overnight at room temperature. Saturated aqueous ammonium chloride solution was added (50 mL). The mixture was extracted with ethyl acetate (3×100 mL) and the combined organic layers were dried over anhydrous sodium sulfate and concentrated under reduced pressure. The residue was purified by silica gel column chromatography eluting with dichloromethane:methanol=10:1 to afford tert-butyl-4-cyano-4-(2-oxo-2,3-dihydrobenzo[d]oxazol-6-ylamino)piperidine-1-carboxylate as a white solid (10 g, 71%).

LCMS (ESI): m/z=359.1 [M+H]$^+$.

tert-Butyl-4-(3-allyl-2-oxo-2,3-dihydrobenzo[d]oxazol-6-ylamino)-4-cyanopiperidine-1-carboxylate

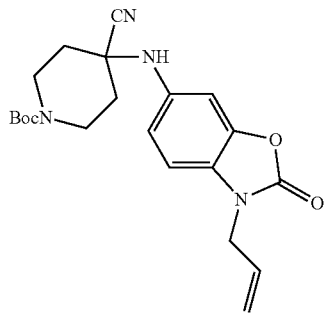 [SMILES: C=CCn1c(=O)oc2cc(NC3(C#N)CCN(C(=O)OC(C)(C)C)CC3)ccc21]

To a solution of tert-butyl-4-cyano-4-(2-oxo-2,3-dihydrobenzo[d]oxazol-6-ylamino)piperidine-1-carboxylate (1.0 g, 0.0027 mol) in N,N-dimethylformamide (10 mL) was added sodium hydride (0.2 g, 60% in oil, 0.00521 mol) at 0° C. After stirring for 15 minutes, 3-bromoprop-1-ene (0.35 g, 0.0029 mol) was added. The resulting mixture was stirred for 15 minutes at room temperature and the reaction was quenched with ice-water (10 mL). The mixture was extracted with ethyl acetate (3×50 mL). The combined organic layers were dried over anhydrous sodium sulfate and concentrated under reduced pressure. The residue was purified by silica gel column chromatography eluting with ethyl acetate:petroleum ether=1:10 to afford tert-butyl-4-(3-allyl-2-oxo-2,3-dihydrobenzo[d]oxazol-6-ylamino)-4-cyanopiperidine-1-carboxylate as a thick oil (600 mg, 58%).

LCMS (ESI): m/z=399.2 [M+H]$^+$.

tert-Butyl-1-(3-allyl-2-oxo-2,3-dihydrobenzo[d]oxazol-6-yl)-2,4-dioxo-1,3,8-triazaspiro[4.5]decane-8-carboxylate

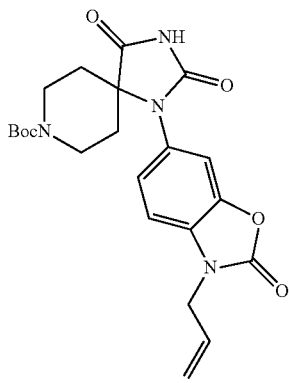 [SMILES: C=CCn1c(=O)oc2cc(N3C(=O)NC(=O)C34CCN(C(=O)OC(C)(C)C)CC4)ccc21]

To a solution of tert-butyl-4-(3-allyl-2-oxo-2,3-dihydrobenzo[d]oxazol-6-ylamino)-4-cyanopiperidine-1-carboxylate (0.6 g, 0.0015 mol) in dichloromethane (10 mL) was added chlorosulfonyl isocyanate (0.32 g, 0.0023 mol) at 0° C. After stirring for 30 minutes at 0° C., the reaction was quenched with a 5% aqueous hydrochloric acid solution (5 mL). The solvent was removed under reduced pressure and ethanol (10 mL) was added. The mixture was stirred for 30 minutes at 80° C. The solvent was removed under reduced pressure and the residue was dissolved in tetrahydrofuran (20 mL). The pH of the resulting mixture was adjusted to 8 by addition of a 15% aqueous potassium carbonate solution. To the resulting mixture was added di-tert-butyl-dicarbonate (213 g, 0.0015 mol). After stirring overnight, the solvent was removed under reduced pressure and the residue was extracted with ethyl acetate (3×10 mL). The combined organic layers were dried over anhydrous sodium sulfate. The solvent was removed under reduced pressure to afford tert-butyl-1-(3-allyl-2-oxo-2,3-dihydrobenzo[d]oxazol-6-yl)-2,4-dioxo-1,3,8-triazaspiro[4.5]decane-8-carboxylate as a yellow oil (400 mg, crude), which was used directly without any further purification.

LCMS (ESI): m/z=443.2 [M+H]$^+$.

$^1$H-NMR (300 MHz, CDCl$_3$): δ=1.46 (s, 9H), 1.73-1.84 (m, 2H), 2.10-2.23 (m, 2H), 3.17-3.30 (m, 2H), 3.92-4.11 (m, 2H), 4.35-4.46 (m, 2H), 5.20-5.34 (m, 2H), 5.79-6.01 (m, 2H), 6.78-6.93 (m, 3H).

tert-Butyl-1-(3-allyl-2-oxo-2,3-dihydrobenzo[d]oxazol-6-yl)-3-methyl-2,4-dioxo-1,3,8-triazaspiro[4.5]decane-8-carboxylate

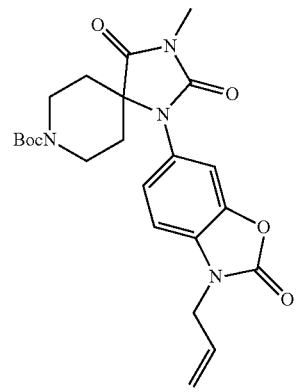 [SMILES: C=CCn1c(=O)oc2cc(N3C(=O)N(C)C(=O)C34CCN(C(=O)OC(C)(C)C)CC4)ccc21]

To a solution of tert-butyl-1-(3-allyl-2-oxo-2,3-dihydrobenzo[d]oxazol-6-yl)-2,4-dioxo-1,3,8-triazaspiro[4.5]decane-8-carboxylate (400 mg, crude) in N,N-dimethylformamide (10 mL) was added sodium hydride (138 mg, 60% in oil, 0.00343 mol) at 0° C. After stirring for 15 minutes, iodomethane (220 mg, 0.0015 mol) was added. The resulting mixture was stirred for 15 minutes at room temperature and the reaction was quenched with ice-water (10 mL). The mixture was extracted with ethyl acetate (3×50 mL). The combined organic layers were dried over anhydrous sodium sulfate and concentrated under reduced pressure. The residue was purified by silica gel column chromatography eluting with dichloromethane:methanol=10:1 to afford tert-butyl-1-(3-allyl-2-oxo-2,3-dihydrobenzo[d]oxazol-6-yl)-3-methyl-2,4-dioxo-1,3,8-triazaspiro[4.5]decane-8-carboxylate as a brown solid (240 mg, 35% over two steps).

LCMS (ESI): m/z=457.2 [M+H]$^+$.

$^1$H-NMR (300 MHz, CDCl$_3$): δ=1.40 (s, 9H), 1.67-1.94 (m, 4H), 3.11 (s, 3H), 3.44-3.58 (m, 2H), 3.93-4.08 (m, 2H), 4.44-4.53 (m, 2H), 5.31-5.47 (m, 2H), 5.81-5.94 (m, 1H), 6.90-7.05 (m, 3H).

(R)-Methyl-2-(2-fluoro-5-(trifluoromethyl)benzamido)-3-methylbutanoate

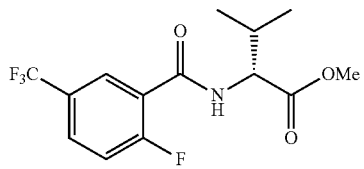 [SMILES: COC(=O)[C@H](NC(=O)c1cc(C(F)(F)F)ccc1F)C(C)C]

To a solution of 2-fluoro-5-(trifluoromethyl)benzoic acid (15.0 g, 0.072 mol) in dichloromethane (500 mL) was added sequentially D-valine methyl ester hydrochloride (12.0 g, 0.072 mol), 1-[bis(dimethylamino)methylene]-1H-1,2,3-triazolo[4,5-b]pyridinium-3-oxide hexafluorophosphate (HATU) (41 g, 0.11 mol) and N,N-diisopropylethylamine (23.3 g, 0.18 mol). Before quenching with ice-water (50 mL), the reaction was stirred for 1 hour. The mixture was extracted with dichloromethane (3×100 mL). The combined organic layers were dried over anhydrous sodium sulfate and the solvent was removed under reduced pressure. The residue was purified by silica gel column chromatography eluting with ethyl acetate:petroleum ether=1:5 to afford (R)-methyl-2-(2-fluoro-5-(trifluoromethyl)benzamido)-3-methylbutanoate as a thick oil (18.6 g, 81%)

LCMS (ESI): m/z=322.1 [M+H]$^+$.

$^1$H-NMR (300 MHz, CD$_3$OD): δ=1.05 (dd, J=6.8, 4.3 Hz, 6H), 2.22-2.35 (m, 1H), 3.79 (s, 3H), 4.58 (d, J=6.0 Hz, 1H), 7.46 (t, J=9.4 Hz, 1H), 7.89 (m, 1H), 8.00 (dd, J=6.2, 2.1 Hz, 1H).

(R)-2-(2-Fluoro-5-(trifluoromethyl)benzamido)-3-methylbutanoic Acid

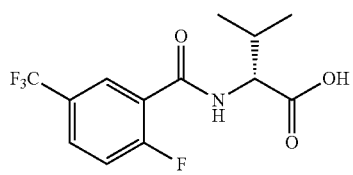 [SMILES: CC(C)[C@@H](NC(=O)c1cc(C(F)(F)F)ccc1F)C(=O)O]

To a solution of (R)-methyl-2-(2-fluoro-5-(trifluoromethyl)benzamido)-3-methylbutanoate (18.6 g, 0.058 mol) in tetrahydrofuran (50 mL) was added an aqueous lithium hydroxide solution (44 mL, 2.0 M, 0.088 mol). Before quenching with ice-water (20 mL), the reaction was stirred 1 hour. The pH of the solution was adjusted to 3 by addition of a 5% aqueous hydrochloric acid solution (5%). The mixture was filtered and the filter cake was washed with petroleum ether (30 mL) and dried under reduced pressure to afford (R)-2-(2-fluoro-5-(trifluoromethyl)benzamido)-3-methylbutanoic acid as a white solid (16.7 g, 94%).

LCMS (ESI): m/z=308.1 [M+H]$^+$.

$^1$H-NMR (300 MHz, DMSO): δ=0.95 (dd, J=6.7, 4.7 Hz, 6H), 2.13-2.17 (m, 1H), 4.31-4.35 (m, 1H), 7.52-7.55 (m, 1H), 7.58-7.85 (m, 2H), 12.77 (br, 1H).

(R)—N-(1-(1-(3-Allyl-2-oxo-2,3-dihydrobenzo[d]oxazol-6-yl)-3-methyl-2,4-dioxo-1,3,8-triazaspiro[4.5]decan-8-yl)-3-methyl-1-oxobutan-2-yl)-2-fluoro-5-(trifluoromethyl)benzamide

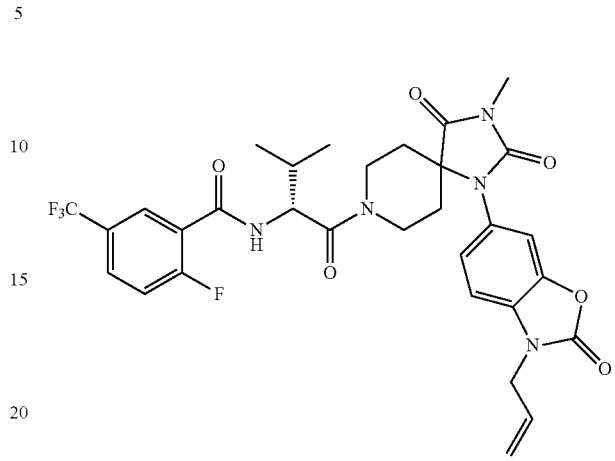

A solution of tert-butyl-1-(3-allyl-2-oxo-2,3-dihydrobenzo[d]oxazol-6-yl)-3-methyl-2,4-dioxo-1,3,8-triazaspiro[4.5]decane-8-carboxylate (100 mg, 0.228 mmol) in hydrochloric acid in dioxane (6.0 M, 5 mL) was stirred for 30 minutes. The solvent was removed under reduced pressure. To the residue was added dichloromethane (5 mL), (R)-2-(2-fluoro-5-(trifluoromethyl)benzamido)-3-methylbutanoic acid (79 mg, 0.26 mmol), 1-[bis(dimethylamino)methylene]-1H-1,2,3-triazolo[4,5-b]pyridinium-3-oxide hexafluorophosphate (HATU) (146 mg, 0.38 mmol) and N,N-diisopropylethylamine (83 mg, 0.64 mmol). The reaction was stirred for 2 hours before it was quenched by addition of with ice-water (10 mL). The mixture was extracted with ethyl acetate (3×10 mL) and the combined organic layers were dried over anhydrous sodium sulfate and concentrated under reduced pressure. The residue was purified by prep-TLC (dichloromethane:methanol=15:1) to afford (R)—N-(1-(1-(3-allyl-2-oxo-2,3-dihydrobenzo[d]oxazol-6-yl)-3-methyl-2,4-dioxo-1,3,8-triazaspiro[4.5]decan-8-yl)-3-methyl-1-oxobutan-2-yl)-2-fluoro-5-(trifluoromethyl)benzamide as a white solid (120 mg, crude), which was used directly without any further purification.

LCMS (ESI): m/z=646.1 [M+H]$^+$.

(R)-2-Fluoro-N-(3-methyl-1-(3-methyl-2,4-dioxo-1-(2-oxo-2,3-dihydrobenzo[d]oxazol-6-yl)-1,3,8-triazaspiro[4.5]decan-8-yl)-1-oxobutan-2-yl)-5-(trifluoromethyl)benzamide

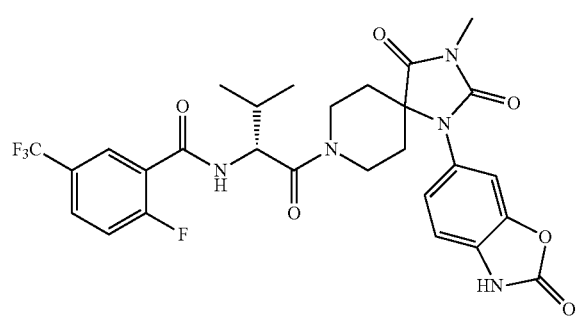 [SMILES: CC(C)[C@@H](NC(=O)c1cc(C(F)(F)F)ccc1F)C(=O)N1CCC2(CC1)C(=O)N(C)C(=O)N2c1ccc2[nH]c(=O)oc2c1]

To a solution of (R)—N-(1-(1-(3-allyl-2-oxo-2,3-dihydrobenzo[d]oxazol-6-yl)-3-methyl-2,4-dioxo-1,3,8-triazaspiro[4.5]decan-8-yl)-3-methyl-1-oxobutan-2-yl)-2-fluoro-5-(trifluoromethyl)benzamide (120 mg, crude) in dioxane/tert-BuOH (1:1) (10 mL) was added a solution of osmium tetroxide in tert-BuOH (0.5 mL, 0.1%) and N-methylmorpholine-N-oxide (170 mg, 1.45 mmol). After stirring for 30 minutes, to the resulting solution was added sodium periodate (300 mg, 1.4 mmol). Before the reaction was quenched by addition of ice-water (10 mL), the mixture was heated at reflux for 1 hour. The solvent was removed under reduced pressure. The residue was extracted with ethyl acetate (3×50 mL). The combined organic layers were dried over anhydrous sodium sulfate and concentrated under reduced pressure. The residue was purified by silica gel column chromatography eluting with dichloromethane:methanol=10:1 to afford (R)-2-fluoro-N-(3-methyl-1-(3-methyl-2,4-dioxo-1-(2-oxo-2,3-dihydrobenzo[d]oxazol-6-yl)-1,3,8-triazaspiro[4.5]decan-8-yl)-1-oxobutan-2-yl)-5-(trifluoromethyl)benzamide as a white solid (8.0 mg, 5% over two steps).

LCMS (ESI): m/z=606.1 [M+H]$^+$.

$^1$H-NMR (400 MHz, CD$_3$OD): δ=0.80-1.01 (m, 6H), 1.70-1.91 (m, 2H), 2.05-2.22 (m, 3H), 3.09 (s, 3H), 3.45-3.50 (m, 1H), 3.86-3.93 (m, 1H), 4.16-4.25 (m, 1H), 4.40-4.48 (m, 1H), 4.81-4.85 (m, 1H), 7.02-7.08 (m, 3H), 7.30-7.37 (m, 1H), 7.79-7.85 (m, 3H), 8.41-8.56 (m, 1H).

The following 5 compounds were synthesized following the general procedure described above from tert-butyl-1-(3-allyl-2-oxo-2,3-dihydrobenzo[d]oxazol-6-yl)-3-methyl-2,4-dioxo-1,3,8-triazaspiro[4.5]decane-8-carboxylate (prepared as described in Example 28-d):

Example 29

(R)-2-Fluoro-N-(3-methyl-1-(3-methyl-2,4-dioxo-1-(2-oxo-2,3-dihydrobenzo[d]oxazol-5-yl)-1,3,8-triazaspiro[4.5]decan-8-yl)-1-oxobutan-2-yl)-5-(trifluoromethyl)benzamide

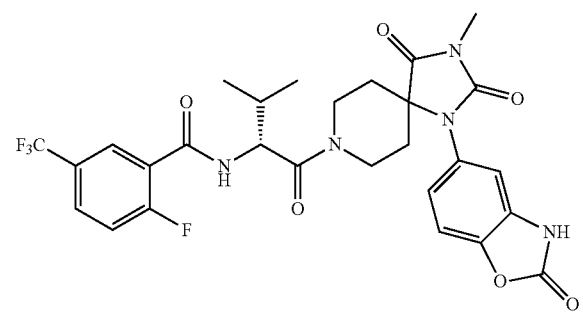 [SMILES: CC(C)[C@@H](NC(=O)c1cc(C(F)(F)F)ccc1F)C(=O)N1CCC2(CC1)C(=O)N(C)C(=O)N2c1ccc2oc(=O)[nH]c2c1]

39.3 mg, yield: 32%, white solid.
LCMS (ESI): m/z=606.2 [M+H]$^+$.

$^1$H-NMR (400 MHz, CD$_3$OD): δ=0.79-1.00 (m, 6H), 1.73-2.16 (m, 5H), 3.08 (s, 3H), 3.44-3.48 (m, 1H), 3.82-3.95 (m, 1H), 4.16-4.24 (m, 1H), 4.39-4.46 (m, 1H), 4.81-4.86 (m, 1H), 6.95-7.05 (m, 2H), 7.15-7.45 (m, 2H), 7.81-7.85 (m, 2H).

Example 30

(R)-2-Fluoro-N-(3-methyl-1-(3-methyl-2,4-dioxo-1-(3-oxo-3,4-dihydro-2H-benzo[b][1,4]oxazin-7-yl)-1,3,8-triazaspiro[4.5]decan-8-yl)-1-oxobutan-2-yl)-5-(trifluoromethyl)benzamide This compound was prepared following the general procedure described above using 4-allyl-7-amino-2H-benzo[b][1,4]oxazin-3(4H)-one

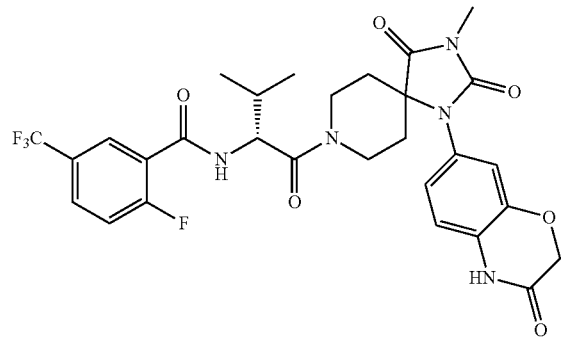 [SMILES: CC(C)[C@@H](NC(=O)c1cc(C(F)(F)F)ccc1F)C(=O)N1CCC2(CC1)C(=O)N(C)C(=O)N2c1ccc2c(c1)OCC(=O)N2]

22.5 mg, yield: 13%, white solid.
LCMS (ESI): m/z=620.2 [M+H]$^+$.

$^1$H-NMR (400 MHz, CD$_3$OD): δ=0.83-1.01 (m, 6H), 1.71-1.74 (m, 1H), 1.84-2.10 (m, 4H), 3.07 (s, 3H), 3.45-3.51 (m, 1H), 3.91-3.97 (m, 1H), 4.18-4.24 (m, 1H), 4.39-4.63 (m, 3H), 5.32-5.42 (m, 1H), 6.80-6.94 (m, 3H), 7.32-7.47 (m, 1H), 7.86-8.48 (m, 2H).

Example 31

(R)-5-Ethyl-2-fluoro-N-(3-methyl-1-(3-methyl-2,4-dioxo-1-(2-oxo-2,3-dihydrobenzo[d]oxazol-6-yl)-1,3,8-triazaspiro[4.5]decan-8-yl)-1-oxobutan-2-yl)benzamide

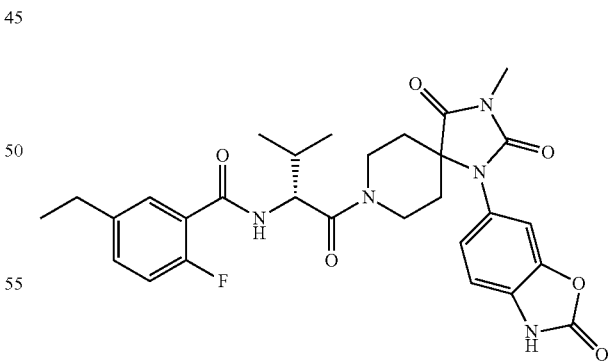

23.4 mg, yield: 39%, white solid.
LCMS (ESI): m/z=566.2 [M+H]$^+$.

$^1$H-NMR (400 MHz, CDCl$_3$): δ=0.87-1.07 (m, 6H), 1.21-1.23 (m, 3H), 1.25-1.99 (m, 8H, 3H), 2.65 (m, 2H), 3.16 (s, 3H), 3.48-3.50 (m, 1H), 3.92-3.97 (m, 2H), 4.67-4.69 (m, 1H), 5.13-5.07 (m, 1H), 6.87-7.02 (m, 1H), 6.99-7.05 (m, 2H), 7.29-7.33 (m, 2H), 7.54-7.74 (m, 2H), 9.37 (m, 1H).

Example 32

(R)—N-(1-(1-(1H-Benzo[d][1,2,3]triazol-5-yl)-3-methyl-2,4-dioxo-1,3,8-triazaspiro[4.5]decan-8-yl)-3-methyl-1-oxobutan-2-yl)-2-fluoro-5-(trifluoromethyl)benzamide

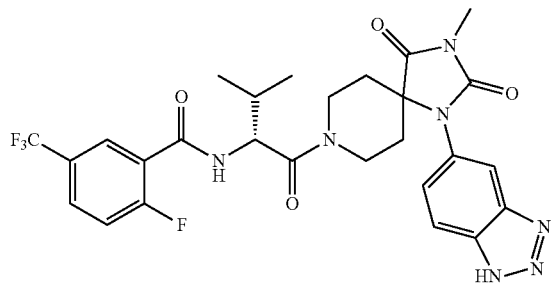 [SMILES: CC(C)[C@@H](NC(=O)c1cc(C(F)(F)F)ccc1F)C(=O)N1CCC2(CC1)C(=O)N(C)C(=O)N2c1ccc2[nH]nnc2c1]

35 mg, 20% yield, white solid.

LCMS (ESI): m/z=590.1 [M+H]$^+$.

$^1$H-NMR (400 MHz, CD$_3$OD): δ=0.69 (d, J=6.8 Hz, 1H), 0.85 (d, J=6.7 Hz, 1H), 0.95-0.99 (m, 4H), 1.75-2.25 (m, 5H), 3.12 (s, 3H), 3.47-3.57 (m, 1H), 3.93-4.02 (m, 1H), 4.20-4.32 (m, 1H), 4.49-4.56 (m, 1H), 4.78-4.84 (m, 1H), 7.16-7.46 (m, 2H), 7.72-8.03 (m, 4H).

Example 33

(R)—N-(3-Methyl-1-(3-methyl-2,4-dioxo-1-phenyl-1,3,8-triazaspiro[4.5]decan-8-yl)-1-oxobutan-2-yl)-3-(trifluoromethyl)benzamide

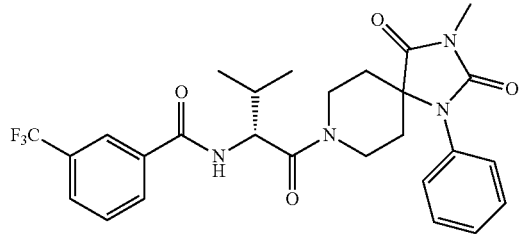 [SMILES: CC(C)[C@@H](NC(=O)c1cccc(C(F)(F)F)c1)C(=O)N1CCC2(CC1)C(=O)N(C)C(=O)N2c1ccccc1]

Representative Scheme:

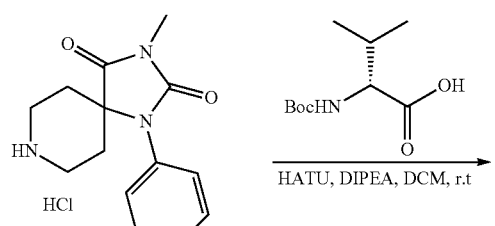

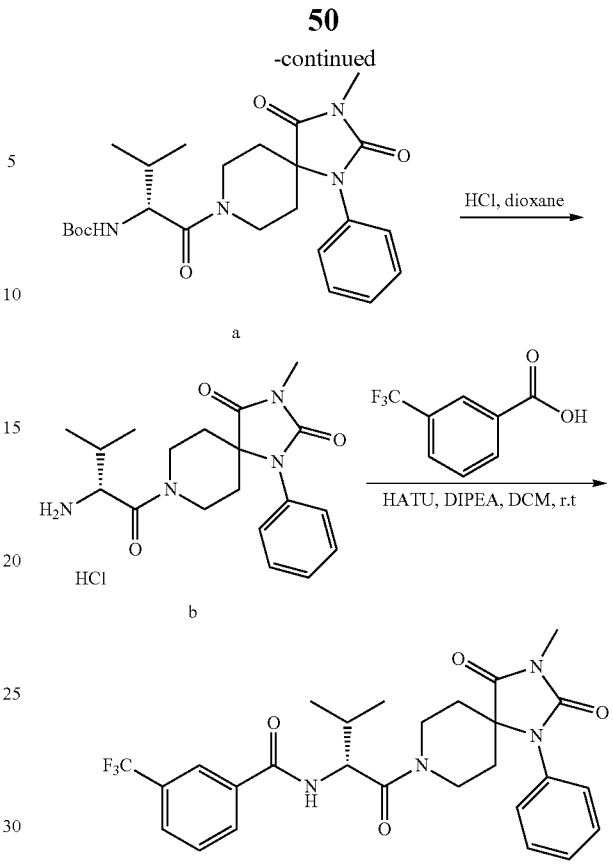

Representative General Procedure (R)-tert-Butyl-3-methyl-1-(3-methyl-2,4-dioxo-1-phenyl-1,3,8-triazaspiro[4.5]decan-8-yl)-1-oxobutan-2-ylcarbamate

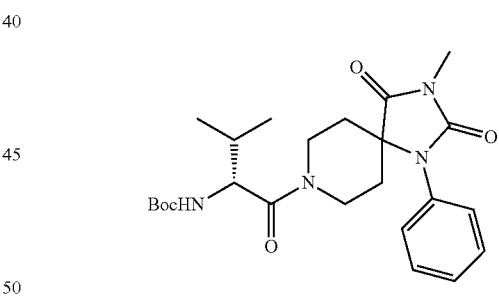

To a mixture of 3-methyl-1-phenyl-1,3,8-triazaspiro[4.5]decane-2,4-dione hydrochloride (prepared as described in Example 1-d) (513 mg, 1.73 mmol) in dichloromethane (30 mL) was added (R)-2-(tert-butoxycarbonylamino)-3-methylbutanoic acid (411 mg, 0.00026 mol), 1-[bis(dimethylamino)methylene]-1H-1,2,3-triazolo[4,5-b]pyridinium-3-oxide hexafluorophosphate (HATU) (900 mg, 2.36 mmol) and N,N-diisopropylethylamine (605 mg, 4.6 mmol). The resulting mixture was stirred for 2 hours at room temperature before the reaction was quenched with ice-water. The mixture was extracted with ethyl acetate (3×10 mL) and the combined organic layers were dried over anhydrous sodium sulfate and concentrated under reduced pressure. The residue was purified by silica gel column chromatography eluting with ethyl acetate:petroleum ether=1:5 to afford (R)-tert-butyl-3-methyl-1-(3-methyl-2,4-dioxo-1-phenyl-1, 3,8-triazaspiro[4.5]decan-8-yl)-1-oxobutan-2-ylcarbamate as a colorless oil (650 mg, 81%).

LCMS (ESI): m/z=459.2 [M+H]$^+$.

$^1$H-NMR (300 MHz, CDCl$_3$): δ=0.65-0.92 (m, 6H), 1.34 (s, 6H), 1.44 (s, 3H), 1.59-1.94 (m, 4H), 3.11 (s, 3H), 3.34-3.51 (m, 1H), 3.83-3.94 (m, 2H), 4.27-4.44 (m, 1H), 4.49-4.61 (m, 1H), 5.15-5.17 (m, 1H), 7.05-7.19 (m, 2H), 7.40-7.45 (m, 3H).

(R)-8-(2-Amino-3-methylbutanoyl)-3-methyl-1-phenyl-1,3,8-triazaspiro[4.5]decane-2,4-dione hydrochloride

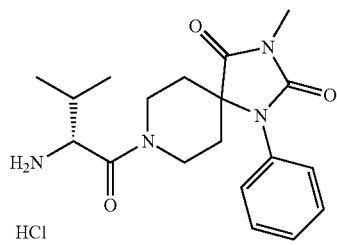 [SMILES: Cl ; CC(C)[C@@H](N)C(=O)N1CCC2(CC1)C(=O)N(C)C(=O)N2c1ccccc1]

A solution of tert-butyl-3-methyl-1-(4-nitrophenyl)-2,4-dioxo-1,3,8-triazaspiro[4.5]decane-8-carboxylate (458 mg, 1.98 mmol) in hydrochloric acid in dioxane (6.0 M, 10 mL) was stirred for 30 minutes. The precipitate was collected by filtration and dried under reduced pressure to afford (R)-8-(2-amino-3-methylbutanoyl)-3-methyl-1-phenyl-1,3,8-triazaspiro[4.5]decane-2,4-dione hydrochloride as a white solid (250 mg, 46%).

LCMS (ESI): m/z=359.2 [M+H]$^+$.

(R)—N-(3-Methyl-1-(3-methyl-2,4-dioxo-1-phenyl-1,3,8-triazaspiro[4.5]decan-8-yl)-1-oxobutan-2-yl)-3-(trifluoromethyl)benzamide

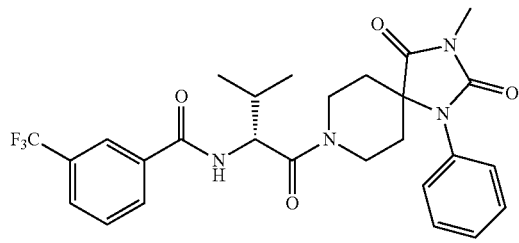 [SMILES: CC(C)[C@@H](NC(=O)c1cccc(C(F)(F)F)c1)C(=O)N1CCC2(CC1)C(=O)N(C)C(=O)N2c1ccccc1]

To a mixture of (R)-8-(2-amino-3-methylbutanoyl)-3-methyl-1-phenyl-1,3,8-triazaspiro[4.5]decane-2,4-dione hydrochloride (52 mg, 0.132 mmol) in dichloromethane (2 mL) was added 3-(trifluoromethyl)benzoic acid (23 mg, 0.12 mmol), 1-[bis(dimethylamino)methylene]-1H-1,2,3-triazolo[4,5-b]pyridinium-3-oxide hexafluorophosphate (HATU) (68 mg, 0.17 mmol) and N,N-diisopropylethylamine (31 mg, 0.24 mmol). The resulting mixture was stirred for 2 hours at room temperature before the reaction was quenched with ice-water (10 mL). The mixture was extracted with ethyl acetate (3×10 mL) and the combined organic layers were dried over anhydrous sodium sulfate and concentrated under reduced pressure. The residue was purified by silica gel column chromatography eluting with ethyl acetate:petroleum ether=1:5 to afford (R)—N-(3-methyl-1-(3-methyl-2,4-dioxo-1-phenyl-1,3,8-triazaspiro[4.5]decan-8-yl)-1-oxobutan-2-yl)-3-(trifluoromethyl)benzamide as a white solid (34.4 mg, 49%).

LCMS (ESI): m/z=531.2 [M+H]$^+$.

$^1$H-NMR (400 MHz, CD$_3$OD): δ=0.92-1.00 (m, 6H), 1.97-2.19 (m, 5H), 3.08 (s, 3H), 3.91-4.48 (m, 4H), 4.77-4.91 (m, 1H), 7.17-7.33 (m, 4H), 7.84-8.07 (m, 4H), 8.12-8.14 (m, 1H).

The following 18 compounds were synthesized following the general procedure described above:

Example 34

(R)-3-Ethyl-2-fluoro-N-(3-methyl-1-(3-methyl-2,4-dioxo-1-phenyl-1,3,8-triazaspiro[4.5]decan-8-yl)-1-oxobutan-2-yl)benzamide

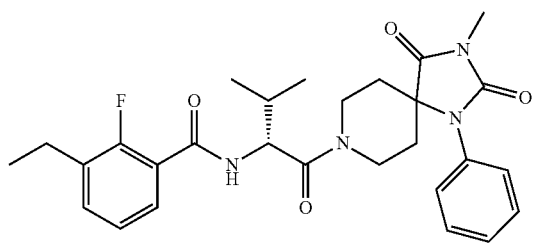 [SMILES: CCc1cccc(C(=O)N[C@@H](C(=O)N2CCC3(CC2)C(=O)N(C)C(=O)N3c2ccccc2)C(C)C)c1F]

31.2 mg, yield: 51%, white solid.

LCMS (ESI): m/z=509.2 [M+H]$^+$.

$^1$H-NMR (400 MHz, CD$_3$OD): δ=0.79-1.09 (m, 6H), 1.17-1.33 (m, 3H), 1.60-2.24 (m, 5H), 2.73 (m, 2H), 3.09 (s, 3H), 3.48 (m, 1H), 3.83-4.04 (m, 1H), 4.24-4.30 (m, 1H), 4.37-4.52 (m, 1H), 4.85-4.89 (m, 1H), 7.10-7.59 (m, 8H).

Example 35

(R)-3,4-Dichloro-N-(3-methyl-1-(3-methyl-2,4-dioxo-1-phenyl-1,3,8-triazaspiro[4.5]decan-8-yl)-1-oxobutan-2-yl)benzamide

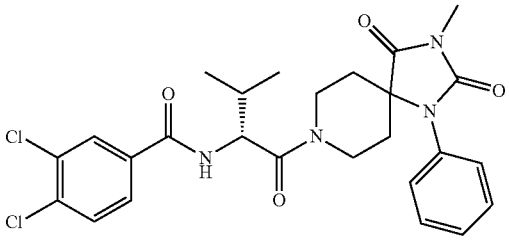 [SMILES: CC(C)[C@@H](NC(=O)c1ccc(Cl)c(Cl)c1)C(=O)N1CCC2(CC1)C(=O)N(C)C(=O)N2c1ccccc1]

33.9 mg, yield: 50%, white solid.

LCMS (ESI): m/z=531.2, 533.2 [M+H]$^+$.

$^1$H-NMR (400 MHz, CD$_3$OD): δ=0.71-0.90 (m, 6H), 1.58-2.30 (m, 5H), 3.09 (s, 3H), 3.48 (m, 1H), 3.84-4.01 (m, 1H), 4.17-4.58 (m, 2H), 4.74 (m, 1H), 7.17-7.84 (m, 8H).

Example 36

(R)-2,5-Dichloro-N-(3-methyl-1-(3-methyl-2,4-dioxo-1-phenyl-1,3,8-triazaspiro[4.5]decan-8-yl)-1-oxobutan-2-yl)benzamide

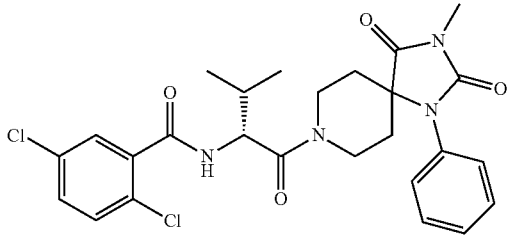 [SMILES: CC(C)[C@@H](NC(=O)c1cc(Cl)ccc1Cl)C(=O)N1CCC2(CC1)C(=O)N(C)C(=O)N2c1ccccc1]

34.4 mg, yield: 51%, white solid.
LCMS (ESI): m/z=531.2, 533.2 [M+H]$^+$.
$^1$H-NMR (400 MHz, CD$_3$OD): δ=0.71-1.10 (m, 6H), 1.61-2.25 (m, 5H), 3.10 (s, 3H), 3.46-3.49 (m, 1H), 3.81-4.04 (m, 1H), 4.11-4.58 (m, 2H), 4.74-4.77 (m, 1H), 7.12-7.57 (m, 8H).

Example 37

5-Ethyl-2-fluoro-N-((2R,3S)-3-methoxy-1-(3-methyl-2,4-dioxo-1-phenyl-1,3,8-triazaspiro[4.5]decan-8-yl)-1-oxobutan-2-yl)benzamide

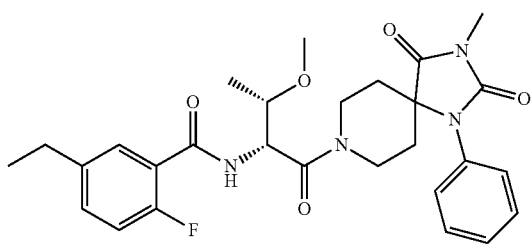 [SMILES: CCc1ccc(F)c(C(=O)N[C@@H](C(=O)N2CCC3(CC2)C(=O)N(C)C(=O)N3c2ccccc2)[C@H](C)OC)c1]

19.8 mg, yield: 29%, white solid.
LCMS (ESI): m/z=525.2 [M+H]$^+$.
$^1$H-NMR (400 MHz, CD$_3$OD): δ=1.22-1.31 (m, 6H), 1.66-2.83 (m, 6H), 3.03 (m, 4H), 3.38 (s, 2H), 3.51-4.51 (m, 5H), 5.01-5.17 (m, 1H), 6.73-7.76 (m, 8H).

Example 38

3-Ethyl-5-fluoro-N-((2R,3S)-3-methoxy-1-(3-methyl-2,4-dioxo-1-phenyl-1,3,8-triazaspiro[4.5]decan-8-yl)-1-oxobutan-2-yl)benzamide

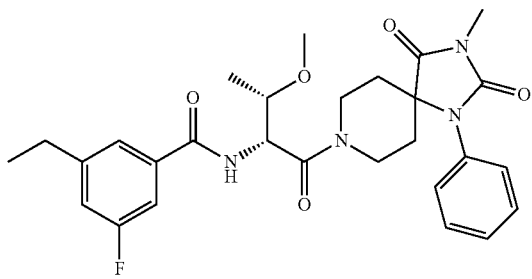 [SMILES: CCc1cc(F)cc(C(=O)N[C@@H](C(=O)N2CCC3(CC2)C(=O)N(C)C(=O)N3c2ccccc2)[C@H](C)OC)c1]

36.0 mg, yield: 54%, white solid.
LCMS (ESI): m/z=525.2 [M+H]$^+$.
$^1$H-NMR (400 MHz, CD$_3$OD): δ=1.00-1.19 (m, 6H), 1.66-2.71 (m, 6H), 3.08 (s, 3H), 3.11 (s, 1H), 3.30 (s, 2H), 3.46-4.47 (m, 5H), 5.03-5.11 (m, 1H), 6.69-7.76 (m, 8H).

Example 39

(R)-5-Ethyl-2-fluoro-N-(3-methyl-1-(3-methyl-2,4-dioxo-1-phenyl-1,3,8-triazaspiro[4.5]decan-8-yl)-1-oxobutan-2-yl)benzamide

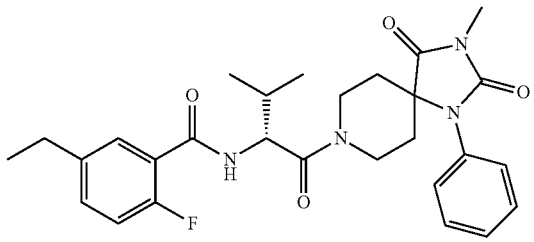 [SMILES: CCc1ccc(F)c(C(=O)N[C@@H](C(=O)N2CCC3(CC2)C(=O)N(C)C(=O)N3c2ccccc2)C(C)C)c1]

10.0 mg, yield: 17%, white solid.
LCMS (ESI): m/z=509.2 [M+H]$^+$.
$^1$H-NMR (400 MHz, CD$_3$OD): δ=0.79-1.09 (m, 6H), 1.26-1.30 (m, 3H), 1.57-2.27 (m, 5H), 2.63-2.75 (m, 2H), 3.09 (s, 3H), 3.42-3.56 (m, 1H), 4.14-4.32 (m, 2H), 4.37-4.53 (m, 1H), 4.82-4.88 (m, 1H), 7.05-7.61 (m, 8H).

Example 40

5-Ethyl-2-fluoro-N-((2R,3R)-3-methoxy-1-(1-(4-methoxyphenyl)-3-methyl-2,4-dioxo-1,3,8-triazaspiro[4.5]decan-8-yl)-1-oxobutan-2-yl)benzamide

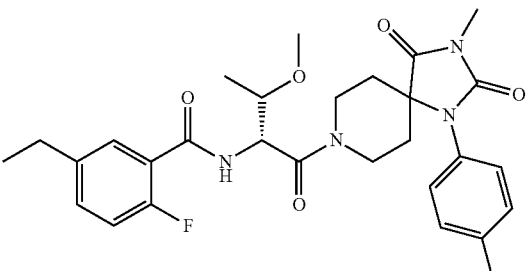

10.0 mg, yield: 15%, white solid.
LCMS (ESI): m/z=555.2 [M+H]$^+$.
$^1$H-NMR (400 MHz, CD$_3$OD): δ=1.02-1.27 (m, 6H), 1.65-2.05 (m, 4H), 2.66-2.73 (m, 2H), 3.08 (s, 3H), 3.12-3.20 (m, 1H), 3.44-3.47 (m, 1H), 3.52-3.88 (m, 6H), 4.17-4.25 (m, 1H), 4.31-4.49 (m, 1H), 5.06-5.17 (m, 1H), 6.93-7.20 (m, 5H), 7.39-7.57 (m, 2H).

Example 41

3-Fluoro-N-((2R,3R)-1-(1-(4-methoxyphenyl)-3-methyl-2,4-dioxo-1,3,8-triazaspiro[4.5]decan-8-yl)-3-methyl-1-oxopentan-2-yl)-5-methylbenzamide

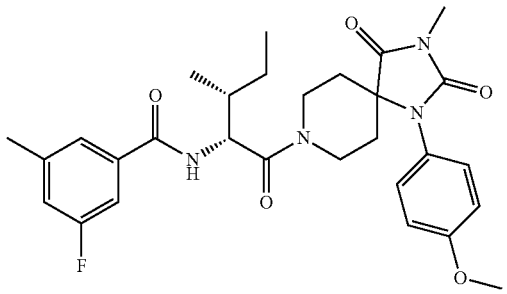

12.8 mg, yield: 11%, white solid.
LCMS (ESI): m/z=539.2 [M+H]⁺.
¹H-NMR (400 MHz, CD₃OD): δ=0.67-0.98 (m, 6H), 1.12-1.25 (m, 1H), 1.45-1.48 (m, 1H), 1.62-2.15 (m, 5H), 2.41 (s, 3H), 3.07 (s, 3H), 3.47-3.51 (m, 1H), 3.75 (s, 2H), 3.84 (s, 1H), 3.85-4.51 (m, 3H), 4.89-4.91 (m, 1H), 6.84-7.52 (m, 7H).

Example 42

(R)-5-Cyclopropyl-2-fluoro-N-(3-methyl-1-(3-methyl-2,4-dioxo-1-phenyl-1,3,8-triazaspiro[4.5]decan-8-yl)-1-oxobutan-2-yl)benzamide

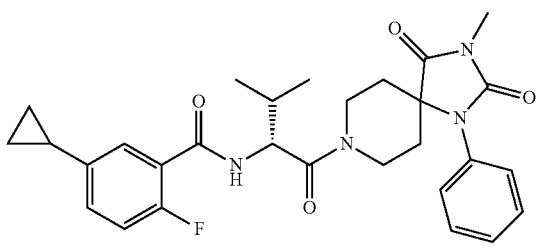 [SMILES: CC(C)[C@@H](NC(=O)c1cc(C2CC2)ccc1F)C(=O)N1CCC2(CC1)C(=O)N(C)C(=O)N2c1ccccc1]

34.0 mg, yield: 39%, white solid.
LCMS (ESI): m/z=521.2 [M+H]⁺.
¹H-NMR (400 MHz, CD₃OD): δ=0.67-0.98 (m, 10H), 1.65-2.15 (m, 6H), 3.08 (s, 3H), 3.47-3.51 (m, 1H), 3.91-3.94 (m, 1H), 4.23-4.49 (m, 2H), 4.80-4.90 (m, 1H), 7.05-7.51 (m, 8H).

Example 43

(R)-5-Chloro-2-fluoro-N-(3-methyl-1-(3-methyl-2,4-dioxo-1-phenyl-1,3,8-triazaspiro[4.5]decan-8-yl)-1-oxobutan-2-yl)benzamide

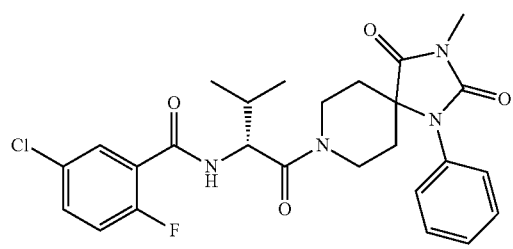

42.0 mg, yield: 48%, white solid.
LCMS (ESI): m/z=515.2[M+H]⁺.
¹H-NMR (400 MHz, CD₃OD): δ=0.76-1.01 (m, 6H), 1.65-2.15 (m, 5H), 3.09 (s, 3H), 3.47-3.51 (m, 1H), 3.90-3.95 (m, 1H), 4.17-4.47 (m, 2H), 4.80-4.82 (m, 1H), 7.22-7.75 (m, 8H).

Example 44

(R)-2-Fluoro-N-(3-methyl-1-(3-methyl-2,4-dioxo-1-phenyl-1,3,8-triazaspiro[4.5]decan-8-yl)-1-oxobutan-2-yl)-5-(trifluoromethyl)benzamide

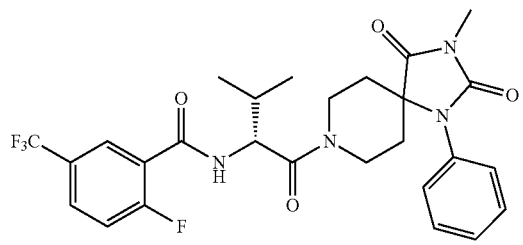 [SMILES: CC(C)[C@@H](NC(=O)c1cc(C(F)(F)F)ccc1F)C(=O)N1CCC2(CC1)C(=O)N(C)C(=O)N2c1ccccc1]

26.9 mg, yield: 55%, white solid.
LCMS (ESI): m/z=549.2 [M+H]⁺.
¹H-NMR (400 MHz, CD₃OD): δ=0.77-1.03 (m, 6H), 1.68-2.22 (m, 5H), 3.09 (s, 3H), 3.46-3.53 (m, 1H), 3.93-3.99 (m, 1H), 4.18-4.30 (m, 1H), 4.40-4.52 (m, 1H), 4.83-4.86 (m, 1H), 7.23-7.53 (m, 6H), 7.85-8.02 (m, 2H).

Example 45

(R)-5-Cyclopropyl-2-fluoro-N-(1-(1-(4-methoxyphenyl)-3-methyl-2,4-dioxo-1,3,8-triazaspiro[4.5]decan-8-yl)-3-methyl-1-oxobutan-2-yl)benzamide

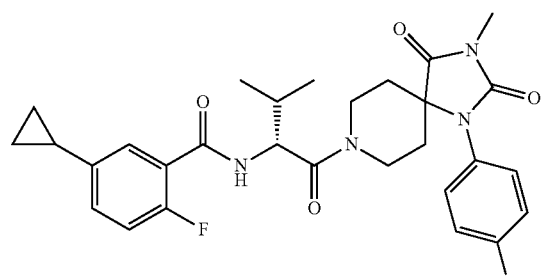

23.0 mg, yield: 36%, white solid.
LCMS (ESI): m/z=551.2 [M+H]⁺.
¹H-NMR (400 MHz, CD₃OD): δ=0.68-0.98 (m, 10H), 1.86-2.16 (m, 6H), 3.32 (s, 3H), 3.47-3.51 (m, 1H), 3.75-3.77 (m, 2H), 3.81-3.88 (m, 1H), 3.93-4.49 (m, 3H), 4.84-4.90 (m, 1H), 6.88-7.34 (m, 7H).

Example 46

(R)-3-Ethyl-N-(3-methyl-1-(3-methyl-2,4-dioxo-1-phenyl-1,3,8-triazaspiro[4.5]decan-8-yl)-1-oxobutan-2-yl)benzamide

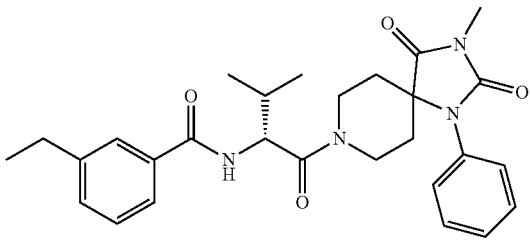 [SMILES: CCc1cccc(C(=O)N[C@@H](C(=O)N2CCC3(CC2)C(=O)N(C)C(=O)N3c2ccccc2)C(C)C)c1]

29.5 mg, yield: 50%, white solid.
LCMS (ESI): m/z=491 [M+H]$^+$.
$^1$H-NMR (400 MHz, CD$_3$OD): δ=0.72-0.97 (m, 6H), 1.23-1.28 (m, 3H), 1.60-2.18 (m, 5H), 2.67-2.73 (m, 2H), 3.07 (s, 3H), 3.49-3.52 (m, 1H), 3.90-4.00 (m, 1H), 4.31-4.49 (m, 2H), 4.76-4.88 (m, 1H), 7.16-7.49 (m, 8H).

Example 47

(R)-3-Ethyl-5-fluoro-N-(3-methyl-1-(3-methyl-2,4-dioxo-1-phenyl-1,3,8-triazaspiro[4.5]decan-8-yl)-1-oxobutan-2-yl)benzamide

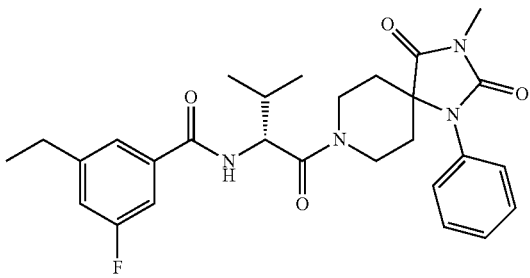 [SMILES: CCc1cc(F)cc(C(=O)N[C@@H](C(=O)N2CCC3(CC2)C(=O)N(C)C(=O)N3c2ccccc2)C(C)C)c1]

27.6 mg, yield: 45%, white solid.
LCMS (ESI): m/z=509 [M+H]$^+$.
$^1$H-NMR (400 MHz, CD$_3$OD): δ=0.71-0.96 (m, 6H), 1.24 (m, 3H), 1.65-1.68 (m, 1H), 1.91-2.09 (m, 4H), 2.70-2.72 (m, 2H) 3.07 (s, 3H), 3.45-3.47 (m, 1H), 3.90-3.96 (m, 1H), 4.30-4.47 (m, 2H), 4.73 (m, 1H), 7.14-7.50 (m, 9H).

Example 48

(R)-3,5-Dichloro-N-(3-methyl-1-(3-methyl-2,4-dioxo-1-phenyl-1,3,8-triazaspiro[4.5]decan-8-yl)-1-oxobutan-2-yl)benzamide

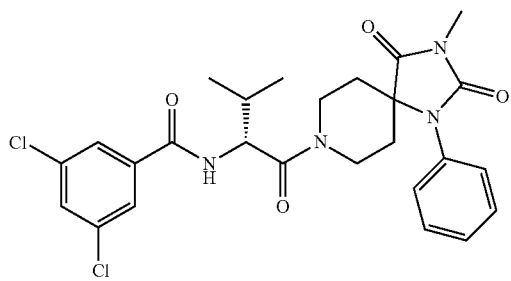 [SMILES: CC(C)[C@@H](NC(=O)c1cc(Cl)cc(Cl)c1)C(=O)N1CCC2(CC1)C(=O)N(C)C(=O)N2c1ccccc1]

18.5 mg, yield: 29%, white solid.
LCMS (ESI): m/z=531 [M+H]$^+$.
$^1$H-NMR (400 MHz, CD$_3$OD): δ=0.71-0.96 (m, 6H), 1.63-1.73 (m, 1H), 1.81-2.61 (m, 4H), 3.08 (s, 3H), 3.47 (m, 1H), 3.89 (m, 1H), 4.22-4.51 (m, 2H), 4.71 (m, 1H), 7.18-8.65 (m, 8H).

Example 49

5-Cyclopropyl-2-fluoro-N-((2R,3R)-3-methoxy-1-(1-(4-methoxyphenyl)-3-methyl-2,4-dioxo-1,3,8-triazaspiro[4.5]decan-8-yl)-1-oxobutan-2-yl)benzamide

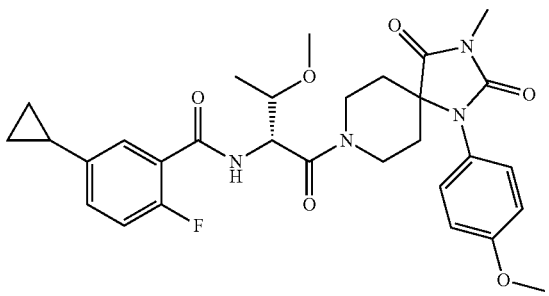 [SMILES: COc1ccc(N2C(=O)N(C)C(=O)C23CCN(C(=O)[C@H](NC(=O)c2cc(C4CC4)ccc2F)C(C)OC)CC3)cc1]

27.2 mg, yield: 31%, white solid.
LCMS (ESI): m/z=567 [M+H]$^+$.
$^1$H-NMR (400 MHz, CD$_3$OD): δ=0.70-0.82 (m, 2H), 0.91-1.03 (m, 4H), 1.14-1.32 (m, 2H), 1.60-1.79 (m, 1H), 1.83-2.17 (m, 4H), 2.99-3.11 (m, 3H), 3.13-3.15 (m, 2H), 3.71-4.01 (m, 6H), 4.14 (m, 1H), 4.47-4.49 (m, 1H), 5.03-5.26 (m, 1H), 6.95-7.01 (m, 1H), 7.02-7.33 (m, 5H), 7.50-7.71 (m, 1H).

Example 50

(R)-5-Ethyl-2-fluoro-N-(1-(1-(4-methoxyphenyl)-3-methyl-2,4-dioxo-1,3,8-triazaspiro[4.5]decan-8-yl)-3-methyl-1-oxobutan-2-yl)benzamide

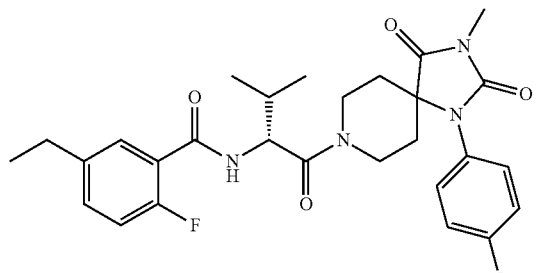

43.7 mg, yield: 68%, white solid.
LCMS (ESI): m/z=539 [M+H]$^+$.
$^1$H-NMR (400 MHz, CD$_3$OD): δ=0.74-1.08 (m, 6H), 1.21-1.38 (m, 3H), 1.60-1.75 (m, 1H), 1.78-2.25 (m, 4H), 2.62-2.80 (m, 2H), 3.08 (s, 3H), 3.41-3.48 (m, 1H), 3.56-3.76 (m, 2H), 3.84-3.93 (m, 1H), 4.18-4.27 (m, 2H), 4.48-4.86 (m, 2H), 6.90-6.92 (m, 1H), 7.00-7.26 (m, 4H), 7.45 (m, 2H).

Example 51
(R)-2-Fluoro-N-(1-(1-(4-methoxyphenyl)-3-methyl-2,4-dioxo-1,3,8-triazaspiro[4.5]decan-8-yl)-3-methyl-1-oxobutan-2-yl)-5-(trifluoromethyl)benzamide
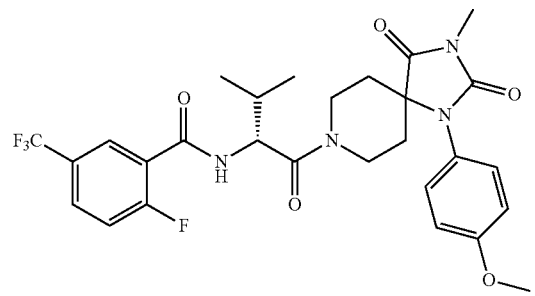 [SMILES: COc1ccc(N2C(=O)N(C)C(=O)C23CCN(C(=O)[C@H](NC(=O)c2cc(C(F)(F)F)ccc2F)C(C)C)CC3)cc1]
40.0 mg, yield: 47%, white solid.
LCMS (ESI): m/z=579 [M+H]$^+$.
$^1$H-NMR (400 MHz, CD$_3$OD): δ=0.79-1.01 (m, 6H), 1.66-2.17 (m, 5H), 3.06 (s, 3H), 3.49 (m, 1H), 3.75 (s, 2H), 3.85 (s, 1H), 3.94-4.22 (m, 2H), 4.44-4.50 (m, 1H), 4.86-4.94 (m, 1H), 6.90-6.93 (m, 1H), 7.13 (m, 3H), 7.43 (m, 1H), 7.94 (m, 2H).
Example 52
(R)—N-(1-(1-(1H-indazol-5-yl)-3-methyl-2,4-dioxo-1,3,8-triazaspiro[4.5]decan-8-yl)-3-methyl-1-oxobutan-2-yl)-2-fluoro-5-(trifluoromethyl)benzamide
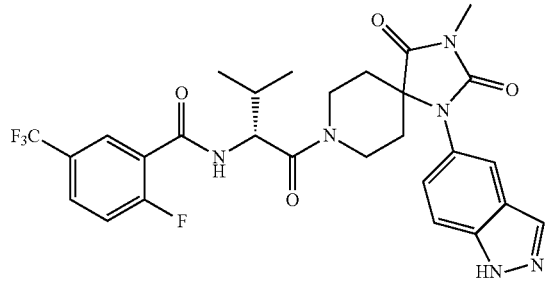
Representative Scheme:
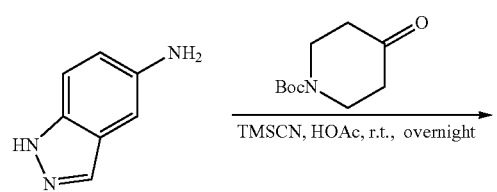
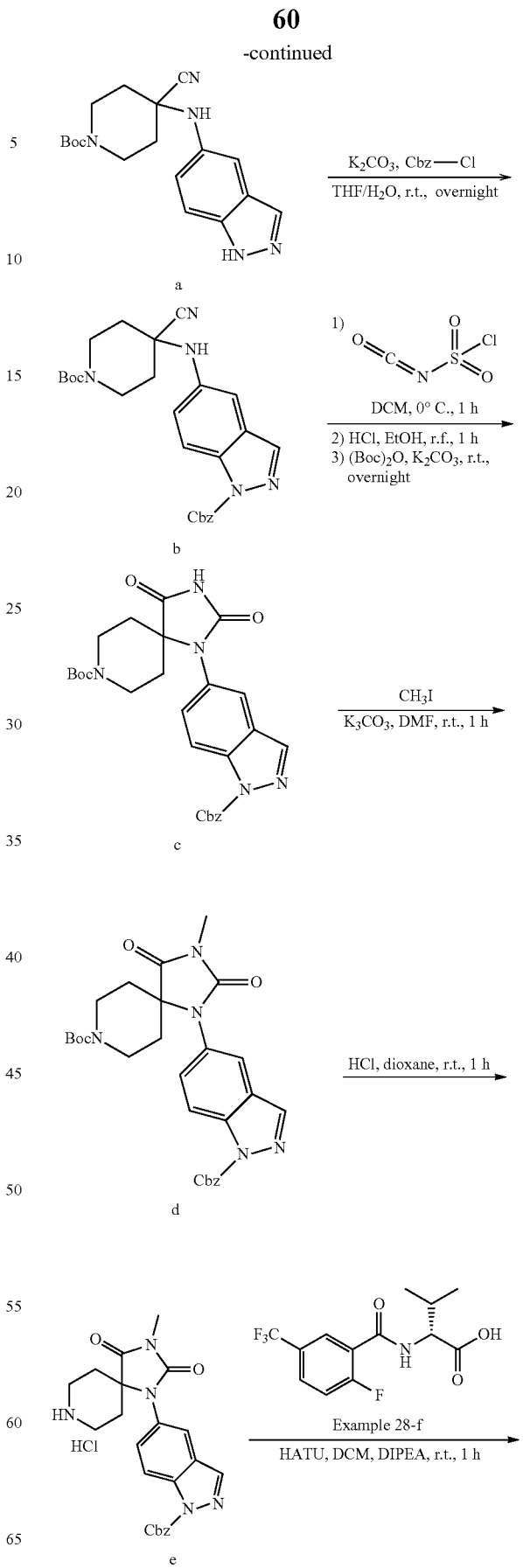

-continued

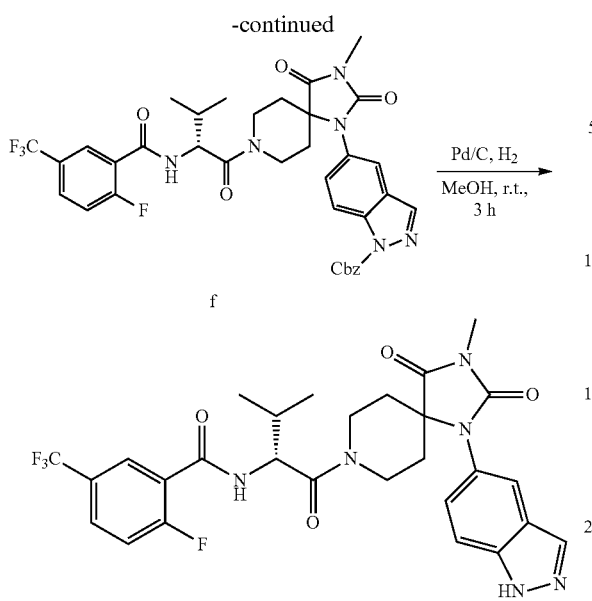

Representative General Procedure tert-Butyl-4-(1H-indazol-5-ylamino)-4-cyanopiperidine-1-carboxylate

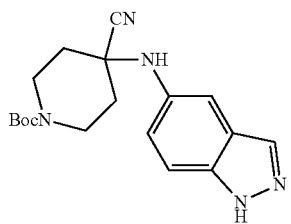 [SMILES: CC(C)(C)OC(=O)N1CCC(C#N)(Nc2ccc3[nH]ncc3c2)CC1]

To a solution of 1H-indazol-5-amine (25.0 g, 0.19 mol) in acetic acid (300 mL) was added tert-butyl-4-oxopiperidine-1-carboxylate (45.0 g, 0.22 mol). The resulting mixture was cooled to 0° C. and trimethylsilyl cyanide (37.0 g, 0.37 mol) was added. The resulting solution was stirred overnight at room temperature. Saturated aqueous ammonium chloride solution (500 mL) was added. The resulting mixture was filtered and the filter cake was washed with water (3×50 mL) to afford tert-butyl-4-(1H-indazol-5-ylamino)-4-cyanopiperidine-1-carboxylate as a brown solid (60.0 g, 93%).

LCMS (ESI): m/z=342.1 [M+H]$^+$.

$^1$H-NMR (300 MHz, DMSO-d$_6$): δ=1.41 (s, 9H), 1.76-1.85 (m, 2H), 2.20-2.24 (m, 2H), 3.15 (t, J=10.8 Hz, 2H), 3.78-3.82 (m, 2H), 5.74 (s, 1H), 6.95-7.05 (m, 1H), 7.12-7.20 (m, 1H), 7.29-7.42 (m, 1H), 7.92 (s, 1H), 12.8 (br, 1H).

Benzyl-5-((1-(tert-butoxycarbonyl)-4-cyanopiperidin-4-yl)amino)-1H-indazole-1-carboxylate

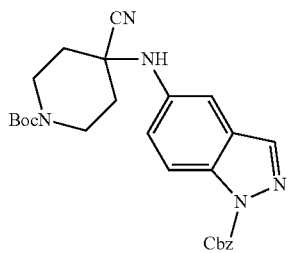 [SMILES: CC(C)(C)OC(=O)N1CCC(C#N)(Nc2ccc3c(cnn3C(=O)OCc3ccccc3)c2)CC1]

To a solution of tert-butyl-4-(1H-indazol-5-ylamino)-4-cyanopiperidine-1-carboxylate (60.0 g, 0.18 mol) in tetrahydrofuran:water (300 mL, 1:1) was added potassium carbonate (57.0 g, 0.41 mol) and benzyl chloroformate (53.0 g, 0.31 mol) at 0° C. After stirring overnight, the organic layer was isolated and the aqueous was extracted with ethyl acetate (3×100 mL). The combined layers were washed with water (3×50 mL) and brine (3×50 mL). The organic layers were dried over anhydrous sodium sulfate and concentrated under reduced pressure. The residue was purified by silica gel column chromatography eluting with ethyl acetate:dichloromethane:petroleum ether=1:2:2 to afford benzyl-5-((1-(tert-butoxycarbonyl)-4-cyanopiperidin-4-yl)amino)-1H-indazole-1-carboxylate as a brown solid (60.0 g, 70%).

LCMS (ESI): m/z=476.1 [M+H]$^+$.

Benzyl-5-(8-(tert-butoxycarbonyl)-2,4-dioxo-1,3,8-triazaspiro[4.5]decan-1-yl)-1H-indazole-1-carboxylate

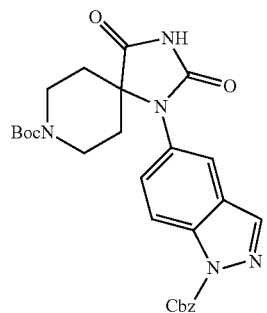 [SMILES: CC(C)(C)OC(=O)N1CCC2(CC1)C(=O)NC(=O)N2c1ccc2c(cnn2C(=O)OCc2ccccc2)c1]

To a solution of benzyl-5-((1-(tert-butoxycarbonyl)-4-cyanopiperidin-4-yl)amino)-1H-indazole-1-carboxylate (10.0 g, 0.021 mol) in dichloromethane (200 mL) was added chlorosulfonyl isocyanate (20 mL, 0.23 mol) at 0° C. After stirring for 30 minutes at 0° C., the reaction was quenched by addition of a 5% aqueous hydrochloric acid solution (100 mL). The solvent was removed under reduced pressure and ethanol (100 mL) was added. The mixture was stirred for 30 minutes at 80° C. The solvent was removed under reduced pressure and the residue was added to tetrahydrofuran (20 mL) and the pH was adjusted to 8 by addition of a 15% aqueous potassium carbonate solution. Then di-tert-butyl-dicarbonate (5.9 g, 0.027 mol) in tetrahydrofuran (100 mL) was added. After stirring overnight, the solvent was removed under reduced pressure and the residue was purified by silica gel column chromatography eluting with dichloromethane:methanol=50:1 to afford benzyl-5-(8-(tert-butoxycarbonyl)-2,4-dioxo-1,3,8-triazaspiro[4.5]decan-1-yl)-1H-indazole-1-carboxylate as a yellow solid (3.0 g, 27%).

LCMS (ESI): m/z=520.1 [M+H]$^+$.

$^1$H-NMR (300 MHz, CDCl$_3$): δ=1.36 (s, 9H), 1.74-1.81 (m, 2H), 1.96-2.00 (m, 2H), 3.43-3.55 (m, 2H), 4.02 (br, 2H), 5.56 (s, 2H), 7.25-7.41 (m, 5H), 7.51-7.57 (m, 3H), 8.21 (s, 1H), 8.29-8.32 (d, 1H, J=9.2 Hz).

Benzyl-5-(8-(tert-butoxycarbonyl)-3-methyl-2,4-dioxo-1,3,8-triazaspiro[4.5]decan-1-yl)-1H-indazole-1-carboxylate

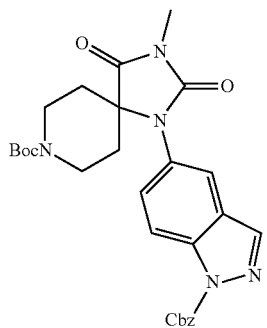 [SMILES: CN1C(=O)N(c2ccc3c(cnn3C(=O)OCc3ccccc3)c2)C2(CCN(C(=O)OC(C)(C)C)CC2)C1=O]

To a solution of benzyl-5-(8-(tert-butoxycarbonyl)-2,4-dioxo-1,3,8-triazaspiro[4.5]decan-1-yl)-1H-indazole-1-carboxylate (10.0 g, 0.019 mol) in N,N-dimethylformamide (100 mL) was added potassium carbonate (5.32 g, 0.039 mol) at 0° C. After stirring for 15 minutes, iodomethane (1.58 mL, 0.025 mol) was added. After stirring for 1 hour, the reaction was quenched by addition of ice-water (50 mL). The mixture was extracted with ethyl acetate (3×50 mL) and the combined organic layers were dried over anhydrous sodium sulfate and concentrated under reduced pressure. The residue was purified by silica gel column chromatography eluting with dichloromethane:methanol=40:1 to afford benzyl-5-(8-(tert-butoxycarbonyl)-3-methyl-2,4-dioxo-1,3,8-triazaspiro[4.5]decan-1-yl)-1H-indazole-1-carboxylate as a white solid (7.5 g, 73%).

LCMS (ESI): m/z=534.1 [M+H]$^+$.

$^1$H-NMR (300 MHz, CDCl$_3$): δ=1.35 (s, 9H), 1.72-1.77 (m, 4H), 1.86-1.90 (m, 2H), 3.11 (s, 3H), 3.51 (br, 2H), 3.86-4.10 (m, 2H), 5.55 (s, 2H), 7.29 (dd, 1H, J=8.9 Hz, J=1.9 Hz), 7.40 (m, 3H), 7.53 (m, 3H), 8.20 (d, 1H, J=0.7 Hz), 8.28 (d, 1H, J=8.6 Hz).

Benzyl-5-(3-methyl-2,4-dioxo-1,3,8-triazaspiro[4.5]decan-1-yl)-1H-indazole-1-carboxylate hydrochloride

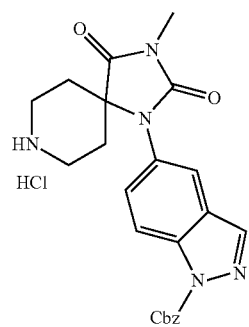 [SMILES: Cl ; CN1C(=O)N(c2ccc3c(cnn3C(=O)OCc3ccccc3)c2)C2(CCNCC2)C1=O]

A solution of benzyl-5-(8-(tert-butoxycarbonyl)-3-methyl-2,4-dioxo-1,3,8-triazaspiro[4.5]decan-1-yl)-1H-indazole-1-carboxylate (3.50 g, 0.00657 mol) in hydrochloric acid in dioxane (10 mL, 6.0 M) was stirred 1 hour. The mixture was filtered, and the filter cake was washed with petroleum ether (3×10 mL) to afford benzyl-5-(3-methyl-2,4-dioxo-1,3,8-triazaspiro[4.5]decan-1-yl)-1H-indazole-1-carboxylate hydrochloride as a white solid (1.98 g, 70%).

LCMS (ESI): m/z=434.1 [M+H]$^+$.

(R)-Benzyl-5-(8-(2-(2-fluoro-5-(trifluoromethyl)benzamido)-3-methylbutanoyl)-3-methy-2,4-dioxo-1,3,8-triazaspiro[4.5]decan-1-yl)-1H-indazole-1-carboxylate

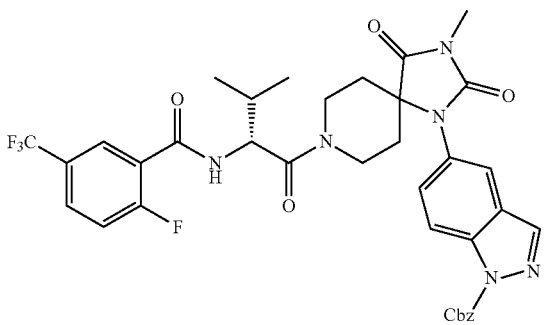 [SMILES: CC(C)[C@@H](NC(=O)c1cc(C(F)(F)F)ccc1F)C(=O)N1CCC2(CC1)C(=O)N(C)C(=O)N2c1ccc2c(cnn2C(=O)OCc2ccccc2)c1]

To a solution of benzyl-5-(3-methyl-2,4-dioxo-1,3,8-triazaspiro[4.5]decan-1-yl)-1H-indazole-1-carboxylate hydrochloride (5.0 g, 0.011 mol) in dichloromethane (100 mL) was added sequentially (R)-2-(2-fluoro-5-(trifluoromethyl)benzamido)-3-methylbutanoic acid (prepared as described in Example 26-f) (2.9 g, 0.0094 mol), 1-[bis(dimethylamino)methylene]-1H-1,2,3-triazolo[4,5-b]pyridinium-3-oxide hexafluorophosphate (HATU) (5.33 g, 0.01406 mol), N,N-diisopropylethylamine (3.0 g, 0.024 mol). The reaction was stirred for 2 hours before quenching with ice-water (10 mL). The mixture was extracted with ethyl acetate (3×50 mL) and the combined organic layers were dried over anhydrous sodium sulfate and concentrated under reduced pressure. The residue was purified by prep-TLC with dichloromethane:methanol=15:1 to afford (R)-benzyl-5-(8-(2-(2-fluoro-5-(trifluoromethyl)benzamido)-3-methylbutanoyl)-3-methyl-2,4-dioxo-1,3,8-triazaspiro[4.5]decan-1-yl)-1H-indazole-1-carboxylate as a white solid (5.1 g, 76%).

LCMS (ESI): m/z=723.0 [M+H]$^+$.

(R)—N-(1-(1-(1H-Indazol-5-yl)-3-methyl-2,4-dioxo-1,3,8-triazaspiro[4.5]decan-8-yl)-3-methyl-1-oxobutan-2-yl)-2-fluoro-5-(trifluoromethyl)benzamide

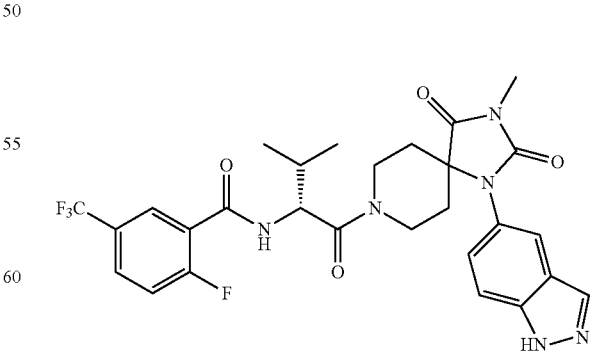

A mixture of (R)-benzyl-5-(8-(2-(2-fluoro-5-(trifluoromethyl)benzamido)-3-methyl butanoyl)-3-methyl-2,4-dioxo-1,3,8-triazaspiro[4.5]decan-1-yl)-1H-indazole-1-carboxylate (350 mg, 0.48 mmol) and palladium on carbon (50 mg, 5%) in methanol (50 mL) was stirred for 3 hours under a hydrogen atmosphere. The resulting mixture was filtered and the filter cake was washed with methanol (5×10 mL). The filtrate was concentrated under reduced pressure. The residue was purified by prep-HPLC (acetonitrile and water, acetonitrile from 5% to 60%) to afford (R)—N-(1-(1-(1H-indazol-5-yl)-3-methyl-2,4-dioxo-1,3,8-triazaspiro[4.5]decan-8-yl)-3-methyl-1-oxobutan-2-yl)-2-fluoro-5-(trifluoromethyl)benzamide as a white solid (78 mg, 27%).

LCMS (ESI): m/z=589.2 [M+H]+.

1H-NMR (400 MHz, CD3OD): δ=0.67-0.99 (m, 6H), 1.74-2.26 (m, 5H), 3.11 (s, 3H), 3.48-3.54 (m, 1H), 3.94-4.00 (m, 1H), 4.18-4.52 (m, 2H), 4.80-4.84 (m, 1H), 7.16-7.68 (m, 3H), 7.75-7.87 (m, 2H), 7.87-8.15 (m, 1H), 8.46-8.51 (m, 1H).

The following 22 compounds were synthesized following the general procedure described above:

Example 53

(R)—N-(1-(1-(1H-Indazol-6-yl)-3-methyl-2,4-dioxo-1,3,8-triazaspiro[4.5]decan-8-yl)-3-methyl-1-oxobutan-2-yl)-2-fluoro-5-(trifluoromethyl)benzamide

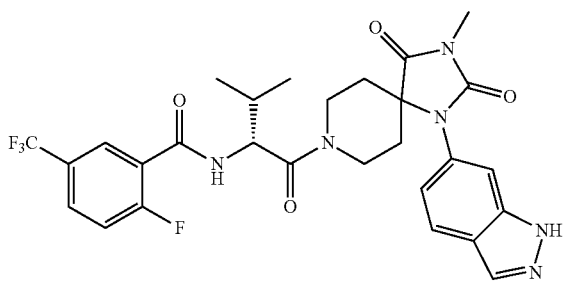 [SMILES: CC(C)[C@@H](NC(=O)c1cc(C(F)(F)F)ccc1F)C(=O)N1CCC2(CC1)C(=O)N(C)C(=O)N2c1ccc2cn[nH]c2c1]

73.2 mg, yield: 30%, white solid.
LCMS (ESI): m/z=589.0 [M+H]+.

1H-NMR (400 MHz, CD3OD): δ=0.79-1.04 (m, 6H), 1.84-2.13 (m, 5H), 3.18 (s, 3H), 3.48-3.54 (m, 1H), 4.02-4.06 (m, 2H), 4.60-4.64 (m, 1H), 4.97-5.01 (m, 1H), 6.91-6.96 (m, 1H), 7.15-7.24 (m, 1H), 7.42-8.01 (m, 4H), 8.13-8.34 (m, 1H).

Example 54

(R)—N-(1-(1-(1H-Indazol-5-yl)-3-methyl-2,4-dioxo-1,3,8-triazaspiro[4.5]decan-8-yl)-3-methyl-1-oxobutan-2-yl)-5-cyclopropyl-2-fluorobenzamide

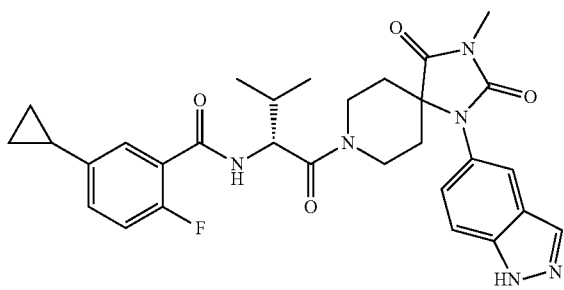 [SMILES: CC(C)[C@@H](NC(=O)c1cc(C2CC2)ccc1F)C(=O)N1CCC2(CC1)C(=O)N(C)C(=O)N2c1ccc2[nH]ncc2c1]

29.7 mg, yield: 37%, white solid.
LCMS (ESI): m/z=561.2 [M+H]+.

1H-NMR (400 MHz, CD3OD): δ=0.63-1.00 (m, 10H), 1.72-2.25 (m, 6H), 3.11 (s, 3H), 3.47-3.53 (m, 1H), 3.93-3.99 (m, 1H), 4.16-4.51 (m, 2H), 4.80-4.82 (m, 1H), 6.89-7.11 (m, 1H), 7.17-7.30 (m, 2H), 7.40-7.53 (m, 1H), 7.65-7.67 (m, 1H), 7.77-8.03 (m, 1H), 8.10-8.15 (m, 1H).

Example 55

(R)—N-(1-(1-(1H-Indazol-5-yl)-3-methyl-2,4-dioxo-1,3,8-triazaspiro[4.5]decan-8-yl)-3-methyl-1-oxobutan-2-yl)-5-ethyl-2-fluorobenzamide

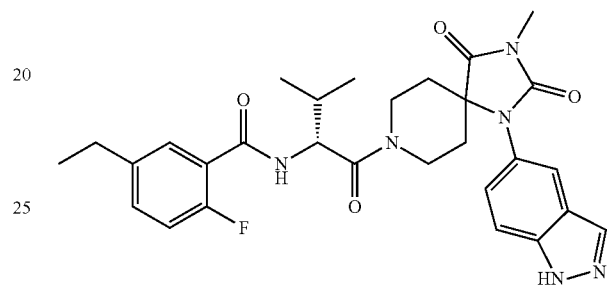

29.4 mg, yield: 46%, white solid.
LCMS (ESI): m/z=549.2 [M+H]+.

1H-NMR (400 MHz, CD3OD): δ=0.67-1.04 (m, 6H), 1.18-1.31 (m, 3H), 1.73-2.25 (m, 5H), 2.58-2.70 (m, 2H), 3.10 (s, 3H), 3.47-3.50 (m, 1H), 3.93-3.99 (m, 1H), 4.16-4.51 (m, 2H), 4.81-4.88 (m, 1H), 6.90-6.94 (m, 1H), 7.09-7.17 (m, 1H), 7.24-7.35 (m, 2H), 7.51-7.56 (m, 1H), 7.65-7.77 (m, 1H), 8.03-8.15 (m, 1H).

Example 56

(R)—N-(1-(1-(1H-Indazol-5-yl)-3-methyl-2,4-dioxo-1,3,8-triazaspiro[4.5]decan-8-yl)-3-methyl-1-oxobutan-2-yl)-2-fluoro-5-methylbenzamide

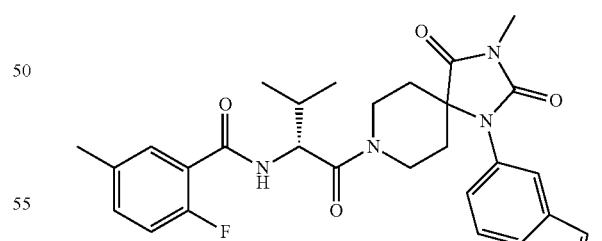

25.2 mg, yield: 39%, white solid.
LCMS (ESI): m/z=535.2 [M+H]+.

1H-NMR (400 MHz, CD3OD): δ=0.66-0.97 (m, 6H), 1.72-2.34 (m, 8H), 3.10 (s, 3H), 3.45-3.54 (m, 1H), 3.92-3.98 (m, 1H), 4.25-4.50 (m, 2H), 4.80-4.82 (m, 1H), 6.86-7.09 (m, 1H), 7.17-7.28 (m, 3H), 7.50-7.52 (m, 1H), 7.64-7.76 (m, 1H), 8.04-8.15 (m, 1H).

Example 57

(R)—N-(2-(1-(1H-Indazol-5-yl)-3-methyl-2,4-dioxo-1,3,8-triazaspiro[4.5]decan-8-yl)-1-cyclopentyl-2-oxoethyl)-2-fluoro-5-(trifluoromethyl)benzamide

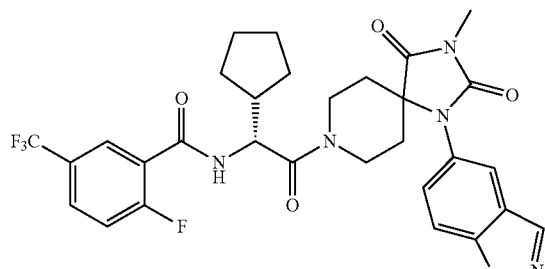

33.7 mg, yield: 41%, white solid.

LCMS (ESI): m/z=615.2 [M+H]⁺.

¹H-NMR (400 MHz, CDCl₃): δ=1.23-1.96 (m, 10H), 2.09-2.23 (m, 2H), 2.34-2.40 (m, 1H), 3.10 (s, 3H), 3.48-3.54 (m, 1H), 3.92-4.00 (m, 1H), 4.30-4.33 (m, 1H), 4.47-4.51 (m, 1H), 4.83-4.84 (m, 1H), 7.14-7.30 (m, 2H), 7.39-7.52 (m, 1H), 7.66-7.68 (m, 1H), 7.74-7.86 (m, 2H), 7.96-8.15 (m, 1H).

Example 58

(R)—N-(2-(1-(1H-Indazol-5-yl)-3-methyl-2,4-dioxo-1,3,8-triazaspiro[4.5]decan-8-yl)-1-cyclobutyl-2-oxoethyl)-2-fluoro-5-(trifluoromethyl)benzamide

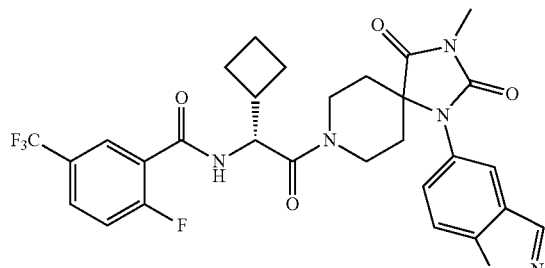

33.6 mg, yield: 41%, white solid.

LCMS (ESI): m/z=601.2 [M+H]⁺.

¹H-NMR (400 MHz, CDCl₃): δ=1.58-1.88 (m, 10H), 2.54-2.77 (m, 1H), 3.18 (s, 3H), 3.48-3.54 (m, 1H), 3.92-4.09 (m, 2H), 4.48-4.61 (m, 1H), 5.09-5.12 (m, 1H), 7.00-7.35 (m, 3H), 7.44-7.62 (m, 2H), 7.71-7.74 (m, 1H), 7.98-8.08 (m, 1H).

Example 59

(R)—N-(1-(1-(1H-Indazol-5-yl)-3-methyl-2,4-dioxo-1,3,8-triazaspiro[4.5]decan-8-yl)-3-methyl-1-oxobutan-2-yl)-3-(trifluoromethyl)benzamide (This Compound was Obtained as the Des-Chloro by-Product of Example 57)

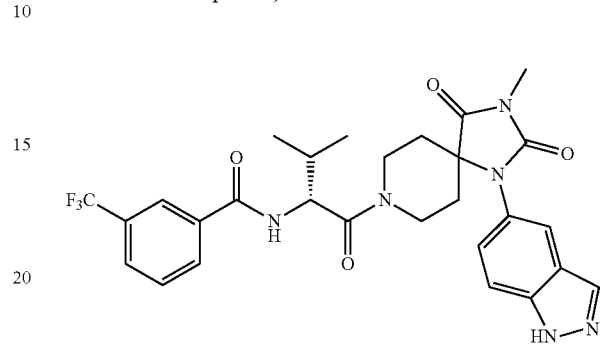

6.9 mg, yield: 11%, white solid.

LCMS (ESI): m/z=571.2 [M+H]⁺.

¹H-NMR (400 MHz, CD₃OD): δ=0.61-0.62 (m, 1H), 0.86-0.88 (m, 1H), 0.94-1.09 (m, 4H), 1.75-2.25 (m, 5H), 3.10 (s, 3H), 3.46-3.53 (m, 1H), 3.92-3.99 (m, 1H), 4.42-4.52 (m, 2H), 4.74-4.78 (m, 1H), 7.15-7.29 (m, 1H), 7.47-7.51 (m, 1H), 7.58-7.67 (m, 2H), 7.77-7.96 (m, 2H), 8.01-8.18 (m, 2H).

Example 60

(R)—N-(1-(1-(1H-Indazol-5-yl)-3-methyl-2,4-dioxo-1,3,8-triazaspiro[4.5]decan-8-yl)-3-methyl-1-oxobutan-2-yl)-3-chloro-5-(trifluoromethyl)benzamide

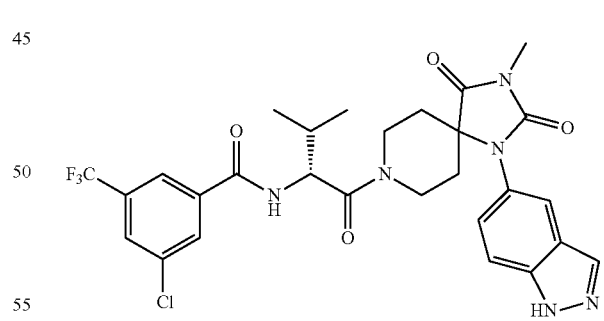

8.8 mg, yield: 14%, white solid.

LCMS (ESI): m/z=605.2 [M+H]⁺.

¹H-NMR (400 MHz, CD₃OD): δ=0.85-0.87 (m, 1H), 0.95-0.99 (m, 4H), 1.06-1.08 (m, 1H), 1.70-1.78 (m, 1H), 1.89-1.99 (m, 1H), 2.07-2.34 (m, 3H), 3.10 (s, 3H), 3.50-3.54 (m, 1H), 3.91-3.99 (m, 1H), 4.23-4.52 (m, 2H), 4.74-4.77 (m, 1H), 7.14-7.17 (m, 1H), 7.48-7.50 (m, 1H), 7.64-7.65 (m, 1H), 7.77-7.89 (m, 3H), 7.97-7.98 (m, 1H), 8.07-8.15 (m, 1H).

Example 61

(R)—N-(1-(1-(1H-Indazol-5-yl)-3-methyl-2,4-dioxo-1,3,8-triazaspiro[4.5]decan-8-yl)-3-methyl-1-oxobutan-2-yl)-2-methyl-5-(trifluoromethyl)benzamide

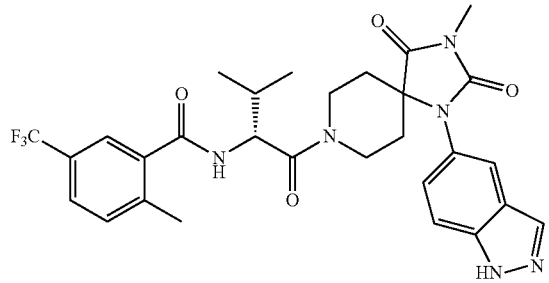 [SMILES: Cc1ccc(C(F)(F)F)cc1C(=O)N[C@@H](C(=O)N1CCC2(CC1)C(=O)N(C)C(=O)N2c1ccc2[nH]ncc2c1)C(C)C]

22.0 mg, yield: 54%, white solid.

LCMS (ESI): m/z=585.2 [M+H]$^+$.

$^1$H-NMR (400 MHz, CD$_3$OD): δ=0.58-1.10 (m, 6H), 1.70-1.89 (m, 3H), 2.10-2.12 (m, 4H), 2.34-2.43 (m, 1H), 3.12 (s, 3H), 3.51-3.54 (m, 1H), 3.98-4.00 (m, 1H), 4.17-4.62 (m, 2H), 4.78-4.82 (m, 1H), 7.17-7.25 (m, 2H), 7.40-7.44 (m, 1H), 7.50-7.84 (m, 3H), 8.00-8.10 (m, 1H).

Example 62

(R)—N-(1-(1-(1H-Indazol-5-yl)-3-methyl-2,4-dioxo-1,3,8-triazaspiro[4.5]decan-8-yl)-3-methyl-1-oxobutan-2-yl)-2-fluoro-5-(trifluoromethoxy)benzamide

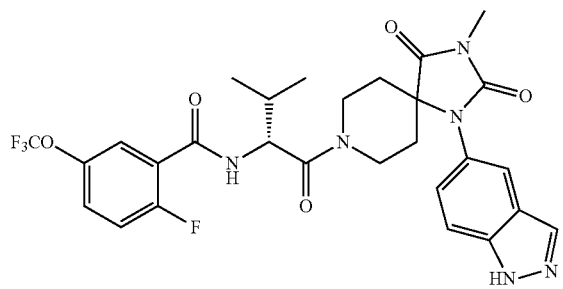 [SMILES: CC(C)[C@@H](NC(=O)c1cc(OC(F)(F)F)ccc1F)C(=O)N1CCC2(CC1)C(=O)N(C)C(=O)N2c1ccc2[nH]ncc2c1]

18.4 mg, yield: 28%, white solid.

LCMS (ESI): m/z=605.2 [M+H]$^+$.

$^1$H-NMR (400 MHz, CD$_3$OD): δ=0.67-0.97 (m, 6H), 1.71-2.12 (m, 5H), 3.10 (s, 3H), 3.47-3.50 (m, 1H), 3.91-3.96 (m, 1H), 4.15-4.23 (m, 1H), 4.38-4.48 (m, 1H), 4.81-4.83 (m, 1H), 7.07-7.41 (m, 6H), 8.03-8.15 (m, 1H).

Example 63

(R)—N-(1-(1-(1H-Indazol-5-yl)-3-methyl-2,4-dioxo-1,3,8-triazaspiro[4.5]decan-8-yl)-3-methyl-1-oxobutan-2-yl)-2-fluoro-5-methoxybenzamide

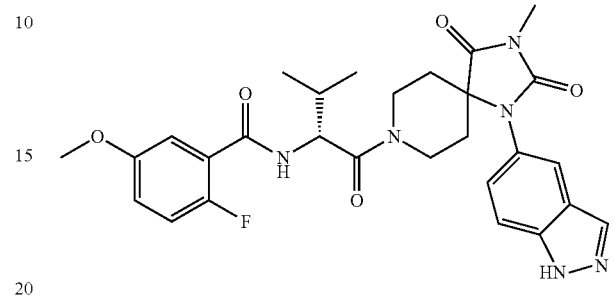

22.2 mg, yield: 34%, white solid.

LCMS (ESI): m/z=551.2 [M+H]$^+$.

$^1$H-NMR (400 MHz, CD$_3$OD): δ=0.67-0.68 (m, 1H), 0.80-0.82 (m, 1H), 0.95-0.97 (m, 4H), 1.72-1.79 (m, 1H), 1.88-1.92 (m, 1H), 2.07-2.23 (m, 3H), 3.10 (s, 3H), 3.46-3.52 (m, 1H), 3.76-3.80 (m, 3H), 3.92-3.98 (m, 1H), 4.15-4.27 (m, 1H), 4.37-4.51 (m, 1H), 4.81-4.83 (m, 1H), 6.90-7.28 (m, 4H), 7.50-7.66 (m, 1H), 7.64-7.76 (m, 1H), 8.03-8.15 (m, 1H).

Example 64

(R)—N-(1-(1-(1H-Indazol-5-yl)-3-methyl-2,4-dioxo-1,3,8-triazaspiro[4.5]decan-8-yl)-3-methyl-1-oxobutan-2-yl)-5-(difluoromethoxy)-2-fluorobenzamide

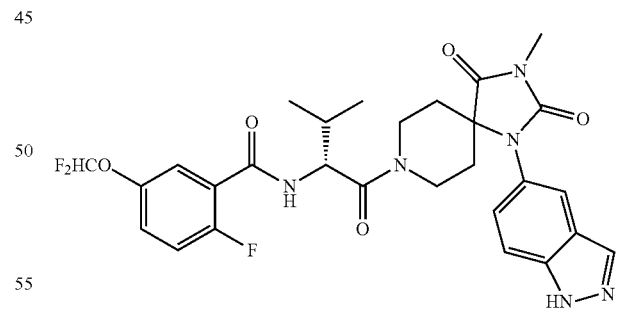

3.5 mg, 6.7% yield, white solid.

LCMS (ESI): m/z=507.2 [M+H]$^+$.

$^1$H-NMR (400 MHz, CD$_3$OD): δ=0.67-0.98 (m, 6H), 1.73-1.79 (m, 1H), 1.88-1.91 (m, 1H), 1.95-2.09 (m, 3H), 3.33 (s, 1H), 3.11 (s, 2H), 3.48-3.54 (m, 1H), 3.93-3.96 (m, 1H), 4.16-4.28 (m, 1H), 4.37-4.52 (m, 1H), 4.79-4.88 (m, 1H), 6.63-6.81 (m, 1H), 6.99-7.06 (m, 1H), 7.21-7.32 (m, 2H), 7.48-7.55 (m, 1H), 7.68-7.78 (m, 1H), 8.03-8.15 (m, 1H), 8.26-8.31 (m, 1H).

Example 65

(R)—N-(1-(1-(1H-Indazol-5-yl)-3-methyl-2,4-dioxo-1,3,8-triazaspiro[4.5]decan-8-yl)-3-methyl-1-oxobutan-2-yl)-2,5-dichlorobenzamide

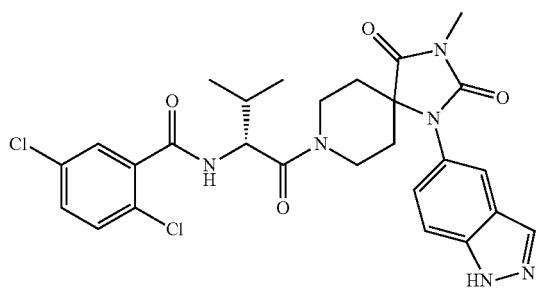 [SMILES: CC(C)[C@@H](NC(=O)c1cc(Cl)ccc1Cl)C(=O)N1CCC2(CC1)C(=O)N(C)C(=O)N2c1ccc2[nH]ncc2c1]

41.2 mg, 29% yield, white solid.

LCMS (ESI): m/z=571.1, 573.1 [M+H]$^+$.

$^1$H-NMR (400 MHz, CD$_3$OD): δ=0.63-1.00 (m, 6H), 1.68-2.23 (m, 5H), 3.10 (s, 3H), 3.32-3.51 (m, 1H), 3.92-3.98 (m, 1H), 4.17-4.50 (m, 2H), 4.72-4.77 (m, 1H), 7.14-7.21 (m, 2H), 7.26-7.35 (m, 1H), 7.43-7.46 (m, 1H), 7.53-7.76 (m, 2H), 8.03-8.15 (m, 1H).

Example 66

(R)—N-(1-(1-(1H-Indazol-5-yl)-3-methyl-2,4-dioxo-1,3,8-triazaspiro[4.5]decan-8-yl)-3-methyl-1-oxobutan-2-yl)-2,5-difluorobenzamide

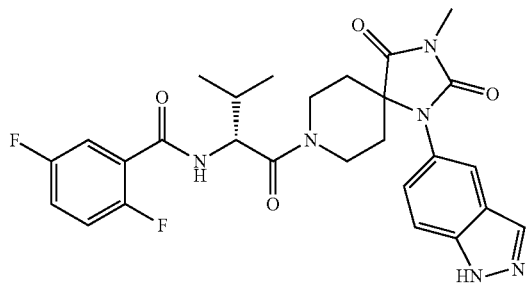 [SMILES: CC(C)[C@@H](NC(=O)c1cc(F)ccc1F)C(=O)N1CCC2(CC1)C(=O)N(C)C(=O)N2c1ccc2[nH]ncc2c1]

20.9 mg, 31.3% yield, white solid.

LCMS (ESI): m/z=539.1 [M+H]$^+$.

$^1$H-NMR (400 MHz, CD$_3$OD): δ=0.67-0.98 (m, 6H), 1.72-1.80 (m, 1H), 1.88-1.95 (m, 1H), 2.08-2.24 (m, 3H), 3.10 (s, 1H), 3.46-3.53 (m, 1H), 4.15-4.29 (m, 1H), 4.48-4.52 (m, 1H), 4.80-4.81 (m, 1H), 4.90-4.91 (m, 1H), 7.00-7.07 (m, 4H), 7.65-7.74 (m, 1H), 8.03-8.15 (m, 2H).

Example 67

(R)—N-(1-(1-(1H-Indazol-5-yl)-3-methyl-2,4-dioxo-1,3,8-triazaspiro[4.5]decan-8-yl)-3-methyl-1-oxobutan-2-yl)-1-admantanecarboxly amide

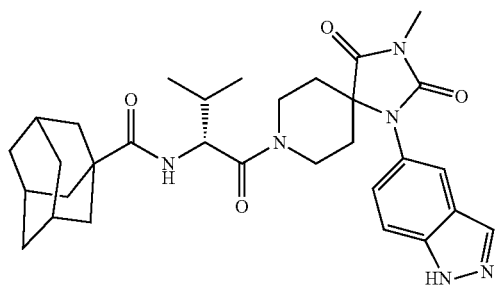 [SMILES: CC(C)[C@@H](NC(=O)C12CC3CC(CC(C3)C1)C2)C(=O)N1CCC2(CC1)C(=O)N(C)C(=O)N2c1ccc2[nH]ncc2c1]

2.5 mg, 10.3% yield, white solid.

LCMS (ESI): m/z=561.3 [M+H]$^+$.

$^1$H-NMR (400 MHz, CD$_3$OD): δ=0.58-0.88 (m, 6H), 1.45-1.92 (m, 20H), 3.32 (s, 3H), 3.43-3.53 (m, 1H), 3.85-3.93 (m, 1H), 4.05-4.25 (m, 1H), 4.38-4.55 (m, 1H), 4.84-4.88 (m, 1H), 7.00-7.12 (m, 1H), 7.22-7.29 (m, 1H), 7.62-7.67 (m, 1H), 8.13-8.14 (m, 1H).

Example 68

(R)—N-(1-(1-(1H-Indazol-5-yl)-3-methyl-2,4-dioxo-1,3,8-triazaspiro[4.5]decan-8-yl)-3-methyl-1-oxobutan-2-yl)-2-chloro-5-(trifluoromethyl)benzamide

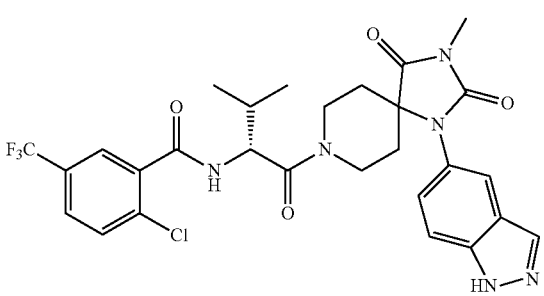 [SMILES: CC(C)[C@@H](NC(=O)c1cc(C(F)(F)F)ccc1Cl)C(=O)N1CCC2(CC1)C(=O)N(C)C(=O)N2c1ccc2[nH]ncc2c1]

50 mg, 67% yield, white solid.

LCMS (ESI): m/z=605.1, 607.1 [M+H]$^+$.

$^1$H-NMR (400 MHz, CD$_3$OD): δ=0.99-0.66 (m, 6H), 1.71-1.80 (m, 1H), 2.00-2.28 (m, 4H), 3.12 (s, 3H), 3.48-3.58 (m, 1H), 3.94-4.05 (m, 1H), 4.34-4.54 (m, 2H), 4.74-4.82 (m, 1H), 7.18-7.34 (m, 1H), 7.40-7.45 (m, 1H), 7.68-7.78 (m, 3H), 8.00-8.16 (m, 1H).

Example 69

(S)—N-(1-(1-(1H-Indazol-5-yl)-3-methyl-2,4-dioxo-1,3,8-triazaspiro[4.5]decan-8-yl)-3-methyl-1-oxobutan-2-yl)-2-fluoro-5-(trifluoromethyl)benzamide

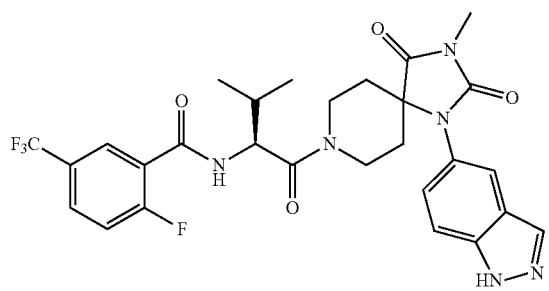 [SMILES: CC(C)[C@H](NC(=O)c1cc(C(F)(F)F)ccc1F)C(=O)N1CCC2(CC1)C(=O)N(C)C(=O)N2c1ccc2[nH]ncc2c1]

81.1 mg, 57% yield, white solid.

LCMS (ESI): m/z=589.2 [M+H]$^+$.

$^1$H-NMR (400 MHz, CD$_3$OD): δ=0.67-0.99 (m, 6H), 1.74-2.16 (m, 5H), 3.11 (s, 3H), 3.48-3.55 (m, 1H), 3.94-4.52 (m, 3H), 481-4.89 (m, 1H), 7.16-7.21 (m, 1H), 7.28-7.41 (m, 1H), 7.52-7.54 (m, 1H), 7.66-7.68 (m, 1H), 7.76-7.87 (m, 2H), 7.99-8.02 (m, 1H).

Example 70

N-(2-(1-(1H-Indazol-5-yl)-3-methyl-2,4-dioxo-1,3,8-triazaspiro[4.5]decan-8-yl)-2-oxoethyl)-2-fluoro-5-(trifluoromethyl)benzamide

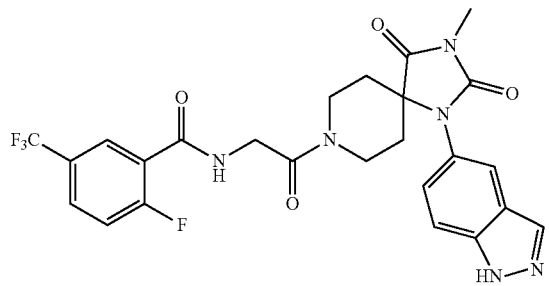 [SMILES: CN1C(=O)N(c2ccc3[nH]ncc3c2)C2(CCN(C(=O)CNC(=O)c3cc(C(F)(F)F)ccc3F)CC2)C1=O]

14.9 mg, 15% yield, white solid.

LCMS (ESI): m/z=547.1 [M+H]$^+$.

$^1$H-NMR (400 MHz, CD$_3$OD): δ=1.80-2.13 (m, 5H), 3.10 (s, 3H), 3.42-3.61 (m, 1H), 3.83-3.91 (m, 2H), 4.21-4.23 (m, 2H), 4.39-4.49 (m, 1H), 7.20-7.23 (m, 1H), 7.34-7.40 (m, 1H), 7.60-7.63 (m, 1H), 7.71-7.72 (m, 1H), 7.82-7.83 (m, 1H), 8.09-8.11 (m, 2H).

Example 71

N-(1-(1-(1H-Indazol-5-yl)-3-methyl-2,4-dioxo-1,3,8-triazaspiro[4.5]decane-8-carbonyl)cyclopropyl)-2-fluoro-5-(trifluoromethyl)benzamide

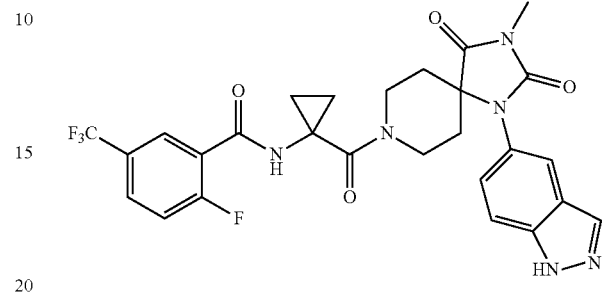

36.8 mg, 11% yield, white solid.

LCMS (ESI): m/z=573.2 [M+H]$^+$.

$^1$H-NMR (400 MHz, CD$_3$OD): δ=1.26-1.36 (m, 4H), 1.76-1.84 (m, 2H), 2.10-2.13 (m, 2H), 3.10 (s, 3H), 3.59-3.80 (m, 2H), 4.31-4.35 (m, 2H), 7.15-7.22 (m, 2H), 7.48-7.50 (m, 1H), 7.64-7.65 (m, 1H), 7.76-7.83 (m, 2H), 8.01 (s, 1H).

Example 72

(R)—N-(1-(1-(1H-Indazol-5-yl)-3-methyl-2,4-dioxo-1,3,8-triazaspiro[4.5]decan-8-yl)-1-oxopropan-2-yl)-2-fluoro-5-(trifluoromethyl)benzamide

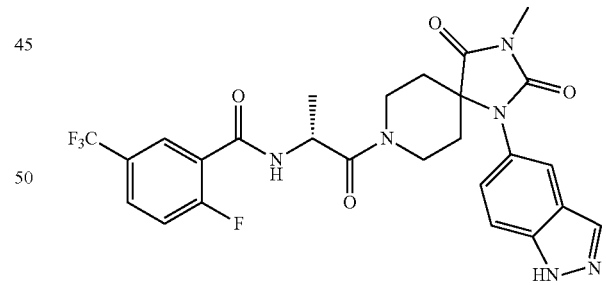

22.2 mg, 14% yield, white solid.

LCMS (ESI): m/z=561.1 [M+H]$^+$.

$^1$H-NMR (400 MHz, CD$_3$OD): δ=1.23-1.37 (m, 3H), 1.78-2.13 (m, 4H), 3.11 (s, 3H), 3.50-3.53 (m, 1H), 3.96-4.08 (m, 2H), 4.46-4.49 (m, 1H), 5.02-5.04 (m, 1H), 7.22-7.29 (m, 1H), 7.41-7.59 (m, 1H), 7.71-7.78. (m, 1H), 7.86-7.91 (m, 2H), 8.07-8.15 (m, 2H).

Example 73

N-(3-(1-(1H-Indazol-5-yl)-3-methyl-2,4-dioxo-1,3,8-triazaspiro[4.5]decane-8-carbonyl)oxetan-3-yl)-2-fluoro-5-(trifluoromethyl)benzamide

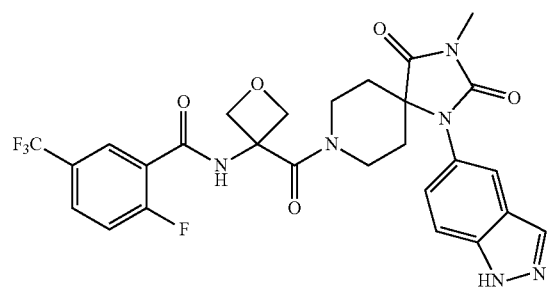 [SMILES: CN1C(=O)N(c2ccc3[nH]ncc3c2)C2(CCN(C(=O)C3(NC(=O)c4cc(C(F)(F)F)ccc4F)COC3)CC2)C1=O]

4.8 mg, 6% yield, yellow solid.

LRMS m/z=588 [M+H]$^+$.

$^1$H-NMR (400 MHz, DMSO-d$_6$): δ=8.61 (s, 1H), 8.51 (d, J=8.7 Hz, 1H), 8.27 (d, J=3.7 Hz, 1H), 8.15-8.09 (m, 1H), 7.94 (d, J=1.4 Hz, 1H), 7.71 (t, J=9.0 Hz, 1H), 7.65 (dd, J=8.7, 1.9 Hz, 1H), 4.76 (dd, J=16.3, 6.0 Hz, 2H), 4.29 (dd, J=28.0, 6.2 Hz, 2H), 3.64-3.44 (m, 2H), 3.28 (m, 2H), 3.01 (s, 3H), 2.21-2.08 (m, 2H), 1.79-1.58 (m, 2H).

Example 74

N-(1-(1-(1H-Indazol-5-yl)-3-methyl-2,4-dioxo-1,3,8-triazaspiro[4.5]decan-8-yl)-2-methyl-1-oxopropan-2-yl)-2-fluoro-5-(trifluoromethyl)benzamide

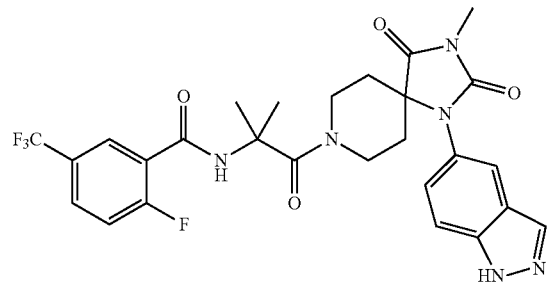 [SMILES: CN1C(=O)N(c2ccc3[nH]ncc3c2)C2(CCN(C(=O)C(C)(C)NC(=O)c3cc(C(F)(F)F)ccc3F)CC2)C1=O]

23.8 mg, 14% yield, white solid.

LCMS (ESI): m/z=597.1 [M+Na]$^+$.

$^1$H-NMR (400 MHz, CD$_3$OD): δ=1.47 (s, 6H), 1.68-1.84 (m, 2H), 2.01-2.05 (m, 2H), 3.06 (s, 3H), 3.55-3.87 (br, 2H), 4.39-4.50 (m, 2H), 7.03-7.06 (m, 1H), 7.29-7.42 (m, 2H), 7.53-7.54 (m, 1H), 7.67-7.69 (m, 1H), 7.81-7.84 (m, 1H), 7.93-7.94 (m, 1H).

Example 75

(R)—N-(1-(1-(Cyclopropylmethyl)-3-methyl-2,4-dioxo-1,3,8-triazaspiro[4.5]decan-8-yl)-3-methyl-1-oxobutan-2-yl)-2-fluoro-5-(trifluoromethyl)benzamide

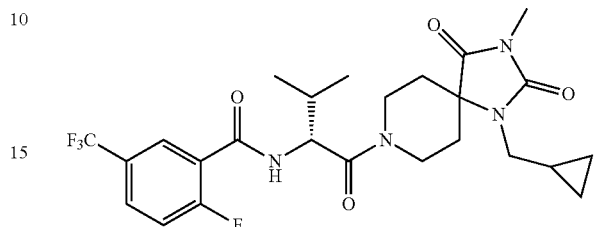

Representative Scheme:

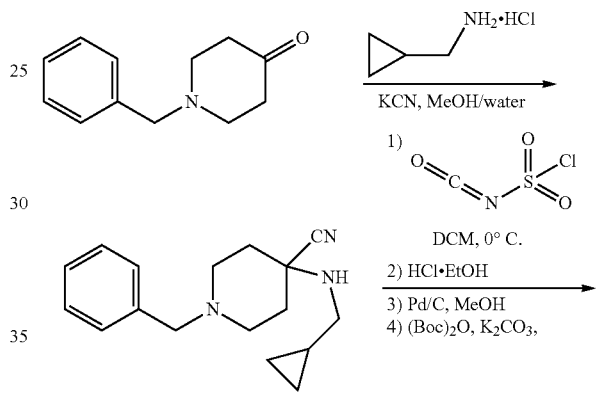

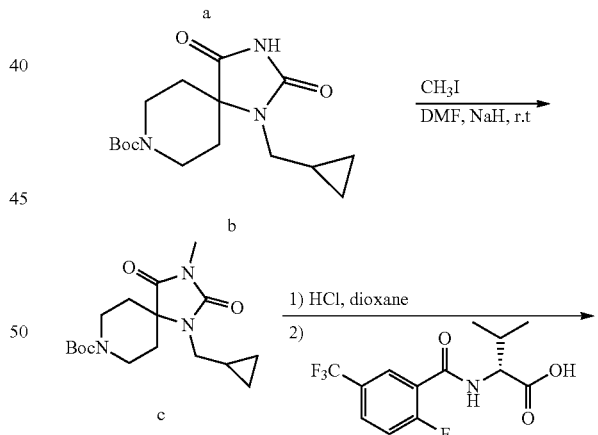

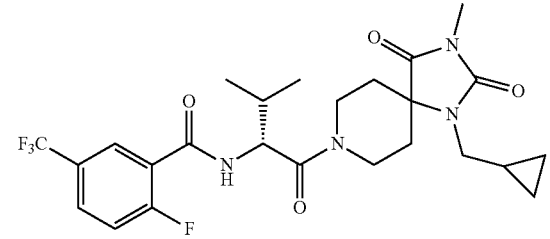

Representative General Procedure

1-Benzyl-4-(cyclopropylmethylamino)piperidine-4-carbonitrile

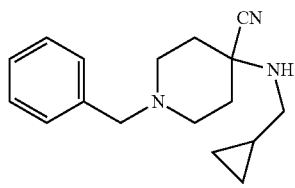 [SMILES: N#CC1(NCC2CC2)CCN(Cc2ccccc2)CC1]

To a mixture of cyclopropylmethanamine hydrochloride (500 mg, 4.7 mmol) in methanol:water (9:1, 50 mL) was added 1-benzylpiperidin-4-one (700 mg, 3.7 mmol) and potassium cyanide (200 mg, 3.0 mmol). The resulting mixture was stirred overnight. The reaction was quenched with aqueous potassium carbonate (10%, 30 mL). The resulting mixture was extracted with ethyl acetate (3×100 mL). The combined organic layers were dried over with anhydrous sodium sulfate. The solvent was removed under reduced pressure and the residue was purified by silica gel column chromatography eluting with dichloromethane:methanol=10:1 to afford 1-benzyl-4-(cyclopropylmethylamino)piperidine-4-carbonitrile as a yellow oil (450 mg, crude), which was used directly without any further purification.

LCMS (ESI): m/z=377.2 [M+H]+.

tert-Butyl-1-(cyclopropylmethyl)-2,4-dioxo-1,3,8-triazaspiro[4.5]decane-8-carboxylate

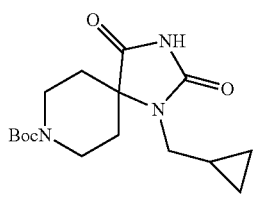 [SMILES: CC(C)(C)OC(=O)N1CCC2(CC1)C(=O)NC(=O)N2CC1CC1]

To a solution of 1-benzyl-4-(cyclopropylmethylamino)piperidine-4-carbonitrile (450 mg, crude) in dichloromethane was added chlorosulfonyl isocyanate (300 mg, 2.11 mmol) at 0° C. After stirring for 30 minutes at 0° C., the reaction was quenched with a 5% aqueous hydrochloric acid solution (5 mL). The solvent was removed under reduced pressure and ethanol (10 mL) was added. The mixture was stirred for 30 minutes at 80° C. The solvent was removed under reduced pressure. The residue was dissolved in methanol. After stirring for 5 minutes, 5% palladium on carbon (150 mg, 50% wet with water) was added. The resulting mixture was stirred under a hydrogen atmosphere for 1 hour. The catalyst was removed by filtration and the filtrate was concentrated under reduced pressure. The residue was added to tetrahydrofuran (20 mL) and the pH was adjusted to 8 by addition of aqueous potassium carbonate (15%). Then di-tert-butyl-dicarbonate (300 mg, 1.37 mmol) in tetrahydrofuran (20 mL) was added. After stirring overnight, the solvent was removed under reduced pressure and the residue was purified by silica gel column chromatography eluting with dichloromethane:methanol=10:1 to afford tert-butyl-1-(cyclopropylmethyl)-2,4-dioxo-1,3,8-triazaspiro[4.5]decane-8-carboxylate as a yellow oil (200 mg, 13% over two steps).

LCMS (ESI): m/z=324.2 [M+H]+.

tert-Butyl-1-(cyclopropylmethyl)-3-methyl-2,4-dioxo-1,3,8-triazaspiro[4.5]decane-8-carboxylate

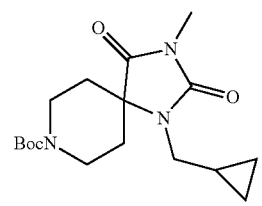 [SMILES: CN1C(=O)N(CC2CC2)C2(CCN(C(=O)OC(C)(C)C)CC2)C1=O]

To a solution of tert-butyl-1-(cyclopropylmethyl)-2,4-dioxo-1,3,8-triazaspiro[4.5]decane-8-carboxylate (200 mg, 0.61 mmol) in N,N-dimethylformamide (2 mL) was added sodium hydride (50 mg, 60% in oil, 1.30 mmol) at 0° C. After stirring for 15 minutes, iodomethane (100 mg, 0.74 mmol) was added. The resulting mixture was stirred for 15 minutes at room temperature and the reaction was quenched with ice-water (10 mL). The mixture was extracted with ethyl acetate (3×50 mL). The combined organic layers were dried over anhydrous sodium sulfate and concentrated under reduced pressure. The residue was purified by prep-HPLC (acetonitrile and water, acetonitrile from 5% to 50%) to afford tert-butyl-1-(cyclopropylmethyl)-3-methyl-2,4-dioxo-1,3,8-triazaspiro[4.5]decane-8-carboxylate as a white solid (110 mg, 52%).

LCMS (ESI): m/z=338.2 [M+H]+.
$^1$H-NMR (300 MHz, CDCl$_3$): δ=0.29-0.35 (m, 2H), 0.46-0.57 (m, 2H), 1.45 (s, 9H), 1.56-1.69 (m, 3H), 1.83-1.94 (m, 2H), 2.98 (s, 3H), 3.08 (d, J=6.9 Hz, 2H), 3.37-3.56 (m, 2H), 3.96-4.12 (m, 2H).

(R)—N-(1-(1-(Cyclopropylmethyl)-3-methyl-2,4-dioxo-1,3,8-triazaspiro[4.5]decan-8-yl)-3-methyl-1-oxobutan-2-yl)-2-fluoro-5-(trifluoromethyl)benzamide

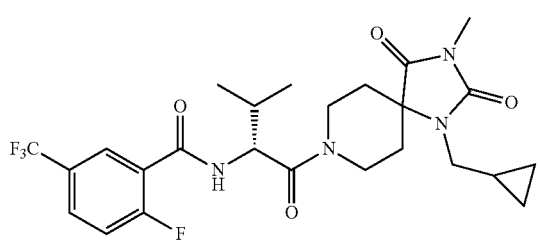 [SMILES: CC(C)[C@@H](NC(=O)c1cc(C(F)(F)F)ccc1F)C(=O)N1CCC2(CC1)C(=O)N(C)C(=O)N2CC1CC1]

A solution of tert-butyl-1-(cyclopropylmethyl)-3-methyl-2,4-dioxo-1,3,8-triazaspiro[4.5]decane-8-carboxylate (110 mg, 0.35 mmol) in hydrochloric acid in dioxane (6.0 M, 10 mL) was stirred for 30 minutes. The solvent was removed under reduced pressure. To the residue was added dichloromethane (5 mL), (R)-2-(2-fluoro-5-(trifluoromethyl)benzamido)-3-methylbutanoic acid (prepared as described in Example 28-f) (100 mg, 0.34 mmol), 1-[bis(dimethylamino)methylene]-1H-1,2,3-triazolo[4,5-b]pyridinium-3-oxide hexafluorophosphate (HATU) (150 mg, 0.39 mmol) and N,N-diisopropylethylamine (150 mg, 1.16 mmol). The resulting mixture was stirred for 2 hours at room temperature before the reaction was quenched with ice-water (5 mL). The mixture was extracted with ethyl acetate (3×10 mL) and the combined organic layers were dried over anhydrous sodium sulfate and concentrated under reduced pressure. The residue was purified by prep-TLC with dichloromethane:methanol=15:1 to afford (R)—N-(1-(1-(cyclopropylmethyl)-3-methyl-2,4-dioxo-1,3,8-triazaspiro[4.5]decan-8-yl)-3-methyl-1-oxobutan-2-yl)-2-fluoro-5-(trifluoromethyl)benzamide as a white solid (44.6 mg, 24%).

LCMS (ESI): m/z=527.2 [M+H]$^+$.

$^1$H-NMR (400 MHz, CD$_3$OD): δ=0.29-0.33 (m, 2H), 0.46-0.54 (m, 3H), 1.04-1.11 (m, 6H), 1.75-1.84 (m, 2H), 1.95-2.05 (m, 1H), 2.15-2.19 (m, 1H), 2.35-2.41 (m, 1H), 3.01 (s, 3H), 3.17-3.20 (m, 2H), 3.42-3.48 (m, 1H), 3.92-3.95 (m, 1H), 4.11-4.33 (m, 1H), 4.57-4.60 (m, 1H), 4.90-4.95 (m, 1H), 7.41-7.48 (m, 1H), 7.91 (s, 1H), 8.04-8.06 (m, 1H), 8.56 (s, 1H).

The following 5 compounds were synthesized following the general procedure described above:

Example 76

(R)—N-(1-(1-Cyclopropyl-3-methyl-2,4-dioxo-1,3,8-triazaspiro[4.5]decan-8-yl)-3-methyl-1-oxobutan-2-yl)-2-fluoro-5-(trifluoromethyl)benzamide

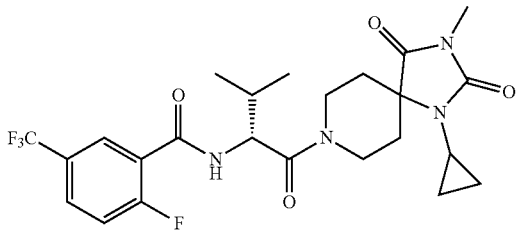 [SMILES: CC(C)[C@@H](NC(=O)c1cc(C(F)(F)F)ccc1F)C(=O)N1CCC2(CC1)C(=O)N(C)C(=O)N2C1CC1]

137.2 mg, yield: 12%, white solid.
LCMS (ESI): m/z=513.1 [M+H]$^+$.

$^1$H-NMR (400 MHz, CD$_3$OD): δ=0.78-0.91 (m, 4H), 1.03-1.11 (m, 6H), 1.80-1.97 (m, 2H), 2.14-2.48 (m, 4H), 2.97 (s, 3H), 3.46-3.52 (m, 1H), 3.93-3.99 (m, 1H), 4.32-4.34 (m, 1H), 4.57-4.61 (m, 1H), 4.95-5.01 (m, 1H), 7.45-7.50 (m, 1H), 7.89-7.90 (m, 1H), 8.03-8.05 (m, 1H), 8.60 (m, 1H).

Example 77

(R)-2-Fluoro-N-(3-methyl-1-(3-methyl-2,4-dioxo-1-(tetrahydro-2H-pyran-4-yl)-1,3,8-triazaspiro[4.5]decan-8-yl)-1-oxobutan-2-yl)-5-(trifluoromethyl)benzamide

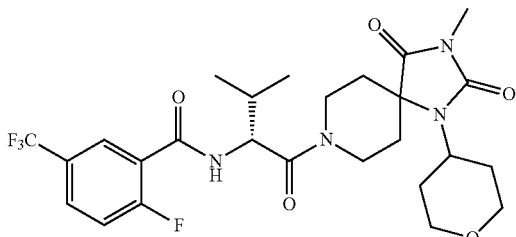

7.8 mg, yield: 4%, white solid.
LCMS (ESI): m/z=557.2 [M+H]$^+$.

$^1$H-NMR (400 MHz, CD$_3$OD): δ=1.05-1.12 (m, 6H), 1.47-1.57 (m, 2H), 1.75-2.02 (m, 3H), 2.12-2.28 (m, 1H), 2.37-2.68 (m, 3H), 2.96 (s, 3H), 3.50-3.53 (m, 4H), 3.88-4.06 (m, 3H), 4.28-4.36 (m, 1H), 4.54-4.66 (m, 1H), 4.87-5.00 (m, 1H), 7.47-7.60 (m, 1H), 7.90-7.92 (m, 1H), 7.95-7.89 (m, 1H).

Example 78

2-Fluoro-N—((R)-3-methyl-1-(3-methyl-2,4-dioxo-1-((S)-1-phenylethyl)-1,3,8-triazaspiro[4.5]decan-8-yl)-1-oxobutan-2-yl)-5-(trifluoromethyl)benzamide

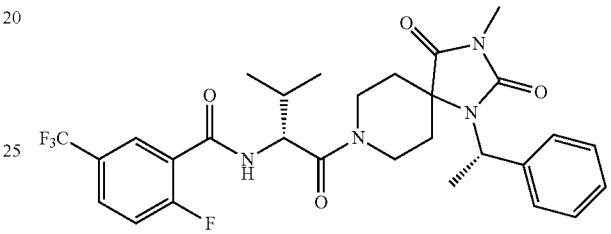

45.0 mg, yield: 36%, white solid.
LCMS (ESI): m/z=577.2 [M+H]$^+$.

$^1$H-NMR (400 MHz, CD$_3$OD): δ=1.02-1.15 (m, 6H), 1.77-2.23 (m, 8H), 3.00 (s, 3H), 3.41-3.47 (m, 1H), 3.91-3.97 (m, 1H), 4.29-4.32 (m, 1H), 4.49-4.68 (m, 2H), 4.87-4.94 (m, 1H), 7.21-7.50 (m, 5H), 7.88-8.08 (m, 2H), 8.47-8.59 (m, 1H).

Example 79

(R)-2-Fluoro-N-(3-methyl-1-(3-methyl-2,4-dioxo-1-((tetrahydro-2H-pyran-4-yl)methyl)-1,3,8-triazaspiro[4.5]decan-8-yl)-1-oxobutan-2-yl)-5-(trifluoromethyl)benzamide

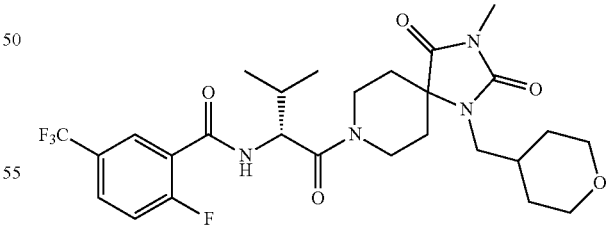

71.7 mg, yield: 42%, white solid.
LCMS (ESI): m/z=571.2 [M+H]$^+$.

$^1$H-NMR (400 MHz, CD$_3$OD): δ=1.04-1.11 (m, 6H), 1.12-1.14 (m, 1H), 1.27-1.30 (m, 2H), 1.61-1.67 (m, 2H), 1.17-2.08 (m, 5H), 2.37-2.44 (m, 1H), 2.99 (s, 3H), 3.12-3.17 (m, 2H), 3.30-3.46 (m, 2H), 3.90-3.97 (m, 3H), 4.30-4.33 (m, 1H), 4.58-4.61 (m, 1H), 4.96-4.98 (m, 2H), 7.45-7.50 (m, 1H), 7.09-7.92 (m, 1H), 8.06-8.07 (m, 1H).

Example 80

2-Fluoro-N—((R)-3-methyl-1-(3-methyl-2,4-dioxo-1-((R)-1-phenylethyl)-1,3,8-triazaspiro[4.5]decan-8-yl)-1-oxobutan-2-yl)-5-(trifluoromethyl)benzamide

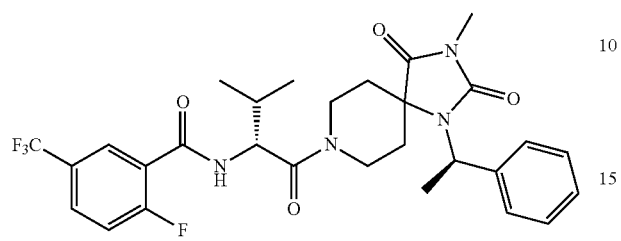

16.0 mg, yield: 14%, white solid.
LCMS (ESI): m/z=577.2 [M+H]$^+$.
$^1$H-NMR (400 MHz, CD$_3$OD): δ=0.95-1.14 (m, 6H), 1.69 (m, 1H), 1.87 (m, 5H), 2.17 (m, 1H), 2.25-2.43 (m, 1H), 3.04 (s, 3H), 3.37-3.61 (m, 1H), 3.90-4.22 (m, 2H), 4.43 (m, 1H), 4.62 (m, 1H), 5.08 (m, 1H), 7.2-7.61 (m, 7H), 7.72-7.84 (m, 1H), 8.29-8.43 (m, 1H).

Example 81

(R)—N-(1-(1-(4-(Azetidin-3-ylmethoxy)phenyl)-3-methyl-2,4-dioxo-1,3,8-triazaspiro[4.5]decan-8-yl)-3-methyl-1-oxobutan-2-yl)-2-fluoro-5-(trifluoromethyl)benzamide trifluoroacetic Acid Salt

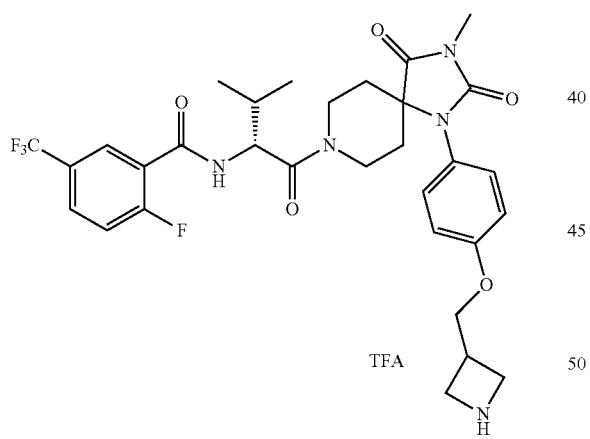

Representative Scheme:

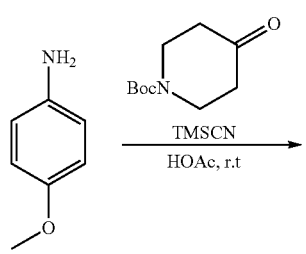

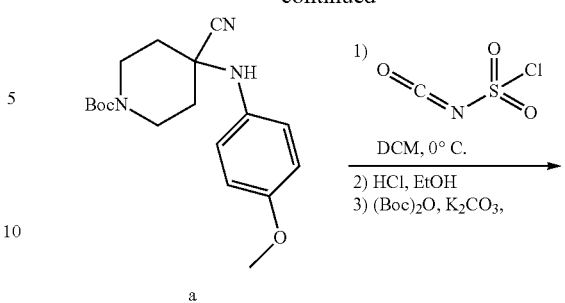

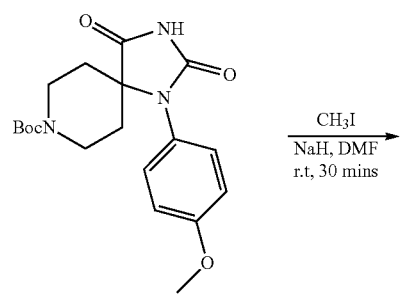

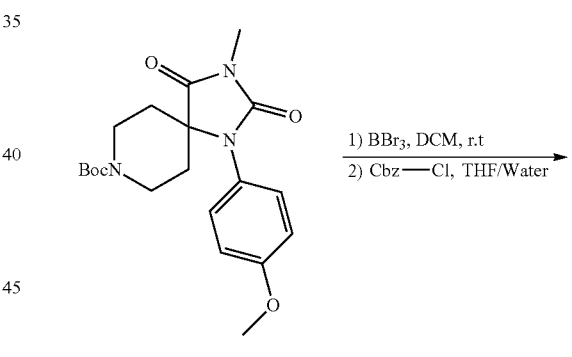

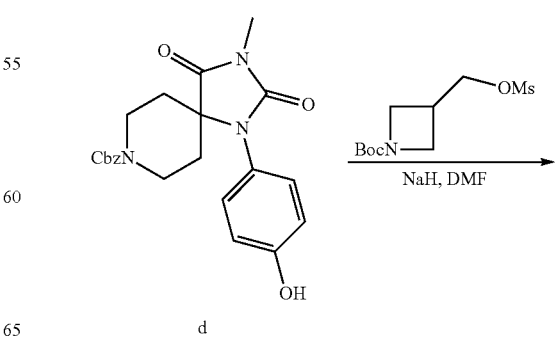

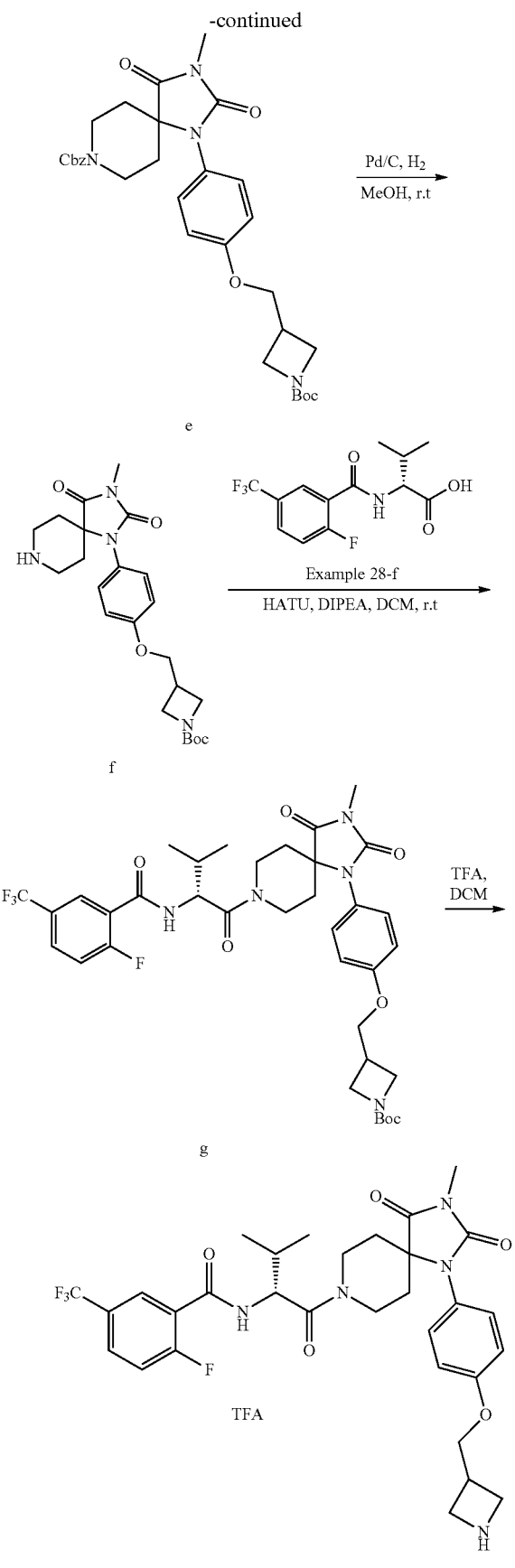

e f g

Representative General Procedure tert-Butyl-4-cyano-4-(4-methoxyphenylamino)piperidine-1-carboxylate

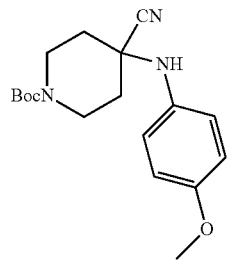

To a solution of 4-methoxyaniline (2 g, 16 mmol) in acetic acid (20 mL) was added tert-butyl-4-oxopiperidine-1-carboxylate (3.5 g, 17.5 mmol). The resulting mixture was cooled to 0° C. and trimethylsilyl cyanide (1.9 g, 19 mmol) was added. The solution was stirred overnight at room temperature. Saturated aqueous ammonium chloride solution was added (50 mL). The mixture was extracted with ethyl acetate (3×50 mL) and the combined organic layers were dried over anhydrous sodium sulfate and concentrated under reduced pressure. The residue was purified by silica gel column chromatography eluting with dichloromethane: petroleum ether=1:1 to afford tert-butyl-4-cyano-4-(4-methoxyphenylamino)piperidine-1-carboxylate as a white solid (5.0 g, 86%).

LCMS (ESI): m/z=332.2 [M+H]$^+$.

$^1$H-NMR (300 MHz, DMSO-$d_6$): δ=1.40 (s, 9H), 1.65-1.89 (m, 2H), 2.06-2.19 (m, 2H), 3.01-3.21 (m, 2H) 3.68 (s, 3H), 3.72-3.88 (m, 2H), 5.50 (s, 1H), 6.80 (d, J=9 Hz, 2H), 6.90 (d, J=9 Hz, 2H).

tert-Butyl-1-(4-methoxyphenyl)-2,4-dioxo-1,3,8-triazaspiro[4.5]decane-8-carboxylate

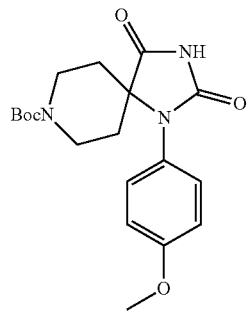 [SMILES: COc1ccc(N2C(=O)NC(=O)C23CCN(C(=O)OC(C)(C)C)CC3)cc1]

To a solution of tert-butyl-4-cyano-4-(4-methoxyphenyl amino)piperidine-1-carboxylate (2.0 g, 6 mmol) in dichloromethane was added chlorosulfonyl isocyanate (2.3 g, 16 mmol) at 0° C. After stirring for 30 minutes at 0° C., the reaction was quenched with a 5% aqueous hydrochloric acid solution (2 mL). The solvent was removed under reduced pressure and ethanol (10 mL) was added. The mixture was stirred for 30 minutes at 80° C. The solvent was removed under reduced pressure and the residue was dissolved in tetrahydrofuran (20 mL) and the pH of the mixture was adjusted to pH 8 by addition of a 10% aqueous potassium carbonate solution. Then di-tert-butyl-dicarbonate (2.5 g, 11 mmol) in tetrahydrofuran (20 mL) was added. After stirring overnight, the solvent was removed under reduced pressure and the residue was purified by silica gel column chromatography eluting with ethyl acetate:petroleum ether=10:1 to afford tert-butyl-1-(4-methoxyphenyl)-2,4-dioxo-1,3,8-triazaspiro[4.5]decane-8-carboxylate as a white solid (1.02 g, 45%).

LCMS (ESI): m/z=376.2 [M+H]⁺.

tert-Butyl-1-(4-methoxyphenyl)-3-methyl-2,4-dioxo-1,3,8-triazaspiro[4.5]decane-8-carboxylate

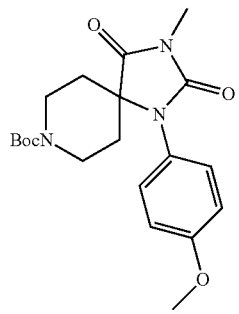

To a solution of tert-butyl-1-(4-methoxyphenyl)-2,4-dioxo-1,3,8-triazaspiro[4.5]decane-8-carboxylate (1.0 mg, 2.6 mmol) in N,N-dimethylformamide (10 mL) was added sodium hydride (0.2 g, 60% in oil, 5.2 mmol) at 0° C. After stirring for 15 minutes, iodomethane (0.37 g, 6 mmol) was added. The resulting mixture was stirred for 15 minutes. The reaction was quenched with ice-water (10 mL). The mixture was extracted with ethyl acetate (3×50 mL) and the combined organic layers were dried over anhydrous sodium sulfate and concentrated under reduced pressure. The residue was purified by silica gel column chromatography eluting with ethyl acetate:petroleum ether=1:3 to afford tert-butyl-1-(4-methoxyphenyl)-3-methyl-2,4-dioxo-1,3,8-triazaspiro[4.5]decane-8-carboxylate as a white solid (140 mg, 67%).

LCMS (ESI): m/z=390.2 [M+H]⁺.
¹H-NMR (300 MHz, CDCl₃): δ=1.39 (s, 9H), 1.62-1.86 (m, 4H), 3.09 (s, 3H), 3.39-3.56 (m, 2H), 3.86 (s, 3H), 3.89-4.00 (m, 2H), 3.78-3.82 (m, 2H), 6.94 (d, J=9 Hz, 2H), 7.07 (d, J=9 Hz, 2H).

Benzyl-1-(4-hydroxyphenyl)-3-methyl-2,4-dioxo-1,3,8-triazaspiro[4.5]decane-8-carboxylate

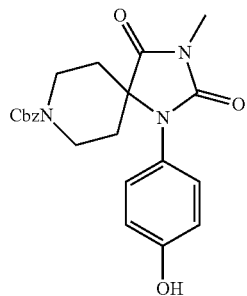 [SMILES: CN1C(=O)N(c2ccc(O)cc2)C2(CCN(C(=O)OCc3ccccc3)CC2)C1=O]

To a solution of tert-butyl-1-(4-methoxyphenyl)-3-methyl-2,4-dioxo-1,3,8-triazaspiro[4.5]decane-8-carboxylate (1.0 g, 2.5 mmol) in dichloromethane (50 mL) was added boron tribromide (4 g, 15 mmol) at 0° C. After stirring overnight, the reaction was quenched by addition of ice-water (5 mL). To the mixture were added benzyl chloroformate (1.56 g, 3.6 mmol) and a 10% aqueous sodium hydroxide solution (12 mL). The mixture was stirred for 2 hours. The organic layer was separated and discarded. The pH of the aqueous layer was adjusted to 2 by addition of 10% aqueous hydrochloric acid solution. The resulting mixture was extracted with dichloromethane (3×50 mL). The combined organic layers were dried over anhydrous sodium sulfate and concentrated under reduced pressure. The residue was washed with ethyl acetate (30 mL) to afford benzyl-1-(4-hydroxyphenyl)-3-methyl-2,4-dioxo-1,3,8-triazaspiro[4.5]decane-8-carboxylate as a white solid (620 mg, 59%)

LCMS (ESI): m/z=410.1 [M+H]⁺.

Benzyl-1-(4-((1-(tert-butoxycarbonyl)azetidin-3-yl)methoxy)phenyl)-3-methyl-2,4-dioxo-1,3,8-triazaspiro[4.5]decane-8-carboxylate

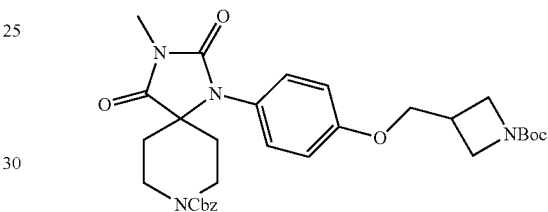

To a solution of benzyl-1-(4-hydroxyphenyl)-3-methyl-2,4-dioxo-1,3,8-triazaspiro[4.5]decane-8-carboxylate (150 mg, 0.367 mmol) in N,N-dimethylformamide (15 mL) was added potassium hydride (50 mg, 1.25 mmol) at 0° C. After stirring for 30 minutes at 0° C., to the resulting solution was added tert-butyl-3-((methylsulfonyloxy)methyl)azetidine-1-carboxylate (243 mg, 0.917 mmol). The resulting mixture was stirred overnight before the reaction was quenched by addition of ice-water (10 mL). The mixture was extracted with ethyl acetate (3×20 mL). The combined organic layers were dried over anhydrous sodium sulfate and concentrated under reduced pressure. The residue was purified by prep-TLC (dichloromethane:methanol=20:1) to afford benzyl-1-(4-((1-(tert-butoxycarbonyl)azetidin-3-yl)methoxy)phenyl)-3-methyl-2,4-dioxo-1,3,8-triazaspiro[4.5]decane-8-carboxylate as a colorless oil (130 mg, 71%).

LCMS (ESI): m/z=579.2 [M+H]⁺.

tert-Butyl-3-((4-(3-methyl-2,4-dioxo-1,3,8-triazaspiro[4.5]decan-1-yl)phenoxy)methyl)azetidine-1-carboxylate

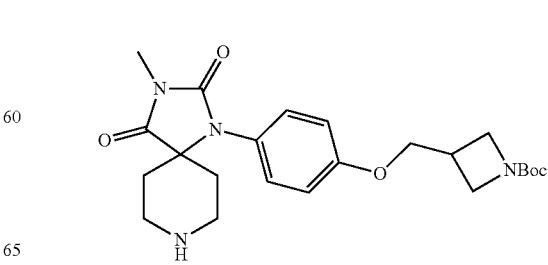

To a solution of benzyl-1-(4-((1-(tert-butoxycarbonyl) azetidin-3-yl)methoxy)phenyl)-3-methyl-2,4-dioxo-1,3,8-triazaspiro[4.5]decane-8-carboxylate (130 mg, 0.225 mmol) in methanol (10 mL) was added 5% palladium on carbon (70 mg). The resulting mixture was stirred for 1 hour under a hydrogen atmosphere. The catalyst was removed by filtration and the solvent was removed under reduced pressure to afford tert-butyl-3-((4-(3-methyl-2,4-dioxo-1,3,8-triazaspiro [4.5]decan-1-yl)phenoxy)methyl)azetidine-1-carboxylate as a white solid (31 mg, 100%).

LCMS (ESI): m/z=445.2 [M+H]$^+$.

(R)-tert-Butyl-3-((4-(8-(2-(2-fluoro-5-(trifluoromethyl)benzamido)-3-methylbutanoyl)-3-methyl-2,4-dioxo-1,3,8-triazaspiro[4.5]decan-1-yl)phenoxy) methyl)azetidine-1-carboxylate

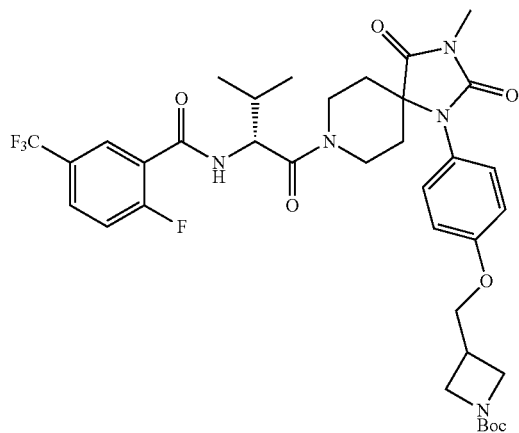 [SMILES: CC(C)[C@@H](NC(=O)c1cc(C(F)(F)F)ccc1F)C(=O)N1CCC2(CC1)C(=O)N(C)C(=O)N2c1ccc(OCC2CN(C(=O)OC(C)(C)C)C2)cc1]

To a solution of tert-butyl-3-((4-(3-methyl-2,4-dioxo-1,3, 8-triazaspiro[4.5]decan-1-yl) phenoxy)methyl)azetidine-1-carboxylate (107 mg, 0.240 mmol) in dichloromethane (10 mL) was added (R)-2-(2-fluoro-5-(trifluoromethyl)benzamido)-3-methylbutanoic acid (prepared as described in Example 28-f) (80 mg, 0.247 mmol), 1-[bis(dimethylamino) methylene]-1H-1,2,3-triazolo[4,5-b]pyridinium-3-oxide hexafluorophosphate (HATU) (128 mg, 0.337 mmol) and N,N-diisopropylethylamine (44 mg, 0.337 mmol). The resulting mixture was stirred for 2 hours at room temperature before the reaction was quenched with ice-water (10 mL). The mixture was extracted with ethyl acetate (3×10 mL) and the combined organic layers were dried over anhydrous sodium sulfate and concentrated under reduced pressure. The residue was purified by prep-TLC with dichloromethane:methanol=15:1 to afford (R)-tert-butyl-3-((4-(8-(2-(2-fluoro-5-(trifluoromethyl)benzamido)-3-methylbutanoyl)-3-methyl-2,4-dioxo-1,3,8-triazaspiro[4.5]decan-1-yl)phenoxy)methyl)azetidine-1-carboxylate as a white solid (80 mg, crude), which was used directly without any further purification.

LCMS (ESI): m/z=734.1 [M+H]$^+$.

(R)—N-(1-(1-(4-(Azetidin-3-ylmethoxy)phenyl)-3-methyl-2,4-dioxo-1,3,8-triazaspiro[4.5]decan-8-yl)-3-methyl-1-oxobutan-2-yl)-2-fluoro-5-(trifluoromethyl)benzamide trifluoroacetic Acid Salt

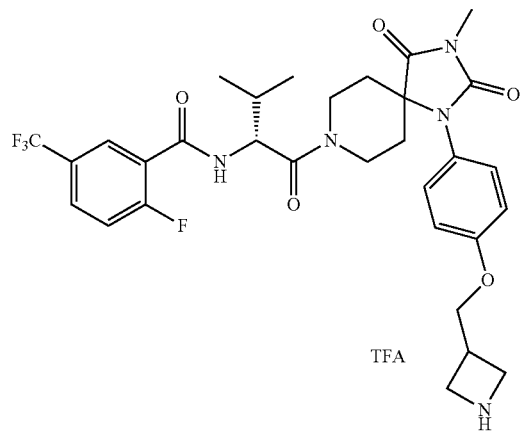 [SMILES: CC(C)[C@@H](NC(=O)c1cc(C(F)(F)F)ccc1F)C(=O)N1CCC2(CC1)C(=O)N(C)C(=O)N2c1ccc(OCC2CNC2)cc1]

To a solution of (R)-tert-butyl-3-((4-(8-(2-(2-fluoro-5-(trifluoromethyl)benzamido)-3-methylbutanoyl)-3-methyl-2,4-dioxo-1,3,8-triazaspiro[4.5]decan-1-yl)phenoxy) methyl)azetidine-1-carboxylate (80 mg, crude) in dichloromethane (10 mL) was added trifluoroacetic acid (2 mL). The resulting mixture was stirred for 2 hours. The solvents were removed under reduced pressure and the residue was purified by prep-HPLC (acetonitrile and water, acetonitrile from 30% to 70%) to afford (R)—N-(1-(1-(4-(azetidin-3-ylmethoxy)phenyl)-3-methyl-2,4-dioxo-1,3,8-triazaspiro[4.5]decan-8-yl)-3-methyl-1-oxobutan-2-yl)-2-fluoro-5-(trifluoromethyl)benzamide trifluoroacetic acid salt as a white solid (48 mg, 26% over two steps).

LCMS (ESI): m/z=634.0 [M+H]$^+$.
$^1$H-NMR (400 MHz, CD$_3$OD): δ=0.82-1.01 (m, 6H), 1.67-2.11 (m, 5H), 3.09 (s, 3H), 3.38-3.51 (m, 2H), 3.97-4.44 (m, 9H), 4.83-4.90 (m, 1H), 7.18-8.50 (m, 8H).

The following 4 compounds were synthesized following the general procedure described above:

Example 82

(R)—N-(1-(1-(4-(cyanomethoxy)phenyl)-3-methyl-2,4-dioxo-1,3,8-triazaspiro[4.5]decan-8-yl)-3-methyl-1-oxobutan-2-yl)-2-fluoro-5-(trifluoromethyl)benzamide

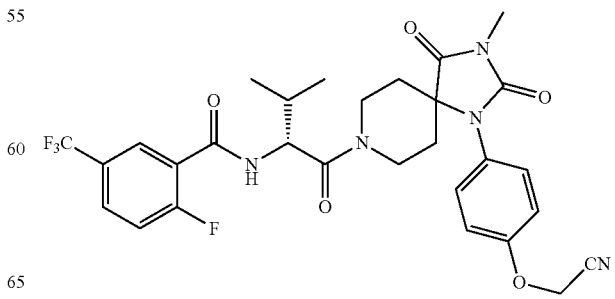

60.3 mg, yield: 25%, white solid.

LCMS (ESI): m/z=604 [M+H]$^+$.

$^1$H-NMR (400 MHz, CD$_3$OD): δ=0.79-1.01 (m, 6H), 1.77-2.12 (m, 5H), 3.09 (s, 3H), 3.31-3.33 (m, 1H), 3.95-4.51 (m, 3H), 4.85-4.97 (m, 2H), 5.07 (s, 1H), 7.06-7.46 (m, 5H), 7.87-8.01 (m, 2H), 8.50-8.53 (m, 1H).

Example 83

(R)-2-Fluoro-N-(3-methyl-1-(3-methyl-1-(4-(oxetan-3-ylmethoxy)phenyl)-2,4-dioxo-1,3,8-triazaspiro[4.5]decan-8-yl)-1-oxobutan-2-yl)-5-(trifluoromethyl)benzamide

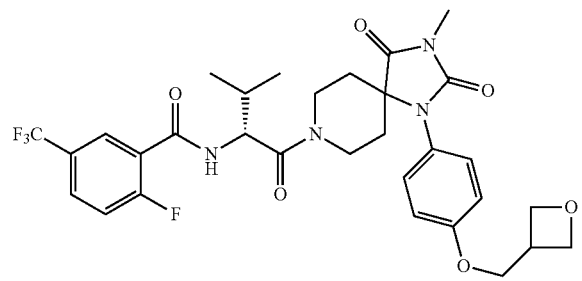 [SMILES: CC(C)[C@@H](NC(=O)c1cc(C(F)(F)F)ccc1F)C(=O)N1CCC2(CC1)C(=O)N(C)C(=O)N2c1ccc(OCC2COC2)cc1]

43.0 mg, yield: 51%, white solid.

LCMS (ESI): m/z=635 [M+H]$^+$.

$^1$H-NMR (400 MHz, CD$_3$OD): δ=0.82-1.02 (m, 6H), 1.31-2.20 (m, 6H), 3.08 (s, 3H), 3.41-3.53 (m, 2H), 3.92-3.98 (m, 1H), 4.12-4.64 (m, 6H), 4.85-4.92 (m, 2H), 6.96-8.51 (m, 8H).

Example 84

(R)-2-Fluoro-N-(1-(1-(4-(2-hydroxyethoxy)phenyl)-3-methyl-2,4-dioxo-1,3,8-triazaspiro[4.5]decan-8-yl)-3-methyl-1-oxobutan-2-yl)-5-(trifluoromethyl)benzamide

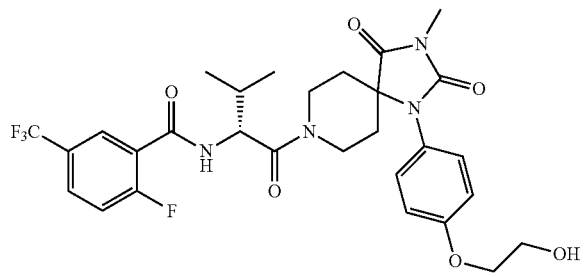 [SMILES: CC(C)[C@@H](NC(=O)c1cc(C(F)(F)F)ccc1F)C(=O)N1CCC2(CC1)C(=O)N(C)C(=O)N2c1ccc(OCCO)cc1]

45.0 mg, yield: 19%, white solid.

LCMS (ESI): m/z=609.2 [M+H]$^+$.

$^1$H-NMR (400 MHz, CD$_3$OD): δ=0.80-1.01 (m, 6H), 1.67-1.88 (m, 2H), 2.05-2.18 (m, 3H), 3.08 (s, 3H), 3.49-3.51 (m, 1H), 3.86-4.05 (m, 4H), 4.11-4.16 (m, 1H), 4.22-4.28 (m, 1H), 4.45 (m, 1H), 4.86-5.01 (m, 1H), 6.94-7.00 (m, 1H), 7.06-7.22 (m, 3H), 7.44-7.49 (m, 1H), 7.94-8.03 (m, 2H).

Example 85

(R)—N-(1-(1-(4-(2-(Dimethylamino)ethoxy)phenyl)-3-methyl-2,4-dioxo-1,3,8-triazaspiro[4.5]decan-8-yl)-3-methyl-1-oxobutan-2-yl)-2-fluoro-5-(trifluoromethyl)benzamide trifluoroacetic Acid Salt

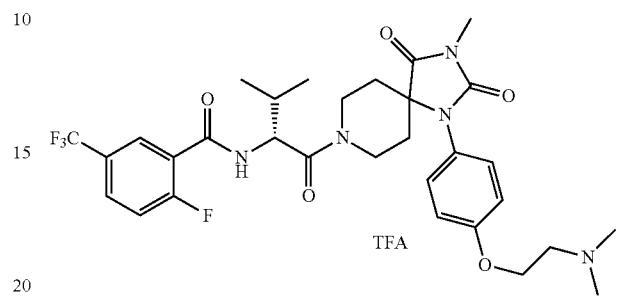

15.9 mg, yield: 20%, white solid.

LCMS (ESI): m/z=635.7 [M+H]$^+$.

$^1$H-NMR (400 MHz, CD$_3$OD): δ=0.80-1.01 (m, 6H), 1.66-1.83 (m, 1H), 2.04-2.17 (m, 4H), 2.99 (s, 4H), 3.02 (s, 2H), 3.12 (s, 3H), 3.50-3.54 (m, 1H), 3.56-3.63 (m, 2H), 3.99-4.02 (m, 1H), 4.21-4.25 (m, 1H), 4.34-4.50 (m, 3H), 4.82-4.90 (m, 1H), 7.06-7.12 (m, 2H), 7.22-7.29 (m, 2H), 7.41-7.47 (m, 1H), 7.88-8.02 (m, 2H).

Example 86

(R)—N-(1-(1-(4-(Azetidin-3-ylamino)phenyl)-3-methyl-2,4-dioxo-1,3,8-triazaspiro[4.5]decan-8-yl)-3-methyl-1-oxobutan-2-yl)-2-fluoro-5-(trifluoromethyl)benzamide trifluoroacetic Acid Salt

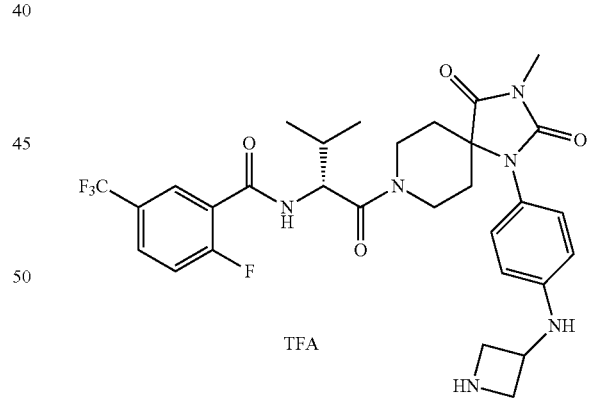

Representative Scheme:

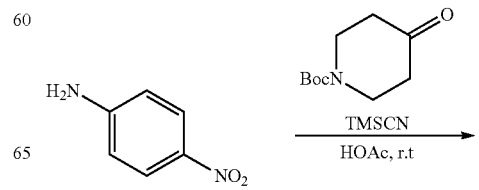

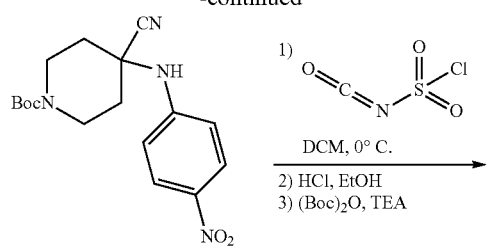
a
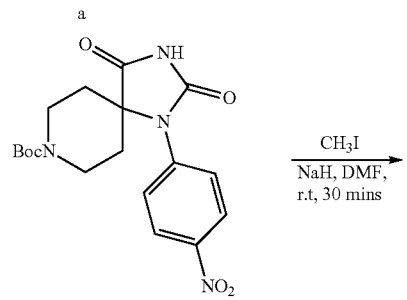
b
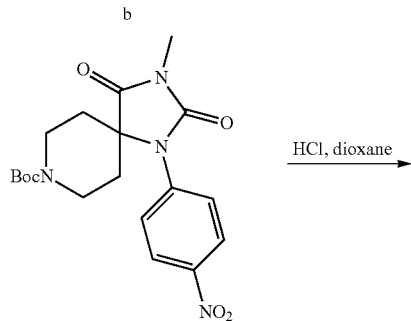
c
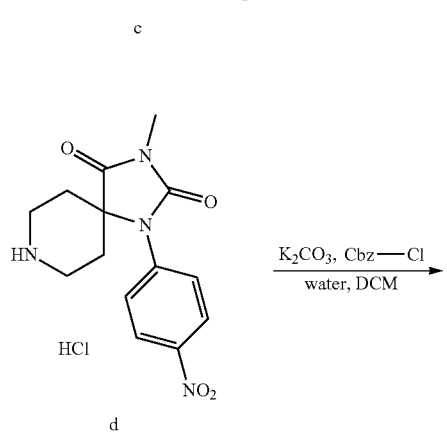
d
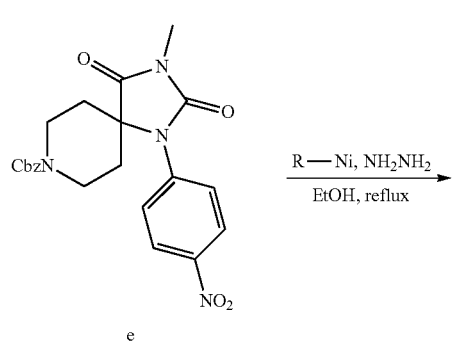
e
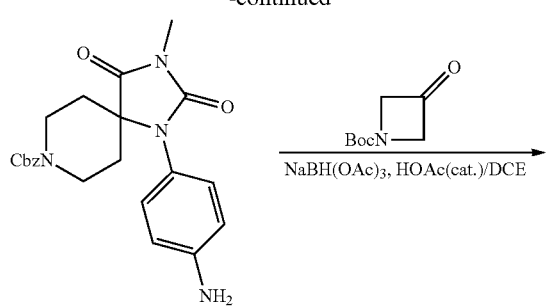
f
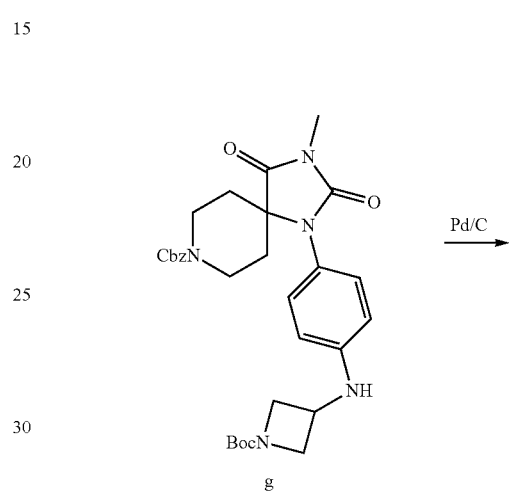
g
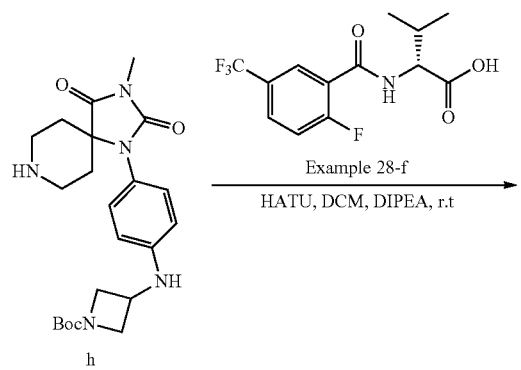
h
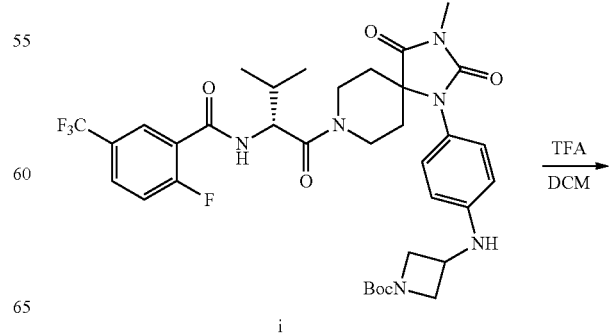
i -continued

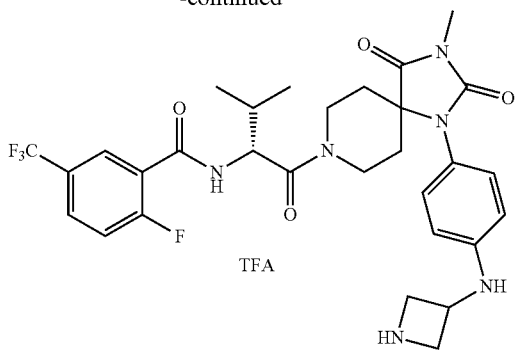

TFA

Representative General Procedure tert-Butyl-4-cyano-4-(4-nitrophenylamino)piperidine-1-carboxylate

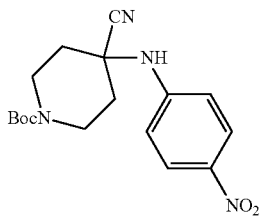 [SMILES: CC(C)(C)OC(=O)N1CCC(C#N)(Nc2ccc([N+](=O)[O-])cc2)CC1]

To a solution of 4-nitroaniline (5 g, 0.036 mol) in acetic acid (80 mL) was added tert-butyl-4-oxopiperidine-1-carboxylate (7.93 g, 0.0399 mol). The resulting mixture was cooled to 0° C. and trimethylsilyl cyanide (4.3 g, 0.043 mol) was added. The resulting solution was stirred overnight at room temperature. To the solution was added saturated aqueous ammonium chloride solution (50 mL). The mixture was filtered and the filter cake was recrystallized from ethyl acetate to afford tert-butyl-4-cyano-4-(4-nitrophenylamino)piperidine-1-carboxylate as a white solid (4 g, 32%).

LCMS (ESI): m/z=347.2 [M+H]$^+$.

tert-Butyl-1-(4-nitrophenyl)-2,4-dioxo-1,3,8-triazaspiro[4.5]decane-8-carboxylate

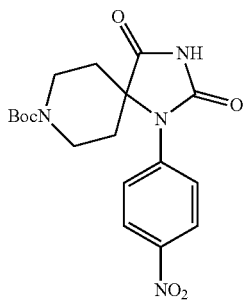 [SMILES: CC(C)(C)OC(=O)N1CCC2(CC1)C(=O)NC(=O)N2c1ccc([N+](=O)[O-])cc1]

To a solution of tert-butyl-4-cyano-4-(4-nitrophenylamino)piperidine-1-carboxylate (3.8 g, 0.0109 mol) in dichloromethane was added chlorosulfonyl isocyanate (3.8 g, 0.026 mol) at 0° C. After stirring for 30 minutes at 0° C., the reaction was quenched with a 5% aqueous hydrochloric acid solution (5 mL). The solvent was removed under reduced pressure and ethanol (20 mL) was added. The mixture was stirred for 30 minutes at 80° C. The solvent was removed under reduced pressure and the residue was added to dichloromethane (20 mL). To the resulting suspensions was added sequentially triethylamine (4.4 g, 0.044 mol), di-tert-butyl-dicarbonate (2.39 g, 0.011 mol). After stirring overnight, the solvent was removed and the residue was recrystallized from ethyl acetate:petroleum ether=1:2 to afford tert-butyl-1-(4-nitrophenyl)-2,4-dioxo-1,3,8-triazaspiro[4.5]decane-8-carboxylate as a yellow oil (2.2 g, 52%).

LCMS (ESI): m/z=391.2 [M+H]$^+$.

tert-Butyl-3-methyl-1-(4-nitrophenyl)-2,4-dioxo-1,3,8-triazaspiro[4.5]decane-8-carboxylate

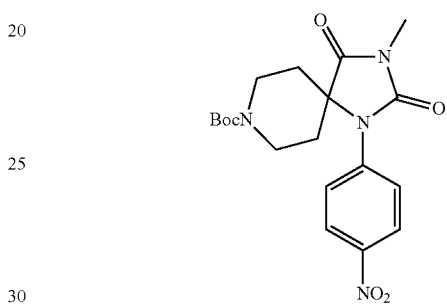

To a solution of tert-butyl-1-(4-nitrophenyl)-2,4-dioxo-1,3,8-triazaspiro[4.5]decane-8-carboxylate (2.2 g, 5.64 mmol) in N,N-dimethylformamide (15 mL) was added sodium hydride (0.237 g, 60% in oil, 6.2 mmol) at 0° C. After stirring for 15 minutes, iodomethane (961 mg, 6.77 mmol) was added. The resulting mixture was stirred for 15 minutes at room temperature and the reaction was quenched with ice-water (10 mL). The mixture was extracted with ethyl acetate (3×50 mL). The combined organic layers were dried over anhydrous sodium sulfate and concentrated under reduced pressure. The residue was recrystallized from ethyl acetate:petroleum ether=1:2 to afford tert-butyl-3-methyl-1-(4-nitrophenyl)-2,4-dioxo-1,3,8-triazaspiro[4.5]decane-8-carboxylate as a yellow solid (1.66 g, 70%).

LCMS (ESI): m/z=405.1 [M+H]$^+$.

3-Methyl-1-(4-nitrophenyl)-1,3,8-triazaspiro[4.5]decane-2,4-dione hydrochloride

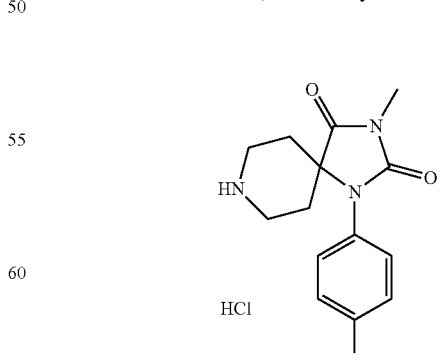

A solution of tert-butyl-3-methyl-1-(4-nitrophenyl)-2,4-dioxo-1,3,8-triazaspiro[4.5]decane-8-carboxylate (800 mg, 1.98 mmol) in hydrochloric acid in dioxane (6.0 M, 10 mL) was stirred for 30 minutes. The precipitate was collected by filtration and dried under reduced pressure to afford 3-methyl-1-(4-nitrophenyl)-1,3,8-triazaspiro[4.5]decane-2,4-dione hydrochloride as a white solid (700 mg, some residual solvent), which was used directly without further purification.

LCMS (ESI): m/z=305.1 [M+H]$^+$.

Benzyl-3-methyl-1-(4-nitrophenyl)-2,4-dioxo-1,3,8-triazaspiro[4.5]decane-8-carboxylate

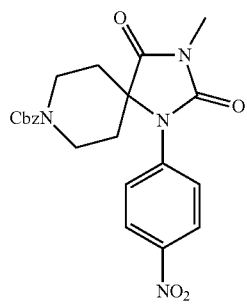 [SMILES: CN1C(=O)N(c2ccc([N+](=O)[O-])cc2)C2(CCN(C(=O)OCc3ccccc3)CC2)C1=O]

To a solution of 3-methyl-1-(4-nitrophenyl)-1,3,8-triazaspiro[4.5]decane-2,4-dione hydrochloride (700 mg, 2.05 mmol) in dichloromethane (10 mL) was added sodium carbonate (652 mg, 6.5 mmol) and water (10 mL). To the mixture was added benzyl chloroformate (350 mg, 2.05 mmol) dropwise. The resulting mixture was stirred for 1 hour at room temperature and the reaction was quenched with ice-water (10 mL). The mixture was extracted with dichloromethane (3×50 mL). The combined organic layers were dried over anhydrous sodium sulfate and concentrated under reduced pressure. The residue was recrystallized from ethyl acetate:petroleum ether=1:2 to afford benzyl-3-methyl-1-(4-nitrophenyl)-2,4-dioxo-1,3,8-triazaspiro[4.5]decane-8-carboxylate as a yellow solid (810 mg, 90%).

LCMS (ESI): m/z=439.1 [M+H]$^+$.

Benzyl-1-(4-aminophenyl)-3-methyl-2,4-dioxo-1,3,8-triazaspiro[4.5]decane-8-carboxylate

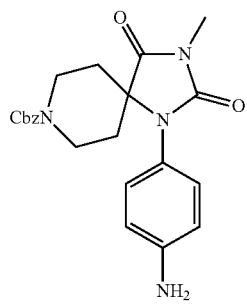 [SMILES: CN1C(=O)N(c2ccc(N)cc2)C2(CCN(C(=O)OCc3ccccc3)CC2)C1=O]

To a solution of benzyl-3-methyl-1-(4-nitrophenyl)-2,4-dioxo-1,3,8-triazaspiro[4.5]decane-8-carboxylate (100 mg, 0.28 mmol) in ethanol (10 mL) was added Raney-Ni (0.1 g, 50% in ethanol). After heating to 50° C., to the resulting mixture hydrazine (0.1 g, 2.5 mmol) was added dropwise. Before removing the Raney-Ni by filtration, the reaction mixture was stirred at 50° C. for 30 minutes. The solvent was removed under reduced pressure and the residue was used directly without further purification.

Benzyl-1-(4-(1-(tert-butoxycarbonyl)azetidin-3-ylamino)phenyl)-3-methyl-2,4-dioxo-1,3,8-triazaspiro[4.5]decane-8-carboxylate

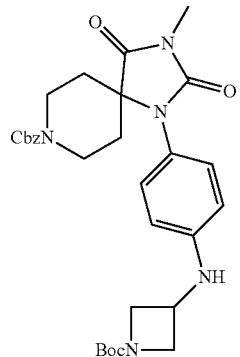 [SMILES: CN1C(=O)N(c2ccc(NC3CN(C(=O)OC(C)(C)C)C3)cc2)C2(CCN(C(=O)OCc3ccccc3)CC2)C1=O]

To a solution of tert-butyl-3-oxoazetidine-1-carboxylate (59 mg, 0.343 mmol) and benzyl-1-(4-aminophenyl)-3-methyl-2,4-dioxo-1,3,8-triazaspiro[4.5]decane-8-carboxylate (140 mg, 0.68 mmol) in dichloromethane (30 mL) was added titaniumisopropoxide (178 mg, 0.68 mmol). The resulting mixture was heated at reflux overnight. After cooling to room temperature, to the resulting solution was added sodium triacetoxyborohydride (210 mg, 1.0 mmol). The reaction was stirred for 2 hours. The reaction was quenched with an aqueous sodium hydroxide solution (1.0 M, 10 mL). The mixture was extracted with ethyl acetate (3×10 mL). The combined organic layers were dried over anhydrous sodium sulfate and concentrated under reduced pressure. The residue was purified by prep-TLC (ethyl acetate:petroleum ether=1:1) to afford benzyl-1-(4-(1-(tert-butoxycarbonyl)azetidin-3-ylamino)phenyl)-3-methyl-2,4-dioxo-1,3,8-triazaspiro[4.5]decane-8-carboxylate as a white solid (30 mg, 15%).

tert-Butyl-3-(4-(3-methyl-2,4-dioxo-1,3,8-triazaspiro[4.5]decan-1-yl)phenylamino)azetidine-1-carboxylate

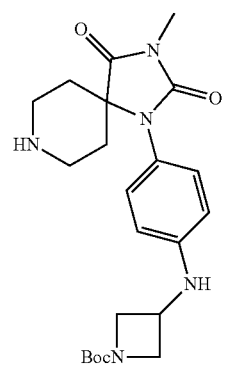 [SMILES: CN1C(=O)N(c2ccc(NC3CN(C(=O)OC(C)(C)C)C3)cc2)C2(CCNCC2)C1=O]

To a solution of benzyl-1-(4-(1-(tert-butoxycarbonyl)azetidin-3-ylamino)phenyl)-3-methyl-2,4-dioxo-1,3,8-triazaspiro[4.5]decane-8-carboxylate (120 mg, 0.213 mmol) in methanol (10 mL) was added 5% palladium on carbon (10 mg, 50% wet with water). The resulting mixture was stirred under a hydrogen atmosphere for 1 hour. The catalyst was removed by filtration and the filtrate was concentrated under reduced pressure to afford tert-butyl-3-(4-(3-methyl-2,4-dioxo-1,3,8-triazaspiro[4.5]decan-1-yl)phenylamino)azetidine-1-carboxylate as a thick oil (90 mg, crude), which was used directly without any further purification.

(R)-tert-Butyl-3-(4-(8-(2-(2-fluoro-5-(trifluoromethyl)benzamido)-3-methylbutanoyl)-3-methyl-2,4-dioxo-1,3,8-triazaspiro[4.5]decan-1-yl)phenylamino)azetidine-1-carboxylate

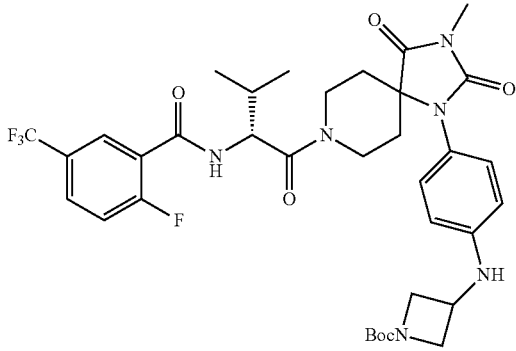 [SMILES: CC(C)[C@@H](NC(=O)c1cc(C(F)(F)F)ccc1F)C(=O)N1CCC2(CC1)C(=O)N(C)C(=O)N2c1ccc(NC2CN(C(=O)OC(C)(C)C)C2)cc1]

To a solution of tert-butyl-3-(4-(3-methyl-2,4-dioxo-1,3,8-triazaspiro[4.5]decan-1-yl) phenylamino)azetidine-1-carboxylate (90 mg, 0.21 mmol) in dichloromethane (5 mL) was added sequentially (R)-2-(2-fluoro-5-(trifluoromethyl)benzamido)-3-methylbutanoic acid (prepared as described in Example 28-f) (65 mg, 0.21 mmol), 1-[bis(dimethylamino)methylene]-1H-1,2,3-triazolo[4,5-b]pyridinium-3-oxide hexafluorophosphate (HATU) (260 mg, 0.68 mmol) and N,N-diisopropylethylamine (180 mg, 1.36 mmol). The resulting mixture was stirred for 2 hours at room temperature before the reaction was quenched with ice-water. The mixture was extracted with ethyl acetate (3×10 mL) and the combined organic layers were dried over anhydrous sodium sulfate and concentrated under reduced pressure. The residue was purified by prep-TLC with dichloromethane:methanol=15:1 to afford (R)-tert-butyl-3-(4-(8-(2-(2-fluoro-5-(trifluoromethyl)benzamido)-3-methylbutanoyl)-3-methyl-2,4-dioxo-1,3,8-triazaspiro[4.5]decan-1-yl)phenylamino)azetidine-1-carboxylate as a white solid (50 mg, 33%).

LCMS (ESI): m/z=719.0 [M+H]$^+$.

(R)—N-(1-(1-(4-(Azetidin-3-ylamino)phenyl)-3-methyl-2,4-dioxo-1,3,8-triazaspiro[4.5]decan-8-yl)-3-methyl-1-oxobutan-2-yl)-2-fluoro-5-(trifluoromethyl)benzamide trifluoroacetic Acid Salt

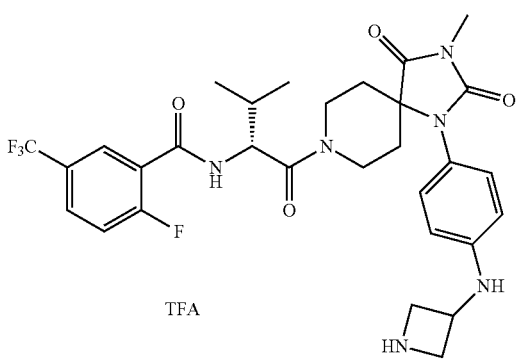 [SMILES: CC(C)[C@@H](NC(=O)c1cc(C(F)(F)F)ccc1F)C(=O)N1CCC2(CC1)C(=O)N(C)C(=O)N2c1ccc(NC2CNC2)cc1]

To a solution of (R)-tert-butyl-3-(4-(8-(2-(2-fluoro-5-(trifluoromethyl)benzamido)-3-methylbutanoyl)-3-methyl-2,4-dioxo-1,3,8-triazaspiro[4.5]decan-1-yl)phenylamino)azetidine-1-carboxylate (50 mg, 0.21 mmol) in dichloromethane (5 mL) was added trifluoroacetic acid (2 mL) at 0° C. The reaction was stirred 3 hours at room temperature. The solvent was removed under reduced pressure and the residue was purified by prep-HPLC (acetonitrile and water, acetonitrile from 30% to 60%) to afford (R)—N-(1-(1-(4-(azetidin-3-ylamino)phenyl)-3-methyl-2,4-dioxo-1,3,8-triazaspiro[4.5]decan-8-yl)-3-methyl-1-oxobutan-2-yl)-2-fluoro-5-(trifluoromethyl)benzamide trifluoroacetic acid salt as a white solid (17.8 mg, 35%).

LCMS (ESI): m/z=619.0 [M+H]$^+$.

$^1$H-NMR (400 MHz, CD$_3$OD): δ=0.80-1.01 (m, 6H), 1.68-2.03 (m, 6H), 3.07 (s, 3H), 3.45-3.52 (m, 1H), 3.93-4.46 (m, 7H), 4.83-4.85 (m, 1H), 6.58-6.69 (m, 2H), 7.01-7.07 (m, 2H), 7.41-7.46 (m, 1H), 7.87-8.00 (m, 2H), 8.48-8.53 (m, 1H).

The following compound was synthesized following the general procedure described above:

Example 87

(R)-2-Fluoro-N-(3-methyl-1-(3-methyl-1-(4-(oxetan-3-ylamino)phenyl)-2,4-dioxo-1,3,8-triazaspiro[4.5]decan-8-yl)-1-oxobutan-2-yl)-5-(trifluoromethyl)benzamide

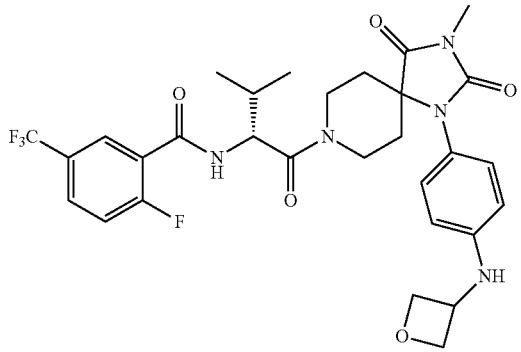 [SMILES: CC(C)[C@@H](NC(=O)c1cc(C(F)(F)F)ccc1F)C(=O)N1CCC2(CC1)C(=O)N(C)C(=O)N2c1ccc(NC2COC2)cc1]

32.6 mg, yield: 43%, white solid
LCMS (ESI): m/z=620.0 [M+H]$^+$.
$^1$H-NMR (400 MHz, CDCl$_3$): δ=0.80-1.01 (m, 6H), 1.67-2.03 (m, 5H), 3.06 (s, 3H), 3.42-3.48 (m, 1H), 3.94-4.53 (m, 7H), 4.88-5.01 (m, 2H), 6.47-6.62 (m, 2H), 6.93-7.01 (m, 2H), 7.41-7.46 (m, 1H), 7.86-7.95 (m, 2H).

Example 88

(R)—N-(1-(1-(4-Cyanobenzyl)-3-methyl-2,4-dioxo-1,3,8-triazaspiro[4.5]decan-8-yl)-3-methyl-1-oxobutan-2-yl)-2-fluoro-5-(trifluoromethyl)benzamide

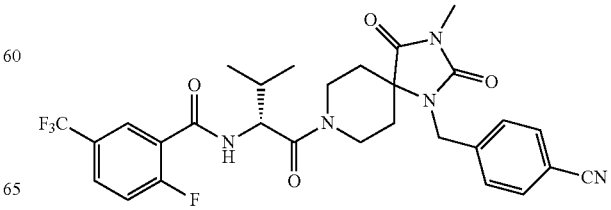

Representative Scheme:

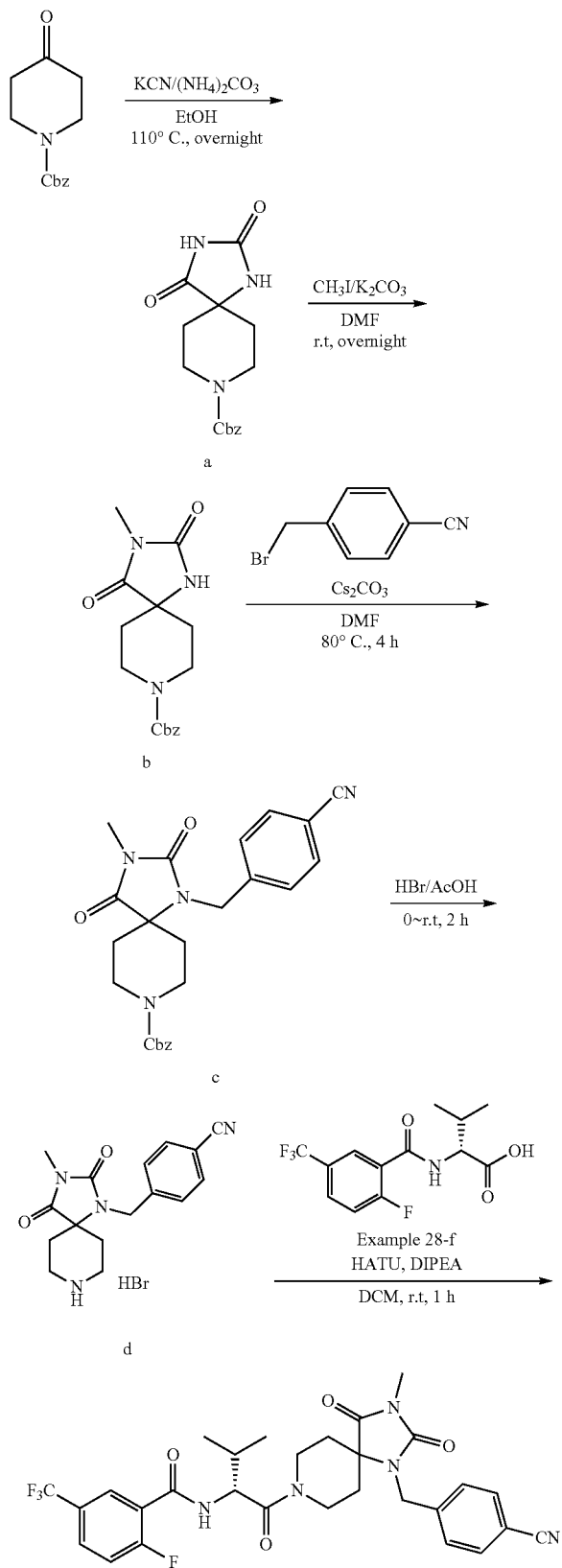

Representative General Procedure

Benzyl-2,4-dioxo-1,3,8-triazaspiro[4.5]decane-8-carboxylate

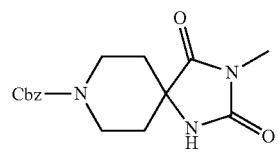 [SMILES: CN1C(=O)NC2(CCN(C(=O)OCc3ccccc3)CC2)C1=O]

A mixture of benzyl-4-oxopiperidine-1-carboxylate (11.7 g, 50 mmol), potassium cyanide (4.87 g, 75 mmol) and ammonium carbonate (24 g, 250 mmol) in ethanol (100 mL), was placed in a stainless steel bomb and heated at 110° C. overnight. The reaction mixture was poured into ice-water (300 mL) and the resulting mixture was filtered. The pH of the mixture in water (100 mL) was adjusted to 2 by addition of an aqueous hydrochloric acid solution (6.0 M). The mixture was filtered and the filter cake was recrystallized from methanol:diethyl ether=1:1 to afford benzyl-2,4-dioxo-1,3,8-triazaspiro[4.5]decane-8-carboxylate as a white solid (10.0 g, 66%).

LCMS (ESI): m/z=304.1 [M+H]$^+$.

$^1$H-NMR (300 MHz, DMSO-d$_6$): δ=1.43-1.56 (m, 2H), 1.63-1.85 (m, 2H), 2.45-2.60 (m, 2H), 3.33 (s, 2H), 3.88 (dd, J=9.7, 4.0 Hz, 2H), 5.09 (s, 2H), 7.20-7.53 (m, 5H), 8.54 (s, 1H), 10.66 (s, 1H).

Benzyl-3-methyl-2,4-dioxo-1,3,8-triazaspiro[4.5]decane-8-carboxylate

To a solution of benzyl-2,4-dioxo-1,3,8-triazaspiro[4.5]decane-8-carboxylate (3.03 g, 10 mmol) in N,N-dimethylformamide (20 mL), was added potassium carbonate (2.76 g, 20 mmol). After stirring for 15 minutes, iodomethane (1.42 g, 10 mmol) was added. Before quenching with ice-water (10 mL), the resulting mixture was stirred at room temperature overnight. The mixture was extracted with dichloromethane (3×150 mL). The combined organic layers were dried over anhydrous sodium sulfate and concentrated under reduced pressure. The residue was purified by silica gel column chromatography eluting with dichloromethane:methanol=50:1) to afford benzyl-3-methyl-2,4-dioxo-1,3,8-triazaspiro[4.5]decane-8-carboxylate as a white solid (1.0 g, 32%).

LCMS (ESI): m/z=318.1 [M+H]$^+$.

$^1$H-NMR (300 MHz, CDCl$_3$): δ=1.57 (m, 2H), 1.70-1.85 (m, 2H), 2.84 (s, 3H), 3.24 (s, 2H), 3.84-3.90 (m, 2H), 5.10 (s, 2H), 7.29-7.45 (m, 5H), 8.81 (s, 1H).

Benzyl-1-(4-cyanobenzyl)-3-methyl-2,4-dioxo-1,3,8-triazaspiro[4.5]decane-8-carboxylate

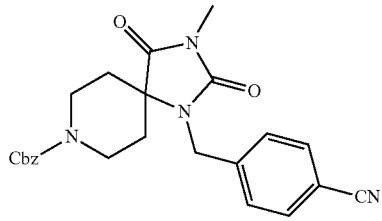 [SMILES: CN1C(=O)N(Cc2ccc(C#N)cc2)C2(CCN(C(=O)OCc3ccccc3)CC2)C1=O]

To a solution of benzyl-3-methyl-2,4-dioxo-1,3,8-triazaspiro[4.5]decane-8-carboxylate (110 mg, 0.347 mmol) in N,N-dimethylformamide (5 mL), was added cesium carbonate (452 mg, 1.39 mmol), and 4-(bromomethyl)benzonitrile (136 mg, 0.69 mmol). The resulting mixture was stirred at 80° C. for 4 hours, before the reaction was quenched with ice-water (10 mL). The mixture was extracted with dichloromethane (3×50 mL). The combined organic layers were dried over anhydrous sodium sulfate and concentrated under reduced pressure. The residue was purified by silica gel column chromatography eluting (ethyl acetate:petroleum ether=1:2) to afford benzyl-1-(4-cyanobenzyl)-3-methyl-2,4-dioxo-1,3,8-triazaspiro[4.5]decane-8-carboxylate as a white solid (130 mg, 86%).

LCMS (ESI): m/z=433.1 [M+H]$^+$.

$^1$H-NMR (300 MHz, CDCl$_3$): δ=1.70 (m, 4H), 3.07 (s, 3H), 3.52 (s, 2H), 4.11 (dd, J=14.3 Hz, J=7.1 Hz, 2H), 4.48 (s, 2H), 5.11 (s, 2H), 7.33-7.42 (m, 2H), 7.55-7.66 (m, 2H).

4-((3-Methyl-2,4-dioxo-1,3,8-triazaspiro[4.5]decan-1-yl)methyl)benzonitrile hydrobromide

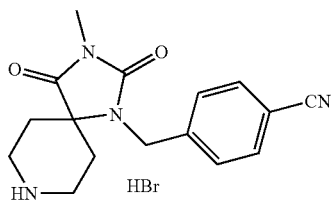 [SMILES: CN1C(=O)N(Cc2ccc(C#N)cc2)C2(CCNCC2)C1=O ; Br]

To a solution of benzyl-1-(4-cyanobenzyl)-3-methyl-2,4-dioxo-1,3,8-triazaspiro[4.5]decane-8-carboxylate (130 mg, 0.3 mmol) in dichloromethane (1 mL) was added hydrobromic acid (2 mL, 38% in acetic acid) at 0° C. Then the reaction was warmed to room temperature and stirred for 2 hours. The solvent was removed under reduced pressure to afford 4-((3-methyl-2,4-dioxo-1,3,8-triazaspiro[4.5]decan-1-yl)methyl)benzonitrile hydrobromide as a white solid (100 mg, crude), which was used directly without any further purification.

LCMS (ESI): m/z=299.2 [M+H]$^+$.

(R)—N-(1-(1-(4-Cyanobenzyl)-3-methyl-2,4-dioxo-1,3,8-triazaspiro[4.5]decan-8-yl)-3-methyl-1-oxobutan-2-yl)-2-fluoro-5-(trifluoromethyl)benzamide

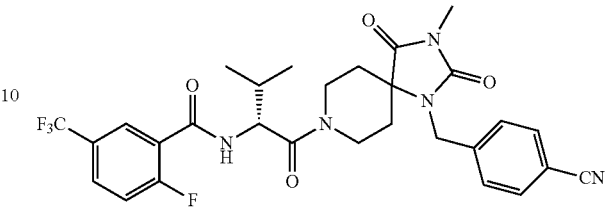

To the mixture of 4-((3-methyl-2,4-dioxo-1,3,8-triazaspiro[4.5]decan-1-yl)methyl)benzonitrile hydrobromide (100 mg, crude) was added dichloromethane (5 mL), (R)-2-(2-fluoro-5-(trifluoromethyl)benzamido)-3-methylbutanoic acid (prepared as described in Example 28-f) (81 mg, 0.26 mmol), 1-[bis(dimethylamino)methylene]-1H-1,2,3-triazolo[4,5-b]pyridinium-3-oxide hexafluorophosphate (HATU) (146 mg, 0.38 mmol) and N,N-diisopropylethylamine (83 mg, 0.64 mmol). The resulting mixture was stirred for 2 hours at room temperature before the reaction was quenched with ice-water. The mixture was extracted with dichloromethane (3×10 mL) and the combined organic layers were dried over anhydrous sodium sulfate and concentrated under reduced pressure. The residue was purified by prep-TLC with dichloromethane:methanol=15:1 to afford (R)—N-(1-(1-(4-cyanobenzyl)-3-methyl-2,4-dioxo-1,3,8-triazaspiro[4.5]decan-8-yl)-3-methyl-1-oxobutan-2-yl)-2-fluoro-5-(trifluoromethyl)benzamide as a white solid (56 mg, 41%).

LCMS (ESI): m/z=588.0 [M+H]$^+$.

$^1$H-NMR (400 MHz, CD$_3$OD): δ=0.89-0.96 (m, 6H), 1.62-2.22 (m, 5H), 2.95 (s, 3H), 3.25-3.31 (m, 1H), 3.75-3.82 (m, 1H), 4.13-4.16 (m, 1H), 4.39-4.54 (m, 3H), 4.74-4.79 (m, 1H), 7.34-7.62 (m, 5H), 7.79-7.95 (m, 2H), 8.35-8.44 (m, 1H).

The following 38 compounds were synthesized following the general procedure described above:

Example 89

(R)—N-(1-(1-Benzyl-3-methyl-2,4-dioxo-1,3,8-triazaspiro[4.5]decan-8-yl)-3-methyl-1-oxobutan-2-yl)-2-fluoro-5-(trifluoromethyl)benzamide

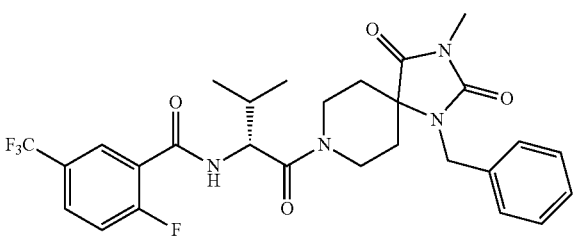

140.8 mg, yield: 57%, white solid.
LCMS (ESI): m/z=562.9 [M+H]$^+$.
$^1$H-NMR (400 MHz, CD$_3$OD): δ=1.00-1.06 (m, 6H), 1.65-1.87 (m, 3H), 2.05-2.17 (m, 1H), 2.30-2.38 (m, 1H), 3.07 (s, 3H), 3.32-3.33 (m, 2H), 3.37-3.44 (m, 1H), 3.87-

3.93 (m, 1H), 4.12-4.27 (m, 1H), 4.45-4.72 (m, 2H), 7.21-7.33 (m, 5H), 7.42-7.51 (m, 1H), 7.87-8.10 (m, 2H), 8.50 (m, 1H).

Example 90

(R)-2-Fluoro-N-(1-(1-(4-fluorobenzyl)-3-methyl-2,4-dioxo-1,3,8-triazaspiro[4.5]decan-8-yl)-3-methyl-1-oxobutan-2-yl)-5-(trifluoromethyl)benzamide

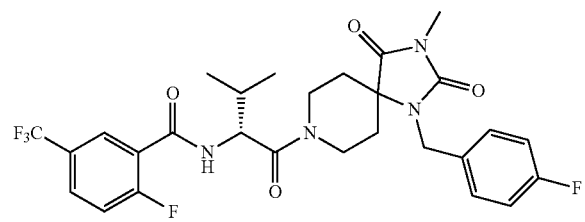 [SMILES: CC(C)[C@@H](NC(=O)c1cc(C(F)(F)F)ccc1F)C(=O)N1CCC2(CC1)C(=O)N(C)C(=O)N2Cc1ccc(F)cc1]

100.0 mg, yield: 45%, white solid.
LCMS (ESI): m/z=581.1[M+H]⁺.
¹H-NMR (400 MHz, CD₃OD): δ=1.01-1.07 (m, 6H), 1.66-1.89 (m, 3H), 2.12-2.39 (m, 2H), 3.06 (s, 3H), 3.36-3.44 (m, 1H), 3.87-3.93 (m, 1H), 4.11-4.32 (m, 1H), 4.48-4.65 (m, 3H), 4.85-4.90 (m, 1H), 6.95-7.10 (m, 2H), 7.37-7.47 (m, 3H), 7.91-8.06 (m, 2H), 8.53 (s, 1H).

Example 91

(R)-2-Fluoro-N-(1-(1-(4-methoxybenzyl)-3-methyl-2,4-dioxo-1,3,8-triazaspiro[4.5]decan-8-yl)-3-methyl-1-oxobutan-2-yl)-5-(trifluoromethyl)benzamide

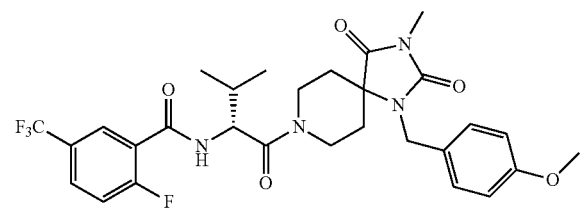 [SMILES: COc1ccc(CN2C(=O)N(C)C(=O)C23CCN(C(=O)[C@H](NC(=O)c2cc(C(F)(F)F)ccc2F)C(C)C)CC3)cc1]

48.5 mg, yield: 40%, white solid.
LCMS (ESI): m/z=593.2 [M+H]⁺.
¹H-NMR (400 MHz, CD₃OD): δ=1.01-1.06 (m, 6H), 1.60-2.38 (m, 5H), 3.32-3.39 (m, 2H), 3.79-3.84 (m, 3H), 3.89-3.93 (m, 1H), 4.11-4.26 (m, 1H), 4.42-4.66 (m, 2H), 6.77-6.90 (m, 2H), 7.24-7.26 (m, 2H), 7.41-7.53 (m, 1H), 7.44-7.51 (m, 1H), 7.87-7.90 (m, 1H), 8.10-8.12 (m, 1H).

Example 92

2-Fluoro-N-((2R)-3-methyl-1-(3-methyl-2,4-dioxo-1-(1-phenylethyl)-1,3,8-triazaspiro[4.5]decan-8-yl)-1-oxobutan-2-yl)-5-(trifluoromethyl)benzamide

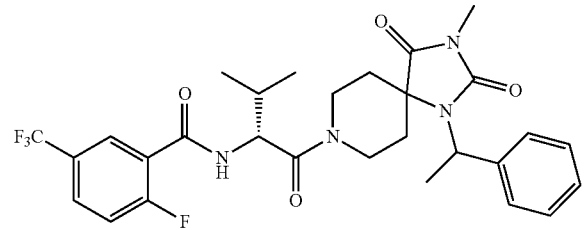 [SMILES: CC(C)[C@@H](NC(=O)c1cc(C(F)(F)F)ccc1F)C(=O)N1CCC2(CC1)C(=O)N(C)C(=O)N2C(C)c1ccccc1]

27.9 mg, yield: 14%, white solid.
LCMS (ESI): m/z=577.2 [M+H]⁺.
¹H-NMR (400 MHz, CD₃OD): δ=1.02-1.15 (m, 6H), 1.67-2.18 (m, 5H), 3.00 (s, 3H), 3.07 (s, 3H), 3.41-3.47 (m, 1H), 3.91-3.97 (m, 1H), 4.29-4.32 (m, 1H), 4.49-4.68 (m, 2H), 4.87-4.94 (m, 1H), 7.21-7.50 (m, 5H), 7.88-8.08 (m, 2H), 8.47-8.59 (m, 1H).

Example 93

(R)-2-Fluoro-N-(3-methyl-1-(3-methyl-1-(4-(methylsulfonyl)benzyl)-2,4-dioxo-1,3,8-triazaspiro[4.5]decan-8-yl)-1-oxobutan-2-yl)-5-(trifluoromethyl)benzamide

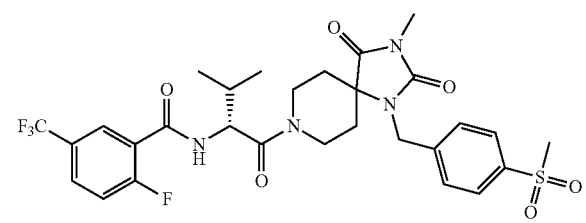 [SMILES: CC(C)[C@@H](NC(=O)c1cc(C(F)(F)F)ccc1F)C(=O)N1CCC2(CC1)C(=O)N(C)C(=O)N2Cc1ccc(S(C)(=O)=O)cc1]

37.5 mg, yield: 40%, white solid.
LCMS (ESI): m/z=641.2 [M+H]⁺.
¹H-NMR (400 MHz, CD₃OD): δ=0.99-1.07 (m, 6H), 1.75-2.32 (m, 5H), 3.13-3.17 (m, 6H), 3.87-3.93 (m, 1H), 4.25-4.28 (m, 1H), 4.51-4.54 (m, 1H), 4.75-4.65 (m, 2H), 4.84-4.90 (m, 2H), 7.65-7.61 (m, 3H), 8.06-8.08 (m, 3H), 8.47-8.59 (m, 1H).

Example 94

(R)-2-Fluoro-N-(1-(1-((2-methoxypyridin-4-yl)methyl)-3-methyl-2,4-dioxo-1,3,8-triazaspiro[4.5]decan-8-yl)-3-methyl-1-oxobutan-2-yl)-5-(trifluoromethyl)benzamide

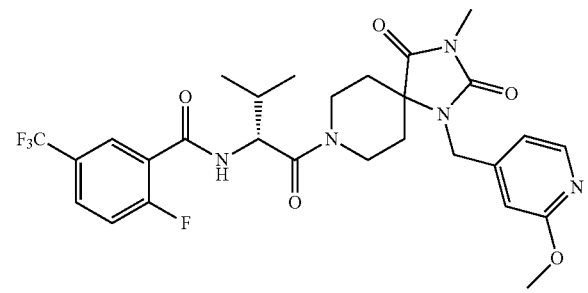 [SMILES: COc1cc(CN2C(=O)N(C)C(=O)C23CCN(C(=O)[C@H](NC(=O)c2cc(C(F)(F)F)ccc2F)C(C)C)CC3)ccn1]

52.3 mg, yield: 20%, white solid.
LCMS (ESI): m/z=594.2 [M+H]⁺.
¹H-NMR (400 MHz, CD₃OD): δ=1.01-1.07 (m, 6H), 1.83-2.15 (m, 5H), 2.65-2.94 (m, 1H), 3.08 (s, 3H), 3.33-3.44 (m, 1H), 3.94-3.97 (m, 4H), 4.25-4.27 (m, 1H), 4.55-4.64 (m, 2H), 4.84-4.88 (m, 1H), 6.96-7.11 (m, 2H), 7.45-7.47 (m, 1H), 7.91-8.10 (m, 3H).

Example 95

(R)-2-Fluoro-N-(3-methyl-1-(3-methyl-1-((2-methylpyridin-4-yl)methyl)-2,4-dioxo-1,3,8-triazaspiro[4.5]decan-8-yl)-1-oxobutan-2-yl)-5-(trifluoromethyl)benzamide

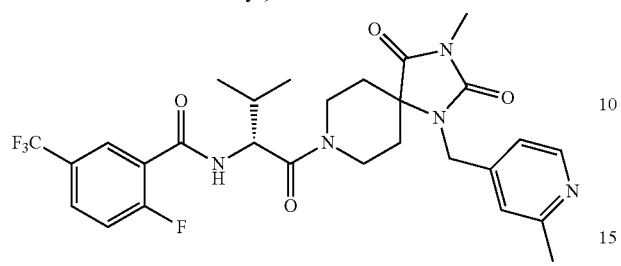

41.6 mg, yield: 43%, white solid.
LCMS (ESI): m/z=578.2 [M+H]$^+$.
$^1$H-NMR (400 MHz, CD$_3$OD): δ=1.02-1.08 (m, 6H), 1.86-2.24 (m, 5H), 2.73 (s, 3H), 3.09 (s, 3H), 3.43-3.47 (m, 1H), 3.90-3.96 (m, 1H), 4.26-4.30 (m, 1H), 4.57-4.60 (m, 1H), 4.79-4.84 (m, 3H), 7.45-7.48 (m, 1H), 7.87-8.02 (m, 4H), 8.58-8.65 (m, 1H).

Example 96

(R)—N-(1-(1-((2,3-Dihydrobenzo[b][1,4]dioxin-6-yl)methyl)-3-methyl-2,4-dioxo-1,3,8-triazaspiro[4.5]decan-8-yl)-3-methyl-1-oxobutan-2-yl)-2-fluoro-5-(trifluoromethyl)benzamide

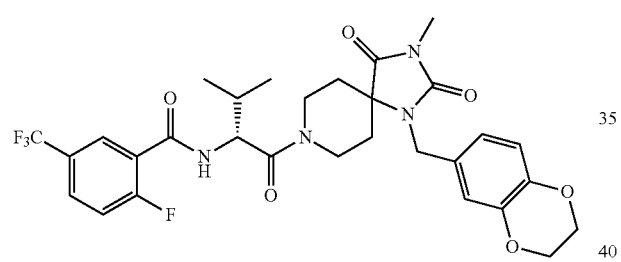

38.8 mg, yield: 22%, white solid.
LCMS (ESI): m/z=621.0 [M+H]$^+$.
$^1$H-NMR (400 MHz, CD$_3$OD): δ=1.02-1.07 (m, 6H), 1.61-1.77 (m, 3H), 2.11-2.35 (m, 2H), 3.05 (s, 3H), 3.32-3.37 (m, 2H), 3.87-3.89 (m, 1H), 4.15-4.40 (m, 4H), 4.38-4.49 (m, 3H), 4.87-4.91 (m, 1H), 6.67-6.80 (m, 3H), 7.43-7.49 (m, 1H), 7.89-8.12 (m, 2H).

Example 97

(R)-2-Fluoro-N-(1-(1-((6-methoxypyridin-3-yl)methyl)-3-methyl-2,4-dioxo-1,3,8-triazaspiro[4.5]decan-8-yl)-3-methyl-1-oxobutan-2-yl)-5-(trifluoromethyl)benzamide

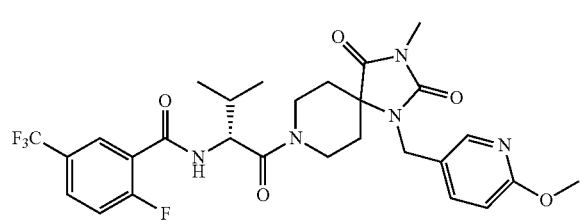 [SMILES: COc1ccc(CN2C(=O)N(C)C(=O)C23CCN(C(=O)[C@H](NC(=O)c2cc(C(F)(F)F)ccc2F)C(C)C)CC3)cn1]

61.5 mg, yield: 32%, white solid.
LCMS (ESI): m/z=594.2 [M+H]$^+$.
$^1$H-NMR (400 MHz, CD$_3$OD): δ=1.03-1.08 (m, 6H), 1.71-1.94 (m, 3H), 2.13-2.18 (m, 1H), 2.34-2.42 (m, 1H), 3.04 (s, 3H), 3.37-3.46 (m, 1H), 3.88-3.94 (m, 4H), 4.18-4.30 (m, 1H), 4.50-4.65 (m, 3H), 4.80 (s, 1H), 6.84-6.87 (m, 1H), 7.43-7.51 (m, 1H), 7.74-8.55 (m, 5H).

Example 98

(R)—N-(1-(1-((1H-Indazol-5-yl)methyl)-3-methyl-2,4-dioxo-1,3,8-triazaspiro[4.5]decan-8-yl)-3-methyl-1-oxobutan-2-yl)-2-fluoro-5-(trifluoromethyl)benzamide

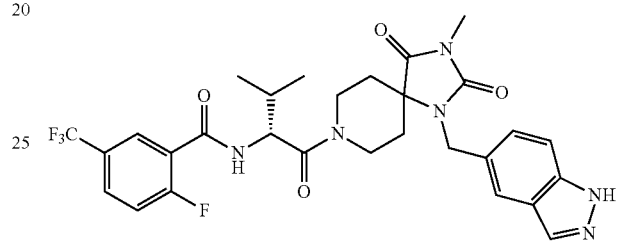

2.9 mg, yield: 7%, white solid.
LCMS (ESI): m/z=603.2 [M+H]$^+$.
$^1$H-NMR (400 MHz, CD$_3$OD): δ=0.92-1.05 (m, 6H), 1.65-2.42 (m, 5H), 3.09 (s, 3H), 3.33-3.44 (m, 2H), 3.85-4.48 (m, 2H), 4.62-4.79 (m, 2H), 4.80-4.81 (m, 1H), 7.40-7.58 (m, 3H), 7.74-7.75 (m, 1H), 7.23-8.54 (m, 3H).

Example 99

(R)—N-(1-(1-(4-Chlorobenzyl)-3-methyl-2,4-dioxo-1,3,8-triazaspiro[4.5]decan-8-yl)-3-methyl-1-oxobutan-2-yl)-2-fluoro-5-(trifluoromethyl)benzamide

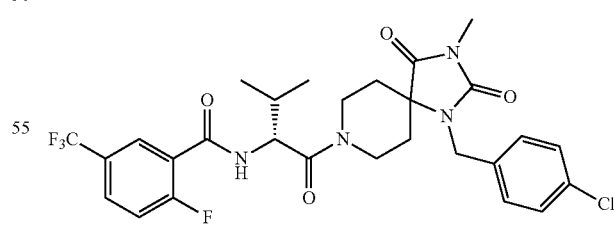

51.0 mg, yield: 47%, white solid.
LCMS (ESI): m/z=597.2 [M+H]$^+$.
$^1$H-NMR (400 MHz, CD$_3$OD): δ=1.02-1.07 (m, 6H), 1.67-2.33 (m, 5H), 3.06 (s, 3H), 3.33-3.41 (m, 1H), 3.90-4.21 (m, 2H), 4.52-4.60 (m, 2H), 4.64-4.87 (m, 2H), 7.24-7.47 (m, 5H), 7.91-8.09 (m, 2H).

Example 100

(R)-2-Fluoro-N-(3-methyl-1-(3-methyl-2,4-dioxo-1-(quinoxalin-6-ylmethyl)-1,3,8-triazaspiro[4.5]decan-8-yl)-1-oxobutan-2-yl)-5-(trifluoromethyl)benzamide

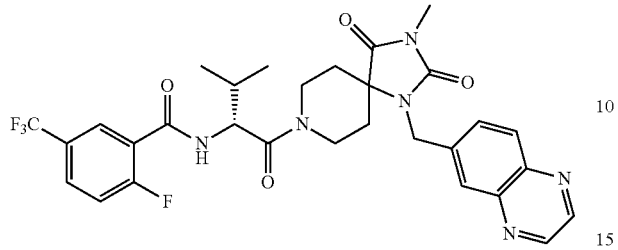

25.0 mg, yield: 20%, white solid.
LCMS (ESI): m/z=615.2 [M+H]$^+$.
$^1$H-NMR (400 MHz, CD$_3$OD): δ=1.00-1.06 (m, 6H), 1.75-2.38 (m, 5H), 3.11 (s, 3H), 3.42-3.43 (m, 1H), 3.91-4.50 (m, 3H), 4.87-4.79 (m, 2H), 4.90-5.00 (m, 1H), 7.38-7.52 (m, 1H), 7.82-7.94 (m, 2H), 7.98-8.15 (m, 3H), 8.82-8.96 (m, 2H).

Example 101

(R)—N-(1-(1-(3-Cyanobenzyl)-3-methyl-2,4-dioxo-1,3,8-triazaspiro[4.5]decan-8-yl)-3-methyl-1-oxobutan-2-yl)-2-fluoro-5-(trifluoromethyl)benzamide

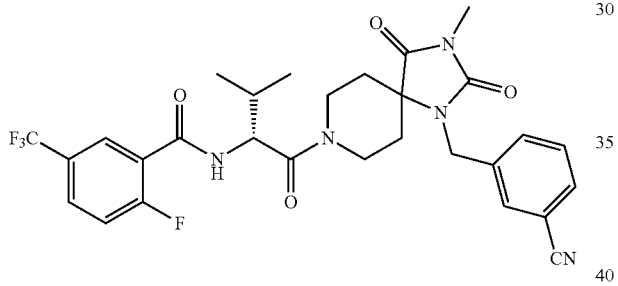

28.0 mg, yield: 18%, white solid.
LCMS (ESI): m/z=588.2 [M+H]$^+$.
$^1$H-NMR (400 MHz, CD$_3$OD): δ=1.01-1.06 (m, 6H), 1.83-2.34 (m, 5H), 3.06 (s, 3H), 3.33-3.43 (m, 1H), 3.90-4.25 (m, 2H), 4.63-4.50 (m, 3H), 4.84-4.86 (m, 1H), 7.47-7.70 (m, 5H), 7.89-8.08 (m, 2H), 8.52 (s, 1H).

Example 102

(R)-2-Fluoro-N-(1-(1-(imidazo[1,2-a]pyridin-7-ylmethyl)-3-methyl-2,4-dioxo-1,3,8-triazaspiro[4.5]decan-8-yl)-3-methyl-1-oxobutan-2-yl)-5-(trifluoromethyl)benzamide

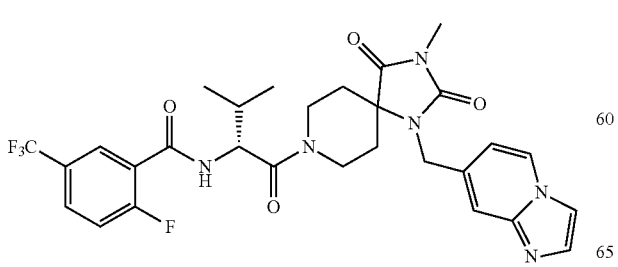

26.3 mg, yield: 16%, white solid.
LCMS (ESI): m/z=603.2 [M+H]$^+$.
$^1$H-NMR (400 MHz, CD$_3$OD): δ=1.03-1.08 (m, 6H), 1.83-2.03 (m, 3H), 2.12-2.19 (m, 1H), 2.33-2.40 (m, 1H), 3.08 (s, 3H), 3.42-3.49 (m, 1H), 3.89-3.96 (m, 1H), 4.24-4.28 (m, 1H), 4.57-4.60 (m, 1H), 4.69-4.84 (m, 3H), 7.46-7.51 (m, 1H), 7.87-8.21 (m, 6H), 8.30-8.62 (m, 1H).

Example 103

(R)-2-Fluoro-N-(3-methyl-1-(3-methyl-1-(3-(methylsulfonyl)benzyl)-2,4-dioxo-1,3,8-triazaspiro[4.5]decan-8-yl)-1-oxobutan-2-yl)-5-(trifluoromethyl)benzamide

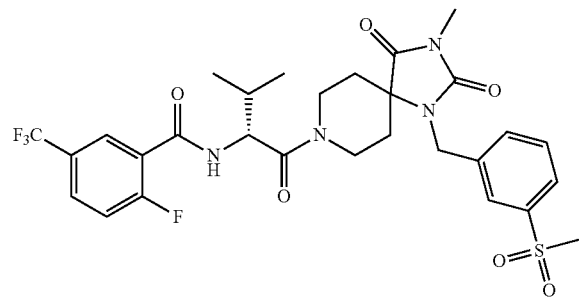 [SMILES: CC(C)[C@@H](NC(=O)c1cc(C(F)(F)F)ccc1F)C(=O)N1CCC2(CC1)C(=O)N(C)C(=O)N2Cc1cccc(S(C)(=O)=O)c1]

22.9 mg, yield: 19%, white solid.
LCMS (ESI): m/z=641.0 [M+H]$^+$.
$^1$H-NMR (400 MHz, CD$_3$OD): δ=1.02-1.07 (m, 6H), 1.74-1.91 (m, 4H), 2.28-2.35 (m, 1H), 3.07-3.14 (m, 6H), 3.43-3.49 (m, 1H), 3.87-3.94 (m, 1H), 4.11-4.28 (m, 2H), 4.51-4.55 (m, 1H), 4.64-4.78 (m, 2H), 7.45-7.57 (m, 2H), 7.62-7.72 (m, 2H), 7.83-8.09 (m, 3H).

Example 104

(R)—N-(1-(1-(3-Chlorobenzyl)-3-methyl-2,4-dioxo-1,3,8-triazaspiro[4.5]decan-8-yl)-3-methyl-1-oxobutan-2-yl)-2-fluoro-5-(trifluoromethyl)benzamide

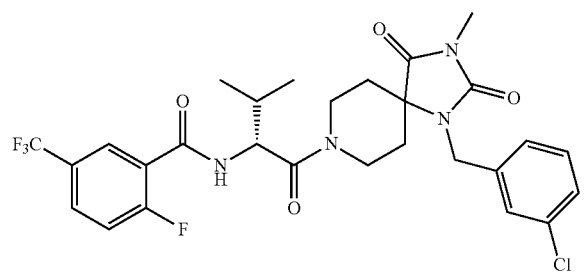 [SMILES: CC(C)[C@@H](NC(=O)c1cc(C(F)(F)F)ccc1F)C(=O)N1CCC2(CC1)C(=O)N(C)C(=O)N2Cc1cccc(Cl)c1]

13.6 mg, yield: 8%, white solid.
LCMS (ESI): m/z=597.1 [M+H]$^+$.
$^1$H-NMR (400 MHz, CD$_3$OD): δ=1.02-1.07 (m, 6H), 1.67-1.85 (m, 3H), 2.05-2.15 (m, 1H), 2.34-2.38 (m, 1H), 3.06 (s, 3H), 3.38-4.44 (m, 1H), 3.86-4.28 (m, 3H), 4.50-4.54 (m, 1H), 4.61-4.71 (m, 1H), 4.86-4.90 (m, 1H), 7.23-7.50 (m, 5H), 7.89-8.02 (m, 1H), 8.09-8.11 (m, 1H), 8.50 (br, 1H).

Example 105

(R)-2-Fluoro-N-(3-methyl-1-(3-methyl-1-((3-methyl-2-oxo-2,3-dihydrobenzo[d]oxazol-5-yl)methyl)-2,4-dioxo-1,3,8-triazaspiro[4.5]decan-8-yl)-1-oxobutan-2-yl)-5-(trifluoromethyl)benzamide

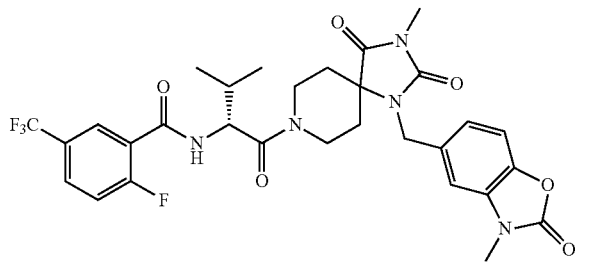 [SMILES: CC(C)[C@@H](NC(=O)c1cc(C(F)(F)F)ccc1F)C(=O)N1CCC2(CC1)C(=O)N(C)C(=O)N2Cc1ccc2oc(=O)n(C)c2c1]

36.0 mg, yield: 15%, white solid.
LCMS (ESI): m/z=634.2 [M+H]⁺.
¹H-NMR (400 MHz, CD₃OD): δ=0.92-1.06 (m, 6H), 1.68-2.37 (m, 5H), 3.06 (s, 3H), 3.28 (s, 3H), 3.30-3.36 (m, 2H), 3.86-4.24 (m, 1H), 4.62-4.70 (m, 3H), 4.85-4.87 (m, 1H), 7.06-7.16 (m, 3H), 7.41-7.46 (m, 1H), 7.99-8.09 (m, 2H).

Example 106

(R)-2-Fluoro-N-(3-methyl-1-(3-methyl-1-((2-methyl-1H-benzo[d]imidazol-6-yl)methyl)-2,4-dioxo-1,3,8-triazaspiro[4.5]decan-8-yl)-1-oxobutan-2-yl)-5-(trifluoromethyl)benzamide

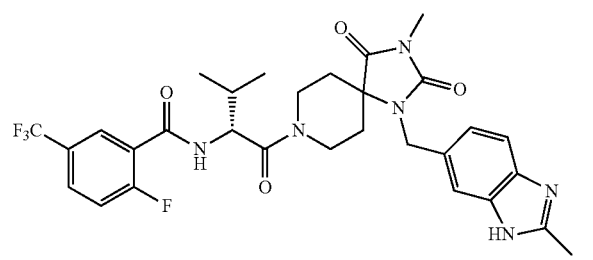

7.2 mg, yield: 6%, white solid.
LCMS (ESI): m/z=617.2 [M+H]⁺.
¹H-NMR (400 MHz, CD₃OD): δ=1.02 (m, 6H), 1.31-2.16 (m, 5H), 2.88 (m, 4H), 3.08 (s, 3H), 3.42-4.25 (m, 4H), 4.49-4.75 (m, 2H), 7.47-7.74 (m, 4H), 7.91-8.05 (m, 2H).

Example 107

(R)-2-Fluoro-N-(1-(1-(2-fluoro-5-methoxybenzyl)-3-methyl-2,4-dioxo-1,3,8-triazaspiro[4.5]decan-8-yl)-3-methyl-1-oxobutan-2-yl)-5-(trifluoromethyl)benzamide

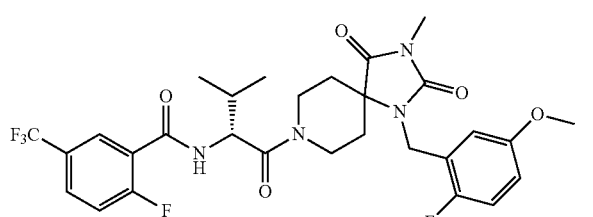

21.4 mg, yield: 18%, white solid.
LCMS (ESI): m/z=611.2 [M+H]⁺.
¹H-NMR (400 MHz, CD₃OD): δ=1.01-1.04 (m, 6H), 1.71-1.93 (m, 3H), 2.08-2.15 (m, 2H), 3.06 (s, 3H), 3.36-3.43 (m, 1H), 3.71-3.77 (m, 3H), 3.88-3.91 (m, 1H), 4.17-4.27 (m, 1H), 4.48-4.57 (m, 3H), 4.84-4.94 (m, 1H), 6.77-7.01 (m, 3H), 7.43-7.46 (m, 1H), 7.50-8.85 (m, 2H).

Example 108

(R)-2-Fluoro-N-(1-(1-(2-fluoro-4-methoxybenzyl)-3-methyl-2,4-dioxo-1,3,8-triazaspiro[4.5]decan-8-yl)-3-methyl-1-oxobutan-2-yl)-5-(trifluoromethyl)benzamide

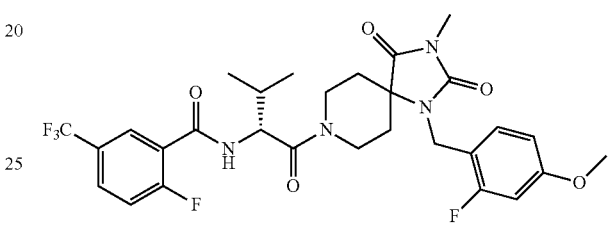

22.5 mg, yield: 5.3%, white solid.
LCMS (ESI): m/z=610.7 [M+H]⁺.
¹H-NMR (400 MHz, CD₃OD): δ=1.01-1.06 (m, 6H), 1.68-1.84 (m, 3H), 2.10-2.28 (m, 2H), 3.03 (s, 3H), 3.36-3.45 (m, 1H), 3.75-3.80 (m, 3H), 3.86-3.90 (m, 1H), 4.16-4.30 (m, 1H), 4.48-4.65 (m, 3H), 4.89-4.95 (m, 1H), 6.54-6.76 (m, 2H), 7.26-7.50 (m, 2H), 7.87-7.92 (m, 1H), 8.02-8.12 (m, 1H), 8.49-8.51 (s, 1H).

Example 109

(R)—N-(1-Cyclopropyl-2-(3-methyl-2,4-dioxo-1-(quinoxalin-6-ylmethyl)-1,3,8-triazaspiro[4.5]decan-8-yl)-2-oxoethyl)-2-fluoro-5-(trifluoromethyl)benzamide

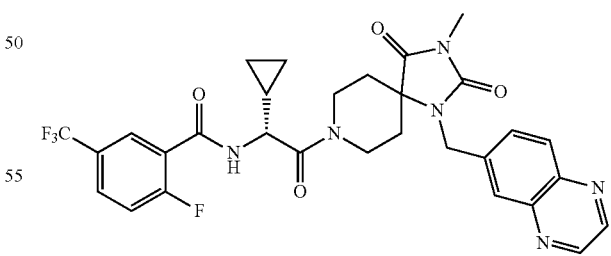

49.2 mg, yield: 34%, white solid.
LCMS (ESI): m/z=613.2 [M+H]⁺.
¹H-NMR (400 MHz, CD₃OD): δ=0.30-0.63 (m, 4H), 1.11-1.27 (m, 1H), 1.70-1.85 (m, 1H), 2.15-2.21 (m, 1H), 3.14 (s, 3H), 3.41-3.48 (m, 1H), 3.89-3.99 (m, 2H), 4.57-4.90 (m, 4H), 7.24-7.32 (m, 1H), 7.75-7.77 (m, 3H), 7.96-8.14 (m, 2H), 8.40-8.41 (m, 1H), 8.82-8.88 (m, 2H).

Example 110

(R)—N-(1-Cyclobutyl-2-(3-methyl-2,4-dioxo-1-(quinoxalin-6-ylmethyl)-1,3,8-triazaspiro[4.5]decan-8-yl)-2-oxoethyl)-2-fluoro-5-(trifluoromethyl)benzamide

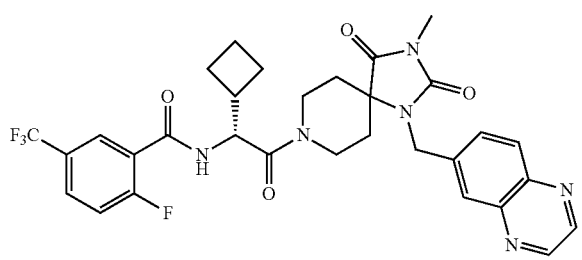 [SMILES: CN1C(=O)N(Cc2ccc3nccnc3c2)C2(CCN(C(=O)[C@H](NC(=O)c3cc(C(F)(F)F)ccc3F)C3CCC3)CC2)C1=O]

69.1 mg, yield: 26%, white solid.

LCMS (ESI): m/z=627.2 [M+H]⁺.

¹H-NMR (400 MHz, CD₃OD): δ=1.73-2.17 (m, 10H), 2.62-2.77 (m, 1H), 3.15 (s, 3H), 3.38-3.49 (m, 1H), 3.89-4.04 (m, 2H), 4.54-4.58 (m, 1H), 4.65-4.95 (m, 2H), 5.05-5.12 (m, 1H), 7.29-7.33 (m, 1H), 7.51-7.58 (m, 1H), 7.73-7.79 (m, 2H), 7.98 (s, 1H), 8.08-8.16 (m, 1H), 8.33-8.43 (m, 1H), 8.82-8.89 (m, 2H).

Example 111

(R)-2-Fluoro-N-(3-methyl-1-(3-methyl-2,4-dioxo-1-(pyrimidin-2-ylmethyl)-1,3,8-triazaspiro[4.5]decan-8-yl)-1-oxobutan-2-yl)-5-(trifluoromethyl)benzamide

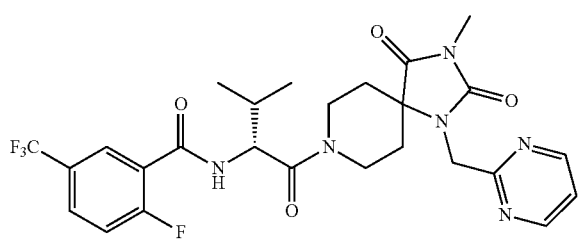 [SMILES: CC(C)[C@@H](NC(=O)c1cc(C(F)(F)F)ccc1F)C(=O)N1CCC2(CC1)C(=O)N(C)C(=O)N2Cc1ncccn1]

16.6 mg, yield: 12%, white solid.

LCMS (ESI): m/z=565.1 [M+H]⁺.

¹H-NMR (400 MHz, CD₃OD): δ=1.01-1.08 (m, 6H), 1.75-2.36 (m, 5H), 3.05 (s, 3H), 3.42-3.49 (m, 1H), 3.88-3.96 (m, 1H), 4.18-4.27 (m, 1H), 4.46-4.55 (m, 1H), 4.65-4.77 (m, 2H), 4.86-4.89 (m, 1H), 7.33-7.48 (m, 2H), 7.83-8.04 (m, 2H), 8.69-8.77 (m, 2H).

Example 112

(R)—N-(1-Cyclopentyl-2-(3-methyl-2,4-dioxo-1-(quinoxalin-6-ylmethyl)-1,3,8-triazaspiro[4.5]decan-8-yl)-2-oxoethyl)-2-fluoro-5-(trifluoromethyl)benzamide

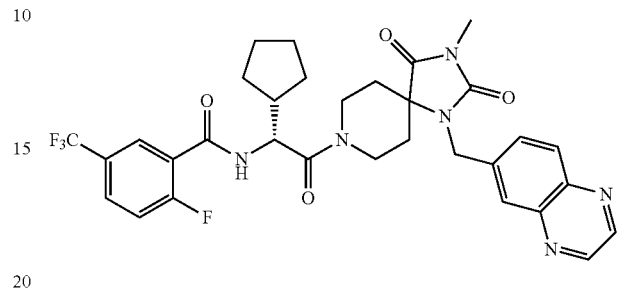

91.5 mg, yield: 55%, white solid.

LCMS (ESI): m/z=641.2 [M+H]⁺.

¹H-NMR (400 MHz, CD₃OD): δ=1.21-1.80 (m, 9H), 1.85-1.95 (m, 3H), 2.30-2.43 (m, 2H), 3.10 (s, 3H), 3.40-3.46 (m, 1H), 3.88-3.95 (m, 1H), 4.17-4.34 (m, 2H), 4.91-5.02 (m, 1H), 7.40-7.45 (m, 1H), 7.85-7.89 (m, 2H), 7.97-8.13 (m, 3H), 8.85-8.90 (m, 2H).

Example 113

(R)—N-(1-Cyclopentyl-2-(3-methyl-1-((2-methyl-[1,2,4]triazolo[1,5-a]pyridin-7-yl)methyl)-2,4-dioxo-1,3,8-triazaspiro[4.5]decan-8-yl)-2-oxoethyl)-2-fluoro-5-(trifluoromethyl)benzamide

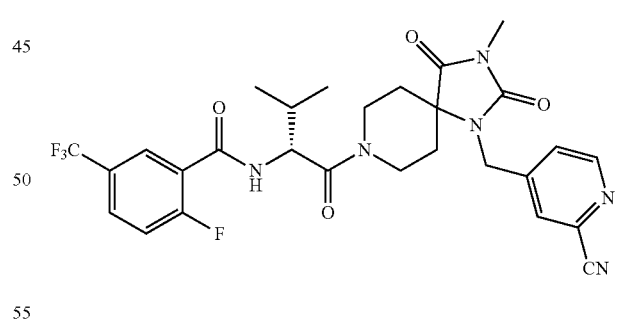

13.7 mg, yield: 5%, white solid.

LCMS (ESI): m/z=589.2 [M+H]⁺.

¹H-NMR (400 MHz, CD₃OD): δ=1.03-1.08 (m, 6H), 1.78-1.96 (m, 3H), 2.10-2.21 (m, 1H), 2.27-2.35 (m, 1H), 3.05 (s, 3H), 3.32-3.43 (m, 1H), 3.88-3.94 (m, 1H), 4.19-4.29 (m, 1H), 4.34-4.58 (m, 1H), 4.67-4.73 (m, 2H), 4.83-4.85 (m, 1H, contained in solvent signal), 7.43-7.50 (m, 1H), 7.80-7.78 (m, 1H), 7.85-7.92 (m, 1H), 7.98-8.08 (m, 2H), 8.51-8.55 (m, 1H), 8.71-8.73 (m, 1H).

Example 114

(R)-2-Fluoro-N-(3-methyl-1-(3-methyl-1-((2-methyl-[1,2,4]triazolo[1,5-a]pyridin-7-yl)methyl)-2,4-dioxo-1,3,8-triazaspiro[4.5]decan-8-yl)-1-oxobutan-2-yl)-5-(trifluoromethyl)benzamide

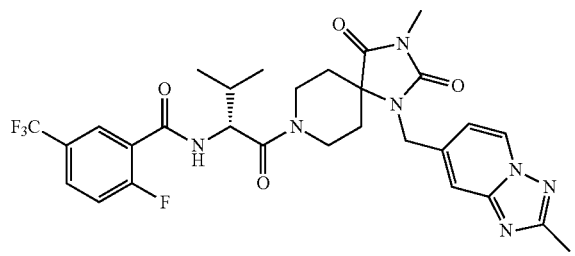 [SMILES: Cc1nc2cc(CN3C(=O)N(C)C(=O)C34CCN(C(=O)[C@H](NC(=O)c3cc(C(F)(F)F)ccc3F)C(C)C)CC4)ccn2n1]

53.7 mg, yield: 18%, white solid.

LCMS (ESI): m/z=618.2 [M+H]$^+$.

$^1$H-NMR (400 MHz, CD$_3$OD): δ=0.98-1.06 (m, 6H), 1.84-1.97 (m, 3H), 2.12-2.16 (m, 1H), 2.26-2.34 (m, 1H), 2.60 (s, 3H), 3.08 (s, 3H), 3.41-3.48 (m, 1H), 3.89-3.96 (m, 1H), 4.19-4.28 (m, 1H), 4.51-4.58 (m, 1H), 4.75-4.80 (m, 2H), 4.84-4.86 (m, 1H, contained in solvent signal), 7.27-7.36 (m, 1H), 7.43-7.48 (m, 1H), 7.71-7.76 (m, 1H), 7.88-7.91 (m, 1H), 8.77-8.71 (m, 1H), 8.06-8.01 (m, 1H).

Example 115

(R)-2-Fluoro-N-(3-methyl-1-(3-methyl-1-((1-methyl-1H-pyrazol-4-yl)methyl)-2,4-dioxo-1,3,8-triazaspiro[4.5]decan-8-yl)-1-oxobutan-2-yl)-5-(trifluoromethyl)benzamide

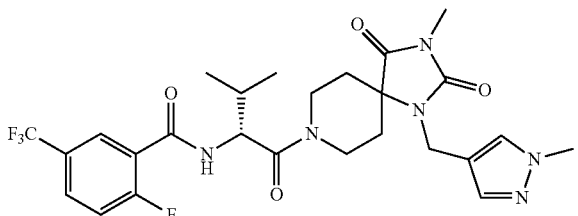

2.5 mg, yield: 6%, white solid.

LCMS (ESI): m/z=567.2 [M+H]$^+$.

$^1$H-NMR (400 MHz, CD$_3$OD): δ=1.04-1.09 (m, 6H), 1.69-1.76 (m, 2H), 1.95-2.03 (m, 1H), 2.14-2.21 (m, 1H), 2.47-2.99 (m, 1H), 3.03 (s, 3H), 3.40-3.46 (m, 1H), 3.81 (s, 3H), 3.86-3.93 (m, 1H), 4.26-4.58 (m, 3H), 4.86-4.95 (m, 2H), 7.46-7.51 (m, 2H), 7.60-7.64 (m, 1H), 7.91 (m, 1H), 8.03-8.11 (m, 1H), 8.55 (m, 1H).

Example 116

(R)-2-Fluoro-N-(3-methyl-1-(3-methyl-1-((2-methylbenzo[d]oxazol-5-yl)methyl)-2,4-dioxo-1,3,8-triazaspiro[4.5]decan-8-yl)-1-oxobutan-2-yl)-5-(trifluoromethyl)benzamide

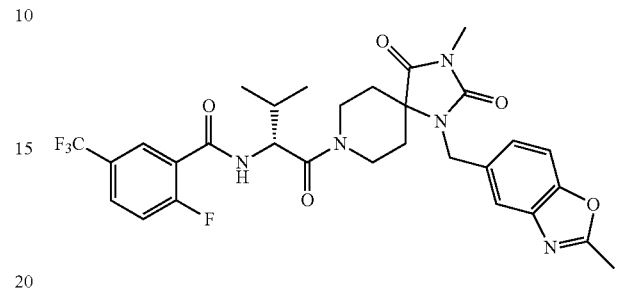

55.0 mg, yield: 28%, white solid.

LCMS (ESI): m/z=618.0 [M+H]$^+$.

$^1$H-NMR (400 MHz, CD$_3$OD): δ=0.94-1.10 (m, 6H), 1.67-1.90 (m, 3H), 2.08-2.40 (m, 2H), 2.59-2.71 (m, 3H), 3.08 (s, 3H), 3.33-3.42 (m, 1H), 3.92-4.26 (m, 3H), 4.48-4.71 (m, 3H), 7.37-7.61 (m, 4H), 7.85-8.06 (m, 2H).

Example 117

(R)-2-Fluoro-N-(3-methyl-1-(3-methyl-1-((4-methylthiazol-2-yl)methyl)-2,4-dioxo-1,3,8-triazaspiro[4.5]decan-8-yl)-1-oxobutan-2-yl)-5-(trifluoromethyl)benzamide

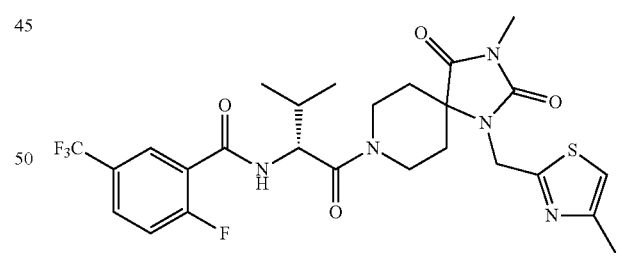

40.0 mg, yield: 22%, white solid.

LCMS (ESI): m/z=584.2 [M+H]$^+$.

$^1$H-NMR (400 MHz, CD$_3$OD): δ=1.05 (m, 6H), 1.76-2.01 (m, 3H), 2.17-2.19 (m, 2H), 2.39-2.41 (m, 3H), 3.05 (s, 3H), 3.44-3.92 (m, 2H), 4.28-4.57 (m, 2H), 4.85-4.87 (m, 2H), 4.91-5.01 (m, 1H), 7.12-7.15 (m, 1H), 7.46-7.52 (m, 1H), 7.85-8.07 (m, 2H).

Example 118

(R)-2-Fluoro-N-(3-methyl-1-(3-methyl-1-((2-methylbenzo[d]oxazol-6-yl)methyl)-2,4-dioxo-1,3,8-triazaspiro[4.5]decan-8-yl)-1-oxobutan-2-yl)-5-(trifluoromethyl)benzamide

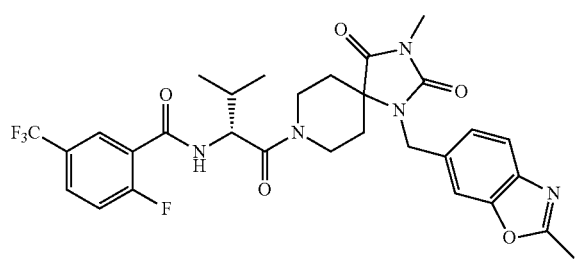 [SMILES: Cc1nc2ccc(CN3C(=O)N(C)C(=O)C34CCN(C(=O)[C@H](NC(=O)c3cc(C(F)(F)F)ccc3F)C(C)C)CC4)cc2o1]

11.5 mg, yield: 11%, white solid.

LCMS (ESI): m/z=544.1 [M+H]$^+$.

$^1$H-NMR (400 MHz, CD$_3$OD): δ=0.90-1.03 (m, 6H), 1.65-2.34 (m, 5H), 2.59-2.64 (m, 3H), 3.05 (s, 3H), 3.32-3.40 (m, 1H), 3.85-3.90 (m, 1H), 4.14-4.23 (m, 1H), 4.46-4.68 (m, 1H), 4.72-4.78 (m, 2H), 4.81-4.86 (m, 1H), 7.33-7.42 (m, 1H), 7.46-7.51 (m, 2H), 8.20-8.25 (m, 1H), 7.78-7.80 (m, 2H).

Example 119

(R)—N-(1-(1-(2-Chloro-4-methoxybenzyl)-3-methyl-2,4-dioxo-1,3,8-triazaspiro[4.5]decan-8-yl)-3-methyl-1-oxobutan-2-yl)-2-fluoro-5-(trifluoromethyl)benzamide

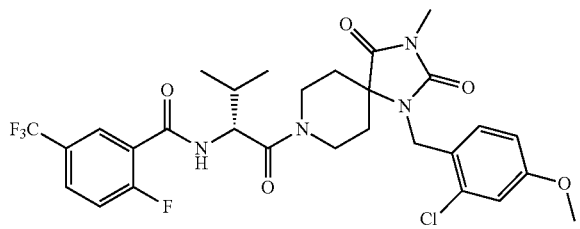 [SMILES: COc1ccc(CN2C(=O)N(C)C(=O)C23CCN(C(=O)[C@H](NC(=O)c2cc(C(F)(F)F)ccc2F)C(C)C)CC3)c(Cl)c1]

38.5 mg, yield: 25%, white solid.

LCMS (ESI): m/z=627.1 [M+H]$^+$.

$^1$H-NMR (400 MHz, CD$_3$OD): δ=1.00-1.04 (m, 6H), 1.73-1.82 (m, 3H), 2.05-2.14 (m, 2H), 3.06 (s, 3H), 3.32-3.39 (m, 1H), 3.75-3.81 (m, 3H), 3.87-3.90 (m, 1H), 4.22-4.28 (m, 2H), 4.46-4.59 (m, 2H), 4.91-4.93 (m, 1H), 6.78-6.88 (m, 2H), 7.39-7.90 (m, 2H), 8.02-8.04 (m, 1H), 8.10-8.12 (m, 1H).

Example 120

(R)-2-Fluoro-N-(3-methyl-1-(3-methyl-1-((1-methyl-6-oxo-1,6-dihydropyridin-3-yl)methyl)-2,4-dioxo-1,3,8-triazaspiro[4.5]decan-8-yl)-1-oxobutan-2-yl)-5-(trifluoromethyl)benzamide

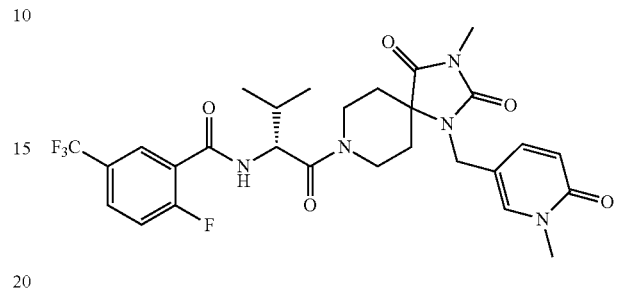

50.0 mg, yield: 27%, white solid.

LCMS (ESI): m/z=594.2 [M+H]$^+$.

$^1$H-NMR (400 MHz, CD$_3$OD): δ=1.07-1.09 (m, 6H), 1.69-2.08 (m, 3H), 2.16-2.42 (m, 2H), 3.04 (s, 3H), 3.52-3.91 (m, 6H), 4.31-4.37 (m, 2H), 4.40-4.66 (m, 1H), 4.86-4.90 (m, 1H), 6.53-6.55 (m, 1H), 7.49-7.78 (m, 3H), 7.86-7.95 (m, 1H), 8.11-8.13 (m, 1H).

Example 121

(R)—N-(1-(1-((1-Acetylazetidin-3-yl)methyl)-3-methyl-2,4-dioxo-1,3,8-triazaspiro[4.5]decan-8-yl)-3-methyl-1-oxobutan-2-yl)-2-fluoro-5-(trifluoromethyl)benzamide

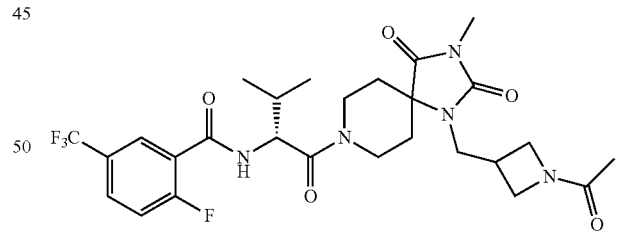

40.0 mg, yield: 32%, white solid.

LCMS (ESI): m/z=584.2 [M+H]$^+$.

$^1$H-NMR (400 MHz, CD$_3$OD): δ=1.04-1.16 (m, 6H), 1.77-2.38 (m, 8H), 2.99-3.01 (m, 4H), 3.42-3.56 (m, 4H), 3.76-4.09 (m, 4H), 4.21-4.32 (m, 1H), 4.55-4.62 (m, 1H), 4.89-5.00 (m, 1H), 7.45-7.50 (m, 1H), 7.89-7.91 (m, 1H), 8.05-8.06 (m, 1H).

Example 122

(R)—N-(1-(1,3-Dimethyl-2,4-dioxo-1,3,8-triazaspiro[4.5]decan-8-yl)-3-methyl-1-oxobutan-2-yl)-2-fluoro-5-(trifluoromethyl)benzamide

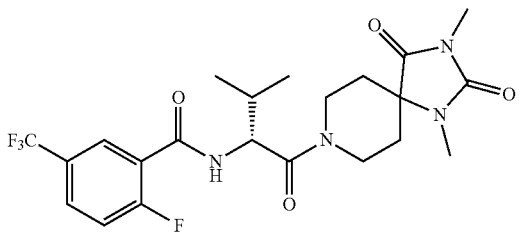 [SMILES: CC(C)[C@@H](NC(=O)c1cc(C(F)(F)F)ccc1F)C(=O)N1CCC2(CC1)C(=O)N(C)C(=O)N2C]

70 mg, 75% yield, white solid.
LCMS (ESI): m/z=487.1 [M+H]⁺.
¹H-NMR (400 MHz, CDCl₃): δ=1.01-1.11 (m, 6H), 1.69-2.19 (m, 5H), 2.85-2.89 (m, 3H), 3.06 (s, 3H), 3.44-3.52 (m, 1H), 3.96-4.13 (m, 2H), 4.67-4.71 (m, 1H), 5.09-5.12 (m, 1H), 7.29-7.34 (m, 1H), 7.52-7.57 (m, 1H), 7.77-7.80 (m, 1H), 8.35-8.37 (m, 1H).

Example 123

(R)—N-(1-(1-Ethyl-3-methyl-2,4-dioxo-1,3,8-triazaspiro[4.5]decan-8-yl)-3-methyl-1-oxobutan-2-yl)-2-fluoro-5-(trifluoromethyl)benzamide

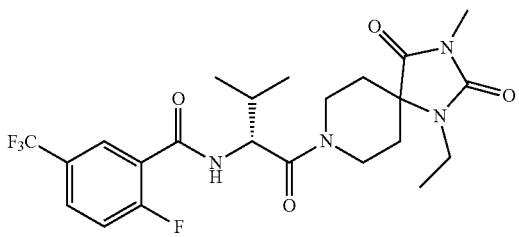 [SMILES: CCN1C(=O)N(C)C(=O)C12CCN(C(=O)[C@H](NC(=O)c1cc(C(F)(F)F)ccc1F)C(C)C)CC2]

62 mg, 45% yield, white solid.
LCMS (ESI): m/z=501.2 [M+H]⁺.
¹H-NMR (400 MHz, CDCl₃): δ=1.02-1.12 (m, 6H), 1.21-1.29 (m, 3H), 1.73-1.91 (m, 3H), 2.01-2.19 (m, 2H), 3.05 (s, 3H), 3.26-3.32 (m, 2H), 3.46-3.53 (m, 1H), 4.00-4.12 (m, 2H), 4.67-4.69 (m, 1H), 5.09-5.15 (m, 1H), 7.29-7.35 (m, 1H), 7.53-7.58 (m, 1H), 7.78-7.79 (m, 1H), 8.35-8.36 (m, 1H).

Example 124

(R)-2-Fluoro-N-(1-(1-isopentyl-3-methyl-2,4-dioxo-1,3,8-triazaspiro[4.5]decan-8-yl)-3-methyl-1-oxobutan-2-yl)-5-(trifluoromethyl)benzamide

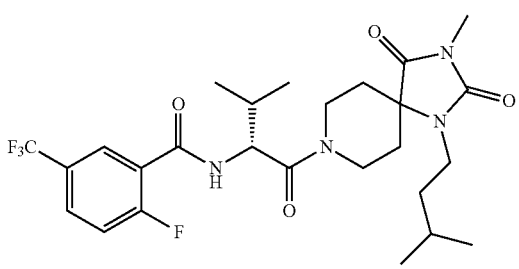 [SMILES: CC(C)CCN1C(=O)N(C)C(=O)C12CCN(C(=O)[C@H](NC(=O)c1cc(C(F)(F)F)ccc1F)C(C)C)CC2]

97 mg, 37% yield, white solid.
LCMS (ESI): m/z=543.2 [M+H]⁺.
¹H-NMR (400 MHz, CDCl₃): δ=0.91-1.12 (m, 12H), 1.50-1.95 (m, 6H), 2.03-2.18 (m, 2H), 3.15 (s, 3H), 3.18-3.22 (m, 2H), 3.43-3.51 (m, 1H), 3.97-4.10 (m, 2H), 4.67-4.70 (m, 1H), 5.08-5.14 (m, 1H), 7.29-7.34 (m, 1H), 7.46-7.51 (m, 1H), 7.75-7.79 (m, 1H), 8.36-8.37 (m, 1H).

Example 125

(R)—N-(1-(1-Cyclopentyl-3-methyl-2,4-dioxo-1,3,8-triazaspiro[4.5]decan-8-yl)-3-methyl-1-oxobutan-2-yl)-2-fluoro-5-(trifluoromethyl)benzamide

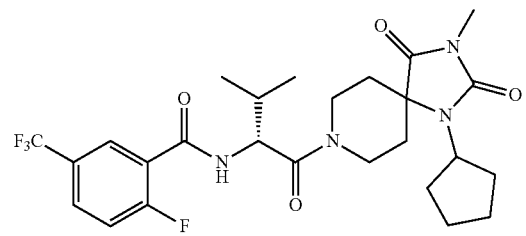 [SMILES: CC(C)[C@@H](NC(=O)c1cc(C(F)(F)F)ccc1F)C(=O)N1CCC2(CC1)C(=O)N(C)C(=O)N2C1CCCC1]

36 mg, 18% yield, white solid.
LCMS (ESI): m/z=541.2 [M+H]⁺.
¹H-NMR (400 MHz, CDCl₃): δ=0.94-1.16 (m, 6H), 1.47-1.60 (m, 2H), 1.67-1.98 (m, 7H), 2.06-2.23 (m, 4H), 3.02 (s, 3H), 3.36-350 (m, 2H), 3.96-4.06 (m, 2H), 4.66-4.69 (m, 1H), 5.09-5.15 (m, 1H), 7.29-7.35 (m, 1H), 7.47-7.58 (m, 1H), 7.76-7.83 (m, 1H), 8.33-8.40 (m, 1H).

Example 126

(R)-2-Fluoro-N-(3-methyl-1-(3-methyl-2,4-dioxo-1,3,8-triazaspiro[4.5]decan-8-yl)-1-oxobutan-2-yl)-5-(trifluoromethyl)benzamide

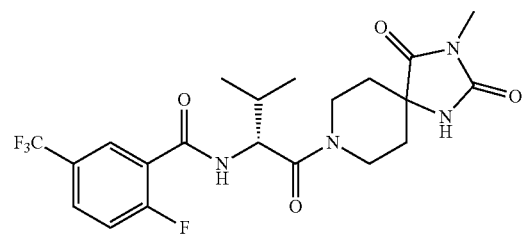 [SMILES: CC(C)[C@@H](NC(=O)c1cc(C(F)(F)F)ccc1F)C(=O)N1CCC2(CC1)NC(=O)N(C)C2=O]

58 mg, 35% yield, white solid.
LCMS (ESI): m/z=473.1 [M+H]⁺.
¹H-NMR (400 MHz, CDCl₃): δ=1.00-1.09 (m, 6H), 1.70-1.91 (m, 2H), 1.89-2.14 (m, 3H), 3.04 (s, 3H), 3.35-3.60 (m, 1H), 3.75-3.78 (m, 1H), 4.07-4.11 (m, 1H), 4.12-4.41 (m, 1H), 5.07-5.16 (m, 1H), 7.05 (s, 1H), 7.29-7.37 (m, 1H), 7.58-7.62 (m, 1H), 7.76-7.80 (m, 1H), 8.31-8.36 (m, 1H).

Example 127

(R)-Methyl-4-(8-(2-(2-fluoro-5-(trifluoromethyl)benzamido)-3-methylbutanoyl)-3-methyl-2,4-dioxo-1,3,8-triazaspiro[4.5]decan-1-yl)phenylcarbamate

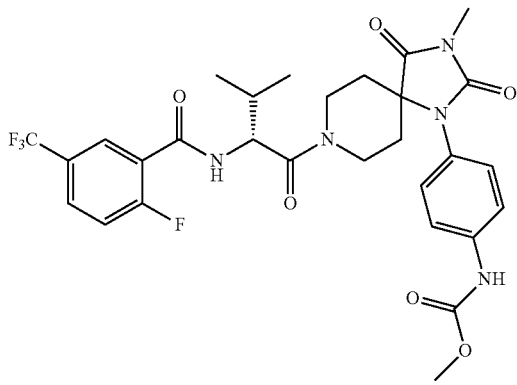 [SMILES: COC(=O)Nc1ccc(N2C(=O)N(C)C(=O)C23CCN(C(=O)[C@H](NC(=O)c2cc(C(F)(F)F)ccc2F)C(C)C)CC3)cc1]

Representative Scheme:

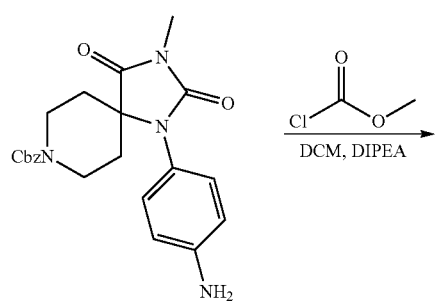

Example 86-f

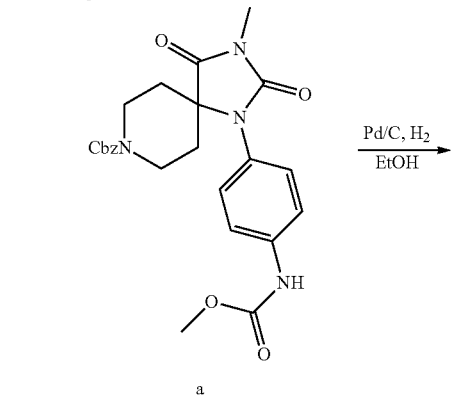

a

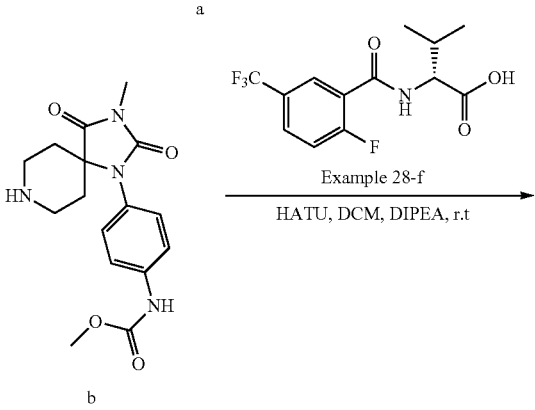

b

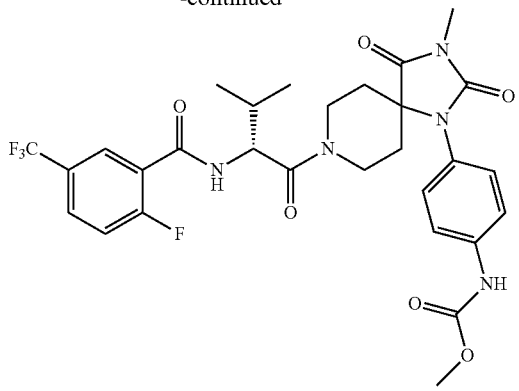

Representative General Procedure

Benzyl-1-(4-(methoxycarbonylamino)phenyl)-3-methyl-2,4-dioxo-1,3,8-triazaspiro[4.5]decane-8-carboxylate

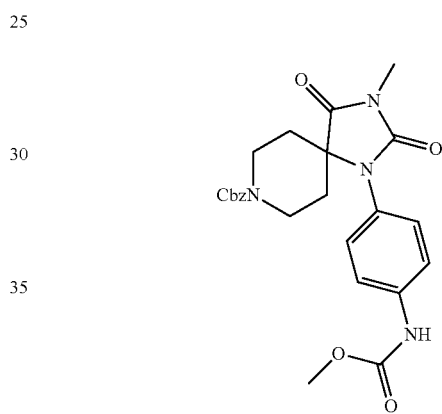

To a solution of benzyl-1-(4-aminophenyl)-3-methyl-2,4-dioxo-1,3,8-triazaspiro[4.5]decane-8-carboxylate (prepared as described in Example 86-f) (150 mg, 0.37 mmol) in dichloromethane (15 mL) was added triethylamine (92 mg, 0.92 mmol). The resulting mixture was cooled to 0° C. and methyl chloroformate (42 mg, 0.44 mmol) was added. The resulting mixture was stirred for 1 hour. After quenching by addition of ice-water (10 mL), the resulting mixture was extracted with dichloromethane (3×10 mL) and the combined organic layers were dried over anhydrous sodium sulfate and concentrated under reduced pressure. The residue was purified by silica gel column chromatography eluting with dichloromethane:methanol=20:1 to afford benzyl-1-(4-(methoxycarbonylamino)phenyl)-3-methyl-2,4-dioxo-1,3,8-triazaspiro[4.5]decane-8-carboxylate as a white solid (95 mg, 51%).

LCMS (ESI): m/z=467.2 [M+H]$^+$.

Methyl-4-(3-methyl-2,4-dioxo-1,3,8-triazaspiro[4.5]decan-1-yl)phenylcarbamate

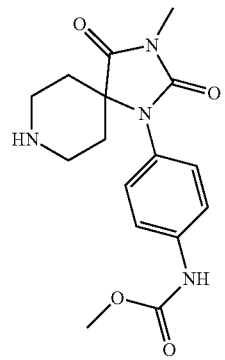 [SMILES: COC(=O)Nc1ccc(N2C(=O)N(C)C(=O)C23CCNCC3)cc1]

To a solution of benzyl-1-(4-(methoxycarbonylamino)phenyl)-3-methyl-2,4-dioxo-1,3,8-triazaspiro[4.5]decane-8-carboxylate (95 mg, 0.20 mmol) in ethanol (15 mL) was added 5% palladium on carbon (15 mg). After stirring for 3 hours, the mixture was filtered. The filtrate was concentrated under reduced pressure to afford methyl-4-(3-methyl-2,4-dioxo-1,3,8-triazaspiro[4.5]decan-1-yl)phenylcarbamate as a white solid (55 mg, 82%).

LCMS (ESI): m/z=333.2 [M+H]$^+$.

(R)-Methy-4-(8-(2-(2-fluoro-5-(trifluoromethyl)benzamido)-3-methylbutanoyl)-3-methyl-2,4-dioxo-1,3,8-triazaspiro[4.5]decan-1-yl)phenylcarbamate

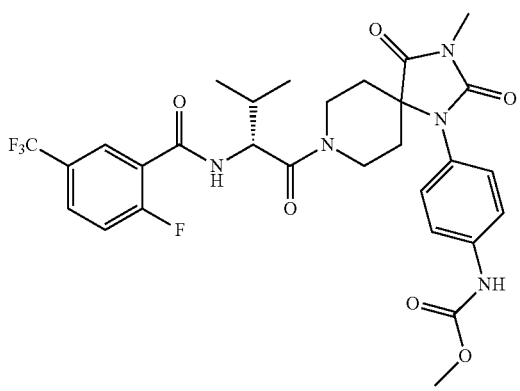 [SMILES: COC(=O)Nc1ccc(N2C(=O)N(C)C(=O)C23CCN(C(=O)[C@H](NC(=O)c2cc(C(F)(F)F)ccc2F)C(C)C)CC3)cc1]

To a solution of methyl-4-(3-methyl-2,4-dioxo-1,3,8-triazaspiro[4.5]decan-1-yl)phenylcarbamate (55 mg, 0.17 mmol) in dichloromethane (5 mL) was added sequentially (R)-2-(2-fluoro-5-(trifluoromethyl)benzamido)-3-methylbutanoic acid (prepared as described in Example 28-f) (51 mg, 0.17 mmol), 1-[bis(dimethylamino)methylene]-1H-1,2,3-triazolo[4,5-b]pyridinium-3-oxide hexafluorophosphate (HATU) (90 mg, 0.23 mmol) and N,N-diisopropylethylamine (32 mg, 0.23 mmol). The reaction was stirred for 2 hours at room temperature before quenching with ice-water (5 mL). The mixture was extracted with ethyl acetate (3×10 mL) and the combined organic layers were dried over anhydrous sodium sulfate and concentrated under reduced pressure. The residue was purified by prep-TLC with dichloromethane:methanol=15:1 to afford (R)-methyl-4-(8-(2-(2-fluoro-5-(trifluoromethyl)benzamido)-3-methylbutanoyl)-3-methyl-2,4-dioxo-1,3,8-triazaspiro[4.5]decan-1-yl)phenylcarbamate as a white solid (16 mg, 15%).

LCMS (ESI): m/z=622.1 [M+H]$^+$.

$^1$H-NMR (400 MHz, CD$_3$OD): δ=0.82-1.09 (m, 6H), 1.58-2.47 (m, 5H), 3.08 (s, 3H), 3.43-3.54 (m, 1H), 3.76-3.77 (m, 3H), 3.91-4.01 (m, 1H), 4.16-4.53 (m, 3H), 7.11-7.18 (m, 1H), 7.18-7.23 (m, 1H), 7.40-7.47 (m, 2H), 7.58-7.61 (m, 1H), 7.87-8.00 (m, 2H).

The following compound was synthesized following the general procedure described above:

Example 128

(R)—N-(1-(1-(4-(Cyclopropanecarboxamido)phenyl)-3-methyl-2,4-dioxo-1,3,8-triazaspiro[4.5]decan-8-yl)-3-methyl-1-oxobutan-2-yl)-2-fluoro-5-(trifluoromethyl)benzamide

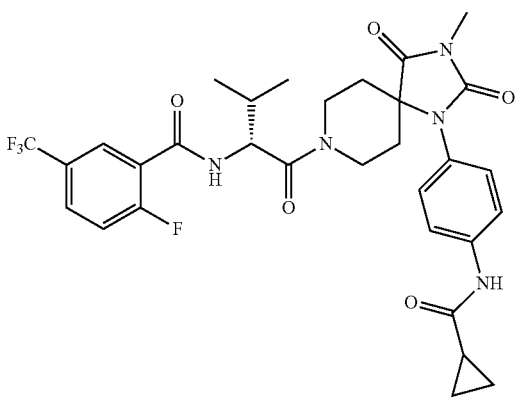 [SMILES: CC(C)[C@@H](NC(=O)c1cc(C(F)(F)F)ccc1F)C(=O)N1CCC2(CC1)C(=O)N(C)C(=O)N2c1ccc(NC(=O)C2CC2)cc1]

44.2 mg, yield: 22%, white solid

LCMS (ESI): m/z=632.1 [M+H]$^+$.

$^1$H-NMR (400 MHz, CD$_3$OD): δ=0.72-1.05 (m, 10H), 1.66-2.27 (m, 6H), 3.08 (s, 3H), 3.46-3.59 (m, 1H), 3.90-3.54 (m, 3H), 4.83-4.87 (m, 1H), 7.09-7.32 (m, 2H), 7.34-7.52 (m, 1H), 7.59-7.74 (m, 2H), 7.81-8.05 (m, 2H).

Example 129

(R)-3-Methyl-N-(2-(3-methyl-4-oxo-1-phenyl-1,3,8-triazaspiro[4.5]decan-8-yl)-2-oxo-1-(tetrahydro-2H-pyran-4-yl)ethyl)benzamide

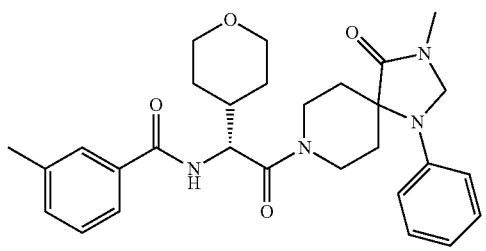 [SMILES: Cc1cccc(C(=O)N[C@@H](C(=O)N2CCC3(CC2)C(=O)N(C)CN3c2ccccc2)C2CCOCC2)c1]

Representative Scheme:
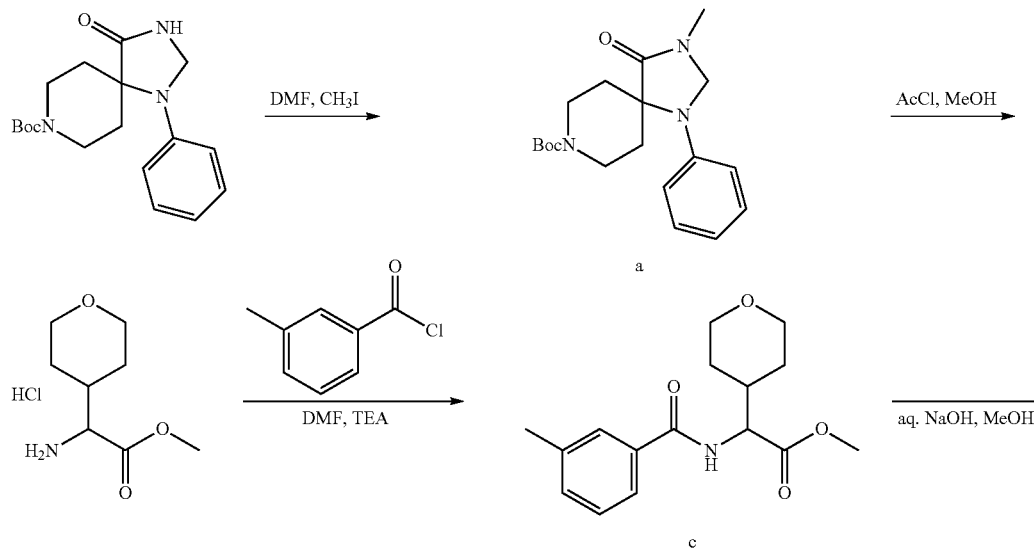
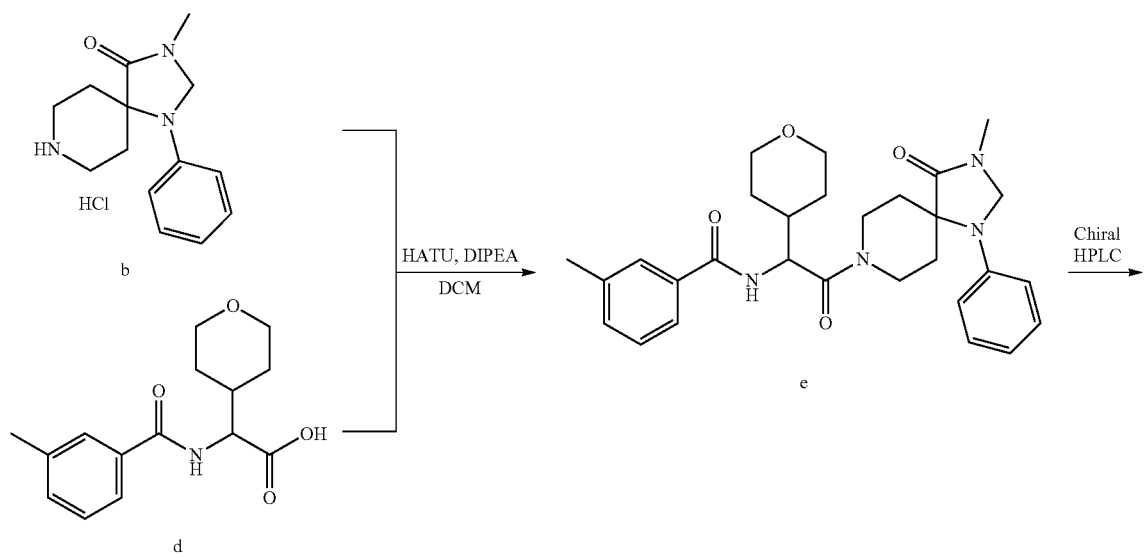
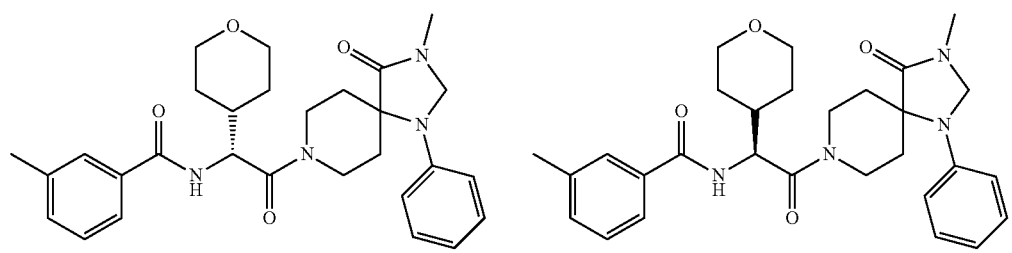

Representative General Procedure tert-Butyl-3-methyl-4-oxo-1-phenyl-1,3,8-triazaspiro[4.5]decane-8-carboxylate

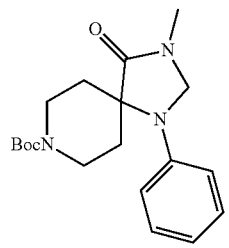 [SMILES: CN1CN(c2ccccc2)C2(CCN(C(=O)OC(C)(C)C)CC2)C1=O]

To a solution of tert-butyl-4-oxo-1-phenyl-1,3,8-triazaspiro[4.5]decane-8-carboxylate (920 mg, 2.78 mmol) in N,N-dimethylformamide (10 mL) was added sodium hydride (138 mg, 60% in oil, 3.34 mmol) at 0° C. After stirring for 15 minutes, iodomethane (789 mg, 5.56 mmol) was added. The resulting mixture was stirred for 15 minutes at room temperature and the reaction was quenched with ice-water (10 mL). The mixture was extracted with ethyl acetate (3×50 mL). The combined organic layers were dried over anhydrous sodium sulfate and concentrated under reduced pressure. The residue was purified by silica gel column chromatography eluting with ethyl acetate:petroleum ether=1:3 to afford tert-butyl-3-methyl-4-oxo-1-phenyl-1,3,8-triazaspiro[4.5]decane-8-carboxylate as a white solid (900 mg, 93%).

LCMS (ESI): m/z=346.4 [M+H]$^+$.

$^1$H-NMR (300 MHz, CDCl$_3$): δ=1.51, (s, 9H), 1.54-1.67 (m, 2H), 2.56-2.57 (m, 2H), 3.01 (s, 3H), 3.50-3.64 (m, 2H), 3.96-4.12 (m, 2H), 4.69-4.75 (m, 2H), 6.72-6.77 (m, 2H), 6.83-6.87 (m, 1H), 7.22-7.25 (m, 1H), 7.27-7.28 (m, 1H).

3-Methyl-1-phenyl-1,3,8-triazaspiro[4.5]decan-4-one hydrochloride

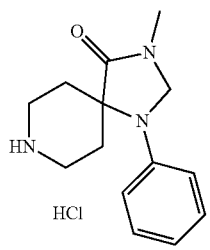 [SMILES: CN1CN(c2ccccc2)C2(CCNCC2)C1=O ; Cl]

To a solution of tert-Butyl-3-methyl-4-oxo-1-phenyl-1,3,8-triazaspiro[4.5]decane-8-carboxylate (300 mg, 1.89 mmol) in methanol (50 mL) was added dropwise acetyl chloride (1.49 g, 18.87 mmol). The resulting mixture was stirred for 2 hours. The precipitate was collected by filtration and dried under reduced pressure to afford 3-methyl-1-phenyl-1,3,8-triazaspiro[4.5]decan-4-one hydrochloride as a white solid (173 mg, 70%).

LCMS (ESI): m/z=246.4 [M+H]$^+$.

Methyl-2-(3-methylbenzamido)-2-(tetrahydro-2H-pyran-4-yl)acetate

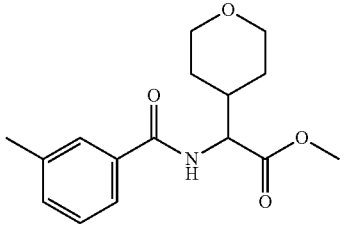

To a suspension of methyl-2-amino-2-(tetrahydro-2H-pyran-4-yl)acetate hydrochloride (210 mg, 1.0 mmol) in dichloromethane (20 mL) was added triethylamine (303 mg, 3.0 mmol). To the mixture was added dropwise a solution of 3-methylbenzoyl chloride (170 mg, 1.1 mmol) in dichloromethane (5 mL) at 0° C. The mixture was stirred for 1 hour before the reaction was quenched with ice-water (10 mL). The organic layer was collected and the aqueous layer was extracted with ethyl acetate (3×20 mL). The combined organic layers were dried over anhydrous sodium sulfate and the solvent was removed under reduced pressure. The residue was purified by silica gel column chromatography eluting with ethyl acetate:petroleum ether=1:1 to afford methyl-2-(3-methylbenzamido)-2-(tetrahydro-2H-pyran-4-yl)acetate as a colorless oil (200 mg, 68%).

LCMS (ESI): m/z=292.1 [M+H]$^+$.

$^1$H-NMR (300 MHz, CDCl$_3$): δ=1.45-1.71 (m, 4H), 2.10-2.25 (m, 1H), 2.41 (s, 3H), 3.31-3.46 (m, 2H), 3.80 (s, 3H), 3.91-4.06 (m, 2H), 4.83-4.94 (m, 1H), 6.61-6.75 (m, 1H), 7.31-7.34 (m, 2H), 7.51-7.68 (m, 2H).

2-(3-Methylbenzamido)-2-(tetrahydro-2H-pyran-4-yl)acetic Acid

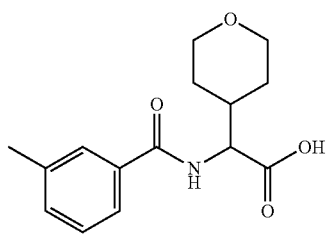 [SMILES: Cc1cccc(C(=O)NC(C(=O)O)C2CCOCC2)c1]

To a solution of methyl-2-(3-methylbenzamido)-2-(tetrahydro-2H-pyran-4-yl)acetate (200 mg, 0.68 mmol) in methanol (10 mL) was added a 10% aqueous sodium hydroxide solution (5 mL). The reaction was heated at reflux for 2 hours before it was cooled to room temperature. The pH of the mixture was adjusted to 2 by addition of a 10% aqueous hydrochloric acid solution. The resulting mixture was dried over anhydrous sodium sulfate and the solvent was removed under reduced pressure to afford 2-(3-methylbenzamido)-2-(tetrahydro-2H-pyran-4-yl)acetic acid as a thick oil (180 mg, crude), which used directly in the next step without further purification.

LCMS (ESI): m/z=278.1 [M+H]$^+$.

3-Methyl-N-(2-(3-methyl-4-oxo-1-phenyl-1,3,8-triazaspiro[4.5]decan-8-yl)-2-oxo-1-(tetrahydro-2H-pyran-4-yl)ethyl)benzamide

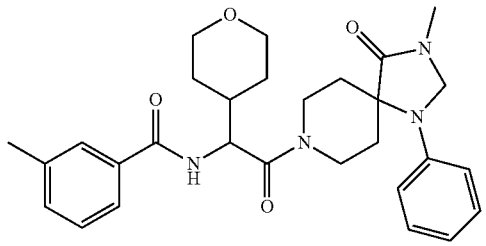 [SMILES: Cc1cccc(C(=O)NC(C(=O)N2CCC3(CC2)C(=O)N(C)CN3c2ccccc2)C2CCOCC2)c1]

To a solution of 3-methyl-1-phenyl-1,3,8-triazaspiro[4.5]decan-4-one hydrochloride (106 mg, 0.379 mmol) in dichloromethane (10 mL) was added sequentially 2-(3-methylbenzamido)-2-(tetrahydro-2H-pyran-4-yl)acetic acid (70 mg, 0.25 mmol), 1-[bis(dimethylamino)methylene]-1H-1,2,3-triazolo[4,5-b]pyridinium-3-oxide hexafluorophosphate (HATU) (144 mg, 0.38 mmol) and N,N-diisopropylethylamine (98 mg, 0.75 mmol). The reaction was stirred for 2 hours before it was quenched by addition of with ice-water (10 mL). The mixture was extracted with ethyl acetate (3×10 mL) and the combined organic layers were dried over anhydrous sodium sulfate and concentrated under reduced pressure. The residue was purified by prep-TLC with ethyl acetate:petroleum ether=1:1 to afford 3-methyl-N-(2-(3-methyl-4-oxo-1-phenyl-1,3,8-triazaspiro[4.5]decan-8-yl)-2-oxo-1-(tetrahydro-2H-pyran-4-yl)ethyl)benzamide as a white solid (50 mg, 39%).

LCMS (ESI): m/z=505.2 [M+H]$^+$.

3-Methyl-N-(2-(3-methyl-4-oxo-1-phenyl-1,3,8-triazaspiro[4.5]decan-8-yl)-2-oxo-1-(tetrahydro-2H-pyran-4-yl)ethyl)benzamide was separated by chiral-HPLC (column: CHIRALPAK* (Daicel) IB (250 mm×20 mm, 5 μm). Mobile phase: hexane:ethanol (0.1% FA)=70:30, flow rate: 20 mL/min) to afford two isomers.

Their confirmations were tentatively assigned as drawn.

(R)-3-Methyl-N-(2-(3-methyl-4-oxo-1-phenyl-1,3,8-triazaspiro[4.5]decan-8-yl)-2-oxo-1-(tetrahydro-2H-pyran-4-yl)ethyl)benzamide

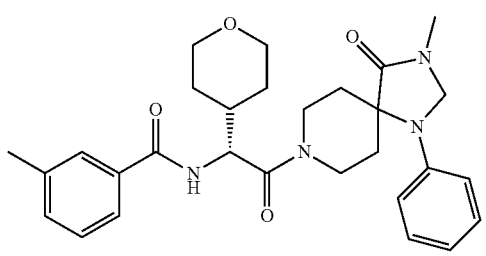 [SMILES: Cc1cccc(C(=O)N[C@@H](C(=O)N2CCC3(CC2)C(=O)N(C)CN3c2ccccc2)C2CCOCC2)c1]

Retention time: 7.481 minutes, ee=97.1%.
LCMS (ESI): m/z=505.2 [M+H]$^+$.
$^1$H-NMR (400 MHz, CDCl$_3$): δ=1.54-1.90 (m, 7H), 2.42-2.66 (m, 5H), 3.05 (s, 3H), 3.36-3.45 (m, 2H), 3.54-3.64 (m, 2H), 3.97-4.14 (m, 4H), 4.54-4.66 (m, 1H), 4.71-4.76 (m, 2H), 5.17-5.23 (m, 1H), 6.98-7.24 (m, 5H), 7.62-7.66 (m, 4H).

Example 130

(S)-3-Methyl-N-(2-(3-methyl-4-oxo-1-phenyl-1,3,8-triazaspiro[4.5]decan-8-yl)-2-oxo-1-(tetrahydro-2H-pyran-4-yl)ethyl)benzamide

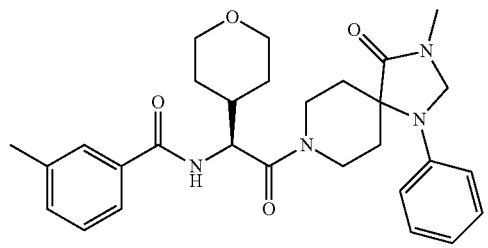 [SMILES: Cc1cccc(C(=O)N[C@H](C(=O)N2CCC3(CC2)C(=O)N(C)CN3c2ccccc2)C2CCOCC2)c1]

Retention time: 14.04 minutes, ee=95%
LCMS (ESI): m/z=505.2 [M+H]$^+$.
$^1$H-NMR (400 MHz, CDCl$_3$): δ=1.54-1.90 (m, 7H), 2.42-2.66 (m, 5H), 3.05 (s, 3H), 3.36-3.45 (m, 2H), 3.54-3.64 (m, 2H), 3.97-4.14 (m, 4H), 4.54-4.66 (m, 1H), 4.71-4.76 (m, 2H), 5.17-5.23 (m, 1H), 6.98-7.24 (m, 5H), 7.62-7.66 (m, 4H).

The following compound was synthesized following the general procedure described above using chiral amino acid.

Example 131

(R)—N-(1-Cyclohexyl-2-(3-methyl-4-oxo-1-phenyl-1,3,8-triazaspiro[4.5]decan-8-yl)-2-oxoethyl)-6-methylpicolinamide trifluoroacetic Acid Salt

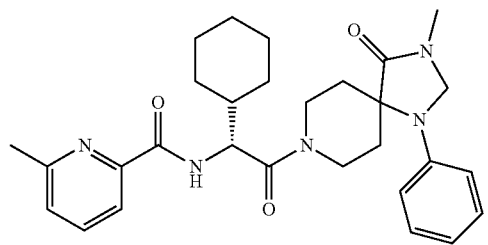

14.6 mg, yield: 20%, white solid.
LCMS (ESI): m/z=504.2 [M+H]$^+$.
$^1$H-NMR (400 MHz, CD$_3$OD): δ=1.0-1.44 (m, 5H), 1.51-2.00 (m, 8H), 2.41-2.76 (m, 5H), 3.02 (s, 3H), 3.50-3.55 (m, 1H), 3.96-4.01 (m, 1H), 4.19-4.39 (m, 1H), 4.48-4.50 (m, 1H), 4.75 (m, 2H), 5.07 (m, 1H), 6.56-6.73 (m, 2H), 6.80-7.00 (m, 2H), 7.26-7.35 (m, 1H), 7.53-7.55 (m, 1H), 7.77-8.01 (m, 2H).

The following compound was synthesized following the general procedure described for Example 236.

Example 132

(R)—N,3-Dimethyl-N-(3-methyl-1-(3-methyl-4-oxo-1-phenyl-1,3,8-triazaspiro[4.5]decan-8-yl)-1-oxobutan-2-yl)benzamide

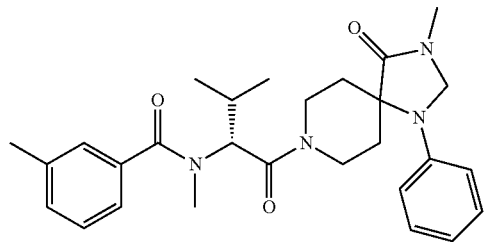 [SMILES: Cc1cccc(C(=O)N(C)[C@@H](C(=O)N2CCC3(CC2)C(=O)N(C)CN3c2ccccc2)C(C)C)c1]

26.4 mg, yield: 58%, white solid.

LCMS (ESI): m/z=464.2 [M+H]$^+$.

$^1$H-NMR (400 MHz, CDCl$_3$): δ=1.00-1.04 (m, 6H), 1.75-1.87 (m, 2H), 2.25-2.39 (two singlets, 3H), 2.45-2.54 (m, 3H), 2.86-2.96 (two singlets, 3H), 3.05 (s, 3H), 3.52-4.75 (m, 6H), 5.26-5.28 (m, 1H), 6.75-7.27 (m, 9H).

Example 133

5-Ethyl-2-fluoro-N-((2R,3S)-3-methoxy-1-(3-methyl-4-oxo-1-phenyl-1,3,8-triazaspiro[4.5]decane-8-yl)-1-oxobutan-2-yl)benzamide

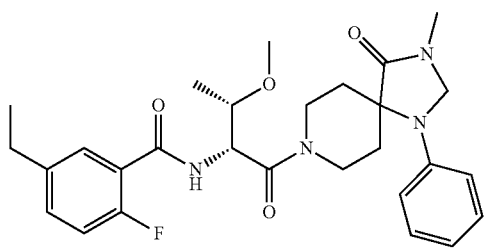 [SMILES: CCc1ccc(F)c(C(=O)N[C@@H](C(=O)N2CCC3(CC2)C(=O)N(C)CN3c2ccccc2)[C@H](C)OC)c1]

Representative Scheme:

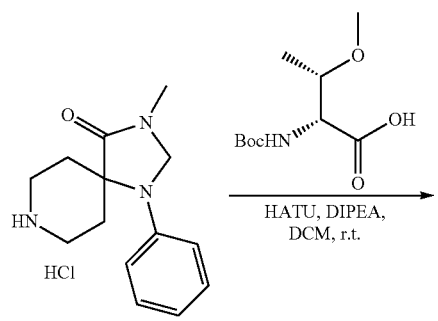

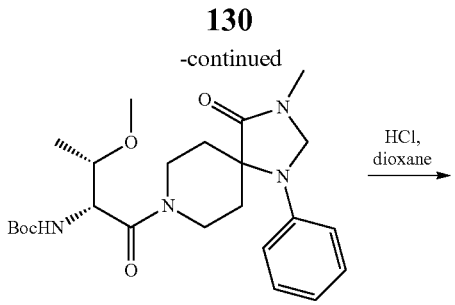

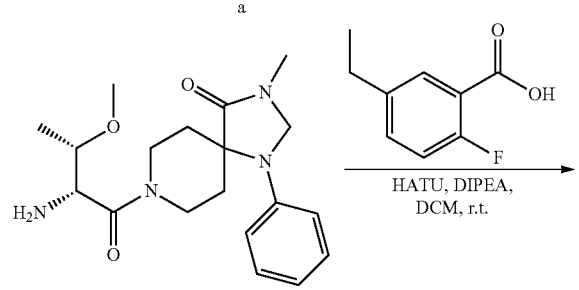

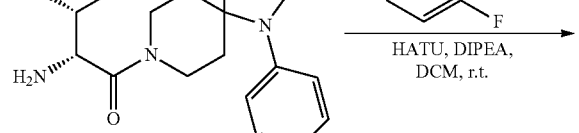

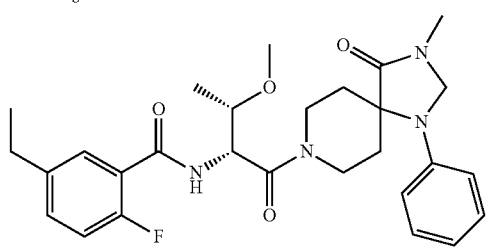

Representative General Procedure tert-Butyl-(2R,3S)-3-methoxy-1-(3-methyl-4-oxo-1-phenyl-1,3,8-triazaspiro[4.5]decan-8-yl)-1-oxobutan-2-ylcarbamate

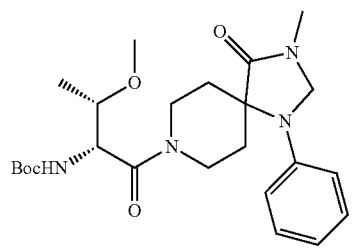 [SMILES: CO[C@@H](C)[C@@H](NC(=O)OC(C)(C)C)C(=O)N1CCC2(CC1)C(=O)N(C)CN2c1ccccc1]

To a mixture of 3-methyl-1-phenyl-1,3,8-triazaspiro[4.5]decan-4-one hydrochloride (prepared as described in Example 129-b) (296 mg, 0.47 mmol) in dichloromethane (30 mL) was added (2R,3S)-2-(tert-butoxycarbonylamino)-3-methoxybutanoic acid (100 mg, 0.43 mmol), 1-[bis(dimethylamino)methylene]-1H-1,2,3-triazolo[4,5-b]pyridinium-3-oxide hexafluorophosphate (HATU) (243 mg, 0.64 mmol) and N,N-diisopropylethylamine (139 mg, 1.07 mmol). The reaction was stirred for 2 hours before it was quenched with ice-water (5 mL). The mixture was extracted with ethyl acetate (3×10 mL) and the combined organic layers were dried over anhydrous sodium sulfate and concentrated under reduced pressure. The residue was purified by silica gel column chromatography eluting with ethyl acetate:petroleum ether=1:5 to afford tert-butyl-(2R,3S)-3- methoxy-1-(3-methyl-4-oxo-1-phenyl-1,3,8-triazaspiro[4.5]decan-8-yl)-1-oxobutan-2-ylcarbamate as a colorless oil (197 mg, 100%).

LCMS (ESI): m/z=461.2 [M+H]⁺.

¹H-NMR (400 MHz, CDCl₃): δ=0.83-1.12 (m, 3H), 1.38 (s, 6H), 1.45 (s, 3H), 1.59-1.64 (m, 4H), 2.83 (s, 3H), 3.06 (s, 1H), 3.14 (s, 2H), 3.34 (s, 2H), 3.30-3.57 (m, 2H), 3.83-4.01 (m, 2H), 4.51-4.75 (m, 2H), 5.47-5.59 (m, 1H), 7.13-7.20 (m, 2H), 7.40-7.52 (m, 3H).

8-((2R,3S)-2-Amino-3-methoxybutanoyl)-3-methyl-1-phenyl-1,3,8-triazaspiro[4.5]decan-4-one hydrochloride

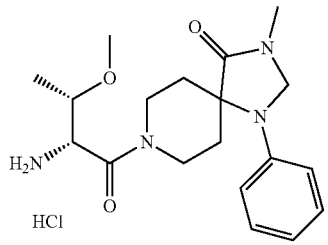 [SMILES: CO[C@@H](C)[C@@H](N)C(=O)N1CCC2(CC1)C(=O)N(C)CN2c1ccccc1 ; Cl]

A solution of tert-butyl-(2R,3S)-3-methoxy-1-(3-methyl-4-oxo-1-phenyl-1,3,8-triazaspiro[4.5]decan-8-yl)-1-oxobutan-2-ylcarbamate (197 mg, 0.43 mmol) in hydrochloric acid in dioxane (6.0 M, 10 mL) was stirred for 30 minutes. The precipitate was collected by filtration and dried under reduced pressure to afford 8-((2R,3S)-2-amino-3-methoxybutanoyl)-3-methyl-1-phenyl-1,3,8-triazaspiro[4.5]decan-4-one hydrochloride as a white solid (120 mg, 60%).

LCMS (ESI): m/z=361.2 [M+H]⁺.

5-Ethyl-2-fluoro-N-((2R,3S)-3-methoxy-1-(3-methyl-4-oxo-1-phenyl-1,3,8-triazaspiro[4.5]decane-8-yl)-1-oxobutan-2-yl)benzamide

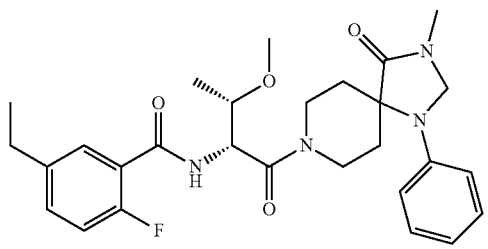 [SMILES: CCc1ccc(F)c(C(=O)N[C@@H](C(=O)N2CCC3(CC2)C(=O)N(C)CN3c2ccccc2)[C@H](C)OC)c1]

To a mixture of 8-((2R,3S)-2-amino-3-methoxybutanoyl)-3-methyl-1-phenyl-1,3,8-triazaspiro[4.5]decan-4-one hydrochloride (52 mg, 0.135 mmol) in dichloromethane (10 mL) was added 5-ethyl-2-fluorobenzoic acid (24 mg, 0.144 mmol), 1-[bis(dimethylamino)methylene]-1H-1,2,3-triazolo[4,5-b]pyridinium-3-oxide hexafluorophosphate (HATU) (75 mg, 0.196 mmol) and N,N-diisopropylethylamine (51 mg, 0.39 mmol). The resulting mixture was stirred for 2 hours at room temperature before the reaction was quenched with ice-water (10 mL). The mixture was extracted with ethyl acetate (3×10 mL) and the combined organic layers were dried over anhydrous sodium sulfate and concentrated under reduced pressure. The residue was purified by silica gel column chromatography eluting with ethyl acetate:petroleum ether=1:5 to afford 5-ethyl-2-fluoro-N-((2R,3S)-3-methoxy-1-(3-methyl-4-oxo-1-phenyl-1,3,8-triazaspiro[4.5]decane-8-yl)-1-oxobutan-2-yl)benzamide as a colorless oil (11.2 mg, 15%). 11.2 mg, yield: 15%, white solid LCMS (ESI): m/z=511.2 [M+H]⁺.

¹H-NMR (400 MHz, CD₃OD): δ=1.22-1.31 (m, 6H), 1.66-2.83 (m, 6H), 3.03 (s, 3H), 3.11 (s, 3H), 3.83 (s, 3H), 3.38-4.78 (m, 7H), 5.17-5.3 (m, 1H), 6.73-7.76 (m, 8H).

The following 3 compounds were synthesized following the general procedure described above:

Example 134

N-((2R,3S)-3-Methoxy-1-(3-methyl-4-oxo-1-phenyl-1,3,8-triazaspiro[4.5]decan-8-yl)-1-oxobutan-2-yl)-3-methylbenzamide

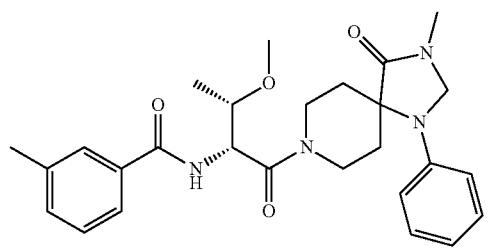 [SMILES: CO[C@@H](C)[C@@H](NC(=O)c1cccc(C)c1)C(=O)N1CCC2(CC1)C(=O)N(C)CN2c1ccccc1]

10.1 mg, yield: 9%, white solid

LCMS (ESI): m/z=479 [M+H]⁺.

¹H-NMR (400 MHz, CDCl₃): δ=1.22-1.27 (m, 3H), 1.70-1.83 (m, 2H), 2.43 (s, 3H), 2.56-2.66 (m, 1H), 2.80-2.94 (m, 1H), 3.06 (s, 3H), 3.41 (s, 3H), 3.46-4.22 (m, 4H), 4.45-4.84 (m, 3H), 5.08-5.51 (m, 1H), 6.85-6.90 (m, 3H), 7.22-7.24 (m, 1H), 7.38-7.50 (m, 3H), 7.67-7.69 (m, 2H).

Example 135

3-Ethyl-N-((2R,3S)-3-methoxy-1-(3-methyl-4-oxo-1-phenyl-1,3,8-triazaspiro[4.5]decan-8-yl)-1-oxobutan-2-yl)benzamide

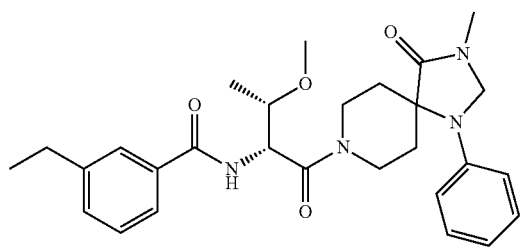 [SMILES: CCc1cccc(C(=O)N[C@@H](C(=O)N2CCC3(CC2)C(=O)N(C)CN3c2ccccc2)[C@H](C)OC)c1]

9.0 mg, yield: 14%, white solid

LCMS (ESI): m/z=493.2 [M+H]⁺.

¹H-NMR (400 MHz, CDCl₃): δ=1.22-1.26 (m, 6H), 1.66-1.85 (m, 2H), 2.45-2.79 (m, 4H), 2.98 (s, 3H), 3.42 (s, 3H), 3.53-3.64 (m, 1H), 4.03-4.36 (m, 2H), 4.42-4.77 (m, 7H), 5.18-5.29 (m, 1H), 6.69-7.76 (m, 9H).

Example 136

3-Ethyl-5-fluoro-N-((2R,3S)-3-methoxy-1-(3-methyl-4-oxo-1-phenyl-1,3,8-triazaspiro[4.5]decan-8-yl)-1-oxobutan-2-yl)benzamide

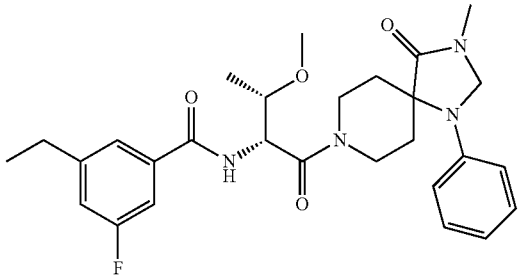 [SMILES: CCc1cc(F)cc(C(=O)N[C@@H](C(=O)N2CCC3(CC2)C(=O)N(C)CN3c2ccccc2)[C@H](C)OC)c1]

8.0 mg, yield: 12%, white solid
LCMS (ESI): m/z=511.2 [M+H]+.
$^1$H-NMR (400 MHz, CD$_3$OD): δ=1.14-1.37 (m, 6H), 1.75-1.81 (m, 2H), 2.50-2.59 (m, 1H), 2.63-2.86 (m, 3H), 3.03 (s, 3H), 3.50 (s, 3H), 3.52-3.59 (m, 1H), 3.74-4.10 (m, 2H), 4.34-4.49 (m, 2H), 4.74-4.77 (m, 2H), 5.21-5.26 (m, 1H), 7.24-7.80 (m, 8H).

The following 8 compounds were synthesized following the general procedure described above using D-Valine:

Example 137

(R)-2-Methyl-N-(3-methyl-1-(3-methyl-4-oxo-1-phenyl-1,3,8-triazaspiro[4.5]decan-8-yl)-1-oxobutan-2-yl)isonicotinamide

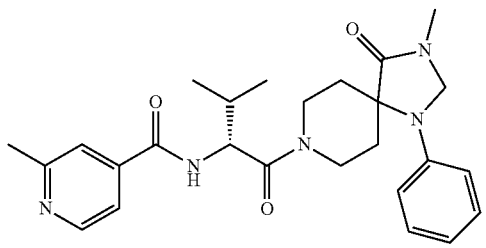

5.0 mg, yield: 7%, white solid
LCMS (ESI): m/z=464.2 [M+H]+.
$^1$H-NMR (400 MHz, CDCl$_3$): δ=1.02-1.09 (m, 6H), 1.24-1.28 (m, 1H), 1.75-2.24 (m, 4H), 2.98-3.06 (m, 6H), 3.51-3.54 (m, 1H), 3.94-4.12 (m, 2H), 4.57-4.62 (m, 1H), 4.72-4.77 (m, 2H), 5.20-5.24 (m, 1H), 5.35-5.45 (m, 1H), 6.75-6.77 (m, 1H), 6.84-6.88 (m, 1H), 7.17-7.19 (m, 1H), 7.35-7.37 (m, 2H), 7.82-7.95 (m, 2H), 8.73-8.75 (m, 1H).

Example 138

(R)-3-Ethyl-N-(3-methyl-1-(3-methyl-4-oxo-1-phenyl-1,3,8-triazaspiro[4.5]decan-8-yl)-1-oxobutan-2-yl)benzamide

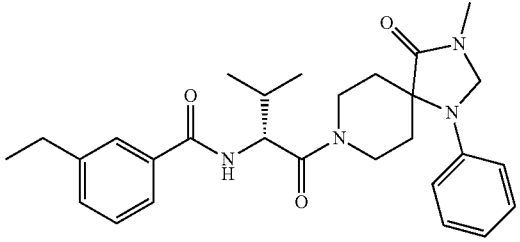 [SMILES: CCc1cccc(C(=O)N[C@@H](C(=O)N2CCC3(CC2)C(=O)N(C)CN3c2ccccc2)C(C)C)c1]

10.0 mg, yield: 16%, white solid
LCMS (ESI): m/z=477.2 [M+H]+.
$^1$H-NMR (400 MHz, CDCl$_3$): δ=1.01-1.14 (m, 6H), 1.25-1.29 (m, 3H), 1.74-1.83 (m, 2H), 2.16-2.18 (m, 1H), 2.68-2.71 (m, 4H), 3.02 (s, 3H), 3.52-3.56 (m, 1H), 3.99-4.08 (m, 2H), 4.54-4.71 (m, 3H), 5.09-5.15 (m, 1H), 6.67-7.24 (m, 6H), 7.34-7.36 (m, 2H), 7.62-7.67 (m, 2H).

Example 139

(R)-4-Fluoro-3-methyl-N-(3-methyl-1-(3-methyl-4-oxo-1-phenyl-1,3,8-triazaspiro[4.5]decan-8-yl)-1-oxobutan-2-yl)benzamide

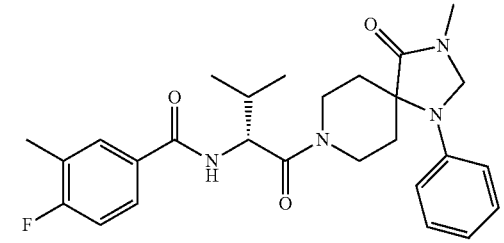 [SMILES: Cc1cc(C(=O)N[C@@H](C(=O)N2CCC3(CC2)C(=O)N(C)CN3c2ccccc2)C(C)C)ccc1F]

20.0 mg, yield: 32%, white solid
LCMS (ESI): m/z=481.2 [M+H]+.
$^1$H-NMR (400 MHz, CDCl$_3$): δ=0.98-1.04 (m, 6H), 1.83-1.97 (m, 2H), 2.03-2.23 (m, 1H), 2.46-2.61 (m, 5H), 3.02 (s, 3H), 3.52-3.57 (m, 1H), 4.03-4.06 (m, 2H), 4.57-4.71 (m, 3H), 5.04-5.08 (m, 1H), 6.69-7.13 (m, 6H), 7.65-7.70 (m, 2H).

Example 140

(R)-3-Fluoro-5-methyl-N-(3-methyl-1-(3-methyl-4-oxo-1-phenyl-1,3,8-triazaspiro[4.5]decan-8-yl)-1-oxobutan-2-yl)benzamide

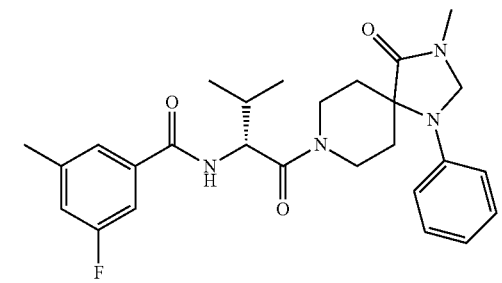 [SMILES: Cc1cc(F)cc(C(=O)N[C@@H](C(=O)N2CCC3(CC2)C(=O)N(C)CN3c2ccccc2)C(C)C)c1]

13.0 mg, yield: 19%, white solid

LCMS (ESI): m/z=481.2 [M+H]$^+$.

$^1$H-NMR (400 MHz, CDCl$_3$): δ=0.97-1.06 (m, 6H), 1.74-1.79 (m, 2H), 1.81-1.83 (m, 1H), 2.40-2.59 (m, 5H), 3.03 (s, 3H), 3.53-3.56 (m, 1H), 4.02-4.05 (m, 2H), 4.57-4.71 (m, 3H), 5.09-5.18 (m, 1H), 6.70-7.39 (m, 8H).

Example 141

(R)-2-Fluoro-5-methyl-N-(3-methyl-1-(3-methyl-4-oxo-1-phenyl-1,3,8-triazaspiro[4.5]decan-8-yl)-1-oxobutan-2-yl)benzamide

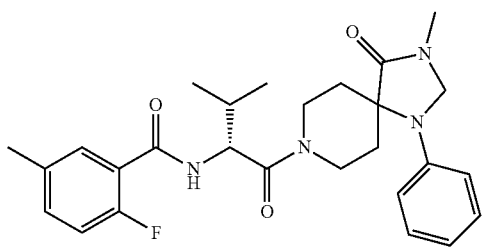

13.0 mg, yield: 11%, white solid

LCMS (ESI): m/z=481.2 [M+H]$^+$.

$^1$H-NMR (400 MHz, CDCl$_3$): δ=0.97-1.06 (m, 6H), 1.74-1.79 (m, 2H), 1.81-1.83 (m, 1H), 2.13 (s, 3H), 2.34-2.50 (m, 2H), 3.02 (s, 3H), 3.50-3.54 (m, 1H), 4.03-4.08 (m, 2H), 4.54-4.71 (m, 3H), 5.09-5.18 (m, 1H), 6.67-7.14 (m, 7H), 7.43-7.46 (m, 1H), 7.79-7.80 (m, 1H).

Example 142

(R)-3-Cyclopropyl-N-(3-methyl-1-(3-methyl-4-oxo-1-phenyl-1,3,8-triazaspiro[4.5]decan-8-yl)-1-oxobutan-2-yl)benzamide

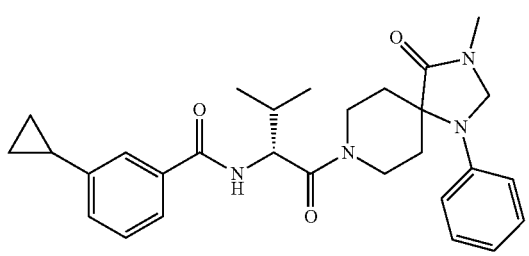 [SMILES: CC(C)[C@@H](NC(=O)c1cccc(C2CC2)c1)C(=O)N1CCC2(CC1)C(=O)N(C)CN2c1ccccc1]

21.0 mg, yield: 29%, white solid

LCMS (ESI): m/z=489.2 [M+H]$^+$.

$^1$H-NMR (400 MHz, CDCl$_3$): δ=0.73-1.10 (m, 10H), 1.78-1.95 (m, 2H), 2.12-2.15 (m, 1H), 2.60-2.64 (m, 3H), 3.02 (s, 3H), 3.51-3.55 (m, 1H), 4.04-4.07 (m, 2H), 4.59-4.70 (m, 3H), 5.08-5.10 (m, 1H), 6.65-7.99 (m, 9H).

Example 143

(R)-3-Chloro-4-cyano-N-(3-methyl-1-(3-methyl-4-oxo-1-phenyl-1,3,8-triazaspiro[4.5]decan-8-yl)-1-oxobutan-2-yl)benzamide

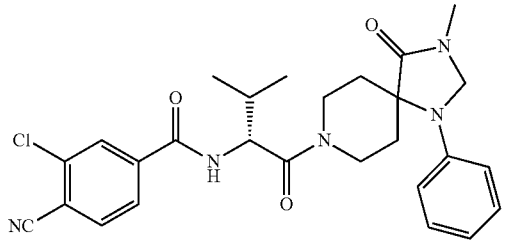 [SMILES: CC(C)[C@@H](NC(=O)c1ccc(C#N)c(Cl)c1)C(=O)N1CCC2(CC1)C(=O)N(C)CN2c1ccccc1]

9.9 mg, yield: 15%, white solid

LCMS (ESI): m/z=509.2 [M+H]$^+$.

$^1$H-NMR (400 MHz, CDCl$_3$): δ=1.02-1.09 (m, 6H), 1.69-2.77 (m, 5H), 3.02 (s, 3H), 3.52-4.34 (m, 4H), 4.74-4.77 (m, 2H), 4.89-4.93 (m, 1H), 6.70-6.78 (m, 2H), 6.86-6.88 (m, 1H), 7.03-7.25 (m, 2H), 7.93-7.96 (m, 2H), 8.09-8.11 (m, 1H).

Example 144

(R)-5-Ethyl-2-fluoro-N-(3-methyl-1-(3-methyl-4-oxo-1-phenyl-1,3,8-triazaspiro[4.5]decan-8-yl)-1-oxobutan-2-yl)benzamide

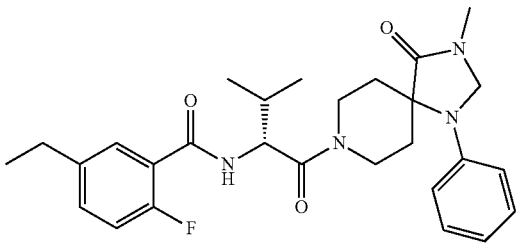 [SMILES: CCc1ccc(F)c(C(=O)N[C@@H](C(=O)N2CCC3(CC2)C(=O)N(C)CN3c2ccccc2)C(C)C)c1]

42.0 mg, yield: 33%, white solid

LCMS (ESI): m/z=495 [M+H]$^+$.

$^1$H-NMR (400 MHz, CDCl$_3$): δ=0.94-1.16 (m, 6H), 1.18-1.38 (m, 3H), 1.60-1.93 (m, 2H), 2.13-2.34 (m, 1H), 2.37-2.62 (m, 1H), 2.62-2.76 (m, 2H), 2.81 (m, 1H), 3.08 (s, 3H), 3.43-3.63 (m, 1H), 3.91-4.10 (m, 1H), 4.20-4.38 (m, 1H), 4.43-4.60 (m, 1H), 4.65-4.76 (m, 2H), 4.96-5.09 (m, 1H), 6.70-6.89 (m, 3H), 7.01-7.32 (m, 3H), 7.34-7.53 (m, 1H), 7.57-7.71 (m, 1H).

Example 145

(R)—N-(1-(1-(4-Carbamoylphenyl)-3-methyl-4-oxo-1,3,8-triazaspiro[4.5]decan-8-yl)-3-methyl-1-oxobutan-2-yl)-2-fluoro-3-methylbenzamide

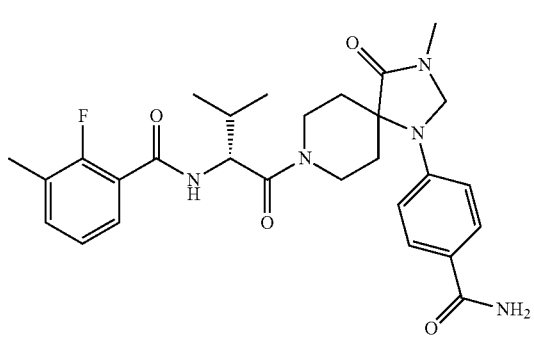 [SMILES: Cc1cccc(C(=O)N[C@@H](C(=O)N2CCC3(CC2)C(=O)N(C)CN3c2ccc(C(N)=O)cc2)C(C)C)c1F]

Representative Scheme:

Representative General Procedure tert-Butyl-1-(4-carbamoylphenyl)-3-methyl-4-oxo-1,3,8-triazaspiro[4.5]decane-8-carboxylate

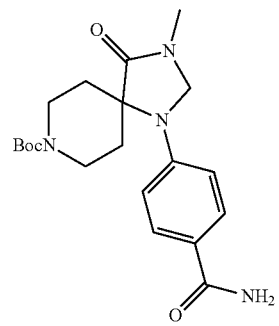 [SMILES: CN1CN(c2ccc(C(N)=O)cc2)C2(CCN(C(=O)OC(C)(C)C)CC2)C1=O]

To a solution of tert-butyl-1-(4-cyanophenyl)-3-methyl-4-oxo-1,3,8-triazaspiro[4.5]decane-8-carboxylate (prepared as described in Example 179-e) (190 mg, 0.15 mmol) in methanol (15 mL) was added an aqueous sodium hydroxide

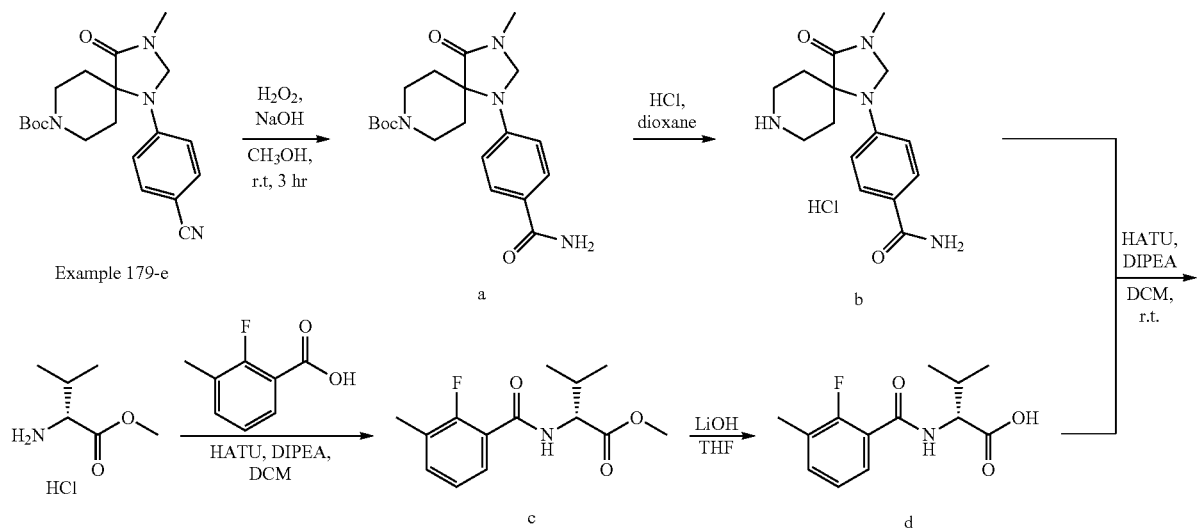

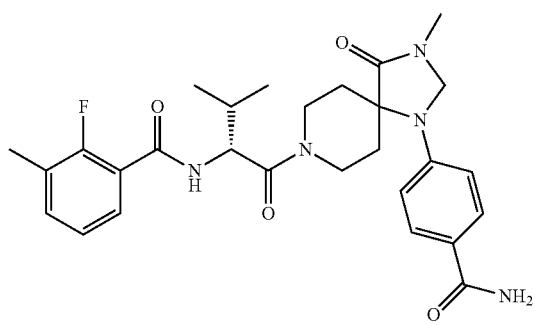

solution (6 mL, 1.0 M). After stirring for 15 minutes, to the resulting solution was added a 30% aqueous hydrogen peroxide (6 mL) dropwise. The resulting mixture was stirred overnight. The solvent was removed under reduced pressure and the residue was diluted with water (40 mL) and ethyl acetate (40 mL). The organic layer was collected and dried over anhydrous sodium sulfate and concentrated under reduced pressure. The residue was purified by silica gel column chromatography eluting with dichloromethane:methanol=200:1 to afford tert-butyl-1-(4-carbamoylphenyl)-3-methyl-4-oxo-1,3,8-triazaspiro[4.5]decane-8-carboxylate as a white solid (160 mg, 80%).
LCMS (ESI): m/z=389.1 [M+H]+.

4-(3-Methyl-4-oxo-1,3,8-triazaspiro[4.5]decan-1-yl)benzamide hydrochloride

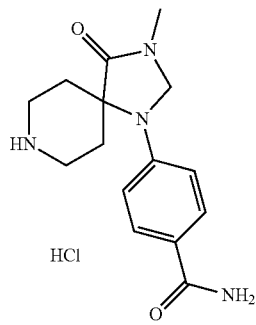 [SMILES: CN1CN(c2ccc(C(N)=O)cc2)C2(CCNCC2)C1=O ; Cl]

A solution of tert-butyl-1-(4-carbamoylphenyl)-3-methyl-4-oxo-1,3,8-triazaspiro[4.5]decane-8-carboxylate (160 mg, 0.41 mmol) in hydrochloric acid in dioxane (6.0 M, 10 mL) was stirred for 30 minutes. The precipitate was collected by filtration and dried under reduced pressure to afford 4-(3-methyl-4-oxo-1,3,8-triazaspiro[4.5]decan-1-yl)benzamide hydrochloride as a white solid (120 mg, 90%).
LCMS (ESI): m/z=289.1 [M+H]+.

(R)-Methyl-2-(2-fluoro-3-methylbenzamido)-3-methylbutanoate

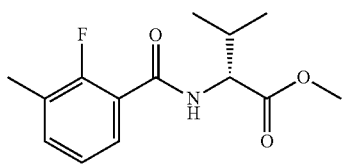

To a solution of 2-fluoro-3-methylbenzoic acid (1.54 g, 10 mmol) in dichloromethane (50 mL) was added sequentially D-valine methyl ester hydrochloride (1.71 g, 10.2 mmol), 1-[bis(dimethylamino)methylene]-1H-1,2,3-triazolo[4,5-b]pyridinium-3-oxide hexafluorophosphate (HATU) (4.2 g, 11.0 mmol) and N,N-diisopropylethylamine (3.9 g, 30 mmol). Before quenching with ice-water (50 mL), the reaction was stirred for 2 hours. The mixture was extracted with dichloromethane (3×100 mL). The combined organic layers were dried over sodium sulfate and the solvent was removed under reduced pressure. The residue was purified by silica gel column chromatography eluting with ethyl acetate:petroleum ether=1:4 to afford (R)-methyl-2-(2-fluoro-3-methylbenzamido)-3-methylbutanoate as a thick oil (3.5 g, crude), which was used directly without further purification.
LCMS (ESI): m/z=268.2 [M+H]+.

(R)-2-(2-Fluoro-3-methylbenzamido)-3-methylbutanoic Acid

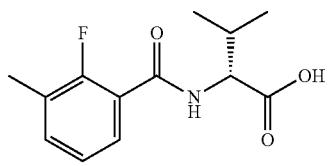 [SMILES: Cc1cccc(C(=O)N[C@@H](C(=O)O)C(C)C)c1F]

To a solution of (R)-methyl-2-(2-fluoro-3-methylbenzamido)-3-methylbutanoate (3.9 g, crude) in methanol (30 mL) was added an aqueous lithium hydroxide solution (20 mL, 2.0 M, 0.044 mol). Before quenching with ice-water (20 mL), the reaction was stirred for 1 hour. The pH of the solution was adjusted to 3 by addition of a 5% aqueous hydrochloric acid solution. The mixture was filtered and the filter cake was washed with petroleum ether (30 mL) and dried under reduced pressure to afford (R)-2-(2-fluoro-3-methylbenzamido)-3-methylbutanoic acid as a thick oil (2.40 g, 94% over two steps).
LCMS (ESI): m/z=254.1 [M+H]+.
$^1$H-NMR (300 MHz, CDCl$_3$): δ=1.05 (t, J=7.8 Hz, 6H), 2.32 (s, 3H), 2.34-2.44 (m, 1H), 4.78-4.82 (m, 1H), 7.06-7.13 (m, 1H), 7.27-7.35 (m, 1H), 7.79-7.91 (m, 1H).

(R)—N-(1-(1-(4-Carbamoylphenyl)-3-methyl-4-oxo-1,3,8-triazaspiro[4.5]decan-8-yl)-3-methyl-1-oxobutan-2-yl)-2-fluoro-3-methylbenzamide

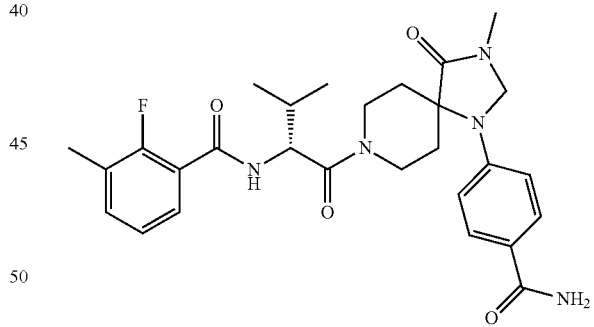

To a mixture of 4-(3-methyl-4-oxo-1,3,8-triazaspiro[4.5]decan-1-yl)benzamide hydrochloride (100 mg, 0.3 mmol) in dichloromethane (5 mL) was added (R)-2-(2-fluoro-3-methylbenzamido)-3-methylbutanoic acid (94 mg, 0.34 mmol), 1-[bis(dimethylamino)methylene]-1H-1,2,3-triazolo[4,5-b]pyridinium-3-oxide hexafluorophosphate (HATU) (177 mg, 0.46 mmol) and N,N-diisopropylethylamine (80 mg, 0.62 mmol). The resulting mixture was stirred for 2 hours at room temperature before the reaction was quenched with ice-water (10 mL). The mixture was extracted with ethyl acetate (3×10 mL) and the combined organic layers were dried over anhydrous sodium sulfate and concentrated under reduced pressure. The residue was purified by prep-TLC with dichloromethane:methanol=15:1 to afford (R)—N-(1-(1-(4-carbamoylphenyl)-3-methyl-4-oxo-1,3,8-triazaspiro[4.5]decan-8-yl)-3-methyl-1-oxobutan-2-yl)-2-fluoro-3-methylbenzamide as a white solid (11.8 mg, 7.3%).

LCMS (ESI): m/z=524.2 [M+H]+.

1H-NMR (400 MHz, CD3OD): δ=0.96-1.25 (m, 6H), 1.68-1.96 (m, 2H), 2.18-2.26 (m, 4H), 2.70-2.71 (m, 1H), 2.89-2.92 (m, 1H), 3.04 (s, 3H), 3.56-3.58 (m, 1H), 3.99-4.03 (m, 1H), 4.37-4.39 (m, 1H), 4.54-4.58 (m, 1H), 4.79-4.82 (m, 2H), 4.95-5.16 (m, 1H), 6.74-6.80 (m, 2H), 7.14-7.17 (m, 1H), 7.38-7.40 (m, 1H), 7.47-7.81 (m, 3H).

The following compound was synthesized following the general procedure described above:

Example 146

(R)—N-(1-(1-(3-Carbamoylphenyl)-3-methyl-4-oxo-1,3,8-triazaspiro[4.5]decan-8-yl)-3-methyl-1-oxobutan-2-yl)-2-fluoro-3-methylbenzamide 24.2 mg, yield: 17%, white solid.

LCMS (ESI): m/z=524.0 [M+H]+.

1H-NMR (400 MHz, CDCl3): δ=0.94-1.19 (m, 6H), 1.69-1.86 (m, 2H), 2.17-2.26 (m, 1H), 2.33 (s, 3H), 2.54-2.69 (m, 1H), 2.75-2.87 (m, 1H), 3.07 (s, 3H), 3.49-3.65 (m, 1H), 4.04-4.19 (m, 2H), 4.60-4.67 (m, 1H), 4.78 (s, 2H), 5.01-5.24 (m, 1H), 6.19-6.34 (m, 2H), 6.92-7.00 (m, 1H), 7.09-7.22 (m, 3H), 7.35 (s, 1H), 7.50-7.63 (m, 1H), 7.70-7.85 (m, 1H).

Example 147

(R)-4-(8-(2-(2-Fluoro-3-methylbenzamido)-3-methylbutanoyl)-3-methyl-4-oxo-1,3,8-triazaspiro[4.5]decan-1-yl)phenylboronic Acid

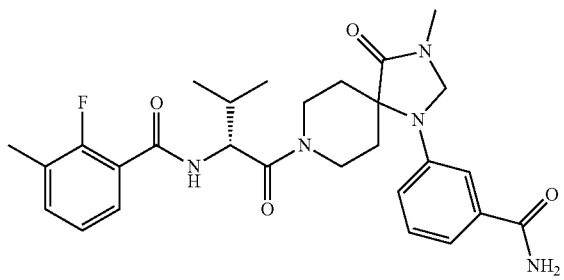 [SMILES: Cc1cccc(C(=O)N[C@@H](C(=O)N2CCC3(CC2)C(=O)N(C)CN3c2cccc(C(N)=O)c2)C(C)C)c1F]

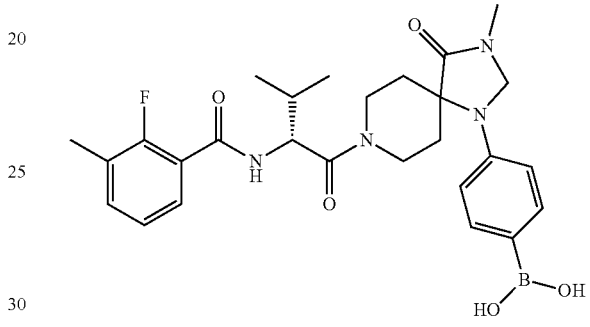

Representative Scheme:

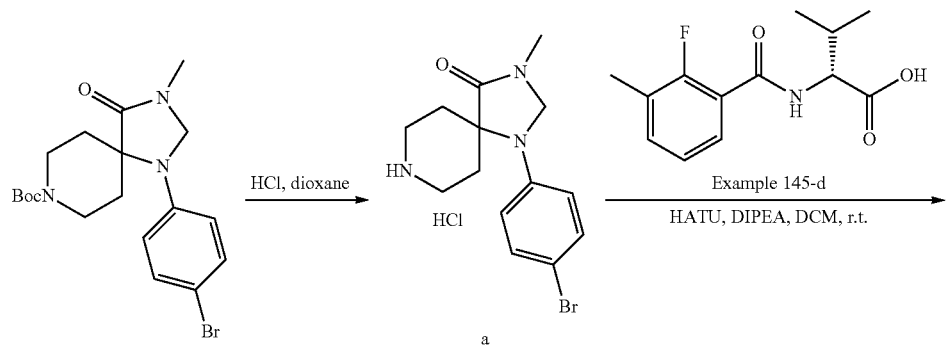

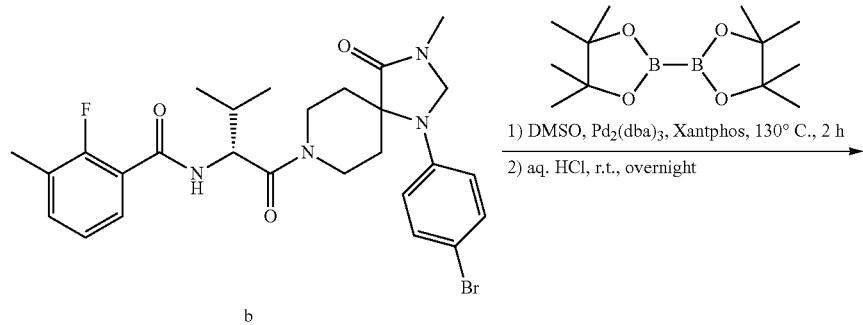

-continued

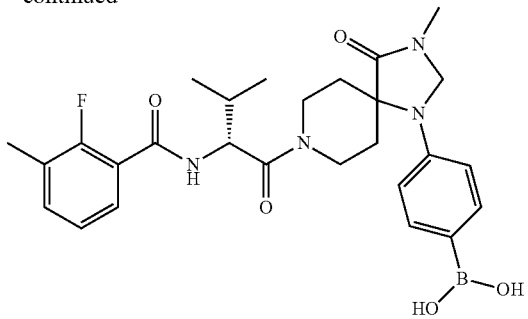

Representative General Procedure

1-(4-Bromophenyl)-3-methyl-1,3,8-triazaspiro[4.5]decan-4-one hydrochloride

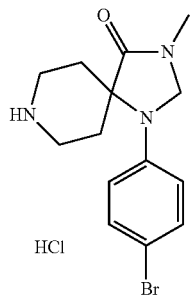

A solution of tert-butyl-1-(4-bromophenyl)-3-methyl-4-oxo-1,3,8-triazaspiro[4.5]decane-8-carboxylate (prepared as described in Example 179-d) (250 mg, 0.00041 mol) in hydrochloric acid in dioxane (6.0 M, 10 mL) was stirred for 30 minutes. The precipitate was collected by filtration and dried under reduced pressure to afford 1-(4-bromophenyl)-3-methyl-1,3,8-triazaspiro[4.5]decan-4-one hydrochloride as a white solid (180 mg, 85%).
LCMS (ESI): m/z=324.1, 326.1 [M+H]$^+$.

(R)—N-(1-(1-(4-Bromophenyl)-3-methyl-4-oxo-1,3,8-triazaspiro[4.5]decan-8-yl)-3-methyl-1-oxobutan-2-yl)-2-fluoro-3-methylbenzamide

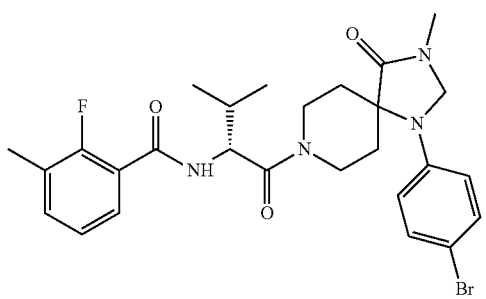 [SMILES: Cc1cccc(C(=O)N[C@@H](C(=O)N2CCC3(CC2)C(=O)N(C)CN3c2ccc(Br)cc2)C(C)C)c1F]

To a mixture of 1-(4-bromophenyl)-3-methyl-1,3,8-triazaspiro[4.5]decan-4-one hydrochloride (167 mg, 0.465 mmol) in dichloromethane (10 mL) was added (R)-2-(2-fluoro-3-methylbenzamido)-3-methylbutanoic acid (prepared as described in Example 145-d) (140 mg, 0.511 mmol), 1-[bis(dimethylamino)methylene]-1H-1,2,3-triazolo[4,5-b]pyridinium-3-oxide hexafluorophosphate (HATU) (292 mg, 0.767 mmol) and N,N-diisopropylethylamine (150 mg, 1.16 mmol). The resulting mixture was stirred for 2 hours before the reaction was quenched with ice-water (10 mL). The mixture was extracted with ethyl acetate (3×10 mL) and the combined organic layers were dried over anhydrous sodium sulfate and concentrated under reduced pressure. The residue was purified by silica gel column chromatography eluting with ethyl acetate:petroleum ether=1:5 to afford (R)—N-(1-(1-(4-Bromophenyl)-3-methyl-4-oxo-1,3,8-triazaspiro[4.5]decan-8-yl)-3-methyl-1-oxobutan-2-yl)-2-fluoro-3-methylbenzamide as a colorless oil (220 mg, 85%).
LCMS (ESI): m/z=559.2, 561.2 [M+H]$^+$.

(R)-4-(8-(2-(2-Fluoro-3-methylbenzamido)-3-methylbutanoyl)-3-methyl-4-oxo-1,3,8-triazaspiro[4.5]decan-1-yl)phenylboronic Acid

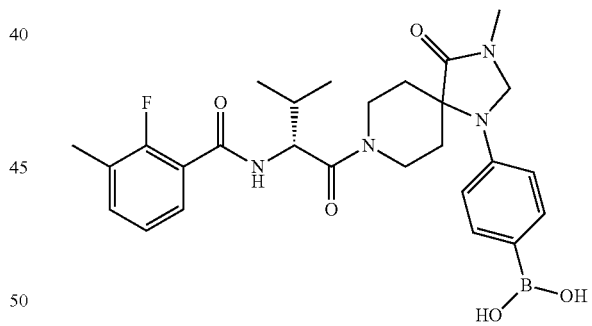

To a solution of (R)—N-(1-(1-(4-bromophenyl)-3-methyl-4-oxo-1,3,8-triazaspiro[4.5]decan-8-yl)-3-methyl-1-oxobutan-2-yl)-2-fluoro-3-methylbenzamide (220 mg, 0.39 mmol) in DMSO (10 mL) was added sequentially bis(pinacolato)diboron (300 mg, 1.18 mmol), tris(dibenzylideneacetone)dipalladium (36 mg, 0.039 mmol), 4,5-bis(diphenylphosphino)-9,9-dimethylxanthene (Xantphos) (46 mg, 0.047 mmol) and potassium acetate (78 mg, 0.788 mmol) under an argon atmosphere. The reaction mixture was stirred at 130° C. for 2 hours. After quenching with ice-water (5 mL), the reaction mixture was extracted with ethyl acetate (3×15 mL). The combined organic layers were dried over anhydrous sodium sulfate and concentrated under reduced pressure. To the residue were added ethanol (3 mL) and an aqueous hydrochloric acid solution (3 mL, 1.0 M). The resulting mixture was stirred overnight. The solvents were removed under reduced pressure. The residue was purified by prep-HPLC (acetonitrile and water, acetonitrile from 5% to 75%) to afford (R)-4-(8-(2-(2-fluoro-3-methylbenzamido)-3-methylbutanoyl)-3-methyl-4-oxo-1,3,8-triazaspiro[4.5]decan-1-yl)phenylboronic acid as a brown oil (14 mg, 7%).

LCMS (ESI): m/z=525.2 [M+H]⁺.

¹H-NMR (400 MHz, CD₃OD): δ=1.03-1.19 (m, 6H), 1.71-1.82 (m, 2H), 2.20-2.40 (m, 4H), 2.63-2.78 (m, 1H), 2.92-2.96 (m, 1H), 3.04 (s, 3H), 3.48-3.62 (m, 1H), 4.00-4.03 (m, 1H), 4.29-4.65 (m, 2H), 4.78-4.86 (m, 2H), 4.94-5.03 (m, 1H), 6.72-6.76 (m, 2H), 7.04-7.26 (m, 1H), 7.32-7.63 (m, 2H), 7.82-7.85 (m, 2H).

The following compound was synthesized following the general procedure described above:

Example 148

(R)-3-(8-(2-(2-Fluoro-3-methylbenzamido)-3-methylbutanoyl)-3-methyl-4-oxo-1,3,8-triazaspiro[4.5]decan-1-yl)phenylboronic Acid

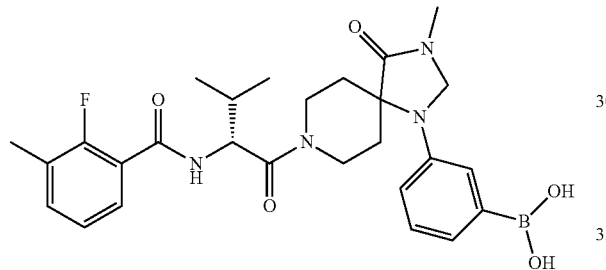

2.0 mg, yield: 8%, white solid.

LCMS (ESI): m/z=525.2 [M+H]⁺.

¹H-NMR (400 MHz, CDCl₃): δ=0.94-1.16 (m, 6H), 1.61-1.95 (m, 3H), 2.09-2.35 (m, 3H), 2.47-2.90 (m, 2H), 2.93-3.16 (m, 3H), 3.55-3.60 (m, 1H), 3.95-4.19 (m, 2H), 4.46-4.84 (m, 3H), 4.98-5.20 (m, 1H), 6.63-7.19 (m, 4H), 7.34-7.85 (m, 3H).

Example 149

(R)-4-(8-(2-(2-Fluoro-5-(trifluoromethyl)benzamido)-3-methylbutanoyl)-3-methyl-4-oxo-1,3,8-triazaspiro[4.5]decan-1-yl)benzoic Acid

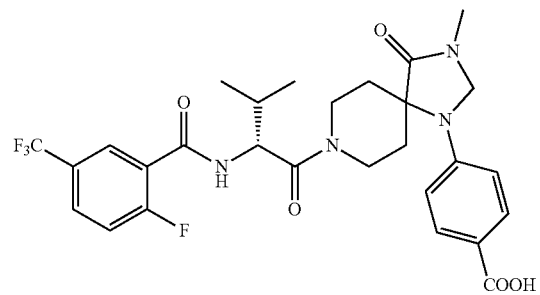 [SMILES: CC(C)[C@@H](NC(=O)c1cc(C(F)(F)F)ccc1F)C(=O)N1CCC2(CC1)C(=O)N(C)CN2c1ccc(C(=O)O)cc1]

Representative Scheme:

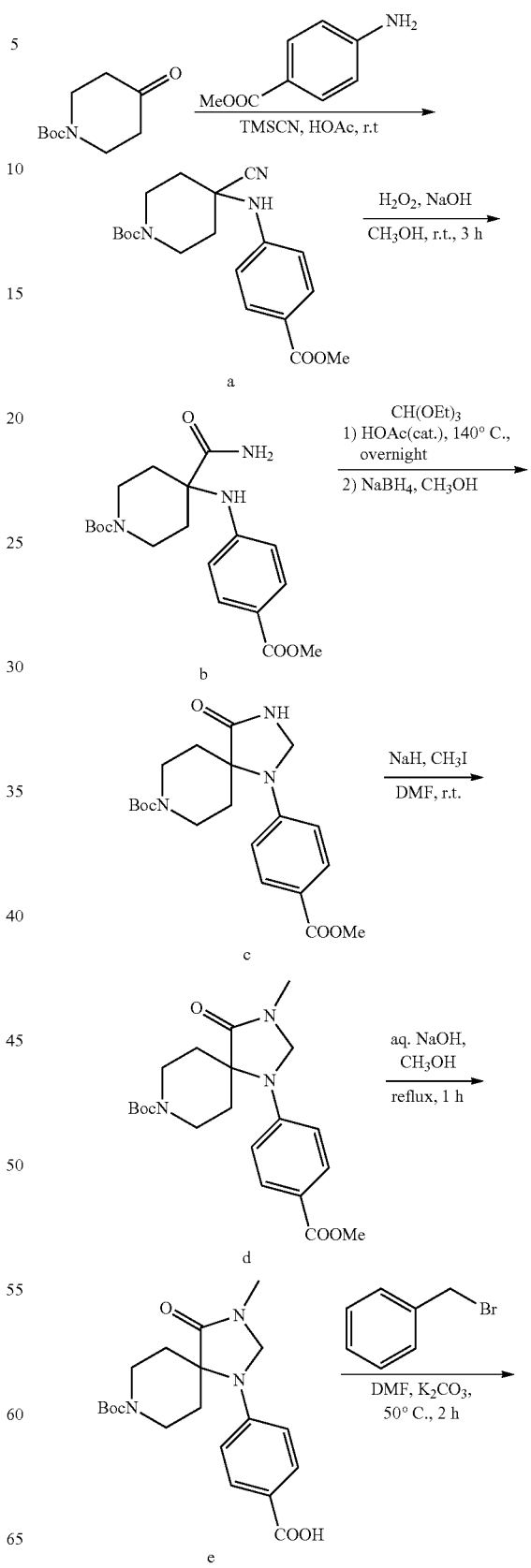

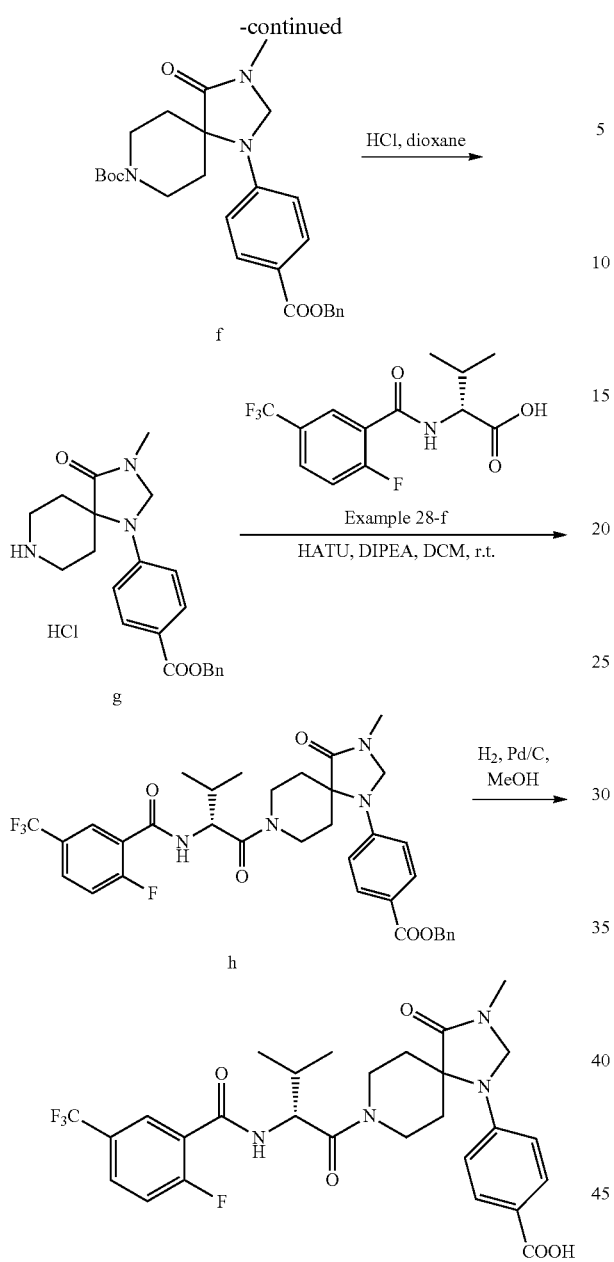

f g h

Representative General Procedure tert-Butyl-4-cyano-4-(4-(methoxycarbonyl)phe-nylamino)piperidine-1-carboxylate

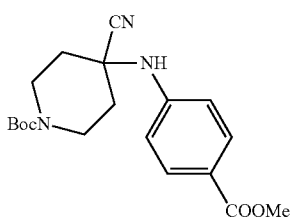 [SMILES: COC(=O)c1ccc(NC2(C#N)CCN(C(=O)OC(C)(C)C)CC2)cc1]

To a solution of methyl-4-aminobenzoate (16.46 g, 0.109 mol) in acetic acid (160 mL) was added tert-butyl-4-oxopi-peridine-1-carboxylate (23.8 g, 0.12 mol). The resulting mixture was cooled to 0° C. and trimethylsilyl cyanide (12.95 g, 0.131 mol) was added. The resulting solution was stirred overnight at room temperature. Saturated aqueous ammonium chloride solution was added (200 mL). After stirring at room temperature for 10 minutes, the mixture was filtered. The filter cake was dried under reduced pressure to afford tert-butyl-4-cyano-4-(4-(methoxycarbonyl)phe-nylamino)piperidine-1-carboxylate as a white solid (39.1 g, 100%).

LCMS (ESI): m/z=360.2 [M+H]$^+$.

tert-Butyl-4-carbamoyl-4-(4-(methoxycarbonyl)phe-nylamino)piperidine-1-carboxylate

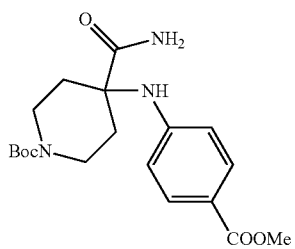 [SMILES: COC(=O)c1ccc(NC2(C(N)=O)CCN(C(=O)OC(C)(C)C)CC2)cc1]

To a solution of tert-butyl-4-cyano-4-(4-(methoxycarbo-nyl)phenylamino)piperidine-1-carboxylate (20.0 g, 0.0557 mol) in methanol (300 mL) was added an aqueous sodium hydroxide solution (100 mL, 1.0 M). After stirring for 15 minutes, to the resulting solution was added a 30% aqueous hydrogen peroxide solution (8 mL) dropwise. After stirring overnight, the resulting mixture was filtered. The filter cake was washed with water (3×100 mL) and dried under reduced pressure to afford tert-butyl-4-carbamoyl-4-(4-(methoxycar-bonyl)phenylamino)piperidine-1-carboxylate as a white solid (18.0 g, 79%).

LCMS (ESI): m/z=378.2 [M+H]$^+$.

$^1$H-NMR (400 MHz, DMSO-d$_6$): δ=1.39 (s, 9H), 1.82-1.92 (m, 4H), 3.14-3.17 (m, 2H), 3.61-3.64 (m, 2H), 3.78 (s, 3H), 6.57 (s, 1H), 6.62-6.70 (m, 2H), 7.15 (s, 1H), 7.41 (s, 1H), 7.62-7.77 (m, 2H).

tert-Butyl-1-(4-(methoxycarbonyl)phenyl)-4-oxo-1,3,8-triazaspiro[4.5]decane-8-carboxylate

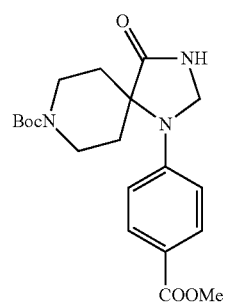 [SMILES: COC(=O)c1ccc(N2CNC(=O)C23CCN(C(=O)OC(C)(C)C)CC3)cc1]

To a solution of tert-butyl-4-carbamoyl-4-(4-(methoxy-carbonyl)phenylamino)piperidine-1-carboxylate (20.0 g, 0.053 mol) in triethyl orthoformate (200 mL) was added acetic acid (1 mL, cat.). The resulting mixture was stirred at 150° C. for 30 hours. The solvent was removed under reduced pressure. The residue was dissolved in methanol (200 mL). To the resulting solution was added sodium borohydride (2.62 g, 0.069 mol) at 0° C. The resulting mixture was stirred for 30 minutes. The solvent was removed under reduced pressure and the residue was diluted with water (200 mL) and ethyl acetate (150 mL). The organic layer was collected and the aqueous layer was extracted with ethyl acetate (3×100 mL). The combined organic layers were dried over anhydrous sodium sulfate and concentrated under reduced pressure. The residue was purified by silica gel column chromatography eluting with dichloromethane:methanol=100:1 to afford tert-butyl-1-(4-(methoxycarbonyl)phenyl)-4-oxo-1,3,8-triazaspiro[4.5]decane-8-carboxylate as a white solid (10 g, 48%).

LCMS (ESI): m/z=390.2 [M+H]$^+$.

$^1$H-NMR (400 MHz, DMSO-d$_6$): δ=1.40 (s, 9H), 1.72-1.75 (m, 2H), 2.47-2.50 (m, 2H), 3.35-3.42 (m, 2H), 3.78 (s, 3H), 3.97-4.01 (m, 2H), 4.70 (s, 3H), 6.68 (d, J=8.8 Hz, 2H), 7.75 (d, J=8.8 Hz, 2H), 8.94 (s, 1H).

tert-Butyl-1-(4-(methoxycarbonyl)phenyl)-3-methyl-4-oxo-1,3,8-triazaspiro[4.5]decane-8-carboxylate

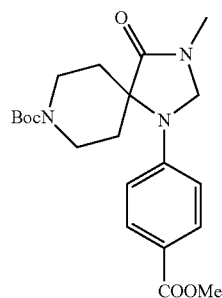 [SMILES: COC(=O)c1ccc(N2CN(C)C(=O)C23CCN(C(=O)OC(C)(C)C)CC3)cc1]

To a solution of tert-butyl-1-(4-(methoxycarbonyl)phenyl)-4-oxo-1,3,8-triazaspiro[4.5]decane-8-carboxylate (1.0 g, 0.00258 mol) in N,N-dimethylformamide (10 mL) was added sodium hydride (180 mg, 60% in oil, 0.00437 mol) at 0° C. After stirring for 15 minutes, iodomethane (0.55 g, 0.00386 mol) was added. The resulting mixture was stirred for 15 minutes at room temperature and the reaction was quenched with ice-water (10 mL). The mixture was extracted with ethyl acetate (3×50 mL). The combined organic layers were dried over anhydrous sodium sulfate and concentrated under reduced pressure. The residue was purified by silica gel column chromatography eluting with ethyl acetate:petroleum ether=1:1 to afford tert-butyl-1-(4-(methoxycarbonyl)phenyl)-3-methyl-4-oxo-1,3,8-triazaspiro[4.5]decane-8-carboxylate as a white solid (0.95 g, 94%).

LCMS (ESI): m/z=404.2 [M+H]$^+$.

4-(8-(tert-Butoxycarbonyl)-3-methyl-4-oxo-1,3,8-triazaspiro[4.5]decan-1-yl)benzoic Acid

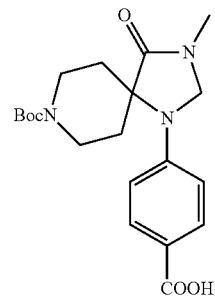

To a solution of tert-butyl-1-(4-(methoxycarbonyl)phenyl)-3-methyl-4-oxo-1,3,8-triazaspiro[4.5]decane-8-carboxylate (1.0 g, 0.00248 mol) in methanol (10 mL) was added a 15% aqueous sodium hydroxide solution (15 mL). The reaction was heated at reflux for 1 hour before cooling to room temperature. The pH of the resulting solution was adjusted to 1 by addition of 10% aqueous hydrochloric acid solution. The mixture was filtered and the filter cake was washed with water (10 mL) and then dried under reduced pressure to afford 4-(8-(tert-butoxycarbonyl)-3-methyl-4-oxo-1,3,8-triazaspiro[4.5]decan-1-yl)benzoic acid as a white solid (0.92 g, 94%).

LCMS (ESI): m/z=390.2 [M+H]$^+$.

tert-Butyl-1-(4-(benzyloxycarbonyl)phenyl)-3-methyl-4-oxo-1,3,8-triazaspiro[4.5]decane-8-carboxylate

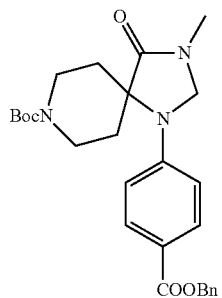

To a solution of 4-(8-(tert-butoxycarbonyl)-3-methyl-4-oxo-1,3,8-triazaspiro[4.5]decan-1-yl)benzoic acid (0.92 g, 0.00236 mol) in N,N-dimethylformamide (10 mL) was added potassium carbonate (0.51 g, 0.00372 mol) and benzyl bromide (0.55 g, 0.00322 mol). Before the reaction was quenched by addition of ice-water (10 mL), the mixture was heated for 2 hours at 50° C. The mixture was extracted with ethyl acetate (3×30 mL). The combined organic layers were dried over anhydrous sodium sulfate and concentrated under reduced pressure. The residue was purified by silica gel column chromatography eluting with ethyl acetate:petroleum ether=1:1 to afford tert-butyl-1-(4-(benzyloxycarbonyl)phenyl)-3-methyl-4-oxo-1,3,8-triazaspiro[4.5]decane-8-carboxylate as a white solid (0.9 g, 81%).

LCMS (ESI): m/z=480.2 [M+H]$^+$.

$^1$H-NMR (300 MHz, CDCl$_3$): δ=1.53 (s, 9H), 1.62-1.65 (m, 2H), 2.57-2.79 (m, 2H), 3.03 (s, 3H), 3.66-4.49 (m, 2H), 4.05-4.16 (m, 2H), 4.74 (s, 2H), 5.33 (s, 2H), 6.65 (d, J=9.1 Hz, 2H), 7.30-7.48 (m, 5H), 7.75 (d, J=9.1 Hz, 2H).

Benzyl-4-(3-methyl-4-oxo-1,3,8-triazaspiro[4.5]decan-1-yl)benzoate hydrochloride

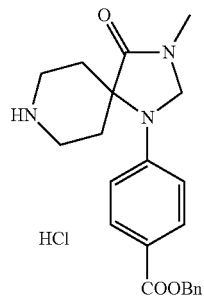

A solution of tert-butyl-1-(4-(benzyloxycarbonyl)phenyl)-3-methyl-4-oxo-1,3,8-triazaspiro[4.5]decane-8-carboxylate (0.9 g, 0.00187 mol) in hydrochloric acid in dioxane (6.0 M, 20 mL) was stirred for 30 minutes. The precipitate was collected by filtration and dried under reduced pressure to afford benzyl-4-(3-methyl-4-oxo-1,3,8-triazaspiro[4.5]decan-1-yl)benzoate hydrochloride as a white solid (0.92 g, 80%).

LCMS (ESI): m/z=380.2 [M+H]⁺.

(R)-Benzyl-4-(8-(2-(2-fluoro-5-(trifluoromethyl)benzamido)-3-methylbutanoyl)-3-methyl-4-oxo-1,3,8-triazaspiro[4.5]decan-1-yl)benzoate

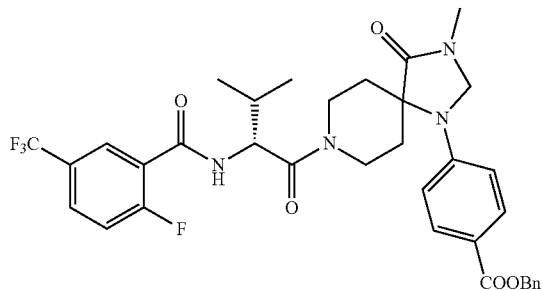

To a mixture of benzyl-4-(3-methyl-4-oxo-1,3,8-triazaspiro[4.5]decan-1-yl)benzoate hydrochloride (120 mg, 0.28 mmol) in dichloromethane (5 mL) was added sequentially (R)-2-(2-fluoro-5-(trifluoromethyl)benzamido)-3-methylbutanoic acid (prepared as described in Example 28-f) (99 mg, 0.32 mmol), (1-[bis(dimethylamino)methylene]-1H-1,2,3-triazolo[4,5-b]pyridinium-3-oxide hexafluorophosphate (HATU) (190 mg, 0.50 mmol) and N,N-diisopropylethylamine (150 mg, 1.164 mmol). The resulting mixture was stirred for 2 hours at room temperature before the reaction was quenched by addition of with ice-water (5 mL). The mixture was extracted with ethyl acetate (3×10 mL) and the combined organic layers were dried over anhydrous sodium sulfate and concentrated under reduced pressure. The residue was purified by prep-TLC with dichloromethane:methanol=15:1 to afford (R)-benzyl-4-(8-(2-(2-fluoro-5-(trifluoromethyl)benzamido)-3-methylbutanoyl)-3-methyl-4-oxo-1,3,8-triazaspiro[4.5]decan-1-yl)benzoate as a thick oil (112 mg, crude).

LCMS (ESI): m/z=669.2 [M+H]⁺.

(R)-4-(8-(2-(2-Fluoro-5-(trifluoromethyl)benzamido)-3-methylbutanoyl)-3-methy-4-oxo-1,3,8-triazaspiro[4.5]decan-1-yl)benzoic Acid

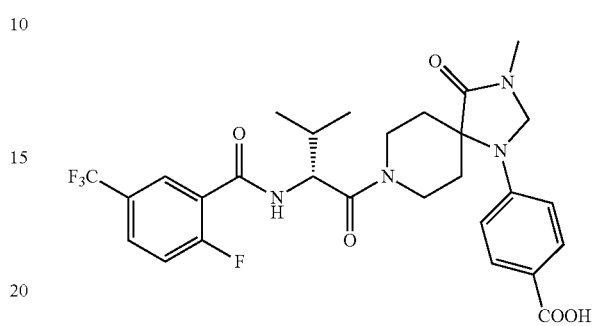

To a solution of ((R)-benzyl-4-(8-(2-(2-fluoro-5-(trifluoromethyl)benzamido)-3-methylbutanoyl)-3-methyl-4-oxo-1,3,8-triazaspiro[4.5]decan-1-yl)benzoate (112 mg, 80% purity, 0.134 mmol) in methanol (15 mL) was added 5% palladium on carbon (50 mg, 50% wet with water). The mixture was stirred under a hydrogen atmosphere for 40 minutes. The catalyst was removed by filtration and the filtrate was concentrated under reduced pressure. The residue was purified by prep-HPLC (acetonitrile and water, acetonitrile from 20% to 60%) to afford (R)-4-(8-(2-(2-fluoro-5-(trifluoromethyl)benzamido)-3-methylbutanoyl)-3-methyl-4-oxo-1,3,8-triazaspiro[4.5]decan-1-yl)benzoic acid as a white solid (64 mg, 38% over two steps).

LCMS (ESI): m/z=579.2 [M+H]⁺.

¹H-NMR (400 MHz, CD₃OD): δ=1.05-1.28 (m, 6H), 1.68-1.91 (m, 2H), 2.19-2.35 (m, 1H), 2.36-2.82 (m, 1H), 2.88-3.00 (m, 1H), 3.04 (s, 3H), 3.50-3.63 (m, 1H), 3.92-4.01 (m, 1H), 4.03-4.10 (m, 1H), 4.29-4.48 (m, 1H), 4.50-4.66 (m, 2H), 4.93-5.18 (m, 1H), 6.74-6.79 (m, 2H), 6.79-7.49 (m, 1H), 7.70-7.72 (m, 1H), 7.88-7.89 (m, 1H), 8.02-8.05 (m, 1H).

The following 18 compounds were synthesized following the general procedure described above:

Example 150

(R)-4-(8-(2-(2-Fluoro-3-methylbenzamido)-3-methylbutanoyl)-3-methyl-4-oxo-1,3,8-triazaspiro[4.5]decan-1-yl)benzoic Acid

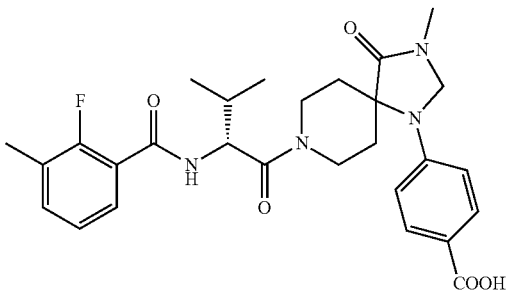 [SMILES: Cc1cccc(C(=O)N[C@@H](C(=O)N2CCC3(CC2)C(=O)N(C)CN3c2ccc(C(=O)O)cc2)C(C)C)c1F]

12.0 mg, yield: 28%, white solid.
LCMS (ESI): m/z=525.2 [M+H]$^+$.
$^1$H-NMR (400 MHz, CD$_3$OD): δ=0.86-1.25 (m, 6H), 1.60-1.94 (m, 2H), 2.16-2.43 (m, 4H), 2.60-2.85 (m, 1H), 2.85-3.00 (m, 1H), 3.07 (s, 3H), 3.54-3.60 (m, 2H), 4.04-4.36 (m, 2H), 4.60-4.85 (m, 2H), 5.10-5.25 (m, 1H), 6.66-6.71 (m, 2H), 7.00-7.20 (m, 1H), 7.29-7.33 (m, 1H), 7.53-7.73 (m, 1H), 7.73-8.08 (m, 3H).

Example 151

(R)-4-(8-(2-(2-Fluoro-5-(trifluoromethyl)benzamido)-3-methylbutanoyl)-4-oxo-1,3,8-triazaspiro[4.5]decan-1-yl)-2-methoxybenzoic Acid

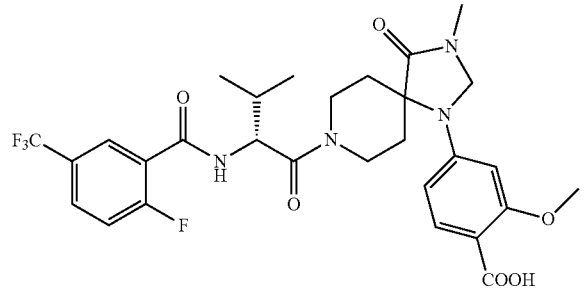 [SMILES: COc1cc(N2CN(C)C(=O)C23CCN(C(=O)[C@H](NC(=O)c2cc(C(F)(F)F)ccc2F)C(C)C)CC3)ccc1C(=O)O]

54.9 mg, yield: 27%, white solid.
LCMS (ESI): m/z=609.2 [M+H]$^+$.
$^1$H-NMR (400 MHz, CD$_3$OD): δ=1.08-1.17 (m, 6H), 1.76-1.88 (m, 2H), 2.22-2.94 (m, 1H), 2.71-2.88 (m, 2H), 3.05 (s, 3H), 3.55-3.60 (m, 1H), 3.85 (s, 3H), 4.02-4.07 (m, 1H), 4.38-4.40 (m, 1H), 4.56-4.58 (m, 1H), 4.71-4.82 (m, 2H), 5.02-5.05 (m, 1H), 6.20-6.27 (m, 1H), 6.43-6.45 (m, 1H), 7.46-7.50 (m, 1H), 7.57-7.78 (m, 1H), 7.89 (m, 1H), 8.03-8.04 (m, 1H), 8.63-8.68 (m, 1H).

Example 152

(R)-4-(8-(2-(5-Ethyl-2-fluorobenzamido)-3-methylbutanoyl)-3-methyl-4-oxo-1,3,8-triazaspiro[4.5]decan-1-yl)benzoic Acid

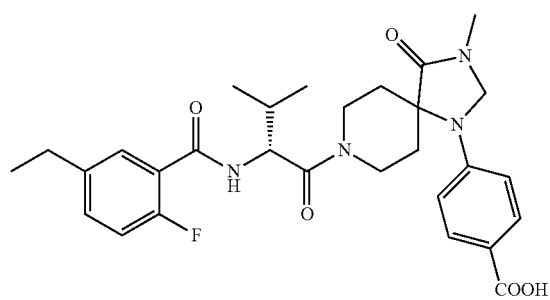 [SMILES: CCc1ccc(F)c(C(=O)N[C@@H](C(=O)N2CCC3(CC2)C(=O)N(C)CN3c2ccc(C(=O)O)cc2)C(C)C)c1]

24.0 mg, yield: 31%, white solid.
LCMS (ESI): m/z=539.2 [M+H]$^+$.
$^1$H-NMR (400 MHz, CD$_3$OD): δ=1.03-1.34 (m, 9H), 1.64-1.90 (m, 2H), 2.15-2.28 (m, 1H), 2.61-2.74 (m, 3H), 2.84-2.98 (m, 1H), 3.03 (s, 3H), 3.46-3.61 (m, 1H), 3.95-4.11 (m, 1H), 4.31-4.42 (m, 1H), 4.54-4.65 (m, 1H), 4.13-4.84 (m, 2H), 4.96-4.98 (m, 1H), 6.52-6.79 (m, 1H), 7.10-7.19 (m, 1H), 7.31-7.40 (m, 1H), 7.61-7.65 (m, 1H), 7.74-7.90 (m, 2H).

Example 153

(R)-4-(8-(2-(5-Cyclopropyl-2-fluorobenzamido)-3-methylbutanoyl)-3-methyl-4-oxo-1,3,8-triazaspiro[4.5]decan-1-yl)benzoic Acid

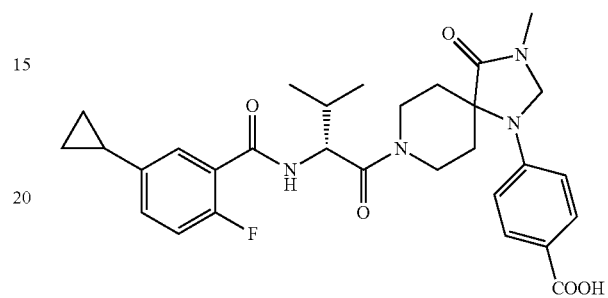

23.5 mg, yield: 49%, white solid.
LCMS (ESI): m/z=551.2 [M+H]$^+$.
$^1$H-NMR (400 MHz, CD$_3$OD): δ=0.55-0.73 (m, 2H), 0.89-1.00 (m, 2H), 1.03-1.04 (m, 3H), 1.09-1.14 (m, 4H), 1.71-1.74 (m, 1H), 1.80-1.84 (m, 1H), 1.91-2.02 (m, 1H), 2.20-2.33 (m, 1H), 2.67-2.83 (m, 1H), 2.92-3.00 (m, 1H), 3.04 (s, 3H), 3.52-3.59 (m, 1H), 3.99-4.05 (m, 1H), 4.33-4.43 (m, 1H), 4.54-4.63 (m, 1H), 4.81-4.83 (m, 1H), 4.97-5.05 (m, 1H), 6.76-6.80 (m, 2H), 7.09-7.29 (m, 2H), 7.46-7.50 (m, 1H), 7.74-7.90 (m, 2H), 8.24-8.32 (m, 1H).

Example 154

(R)-2-Chloro-4-(8-(2-(2-fluoro-5-(trifluoromethyl)benzamido)-3-methylbutanoyl)-3-methyl-4-oxo-1,3,8-triazaspiro[4.5]decan-1-yl)benzoic Acid

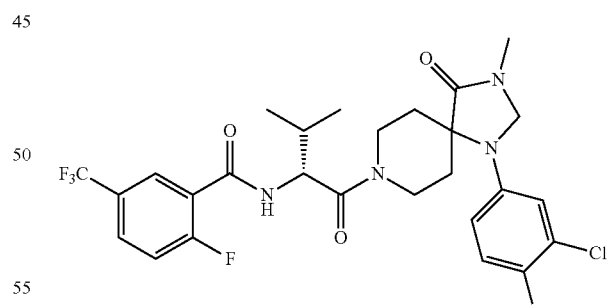

13.0 mg, yield: 12%, white solid.
LCMS (ESI): m/z=613.0 [M+H]$^+$.
$^1$H-NMR (400 MHz, CD$_3$OD): δ=1.05-1.20 (m, 6H), 1.4-1.88 (m, 2H), 2.22-2.29 (m, 1H), 2.63-2.70 (m, 1H), 2.89-2.94 (m, 1H), 3.04 (s, 3H), 3.53-3.60 (m, 1H), 4.01-4.08 (m, 1H), 4.39-4.42 (m, 1H), 4.57-4.59 (m, 1H), 4.80-4.84 (m, 2H), 5.05-5.10 (m, 1H), 6.68-6.72 (m, 1H), 6.79-6.82 (m, 1H), 7.44-7.49 (m, 1H), 7.65-7.67 (m, 1H), 7.88-7.90 (m, 1H), 8.05-8.07 (m, 1H), 8.58-8.67 (m, 1H).

Example 155

(R)-4-(3-(Cyclopropylmethyl)-8-(2-(2-fluoro-5-(trifluoromethyl)benzamido)-3-methylbutanoyl)-4-oxo-1,3,8-triazaspiro[4.5]decan-1-yl)benzoic Acid

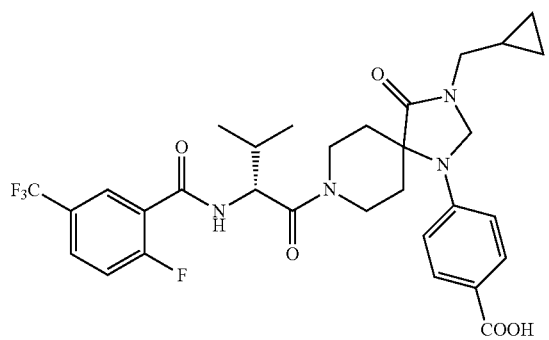 [SMILES: CC(C)[C@@H](NC(=O)c1cc(C(F)(F)F)ccc1F)C(=O)N1CCC2(CC1)C(=O)N(CC1CC1)CN2c1ccc(C(=O)O)cc1]

36.5 mg, yield: 33%, white solid.

LCMS (ESI): m/z=619.2 [M+H]$^+$.

$^1$H-NMR (400 MHz, CD$_3$OD): δ=0.35-0.38 (m, 2H), 0.63-0.67 (m, 2H), 1.05-1.12 (m, 7H), 1.71-1.92 (m, 2H), 2.23-2.27 (m, 1H), 2.69-2.80 (m, 1H), 2.93-3.00 (m, 1H), 3.31-3.33 (m, 2H), 3.52-3.59 (m, 1H), 3.99-4.07 (m, 1H), 4.33-4.42 (m, 1H), 4.56-4.60 (m, 1H), 4.94-5.05 (m, 4H), 6.79-6.81 (m, 2H), 7.45-7.47 (m, 1H), 7.73-7.89 (m, 3H), 8.03-8.06 (m, 1H), 8.55-8.67 (m, 1H).

Example 156

(R)-4-(8-(2-Cyclopentyl-2-(2-fluoro-5-(trifluoromethyl)benzamido)acetyl)-3-methyl-4-oxo-1,3,8-triazaspiro[4.5]decan-1-yl)benzoic Acid

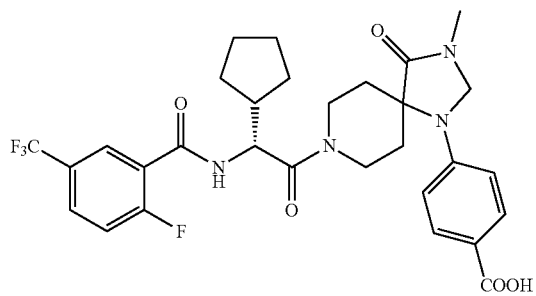 [SMILES: CN1CN(c2ccc(C(=O)O)cc2)C2(CCN(C(=O)[C@H](NC(=O)c3cc(C(F)(F)F)ccc3F)C3CCCC3)CC2)C1=O]

29.0 mg, yield: 35%, white solid.

LCMS (ESI): m/z=605.2 [M+H]$^+$.

$^1$H-NMR (400 MHz, CD$_3$OD): δ=1.32-1.40 (m, 1H), 1.45-1.58 (m, 1H), 1.65-1.81 (m, 6H), 1.93-1.95 (m, 1H), 2.50-2.56 (m, 1H), 2.67-2.76 (m, 2H), 2.95-3.01 (m, 1H), 3.04 (s, 3H), 3.51-3.60 (m, 1H), 4.00-4.08 (m, 1H), 4.39-4.50 (m, 1H), 4.56-4.59 (m, 1H), 4.83-4.88 (m, 2H, 1H contained in solvent signal), 5.04-5.07 (m, 1H), 6.74-6.83 (m, 2H), 7.43-7.48 (m, 1H), 7.69-7.71 (m, 1H), 7.86-8.06 (m, 3H).

Example 157

(R)—N-(1-(1-(4-Carbamoylphenyl)-3-methyl-4-oxo-1,3,8-triazaspiro[4.5]decan-8-yl)-3-methyl-1-oxobutan-2-yl)-2-fluoro-5-(trifluoromethyl)benzamide

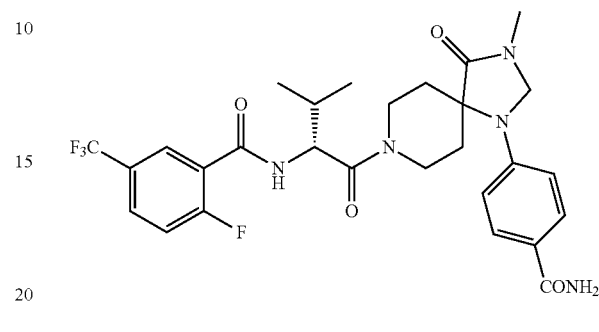

23.1 mg, yield: 9%, white solid.

LCMS (ESI): m/z=578.2 [M+H]$^+$.

$^1$H-NMR (400 MHz, CD$_3$OD): δ=1.05-1.20 (m, 6H), 1.73-1.85 (m, 2H), 2.25-2.28 (m, 1H), 2.69-2.73 (m, 1H), 2.95-2.98 (m, 1H), 3.05 (s, 3H), 3.54-3.61 (m, 1H), 4.04-4.05 (m, 1H), 4.35-4.38 (m, 1H), 4.46-4.49 (m, 1H), 4.56-4.58 (m, 2H), 4.99-5.06 (m, 1H), 6.78-6.81 (m, 2H), 7.46-7.51 (m, 1H), 7.63-7.65 (m, 1H), 7.80-7.82 (m, 1H), 7.88-7.89 (m, 1H), 8.04-8.05 (m, 1H).

Example 158

(R)-4-(8-(2-(2-Fluoro-5-(trifluoromethyl)benzamido)-3-methylbutanoyl)-3-methy-4-oxo-1,3,8-triazaspiro[4.5]decan-1-yl)-2-methylbenzoic Acid

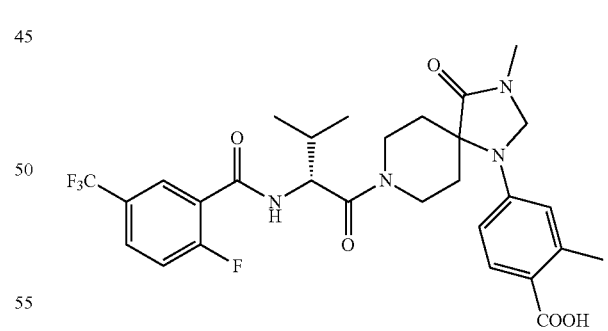

25.0 mg, yield: 32%, white solid.

LCMS (ESI): m/z=593.2 [M+H]$^+$.

$^1$H-NMR (400 MHz, CD$_3$OD): δ=0.99-1.16 (m, 6H), 1.78-1.80 (m, 2H), 2.22-2.30 (m, 1H), 2.36-2.39 (m, 2H), 2.44-2.59 (m, 2H), 2.63-2.72 (m, 1H), 3.03 (s, 3H), 3.58-3.65 (m, 1H), 3.94-4.10 (m, 1H), 4.31-4.35 (m, 1H), 4.44-4.49 (m, 1H), 4.73-4.78 (m, 2H), 4.98-5.03 (m, 1H), 6.91-7.02 (m, 2H), 7.21 (m, 1H), 7.39-7.51 (m, 1H), 7.84-8.09 (m, 2H).

Example 159

(R)-4-(8-(2-(2-Fluoro-5-(trifluoromethyl)benzamido)-3,3-dime-3-methy-4-oxo-1,3,8-triazaspiro[4.5]decan-1-yl)benzoic Acid

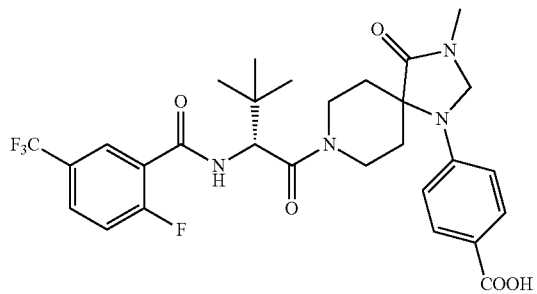

4.1 mg, yield: 6%, white solid.

LCMS (ESI): m/z=593.2 [M+H]$^+$.

$^1$H-NMR (400 MHz, CDCl$_3$): δ=1.06-1.15 (m, 6H), 1.21-1.23 (m, 2H), 1.27-1.29 (m, 1H), 1.66-1.70 (m, 1H), 1.82-1.85 (m, 1H), 2.70-2.74 (m, 1H), 2.87-2.91 (m, 1H), 3.07 (s, 3H), 3.54-3.57 (m, 1H), 4.12-4.17 (m, 1H), 4.29-4.32 (m, 1H), 4.66-4.69 (m, 1H), 4.76-4.85 (m, 2H), 5.22-5.32 (m, 1H), 6.59-6.73 (m, 2H), 7.28-7.52 (m, 1H), 7.68-7.98 (m, 4H), 8.33-8.39 (m, 1H).

Example 160

(R)-4-(8-(2-(3-Chloro-5-(trifluoromethyl)benzamido)-3-methylbutanoyl)-3-methyl-4-oxo-1,3,8-triazaspiro[4.5]decan-1-yl)benzoic Acid

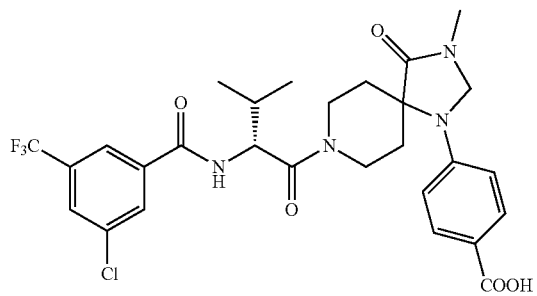 [SMILES: CC(C)[C@@H](NC(=O)c1cc(Cl)cc(C(F)(F)F)c1)C(=O)N1CCC2(CC1)C(=O)N(C)CN2c1ccc(C(=O)O)cc1]

18.5 mg, yield: 30%, white solid.

LCMS (ESI): m/z=595.1 [M+H]$^+$.

$^1$H-NMR (400 MHz, CD$_3$OD): δ=1.03-1.20 (m, 6H), 1.69-1.90 (m, 2H), 2.27-2.35 (m, 1H), 2.64-2.73 (m, 1H), 2.94-2.99 (m, 1H), 3.04 (s, 3H), 3.51-3.58 (m, 1H), 3.99-4.06 (m, 1H), 4.43-4.60 (m, 2H), 4.80-4.84 (m, 3H, 1H contained in solvent signal), 6.70-6.80 (m, 2H), 7.58-7.61 (m, 2H), 7.87-7.90 (m, 1H), 8.13-8.17 (m, 2H), 8.82-8.99 (m, 1H).

Example 161

(R)-4-(3-Methyl-8-(3-methyl-2-(2-methyl-5-(trifluoromethyl)benzamido)butanoyl)-4-oxo-1,3,8-triazaspiro[4.5]decan-1-yl)benzoic Acid

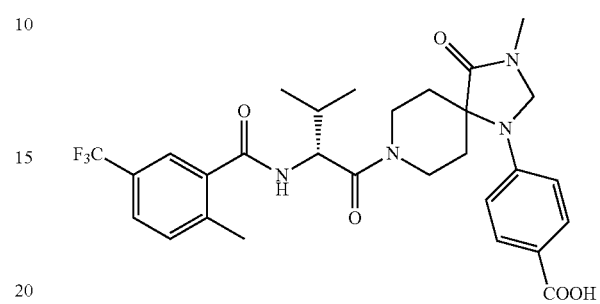

15.0 mg, yield: 35%, white solid.

LCMS (ESI): m/z=575.2 [M+H]$^+$.

$^1$H-NMR (400 MHz, CD$_3$OD): δ=1.13-1.15 (m, 6H), 1.69-1.80 (m, 2H), 2.22-2.35 (m, 1H), 2.50-2.54 (m, 3H), 2.67-2.84 (m, 1H), 3.00-3.13 (m, 4H), 3.54-3.58 (m, 1H), 4.06-4.11 (m, 1H), 4.39-4.43 (m, 1H), 4.54-4.67 (m, 1H), 4.84-4.92 (m, 2H), 4.94-5.05 (m, 1H), 6.80-6.83 (m, 2H), 7.48-7.53 (m, 1H), 7.64-7.67 (m, 1H), 7.71-7.81 (m, 2H), 7.89-8.00 (m, 1H).

Example 162

(R)-4-(8-(2-(2-Fluoro-5-(trifluoromethoxy)benzamido)-3-methylbutanoyl)-3-methyl-4-oxo-1,3,8-triazaspiro[4.5]decan-1-yl)benzoic Acid

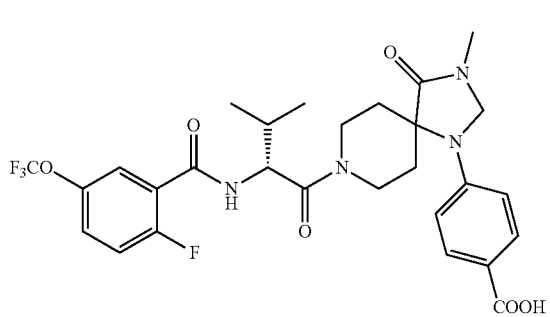 [SMILES: CC(C)[C@@H](NC(=O)c1cc(OC(F)(F)F)ccc1F)C(=O)N1CCC2(CC1)C(=O)N(C)CN2c1ccc(C(=O)O)cc1]

10.6 mg, yield: 15%, white solid.

LCMS (ESI): m/z=595.2 [M+H]$^+$.

$^1$H-NMR (400 MHz, CD$_3$OD): δ=1.75-1.88 (m, 6H), 1.75-1.78 (m, 2H), 2.25-2.36 (m, 2H), 2.90-2.92 (m, 1H), 3.10 (s, 3H), 3.55-3.59 (m, 1H), 4.01-4.03 (m, 1H), 4.31-4.35 (m, 2H), 4.83-4.85 (m, 1H), 4.96-5.00 (m, 2H), 6.75-6.80 (m, 1H), 7.36-7.90 (m, 5H), 8.56-8.61 (m, 1H).

Example 163

(R)-4-(8-(2-(2-Fluoro-5-methoxybenzamido)-3-methylbutanoyl)-3-methyl-4-oxo-1,3,8-triazaspiro[4.5]decan-1-yl)benzoic Acid

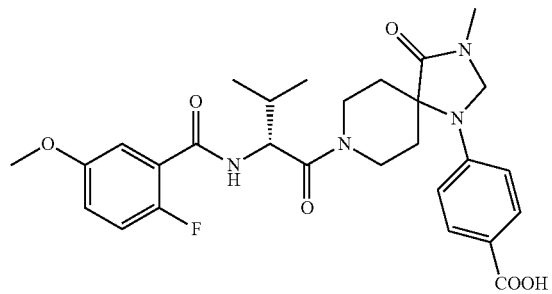 [SMILES: COc1ccc(F)c(C(=O)N[C@@H](C(=O)N2CCC3(CC2)C(=O)N(C)CN3c2ccc(C(=O)O)cc2)C(C)C)c1]

27.5 mg, yield: 26%, white solid.

LCMS (ESI): m/z=541.2 [M+H]$^+$.

$^1$H-NMR (400 MHz, CDCl$_3$): δ=1.08-1.27 (m, 6H), 1.68-1.78 (m, 2H), 2.21-2.24 (m, 1H), 2.27-2.77 (m, 1H), 2.88-2.93 (m, 1H), 3.06 (s, 3H), 3.50-3.57 (m, 1H), 3.78-3.82 (m, 3H), 4.03-4.22 (m, 2H), 4.69-4.80 (m, 3H), 5.07-5.21 (m, 1H), 6.50-6.69 (m, 2H), 6.95-7.12 (m, 2H), 7.53-7.84 (m, 2H), 7.94-7.96 (m, 2H).

Example 164

(R)-4-(8-(2-(1-Admantanecarboxamido)-3-methylbutanoyl)-3-methyl-4-oxo-1,3,8-triazaspiro[4.5]decan-1-yl)benzoic Acid

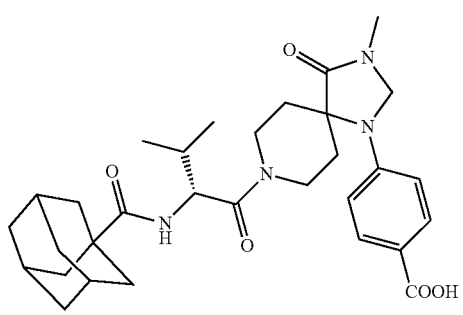 [SMILES: CC(C)[C@@H](NC(=O)C12CC3CC(CC(C3)C1)C2)C(=O)N1CCC2(CC1)C(=O)N(C)CN2c1ccc(C(=O)O)cc1]

29.9 mg, yield: 54%, white solid.

LCMS (ESI): m/z=551.2 [M+H]$^+$.

$^1$H-NMR (400 MHz, CDCl$_3$): δ=0.90-1.03 (m, 6H), 1.72-1.97 (m, 16H), 2.15-2.21 (m, 1H), 2.68-2.83 (m, 3H), 3.04 (s, 3H), 3.50-3.56 (m, 1H), 4.00-4.94 (m, 1H), 4.24-4.26 (m, 1H), 4.52-4.54 (m, 1H), 4.73-4.75 (m, 1H), 4.84-4.86 (m, 2H), 6.77-6.79 (m, 2H), 7.85-7.95 (m, 2H).

Example 165

(R)-4-(8-(2-(5-(Difluoromethoxy)-2-fluorobenzamido)-3-methylbutanoyl)-3-methyl-4-oxo-1,3,8-triazaspiro[4.5]decan-1-yl)benzoic Acid

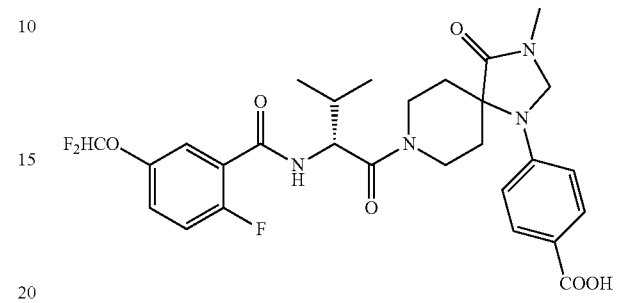

36.0 mg, yield: 51%, white solid.

LCMS (ESI): m/z=577.2 [M+H]$^+$.

$^1$H-NMR (400 MHz, CDCl$_3$): δ=1.04-1.15 (m, 6H), 1.72-1.81 (m, 2H), 2.24-2.29 (m, 1H), 2.67-2.94 (m, 2H), 3.04 (s, 3H), 3.52-3.59 (m, 1H), 4.03-4.06 (m, 1H), 4.32-4.34 (m, 1H), 4.55-4.58 (m, 1H), 4.86-4.91 (m, 1H), 4.97-5.05 (m, 2H), 6.75-6.77 (m, 2H), 6.85-6.94 (m, 1H), 7.28-7.31 (m, 1H), 7.52-7.55 (m, 1H), 7.72-7.79 (m, 1H), 7.88-7.90 (m, 1H), 8.39-8.46 (m, 1H).

Example 166

(R)-4-(8-(2-(5-(Difluoromethoxy)-2-fluorobenzamido)-3-methylbutanoyl)-3-methyl-2,4-dioxo-1,3,8-triazaspiro[4.5]decan-1-yl)benzoic Acid

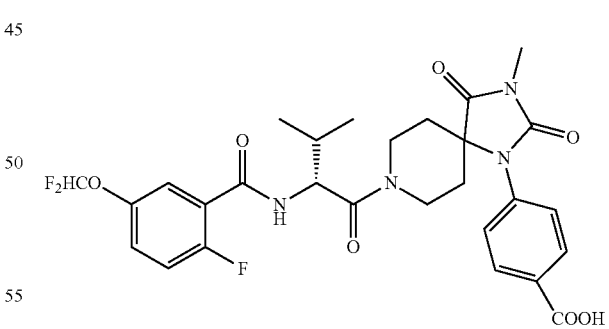

19.9 mg, 77% yield, white solid.

LCMS (ESI): m/z=591.1 [M+H]$^+$.

$^1$H-NMR (400 MHz, CD$_3$OD): δ=0.79-1.01 (m, 6H), 1.71-2.19 (m, 5H), 3.09 (s, 3H), 3.46-3.52 (m, 1H), 3.89-4.04 (m, 1H), 4.15-4.56 (m, 2H), 4.79-4.84 (m, 1H), 6.66-7.00 (m, 1H), 7.21-7.49 (m, 5H), 8.02-8.17 (m, 2H).

Example 167
(R)-4-(8-(2-(2-Fluoro-5-(trifluoromethoxy)benzamido)-3-methylbutanoyl)-3-methyl-2,4-dioxo-1,3,8-triazaspiro[4.5]decan-1-yl)benzoic Acid
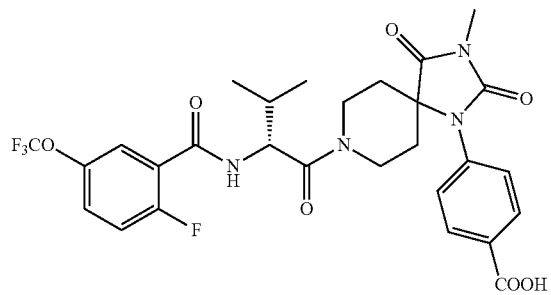 [SMILES: CC(C)[C@@H](NC(=O)c1cc(OC(F)(F)F)ccc1F)C(=O)N1CCC2(CC1)C(=O)N(C)C(=O)N2c1ccc(C(=O)O)cc1]
57.4 mg, 66% yield, white solid.
LCMS (ESI): m/z=609.2 [M+H]$^+$.
$^1$H-NMR (400 MHz, CD$_3$OD): δ=0.80-1.01 (m, 6H), 1.70-2.27 (m, 5H), 3.10 (s, 3H), 3.46-3.54 (m, 1H), 3.91-3.99 (m, 1H), 4.26-4.58 (m, 2H), 4.78-4.83 (m, 1H), 7.26-7.65 (m, 5H), 8.04-8.16 (m, 2H).
Example 168
(R)-2-(4-(8-(2-(5-Ethyl-2-fluorobenzamido)-3-methylbutanoyl)-3-methyl-4-oxo-1,3,8-triazaspiro[4.5]decan-1-yl)phenoxy)acetic Acid
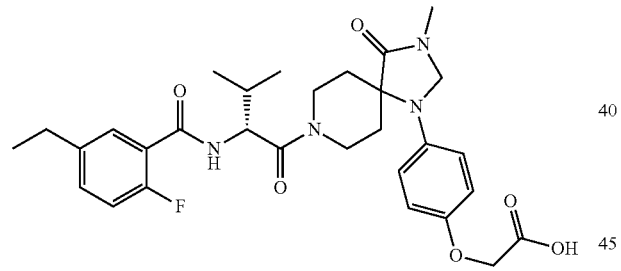
Representative Scheme:
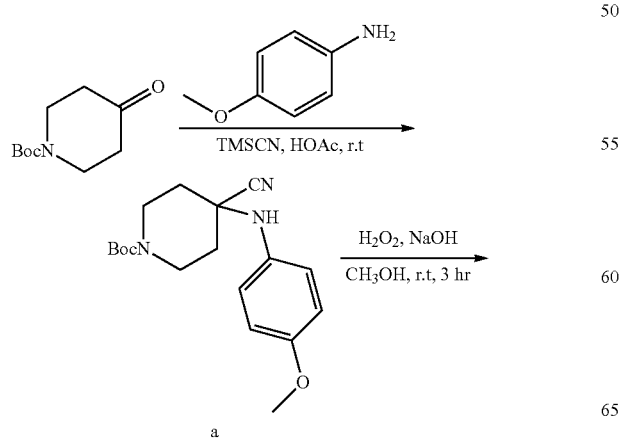
a
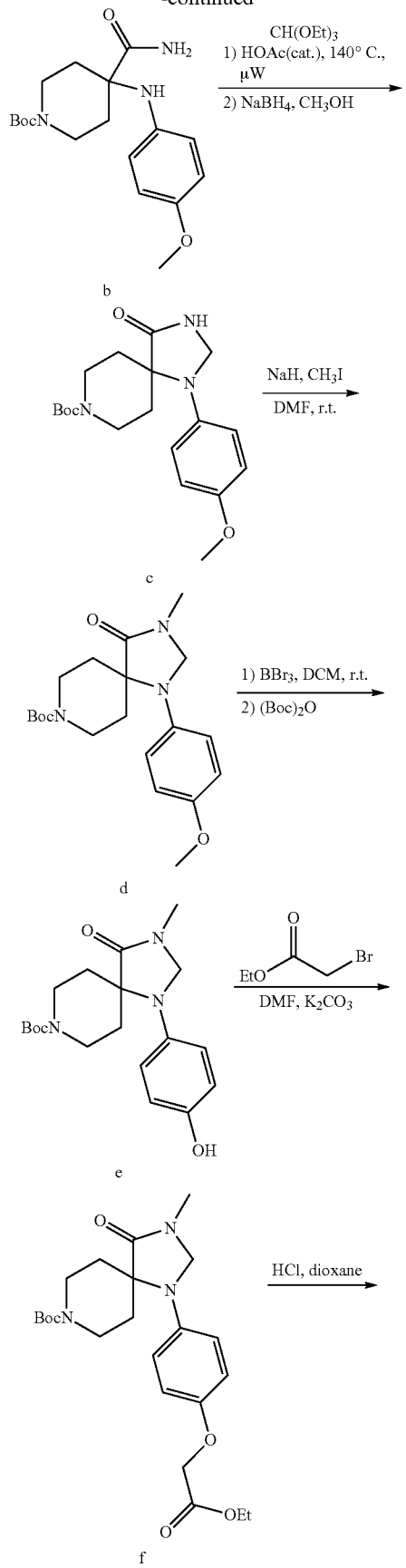
b
c
d
e
f 163
-continued 164
Representative General Procedure:

tert-Butyl-4-cyano-4-(4-methoxyphenylamino)piperidine-1-carboxylate

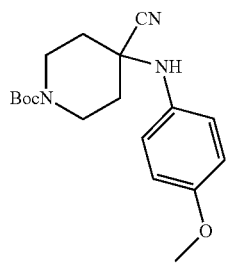 [SMILES: COc1ccc(NC2(C#N)CCN(C(=O)OC(C)(C)C)CC2)cc1]

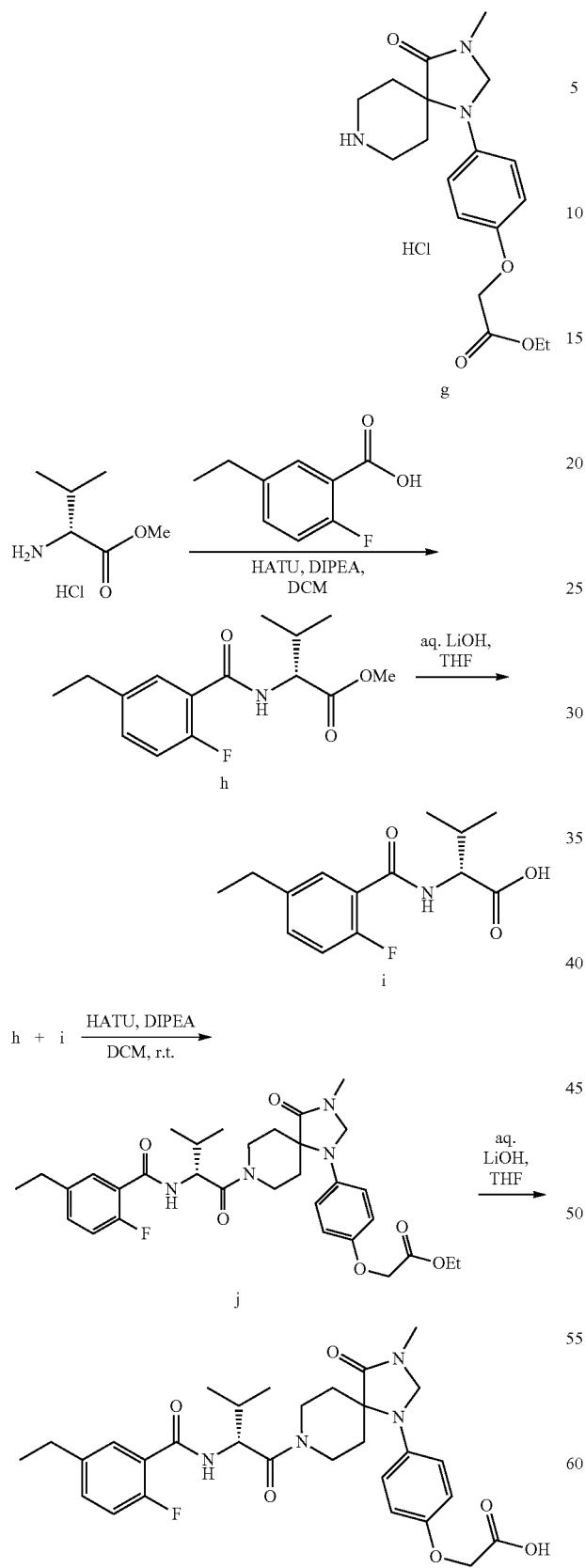

To a solution of 4-methoxyaniline (5.0 g, 0.040 mol) in acetic acid (30 mL) was added tert-butyl-4-oxopiperidine-1-carboxylate (8.8 g, 0.044 mol). The resulting mixture was cooled to 0° C. and trimethylsilyl cyanide (4.36 g, 0.040 mol) was added. The solution was stirred overnight. Saturated aqueous ammonium chloride solution was added (50 mL). The mixture was filtered, the filter cake was washed with water (3×10 mL) and dried under reduced pressure to afford tert-butyl-4-cyano-4-(4-methoxyphenylamino)piperidine-1-carboxylate as a white solid (12.1 g, 93%).

LCMS (ESI): m/z=332.1 [M+H]$^+$.

tert-Butyl-4-carbamoyl-4-(4-methoxyphenylamino)piperidine-1-carboxylate

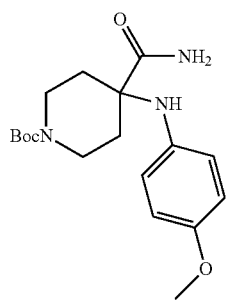 [SMILES: COc1ccc(NC2(C(N)=O)CCN(C(=O)OC(C)(C)C)CC2)cc1]

To a solution of tert-butyl-4-cyano-4-(4-methoxyphenylamino)piperidine-1-carboxylate (3.0 g, 9.06 mmol) in methanol (16 mL) was added an aqueous sodium hydroxide solution (10 mL, 1.0 M). After stirring for 15 minutes, to the resulting solution was added a 30% aqueous hydrogen peroxide solution (10 mL) dropwise. The resulting mixture was stirred overnight and filtered. The white solid was washed with water (3×10 mL) and dried under reduced pressure to afford tert-butyl-4-carbamoyl-4-(4-methoxyphenylamino)piperidine-1-carboxylate as a white solid (2.8 g, crude), which was used directly without any further purification.

LCMS (ESI): m/z=350.2 [M+H]$^+$.

tert-Butyl-1-(4-methoxyphenyl)-4-oxo-1,3,8-triazaspiro[4.5]decane-8-carboxylate

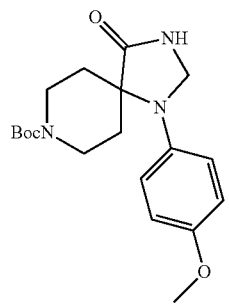 [SMILES: COc1ccc(N2CNC(=O)C23CCN(C(=O)OC(C)(C)C)CC3)cc1]

To a solution of tert-butyl-4-carbamoyl-4-(4-methoxyphenylamino)piperidine-1-carboxylate (450 mg, 1.3 mmol) in triethyl orthoformate (4 mL) was added acetic acid (2 drops, cat.). The mixture was heated at 140° C. for 30 minutes in a microwave reactor. The solvent was removed under reduced pressure and the residue was dissolved in methanol (10 mL). To the resulting solution was added sodium borohydride (100 mg, 2.6 mmol) at 0° C. The resulting mixture was stirred for 30 minutes. The solvent was removed under reduced pressure and the residue was diluted with water (10 mL) and ethyl acetate (15 mL). The organic layer was collected and the aqueous layer was extracted with ethyl acetate (3×50 mL). The combined organic layers were dried over anhydrous sodium sulfate and concentrated under reduced pressure. The residue was purified by silica gel column chromatography eluting with dichloromethane:methanol=200:1 to afford tert-butyl-1-(4-methoxyphenyl)-4-oxo-1,3,8-triazaspiro[4.5]decane-8-carboxylate as a white solid (220 mg, 48%).

LCMS (ESI): m/z=362.2 [M+H]$^+$.

tert-Butyl-1-(4-methoxyphenyl)-3-methyl-4-oxo-1,3,8-triazaspiro[4.5]decane-8-carboxylate

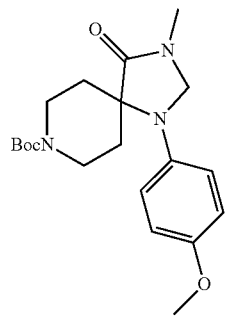 [SMILES: COc1ccc(N2CN(C)C(=O)C23CCN(C(=O)OC(C)(C)C)CC3)cc1]

To a solution of tert-butyl-1-(4-methoxyphenyl)-4-oxo-1,3,8-triazaspiro[4.5]decane-8-carboxylate (240 mg, 0.66 mmol) in N,N-dimethylformamide (5 mL) was added sodium hydride (82 mg, 60% in oil, 2.04 mmol) at 0° C. After stirring for 15 minutes, iodomethane (600 mg, 4.2 mmol) was added. The resulting mixture was stirred for 1 hour. The reaction was quenched with ice-water (10 mL) and the mixture was extracted with ethyl acetate (3×50 mL). The combined organic layers were dried over anhydrous sodium sulfate and concentrated under reduced pressure. The residue was purified by silica gel column chromatography eluting with dichloromethane:methanol=15:1 to afford tert-butyl-1-(4-methoxyphenyl)-3-methyl-4-oxo-1,3,8-triazaspiro[4.5]decane-8-carboxylate as a yellow oil (232 mg, 93%).

LCMS (ESI): m/z=376.1 [M+H]$^+$.

tert-Butyl-1-(4-hydroxyphenyl)-3-methyl-4-oxo-1,3,8-triazaspiro[4.5]decane-8-carboxylate

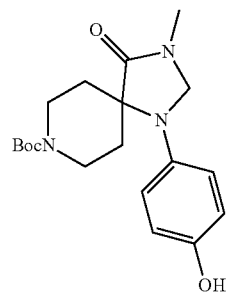

To a solution of tert-butyl 1-(4-methoxyphenyl)-3-methyl-4-oxo-1,3,8-triazaspiro[4.5]decane-8-carboxylate (160 mg, 0.42 mmol) in dichloromethane (15 mL) was added boron tribromide (500 mg, 2.0 mmol) at 0° C. After stirring overnight, the reaction was quenched by addition of ice-water (5 mL). To the mixture was added di-tert-butyl-dicarbonate (300 mg, 1.37 mmol) and potassium carbonate (1 g, 7.24 mmol). The mixture was stirred for 2 hours. The organic layer was isolated and the aqueous layer was extracted with ethyl acetate (3×20 mL). The combined organic layers were dried over anhydrous sodium sulfate and concentrated under reduced pressure. The residue was purified by silica gel column chromatography eluting with dichloromethane:methanol=40:1 to afford tert-butyl-1-(4-hydroxyphenyl)-3-methyl-4-oxo-1,3,8-triazaspiro[4.5]decane-8-carboxylate as a colorless oil (110 mg, 72%).

LCMS (ESI): m/z=362.1 [M+H]$^+$.

tert-Butyl-1-(4-(2-ethoxy-2-oxoethoxy)phenyl)-3-methyl-4-oxo-1,3,8-triazaspiro[4.5]decane-8-carboxylate

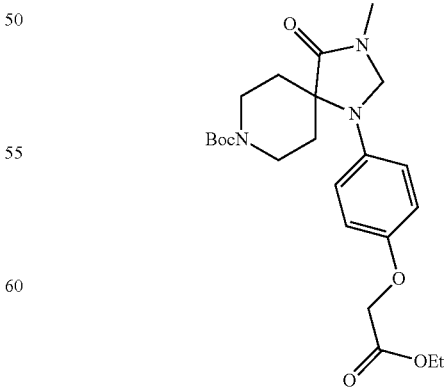

To a solution of tert-butyl-1-(4-hydroxyphenyl)-3-methyl-4-oxo-1,3,8-triazaspiro[4.5]decane-8-carboxylate (50 mg, 0.14 mmol) in N,N-dimethylformamide (15 mL) was added potassium carbonate (38 mg, 0.28 mmol) and ethyl-2-bromoacetate (50 mg, 0.14 mmol). The resulting mixture was stirred overnight. After quenching with ice-water (10 mL), the mixture was extracted with ethyl acetate (3×50 mL). The combined organic layers were dried over anhydrous sodium sulfate and concentrated under reduced pressure. The residue was purified by prep-TLC with ethyl acetate:petroleum ether=1:1 to afford tert-butyl-1-(4-(2-ethoxy-2-oxoethoxy)phenyl)-3-methyl-4-oxo-1,3,8-triazaspiro[4.5]decane-8-carboxylate as a colorless oil (40 mg, 65%).

LCMS (ESI): m/z=448.2 [M+H]+.

Ethyl-2-(4-(3-methyl-4-oxo-1,3,8-triazaspiro[4.5]decan-1-yl)phenoxy)acetate hydrochloride

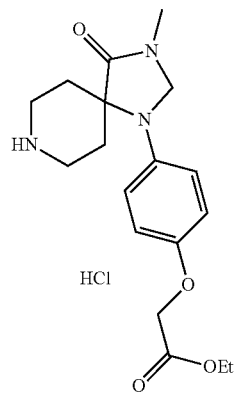 [SMILES: CCOC(=O)COc1ccc(N2CN(C)C(=O)C23CCNCC3)cc1 ; Cl]

A solution of tert-butyl-1-(4-(2-ethoxy-2-oxoethoxy)phenyl)-3-methyl-4-oxo-1,3,8-triazaspiro[4.5]decane-8-carboxylate (40 mg, 0.089 mmol) in hydrochloric acid in dioxane (6.0 M, 10 mL) was stirred for 30 minutes. The precipitate was collected by filtration and dried under reduced pressure to afford ethyl-2-(4-(3-methyl-4-oxo-1,3,8-triazaspiro[4.5]decan-1-yl)phenoxy)acetate hydrochloride as a white solid (31 mg, 100%).

LCMS (ESI): m/z=348.2 [M+H]+.

(R)-Methyl-2-(5-ethyl-2-fluorobenzamido)-3-methylbutanoate

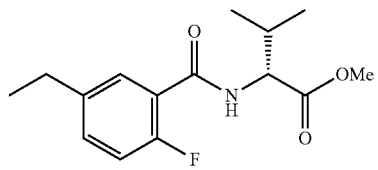 [SMILES: CCc1ccc(F)c(C(=O)N[C@@H](C(=O)OC)C(C)C)c1]

To a solution of 5-ethyl-2-fluorobenzoic acid (1.00 g, 5.95 mmol) in dichloromethane (50 mL) was added sequentially D-valine methyl ester hydrochloride (1.2 g, 7.18 mmol), 1-[bis(dimethylamino)methylene]-1H-1,2,3-triazolo[4,5-b]pyridinium-3-oxide hexafluorophosphate (HATU) (3.4 g, 8.94 mmol) and N,N-diisopropylethylamine (1.9 g, 14.7 mmol). Before quenching with ice-water (50 mL), the reaction was stirred for 2 hours. The mixture was extracted with dichloromethane (3×100 mL). The combined organic layers were dried over anhydrous sodium sulfate and the solvent was removed under reduced pressure. The residue was purified by silica gel column chromatography eluting with ethyl acetate:petroleum ether=1:4 to afford (R)-methyl-2-(5-ethyl-2-fluorobenzamido)-3-methylbutanoate as a thick oil (1.6 g, 95%).

LCMS (ESI): m/z=282.2 [M+H]+.

(R)-2-(5-Ethyl-2-fluorobenzamido)-3-methylbutanoic Acid

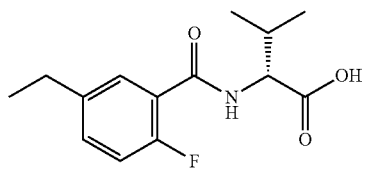 [SMILES: CCc1ccc(F)c(C(=O)N[C@@H](C(=O)O)C(C)C)c1]

To a solution of (R)-methyl-2-(5-ethyl-2-fluorobenzamido)-3-methylbutanoate (1.6 g, crude) in tetrahydrofuran (20 mL) was added an aqueous lithium hydroxide solution (240 mg in 10 mL of water, 17.8 mmol). Before quenching with ice-water (20 mL), the reaction was stirred for 1 hour. The pH of the solution was adjusted to 3 by addition of a 9% aqueous hydrochloric acid solution. The mixture was filtered and the filter cake was washed with petroleum ether (30 mL) and dried under reduced pressure to afford (R)-2-(5-ethyl-2-fluorobenzamido)-3-methylbutanoic acid as a white solid (1.3 g, 94% over two steps).

LCMS (ESI): m/z=268.1 [M+H]+.

$^1$H-NMR (300 MHz, CDCl$_3$): δ=1.05 (dd, J=8.6, 6.9 Hz, 6H), 1.23 (t, J=7.6 Hz, 3H), 2.31-2.45 (m, 1H), 2.65 (q, J=7.8 Hz, 2H), 7.01-7.07 (m, 1H), 7.16-7.33 (m, 2H), 7.85-7.93 (m, 1H).

(R)-Ethyl-2-(4-(8-(2-(5-ethyl-2-fluorobenzamido)-3-methylbutanoyl)-3-methyl-4-oxo-1,3,8-triazaspiro[4.5]decan-1-yl)phenoxy)acetate

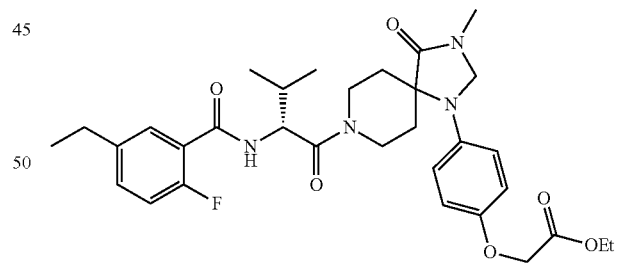

To a mixture of ethyl-2-(4-(3-methyl-4-oxo-1,3,8-triazaspiro[4.5]decan-1-yl)phenoxy)acetate hydrochloride (31 mg, 0.089 mmol) in dichloromethane (5 mL) was added sequentially (R)-2-(5-ethyl-2-fluorobenzamido)-3-methylbutanoic acid (24 mg, 0.089 mmol), 1-[bis(dimethylamino)methylene]-1H-1,2,3-triazolo[4,5-b]pyridinium-3-oxide hexafluorophosphate (HATU) (51 mg, 0.13 mmol) and N,N-diisopropylethylamine (29 mg, 0.22 mmol). The resulting mixture was stirred for 2 hours at room temperature before the reaction was quenched with ice-water. The mixture was extracted with ethyl acetate (3×10 mL) and the combined organic layers were dried over anhydrous sodium sulfate and concentrated under reduced pressure. The residue was purified by prep-TLC with dichloromethane:methanol=15:1 to afford (R)-ethyl-2-(4-(8-(2-(5-ethyl-2-fluorobenzamido)-3-methylbutanoyl)-3-methyl-4-oxo-1,3,8-triazaspiro[4.5]decan-1-yl)phenoxy)acetate as a colorless oil (20 mg, 37%).

LCMS (ESI): m/z=597.1 [M+H]⁺.

(R)-2-(4-(8-(2-(5-Ethyl-2-fluorobenzamido)-3-methylbutanoyl)-3-methyl-4-oxo-1,3,8-triazaspiro[4.5]decan-1-yl)phenoxy)acetic Acid

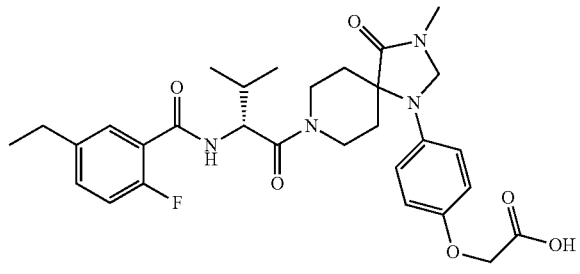 [SMILES: CCc1ccc(F)c(C(=O)N[C@@H](C(=O)N2CCC3(CC2)C(=O)N(C)CN3c2ccc(OCC(=O)O)cc2)C(C)C)c1]

To a solution of (R)-ethyl-2-(4-(8-(2-(5-ethyl-2-fluorobenzamido)-3-methylbutanoyl)-3-methyl-4-oxo-1,3,8-triazaspiro[4.5]decan-1-yl)phenoxy)acetate (20 mg, 0.03 mmol) in tetrahydrofuran (2 mL) was added an aqueous lithium hydroxide solution (2 mL, 2.0 M). The resulting mixture was stirred overnight. The pH of the reaction mixture was adjusted to 3 by addition of an aqueous hydrochloric acid solution (2.0 M). The resulting mixture was extracted with ethyl acetate (3×10 mL). The combined organic layers were dried over anhydrous sodium sulfate and concentrated under reduced pressure. The residue was purified by prep-HPLC (acetonitrile and water, acetonitrile from 30% to 70%) to afford (R)-2-(4-(8-(2-(5-ethyl-2-fluorobenzamido)-3-methylbutanoyl)-3-methyl-4-oxo-1,3,8-triazaspiro[4.5]decan-1-yl)phenoxy)acetic acid as a white solid (7.0 mg, 39%).

LCMS (ESI): m/z=569.2 [M+H]⁺.
¹H-NMR (400 MHz, CDCl₃): δ=0.99-1.04 (m, 9H), 1.73-2.14 (m, 5H), 2.65-2.67 (m, 2H), 3.02 (s, 3H), 3.57-3.60 (m, 1H), 4.02-4.04 (m, 2H), 4.45-4.66 (m, 5H), 5.06-5.10 (m, 1H), 6.75-7.80 (m, 8H).

The following 3 compounds were synthesized following the general procedure described above:

Example 169

(R)—N-(1-(1-(4-(2-Amino-2-oxoethoxy)phenyl)-3-methyl-4-oxo-1,3,8-triazaspiro[4.5]decan-8-yl)-3-methyl-1-oxobutan-2-yl)-5-ethyl-2-fluorobenzamide

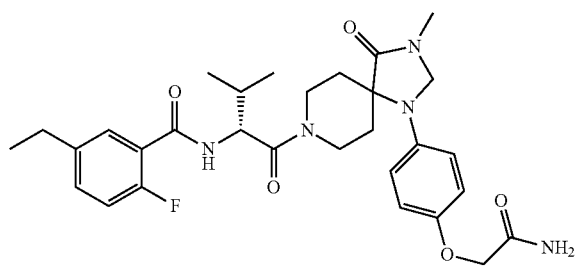 [SMILES: CCc1ccc(F)c(C(=O)N[C@@H](C(=O)N2CCC3(CC2)C(=O)N(C)CN3c2ccc(OCC(N)=O)cc2)C(C)C)c1]

11.0 mg, yield: 17%, white solid.
LCMS (ESI): m/z=568.2 [M+H]⁺.
¹H-NMR (400 MHz, CDCl₃): δ=0.98-1.05 (m, 6H), 1.23-1.27 (m, 3H), 1.73-1.89 (m, 2H), 2.09-2.27 (m, 3H), 2.64-2.71 (m, 2H), 3.03 (s, 3H), 3.53-3.59 (m, 1H), 4.03-4.06 (m, 2H), 4.39-4.89 (m, 3H), 4.63-4.69 (m, 2H), 5.08-5.15 (m, 1H), 6.14-6.17 (m, 1H), 6.57-6.61 (m, 1H), 6.77-6.85 (m, 4H), 7.02-7.08 (m, 1H), 7.28-7.32 (m, 1H), 7.51-7.56 (m, 1H), 7.84-7.85 (m, 1H).

Example 170

(R)—N-(1-(1-(4-(Cyanomethoxy)phenyl)-3-methyl-4-oxo-1,3,8-triazaspiro[4.5]decan-8-yl)-3-methyl-1-oxobutan-2-yl)-5-ethyl-2-fluorobenzamide

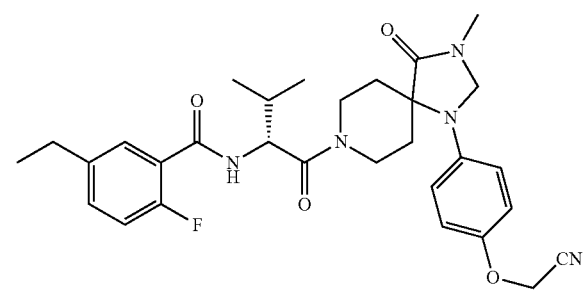 [SMILES: CCc1ccc(F)c(C(=O)N[C@@H](C(=O)N2CCC3(CC2)C(=O)N(C)CN3c2ccc(OCC#N)cc2)C(C)C)c1]

2.0 mg, yield: 4%, white solid.
LCMS (ESI): m/z=550 [M+H]⁺.
¹H-NMR (400 MHz, CD₃OD): δ=0.98-1.00 (m, 6H), 1.24-1.32 (m, 3H), 1.67-1.84 (m, 3H), 2.01-2.21 (m, 4H), 2.47-2.52 (m, 1H), 2.65-2.73 (m, 2H), 3.02 (s, 3H), 3.55-3.65 (m, 2H), 3.95-4.04 (m, 1H), 4.36-4.48 (m, 1H), 4.73-4.75 (m, 2H), 4.79-4.82 (m, 1H), 4.97-5.01 (m, 1H), 6.83-6.89 (m, 3H), 7.03-7.05 (m, 1H), 7.11-7.20 (m, 4H), 7.39-7.44 (m, 1H), 7.58-7.61 (m, 1H), 8.18-8.25 (m, 1H).

Example 171

(R)—N-(1-(1-(4-(2-(Dimethylamino)ethoxy)phenyl)-3-methyl-4-oxo-1,3,8-triazaspiro[4.5]decan-8-yl)-3-methyl-1-oxobutan-2-yl)-2-fluoro-5-(trifluoromethyl)benzamide trifluoroacetic Acid Salt

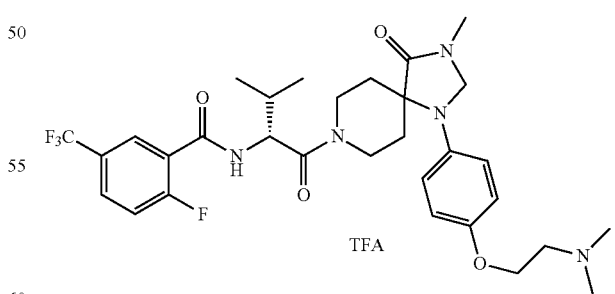

20.8 mg, yield: 24%, white solid.
LCMS (ESI): m/z=621.8 [M+H]⁺.
¹H-NMR (400 MHz, CD₃OD): δ=0.98-1.06 (m, 6H), 1.75-2.21 (m, 4H), 2.48-2.53 (m, 1H), 2.98 (s, 4H), 3.00 (s, 3H), 3.02 (s, 2H), 3.57-3.61 (m, 3H), 3.93-4.11 (m, 1H), 4.22-4.26 (m, 3H), 4.33-4.40 (m, 1H), 4.69-4.72 (m, 2H), 4.94-4.98 (m, 1H), 6.89-7.06 (m, 4H), 7.47-7.53 (m, 1H), 7.92-7.98 (m, 1H), 8.02-8.06 (m, 1H).

Example 172

(R)—N-(1-(1-(4-Acetamidophenyl)-3-methyl-4-oxo-1,3,8-triazaspiro[4.5]decan-8-yl)-3-methyl-1-oxobutan-2-yl)-5-ethyl-2-fluorobenzamide

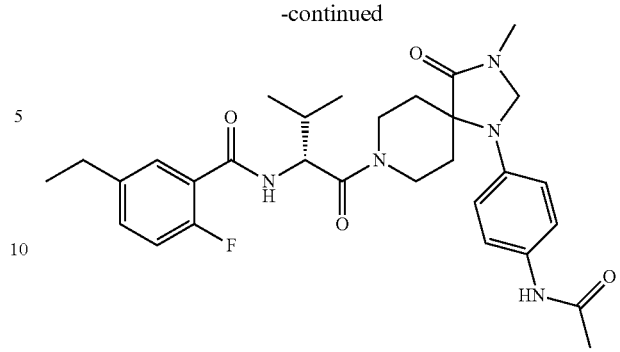

Representative General Procedure tert-Butyl-1-(4-acetamidophenyl)-3-methyl-4-oxo-1,3,8-triazaspiro[4.5]decane-8-carboxylate

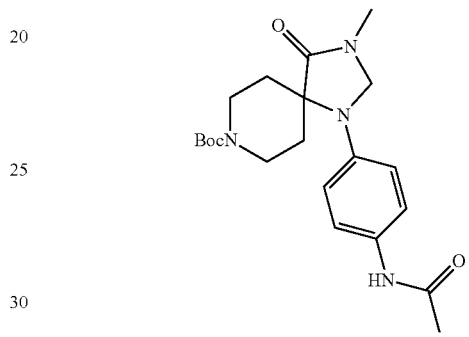

To a solution of tert-butyl-1-(4-aminophenyl)-3-methyl-4-oxo-1,3,8-triazaspiro[4.5]decane-8-carboxylate (prepared as described in Example 218-d) (150 mg, 0.41 mmol) in dichloromethane (15 mL) was added triethylamine (92 mg, 0.92 mmol). The resulting mixture was cooled to 0° C. and acetyl chloride (42 mg, 0.54 mmol) was added. The reaction was stirred for 30 minutes. After the reaction was quenched by addition of ice-water (10 mL), the mixture was extracted with dichloromethane (3×10 mL) and the combined organic layers were dried over anhydrous sodium sulfate and concentrated under reduced pressure. The residue was purified by silica gel column chromatography eluting with ethyl acetate:petroleum ether=1:3 to afford tert-butyl-1-(4-acetamidophenyl)-3-methyl-4-oxo-1,3,8-triazaspiro[4.5]decane-8-carboxylate as a white solid (95 mg, 51%).

LCMS (ESI): m/z=403.2 [M+H]$^+$.

N-(4-(3-Methyl-4-oxo-1,3,8-triazaspiro[4.5]decan-1-yl)phenyl)acetamide hydrochloride

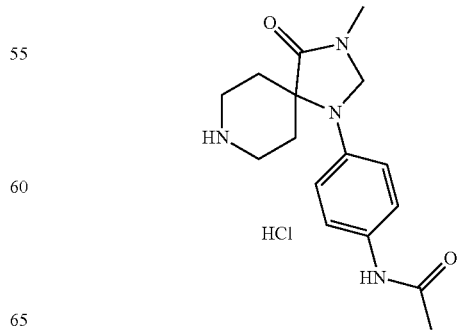

Representative Scheme:

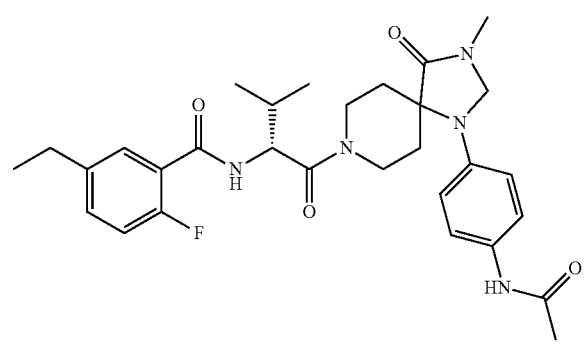 [SMILES: CCc1ccc(F)c(C(=O)N[C@@H](C(=O)N2CCC3(CC2)C(=O)N(C)CN3c2ccc(NC(C)=O)cc2)C(C)C)c1]

Example 218-d

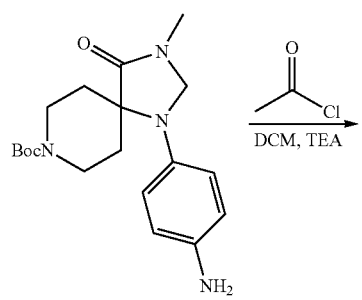

a

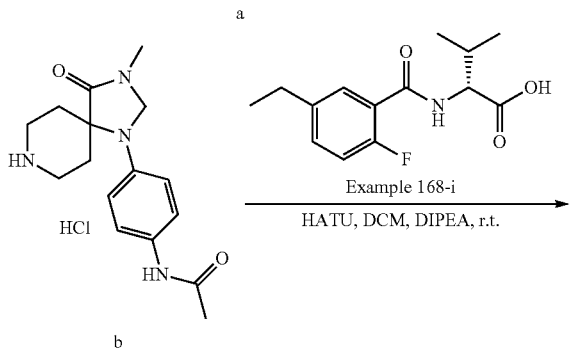

b

To a solution of tert-butyl-1-(4-acetamidophenyl)-3-methyl-4-oxo-1,3,8-triazaspiro[4.5]decane-8-carboxylate (100 mg, 0.248 mmol) in dioxane (2 mL) was added hydrochloric acid in dioxane (4 mL, 6.0 M). The resulting mixture was stirred for 6 hours. The precipitate was collected by filtration and dried under reduced pressure to afford N-(4-(3-methyl-4-oxo-1,3,8-triazaspiro[4.5]decan-1-yl)phenyl)acetamide hydrochloride as a white solid (80 mg, 95%).

LCMS (ESI): m/z=303.2 [M+H]$^+$.

(R)—N-(1-(1-(4-Acetamidophenyl)-3-methyl-4-oxo-1,3,8-triazaspiro[4.5]decan-8-yl)-3-methyl-1-oxobutan-2-yl)-5-ethyl-2-fluorobenzamide

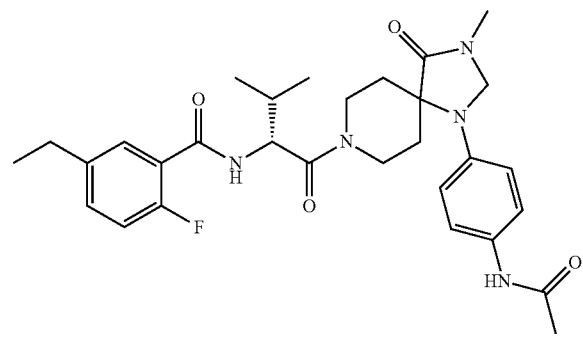 [SMILES: CCc1ccc(F)c(C(=O)N[C@@H](C(=O)N2CCC3(CC2)C(=O)N(C)CN3c2ccc(NC(C)=O)cc2)C(C)C)c1]

To a solution of N-(4-(3-methyl-4-oxo-1,3,8-triazaspiro[4.5]decan-1-yl)phenyl)acetamide hydrochloride (69 mg, 0.206 mmol) in dichloromethane (5 mL) was added sequentially (R)-2-(5-ethyl-2-fluorobenzamido)-3-methylbutanoic acid (prepared as described in Example 168-i) (50 mg, 0.187 mmol), 1-[bis(dimethylamino)methylene]-1H-1,2,3-triazolo[4,5-b]pyridinium-3-oxide hexafluorophosphate (HATU) (142 mg, 0.374 mmol) and N,N-diisopropylethylamine (48 mg, 0.374 mmol). The reaction was stirred for 2 hours at room temperature before quenching with ice-water (5 mL). The mixture was extracted with ethyl acetate (3×10 mL) and the combined organic layers were dried over anhydrous sodium sulfate and concentrated under reduced pressure. The residue was purified by prep-TLC with dichloromethane:methanol=15:1 to afford (R)—N-(1-(1-(4-acetamidophenyl)-3-methyl-4-oxo-1,3,8-triazaspiro[4.5]decan-8-yl)-3-methyl-1-oxobutan-2-yl)-5-ethyl-2-fluorobenzamide as a white solid (16 mg, 16%).

LCMS (ESI): m/z=552.2 [M+H]$^+$.

$^1$H-NMR (400 MHz, CDCl$_3$): δ=1.02-1.07 (m, 6H), 1.20-1.27 (m, 3H), 1.71-1.92 (m, 2H), 2.08-2.11 (m, 3H), 2.17-2.45 (m, 2H), 2.57-2.72 (m, 3H), 3.02 (s, 3H), 3.51-3.58 (m, 1H), 3.95-4.05 (m, 1H), 4.18-4.31 (m, 1H), 4.40-4.48 (m, 1H), 4.73-4.75 (m, 2H), 4.95-4.99 (m, 1H), 6.79-7.62 (m, 8H).

The following 3 compounds were synthesized following the general procedure described above:

Example 173

(R)-5-Ethyl-2-fluoro-N-(3-methyl-1-(3-methyl-1-(4-(methylsulfonamido)phenyl)-4-oxo-1,3,8-triazaspiro[4.5]decan-8-yl)-1-oxobutan-2-yl)benzamide

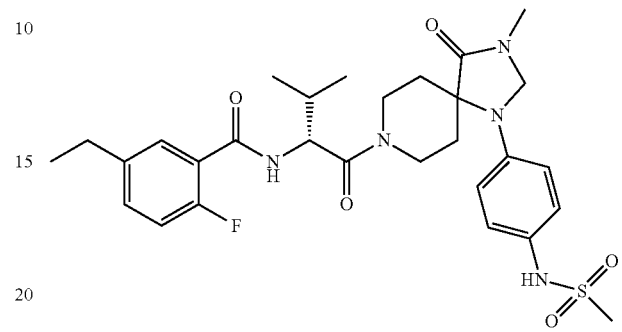

10.6 mg, yield: 10%, white solid.

LCMS (ESI): m/z=588.2 [M+H]$^+$.

$^1$H-NMR (400 MHz, CD$_3$OD): δ=1.03-1.08 (m, 6H), 1.22-1.27 (m, 3H), 1.71-1.92 (m, 2H), 2.18-2.53 (m, 2H), 2.66-2.78 (m, 3H), 2.82-2.91 (m, 3H), 3.03 (s, 3H), 3.51-3.58 (m, 1H), 3.95-4.05 (m, 1H), 4.22-4.33 (m, 1H), 4.44-4.51 (m, 1H), 4.75-4.76 (m, 2H), 4.95-4.99 (m, 1H), 6.81-8.31 (m, 8H).

Example 174

(R)-2-Fluoro-N-(3-methyl-1-(3-methyl-1-(4-(methylsulfonamido)phenyl)-4-oxo-1,3,8-triazaspiro[4.5]decan-8-yl)-1-oxobutan-2-yl)-5-(trifluoromethyl)benzamide

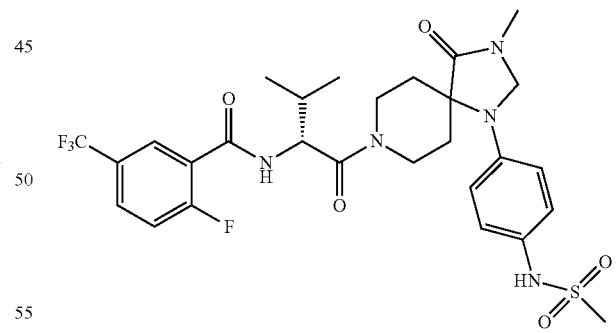

24.6 mg, yield: 22%, white solid.

LCMS (ESI): m/z=628.2 [M+H]$^+$.

$^1$H-NMR (400 MHz, CD$_3$OD): δ=1.04-1.09 (m, 6H), 1.72-1.93 (m, 2H), 2.19-2.24 (m, 1H), 2.33-2.49 (m, 1H), 2.68-2.76 (m, 1H), 2.76-2.91 (m, 3H), 3.03 (s, 3H), 3.54-3.60 (m, 1H), 3.97-4.12 (m, 1H), 4.22-4.31 (m, 1H), 4.43-4.51 (m, 1H), 4.74-4.76 (m, 2H), 4.94-5.02 (m, 1H), 6.81-6.91 (m, 2H), 7.07-7.21 (m, 2H), 7.39-7.52 (m, 1H), 7.85-7.95 (m, 1H), 8.04-8.06 (m, 1H), 8.55-8.63 (m, 1H).

Example 175
(R)-Methyl-4-(8-(2-(2-fluoro-5-(trifluoromethyl)benzamido)-3-methylbutanoyl)-3-methyl-4-oxo-1,3,8-triazaspiro[4.5]decan-1-yl)phenylcarbamate
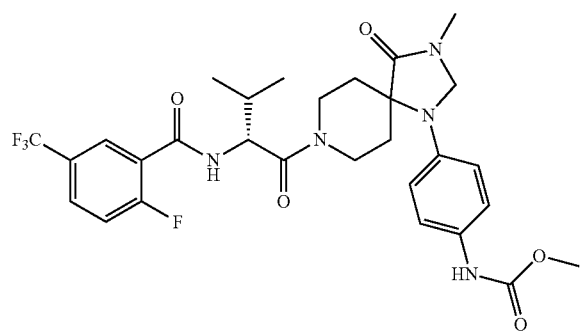 [SMILES: COC(=O)Nc1ccc(N2CN(C)C(=O)C23CCN(C(=O)[C@H](NC(=O)c2cc(C(F)(F)F)ccc2F)C(C)C)CC3)cc1]
58.4 mg, yield: 27%, white solid.
LCMS (ESI): m/z=607.8 [M+H]$^+$.
$^1$H-NMR (400 MHz, CD$_3$OD): δ=1.01-1.05 (m, 6H), 1.68-1.87 (m, 2H), 2.14-2.51 (m, 3H), 2.98 (s, 3H), 3.50-3.56 (m, 1H), 3.70-3.73 (m, 3H), 3.92-4.42 (m, 3H), 4.68-4.71 (m, 2H), 4.95-4.99 (m, 1H), 6.80-6.87 (m, 2H), 7.19-7.44 (m, 3H), 7.86-7.77 (m, 1H), 8.02-8.04 (m, 1H).
Example 176
(R)-2-(8-(2-(3-Fluoro-5-methylbenzamido)-3-methylbutanoyl)-4-oxo-1-phenyl-1,3,8-triazaspiro[4.5]decan-3-yl)acetic Acid
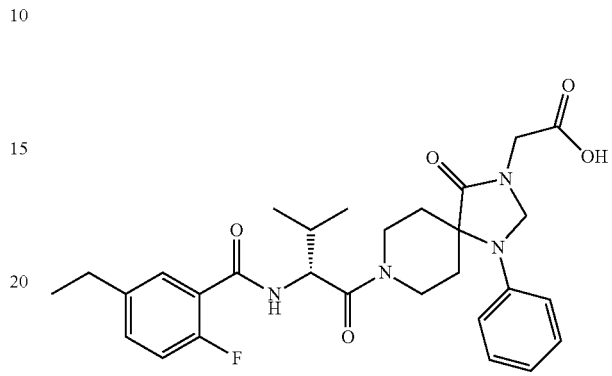
Representative Scheme:
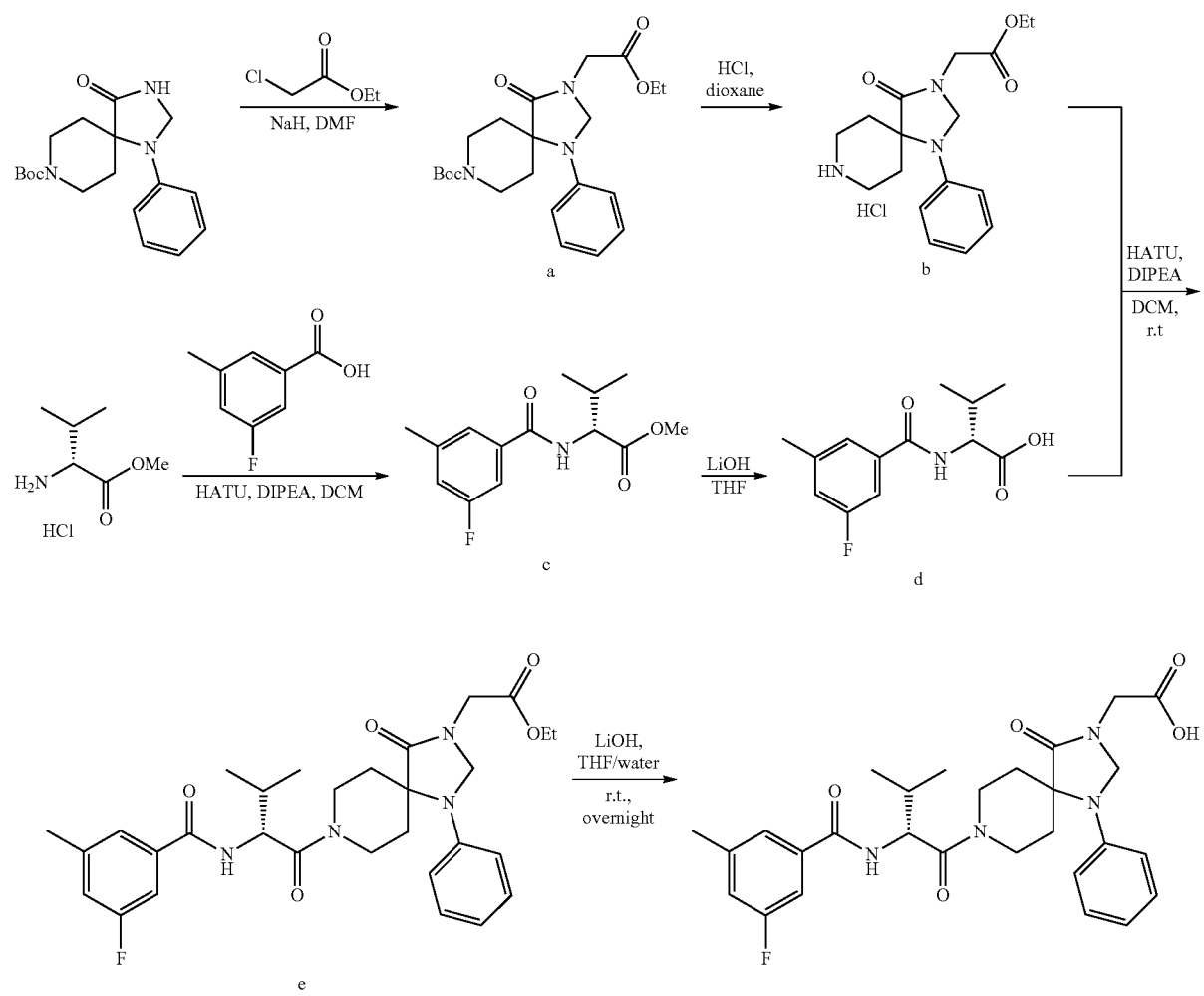

Representative General Procedure tert-Butyl-3-(2-ethoxy-2-oxoethyl)-4-oxo-1-phenyl-1,3,8-triazaspiro[4.5]decane-8-carboxylate

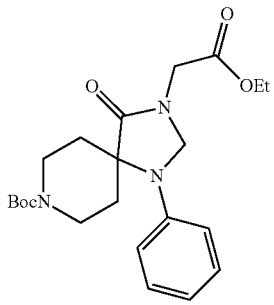 [SMILES: CCOC(=O)CN1CN(c2ccccc2)C2(CCN(C(=O)OC(C)(C)C)CC2)C1=O]

To a solution of tert-butyl-4-oxo-1-phenyl-1,3,8-triazaspiro[4.5]decane-8-carboxylate (150 mg, 0.453 mmol) in N,N-dimethylformamide (20 mL) was added sodium hydride (20 mg, 60% in oil, 0.5 mmol) at 0° C. After stirring for 30 minutes, ethyl-2-chloroacetate (67 mg, 0.543 mmol) was added. The reaction was stirred overnight, before quenching with ice-water (10 mL). The resulting mixture was filtered to afford tert-butyl-3-(2-ethoxy-2-oxoethyl)-4-oxo-1-phenyl-1,3,8-triazaspiro[4.5]decane-8-carboxylate as a white solid (164 mg, 87%).

LCMS (ESI): m/z=418.2 [M+H]$^+$.

Ethyl-2-(4-oxo-1-phenyl-1,3,8-triazaspiro[4.5]decan-3-yl)acetate hydrochloride

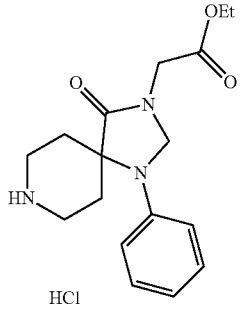

To a solution of tert-butyl-3-(2-ethoxy-2-oxoethyl)-4-oxo-1-phenyl-1,3,8-triazaspiro[4.5]decane-8-carboxylate (80 mg, 0.192 mmol) in dioxane (2 mL) was added hydrochloric acid in dioxane (4 mL, 6.0 M). The resulting mixture was stirred for 6 hours. The precipitate was collected by filtration and dried under reduced pressure to afford ethyl 2-(4-oxo-1-phenyl-1,3,8-triazaspiro[4.5]decan-3-yl)acetate hydrochloride as a white solid (65 mg, 97%).

LCMS (ESI): m/z=318.2 [M+H]$^+$.

(R)-Methyl-2-(3-fluoro-5-methylbenzamido)-3-methylbutanoate

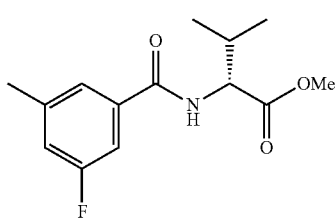 [SMILES: COC(=O)[C@H](NC(=O)c1cc(C)cc(F)c1)C(C)C]

To a solution of 3-fluoro-5-methylbenzoic acid (1.0 g, 6.49 mmol) in dichloromethane (30 mL) was added sequentially D-valine methyl ester hydrochloride (1.2 g, 7.14 mmol), 1-[bis(dimethylamino)methylene]-1H-1,2,3-triazolo[4,5-b]pyridinium-3-oxide hexafluorophosphate (HATU) (3.7 g, 9.74 mmol) and N,N-diisopropylethylamine (2.5 g, 19.48 mmol). Before quenching with ice-water (50 mL), the reaction was stirred for 2 hours. The mixture was extracted with dichloromethane (3×100 mL). The combined organic layers were dried over anhydrous sodium sulfate and the solvent was removed under reduced pressure. The residue was purified by silica gel column chromatography eluting with ethyl acetate:petroleum ether=1:4 to afford (R)-methyl-2-(3-fluoro-5-methylbenzamido)-3-methylbutanoate as a thick oil (0.6 g, 35%).

LCMS (ESI): m/z=268.2 [M+H]$^+$.

(R)-2-(3-Fluoro-5-methylbenzamido)-3-methylbutanoicacid

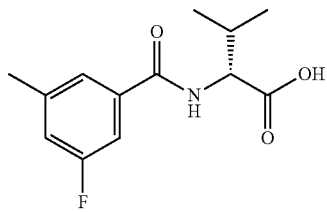 [SMILES: Cc1cc(F)cc(C(=O)N[C@@H](C(=O)O)C(C)C)c1]

To a solution of (R)-methyl-2-(3-fluoro-5-methylbenzamido)-3-methylbutanoate (1.64 g, 6.14 mmol) in tetrahydrofuran (30 mL) was added an aqueous lithium hydroxide solution (0.73 g in 20 mL of water, 30.7 mmol). Before quenching with ice-water (20 mL), the reaction was stirred for 1 hour. The pH of the solution was adjusted to 3 by addition of a 5% aqueous hydrochloric acid solution. The mixture was filtered and the filter cake was washed with petroleum ether (30 mL) and dried under reduced pressure to afford (R)-2-(3-fluoro-5-methylbenzamido)-3-methylbutanoic acid as a thick oil (0.8 g, 53%).

LCMS (ESI): m/z=254.1 [M+H]$^+$.

(R)-Ethyl-2-(8-(2-(3-fluoro-5-methylbenzamido)-3-methylbutanoyl)-4-oxo-1-phenyl-1,3,8-triazaspiro[4.5]decan-3-yl)acetate

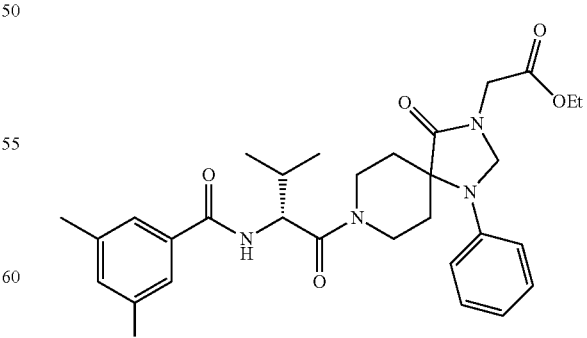

To a mixture of ethyl-2-(4-oxo-1-phenyl-1,3,8-triazaspiro[4.5]decan-3-yl)acetate hydrochloride (65 mg, 0.184 mmol) in dichloromethane (5 mL) was added sequentially (R)-2-

(3-fluoro-5-methylbenzamido)-3-methylbutanoic acid (60 mg, 0.224 mmol), 1-[bis(dimethylamino)methylene]-1H-1,2,3-triazolo[4,5-b]pyridinium-3-oxide hexafluorophosphate (HATU) (140 mg, 0.368 mmol) and N,N-diisopropylethylamine (120 mg, 0.920 mmol). The reaction was stirred for 2 hours at room temperature before quenching with ice-water (5 mL). The mixture was extracted with ethyl acetate (3×10 mL) and the combined organic layers were dried over anhydrous sodium sulfate and concentrated under reduced pressure. The residue was purified by prep-TLC with ethyl acetate:petroleum ether=15:1 to afford (R)-ethyl-2-(8-(2-(3-fluoro-5-methylbenzamido)-3-methylbutanoyl)-4-oxo-1-phenyl-1,3,8-triazaspiro[4.5]decan-3-yl)acetate as a white solid (20 mg, 20%).

LCMS (ESI): m/z=553.2 [M+H]⁺.

(R)-2-(8-(2-(3-Fluoro-5-methylbenzamido)-3-methylbutanoyl)-4-oxo-1-phenyl-1,3,8-triazaspiro[4.5]decan-3-yl)acetic Acid

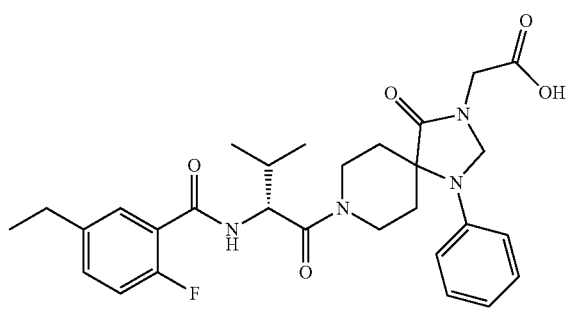 [SMILES: CCc1ccc(F)c(C(=O)N[C@@H](C(=O)N2CCC3(CC2)C(=O)N(CC(=O)O)CN3c2ccccc2)C(C)C)c1]

To a solution of (R)-ethyl-2-(8-(2-(3-fluoro-5-methylbenzamido)-3-methylbutanoyl)-4-oxo-1-phenyl-1,3,8-triazaspiro[4.5]decan-3-yl)acetate (20 mg, 0.036 mmol) in tetrahydrofuran:water=1:1 (10 mL) was added lithium hydroxide (156 mg, 6.5 mmol). The resulting mixture was stirred overnight. The mixture was diluted with water (10 mL) and extracted with ethyl acetate (10 mL). The pH of the aqueous layer was adjusted to 1 by addition of a 5% aqueous hydrochloric acid solution. The resulting mixture was extracted with ethyl acetate (3×10 mL). The combined organic layers were dried over anhydrous sodium sulfate and dried under reduced pressure. The residue was purified by prep-HPLC to afford (R)-2-(8-(2-(3-fluoro-5-methylbenzamido)-3-methylbutanoyl)-4-oxo-1-phenyl-1,3,8-triazaspiro[4.5]decan-3-yl)acetic acid as a white solid (2.7 mg, 15%).

LCMS (ESI): m/z=525.0 [M+H]⁺.

¹H-NMR (400 MHz, CDCl₃): δ=0.99-1.05 (m, 6H), 1.24-1.28 (m, 1H), 1.77-1.87 (m, 2H), 2.16-2.26 (m, 1H), 2.43-2.44 (m, 3H), 2.55-2.67 (m, 3H), 3.50-3.60 (m, 1H), 3.98-4.13 (m, 3H), 4.33-4.66 (m, 4H), 5.22-5.30 (m, 1H), 6.68-7.45 (m, 7H).

The following 2 compounds were synthesized following the general procedure described above:

Example 177

(R)-2-Fluoro-3-methyl-N-(3-methyl-1-(3-(3-(methylsulfonyl)propyl)-4-oxo-1-phenyl-1,3,8-triazaspiro[4.5]decan-8-yl)-1-oxobutan-2-yl)benzamide

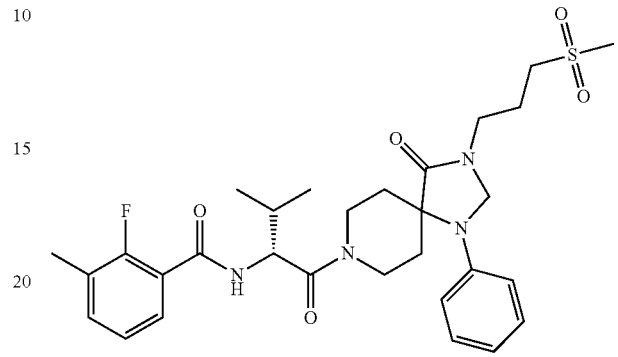

35.0 mg, yield: 29%, white solid.

LCMS (ESI): m/z=587.2 [M+H]⁺.

¹H-NMR (400 MHz, CD₃OD): δ=0.99-1.09 (m, 6H), 1.74-1.87 (m, 2H), 2.16-2.23 (m, 3H), 2.35 (s, 3H), 2.49-2.74 (m, 2H), 3.02 (s, 3H), 3.19-3.24 (m, 2H), 3.50-3.98 (m, 3H), 4.01-4.02 (m, 1H), 4.32-4.35 (m, 1H), 4.47-4.51 (m, 1H), 4.73-4.81 (m, 2H), 4.97-5.00 (m, 1H), 6.71-7.52 (m, 8H).

Example 178

(R)—N-(1-(3-(Cyanomethyl)-4-oxo-1-phenyl-1,3,8-triazaspiro[4.5]decan-8-yl)-3-methyl-1-oxobutan-2-yl)-5-ethyl-2-fluorobenzamide

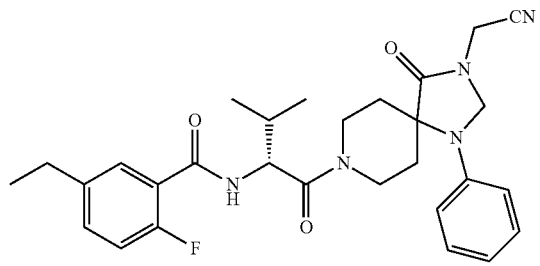 [SMILES: CCc1ccc(F)c(C(=O)N[C@@H](C(=O)N2CCC3(CC2)C(=O)N(CC#N)CN3c2ccccc2)C(C)C)c1]

58.3 mg, yield: 60%, white solid.

LCMS (ESI): m/z=520.2 [M+H]⁺.

¹H-NMR (400 MHz, CD₃OD): δ=1.03-1.08 (m, 6H), 1.22-1.27 (m, 3H), 1.73-1.95 (m, 2H), 2.16-2.53 (m, 2H), 2.65-2.77 (m, 3H), 3.47-3.57 (m, 1H), 3.93-4.05 (m, 1H), 4.21-4.53 (m, 2H), 4.57-4.58 (m, 2H), 4.84-4.86 (m, 2H), 4.97-4.99 (m, 1H), 6.75-7.62 (m, 8H).

Example 179
(R)—N-(1-(1-(4-Cyanophenyl)-3-methyl-4-oxo-1,3,8-triazaspiro[4.5]decan-8-yl)-3-methyl-1-oxobutan-2-yl)-2-fluoro-3-methylbenzamide
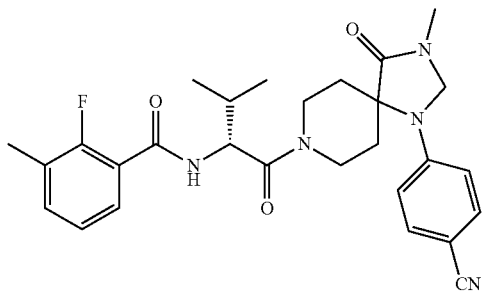 [SMILES: Cc1cccc(C(=O)N[C@@H](C(=O)N2CCC3(CC2)C(=O)N(C)CN3c2ccc(C#N)cc2)C(C)C)c1F]
Representative Scheme:
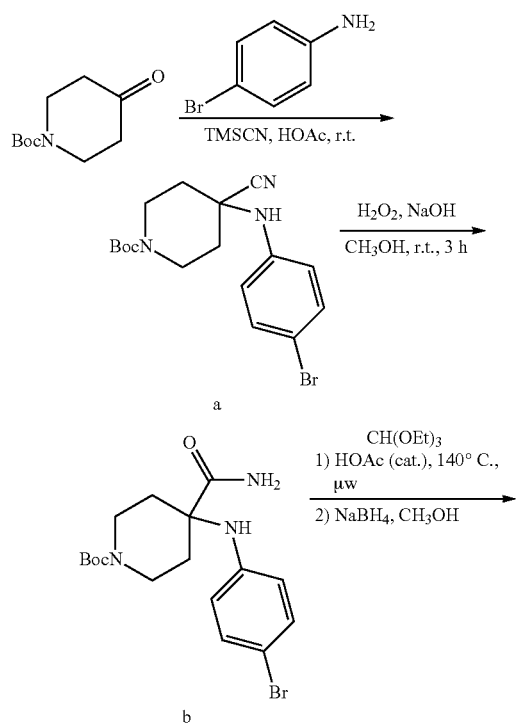
a
b
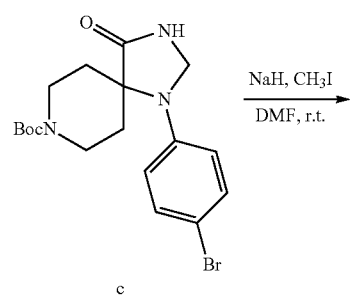
c
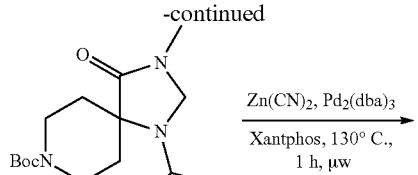
d
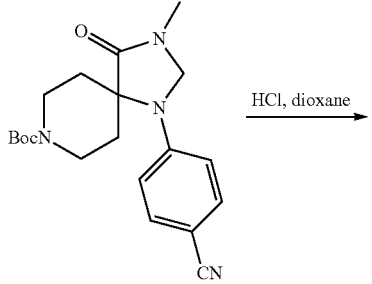
e
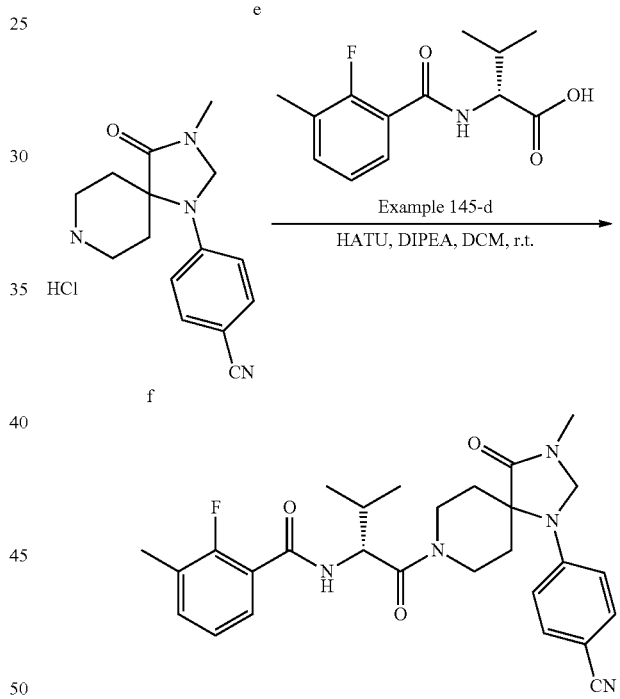
f
Representative General Procedure
tert-Butyl-4-(4-bromophenylamino)-4-cyanopiperidine-1-carboxylate
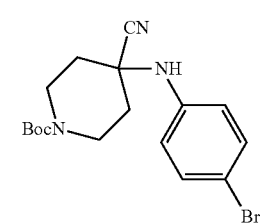 [SMILES: CC(C)(C)OC(=O)N1CCC(C#N)(Nc2ccc(Br)cc2)CC1]

To a solution of 4-bromoaniline (4.17 g, 0.024 mol) in acetic acid (100 mL) was added tert-butyl-4-oxopiperidine-1-carboxylate (5 g, 0.025 mol). The resulting mixture was cooled to 0° C. and trimethylsilyl cyanide (2.71 g, 0.027 mol) was added. The resulting solution was stirred overnight. Saturated aqueous ammonium chloride solution was added (50 mL). The mixture was filtered, the filter cake was washed with water (3×10 mL) and dried under reduced pressure to afford tert-butyl-4-(4-bromophenylamino)-4-cyanopiperidine-1-carboxylate as a white solid (9.0 g, 98%).

LCMS (ESI): m/z=380.1, 383.1 [M+H]$^+$.

$^1$H-NMR (400 MHz, DMSO-d$_6$): δ=1.41 (s, 9H), 1.65-1.85 (m, 2H), 2.28 (d, J=13.6 Hz, 2H), 3.10-3.16 (m, 2H), 3.76 (d, J=14.3 Hz, 2H), 6.34 (s, 1H), 6.74-6.91 (m, 2H), 7.27-7.43 (m, 2H).

tert-Butyl-4-(4-bromophenylamino)-4-carbamoylpiperidine-1-carboxylate

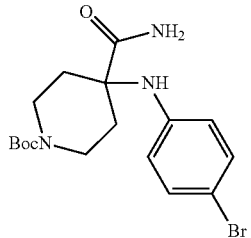 [SMILES: CC(C)(C)OC(=O)N1CCC(Nc2ccc(Br)cc2)(C(N)=O)CC1]

To a solution of tert-butyl-4-(4-bromophenylamino)-4-cyanopiperidine-1-carboxylate (4.0 g, 0.011 mol) in methanol (300 mL) was added an aqueous sodium hydroxide solution (36 mL, 1.0 M). After stirring for 15 minutes, to the resulting solution was added a 30% aqueous hydrogen peroxide solution (29 mL) dropwise. The resulting mixture was stirred overnight and filtered. The precipitate was washed with water (3×100 mL) and dried under reduced pressure to afford tert-butyl-4-(4-bromophenylamino)-4-carbamoylpiperidine-1-carboxylate as a white solid (3.6 g, 85%).

LCMS (ESI): m/z=398.2, 400.2 [M+H]$^+$.

$^1$H-NMR (300 MHz, DMSO-d$_6$): δ=1.39 (s, 9H), 1.59-1.98 (m, 4H), 3.12-3.16 (m, 2H), 3.54-3.60 (m, 2H), 5.92 (s, 1H), 6.53 (d, J=8.9 Hz, 2H), 7.12 (s, 1H), 7.21 (d, J=8.9 Hz, 2H), 7.33 (s, 1H).

tert-Butyl-1-(4-bromophenyl)-4-oxo-1,3,8-triazaspiro[4.5]decane-8-carboxylate

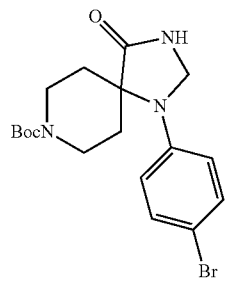 [SMILES: CC(C)(C)OC(=O)N1CCC2(CC1)C(=O)NCN2c1ccc(Br)cc1]

To a solution of tert-butyl-4-(4-bromophenylamino)-4-carbamoylpiperidine-1-carboxylate (0.6 g, 0.0015 mol) in triethyl orthoformate (200 mL) was added acetic acid (1 drop, cat.). The resulting mixture was heated at 170° C. for 30 minutes in a microwave reactor. The solvent was removed under reduced pressure. The residue was dissolved in methanol (200 mL) and to the resulting solution was added sodium borohydride (2.62 g, 0.069 mol) at 0° C. The resulting mixture was stirred for 30 minutes. The solvent was removed under reduced pressure and the residue was diluted with water (200 mL) and ethyl acetate (150 mL). The organic layer was collected and the aqueous layer was extracted with ethyl acetate (3×100 mL). The combined organic layers were dried over anhydrous sodium sulfate and concentrated under reduced pressure. The residue was purified by silica gel column chromatography eluting with dichloromethane:methanol=200:1 to afford tert-butyl-1-(4-bromophenyl)-4-oxo-1,3,8-triazaspiro[4.5]decane-8-carboxylate as a white solid (210 mg, 33%).

LCMS (ESI): m/z=410.1, 413.1 [M+H]$^+$.

tert-Butyl-1-(4-bromophenyl)-3-methyl-4-oxo-1,3,8-triazaspiro[4.5]decane-8-carboxylate

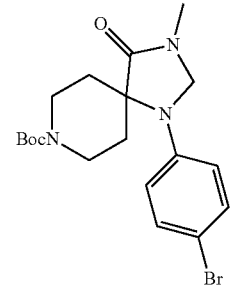

To a solution of tert-butyl-1-(4-bromophenyl)-4-oxo-1,3,8-triazaspiro[4.5]decane-8-carboxylate (210 mg, 0.51 mmol) in N,N-dimethylformamide (3 mL) was added sodium hydride (41 mg, 60% in oil, 1.02 mmol) at 0° C. After stirring for 15 minutes, iodomethane (145 mg, 1.02 mmol) was added. The resulting mixture was stirred for 1 hour. The reaction was quenched with ice-water (10 mL) and the mixture was extracted with ethyl acetate (3×50 mL). The combined organic layers were dried over anhydrous sodium sulfate and concentrated under reduced pressure. The residue was purified by silica gel column chromatography eluting with dichloromethane:methanol=15:1 to afford tert-butyl-1-(4-bromophenyl)-3-methyl-4-oxo-1,3,8-triazaspiro[4.5]decane-8-carboxylate as a white solid (210 mg, 97%).

LCMS (ESI): m/z=424.1, 426.1 [M+H]$^+$.

tert-Butyl-1-(4-cyanophenyl)-3-methyl-4-oxo-1,3,8-triazaspiro[4.5]decane-8-carboxylate

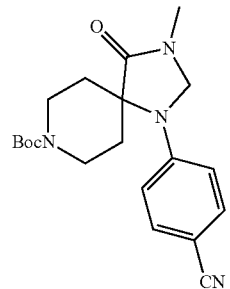

To a solution of tert-butyl-1-(4-bromophenyl)-3-methyl-4-oxo-1,3,8-triazaspiro[4.5]decane-8-carboxylate (100 mg, 0.24 mmol) in N,N-dimethylformamide was added sequentially zinc cyanide (135 mg, 1.18 mmol), tris(dibenzylideneacetone)dipalladium (22 mg, 0.024 mmol), 4,5-bis(diphenylphosphino)-9,9-dimethylxanthene (Xantphos) (27 mg, 0.047 mmol) under an argon atmosphere. The reaction mixture was stirred overnight at 130° C. After quenching with ice-water (5 mL), the reaction mixture was extracted with ethyl acetate (3×15 mL). The combined organic layers were dried over anhydrous sodium sulfate and concentrated under reduced pressure. The residue was purified by silica gel column chromatography eluting with ethyl acetate:petroleum ether=1:1 to afford tert-butyl-1-(4-cyanophenyl)-3-methyl-4-oxo-1,3,8-triazaspiro[4.5]decane-8-carboxylate as a brown oil (50 mg, crude), which was used directly without any further purification.

LCMS (ESI): m/z=371.2 [M+H]+.

4-(3-Methyl-4-oxo-1,3,8-triazaspiro[4.5]decan-1-yl)benzonitrile hydrochloride

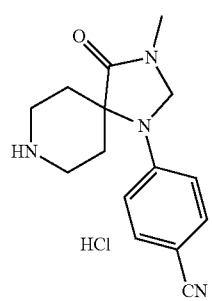 [SMILES: CN1CN(c2ccc(C#N)cc2)C2(CCNCC2)C1=O ; Cl]

A solution of tert-butyl-1-(4-cyanophenyl)-3-methyl-4-oxo-1,3,8-triazaspiro[4.5]decane-8-carboxylate (60 mg, 0.16 mmol) in hydrochloric acid in dioxane (6.0 M, 10 mL) was stirred for 30 minutes. The precipitate was collected by filtration and dried under reduced pressure to afford 4-(3-methyl-4-oxo-1,3,8-triazaspiro[4.5]decan-1-yl)benzonitrile hydrochloride as a white solid (60 mg, crude), which was used directly without any further purification.

LCMS (ESI): m/z=271.1 [M+H]+.

(R)—N-(1-(1-(4-Cyanophenyl)-3-methyl-4-oxo-1,3,8-triazaspiro[4.5]decan-8-yl)-3-methyl-1-oxobutan-2-yl)-2-fluoro-3-methylbenzamide

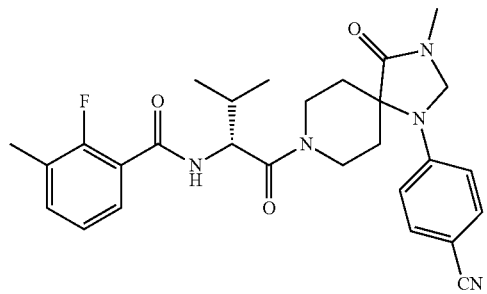 [SMILES: Cc1cccc(C(=O)N[C@@H](C(=O)N2CCC3(CC2)C(=O)N(C)CN3c2ccc(C#N)cc2)C(C)C)c1F]

To a mixture of 4-(3-methyl-4-oxo-1,3,8-triazaspiro[4.5]decan-1-yl)benzonitrile hydrochloride (55 mg, 0.203 mmol) in dichloromethane (5 mL) was added (R)-2-(2-fluoro-3-methylbenzamido)-3-methylbutanoic acid (prepared as described in Example 145-d) (61 mg, 0.223 mmol), 1-[bis(dimethylamino)methylene]-1H-1,2,3-triazolo[4,5-b]pyridinium-3-oxide hexafluorophosphate (HATU) (116 mg, 0.304 mmol) and N,N-diisopropylethylamine (53 mg, 0.406 mmol). The resulting mixture was stirred for 2 hours at room temperature before the reaction was quenched with ice-water. The mixture was extracted with ethyl acetate (3×10 mL) and the combined organic layers were dried over anhydrous sodium sulfate and concentrated under reduced pressure. The residue was purified by prep-TLC with dichloromethane:methanol=15:1 to afford (R)—N-(1-(1-(4-cyanophenyl)-3-methyl-4-oxo-1,3,8-triazaspiro[4.5]decan-8-yl)-3-methyl-1-oxobutan-2-yl)-2-fluoro-3-methylbenzamide as a white solid (19 mg, 18%).

LCMS (ESI): m/z=506.2 [M+H]+.

1H-NMR (400 MHz, CD3OD): δ=1.03-1.19 (m, 6H), 1.7-1.82 (m, 2H), 2.20-2.40 (m, 4H), 2.69-2.69-2.73 (m, 2H), 2.81-2.85 (m, 2H), 3.04 (s, 3H), 3.50-3.53 (m, 1H), 3.98-4.03 (m, 1H), 4.36-4.39 (m, 1H), 4.54-4.59 (m, 1H), 4.79-4.85 (m, 2H), 4.94-4.99 (m, 2H), 6.25-6.78 (m, 2H), 7.14-7.29 (m, 3H), 7.45-7.55 (m, 2H).

The following 12 compounds were synthesized following the general procedure described above:

Example 180

(R)—N-(1-(1-(3-Cyanophenyl)-3-methyl-4-oxo-1,3,8-triazaspiro[4.5]decan-8-yl)-3-methyl-1-oxobutan-2-yl)-2-fluoro-3-methylbenzamide

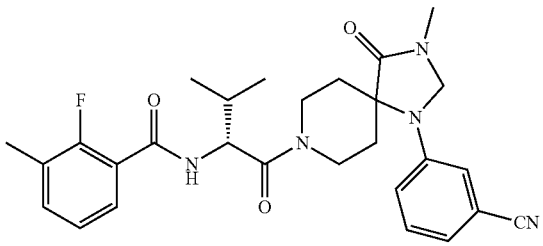 [SMILES: Cc1cccc(C(=O)N[C@@H](C(=O)N2CCC3(CC2)C(=O)N(C)CN3c2cccc(C#N)c2)C(C)C)c1F]

9.2 mg, 8% yield, white solid.

LCMS (ESI): m/z=488.0 [M+H]+.

1H-NMR (400 MHz, CD3OD): δ=1.18-1.03 (m, 6H), 1.80-1.65 (m, 2H), 2.20-2.15 (m, 1H), 2.44 (d, J=4.9 Hz, 3H), 2.60-55 (m, 1H), 2.80-2.78 (m, 1H), 3.08 (s, 3H), 3.63-3.50 (m, 2H), 4.20-4.04 (m, 2H), 4.74-4.62 (m, 2H), 5.18-5.03 (m, 1H), 7.15-6.60 (m, 4H), 7.44-7.30 (m, 2H), 7.67 (d, J=9.2 Hz, 2H).

Example 181

(R)—N-(1-(1-(4-Chlorophenyl)-3-methyl-2,4-dioxo-1,3,8-triazaspiro[4.5]decan-8-yl)-3-methyl-1-oxobutan-2-yl)-2-fluoro-5-(trifluoromethyl)benzamide

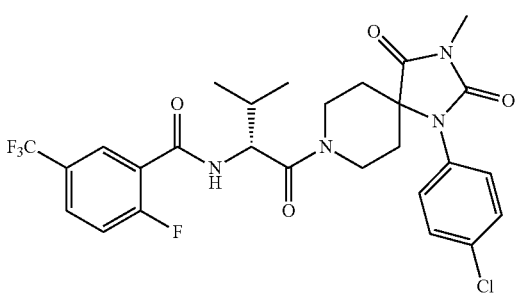

45.1 mg, 47% yield, white solid.

LCMS (ESI): m/z=538.1 [M+H]+.

1H-NMR (400 MHz, CD3OD): δ=0.81-1.02 (m, 6H), 1.65-2.21 (m, 5H), 3.08 (s, 3H), 3.46-3.51 (m, 1H), 3.91-3.98 (m, 1H), 4.19-4.30 (m, 1H), 4.41-4.52 (m, 1H), 4.82-4.85 (m, 1H), 7.22-7.54 (m, 5H), 7.88-8.01 (m, 2H), 8.48-8.49 (m, 1H).

Example 182

(R)-2-Fluoro-N-(1-(1-(4-fluorophenyl)-3-methyl-2,4-dioxo-1,3,8-triazaspiro[4.5]decan-8-yl)-3-methyl-1-oxobutan-2-yl)-5-(trifluoromethyl)benzamide

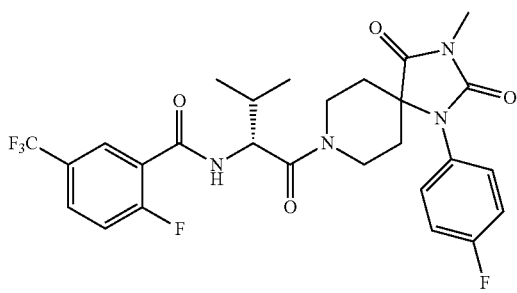 [SMILES: CC(C)[C@@H](NC(=O)c1cc(C(F)(F)F)ccc1F)C(=O)N1CCC2(CC1)C(=O)N(C)C(=O)N2c1ccc(F)cc1]

47.9 mg, 44% yield, white solid.

LCMS (ESI): m/z=567.1 [M+H]+.

1H-NMR (400 MHz, CD3OD): δ=0.80-1.02 (m, 6H), 1.65-2.00 (m, 2H), 2.03-2.21 (m, 3H), 3.08 (s, 3H), 3.45-3.52 (m, 1H), 3.92-3.98 (m, 1H), 4.19-4.30 (m, 1H), 4.41-4.53 (m, 1H), 4.82-4.88 (m, 1H), 7.10-7.14 (m, 1H), 7.23-7.28 (m, 2H), 7.33-7.47 (m, 2H), 7.87-8.01 (m, 2H).

Example 183

(R)—N-(1-(1-(3,4-Dichlorophenyl)-3-methyl-2,4-dioxo-1,3,8-triazaspiro[4.5]decan-8-yl)-3-methyl-1-oxobutan-2-yl)-2-fluoro-5-(trifluoromethyl)benzamide

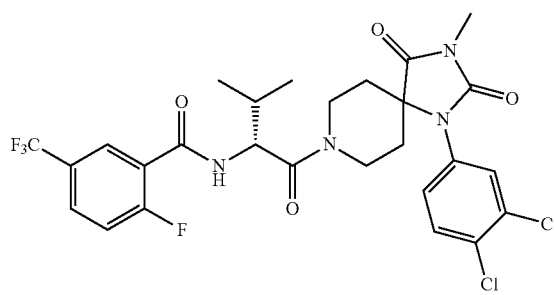

29.5 mg, 27% yield: 27%, white solid.

LCMS (ESI): m/z=617.1 [M+H]+.

1H-NMR (400 MHz, CD3OD): δ=0.83-1.02 (m, 6H), 1.65-1.86 (m, 1H), 1.94-2.22 (m, 4H), 3.08 (s, 3H), 3.32-3.51 (m, 1H), 3.91-3.97 (m, 1H), 4.21-4.31 (m, 1H), 4.43-4.55 (m, 1H), 4.82-4.87 (m, 1H), 7.19-7.27 (m, 1H), 7.38-7.50 (m, 1H), 7.59-7.68 (m, 2H), 7.87-8.02 (m, 2H), 8.47-8.54 (m, 1H).

Example 184

(R)-2-Fluoro-N-(3-methyl-1-(3-methyl-2,4-dioxo-1-p-tolyl-1,3,8-triazaspiro[4.5]decan-8-yl)-1-oxobutan-2-yl)-5-(trifluoromethyl)benzamide

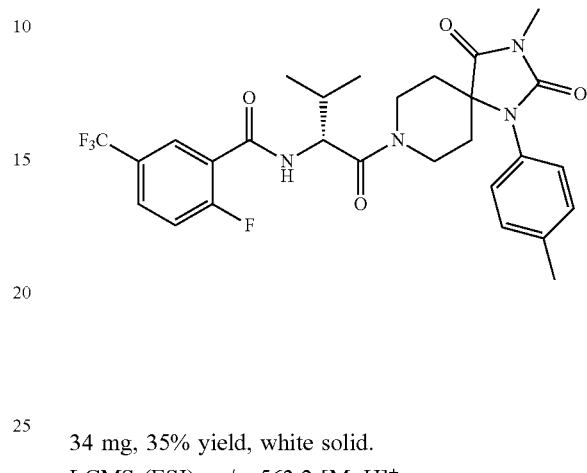

34 mg, 35% yield, white solid.

LCMS (ESI): m/z=563.2 [M+H]+.

1H-NMR (400 MHz, CD3OD): δ=0.78-0.99 (m, 6H), 1.65-2.18 (m, 5H), 2.30-2.41 (m, 3H), 3.08 (s, 3H), 3.44-3.52 (m, 1H), 3.90-3.99 (m, 1H), 4.16-4.50 (m, 2H), 4.84-4.88 (m, 1H), 7.08-7.46 (m, 5H), 7.88-8.02 (m, 2H), 8.43-8.52 (m, 1H).

Example 185

(R)—N-(1-(1-(1H-Indol-5-yl)-3-methyl-2,4-dioxo-1,3,8-triazaspiro[4.5]decan-8-yl)-3-methyl-1-oxobutan-2-yl)-2-fluoro-5-(trifluoromethyl)benzamide

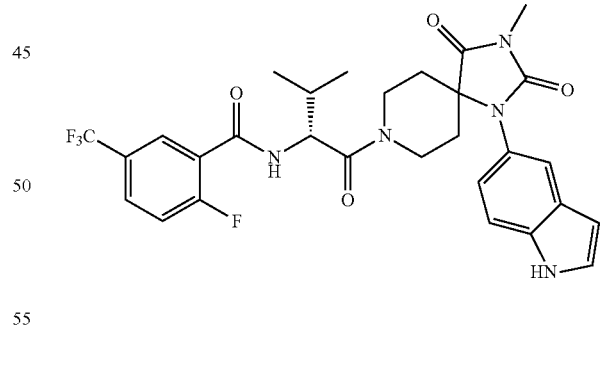

6 mg, 15% yield, white solid.

LCMS (ESI): m/z=588.2 [M+H]+.

1H-NMR (400 MHz, CD3OD): δ=0.77-0.83 (m, 2H), 0.89-0.95 (m, 2H), 1.03 (d, J=6.8 Hz, 2H), 1.83-1.98 (m, 3H), 2.07-2.12 (m, 2H), 3.17 (s, 3H), 3.49-3.55 (m, 1H), 3.97-4.01 (m, 1H), 4.46-4.61 (m, 1.5H), 4.99-5.02 (m, 1H), 5.37 (s, 0.5H), 6.55-6.61 (m, 1H), 6.90-6.97 (m, 1H), 7.21-7.28 (m, 1H), 7.41-7.48 (m, 3H), 7.70-7.73 (m, 1H), 8.22 (d, J=4.9 Hz, 1H), 8.32-8.39 (m, 1H).

Example 186

(R)-2-Fluoro-N-(3-methy-1-(3-methyl-2,4-dioxo-1-(4-(trifluoromethyl)phenyl)-1,3,8-triazaspiro[4.5]decan-8-yl)-1-oxobutan-2-yl)-5-(trifluoromethyl)benzamide

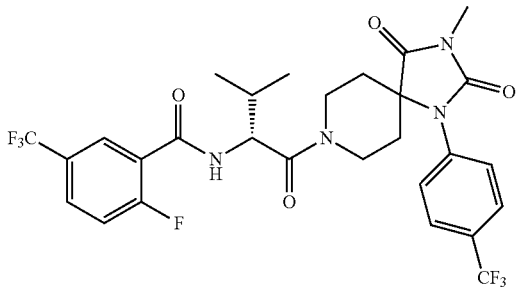

172 mg, 52% yield, white solid.
LCMS (ESI): m/z=617.2 [M+H]$^+$.
$^1$H-NMR (400 MHz, CD$_3$OD): δ=0.87-1.05 (m, 6H), 1.75-1.80 (m, 1H), 1.91-2.12 (m, 4H), 3.15 (s, 3H), 3.45-3.53 (m, 1H), 3.99-4.07 (m, 2H), 4.63-4.66 (m, 1H), 5.00-5.03 (m, 1H), 7.24-7.43 (m, 4H), 7.67-7.78 (m, 3H), 8.27-8.36 (m, 1H).

Example 187

(R)—N-(1-(1-(3-Chlorophenyl)-3-methyl-2,4-dioxo-1,3,8-triazaspiro[4.5]decan-8-yl)-3-methyl-1-oxobutan-2-yl)-2-fluoro-5-(trifluoromethyl)benzamide

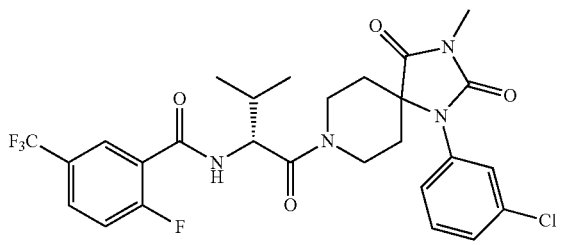 [SMILES: CC(C)[C@@H](NC(=O)c1cc(C(F)(F)F)ccc1F)C(=O)N1CCC2(CC1)C(=O)N(C)C(=O)N2c1cccc(Cl)c1]

120 mg, 79% yield, white solid.
LCMS (ESI): m/z=583.1 [M+H]$^+$.
$^1$H-NMR (400 MHz, CD$_3$OD): δ=0.87-1.05 (m, 6H), 1.77-1.80 (m, 1H), 1.91-2.12 (m, 4H), 3.15 (s, 3H), 3.46-3.53 (m, 1H), 3.98-4.04 (m, 2H), 4.63-4.66 (m, 1H), 4.98-5.01 (m, 1H), 7.05-7.11 (m, 1H), 7.17-7.29 (m, 2H), 7.35-7.46 (m, 3H), 7.75-7.78 (m, 1H), 8.25-8.36 (m, 1H).

Example 188

(R)-2-Fluoro-N-(3-methyl-1-(3-methyl-2,4-dioxo-1-(pyridin-2-yl)-1,3,8-triaza-spiro[4.5]decan-8-yl)-1-oxobutan-2-yl)-5-(trifluoromethyl)benzamide

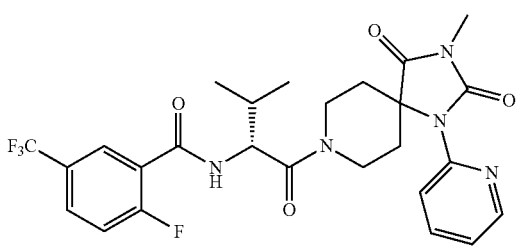 [SMILES: CC(C)[C@@H](NC(=O)c1cc(C(F)(F)F)ccc1F)C(=O)N1CCC2(CC1)C(=O)N(C)C(=O)N2c1ccccn1]

98 mg, 71% yield, white solid.
LCMS (ESI): m/z=550.1 [M+H]$^+$.
$^1$H-NMR (400 MHz, CD$_3$OD): δ=1.00-1.16 (m, 6H), 1.78-1.92 (m, 2H), 2.18-2.24 (m, 1H), 3.07-3.24 (m, 4H), 3.40-3.52 (m, 2H), 3.98-4.14 (m, 2H), 4.62-4.71 (m, 1H), 5.15-5.20 (m, 1H), 7.01-7.10 (m, 1H), 7.28-7.35 (m, 1H), 7.53-7.60 (m, 1H), 7.68-7.81 (m, 2H), 7.98-8.26 (m, 2H), 8.35-8.39 (m, 1H).

Example 189

(R)-2-Fluoro-N-(3-methyl-1-(3-methyl-2,4-dioxo-1-(pyridin-3-yl)-1,3,8-triaza-spiro[4.5]decan-8-yl)-1-oxobutan-2-yl)-5-(trifluoromethyl)benzamide

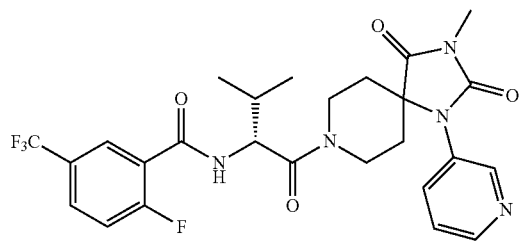 [SMILES: CC(C)[C@@H](NC(=O)c1cc(C(F)(F)F)ccc1F)C(=O)N1CCC2(CC1)C(=O)N(C)C(=O)N2c1cccnc1]

150 mg, 49% yield, white solid.
LCMS (ESI): m/z=550.1 [M+H]$^+$.
$^1$H-NMR (400 MHz, CD$_3$OD): δ=0.88-1.06 (m, 6H), 1.70-1.81 (m, 1H), 1.99-2.23 (m, 4H), 3.18 (s, 3H), 3.48-3.54 (m, 1H), 4.00-4.15 (m, 2H), 4.59-4.70 (m, 1H), 4.86-5.05 (m, 1H), 7.31-7.42 (m, 1H), 7.69-7.78 (m, 2H), 7.85-7.92 (m, 1H), 8.13-8.35 (m, 1H), 8.70-8.77 (m, 1H), 9.31 (s, 1H).

Example 190

(R)-2-Fluoro-N-(3-methyl-1-(3-methyl-2,4-dioxo-1-(4-deuterium-phenyl-1,3,8-triazaspiro[4.5]decan-8-yl)-1-oxobutan-2-yl)-5-(trifluoromethyl)benzamide

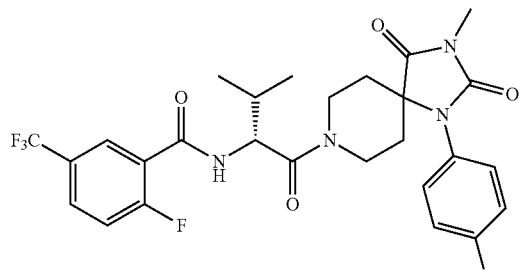

25 mg, 47% yield, white solid.
LCMS (ESI): m/z=550.1 [M+H]$^+$.
$^1$H-NMR (400 MHz, CD$_3$OD): δ=0.75-1.03 (m, 6H), 1.66-2.21 (m, 5H), 3.09 (s, 3H), 3.44-3.53 (m, 1H), 3.91-4.01 (m, 1H), 4.15-4.32 (m, 1H), 4.37-4.54 (m, 1H), 4.83-4.86 (m, 1H), 7.22-7.32 (m 2H), 7.37-7.53 (m 3H), 7.84-8.03 (m 2H).

Example 191
(R)—N-(1-(1-(Benzo[d][1,3]dioxol-5-yl)-3-methyl-2,4-dioxo-1,3,8-triazaspiro[4.5] decan-8-yl)-3-methyl-1-oxobutan-2-yl)-2-fluoro-5-(trifluoromethyl)benzamide
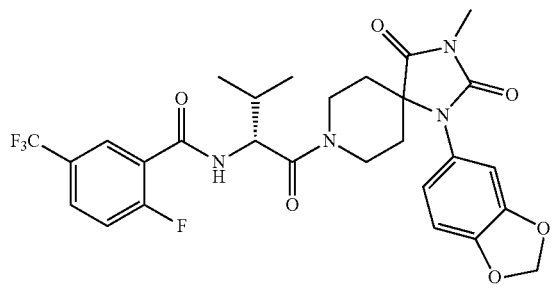
102.6 mg, 35% yield, white solid.
LCMS (ESI): m/z=593.1 [M+H]$^+$.
$^1$H-NMR (300 MHz, DMSO-d$_6$): δ=0.92-1.11 (m, 6H), 1.70-178 (m, 2H), 2.07-2.11 (m, 3H), 3.03-3.12 (m, 5H), 4.13-4.17 (m, 2H), 4.76 (t, 1H), 6.04-6.10 (m, 2H), 6.87-6.71 (m, 3H), 7.50-7.68 (m, 1H), 8.01-7.74 (m, 2H), 8.34 (d, 1H).
Example 192
(R)—N-(1-(1-(3-Chlorophenyl)-3-methyl-4-oxo-1,3,8-triazaspiro[4.5]decan-8-yl)-3-methyl-1-oxobutan-2-yl)-3-methylbenzamide
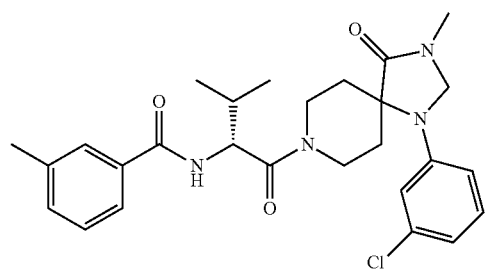 [SMILES: Cc1cccc(C(=O)N[C@@H](C(=O)N2CCC3(CC2)C(=O)N(C)CN3c2cccc(Cl)c2)C(C)C)c1]
Representative Scheme:
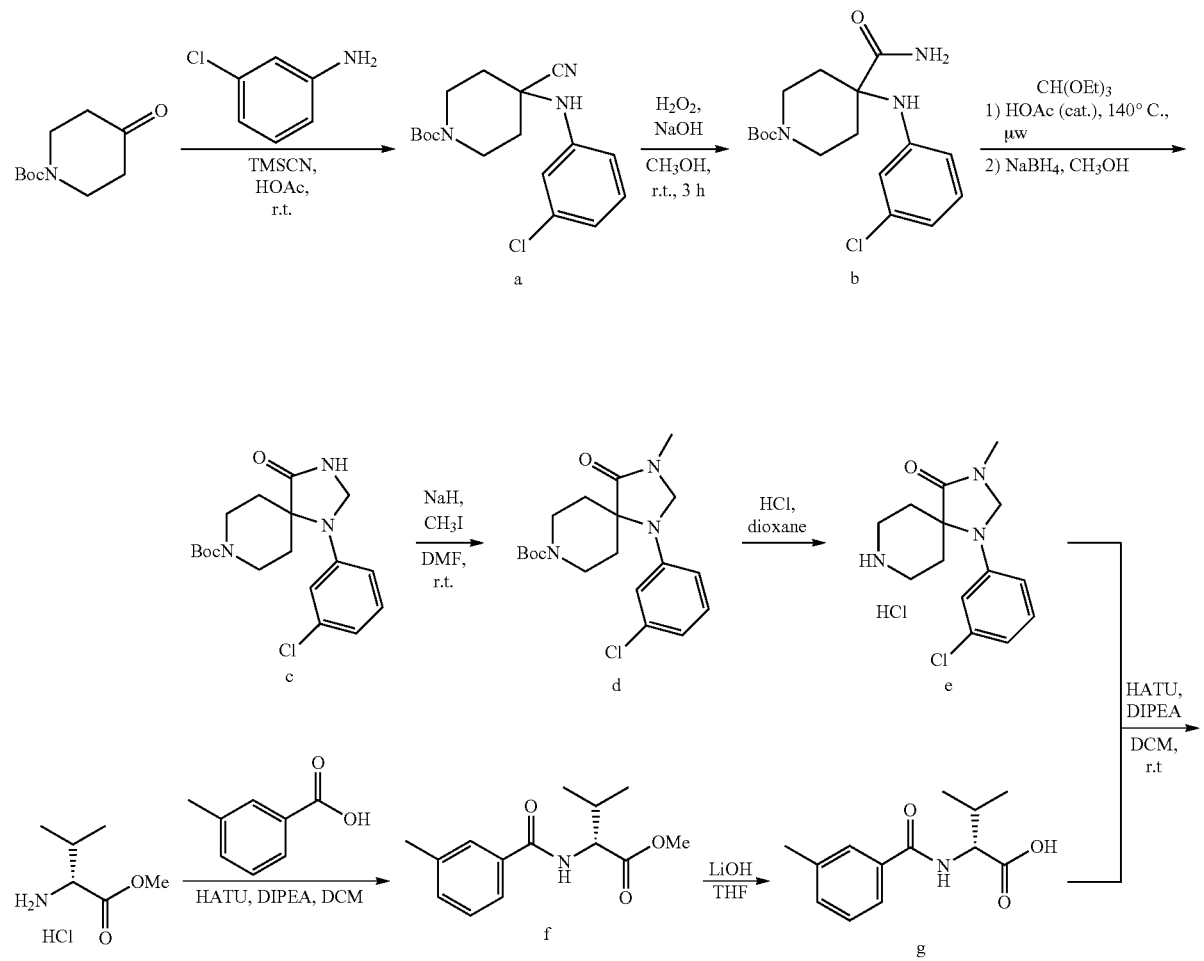

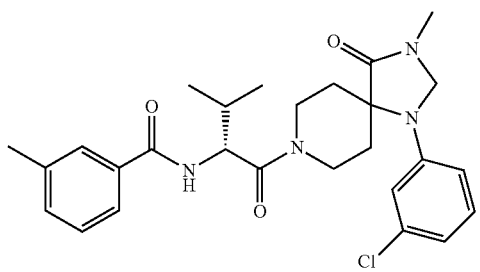

Representative General Procedure tert-Butyl-4-(3-chlorophenylamino)-4-cyanopiperidine-1-carboxylate

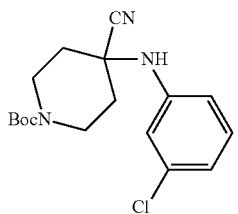 [SMILES: CC(C)(C)OC(=O)N1CCC(C#N)(Nc2cccc(Cl)c2)CC1]

To a solution of 3-chloroaniline (2.0 g, 0.015 mol) in acetic acid (20 mL) was added tert-butyl-4-oxopiperidine-1-carboxylate (3.4 g, 0.016 mol). The resulting mixture was cooled to 0° C. and trimethylsilyl cyanide (1.86 g, 0.017 mol) was added. The solution was stirred overnight. Saturated aqueous ammonium chloride was added (50 mL). The mixture was filtered, the filter cake was washed with water (3×10 mL) and dried under reduced pressure to afford tert-butyl-4-(3-chlorophenylamino)-4-cyanopiperidine-1-carboxylate as a white solid (5.0 g, 100%).

LCMS (ESI): m/z=336.1, 338.1 [M+H]$^+$.

$^1$H-NMR (400 MHz, DMSO-d$_6$): δ=1.41 (s, 9H), 1.64-1.85 (m, 2H), 2.29-2.32 (m, 2H), 3.15-3.17 (m, 2H), 3.77-3.85 (m, 2H), 6.46 (s, 1H), 6.72-6.94 (m, 3H), 7.21-7.29 (m, 1H).

tert-Butyl-4-carbamoyl-4-(3-chlorophenylamino)piperidine-1-carboxylate

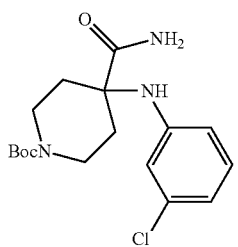 [SMILES: CC(C)(C)OC(=O)N1CCC(Nc2cccc(Cl)c2)(C(N)=O)CC1]

To a solution of tert-butyl-4-(3-chlorophenylamino)-4-cyanopiperidine-1-carboxylate (1.0 g, 2.97 mmol) in methanol (16 mL) was added an aqueous sodium hydroxide solution (10 mL, 1.0 M). After stirring for 15 minutes, to the resulting solution was added a 30% aqueous hydrogen peroxide solution (7 mL) dropwise. The resulting mixture was stirred overnight and filtered. The white solid was washed with water (3×10 mL) and dried under reduced pressure to afford tert-butyl-4-carbamoyl-4-(3-chlorophenylamino)piperidine-1-carboxylate as a white solid (1.0 g, crude), which was used directly without any further purification.

LCMS (ESI): m/z=354.1, 356.1 [M+H]$^+$.

tert-Butyl-1-(3-chlorophenyl)-4-oxo-1,3,8-triazaspiro[4.5]decane-8-carboxylate

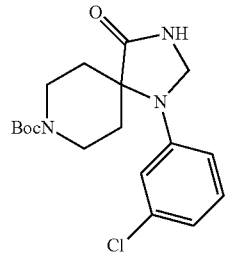 [SMILES: CC(C)(C)OC(=O)N1CCC2(CC1)C(=O)NCN2c1cccc(Cl)c1]

To a solution of tert-butyl-4-carbamoyl-4-(3-chlorophenylamino)piperidine-1-carboxylate (450 mg, 1.2 mmol) in triethyl orthoformate (4 mL) was added acetic acid (2 drops, cat.). The mixture was heated at 140° C. for 30 minutes in a microwave reactor. The solvent was removed under reduced pressure and the residue was dissolved in methanol (10 mL). To the resulting solution was added sodium borohydride (100 mg, 2.6 mmol) at 0° C. The resulting mixture was stirred for 30 minutes. The solvent was removed under reduced pressure and the residue was diluted with water (10 mL) and ethyl acetate (15 mL). The organic layer was collected and the aqueous layer was extracted with ethyl acetate (3×50 mL). The combined organic layers were dried over anhydrous sodium sulfate and concentrated under reduced pressure. The residue was purified by silica gel column chromatography eluting with dichloromethane:methanol=200:1 to afford tert-butyl-1-(3-chlorophenyl)-4-oxo-1,3,8-triazaspiro[4.5]decane-8-carboxylate as a white solid (120 mg, 25%).

LCMS (ESI): m/z=366.1, 368.1 [M+H]$^+$.

$^1$H-NMR (300 MHz, CDCl$_3$): δ=1.51 (s, 9H), 1.61-1.76 (m, 2H), 2.47-2.66 (m, 2H), 3.51-3.62 (m, 2H), 3.99-4.16 (m, 2H), 4.73 (s, 2H), 6.57-6.72 (m, 2H), 6.77-6.87 (m, 1H), 7.06-7.21 (m, 1H).

tert-Butyl-1-(3-chlorophenyl)-3-methyl-4-oxo-1,3,8-triazaspiro[4.5]decane-8-carboxylate

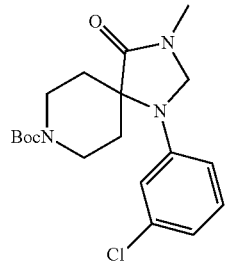 [SMILES: CN1CN(c2cccc(Cl)c2)C2(CCN(C(=O)OC(C)(C)C)CC2)C1=O]

To a solution of tert-butyl-1-(3-chlorophenyl)-4-oxo-1,3,8-triazaspiro[4.5]decane-8-carboxylate (120 mg, 0.33 mmol) in N,N-dimethylformamide (3 mL) was added sodium hydride (41 mg, 60% in oil, 1.02 mmol) at 0° C. After stirring for 15 minutes, iodomethane (233 mg, 1.64 mmol) was added. The resulting mixture was stirred for 1 hour. The reaction was quenched with ice-water (10 mL) and the mixture was extracted with ethyl acetate (3×50 mL). The combined organic layers were dried over anhydrous sodium sulfate and concentrated under reduced pressure. The residue was purified by silica gel column chromatography eluting with dichloromethane:methanol=15:1 to afford tert-butyl-1-(3-chlorophenyl)-3-methyl-4-oxo-1,3,8-triazaspiro[4.5]decane-8-carboxylate as a yellow oil (120 mg, 96%).

LCMS (ESI): m/z=380.1, 382.1 [M+H]$^+$.

1-(3-Chlorophenyl)-3-methyl-1,3,8-triazaspiro[4.5]decan-4-one hydrochloride

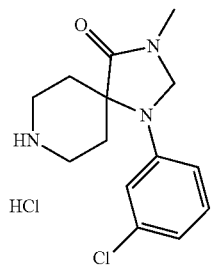 [SMILES: Cl ; CN1CN(c2cccc(Cl)c2)C2(CCNCC2)C1=O]

A solution of tert-butyl-1-(3-chlorophenyl)-3-methyl-4-oxo-1,3,8-triazaspiro[4.5]decane-8-carboxylate (120 mg, 0.13 mmol) in hydrochloric acid in dioxane (6.0 M, 10 mL) was stirred for 30 minutes. The precipitate was collected by filtration and dried under reduced pressure to afford 1-(3-chlorophenyl)-3-methyl-1,3,8-triazaspiro[4.5]decan-4-one hydrochloride as a white solid (80 mg, 80%).

LCMS (ESI): m/z=280.1, 282.1 [M+H]$^+$.

(R)-Methyl-3-methyl-2-(3-methylbenzamido)butanoate

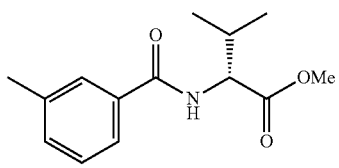 [SMILES: COC(=O)[C@H](NC(=O)c1cccc(C)c1)C(C)C]

To a suspension of (R)-methyl-2-amino-3-methylbutanoate hydrochloride (2.9 g, 17 mmol) in dichloromethane (30 mL) was added N,N-diisopropylethylamine (5.6 g, 40 mmol). To the resulting mixture was added dropwise a solution of 3-methylbenzoyl chloride (3.2 g, 20.6 mmol) in dichloromethane (5 mL) at 0° C. The mixture was stirred for 1 hour before the reaction was quenched with ice-water (10 mL). The organic layer was collected and the aqueous layer was extracted with ethyl acetate (3×20 mL). The combined organic layers were dried over anhydrous sodium sulfate and the solvent was removed under reduced pressure. The residue was purified by silica gel column chromatography eluting with ethyl acetate:petroleum ether=1:10 to afford (R)-methyl-3-methyl-2-(3-methylbenzamido)butanoate as a yellow oil (3.3 g, 78%).

LCMS (ESI): m/z=250.1 [M+H]$^+$.

$^1$H-NMR (300 MHz, CDCl$_3$): δ=1.01 (t, J=7.2 Hz, 6H), 2.19-2.36 (m, 1H), 2.42 (s, 3H), 3.79 (s, 3H), 4.59-4.83 (m, 1H), 6.55-6.66 (m, 1H), 7.30-7.38 (m, 2H), 7.56-7.66 (m, 2H).

(R)-3-Methyl-2-(3-methylbenzamido)butanoic Acid

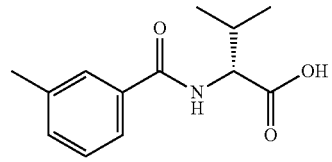 [SMILES: Cc1cccc(C(=O)N[C@@H](C(=O)O)C(C)C)c1]

To a solution of (R)-methyl-3-methyl-2-(3-methylbenzamido)butanoate (1.5 g, 6 mmol) in tetrahydrofuran (12 mL) was added an aqueous lithium hydroxide solution (8 mL, 2.0 M, 0.016 mol). Before quenching with ice-water (20 mL), the reaction was stirred for 1 hour. The pH of the solution was adjusted to 3 by addition of a 5% aqueous hydrochloric acid solution. The mixture was filtered and the filter cake was washed with petroleum ether (30 mL) and dried under reduced pressure to afford (R)-3-methyl-2-(3-methyl benzamido)butanoic acid as a thick oil (1.1 g, 77%).

LCMS (ESI): m/z=236.1 [M+H]$^+$.

(R)—N-(1-(1-(3-Chlorophenyl)-3-methyl-4-oxo-1,3,8-triazaspiro[4.5]decan-8-yl)-3-methyl-1-oxobutan-2-yl)-3-methylbenzamide

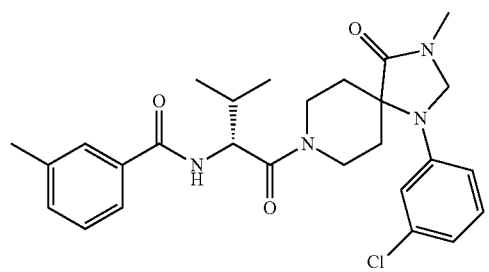 [SMILES: Cc1cccc(C(=O)N[C@@H](C(=O)N2CCC3(CC2)C(=O)N(C)CN3c2cccc(Cl)c2)C(C)C)c1]

To a mixture of 1-(3-chlorophenyl)-3-methyl-1,3,8-triazaspiro[4.5]decan-4-one hydrochloride (45 mg, 0.14 mmol) in dichloromethane (5 mL) was added (R)-3-methyl-2-(3-methylbenzamido)butanoic acid (37 mg, 0.16 mmol), 1-[bis(dimethylamino)methylene]-1H-1,2,3-triazolo[4,5-b]pyridinium-3-oxide hexafluorophosphate (HATU) (81 mg, 0.21 mmol) and N,N-diisopropylethylamine (46 mg, 0.35 mmol). The resulting mixture was stirred for 2 hours at room temperature before the reaction was quenched with ice-water (5 mL). The mixture was extracted with ethyl acetate (3×10 mL) and the combined organic layers were dried over anhydrous sodium sulfate and concentrated under reduced pressure. The residue was purified by prep-TLC with dichloromethane:methanol=15:1 to afford (R)—N-(1-(1-(3-chlorophenyl)-3-methyl-4-oxo-1,3,8-triazaspiro[4.5]decan-8-yl)-3-methyl-1-oxobutan-2-yl)-3-methylbenzamide as a white solid (2.1 mg, 3%).

LCMS (ESI): m/z=497.0, 499.0 [M+H]⁺.

¹H-NMR (400 MHz, CDCl₃): δ=0.97-1.15 (m, 6H), 1.64-2.22 (m, 5H), 2.44 (s, 3H), 2.49-2.75 (m, 1H), 3.03 (s, 3H), 3.50-3.65 (m, 1H), 4.10-4.20 (m, 1H), 4.58-4.73 (m, 3H), 5.25-5.50 (m, 1H), 6.92-7.15 (m, 3H), 7.34-7.36 (m, 3H), 7.49-7.70 (m, 2H).

The following 16 compounds were synthesized following the general procedure described above:

Example 193

(R)—N-(1-(1-(4-Chlorophenyl)-3-methyl-4-oxo-1,3,8-triazaspiro[4.5]decan-8-yl)-3-methyl-1-oxobutan-2-yl)-3-methylbenzamide

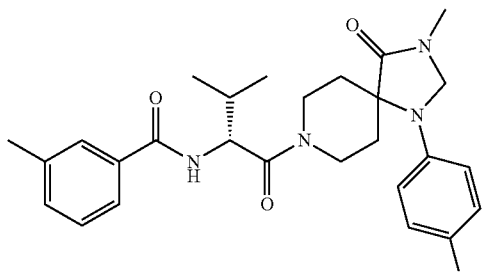

8.7 mg, yield: 16%, white solid.
LCMS (ESI): m/z=496 [M+H]⁺.
¹H-NMR (400 MHz, CDCl₃): δ=0.89-1.22 (m, 6H), 1.61-1.88 (m, 2H), 2.01-2.27 (m, 1H), 2.30-2.77 (m, 5H), 3.15 (s, 3H), 3.43-3.71 (m, 1H), 3.96-4.23 (m, 2H), 4.50-4.83 (m, 3H), 4.97-5.22 (m, 1H), 6.50-6.76 (m, 2H), 6.91-7.12 (m, 2H), 7.13-7.25 (m, 1H), 7.32-7.46 (m, 2H), 7.58-7.72 (m, 2H).

Example 194

(R)—N-(1-(1-(3-Bromophenyl)-3-methyl-4-oxo-1,3,8-triazaspiro[4.5]decan-8-yl)-3-methyl-1-oxobutan-2-yl)-3-methylbenzamide

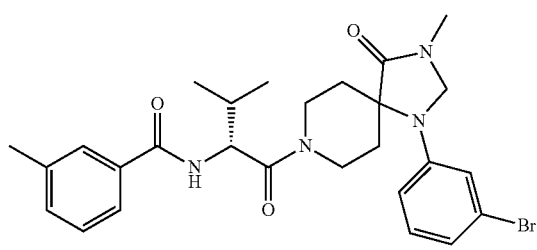 [SMILES: Cc1cccc(C(=O)N[C@@H](C(=O)N2CCC3(CC2)C(=O)N(C)CN3c2cccc(Br)c2)C(C)C)c1]

3.0 mg, yield: 5%, white solid.
LCMS (ESI): m/z=542.2 [M+H]⁺.
¹H-NMR (400 MHz, CDCl₃): δ=0.99-1.16 (m, 6H), 1.63-1.88 (m, 2H), 2.15-2.22 (m, 1H), 2.44 (s, 3H), 2.48-2.82 (m, 2H), 3.05 (s, 3H), 3.55-3.60 (m, 1H), 3.89-4.24 (m, 2H), 4.60-4.71 (m, 3H), 5.00-5.25 (m, 1H), 6.58-6.75 (m, 1H), 6.80-6.96 (m, 1H), 6.96-7.20 (m, 2H), 7.36-7.44 (m, 2H), 7.54-7.77 (m, 2H).

Example 195

(R)-3-Methyl-N-(3-methyl-1-(3-methyl-4-oxo-1-(pyridin-3-yl)-1,3,8-triazaspiro[4.5]decan-8-yl)-1-oxobutan-2-yl)benzamide

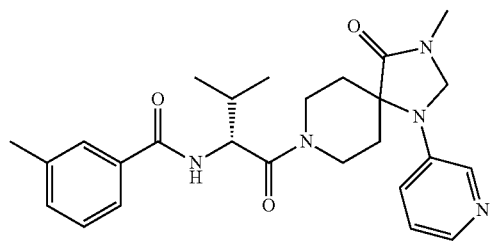 [SMILES: Cc1cccc(C(=O)N[C@@H](C(=O)N2CCC3(CC2)C(=O)N(C)CN3c2cccnc2)C(C)C)c1]

6.6 mg, yield: 14%, white solid.
LCMS (ESI): m/z=464 [M+H]⁺.
¹H-NMR (400 MHz, CDCl₃): δ=1.08-1.13 (m, 6H), 1.66-2.00 (m, 2H), 2.14-2.24 (m, 1H), 2.43-2.50 (m, 4H), 2.90-3.05 (m, 1H), 3.10 (s, 3H), 3.53-3.64 (m, 1H), 4.03-4.36 (m, 2H), 4.56-4.98 (m, 4H), 7.07-7.11 (m, 1H), 7.32-7.44 (m, 3H), 7.60-7.65 (m, 2H), 7.96-8.04 (m, 2H), 8.30-8.40 (m, 1H).

Example 196

(R)—N-(1-(1-(2-Chlorophenyl)-3-methyl-4-oxo-1,3,8-triazaspiro[4.5]decan-8-yl)-3-methyl-1-oxobutan-2-yl)-3-methylbenzamide

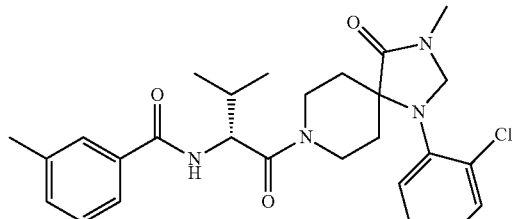

20.0 mg, yield: 23%, white solid.
LCMS (ESI): m/z=497.2, 499.2 [M+H]⁺.
¹H-NMR (400 MHz, CD₃OD): δ=0.78-1.08 (m, 6H), 1.49-2.31 (m, 5H), 2.43 (s, 3H), 2.97 (s, 3H), 3.46-4.23 (m, 4H), 4.62-4.77 (m, 2H), 4.79-4.87 (m, 1H), 7.13-7.72 (m, 8H).

Example 197

(R)—N-(1-(1-(4-Methoxyphenyl)-3-methyl-4-oxo-1,3,8-triazaspiro[4.5]decan-8-yl)-3-methyl-1-oxobutan-2-yl)-3-methylbenzamide

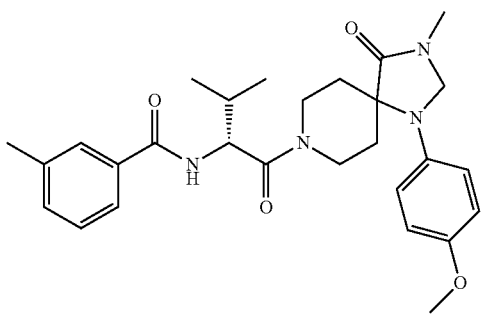 [SMILES: COc1ccc(N2CN(C)C(=O)C23CCN(C(=O)[C@H](NC(=O)c2cccc(C)c2)C(C)C)CC3)cc1]

23.0 mg, yield: 29%, white solid.

LCMS (ESI): m/z=493.2 [M+H]⁺.

¹H-NMR (400 MHz, CD₃OD): δ=0.89-1.04 (m, 6H), 1.65-2.09 (m, 3H), 2.13-2.31 (m, 2H), 2.42 (s, 3H), 2.99 (s, 3H), 3.45-3.61 (m, 1H), 3.63 (s, 2H), 3.79 (s, 1H), 3.87-4.44 (m, 3H), 4.69-4.71 (m, 2H), 4.91-5.04 (m, 1H), 6.64-6.69 (m, 1H), 6.80-7.06 (m, 3H), 7.32-7.46 (m, 2H), 7.67-7.88 (m, 2H).

Example 198

(R)—N-(1-(1-(3-Methoxyphenyl)-3-methyl-4-oxo-1,3,8-triazaspiro[4.5]decan-8-yl)-3-methyl-1-oxobutan-2-yl)-3-methylbenzamide

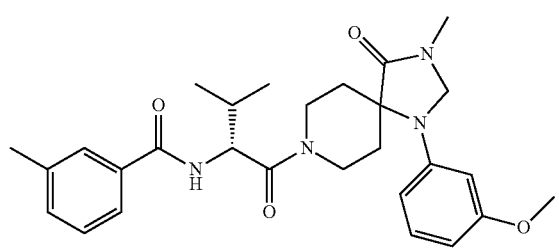

13.0 mg, yield: 17%, white solid.

LCMS (ESI): m/z=493.2 [M+H]⁺.

¹H-NMR (400 MHz, CD₃OD): δ=0.93-1.16 (m, 6H), 1.61-2.01 (m, 2H), 1.97-2.20 (m, 1H), 2.24 (s, 3H), 2.48-2.80 (m, 2H), 3.02 (s, 3H), 3.47-3.57 (m, 3H), 3.59 (s, 1H), 3.78 (s, 1H), 3.84-4.60 (m, 3H), 4.75 (m, 1H), 4.90 (m, 1H), 6.21-6.53 (m, 3H), 6.88-7.13 (m, 1H), 7.38 (m, 2H), 7.58-7.74 (m, 2H).

Example 199

(R)—N-(1-(1-(4-Bromophenyl)-3-methyl-4-oxo-1,3,8-triazaspiro[4.5]decan-8-yl)-3-methyl-1-oxobutan-2-yl)-3-methylbenzamide

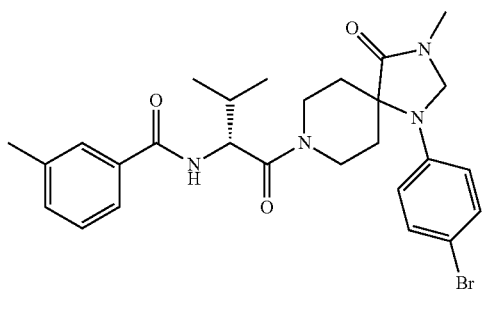

3.2 mg, yield: 4%, white solid.

LCMS (ESI): m/z=542.2 [M+H]⁺.

¹H-NMR (400 MHz, CDCl₃): δ=1.01-1.14 (m, 6H), 1.66-1.78 (m, 2H), 2.32-2.33 (m, 1H), 2.54-2.63 (m, 4H), 2.72-2.75 (m, 1H), 3.01 (s, 3H), 3.48-4.52 (m, 4H), 4.71-4.73 (m, 2H), 4.92-4.95 (m, 1H), 6.57-6.74 (m, 2H), 7.00-7.03 (m, 2H), 7.33-7.46 (m, 2H), 7.69-7.73 (m, 2H).

Example 200

(R)-5-Ethyl-2-fluoro-N-(3-methyl-1-(3-methyl-1-(4-(methylsulfonyl)phenyl)-4-oxo-1,3,8-triazaspiro[4.5]decan-8-yl)-1-oxobutan-2-yl)benzamide

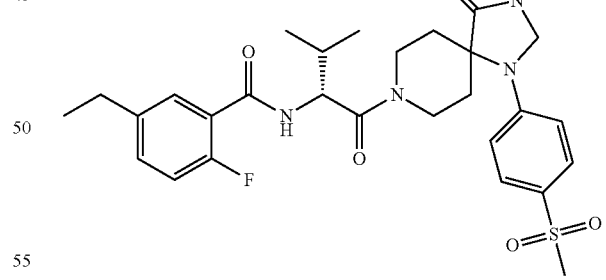

19.2 mg, yield: 17%, white solid.

LCMS (ESI): m/z=573 [M+H]⁺.

¹H-NMR (400 MHz, CDCl₃): δ=1.02-1.12 (m, 9H), 1.69-1.70 (m, 1H), 1.80-1.89 (m, 1H), 2.65-2.70 (m, 5H), 2.94 (s, 3H), 3.07 (s, 3H), 3.53-3.60 (m, 1H), 4.08-4.18 (m, 2H), 4.68 (m, 1H), 4.78-4.89 (m, 2H), 5.01-5.21 (m, 1H), 6.74-7.92 (m, 8H).

Example 201

(R)-5-Ethyl-2-fluoro-N-(3-methyl-1-(3-methyl-1-(1-methyl-6-oxo-1,6-dihydropyridin-3-yl)-4-oxo-1,3,8-triazaspiro[4.5]decan-8-yl)-1-oxobutan-2-yl)benzamide

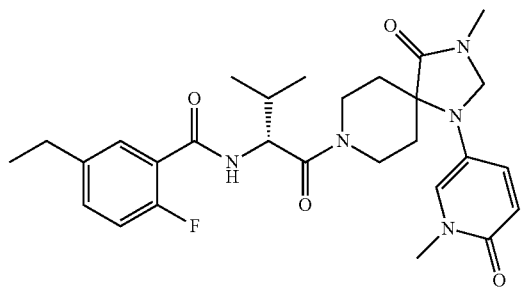 [SMILES: CCc1ccc(F)c(C(=O)N[C@@H](C(=O)N2CCC3(CC2)C(=O)N(C)CN3c2ccc(=O)n(C)c2)C(C)C)c1]

20.0 mg, yield: 34%, white solid.

LCMS (ESI): m/z=526.2 [M+H]+.

$^1$H-NMR (400 MHz, CD$_3$OD): δ=0.84-1.10 (m, 6H), 1.18-1.32 (m, 3H), 1.54-1.75 (m, 1H), 1.77-2.01 (m, 3H), 2.13-2.22 (m, 1H), 2.62-2.77 (m, 2H), 3.09 (s, 3H), 3.48-3.57 (m, 3H), 3.56-3.62 (m, 1H), 3.90-4.07 (m, 1H), 4.15-4.59 (m, 1H), 4.36-4.44 (m, 1H), 4.56-4.61 (m, 2H), 4.87-4.92 (m, 1H), 6.47-6.63 (m, 1H), 7.13-7.21 (m, 1H), 7.40-7.43 (m, 1H), 7.47-7.70 (m, 3H).

Example 202

(R)-5-Ethyl-2-fluoro-N-(1-(1-(4-methoxyphenyl)-3-methyl-4-oxo-1,3,8-triazaspiro[4.5]decan-8-yl)-3-methyl-1-oxobutan-2-yl)benzamide

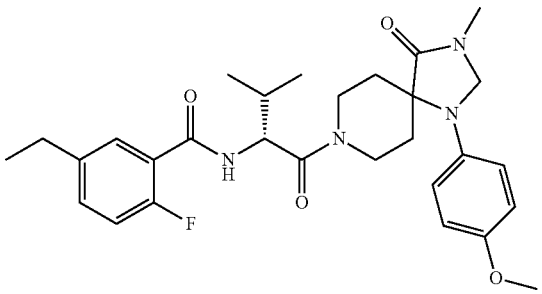 [SMILES: CCc1ccc(F)c(C(=O)N[C@@H](C(=O)N2CCC3(CC2)C(=O)N(C)CN3c2ccc(OC)cc2)C(C)C)c1]

65.3 mg, yield: 47%, white solid.

LCMS (ESI): m/z=525.0 [M+H]+.

$^1$H-NMR (400 MHz, CD$_3$OD): δ=0.88-1.13 (m, 6H), 1.18-1.36 (m, 3H), 1.71-1.92 (m, 2H), 1.93-2.38 (m, 3H), 2.68 (m, 2H), 3.00-3.05 (m, 3H), 3.65 (m, 3H), 3.79 (m, 1H), 3.91-4.09 (m, 1H), 4.20-4.25 (m, 1H), 4.35-4.41 (m, 1H), 4.62-4.76 (m, 2H), 4.94-5.01 (m, 1H), 6.72-6.88 (m, 1H), 6.91-6.98 (m, 2H), 7.13-7.21 (m, 2H), 7.34-7.47 (m, 1H), 7.547.66 (m, 1H).

Example 203

(R)-5-Ethyl-2-fluoro-N-(3-methyl-1-(3-methyl-1-(3-methyl-2-oxo-2,3-dihydrobenzo[d]oxazol-5-yl)-4-oxo-1,3,8-triazaspiro[4.5]decan-8-yl)-1-oxobutan-2-yl)benzamide

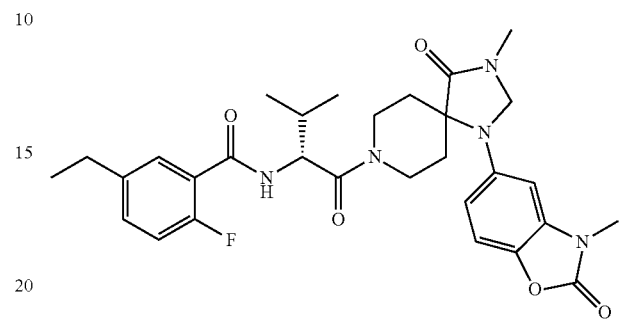

10.0 mg, yield: 19%, white solid.

LCMS (ESI): m/z=566.0 [M+H]+.

$^1$H-NMR (400 MHz, CDCl$_3$): δ=0.99-1.06 (m, 6H), 1.22-1.27 (m, 3H), 1.76-1.88 (m, 2H), 2.11-2.37 (m, 3H), 2.65-2.69 (m, 2H), 3.04 (s, 3H), 3.32 (s, 2H), 3.39 (s, 1H), 3.54-3.59 (m, 1H), 4.05-4.07 (m, 2H), 4.53-4.57 (m, 1H), 4.53-4.72 (m, 2H), 5.07-5.10 (m, 1H), 6.41-6.45 (m, 1H), 6.57-6.59 (m, 1H), 6.97-6.99 (m, 1H), 7.04-7.07 (m, 1H), 7.26-7.73 (m, 1H), 7.47-7.49 (m, 1H), 7.77-7.79 (m, 1H).

Example 204

(R)-2-Fluoro-N-(3-methyl-1-(3-methyl-1-(1-methyl-6-oxo-1,6-dihydropyridin-3-yl)-4-oxo-1,3,8-triazaspiro[4.5]decan-8-yl)-1-oxobutan-2-yl)-5-(trifluoromethyl)benzamide

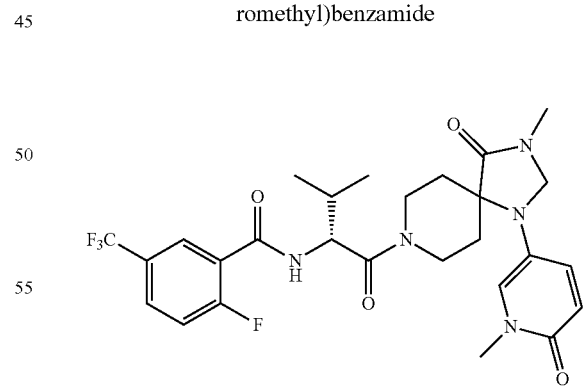

24.7 mg, yield: 27%, white solid.

LCMS (ESI): m/z=566.2 [M+H]+.

$^1$H-NMR (400 MHz, CD$_3$OD): δ=0.91-1.04 (m, 6H), 1.62-2.18 (m, 5H), 2.97 (s, 3H), 3.52-3.64 (m, 4H), 3.99-4.37 (m, 3H), 4.59-4.63 (m, 2H), 4.87 (m, 1H), 6.48-6.58 (m, 1H), 7.42-7.60 (m 3H), 7.97-8.03 (m, 2H).

Example 205

(R)-2-Fluoro-N-(3-methyl-1-(3-methyl-1-(4-(methylsulfonyl)phenyl)-4-oxo-1,3,8-triazaspiro[4.5]decan-8-yl)-1-oxobutan-2-yl)-5-(trifluoromethyl)benzamide

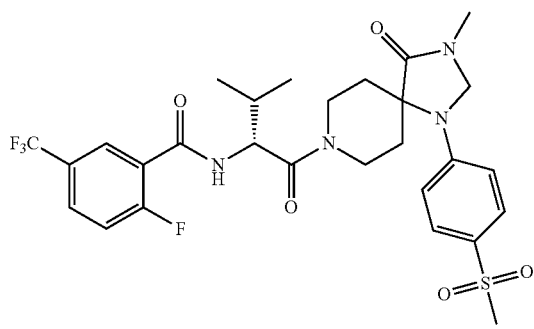 [SMILES: CC(C)[C@@H](NC(=O)c1cc(C(F)(F)F)ccc1F)C(=O)N1CCC2(CC1)C(=O)N(C)CN2c1ccc(S(C)(=O)=O)cc1]

9.3 mg, yield: 6%, white solid.

LCMS (ESI): m/z=613.2 [M+H]+.

1H-NMR (400 MHz, CD3OD): δ=1.06-1.19 (m, 6H), 1.74-1.95 (m, 2H), 2.20-2.33 (m, 1H), 2.66-2.87 (m, 1H), 2.97-3.14 (m, 7H), 3.50-3.61 (m, 1H), 4.02-4.15 (m, 1H), 4.37-4.39 (m, 1H), 4.57-4.60 (m, 1H), 4.83-4.85 (m, 2H, contained in solvent signal), 4.95-5.05 (m, 1H), 6.88-6.94 (m, 2H), 7.45-7.52 (m, 1H), 7.62-7.78 (m, 2H), 7.90-8.09 (m, 2H).

Example 206

(R)-2-Fluoro-N-(1-(1-(imidazo[1,2-a]pyridin-6-yl)-3-methyl-4-oxo-1,3,8-triazaspiro[4.5]decan-8-yl)-3-methyl-1-oxobutan-2-yl)-5-(trifluoromethyl)benzamide trifluoroacetic Acid Salt

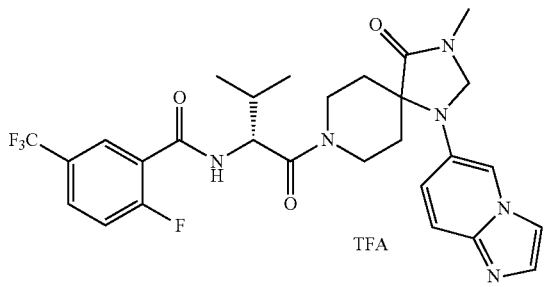 [SMILES: CC(C)[C@@H](NC(=O)c1cc(C(F)(F)F)ccc1F)C(=O)N1CCC2(CC1)C(=O)N(C)CN2c1ccc2nccn2c1]

6.1 mg, yield: 7%, white solid.

LCMS (ESI): m/z=575.2 [M+H]+.

1H-NMR (400 MHz, CD3OD): δ=1.08-1.14 (m, 6H), 1.82-1.94 (m, 2H), 2.17-2.22 (m, 1H), 2.47-2.50 (m, 1H), 2.88-2.91 (m, 1H), 3.07 (s, 3H), 3.56-3.62 (m, 1H), 4.05-4.12 (m, 1H), 4.33-4.36 (m, 1H), 4.61-4.63 (m, 1H), 4.83-4.87 (m, 3H), 7.48-7.52 (m, 1H), 7.72-7.88 (m, 4H), 8.07-8.09 (m, 2H), 8.35 (m, 1H), 8.74-8.75 (m, 1H).

Example 207

(R)-3-Chloro-N-(3-methyl-1-(3-methyl-1-(1-methyl-6-oxo-1,6-dihydropyridin-3-yl)-4-oxo-1,3,8-triazaspiro[4.5]decan-8-yl)-1-oxobutan-2-yl)-5-(trifluoromethyl)benzamide

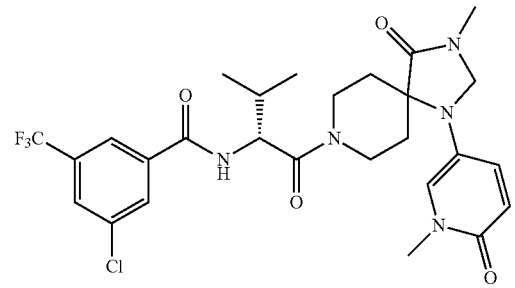 [SMILES: CC(C)[C@@H](NC(=O)c1cc(Cl)cc(C(F)(F)F)c1)C(=O)N1CCC2(CC1)C(=O)N(C)CN2c1ccc(=O)n(C)c1]

59.2 mg, yield: 40%, white solid.

LCMS (ESI): m/z=582.2 [M+H]+.

1H-NMR (400 MHz, CD3OD): δ=0.88-1.06 (m, 6H), 1.56-1.69 (m, 1H), 1.83-1.97 (m, 3H), 2.19-2.21 (m, 1H), 2.97 (s, 3H), 3.51 (s, 3H), 3.55-3.58 (m, 1H), 3.99-4.35 (m, 3H), 4.59-4.63 (m, 2H), 4.80-4.82 (m, 1H), 6.46-6.58 (m, 1H), 7.52-7.66 (m, 2H), 7.92-7.94 (m, 1H), 8.08-8.14 (m, 2H).

Example 208

(R)—N-(1-Cyclopentyl-2-(3-methyl-1-(1-methyl-6-oxo-1,6-dihydropyridin-3-yl)-4-oxo-1,3,8-triazaspiro[4.5]decan-8-yl)-2-oxoethyl)-2-fluoro-5-(trifluoromethyl)benzamide

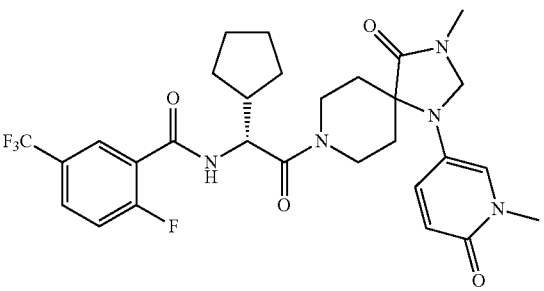 [SMILES: CN1CN(c2ccc(=O)n(C)c2)C2(CCN(C(=O)[C@H](NC(=O)c3cc(C(F)(F)F)ccc3F)C3CCCC3)CC2)C1=O]

53.3 mg, yield: 31%, white solid.

1H-NMR (400 MHz, CD3OD): δ=1.31-1.72 (m, 8H), 1.85-1.91 (m, 4H), 2.35-2.39 (m, 1H), 2.96 (s, 3H), 3.50 (s, 3H), 3.52-3.59 (m, 1H), 3.96-3.99 (m, 1H), 4.19-4.36 (m, 2H), 4.59-4.63 (m, 2H), 4.92-4.95 (m, 1H), 6.46-6.58 (m, 1H), 7.42-7.46 (m, 1H), 7.52-7.67 (m, 2H), 7.87-8.00 (m, 2H).

Example 209

2-Fluoro-N-((2R)-1-(1-(4-methoxyphenyl)-2,3-dimethyl-4-oxo-1,3,8-triazaspiro[4.5]decan-8-yl)-3-methyl-1-oxobutan-2-yl)-5-(trifluoromethyl)benzamide

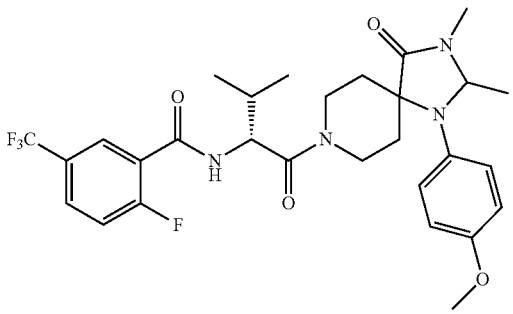 [SMILES: COc1ccc(N2C(C)N(C)C(=O)C23CCN(C(=O)[C@H](NC(=O)c2cc(C(F)(F)F)ccc2F)C(C)C)CC3)cc1]

Representative Scheme:

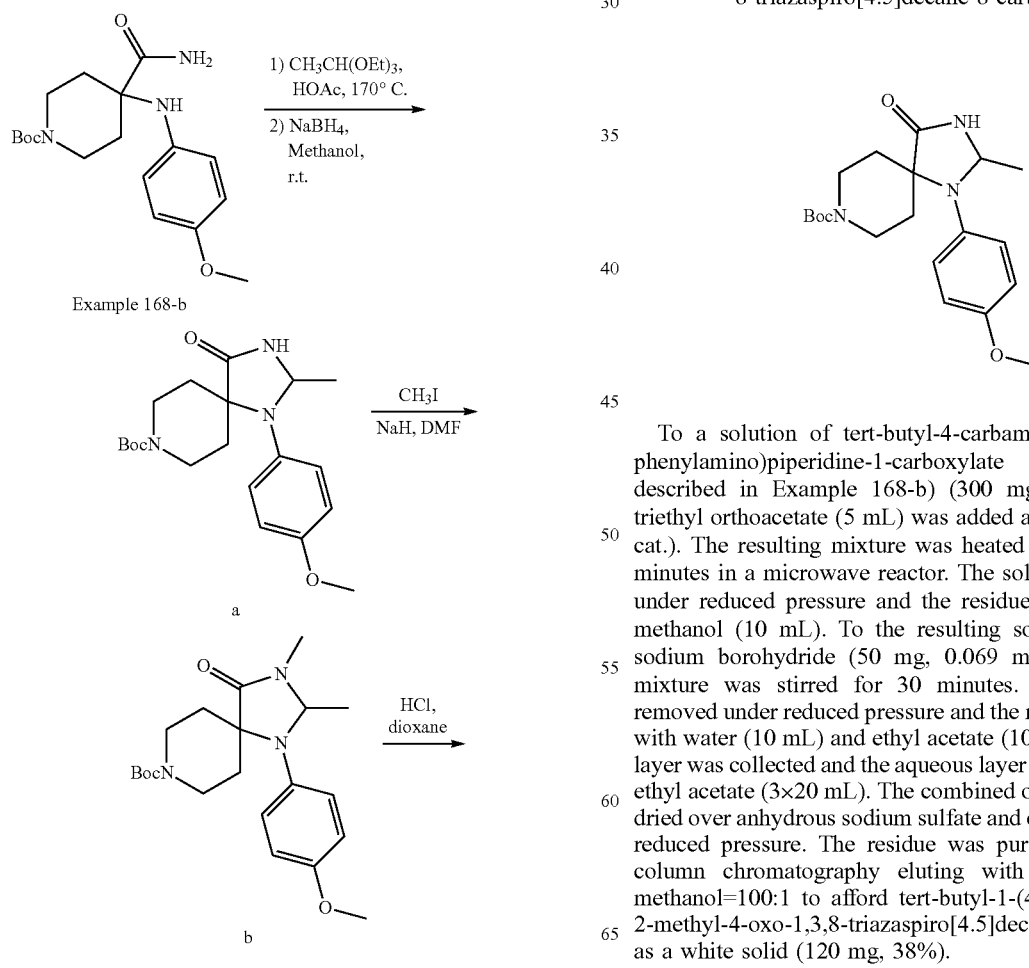

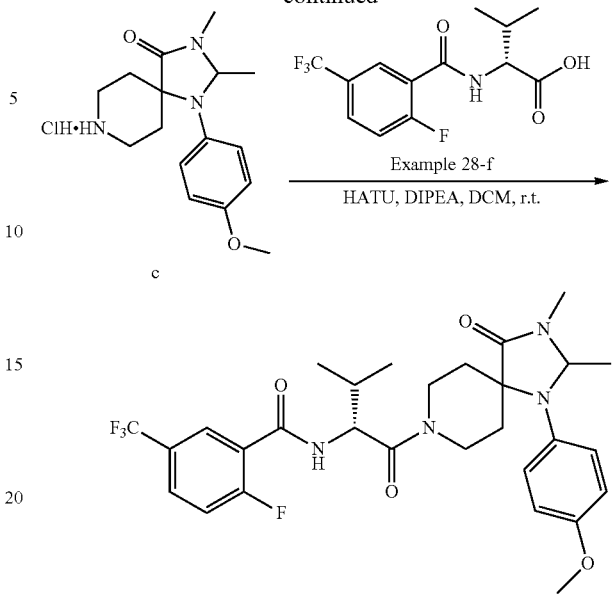

Representative General Procedure tert-Butyl-1-(4-methoxyphenyl)-2-methyl-4-oxo-1,3,8-triazaspiro[4.5]decane-8-carboxylate To a solution of tert-butyl-4-carbamoyl-4-(4-methoxyphenylamino)piperidine-1-carboxylate (prepared as described in Example 168-b) (300 mg, 0.85 mmol) in triethyl orthoacetate (5 mL) was added acetic acid (1 drop, cat.). The resulting mixture was heated at 170° C. for 30 minutes in a microwave reactor. The solvent was removed under reduced pressure and the residue was dissolved in methanol (10 mL). To the resulting solution was added sodium borohydride (50 mg, 0.069 mol) at 0° C. The mixture was stirred for 30 minutes. The solvent was removed under reduced pressure and the residue was diluted with water (10 mL) and ethyl acetate (10 mL). The organic layer was collected and the aqueous layer was extracted with ethyl acetate (3×20 mL). The combined organic layers were dried over anhydrous sodium sulfate and concentrated under reduced pressure. The residue was purified by silica gel column chromatography eluting with dichloromethane:methanol=100:1 to afford tert-butyl-1-(4-methoxyphenyl)-2-methyl-4-oxo-1,3,8-triazaspiro[4.5]decane-8-carboxylate as a white solid (120 mg, 38%).

LCMS (ESI): m/z=376.2 [M+H]$^+$.

207

¹H-NMR (300 MHz, CDCl₃): δ=1.19 (d, J=5.3 Hz, 3H), 1.38 (s, 9H), 1.59-1.85 (m, 4H), 3.25-3.27 (m, 1H), 3.80-3.88 (m, 6H), 5.00-5.19 (m, 1H), 6.85 (d, J=8.9 Hz, 2H), 7.05 (d, J=8.9 Hz, 2H).

tert-Butyl-1-(4-methoxyphenyl)-2,3-dimethyl-4-oxo-1,3,8-triazaspiro[4.5]decane-8-carboxylate

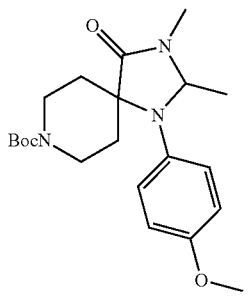 [SMILES: COc1ccc(N2C(C)N(C)C(=O)C23CCN(C(=O)OC(C)(C)C)CC3)cc1]

To a solution of tert-butyl-1-(4-methoxyphenyl)-2-methyl-4-oxo-1,3,8-triazaspiro[4.5]decane-8-carboxylate (120 mg, 0.32 mmol) in N,N-dimethylformamide (10 mL) was added sodium hydride (20 mg, 60% in oil, 0.52 mmol) at 0° C. After stirring for 15 minutes, iodomethane (282 mg, 1.9 mmol) was added. The resulting mixture was stirred for 15 minutes at room temperature and the reaction was quenched with ice-water (10 mL). The mixture was extracted with ethyl acetate (3×50 mL). The combined organic layers were dried over anhydrous sodium sulfate and concentrated under reduced pressure. The residue was purified by silica gel column chromatography eluting with ethyl acetate:petroleum ether=1:1 to afford tert-butyl-1-(4-methoxyphenyl)-2,3-dimethyl-4-oxo-1,3,8-triazaspiro[4.5]decane-8-carboxylate as a white solid (80 mg, 66%).

LCMS (ESI): m/z=390.2 [M+H]⁺.

1-(4-Methoxyphenyl)-2,3-dimethyl-1,3,8-triazaspiro[4.5]decane-4-one hydrochloride

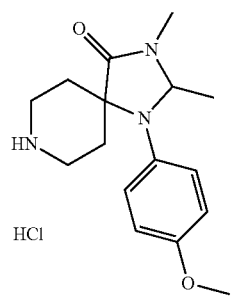 [SMILES: Cl ; COc1ccc(N2C(C)N(C)C(=O)C23CCNCC3)cc1]

A solution of tert-butyl-1-(4-methoxyphenyl)-2,3-dimethyl-4-oxo-1,3,8-triazaspiro[4.5]decane-8-carboxylate (80 mg, 0.2 mmol) in hydrochloric acid in dioxane (6.0 M, 10 mL) was stirred for 30 minutes. The solvent was removed under reduced pressure to afford 1-(4-methoxyphenyl)-2,3-dimethyl-1,3,8-triazaspiro[4.5]decane-4-one hydrochloride as a white solid (60 mg, 90%).

LCMS (ESI): m/z=290.2 [M+H]⁺.

208

2-Fluoro-N-((2R)-1-(1-(4-methoxyphenyl)-2,3-dimethyl-4-oxo-1,3,8-triazaspiro[4.5]decan-8-yl)-3-methyl-1-oxobutan-2-yl)-5-(trifluoromethyl)benzamide

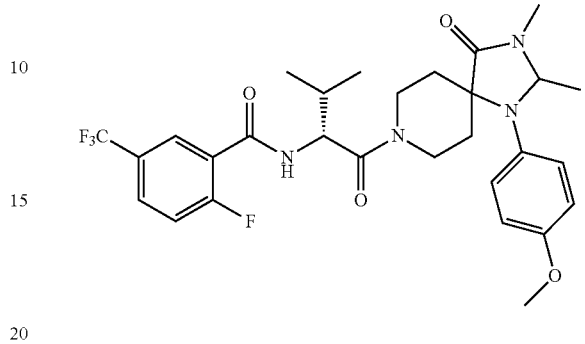

To a mixture of 1-(4-methoxyphenyl)-2,3-dimethyl-1,3,8-triazaspiro[4.5]decane-4-one hydrochloride (60 mg, 0.18 mmol) in dichloromethane (5 mL) was added sequentially (R)-2-(2-fluoro-5-(trifluoromethyl)benzamido)-3-methylbutanoic acid (prepared as described in Example 28-f) (60 mg, 0.19 mmol), 1-[bis(dimethylamino)methylene]-1H-1,2,3-triazolo[4,5-b]pyridinium-3-oxide hexafluorophosphate (HATU) (120 mg, 0.31 mmol) and N,N-diisopropylethylamine (270 mg, 2.0 mmol). The reaction was stirred for 2 hours before the reaction was quenched by addition of ice-water (10 mL). The mixture was extracted with ethyl acetate (3×10 mL) and the combined organic layers were dried over anhydrous sodium sulfate and concentrated under reduced pressure. The residue was purified by prep-TLC with dichloromethane:methanol=15:1 to afford 2-fluoro-N-((2R)-1-(1-(4-methoxyphenyl)-2,3-dimethyl-4-oxo-1,3,8-triazaspiro[4.5]decan-8-yl)-3-methyl-1-oxobutan-2-yl)-5-(trifluoromethyl)benzamide (6.5 mg, 5.9%).

LCMS (ESI): m/z=579.2 [M+H]⁺.

¹H-NMR (400 MHz, CD₃OD): δ=0.72-1.01 (m, 6H), 1.18-1.22 (m, 3H), 1.31-1.52 (m, 1H), 1.78-2.22 (m, 4H), 2.93 (s, 3H), 3.68-3.73 (m, 3H), 3.81-3.82 (m, 1H), 3.97-4.38 (m, 2H), 4.79-4.93 (m, 2H), 5.07-5.12 (m, 1H), 6.76-8.45 (m, 8H).

Example 210

4-((R)-8-((R)-2-(5-Ethyl-2-fluorobenzamido)-3-methylbutanoyl)-2,3-dimethyl-4-oxo-1,3,8-triazaspiro[4.5]decan-1-yl)benzoic Acid

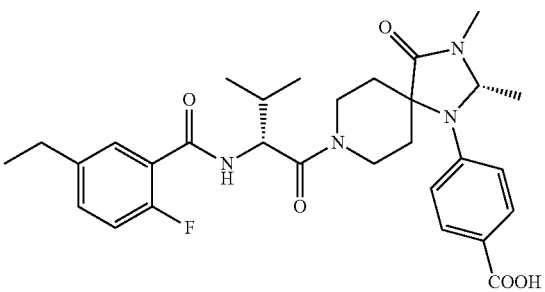 [SMILES: CCc1ccc(F)c(C(=O)N[C@@H](C(=O)N2CCC3(CC2)C(=O)N(C)[C@H](C)N3c2ccc(C(=O)O)cc2)C(C)C)c1]

Representative Scheme:
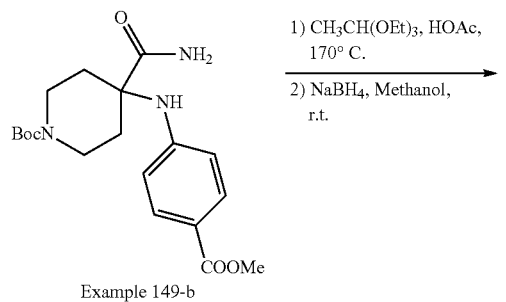
Example 149-b
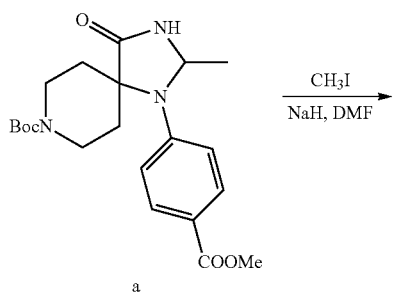
a
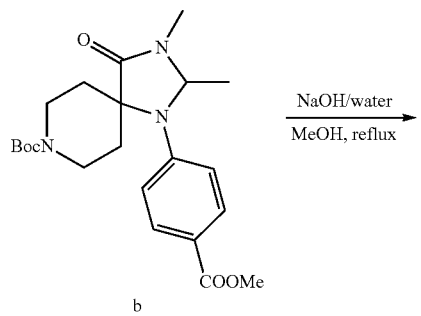
b
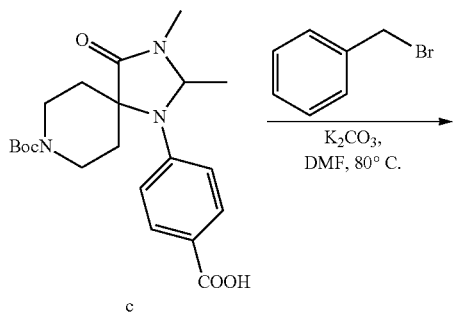
c
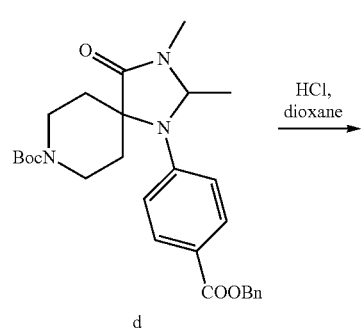
d
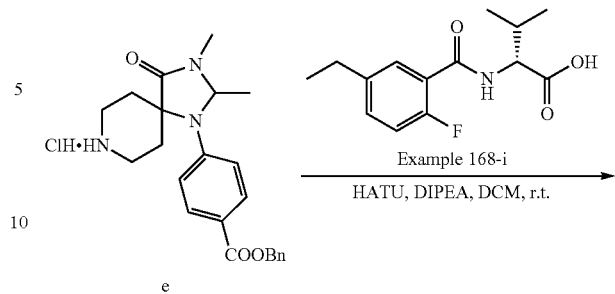
e
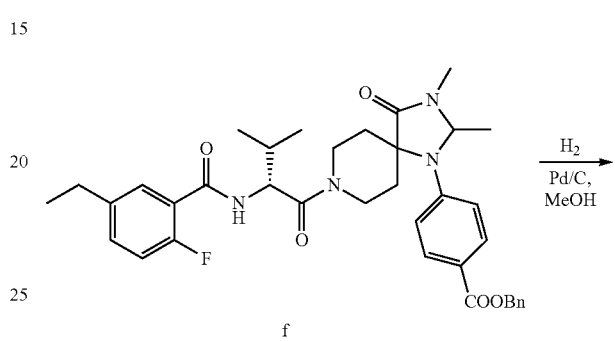
f
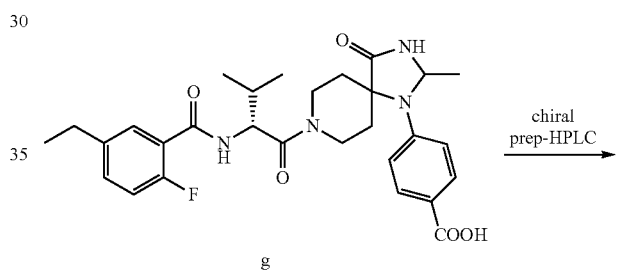
g
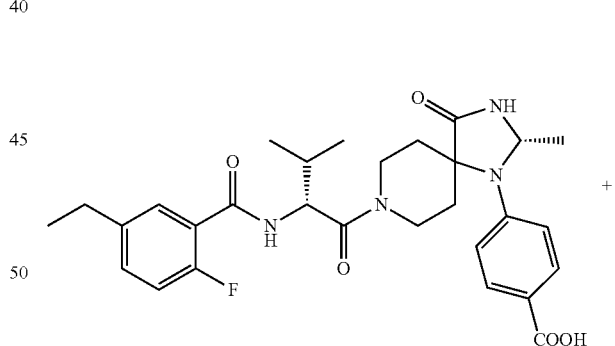
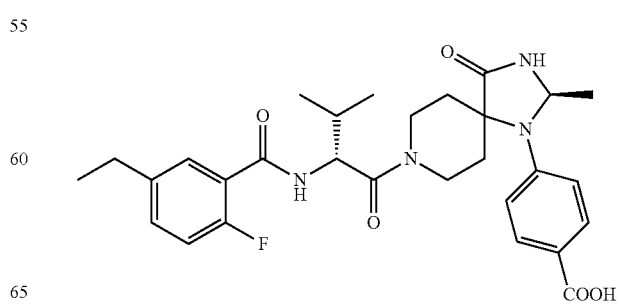

tert-Butyl-1-(4-(methoxycarbonyl)phenyl)-2-methyl-4-oxo-1,3,8-triazaspiro[4.5]decane-8-carboxylate

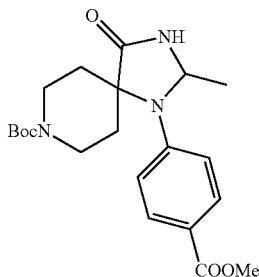 [SMILES: COC(=O)c1ccc(N2C(C)NC(=O)C23CCN(C(=O)OC(C)(C)C)CC3)cc1]

To a solution of tert-butyl-4-carbamoyl-4-(4-(methoxycarbonyl)phenylamino)piperidine-1-carboxylate (prepared as described in Example 149-b) (500 mg, 0.00136 mmol) in triethyl orthoacetate (5 mL) was added acetic acid (1 drop, cat.). The resulting mixture was heated at 170° C. for 30 minutes in a microwave reactor. The solvent was removed under reduced pressure and the residue was dissolved in methanol (10 mL). To the resulting solution was added sodium borohydride (100 mg, 0.0026 mol) at 0° C. The mixture was stirred for 30 minutes. The solvent was removed under reduced pressure and the residue was diluted with water (10 mL) and ethyl acetate (10 mL). The organic layer was collected and the aqueous layer was extracted with ethyl acetate (3×20 mL). The combined organic layers were dried over anhydrous sodium sulfate and concentrated under reduced pressure. The residue was purified by silica gel column chromatography eluting with dichloromethane:methanol=100:1 to afford tert-butyl-1-(4-(methoxycarbonyl)phenyl)-2-methyl-4-oxo-1,3,8-triazaspiro[4.5]decane-8-carboxylate as a white solid (223 mg, 41%).

LCMS (ESI): m/z=404.2 [M+H]$^+$ tert-Butyl-1-(4-(methoxycarbonyl)phenyl)-2,3-dimethyl-4-oxo-1,3,8-triazaspiro[4.5]decane-8-carboxylate

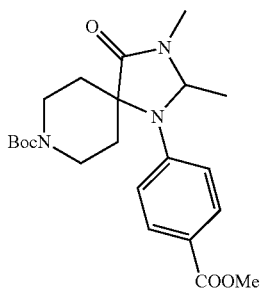 [SMILES: COC(=O)c1ccc(N2C(C)N(C)C(=O)C23CCN(C(=O)OC(C)(C)C)CC3)cc1]

To a solution of tert-butyl-1-(4-(methoxycarbonyl)phenyl)-2-methyl-4-oxo-1,3,8-triazaspiro[4.5]decane-8-carboxylate (500 mg, 1.23 mmol) in N,N-dimethylformamide (10 mL) was added sodium hydride (52 mg, 60% in oil, 1.46 mmol) at 0° C. After stirring for 15 minutes, iodomethane (0.55 g, 3.87 mmol) was added. The resulting mixture was stirred for 15 minutes at room temperature and the reaction was quenched with ice-water (10 mL). The mixture was extracted with ethyl acetate (3×50 mL). The combined organic layers were dried over anhydrous sodium sulfate and concentrated under reduced pressure. The residue was purified by silica gel column chromatography eluting with ethyl acetate:petroleum ether=1:1 to afford tert-butyl 1-(4-(methoxycarbonyl)phenyl)-2,3-dimethyl-4-oxo-1,3,8-triazaspiro[4.5]decane-8-carboxylate as a white solid (432 mg, 83%).

LCMS (ESI): m/z=418.2 [M+H]$^+$.

4-(8-(tert-Butoxycarbonyl)-2,3-dimethyl-4-oxo-1,3,8-triazaspiro[4.5]decan-1-yl)benzoic Acid

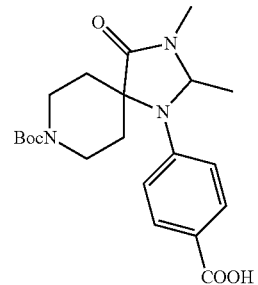 [SMILES: CC1N(C)C(=O)C2(CCN(C(=O)OC(C)(C)C)CC2)N1c1ccc(C(=O)O)cc1]

To a solution of tert-butyl-1-(4-(methoxycarbonyl)phenyl)-2,3-dimethyl-4-oxo-1,3,8-triazaspiro[4.5]decane-8-carboxylate (430 mg, 1.02 mmol) in methanol (10 mL) was added a 15% aqueous sodium hydroxide solution (15 mL). The reaction was heated at reflux for 1 hour before cooling to room temperature. The pH of the resulting solution was adjusted to 1 by addition of 10% aqueous hydrochloric acid solution. The mixture was filtered and the filter cake was washed with water (10 mL) and then dried under reduced pressure to afford 4-(8-(tert-butoxycarbonyl)-2,3-dimethyl-4-oxo-1,3,8-triazaspiro[4.5]decan-1-yl)benzoic acid as a white solid (370 mg, 89%).

LCMS (ESI): m/z=404.1 [M+H]$^+$.

tert-Butyl-1-(4-(benzyloxycarbonyl)phenyl)-2,3-dimethyl-4-oxo-1,3,8-triazaspiro[4.5]decane-8-carboxylate

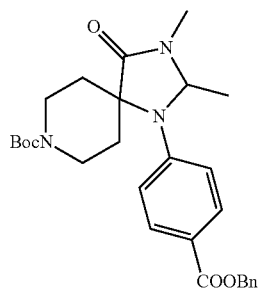

To a solution of 4-(8-(tert-butoxycarbonyl)-2,3-dimethyl-4-oxo-1,3,8-triazaspiro[4.5]decan-1-yl)benzoic acid (370 mg, 0.91 mmol) in N,N-dimethylformamide (10 mL) was added potassium carbonate (490 mg, 3.5 mmol) and benzyl bromide (320 mg, 1.7 mmol). Before the reaction was quenched by addition of ice-water (10 mL), the mixture was heated for 2 hours at 50° C. The mixture was extracted with ethyl acetate (3×30 mL). The combined organic layers were dried over anhydrous sodium sulfate and concentrated under reduced pressure. The residue was purified by silica gel column chromatography eluting with ethyl acetate:petroleum ether=1:1 to afford tert-butyl-1-(4-(benzyloxycarbonyl)phenyl)-2,3-dimethyl-4-oxo-1,3,8-triazaspiro[4.5]decane-8-carboxylate as a white solid (391 mg, 89%).

LCMS (ESI): m/z=494.2 [M+H]+.

Benzyl 4-(2,3-dimethyl-4-oxo-1,3,8-triazaspiro[4.5]decan-1-yl)benzoate hydrochloride

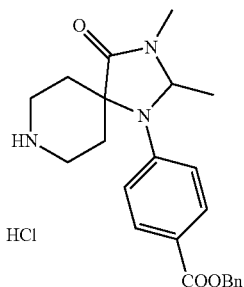

A solution of tert-butyl-1-(4-(benzyloxycarbonyl)phenyl)-2,3-dimethyl-4-oxo-1,3,8-triazaspiro[4.5]decane-8-carboxylate (391 mg, 0.79 mmol) in hydrochloric acid in dioxane (6.0 M, 20 mL) was stirred for 30 minutes. The precipitate was collected by filtration and dried under reduced pressure to afford benzyl-4-(2,3-dimethyl-4-oxo-1,3,8-triazaspiro[4.5]decan-1-yl)benzoate hydrochloride as a white solid (312 mg, 92%).

LCMS (ESI): m/z=394.2 [M+H]+.

Benzyl-4-(8-((R)-2-(5-ethyl-2-fluorobenzamido)-3-methylbutanoyl)-2,3-dimethyl-4-oxo-1,3,8-triazaspiro[4.5]decan-1-yl)benzoate

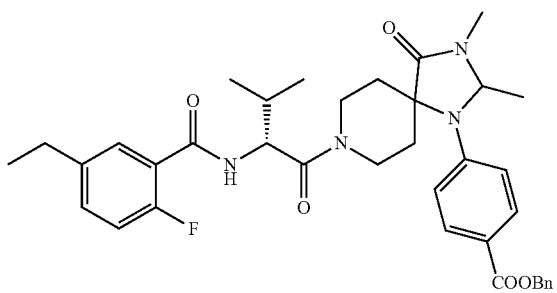

To a mixture of benzyl-4-(2,3-dimethyl-4-oxo-1,3,8-triazaspiro[4.5]decan-1-yl)benzoate hydrochloride (312 mg, 0.73 mmol) in dichloromethane (5 mL) was added sequentially (R)-2-(5-ethyl-2-fluorobenzamido)-3-methylbutanoic acid (prepared as described in Example 168-i) (195 mg, 0.73 mmol), (1-[bis(dimethylamino)methylene]-1H-1,2,3-triazolo[4,5-b]pyridinium-3-oxide hexafluorophosphate (HATU) (277 mg, 1.10 mmol) and N,N-diisopropylethylamine (230 mg, 1.78 mmol). The resulting mixture was stirred for 2 hours at room temperature before the reaction was quenched by addition of with ice-water (5 mL). The mixture was extracted with ethyl acetate (3×10 mL) and the combined organic layers were dried over anhydrous sodium sulfate and concentrated under reduced pressure. The residue was purified by prep-TLC with dichloromethane:methanol=15:1 to afford benzyl-4-(8-((R)-2-(5-ethyl-2-fluorobenzamido)-3-methylbutanoyl)-2,3-dimethyl-4-oxo-1,3,8-triazaspiro[4.5]decan-1-yl)benzoate as a thick oil (251 mg, crude), which was used directly without further purification.

LCMS (ESI): m/z=644.2 [M+H]+.

(4-(8-((R)-2-(5-Ethyl-2-fluorobenzamido)-3-methylbutanoyl)-2-methyl-4-oxo-1,3,8-triazaspiro[4.5]decan-1-yl)benzoic Acid

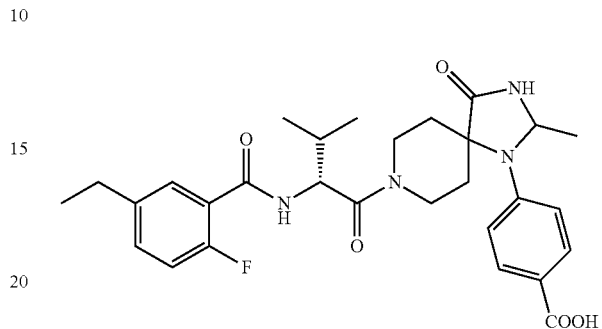

To a solution of benzyl-4-(8-((R)-2-(5-ethyl-2-fluorobenzamido)-3-methylbutanoyl)-2,3-dimethyl-4-oxo-1,3,8-triazaspiro[4.5]decan-1-yl)benzoate (251 mg, crude) in methanol (15 mL) was added 5% palladium on carbon (50 mg, 50% wet with water). The mixture was stirred under a hydrogen atmosphere for 40 minutes. The catalyst was removed by filtration and the filtrate was concentrated under reduced pressure. The residue was purified by prep-HPLC (acetonitrile and water, acetonitrile from 20% to 60%) to afford (4-(8-((R)-2-(5-ethyl-2-fluorobenzamido)-3-methylbutanoyl)-2-methyl-4-oxo-1,3,8-triazaspiro[4.5]decan-1-yl) benzoic acid as a white solid (126 mg, 32% over two steps).

LCMS (ESI): m/z=553.1 [M+H]+.

4-((R)-8-((R)-2-(5-Ethyl-2-fluorobenzamido)-3-methylbutanoyl)-2,3-dimethyl-4-oxo-1,3,8-triazaspiro[4.5]decan-1-yl)benzoic Acid

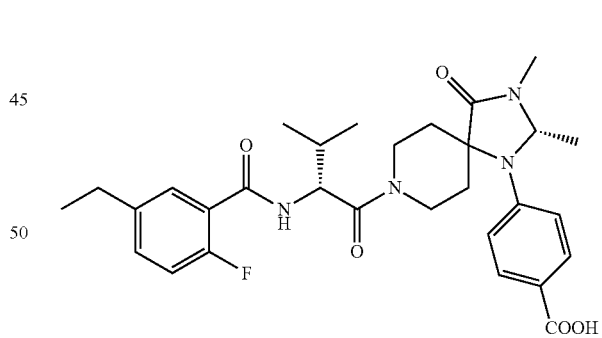

4-((R)-8-((R)-2-(5-Ethyl-2-fluorobenzamido)-3-methylbutanoyl)-2,3-dimethyl-4-oxo-1,3,8-triazaspiro[4.5]decan-1-yl)benzoic acid (126 mg) was separated by chiral prep-HPLC (column: CHIRALPAK* (Daicel) IA (250 mm×20 mm, 5 μm). Mobile phase=hexane:ethanol (0.2% EDA-0.2% FA)=1:1, flow rate: 20 mL/min) to afford as a white solid (31.7 mg, 32%). The conformation was tentatively assigned.

LCMS (ESI): m/z=553.1 [M+H]+.

Chiral HPLC: (CHIRALPAK*IB (205 mm×4.6 mm, 5 μm). Mobile phase=hexane:ethanol (0.2% FA-0.2% DEA)=1:1, retention time: 6.78 minutes), ee=96.1%.

¹H-NMR (400 MHz, CD₃OD): δ=1.00-1.13 (m, 6H), 1.17-1.32 (m, 4H), 1.43-1.45 (m, 3H), 1.60-1.85 (m, 2H), 2.23-2.35 (m, 1H), 2.65-2.83 (m, 4H), 3.01 (s, 3H), 3.53-3.59 (m, 1H), 4.00-4.05 (m, 1H), 4.34-4.39 (m, 1H), 4.54-4.71 (m, 1H), 5.40-5.59 (m, 1H), 6.88-7.00 (m, 2H), 7.12-7.19 (m, 1H), 7.35-7.50 (m, 1H), 7.58-7.77 (m, 1H), 7.82-8.01 (m, 2H).

Example 211

4-((S)-8-((R)-2-(5-Ethyl-2-fluorobenzamido)-3-methylbutanoyl)-2,3-dimethyl-4-oxo-1,3,8-triazaspiro[4.5]decan-1-yl)benzoic Acid

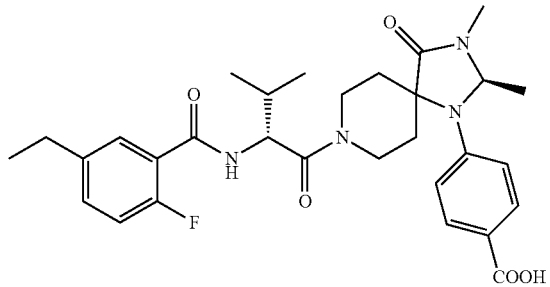 [SMILES: CCc1ccc(F)c(C(=O)N[C@@H](C(=O)N2CCC3(CC2)C(=O)N(C)[C@@H](C)N3c2ccc(C(=O)O)cc2)C(C)C)c1]

4-((S)-8-((R)-2-(5-Ethyl-2-fluorobenzamido)-3-methylbutanoyl)-2,3-dimethyl-4-oxo-1,3,8-triazaspiro[4.5]decan-1-yl)benzoic acid (126 mg) was separated by chiral prep-HPLC (column: CHIRALPAK* (Daicel) IA (250 mm×20 mm, 5 μm). Mobile phase=hexane:ethanol (0.2% EDA-0.2% FA)=1:1, flow rate: 20 mL/min) to afford as a white solid (31.4 mg, 31%). The conformation was tentatively assigned.

LCMS (ESI): m/z=553.0 [M+H]⁺.

Chiral HPLC: (CHIRALPAK*IB (205 mm×4.6 mm, 5 μm). Mobile phase=hexane:ethanol (0.2% FA-0.2% DEA)=1:1, retention time: 10.578 minutes, ee=97%.

¹H-NMR (400 MHz, CD₃OD): δ=1.03-1.11 (m, 6H), 1.18-1.33 (m, 4H), 1.46-1.49 (m, 3H), 1.54-1.94 (m, 2H), 2.22-2.65 (m, 4H), 2.99 (s, 3H), 3.06-3.08 (m, 1H), 3.57-3.59 (m, 1H), 4.03-4.10 (m, 1H), 4.37-4.44 (m, 1H), 4.52-4.59 (m, 1H), 5.42-5.59 (m, 1H), 6.92-7.00 (m, 2H), 7.17-7.19 (m, 1H), 7.39-7.42 (m, 1H), 7.58-7.77 (m, 1H), 7.82-8.01 (m, 2H).

The following 2 compounds were synthesized following the general procedure described above:

Example 212

4-((R)-8-((R)-2-(2-Fluoro-5-(trifluoromethyl)benzamido)-3-methylbutanoyl)-2,3-dimethyl-4-oxo-1,3,8-triazaspiro[4.5]decan-1-yl)benzoic Acid

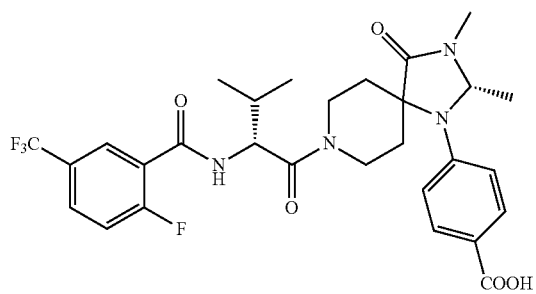 [SMILES: CC(C)[C@@H](NC(=O)c1cc(C(F)(F)F)ccc1F)C(=O)N1CCC2(CC1)C(=O)N(C)[C@H](C)N2c1ccc(C(=O)O)cc1]

35.6 mg, yield: 23%, white solid.

LCMS (ESI): m/z=593 [M+H]⁺.

Chiral HPLC: (CHIRALPAK*IB (205 mm×4.6 mm, 5 μm). Mobile phase=hexane:ethanol (0.2% FA-0.2% DEA)=1:1, retention time: 6.31 minutes, ee=95.1%.

¹H-NMR (400 MHz, CD₃OD): δ=0.99-1.15 (m, 6H), 1.32-1.45 (m, 4H), 1.63-1.87 (m, 2H), 2.26-2.65 (m, 2H), 2.79-2.81 (m, 1H), 2.99 (s, 3H), 3.54-3.59 (m, 1H), 4.06-4.09 (m, 2H), 4.34-4.55 (m, 1H), 5.41-5.59 (m, 1H), 6.89-6.99 (m, 2H), 7.45-7.59 (m, 1H), 7.83-7.99 (m, 3H), 8.02-8.05 (m, 1H).

Example 213

4-((S)-8-((R)-2-(2-Fluoro-5-(trifluoromethyl)benzamido)-3-methylbutanoyl)-2,3-dimethyl-4-oxo-1,3,8-triazaspiro[4.5]decan-1-yl)benzoic Acid

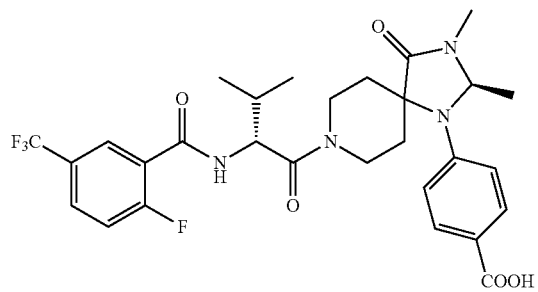

35.7 mg, yield: 24%, white solid.

LCMS (ESI): m/z=593.0 [M+H]⁺.

Chiral HPLC: (CHIRALPAK*IB (205 mm×4.6 mm, 5 μm). Mobile phase=hexane:ethanol (0.2% FA-0.2% DEA)=1:1, retention time: 12.7 minutes, ee=97%.

¹H-NMR (400 MHz, CD₃OD): δ=1.04-1.16 (m, 6H), 1.32-1.35 (m, 2H), 1.45-1.74 (m, 4H), 1.95-2.10 (m, 1H), 2.24-2.35 (m, 1H), 2.61-2.81 (m, 1H), 3.04 (s, 3H), 3.59-3.67 (m, 1H), 4.02-4.37 (m, 2H), 4.53-4.61 (m, 1H), 5.42-5.53 (m, 1H), 6.92-7.01 (m, 2H), 7.48-7.67 (m, 1H), 7.81-7.88 (m, 3H), 8.01-8.07 (m, 1H).

Example 214

(R)—N-(1-(1-(1H-Indazol-5-yl)-3-methyl-4-oxo-1,3,8-triazaspiro[4.5]decan-8-yl)-3-methyl-1-oxobutan-2-yl)-2-fluoro-5-(trifluoromethyl)benzamide

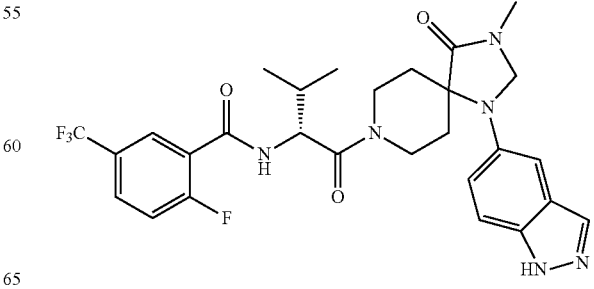

Representative Scheme:

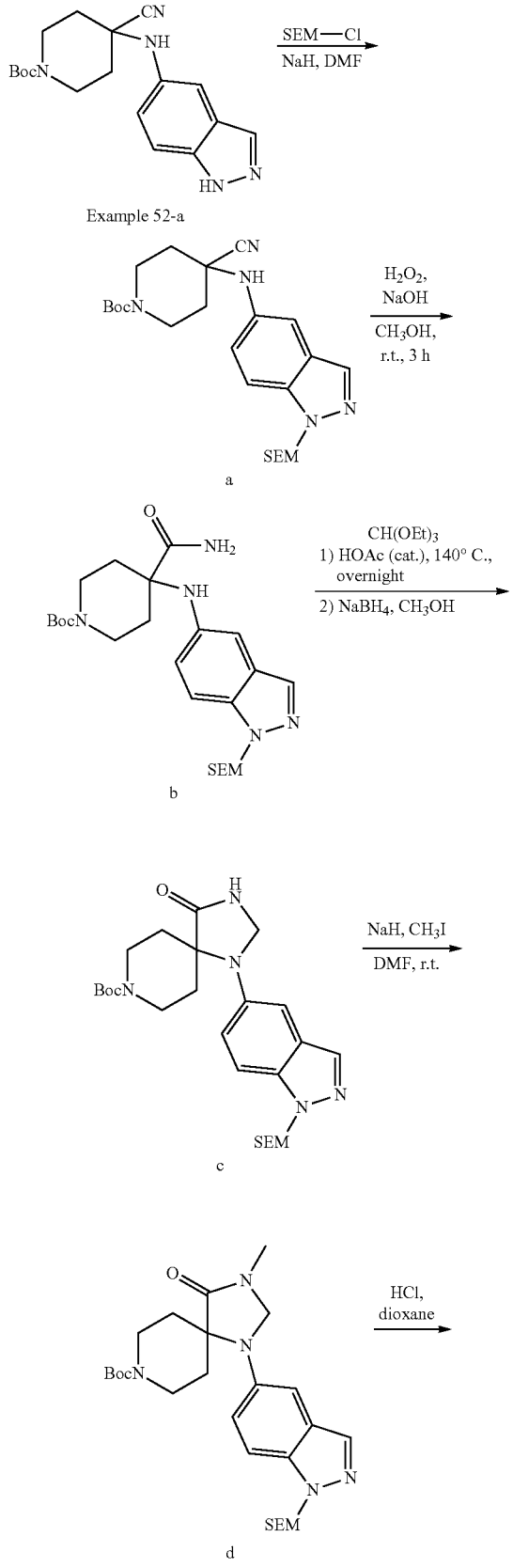

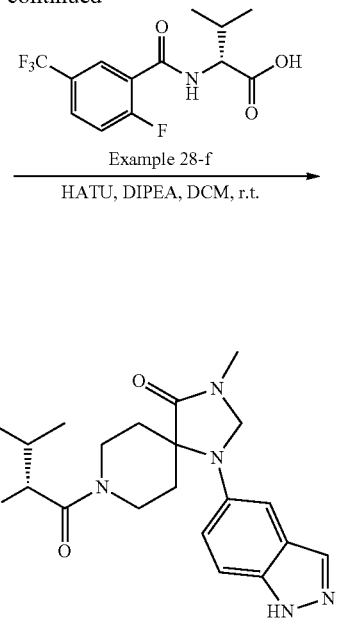

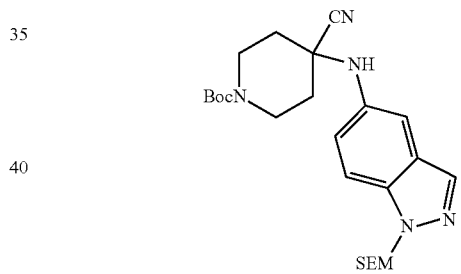

Representative General Procedure tert-Butyl-4-cyano-4-(1-((2-(trimethylsilyl)ethoxy)methyl)-1H-indazol-5-ylamino)piperidine-1-carboxylate To a solution of tert-butyl-4-(1H-indazol-5-ylamino)-4-cyanopiperidine-1-carboxylate (prepared as described in Example 52-a) (1.0 g, 2.92 mmol) in N,N-dimethylformamide (10 mL) was added sodium hydride (0.175 g, 60% in oil, 4.39 mmol) at 0° C. After stirring for 15 minutes at 0° C., 2-(trimethylsilyl) ethoxymethyl chloride (0.54 g, 3.22 mmol) was added. After stirring for 2 hours, the reaction was quenched by addition of ice-water (20 mL). The mixture was extracted with dichloromethane (3×20 mL). The combined organic layers were washed with brine and dried over anhydrous sodium sulfate and concentrated under reduced pressure. The residue was purified by silica gel column chromatography eluting with dichloromethane:methanol=100:1 to afford tert-butyl-4-cyano-4-(1-((2-(trimethylsilyl)ethoxy)methyl)-1H-indazol-5-ylamino)piperidine-1-carboxylate as a white solid (280 mg, 21%).

LCMS (ESI): m/z=472.2 [M+H]$^+$.

$^1$H-NMR (300 MHz, DMSO-d$_6$): δ=0.01-0.02 (m, 9H), 0.8-0.87 (m, 2H), 1.44-1.45 (m, 9H), 1.82-1.87 (m, 2H), 2.29-2.33 (m, 2H), 3.18-3.25 (m, 2H), 3.49-3.57 (m, 2H), 3.78-3.82 (m, 2H), 5.59-5.70 (m, 2H), 5.95 (s, 1H), 6.94-6.98 (m, 2H), 7.51-7.54 (m, 1H), 8.26 (s, 1H).

tert-Butyl-4-carbamoyl-4-(1-((2-(trimethylsilyl)ethoxy)methyl)-1H-indazol-5-ylamino)piperidine-1-carboxylate

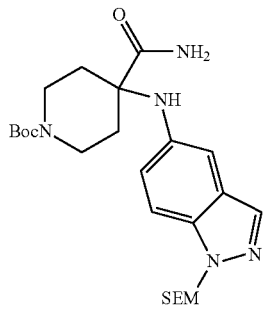 [SMILES: CC(C)(C)OC(=O)N1CCC(Nc2ccc3c(cnn3COCC[Si](C)(C)C)c2)(C(N)=O)CC1]

To a solution of tert-butyl-4-cyano-4-(1-((2-(trimethylsilyl)ethoxy)methyl)-1H-indazol-5-ylamino) piperidine-1-carboxylate (600 mg, 1.73 mmol) in methanol (5 mL) was added an aqueous sodium hydroxide solution (6.67 mL, 1.0 M). After stirring for 15 minutes, to the resulting solution was added a 30% aqueous hydrogen peroxide solution (5.07 mL) dropwise. After stirring overnight, the reaction was quenched with ice-water (50 mL) and the mixture was extracted with ethyl acetate (3×50 mL). The combined organic layers were washed with brine and dried over anhydrous sodium sulfate and concentrated under reduced pressure. The residue was purified by silica gel column chromatography eluting with dichloromethane:methanol=100:1 to afford tert-butyl-4-carbamoyl-4-(1-((2-(trimethylsilyl)ethoxy)methyl)-1H-indazol-5-ylamino)piperidine-1-carboxylate as a white solid (500 mg, 80%).

LCMS (ESI): m/z=490.2 [M+H]$^+$.

tert-Butyl-4-oxo-1-(1-((2-(trimethylsilyl)ethoxy)methyl)-1H-indazol-5-yl)-1,3,8-triazaspiro[4.5]decane-8-carboxylate

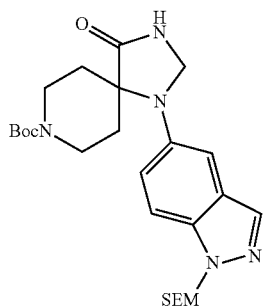 [SMILES: CC(C)(C)OC(=O)N1CCC2(CC1)C(=O)NCN2c1ccc2c(cnn2COCC[Si](C)(C)C)c1]

To a solution of tert-butyl-4-carbamoyl-4-(1-((2-(trimethylsilyl)ethoxy)methyl)-1H-indazol-5-ylamino)piperidine-1-carboxylate (300 mg, 0.613 mmol) in triethyl orthoformate (2 mL) was added acetic acid (1 drop, cat.). The resulting mixture was stirred for 30 minutes at 130° C. in a microwave reactor. The solvent was removed under reduced pressure and the residue was dissolved in methanol (10 mL). To the solution was added sodium borohydride (100 mg, 2.63 mmol) at 0° C. The resulting mixture was stirred for 30 minutes. The solvent was removed under reduced pressure. The residue was purified by silica gel column chromatography eluting with dichloromethane:methanol=100:1 to afford tert-butyl-4-oxo-1-(1-((2-(trimethylsilyl)ethoxy)methyl)-1H-indazol-5-yl)-1,3,8-triazaspiro[4.5]decane-8-carboxylate as a white solid (100 mg, 32%).

LCMS (ESI): m/z=502.2 [M+H]$^+$.

tert-Butyl-3-methyl-4-oxo-1-(1-((2-(trimethylsilyl)ethoxy)methyl)-1H-indazol-5-yl)-1,3,8-triazaspiro[4.5]decane-8-carboxylate

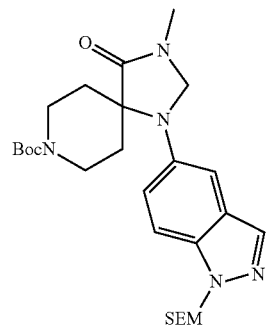 [SMILES: CN1CN(c2ccc3c(cnn3COCC[Si](C)(C)C)c2)C2(CCN(C(=O)OC(C)(C)C)CC2)C1=O]

To a solution of tert-butyl-4-oxo-1-(1-((2-(trimethylsilyl)ethoxy)methyl)-1H-indazol-5-yl)-1,3,8-triazaspiro[4.5]decane-8-carboxylate (200 mg, 0.40 mmol) in N,N-dimethylformamide (5 mL) was added sodium hydride (48 mg, 1.2 mol) at 0° C. After stirring for 15 minutes, iodomethane (283 mg, 2.0 mmol) was added. After stirring for 1 hour, the reaction was quenched by addition of ice-water (10 mL). The mixture was extracted with ethyl acetate (3×20 mL). The combined organic layers were dried over anhydrous sodium sulfate and concentrated under reduced pressure. The residue was purified by silica gel column chromatography eluting with dichloromethane:methanol=100:1 to afford tert-butyl-3-methyl-4-oxo-1-(1-((2-(trimethylsilyl)ethoxy)methyl)-1H-indazol-5-yl)-1,3,8-triazaspiro[4.5]decane-8-carboxylate as a white solid (180 mg, 87%).

LCMS (ESI): m/z=516.2 [M+H]$^+$.

$^1$H-NMR (300 MHz, CDCl$_3$) b=0.01-0.03 (m, 9H), 0.86-0.95 (m, 2H), 1.44 (s, 9H), 1.69-1.74 (m, 2H), 2.12-2.16 (m, 2H), 2.99 (s, 3H), 3.57-3.62 (m, 4H), 3.82-3.94 (m, 2H), 4.68 (s, 2H), 5.27-5.66 (m, 2H), 7.00-7.08 (m, 2H), 7.61-7.64 (m, 1H), 7.88-7.98 (m, 1H).

1-(1H-Indazol-5-yl)-3-methyl-1,3,8-triazaspiro[4.5]decan-4-one hydrochloride

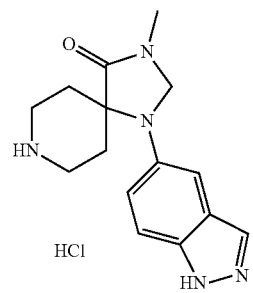 [SMILES: CN1CN(c2ccc3[nH]ncc3c2)C2(CCNCC2)C1=O ; Cl]

A solution of tert-butyl-3-methyl-4-oxo-1-(1-((2-(trimethylsilyl)ethoxy)methyl)-1H-indazol-5-yl)-1,3,8-triazaspiro[4.5]decane-8-carboxylate (180 mg, 0.35 mmol) in hydrochloric acid in dioxane (6.0 M, 20 mL) was stirred for 30 minutes. The precipitate was collected by filtration and dried under reduced pressure to afford 1-(1H-indazol-5-yl)-3-methyl-1,3,8-triazaspiro[4.5]decan-4-one hydrochloride as a white solid (115 mg, crude), which was used directly without any further purification.

LCMS (ESI): m/z=285.2 [M+H]$^+$.

(R)—N-(1-(1-(1H-Indazol-5-yl)-3-methyl-4-oxo-1,3,8-triazaspiro[4.5]decan-8-yl)-3-methyl-1-oxobutan-2-yl)-2-fluoro-5-(trifluoromethyl)benzamide

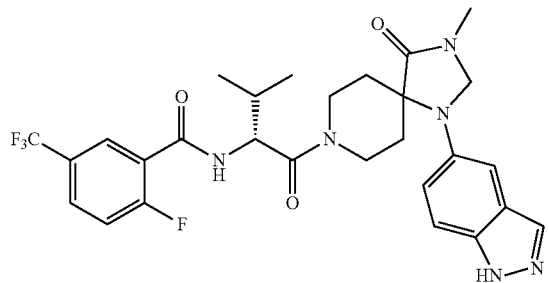 [SMILES: CC(C)[C@@H](NC(=O)c1cc(C(F)(F)F)ccc1F)C(=O)N1CCC2(CC1)C(=O)N(C)CN2c1ccc2[nH]ncc2c1]

To a mixture of 1-(1H-indazol-5-yl)-3-methyl-1,3,8-triazaspiro[4.5]decan-4-one hydrochloride (115 mg, crude) in dichloromethane (10 mL) was added sequentially (R)-2-(2-fluoro-5-(trifluoromethyl)benzamido)-3-methylbutanoic acid (prepared as described in Example 28-f) (129 mg, 0.34 mmol), 1-[bis(dimethylamino)methylene]-1H-1,2,3-triazolo[4,5-b]pyridinium-3-oxide hexafluorophosphate (HATU) (198 mg, 0.52 mmol), N,N-diisopropylethylamine (109 mg, 0.85 mmol). The reaction was stirred for 2 hours before quenching with ice-water (10 mL). The mixture was extracted with dichloromethane (3×10 mL) and the combined organic layers were dried over anhydrous sodium sulfate and concentrated under reduced pressure. The residue was purified by prep-TLC with dichloromethane:methanol=20:1 to afford (R)—N-(1-(1-(1H-indazol-5-yl)-3-methyl-4-oxo-1,3,8-triazaspiro[4.5]decan-8-yl)-3-methyl-1-oxobutan-2-yl)-2-fluoro-5-(trifluoromethyl)benzamide as a white solid (35 mg, 32%).

LCMS (ESI): m/z=575.2 [M+H]$^+$.

$^1$H-NMR (400 MHz, CD$_3$OD): δ=0.85-1.06 (m, 6H), 1.82-2.19 (m, 5H), 3.02 (s, 3H), 3.56-3.66 (m, 1H), 3.94-4.34 (m, 3H), 4.75-4.78 (m, 2H), 4.98-5.01 (m, 1H), 7.17-7.53 (m, 4H), 7.80-7.93 (m, 2H), 8.01-8.21 (m, 1H).

The following 2 compounds were synthesized following the general procedure described above:

Example 215

(R)—N-(1-(1-(1H-Indazol-5-yl)-3-methyl-4-oxo-1,3,8-triazaspiro[4.5]decan-8-yl)-3-methyl-1-oxobutan-2-yl)-5-ethyl-2-fluorobenzamide

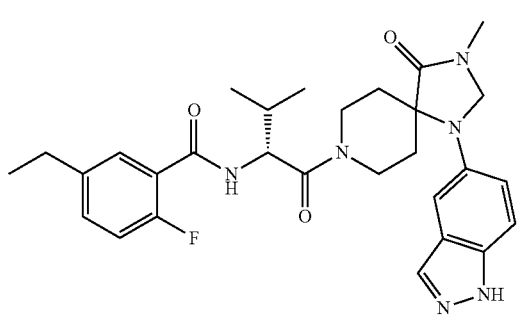 [SMILES: CCc1ccc(F)c(C(=O)N[C@@H](C(=O)N2CCC3(CC2)C(=O)N(C)CN3c2ccc3[nH]ncc3c2)C(C)C)c1]

9.5 mg, yield: 10%, white solid.

LCMS (ESI): m/z=535.0 [M+H]$^+$.

$^1$H-NMR (400 MHz, CDCl$_3$): δ=0.94-1.05 (m, 6H), 1.19-1.26 (m, 3H), 1.85-2.11 (m, 5H), 2.61-2.67 (m, 2H), 3.05 (s, 3H), 3.58-3.63 (m, 1H), 3.98-4.05 (m, 2H), 4.27-4.46 (m, 1H), 4.71-4.76 (m, 2H), 5.10 (s, 1H), 7.00-7.12 (m, 2H), 7.28-7.30 (m, 1H), 7.33-7.79 (m, 2H), 7.94-8.02 (m, 2H).

Example 216

(R)—N-(1-(1-(1H-Benzo[d]imidazol-6-yl)-3-methyl-4-oxo-1,3,8-triazaspiro[4.5]decan-8-yl)-3-methyl-1-oxobutan-2-yl)-5-ethyl-2-fluorobenzamide

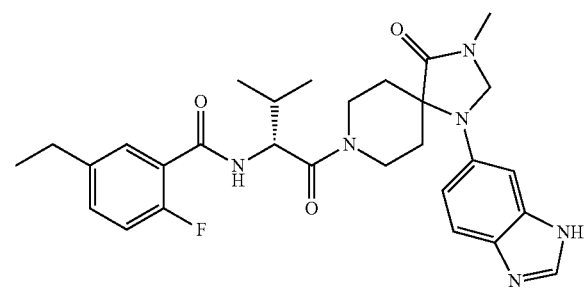 [SMILES: CCc1ccc(F)c(C(=O)N[C@@H](C(=O)N2CCC3(CC2)C(=O)N(C)CN3c2ccc3nc[nH]c3c2)C(C)C)c1]

18.8 mg, yield: 16%, white solid.

LCMS (ESI): m/z=535.0 [M+H]$^+$.

$^1$H-NMR (400 MHz, CD$_3$OD): δ=1.07-1.11 (m, 6H), 1.17-1.22 (m, 3H), 1.79-1.98 (m, 2H), 2.21-2.31 (m, 1H), 2.44-2.68 (m, 3H), 2.81-2.89 (m, 1H), 3.06-3.07 (m, 3H), 3.52-3.65 (m, 1H), 4.00-4.07 (m, 1H), 4.24-4.36 (m, 1H), 4.46-4.57 (m, 1H), 4.85-4.87 (m, 2H) 4.93-4.97 (m, 1H), 7.06-9.22 (m, 7H).

Example 217

(R)-3-Methyl-N-(3-methyl-1-oxo-1-(2-oxo-1-phenyl-3-oxa-1,8-diazaspiro[4.5]decan-8-yl)butan-2-yl)benzamide

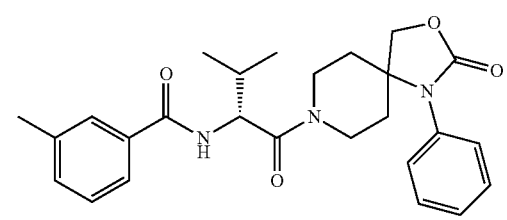 [SMILES: Cc1cccc(C(=O)N[C@@H](C(=O)N2CCC3(CC2)COC(=O)N3c2ccccc2)C(C)C)c1]

Scheme:

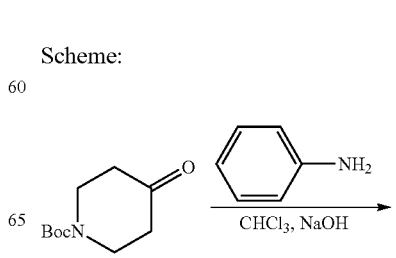

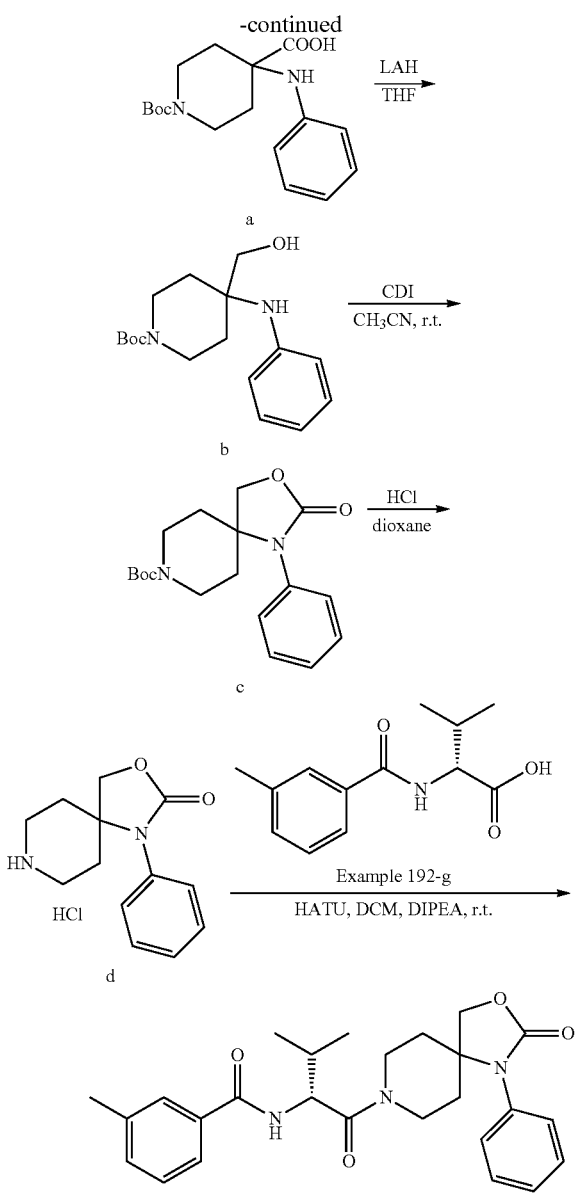

Experimental Procedure 1-(tert-Butoxycarbonyl)-4-(phenylamino)piperidine-4-carboxylic Acid

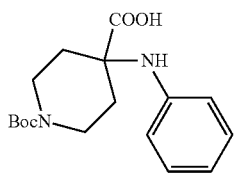 [SMILES: CC(C)(C)OC(=O)N1CCC(Nc2ccccc2)(C(=O)O)CC1]

To a solution of aniline (10 g, 107 mmol) in tetrahydrofuran (800 mL) was added sodium hydroxide (22 g, 537 mmol) at 0° C. After stirring for 10 minutes at 0° C., to the resulting solution was added tert-butyl-4-oxopiperidine-1-carboxylate (42 g, 55 mmol). The resulting suspension was stirred for 20 minutes at 0° C. To the suspension was added chloroform (64 g, 537 mmol). The reaction was stirred overnight before quenching with water (100 mL). The resulting mixture was extracted with ethyl acetate (100 mL). The pH of the aqueous layer was adjusted to 3 by addition of a 5% aqueous hydrochloric acid solution and extracted with ethyl acetate (3×100 mL). The combined organic layers were dried over anhydrous sodium sulfate and the solvent was removed under reduced pressure to afford 1-(tert-butoxycarbonyl)-4-(phenylamino)piperidine-4-carboxylic acid as a yellow solid (18 g, 52%).

LCMS (ESI): m/z=321.2 [M+H]$^+$.

$^1$H-NMR (300 MHz, DMSO-d$_6$): δ=1.39 (s, 9H), 1.82-1.95 (m, 4H), 3.16-3.26 (m, 2H), 3.57-3.61 (m, 2H), 6.52-6.56 (m, 3H), 7.02-7.07 (m, 2H).

tert-Butyl-4-(hydroxymethyl)-4-(phenylamino)piperidine-1-carboxylate

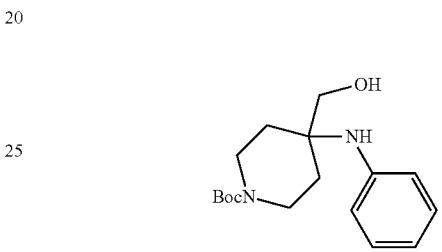

To a solution of 1-(tert-butoxycarbonyl)-4-(phenylamino)piperidine-4-carboxylic acid (2 g, 6.25 mmol) in tetrahydrofuran (10 mL) was added lithium aluminum hydride (4 mL, 2.4 M in tetrahydrofuran, 9.6 mmol). Before quenching by sequential addition of ice-water (4 mL), 15% aqueous sodium hydroxide solution (12 mL) and water (4 mL), the reaction was stirred for 2 hours. The resulting mixture was filtered and the filtrate was concentrated under reduced pressure. The residue was purified by silica gel column chromatography eluting with ethyl acetate:petroleum ether=1:3 to afford tert-butyl-4-(hydroxymethyl)-4-(phenylamino)piperidine-1-carboxylate as a yellow oil (580 mg, 30%).

LCMS (ESI): m/z=307.1 [M+H]$^+$.

tert-Butyl-2-oxo-1-phenyl-3-oxa-1,8-diazaspiro[4.5]decane-8-carboxylate

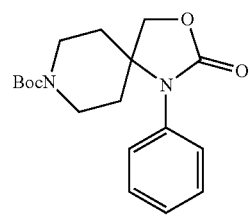 [SMILES: CC(C)(C)OC(=O)N1CCC2(CC1)COC(=O)N2c1ccccc1]

To a solution of tert-butyl-4-(hydroxymethyl)-4-(phenylamino)piperidine-1-carboxylate (250 mg, 0.817 mmol) in acetonitrile (5 mL) was added pyridinium chloride (118 mg, 1.01 mmol) and 1,1'-carbonyldiimidazole (265 mg, 1.63 mmol). Before quenching by addition of ice-water (4 mL), the reaction was stirred for 2 hours at 70° C. The mixture was extracted with ethyl acetate (3×20 mL). The combined organic layers were dried over anhydrous sodium sulfate and concentrated under reduced pressure. The residue was purified by silica gel column chromatography eluting with ethyl acetate:petroleum ether=1:5 to afford the crude product. The crude product was washed with petroleum ether (3×5 mL) to afford tert-butyl-2-oxo-1-phenyl-3-oxa-1,8-diazaspiro[4.5]decane-8-carboxylate as a white solid (170 mg, 62%).

LCMS (ESI): m/z=333.2 [M+H]⁺.

1-Phenyl-3-oxa-1,8-diazaspiro[4.5]decan-2-one hydrochloride

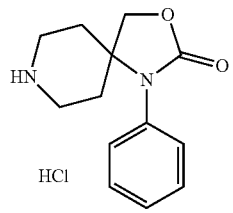 [SMILES: O=C1OCC2(CCNCC2)N1c1ccccc1 ; Cl]

A solution of tert-butyl-2-oxo-1-phenyl-3-oxa-1,8-diazaspiro[4.5]decane-8-carboxylate (70 mg, 0.21 mmol) in hydrochloric acid in dioxane (6.0 M, 10 mL) was stirred for 30 minutes. The precipitate was collected by filtration and dried. The crude product was used directly without further purification.

LCMS (ESI): m/z=233.2 [M+H]⁺.

(R)-3-Methyl-N-(3-methyl-1-oxo-1-(2-oxo-1-phenyl-3-oxa-1,8-diazaspiro[4.5]decan-8-yl)butan-2-yl)benzamide

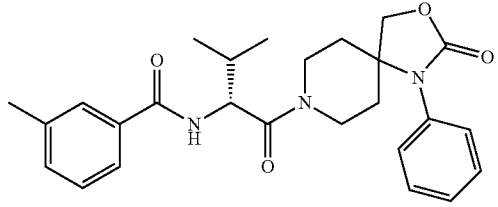 [SMILES: Cc1cccc(C(=O)N[C@@H](C(=O)N2CCC3(CC2)COC(=O)N3c2ccccc2)C(C)C)c1]

To a suspension of 1-phenyl-3-oxa-1,8-diazaspiro[4.5]decan-2-one hydrochloride (45 mg, crude) and (R)-3-methyl-2-(3-methylbenzamido)butanoic acid (prepared as described in Example 192-g) (65 mg, 0.274 mmol) in dichloromethane (5 mL) was added 1-[bis(dimethylamino)methylene]-1H-1,2,3-triazolo[4,5-b]pyridinium-3-oxide hexafluorophosphate (HATU) (111 mg, 0.316 mmol) and N,N-diisopropylethylamine (82 mg, 0.633 mmol). The resulting mixture was stirred for 2 hours at room temperature before the reaction was quenched with ice-water (10 mL). The mixture was extracted with ethyl acetate (3×10 mL) and the combined organic layers were dried over sodium sulfate and concentrated under reduced pressure. The residue was purified by prep-TLC with dichloromethane:methanol=15:1 to afford (R)-3-methyl-N-(3-methyl-1-oxo-1-(2-oxo-1-phenyl-3-oxa-1,8-diazaspiro[4.5]decan-8-yl)butan-2-yl)benzamide as a white solid (13 mg, 13% over two steps).

LCMS (ESI): m/z=450.2 [M+H]⁺.

¹H-NMR (400 MHz, CD₃OD): δ=0.74-0.96 (m, 6H), 1.11-1.28 (m, 1H), 1.46-1.86 (m, 1H), 1.89-2.30 (m, 3H), 2.37-2.42 (m, 3H), 2.68-2.90 (m, 2H), 3.15-3.31 (m, 1H), 4.35-4.39 (m, 1H), 4.59-4.91 (m, 3H), 6.99-7.68 (m, 9H).

Example 218

(R)-2-Fluoro-N-(3-methyl-1-(3-methyl-1-(4-(oxetan-3-ylamino)phenyl)-4-oxo-1,3,8-triazaspiro[4.5]decan-8-yl)-1-oxobutan-2-yl)-5-(trifluoromethyl)benzamide

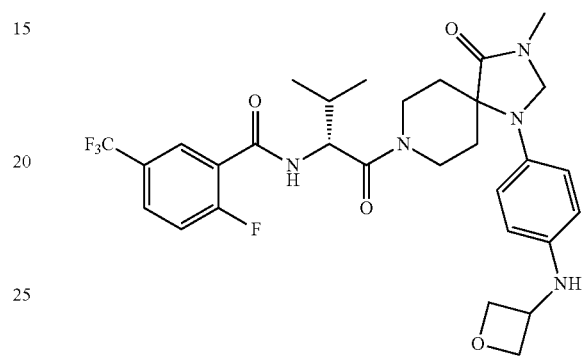

Scheme:

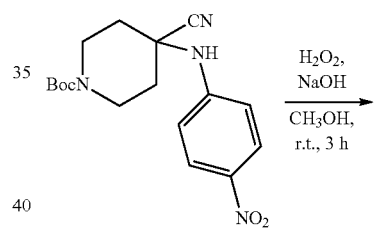

Example 86-a

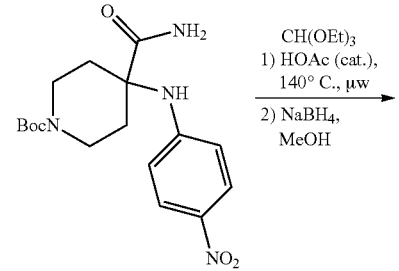

a

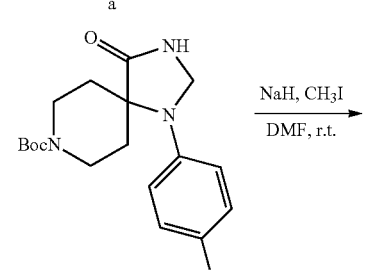

b

-continued

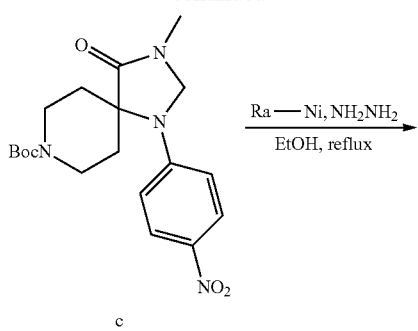

c

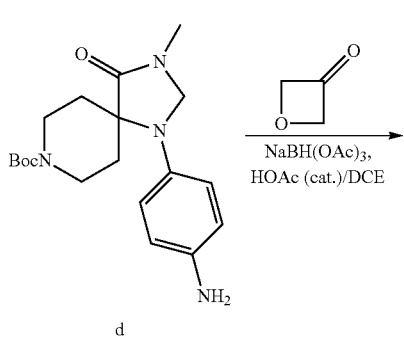

d

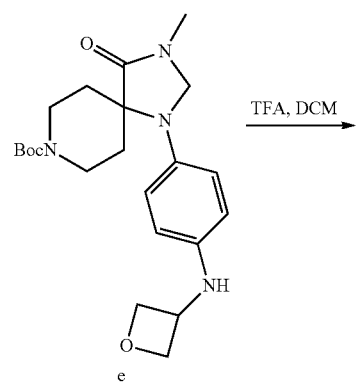

e

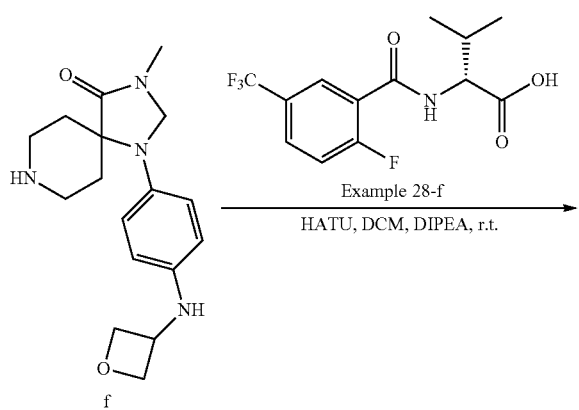

f

-continued

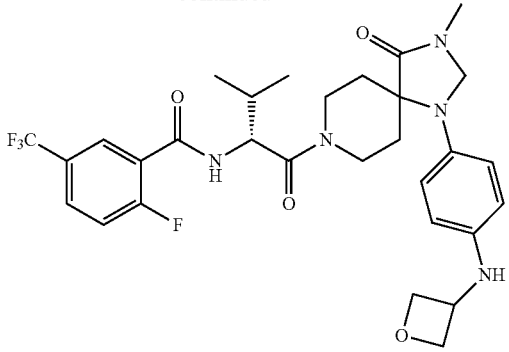

Experimental Procedure tert-Butyl-4-carbamoyl-4-(4-nitrophenylamino)piperidine-1-carboxylate

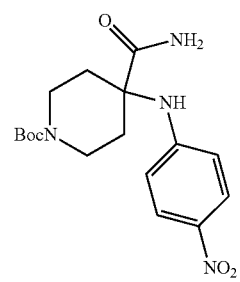 [SMILES: CC(C)(C)OC(=O)N1CCC(Nc2ccc([N+](=O)[O-])cc2)(C(N)=O)CC1]

To a solution of tert-butyl-4-cyano-4-(4-nitrophenylamino)piperidine-1-carboxylate (prepared as described in Example 86-a) (9.0 g, 0.0261 mol) in methanol (100 mL) was added an aqueous sodium hydroxide solution (100 mL, 1.0 M). After stirring for 15 minutes, a 30% aqueous hydrogen peroxide solution (76 mL) was added dropwise. After stirring overnight, the resulting mixture was filtered. The filter cake was washed with water (3×100 mL) and dried under reduced pressure to afford tert-butyl-4-carbamoyl-4-(4-nitrophenylamino)piperidine-1-carboxylate as a white solid (5.2 g, 55%).
LCMS (ESI): m/z=365.2 [M+H]⁺.

tert-Butyl-1-(4-nitrophenyl)-4-oxo-1,3,8-triazaspiro[4.5]decane-8-carboxylate

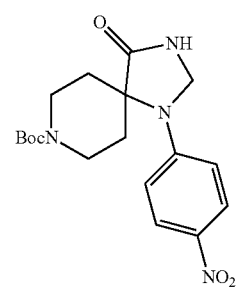 [SMILES: CC(C)(C)OC(=O)N1CCC2(CC1)C(=O)NCN2c1ccc([N+](=O)[O-])cc1]

To a solution of tert-butyl-4-carbamoyl-4-(4-nitrophenylamino)piperidine-1-carboxylate (2.0 g, 0.0055 mol) in triethyl orthoformate (20 mL) was added acetic acid (1 mL, cat.). The resulting mixture was stirred at 140° C. for 30 minutes in a microwave reactor. The solvent was removed under reduced pressure and the residue was dissolved in methanol (30 mL). To the resulting solution was added sodium borohydride (0.5 g, 0.0132 mol) at 0° C. and the mixture was stirred for 30 minutes. The solvent was removed under reduced pressure and the residue was treated with water (20 mL) and ethyl acetate (50 mL). The organic layer was collected and the aqueous layer was extracted with ethyl acetate (3×10 mL). The combined organic layers were dried over anhydrous sodium sulfate and concentrated under reduced pressure. The residue was purified by silica gel column chromatography eluting with dichloromethane:methanol=100:1 to afford tert-butyl-1-(4-nitrophenyl)-4-oxo-1,3,8-triazaspiro[4.5]decane-8-carboxylate as a white solid (1.2 g, 61%).

LCMS (ESI): m/z=377.4 [M+H]$^+$.

tert-Butyl-3-methyl-1-(4-nitrophenyl)-4-oxo-1,3,8-triazaspiro[4.5]decane-8-carboxylate

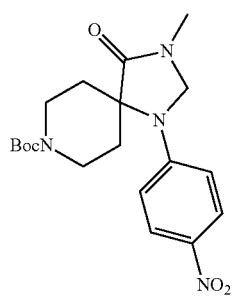 [SMILES: CN1CN(c2ccc([N+](=O)[O-])cc2)C2(CCN(C(=O)OC(C)(C)C)CC2)C1=O]

To a solution of tert-butyl-1-(4-nitrophenyl)-4-oxo-1,3,8-triazaspiro[4.5]decane-8-carboxylate (1.2 g, 0.00319 mol) in N,N-dimethylformamide (10 mL) was added sodium hydride (320 mg, 60% in oil, 0.00798 mol) at 0° C. After stirring for 15 minutes, iodomethane (2.27 g, 0.01598 mol) was added. The resulting mixture was stirred for 60 minutes at room temperature and the reaction was quenched with ice-water (10 mL). The mixture was extracted with ethyl acetate (3×15 mL). The combined organic layers were dried over anhydrous sodium sulfate and concentrated under reduced pressure. The residue was purified by silica gel column chromatography eluting with ethyl acetate:petroleum ether=1:1 to afford tert-butyl-3-methyl-1-(4-nitrophenyl)-4-oxo-1,3,8-triazaspiro[4.5]decane-8-carboxylate as a yellow solid (1.0 g, 81%).

LCMS (ESI): m/z=391.2 [M+H]$^+$.

$^1$H-NMR (400 MHz, CDCl$_3$): δ=1.55 (s, 9H), 1.67-1.74 (m, 2H), 2.56-2.74 (m, 2H), 3.05 (s, 3H), 3.51-3.65 (m, 2H), 4.06-4.16 (m, 2H), 4.79-4.83 (m, 2H), 6.64-6.67 (m, 2H), 8.11-8.14 (m, 2H).

tert-Butyl-1-(4-aminophenyl)-3-methyl-4-oxo-1,3,8-triazaspiro[4.5]decane-8-carboxylate

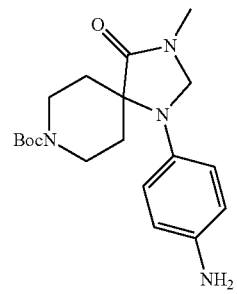 [SMILES: CN1CN(c2ccc(N)cc2)C2(CCN(C(=O)OC(C)(C)C)CC2)C1=O]

To a solution of tert-butyl-3-methyl-1-(4-nitrophenyl)-4-oxo-1,3,8-triazaspiro[4.5]decane-8-carboxylate (500 mg, 1.281 mmol) in ethanol (10 mL) was added Raney-Ni (0.1 g, 50% in ethanol). After heating to 50° C., hydrazine (1.0 mL) was added dropwise to the resulting suspension. Before removing the Raney-Ni by filtration, the reaction mixture was stirred at room temperature for 30 minutes. The solvent was removed under reduced pressure and the residue was used directly without further purification.

LCMS (ESI): m/z=361.2 [M+H]$^+$.

tert-Butyl-3-methyl-1-(4-(oxetan-3-ylamino)phenyl)-4-oxo-1,3,8-triazaspiro[4.5]decane-8-carboxylate

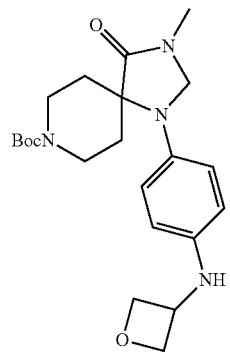

To a solution of oxetan-3-one (99 mg, 1.39 mmol) and tert-butyl-1-(4-aminophenyl)-3-methyl-4-oxo-1,3,8-triazaspiro[4.5]decane-8-carboxylate (100 mg, 0.28 mmol) in 1,2-dichloroethane (30 mL) was added acetic acid (1 drop) at room temperature. After two hours, to the solution was added sodium triacetoxyborohydride (294 mg, 1.39 mmol) at room temperature. The mixture was stirred overnight at room temperature. The reaction was quenched with water (10 mL) and the mixture was extracted with dichloromethane (3×10 mL). The combined organic layers were dried over anhydrous sodium sulfate and concentrated under reduced pressure. The residue was purified by prep-TLC with dichloromethane:methanol=20:1 to afford tert-butyl-3-methyl-1-(4-(oxetan-3-ylamino)phenyl)-4-oxo-1,3,8-triazaspiro[4.5]decane-8-carboxylate as a white solid (50 mg, 42%).

LCMS (ESI): m/z=416.2 [M+H]$^+$.

3-Methyl-1-(4-(oxetan-3-ylamino)phenyl)-1,3,8-triazaspiro[4.5]decan-4-one

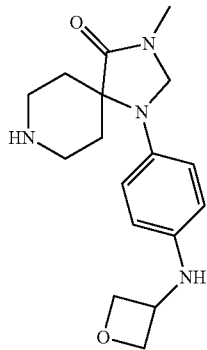 [SMILES: CN1CN(c2ccc(NC3COC3)cc2)C2(CCNCC2)C1=O]

To a solution of tert-butyl-3-methyl-1-(4-(oxetan-3-ylamino)phenyl)-4-oxo-1,3,8-triazaspiro[4.5]decane-8-carboxylate (55 mg, 0.13 mmol) in dichloromethane (2 mL) was added trifluoroacetic acid (1 mL) at room temperature. The reaction was stirred for 30 minutes at room temperature. The solvent was removed under reduced pressure and water (5 mL) was added to the residue. The pH of the suspension was adjusted to 11 by addition of a 10% aqueous sodium carbonate solution. The mixture was extracted with ethyl acetate (3×10 mL) and the combined organic layers were dried over anhydrous sodium sulfate and concentrated under reduced pressure to afford 3-methyl-1-(4-(oxetan-3-ylamino)phenyl)-1,3,8-triazaspiro[4.5]decan-4-one as the crude product (45 mg, crude) which was used directly without further purification.

(R)-2-Fluoro-N-(3-methyl-1-(3-methyl-1-(4-(oxetan-3-ylamino)phenyl)-4-oxo-1,3,8-triazaspiro[4.5]decan-8-yl)-1-oxobutan-2-yl)-5-(trifluoromethyl)benzamide

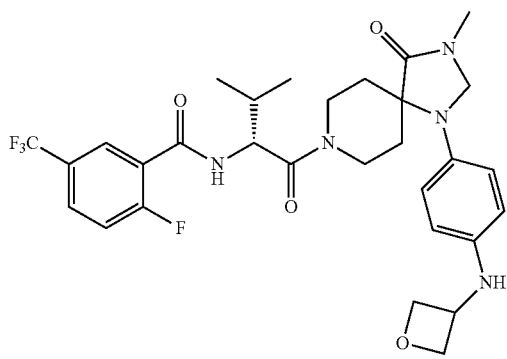 [SMILES: CC(C)[C@@H](NC(=O)c1cc(C(F)(F)F)ccc1F)C(=O)N1CCC2(CC1)C(=O)N(C)CN2c1ccc(NC2COC2)cc1]

To a solution of 3-methyl-1-(4-(oxetan-3-ylamino)phenyl)-1,3,8-triazaspiro[4.5]decan-4-one (45 mg, 0.14 mmol) in dichloromethane (5 mL) was added sequentially (R)-2-(2-fluoro-5-(trifluoromethyl)benzamido)-3-methylbutanoic acid (prepared as described in Example 28-f) (44 mg, 0.14 mmol), 1-[bis(dimethylamino)methylene]-1H-1,2,3-triazolo[4,5-b]pyridinium-3-oxide hexafluorophosphate (HATU) (81 mg, 0.21 mmol) and N,N-diisopropylethylamine (46 mg, 0.36 mmol). The resulting mixture was stirred for one hour at room temperature before the reaction was quenched with ice-water. The mixture was extracted with dichloromethane (3×10 mL) and the combined organic layers were dried over anhydrous sodium sulfate and concentrated under reduced pressure. The residue was purified by prep-TLC with petroleum ether:ethyl acetate=1:2 to afford (R)-2-fluoro-N-(3-methyl-1-(3-methyl-1-(4-(oxetan-3-ylamino)phenyl)-4-oxo-1,3,8-triazaspiro[4.5]decan-8-yl)-1-oxobutan-2-yl)-5-(trifluoromethyl)benzamide as a white solid (11.5 mg, 13% over two steps).

LCMS (ESI): m/z=606.2 [M+H]$^+$.

$^1$H-NMR (400 MHz, CDCl$_3$): δ=0.88-1.04 (m, 6H), 1.76-2.15 (m, 5H), 3.01 (s, 3H), 3.55-3.60 (m, 2H), 3.92-4.08 (m, 2H), 4.40-4.43 (m, 1H), 4.55-4.65 (m, 5H), 4.94-5.09 (m, 2H), 6.54-6.63 (m, 2H), 6.85-6.87 (m, 2H), 7.26-7.34 (m, 1H), 7.51-7.60 (m, 1H), 7.76-7.77 (m, 1H), 8.34-8.36 (m, 1H).

Example 219

(R)-2-Fluoro-N-(1-(1-((3-methoxycyclobutyl)methyl)-3-methyl-2,4-dioxo-1,3,8-triazaspiro[4.5]decan-8-yl)-3-methyl-1-oxobutan-2-yl)-5-(trifluoromethyl)benzamide

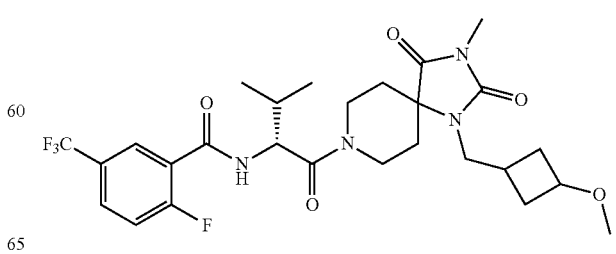

Scheme:

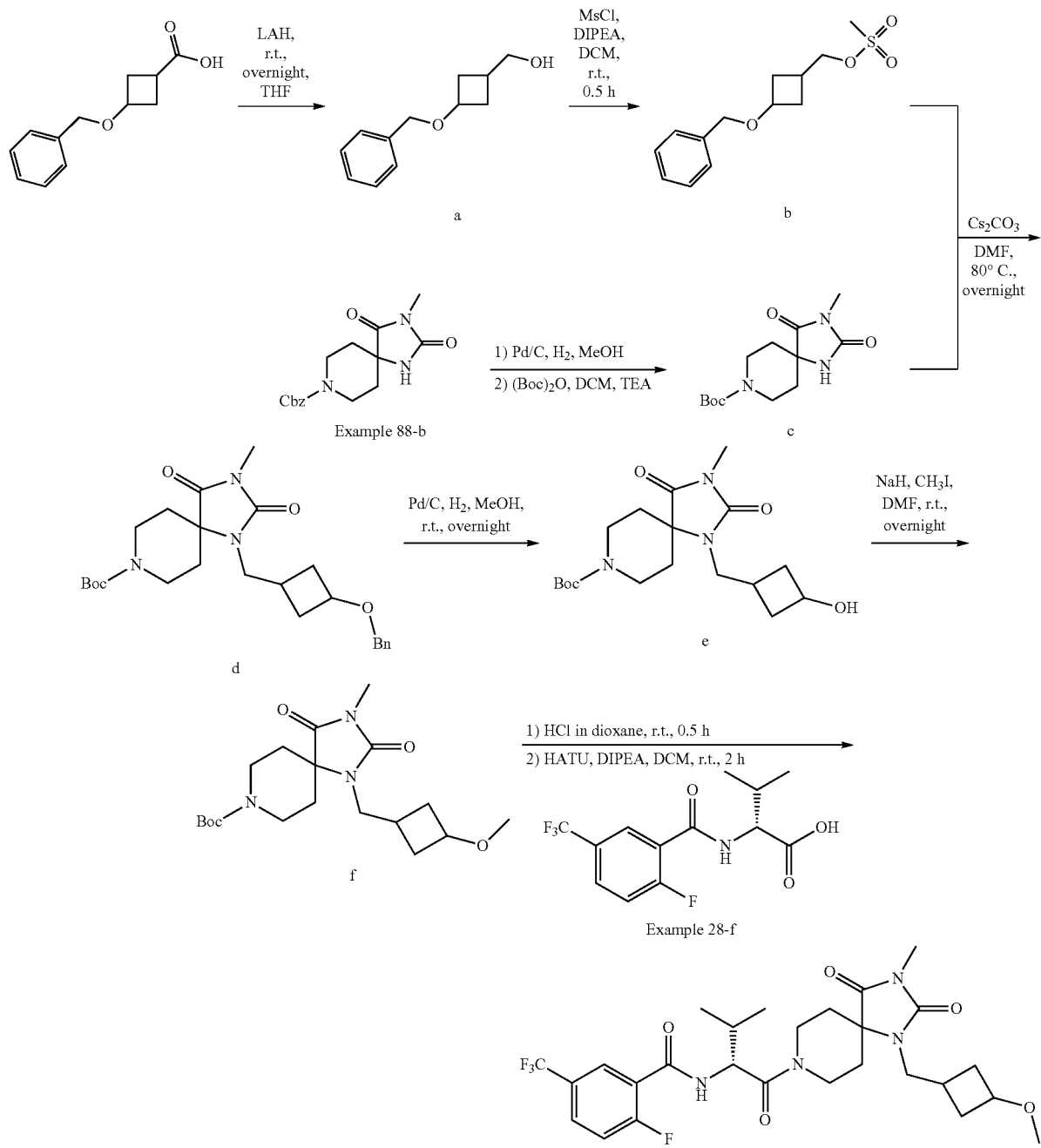

Experimental Procedure (3-(Benzyloxy)cyclobutyl)methanol

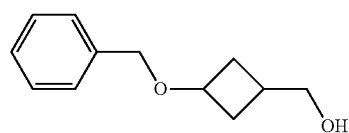 [SMILES: OCC1CC(OCc2ccccc2)C1]

To a solution of 3-(benzyloxy)cyclobutanecarboxylic acid (0.5 g, 2.4 mmol) in tetrahydrofuran (10 mL) was added lithium aluminum hydride (2 mL, 2.4 M in tetrahydrofuran) at 0° C. dropwise. The reaction was stirred overnight at room temperature. After quenching with water (0.2 mL), a 15% aqueous sodium hydroxide solution (0.6 mL) and water (0.2 mL) were added sequentially. The resulting mixture was filtered and the filtrate was concentrated under reduced pressure. The residue was purified by silica gel column chromatography eluting with ethyl acetate:petroleum ether=1:5 to afford (3-(benzyloxy)cyclobutyl)methanol as a colorless oil (420 mg, 90%).

¹H-NMR (300 MHz, CDCl₃): δ=1.68-2.48 (m, 5H), 2.62-3.57 (m, 2H), 3.88-4.17 (m, 1H), 4.40 (m, 2H), 7.24-7.33 (m, 5H).

(3-(Benzyloxy)cyclobutyl)methyl-methanesulfonate

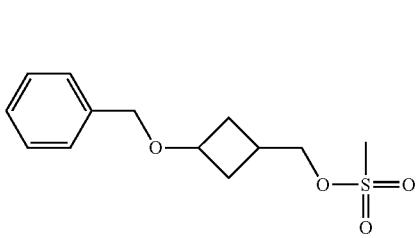 [SMILES: CS(=O)(=O)OCC1CC(OCc2ccccc2)C1]

To a solution of (3-(benzyloxy)cyclobutyl)methanol (200 mg, 1.04 mmol) in dichloromethane (10 mL) was added N,N-diisopropylethylamine (201 mg, 1.56 mmol) and methanesulfonyl chloride (142 mg, 1.25 mmol). The reaction was stirred for 0.5 h at room temperature. Then the reaction was quenched with water (10 mL) and extracted with ethyl acetate (3×10 mL). The combined organic layers were dried over anhydrous sodium sulfate and concentrated under reduced pressure to afford crude (3-(benzyloxy)cyclobutyl)methyl-methanesulfonate (270 mg, crude), which was used directly without further purification.

tert-Butyl-3-methyl-2,4-dioxo-1,3,8-triazaspiro[4.5]decane-8-carboxylate

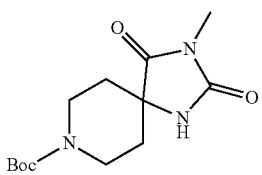 [SMILES: CN1C(=O)NC2(CCN(C(=O)OC(C)(C)C)CC2)C1=O]

To a solution of benzyl-3-methyl-2,4-dioxo-1,3,8-triazaspiro[4.5]decane-8-carboxylate (prepared as described in Example 88-b) (1.5 g, 4.7 mmol) in methanol (50 mL) was added 5% palladium on carbon (0.2 g). The reaction was stirred overnight at room temperature under a hydrogen atmosphere. The catalyst was removed by filtration and the filtrate was concentrated under reduced pressure. To the residue was added sequentially dichloromethane (50 mL), triethylamine (0.56 g, 5.6 mmol), di-tert-butyl dicarbonate (1.2 g, 5.6 mmol). The mixture was stirred for 3 hours before the reaction was quenched with a cold 5% aqueous hydrochloric acid solution (10 mL). The organic layer was collected and dried over anhydrous sodium sulfate. The solvent was removed under reduced pressure. To the residue was added ethyl acetate:petroleum ether=1:3 (10 mL) and the mixture was stirred at 0° C. for 1 hour. The precipitate was collected by filtration and dried under reduced pressure to afford tert-butyl-3-methyl-2,4-dioxo-1,3,8-triazaspiro[4.5]decane-8-carboxylate as a white solid (1.23 g, 92%).

LCMS (ESI): m/z=284.2 [M+H]⁺.

tert-Butyl-1-((3-(benzyloxy)cyclobutyl)methyl)-3-methyl-2,4-dioxo-1,3,8-triazaspiro[4.5]decane-8-carboxylate

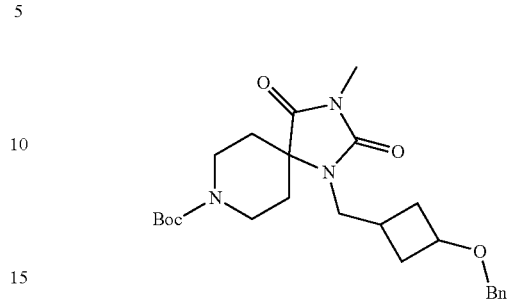

To a solution of (3-(benzyloxy)cyclobutyl)methyl-methanesulfonate (270 mg, crude) in N,N-dimethylformamide (5 mL) was added tert-butyl-3-methyl-2,4-dioxo-1,3,8-triazaspiro[4.5]decane-8-carboxylate (283 mg, 1.0 mmol) and cesium carbonate (650 mg, 2.0 mmol). Before quenching by addition of ice-water (20 mL), the mixture was stirred at 80° C. overnight. The mixture was extracted with ethyl acetate (3×10 mL). The combined organic layers were dried over anhydrous sodium sulfate and concentrated under reduced pressure. The residue was purified by silica gel column chromatography eluting with ethyl acetate:petroleum ether=1:5 to afford tert-butyl-1-((3-(benzyloxy)cyclobutyl)methyl)-3-methyl-2,4-dioxo-1,3,8-triazaspiro[4.5]decane-8-carboxylate as a white solid (290 mg, 63%).

LCMS (ESI): m/z=458.2 [M+H]⁺.

¹H-NMR (300 MHz, CDCl₃): δ=1.46 (s, 9H), 1.54-2.68 (m, 8H), 3.01 (s, 3H), 3.31-3.19 (m, 2H), 4.30-3.40 (m, 6H), 4.41-4.39 (m, 2H), 7.33-7.25 (m, 5H).

tert-Butyl-1-((3-hydroxycyclobutyl)methyl)-3-methyl-2,4-dioxo-1,3,8-triazaspiro[4.5]decane-8-carboxylate

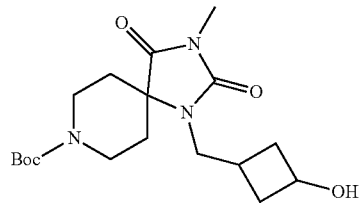 [SMILES: CN1C(=O)N(CC2CC(O)C2)C2(CCN(C(=O)OC(C)(C)C)CC2)C1=O]

To a solution of tert-butyl-1-((3-(benzyloxy)cyclobutyl)methyl)-3-methyl-2,4-dioxo-1,3,8-triazaspiro[4.5]decane-8-carboxylate (290 mg, 0.63 mmol) in methanol (10 mL) was added 5% palladium on carbon (30 mg, 50% wet with water). The reaction was stirred overnight at room temperature under a hydrogen atmosphere. The catalyst was removed by filtration and the filtrate was concentrated under reduced pressure to afford crude tert-butyl-1-((3-hydroxycyclobutyl)methyl)-3-methyl-2,4-dioxo-1,3,8-triazaspiro[4.5]decane-8-carboxylate (220 mg, crude), which was used directly without further purification.

LCMS (ESI): m/z=368.2 [M+H]⁺.

tert-Butyl-1-((3-methoxycyclobutyl)methyl)-3-methyl-2,4-dioxo-1,3,8-triazaspiro[4.5]decane-8-carboxylate

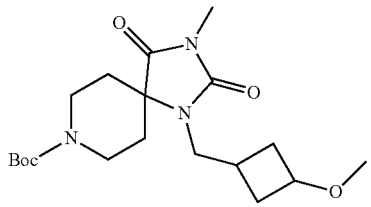 [SMILES: COC1CC(CN2C(=O)N(C)C(=O)C23CCN(C(=O)OC(C)(C)C)CC3)C1]

To a solution of tert-butyl-1-((3-hydroxycyclobutyl)methyl)-3-methyl-2,4-dioxo-1,3,8-triazaspiro[4.5]decane-8-carboxylate (220 mg, crude) in N,N-dimethylformamide (5 mL) was added sodium hydride (50 mg, 1.2 mmol) at room temperature. After stirring for 15 minutes, iodomethane (425 mg, 3.0 mmol) was added. The resulting mixture was stirred overnight and the reaction was quenched with ice-water (10 mL). The mixture was extracted with ethyl acetate (3×50 mL). The combined organic layers were dried over anhydrous sodium sulfate and concentrated under reduced pressure. The residue was purified by silica gel column chromatography eluting with ethyl acetate:petroleum ether=1:3 to afford tert-Butyl-1-((3-methoxycyclobutyl)methyl)-3-methyl-2,4-dioxo-1,3,8-triazaspiro[4.5]decane-8-carboxylate as a white solid (150 mg, crude), which was used directly without further purification.

LCMS (ESI): m/z=382.2 [M+H]$^+$.

(R)-2-Fluoro-N-(1-(1-((3-methoxycyclobutyl)methyl)-3-methyl-2,4-dioxo-1,3,8-triazaspiro[4.5]decan-8-yl)-3-methyl-1-oxobutan-2-yl)-5-(trifluoromethyl)benzamide

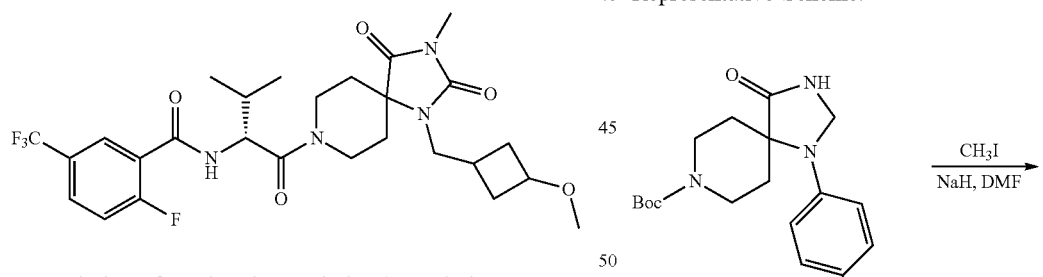

A solution of tert-butyl-3-methyl-1-(1-methyl-6-oxo-1,6-dihydropyridin-3-yl)-2,4-dioxo-1,3,8-triazaspiro[4.5]decane-8-carboxylate (150 mg, crude) in hydrochloric acid in dioxane (6.0 M, 10 mL) was stirred for 30 minutes. The solvent was removed under reduced pressure. To the residue was added dichloromethane (5 mL), (R)-2-(2-fluoro-5-(trifluoromethyl)benzamido)-3-methylbutanoic acid (prepared as described in Example 28-f) (121 mg, 0.39 mmol), 1-[bis(dimethylamino)methylene]-1H-1,2,3-triazolo[4,5-b]pyridinium-3-oxide hexafluorophosphate (HATU) (224 mg, 0.59 mmol) and N,N-diisopropylethylamine (127 mg, 0.98 mmol). The resulting mixture was stirred for 2 hours at room temperature before the reaction was quenched with ice-water. The mixture was extracted with ethyl acetate (3×10 mL) and the combined organic layers were dried over anhydrous sodium sulfate and concentrated under reduced pressure. The residue was purified by prep-TLC with dichloromethane:methanol=15:1 to afford (R)-2-fluoro-N-(1-(1-((3-methoxycyclobutyl)methyl)-3-methyl-2,4-dioxo-1,3,8-triazaspiro[4.5]decan-8-yl)-3-methyl-1-oxobutan-2-yl)-5-(trifluoromethyl)benzamide as a white solid (65.7 mg, 29.5% over three steps).

LCMS (ESI): m/z=571.2 [M+H]$^+$.

$^1$H-NMR (400 MHz, CD$_3$OD): δ=0.98-1.23 (m, 6H), 1.51-2.78 (m, 10H), 2.99 (d, J=2.8 Hz, 3H), 3.09-3.27 (m, 3H), 3.27-4.10 (m, 6H), 4.29 (t, J=13.0 Hz, 1H), 4.59 (d, J=11.0 Hz, 1H), 4.99 (d, J=7.1 Hz, 1H), 7.48 (t, J=9.4 Hz, 1H), 7.84-7.95 (m, 1H), 7.98-8.18 (m, 1H).

Example 220

(R)—N-(1-(1-(4-(1H-1,2,4-Triazol-3-yl)phenyl)-3-methyl-4-oxo-1,3,8-triazaspiro[4.5]decan-8-yl)-3-methyl-1-oxobutan-2-yl)-2-fluoro-5-(trifluoromethyl)benzamide

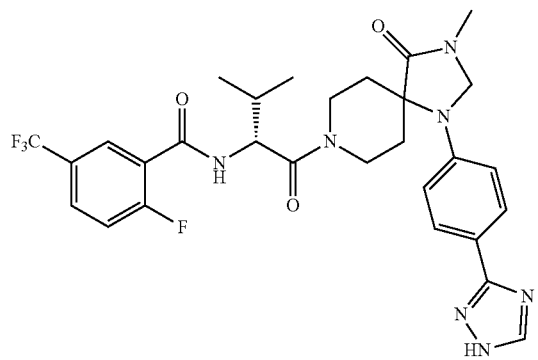 [SMILES: CC(C)[C@@H](NC(=O)c1cc(C(F)(F)F)ccc1F)C(=O)N1CCC2(CC1)C(=O)N(C)CN2c1ccc(-c2nc[nH]n2)cc1]

Representative Scheme:

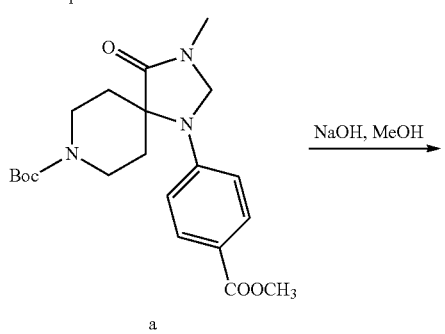

-continued

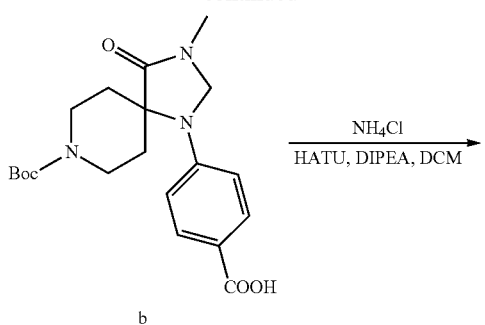

b

NH₄Cl
HATU, DIPEA, DCM →

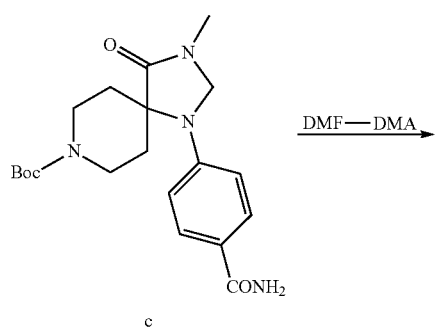

c

DMF—DMA →

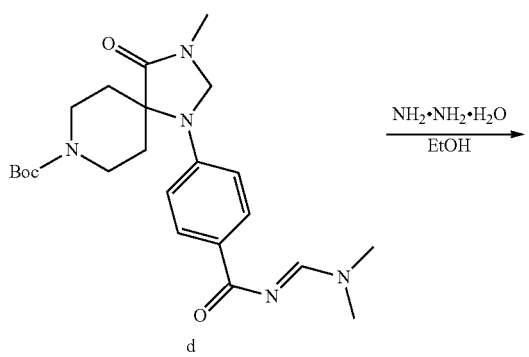

d

NH₂·NH₂·H₂O
EtOH →

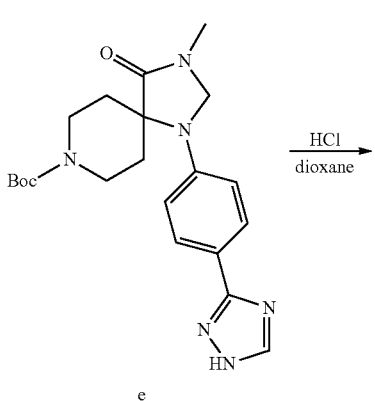

e

HCl
dioxane →

-continued

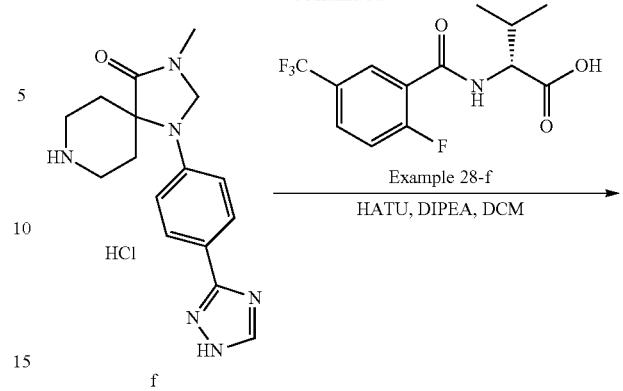

f

Example 28-f
HATU, DIPEA, DCM →

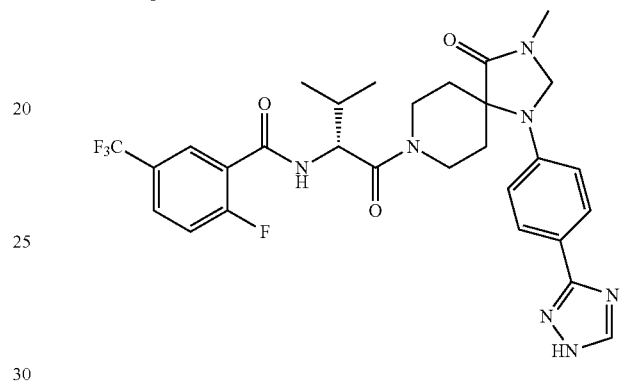

Representative General Procedure tert-Butyl-1-(4-(methoxycarbonyl)phenyl)-3-methyl-4-oxo-1,3,8-triazaspiro[4.5]decane-8-carboxylate

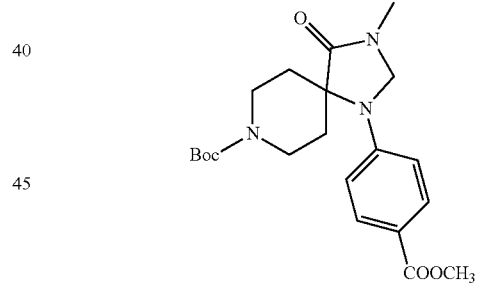

To a solution of tert-butyl-1-(4-(methoxycarbonyl)phenyl)-4-oxo-1,3,8-triazaspiro[4.5]decane-8-carboxylate (prepared as described in Example 149-c) (1000 mg, 2.57 mmol) in N,N-dimethylformamide (10 mL) was added sodium hydride (138 mg, 60% in oil, 3.34 mmol) at 0° C. After stirring for 15 minutes, iodomethane (550 mg, 3.86 mmol) was added. The resulting mixture was stirred for 15 minutes before the reaction was quenched with ice-water (10 mL). The mixture was extracted with ethyl acetate (3×10 mL). The combined organic layers were dried over anhydrous sodium sulfate and concentrated under reduced pressure and the residue was purified by silica gel column chromatography eluting with ethyl acetate:petroleum ether=1:2 to afford tert-butyl-1-(4-(methoxycarbonyl)phenyl)-3-methyl-4-oxo-1,3,8-triazaspiro[4.5]decane-8-carboxylate as a white solid (1000 mg, 96%).

LCMS (ESI): m/z=404.2 [M+H]⁺.

4-(8-(tert-Butoxycarbonyl)-3-methyl-4-oxo-1,3,8-triazaspiro[4.5]decan-1-yl) benzoic Acid

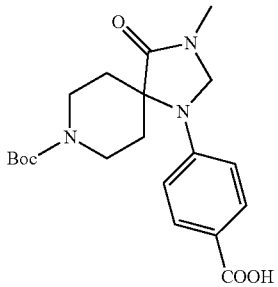 [SMILES: CN1CN(c2ccc(C(=O)O)cc2)C2(CCN(C(=O)OC(C)(C)C)CC2)C1=O]

To a solution of tert-butyl-1-(4-(methoxycarbonyl)phenyl)-3-methyl-4-oxo-1,3,8-triazaspiro[4.5]decane-8-carboxylate (1000 mg, 0.94 mmol) in methanol (20 mL) was added a 15% aqueous sodium hydroxide solution (15 mL). The reaction was heated at reflux for 30 minutes before cooling to room temperature. The pH of the resulting solution was adjusted to 3-4 by addition of 10% aqueous hydrochloric acid solution. The suspension was filtered. The filter cake was washed with petroleum ether (15 mL) and dried under reduced pressure to afford 4-(8-(tert-butoxycarbonyl)-3-methyl-4-oxo-1,3,8-triazaspiro[4.5]decan-1-yl) benzoic acid as a white solid (910 mg, 86%).

LCMS (ESI): m/z=390.4 [M+H]$^+$.

tert-Butyl-1-(4-carbamoylphenyl)-3-methyl-4-oxo-1,3,8-triazaspiro[4.5]decane-8-carboxylate

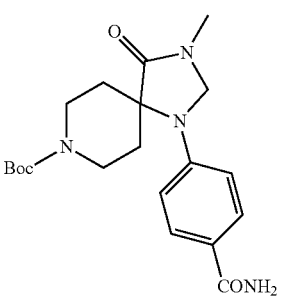 [SMILES: CN1CN(c2ccc(C(N)=O)cc2)C2(CCN(C(=O)OC(C)(C)C)CC2)C1=O]

To a solution of 4-(8-(tert-butoxycarbonyl)-3-methyl-4-oxo-1,3,8-triazaspiro[4.5]decan-1-yl) benzoic acid (910 mg 2.34 mmol) in dichloromethane (15 mL) was added sequentially ammonium chloride (751 mg, 14.03 mmol), 1-[bis(dimethylamino)methylene]-1H-1,2,3-triazolo[4,5-b]pyridinium-3-oxide hexafluorophosphate (HATU) (1.73 g, 3.51 mmol) and N,N-diisopropylethylamine (1.51 g, 11.69 mmol). The resulting mixture was stirred for 2 hours before the reaction was quenched with ice water (10 mL). The mixture was extracted with dichloromethane (3×15 mL). The combined organic layers were dried over anhydrous sodium sulfate and concentrated under reduced pressure. The residue was purified by silica gel column chromatography eluting with dichloromethane:methanol=20:1 to afford tert-butyl-1-(4-carbamoylphenyl)-3-methyl-4-oxo-1,3,8-triazaspiro[4.5]decane-8-carboxylate as a white solid (850 mg, 94%).

LCMS (ESI): m/z=389.2 [M+H]$^+$.

(E)-tert-Butyl-1-(4-(((dimethylamino)methylene)carbamoyl)phenyl)-3-methyl-4-oxo-1,3,8-triazaspiro[4.5]decane-8-carboxylate

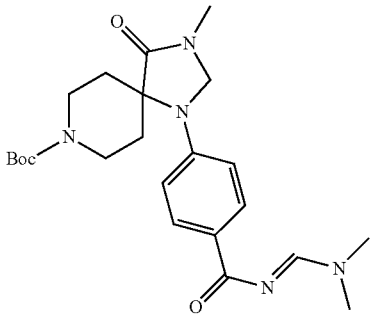 [SMILES: CN(C)/C=N/C(=O)c1ccc(N2CN(C)C(=O)C23CCN(C(=O)OC(C)(C)C)CC3)cc1]

A solution of tert-butyl-1-(4-carbamoylphenyl)-3-methyl-4-oxo-1,3,8-triazaspiro[4.5]decane-8-carboxylate (400 mg 1.03 mmol) in N,N-dimethylformamide/N,N-dimethylacetamide (1:1, 10 mL) was stirred at room temperature overnight. The solvent was removed under reduced pressure and the residue was purified by silica gel column chromatography eluting with ethyl acetate:petroleum ether=1:3 to afford (E)-tert-butyl-1-(4-(((dimethylamino)methylene)carbamoyl)phenyl)-3-methyl-4-oxo-1,3,8-triazaspiro[4.5]decane-8-carboxylate as a yellow solid (290 mg, 85%).

LCMS (ESI): m/z=444.3 [M+H]$^+$.

tert-Butyl-1-(4-(1H-1,2,4-triazol-3-yl)phenyl)-3-methyl-4-oxo-1,3,8-triazaspiro[4.5]decane-8-carboxylate

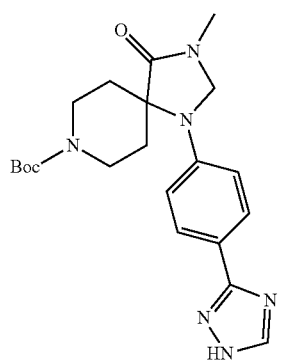 [SMILES: CN1CN(c2ccc(-c3nc[nH]n3)cc2)C2(CCN(C(=O)OC(C)(C)C)CC2)C1=O]

To a solution of (E)-tert-butyl-1-(4-(((dimethylamino)methylene)carbamoyl)phenyl)-3-methyl-4-oxo-1,3,8-triazaspiro[4.5]decane-8-carboxylate (290 mg, 0.65 mmol) in ethanol (20 mL) was added hydrazine hydrate (0.3 mL, 80% in water). The reaction was stirred at room temperature overnight. Then the solvent was removed under reduced pressure and the residue was purified by silica gel column chromatography eluting with dichloromethane:methanol=20:1 to afford tert-butyl-1-(4-(1H-1,2,4-triazol-3-yl)phenyl)-3-methyl-4-oxo-1,3,8-triazaspiro[4.5]decane-8-carboxylate as a thick oil (210 mg, 77%).

LCMS (ESI): m/z=413.4 [M+H]$^+$.

$^1$H-NMR (400 MHz, CD$_3$OD): δ=1.52 (s, 9H), 1.61-1.65 (m, 2H), 2.55-2.73 (m, 2H), 3.01 (m, 3H), 3.48-3.68 (m,

2H), 3.95-4.21 (m, 2H), 4.65-4.73 (m, 2H), 6.71-6.75 (m, 2H), 7.88-7.89 (m, 2H), 8.13 (s, 1H).

1-(4-(1H-1,2,4-Triazol-3-yl)phenyl)-3-methyl-1,3,8-triazaspiro[4.5]decan-4-one hydrochloride

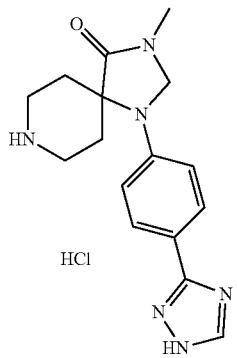 [SMILES: CN1CN(c2ccc(-c3nc[nH]n3)cc2)C2(CCNCC2)C1=O ; Cl]

A solution of tert-butyl-1-(4-(1H-1,2,4-triazol-3-yl)phenyl)-3-methyl-4-oxo-1,3,8-triazaspiro[4.5]decane-8-carboxylate (110 mg, 0.26 mmol) in hydrochloric acid in dioxane (6.0 M, 10 mL) was stirred for 30 minutes. The precipitate was collected by filtration and dried under reduced pressure to afford 1-(4-(1H-1,2,4-triazol-3-yl)phenyl)-3-methyl-1,3,8-triazaspiro[4.5]decan-4-one hydrochloride as a white solid (90 mg, 95%).

LCMS (ESI): m/z=313.4 [M+H]$^+$.

(R)—N-(1-(1-(4-(1H-1,2,4-Triazol-3-yl)phenyl)-3-methyl-4-oxo-1,3,8-triazaspiro[4.5]decan-8-yl)-3-methyl-1-oxobutan-2-yl)-2-fluoro-5-(trifluoromethyl)benzamide

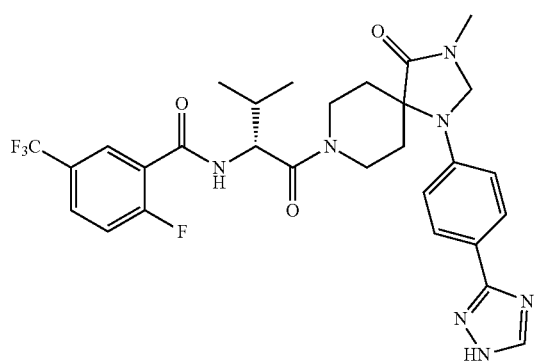 [SMILES: CC(C)[C@@H](NC(=O)c1cc(C(F)(F)F)ccc1F)C(=O)N1CCC2(CC1)C(=O)N(C)CN2c1ccc(-c2nc[nH]n2)cc1]

To a suspension of 1-(4-(1H-1,2,4-triazol-3-yl)phenyl)-3-methyl-1,3,8-triazaspiro[4.5]decan-4-one hydrochloride (90 mg, 0.26 mmol) in dichloromethane (5 mL) was added (R)-2-(2-fluoro-5-(trifluoromethyl)benzamido)-3-methylbutanoic acid (prepared as described in Example 28-f) (82 mg, 0.26 mmol), 1-[bis(dimethylamino)methylene]-1H-1,2,3-triazolo[4,5-b]pyridinium-3-oxide hexafluorophosphate (HATU) (153 mg, 0.40 mmol) and N,N-diisopropylethylamine (104 mg, 0.80 mmol). The resulting mixture was stirred for 2 hours at room temperature before the reaction was quenched with ice-water (10 mL). The mixture was extracted with ethyl acetate (3×10 mL) and the combined organic layers were dried over anhydrous sodium sulfate and concentrated under reduced pressure. The residue was purified by prep-TLC with dichloromethane:methanol=15:1 to afford (R)—N-(1-(1-(4-(1H-1,2,4-triazol-3-yl)phenyl)-3-methyl-4-oxo-1,3,8-triazaspiro[4.5]decan-8-yl)-3-methyl-1-oxobutan-2-yl)-2-fluoro-5-(trifluoromethyl)benzamide as a white solid (55 mg, 35%).

LCMS (ESI): m/z=602.2 [M+H]$^+$.

$^1$H-NMR (400 MHz, CD$_3$OD): δ=1.06-1.20 (m, 6H), 1.76-1.94 (m, 2H), 2.21-2.32 (m, 1H), 2.64-2.76 (m, 1H), 2.87-3.01 (m, 1H), 3.05 (s, 3H), 3.54-3.58 (m, 1H), 3.99-4.14 (m, 1H), 4.32-4.39 (m, 1H), 4.57-4.60 (m, 1H), 4.85-4.87 (m, 2H), 4.97-4.99 (m, 1H), 6.94-6.97 (m, 2H), 7.44-7.50 (m, 1H), 7.71-7.91 (m, 3H), 8.05-8.06 (m, 1H), 8.81-8.88 (m, 1H).

Example 221

(R)-Methyl-4-(8-(2-(2-fluoro-5-(trifluoromethyl)benzamido)-3-methylbutanoyl)-3-methyl-2,4-dioxo-1,3,8-triazaspiro[4.5]decan-1-yl)benzoate

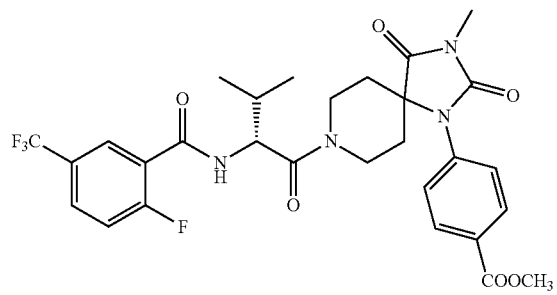 [SMILES: COC(=O)c1ccc(N2C(=O)N(C)C(=O)C23CCN(C(=O)[C@H](NC(=O)c2cc(C(F)(F)F)ccc2F)C(C)C)CC3)cc1]

Representative Scheme:

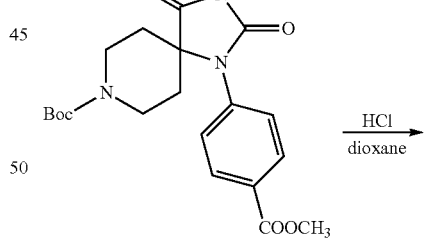

Example 223-c

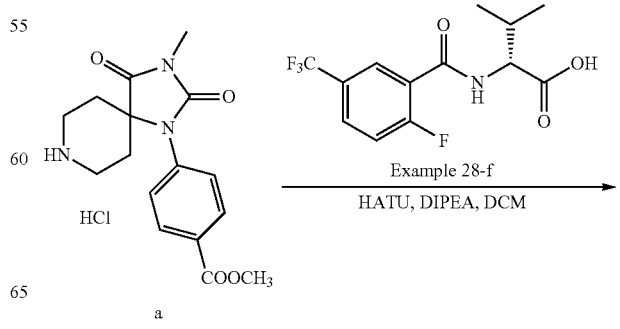

a

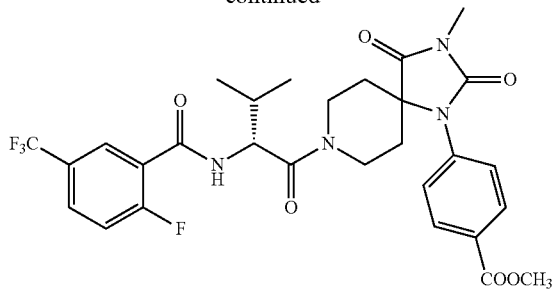

Representative General Procedure 4-(3-Methyl-2,4-dioxo-1,3,8-triazaspiro[4.5]decan-1-yl)benzoic acid hydrochloride

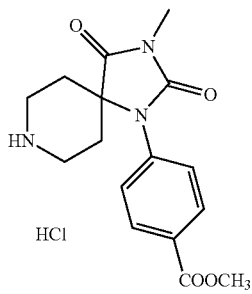 [SMILES: COC(=O)c1ccc(N2C(=O)N(C)C(=O)C23CCNCC3)cc1 ; Cl]

A solution of tert-butyl-1-(4-(methoxycarbonyl)phenyl)-3-methyl-2,4-dioxo-1,3,8-triazaspiro[4.5]decane-8-carboxylate (prepared as described in Example 223-c) (120 mg, 0.28 mmol) in hydrochloric acid in dioxane (6.0 M, 10 mL) was stirred for 30 minutes. The precipitate was collected by filtration and dried under reduced pressure to afford 4-(3-methyl-2,4-dioxo-1,3,8-triazaspiro[4.5]decan-1-yl)benzoic acid hydrochloride as a white solid (100 mg, 97%).

LCMS (ESI): m/z=317.1 [M+H]$^+$.

(R)-Methyl-4-(8-(2-(2-fluoro-5-(trifluoromethyl)benzamido)-3-methylbutanoyl)-3-methyl-2,4-dioxo-1,3,8-triazaspiro[4.5]decan-1-yl)benzoate

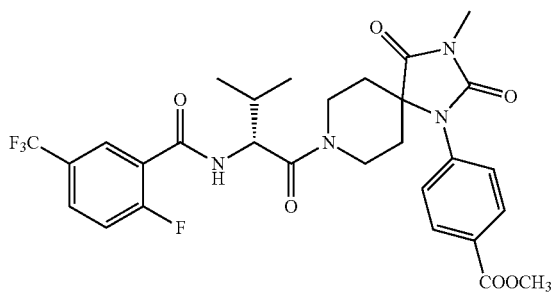 [SMILES: COC(=O)c1ccc(N2C(=O)N(C)C(=O)C23CCN(C(=O)[C@H](NC(=O)c2cc(C(F)(F)F)ccc2F)C(C)C)CC3)cc1]

To a solution of 4-(3-methyl-2,4-dioxo-1,3,8-triazaspiro[4.5]decan-1-yl)benzoic acid hydrochloride (2) (100 mg, 0.28 mmol) in dichloromethane (5 mL) was added (R)-2-(2-fluoro-5-(trifluoromethyl)benzamido)-3-methylbutanoic acid (prepared as described in Example 28-f) (89 mg, 0.28 mmol), 1-[bis(dimethylamino)methylene]-1H-1,2,3-triazolo[4,5-b]pyridinium-3-oxide hexafluorophosphate (HATU) (165 mg, 0.43 mmol) and N,N-diisopropylethylamine (114 mg, 0.86 mmol). The resulting mixture was stirred for 2 hours at room temperature before the reaction was quenched with ice-water (10 mL). The mixture was extracted with ethyl acetate (3×10 mL) and the combined organic layers were dried over anhydrous sodium sulfate and concentrated under reduced pressure. The residue was purified by prep-HPLC (Gradient: 95% water, 5% acetonitrile, 30-50 min gradient to 25% water, 85% acetonitrile) to afford (R)-methyl-4-(8-(2-(2-fluoro-5-(trifluoromethyl)benzamido)-3-methylbutanoyl)-3-methyl-2,4-dioxo-1,3,8-triazaspiro[4.5]decan-1-yl)benzoate as a white solid (46.1 mg, 27%).

LCMS (ESI): m/z=607.2 [M+H]$^+$.

$^1$H-NMR (400 MHz, CD$_3$OD): δ=0.81-1.00 (m, 6H), 1.71-1.86 (m, 1H), 1.96-2.22 (m, 4H), 3.11 (s, 3H), 3.49-3.53 (m, 1H), 3.91-3.93 (m, 3H), 3.95-3.97 (m, 1H), 4.15-4.26 (m, 1H), 4.43-4.55 (m, 1H), 4.85-4.87 (m, 1H), 7.33-7.42 (m, 3H), 7.77-7.94 (m, 2H), 8.02-8.07 (m, 2H), 8.13-8.30 (m, 1H).

The following compound was synthesized following the general procedure described above:

Example 222

(R)-4-(8-(2-(5-Cyclopropyl-2-fluorobenzamido)-3-methylbutanoyl)-3-methyl-2,4-dioxo-1,3,8-triazaspiro[4.5]decan-1-yl)benzoic Acid

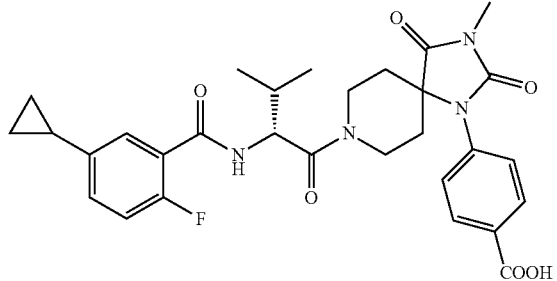 [SMILES: CC(C)[C@@H](NC(=O)c1cc(C2CC2)ccc1F)C(=O)N1CCC2(CC1)C(=O)N(C)C(=O)N2c1ccc(C(=O)O)cc1]

10.6 mg, 48% yield, white solid.

LCMS (ESI): m/z=564.7 [M+H]$^+$.

$^1$H-NMR (400 MHz, CD$_3$OD): δ=0.64-0.73 (m, 2H), 0.80-0.90 (m, 2H), 0.94-1.05 (m, 6H), 1.64-1.79 (m, 1H), 1.81-1.91 (m, 1H), 1.91-2.02 (m, 1H), 2.05-2.25 (m, 2H), 3.10 (d, 3H), 3.49-3.50 (m, 1H), 3.75 (m, 1H), 3.94-4.30 (m, 2H), 4.39-4.51 (m, 1H), 4.77-4.87 (m, 1H), 6.99-7.14 (m, 1H), 7.19-7.27 (m, 1H), 7.29-7.37 (m, 2H), 7.43 (dd, 1H), 8.08 (dd, 2H).

Example 223

(R)-4-(8-(2-(2-Fluoro-5-(trifluoromethyl)benzamido)-3-methylbutanoyl)-3-methyl-2,4-dioxo-1,3,8-triazaspiro[4.5]decan-1-yl)benzoic Acid

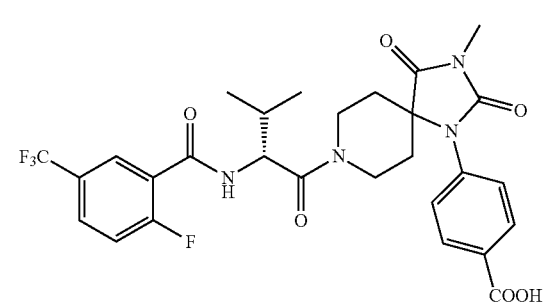 [SMILES: CC(C)[C@@H](NC(=O)c1cc(C(F)(F)F)ccc1F)C(=O)N1CCC2(CC1)C(=O)N(C)C(=O)N2c1ccc(C(=O)O)cc1]

Representative Scheme:
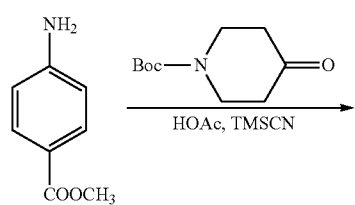
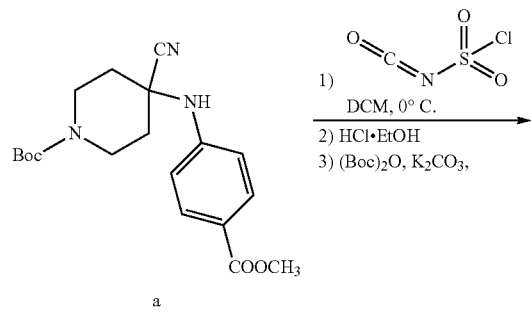
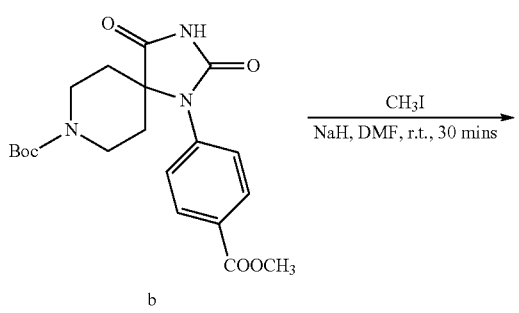
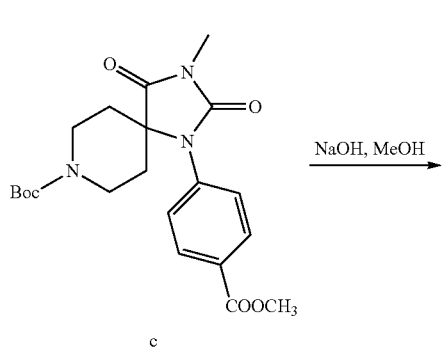
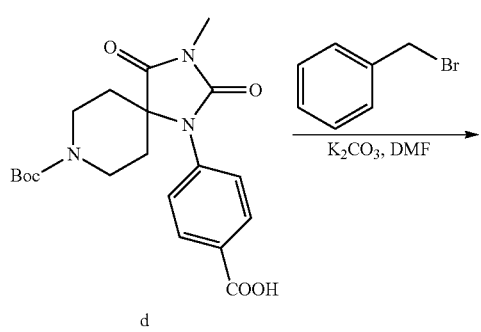
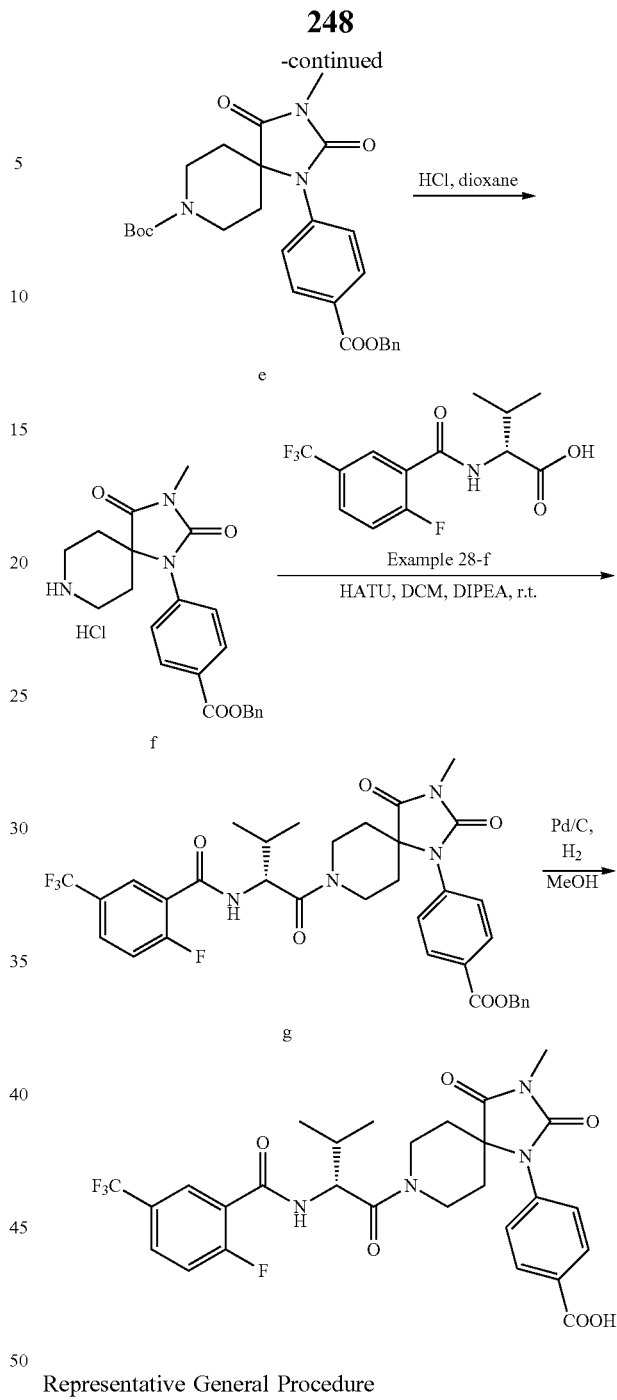
Representative General Procedure
tert-Butyl-4-cyano-4-(4-(methoxycarbonyl)phenylamino)piperidine-1-carboxylate
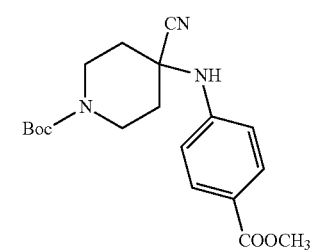 [SMILES: COC(=O)c1ccc(NC2(C#N)CCN(C(=O)OC(C)(C)C)CC2)cc1]
To a solution of methyl-4-aminobenzoate (16.46 g, 0.109 mol) in acetic acid (160 mL) was added tert-butyl-4-oxopiperidine-1-carboxylate (23.8 g, 0.12 mol). The resulting mixture was cooled to 0° C. and trimethylsilyl cyanide (12.95 g, 0.131 mol) was added. The resulting solution was stirred overnight at room temperature. Saturated aqueous ammonium chloride solution was added (200 mL). After stirring at room temperature for 10 minutes, the suspension was filtered. The filter cake was dried under reduced pressure to afford tert-butyl-4-cyano-4-(4-(methoxycarbonyl) phenylamino)piperidine-1-carboxylate as a white solid (39.1 g, 100%).

LCMS (ESI): m/z=360.2 [M+H]$^+$.

$^1$H-NMR (300 MHz, DMSO-d$_6$): δ=2.18-2.28 (m, 4H), 2.96-3.25 (m, 4H), 4.25-4.35 (m, 2H), 6.48-6.68 (m, 3H), 7.04-7.18 (m, 2H), 7.40-7.50 (m, 3H), 7.56-7.73 (m, 2H).

tert-Butyl-1-(4-(methoxycarbonyl)phenyl)-2,4-di-oxo-1,3,8-triazaspiro[4.5]decane-8-carboxylate

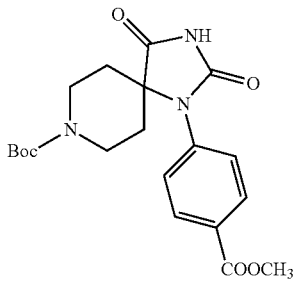 [SMILES: COC(=O)c1ccc(N2C(=O)NC(=O)C23CCN(C(=O)OC(C)(C)C)CC3)cc1]

To a solution of tert-butyl-4-cyano-4-(4-(methoxycarbonyl)phenylamino)piperidine-1-carboxylate (6.0 g 16.7 mmol) in dichloromethane (70 mL) was added chlorosulfonyl isocyanate (4.0 g 28.4 mmol) at 0° C. After stirring for 30 minutes at 0° C., the reaction was quenched with a 5% aqueous hydrochloric acid solution (20 mL). The solvent was removed under reduced pressure and ethanol (35 mL) was added. The suspension was stirred 30 minutes at 80° C. The solvent was removed under reduced pressure and the residue was added to tetrahydrofuran (50 mL) and the pH of the suspension was adjusted to pH 8 by addition of a 10% aqueous potassium carbonate solution. Then di-tert-butyl dicarbonate (6.20 g, 28.4 mmol) in tetrahydrofuran (50 mL) was added. After stirring overnight, the solvent was removed under reduced pressure and the residue was purified by silica gel column chromatography eluting with ethyl acetate:petroleum ether=10:1 to afford tert-butyl-1-(4-(methoxycarbonyl)phenyl)-2,4-dioxo-1,3,8-triazaspiro[4.5]decane-8-carboxylate as a white solid (4.0 g, 60%).

LCMS (ESI): m/z=404.4 [M+H]$^+$.

tert-Butyl-1-(4-(methoxycarbonyl)phenyl)-3-methyl-2,4-dioxo-1,3,8-triazaspiro[4.5]decane-8-carboxylate

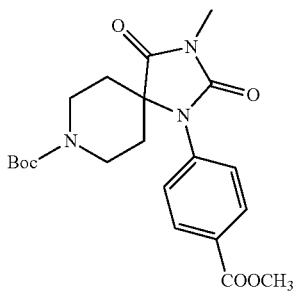 [SMILES: COC(=O)c1ccc(N2C(=O)N(C)C(=O)C23CCN(C(=O)OC(C)(C)C)CC3)cc1]

To a solution of tert-butyl-1-(4-(methoxycarbonyl)phenyl)-2,4-dioxo-1,3,8-triazaspiro[4.5]decane-8-carboxylate (3.45 g, 8.56 mmol) in N,N-dimethylformamide (40 mL) was added sodium hydride (685 mg, 60% in oil, 17.2 mmol) at 0° C., After stirring for 15 minutes, iodomethane (1.83 g, 12.84 mmol) was added. The resulting mixture was stirred for 15 minutes. The reaction was quenched with ice-water (20 mL) and the mixture was extracted with ethyl acetate (3×50 mL). The combined organic layers were dried over anhydrous sodium sulfate and concentrated under reduced pressure. The residue was purified by silica gel column chromatography eluting with ethyl acetate:petroleum ether=1:3 to afford tert-butyl-1-(4-(methoxycarbonyl)phenyl)-3-methyl-2,4-dioxo-1,3,8-triazaspiro[4.5]decane-8-carboxylate as a white solid (3.0 g, 84%). LCMS (ESI): m/z=418.2 [M+H]$^+$.

4-(8-(tert-Butoxycarbonyl)-3-methyl-2,4-dioxo-1,3,8-triazaspiro[4.5]decan-1-yl)benzoic Acid

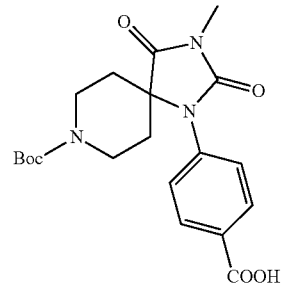

To a solution of tert-butyl-1-(4-(methoxycarbonyl)phenyl)-3-methyl-2,4-dioxo-1,3,8-triazaspiro[4.5]decane-8-carboxylate (1300 mg, 3.12 mmol) in methanol (30 mL) was added a 15% aqueous sodium hydroxide solution (15 mL). The reaction was heated at reflux for 30 minutes before cooling to room temperature. The pH of the resulting solution was adjusted to 3-4 by addition of 10% aqueous hydrochloric acid solution. The suspension was filtered. The filter cake was washed with petroleum ether and dried under reduced pressure to afford 4-(8-(tert-butoxycarbonyl)-3-methyl-2,4-dioxo-1,3,8-triazaspiro[4.5]decan-1-yl)benzoic acid as a white solid (1150 mg, 892%).

LCMS (ESI): m/z=404.4 [M+H]$^+$.

tert-Butyl-1-(4-((benzyloxy)carbonyl)phenyl)-3-methyl-2,4-dioxo-1,3,8-triazaspiro[4.5]decane-8-carboxylate

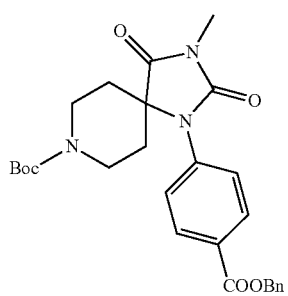

To a solution of 4-(8-(tert-butoxycarbonyl)-3-methyl-2,4-dioxo-1,3,8-triazaspiro[4.5]decan-1-yl)benzoic acid (400 mg, 0.99 mmol) in N,N-dimethylformamide (6 mL) was added potassium carbonate (274 mg, 1.99 mmol) and benzyl bromide (177 mg, 1.29 mmol). Before the reaction was quenched by addition of ice-water (10 mL), the resulting suspension was heated for 2 hours at 50° C. The mixture was extracted with ethyl acetate (3×30 mL) and then the combined organic layers were dried over anhydrous sodium sulfate and concentrated under reduced pressure. The residue was purified by silica gel column chromatography eluting with ethyl acetate:petroleum ether=1:2 to afford tert-butyl-1-(4-((benzyloxy)carbonyl)phenyl)-3-methyl-2,4-dioxo-1,3,8-triazaspiro[4.5]decane-8-carboxylate as a white solid (500 mg, 91%).

LCMS (ESI): m/z=493.4 [M+H]$^+$.

$^1$H-NMR (300 MHz, DMSO-d$_6$): δ=1.41 (s, 2H), 1.62-1.86 (m, 4H), 3.13 (s, 3H), 3.53-3.68 (m, 2H), 4.03-4.13 (m, 2H), 5.41 (s, 2H), 7.26-7.29 (m, 2H), 7.37-7.42 (m, 5H), 8.17-8.19 (m, 2H).

Benzyl-4-(3-methyl-2,4-dioxo-1,3,8-triazaspiro[4.5]decan-1-yl)benzoate hydrochloride

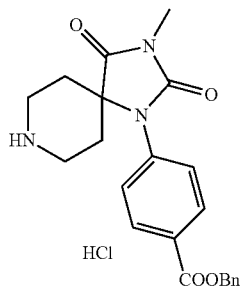

A solution of tert-butyl-1-(4-((benzyloxy)carbonyl)phenyl)-3-methyl-2,4-dioxo-1,3,8-triazaspiro[4.5]decane-8-carboxylate (120 mg, 0.24 mmol) in hydrochloric acid in dioxane (6.0 M, 10 mL) was stirred for 30 minutes. The precipitate was collected by filtration and dried under reduced pressure to afford benzyl 4-(3-methyl-2,4-dioxo-1,3,8-triazaspiro[4.5]decan-1-yl)benzoate hydrochloride as a white solid (110 mg, 98%).

LCMS (ESI): m/z=393.4 [M+H]$^+$.

(R)-Benzyl-4-(8-(2-(2-fluoro-5-(trifluoromethyl)benzamido)-3-methylbutanoyl)-3-methyl-2,4-dioxo-1,3,8-triazaspiro[4.5]decan-1-yl)benzoate

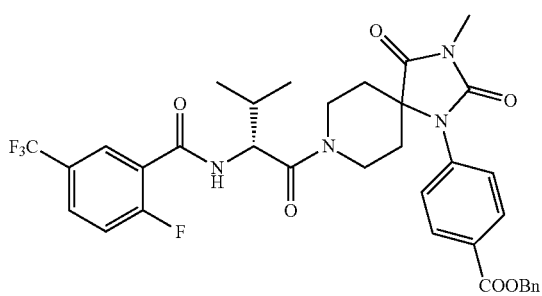

To a suspension of benzyl 4-(3-methyl-2,4-dioxo-1,3,8-triazaspiro[4.5]decan-1-yl)benzoate hydrochloride (90 mg, 0.26 mmol) in dichloromethane (5 mL) was added (R)-2-(2-fluoro-5-(trifluoromethyl)benzamido)-3-methylbutanoic acid (prepared as described in Example 28-f) (82 mg, 0.26 mmol), 1-[bis(dimethylamino)methylene]-1H-1,2,3-triazolo[4,5-b]pyridinium-3-oxide hexafluorophosphate (HATU) (153 mg, 0.40 mmol) and N,N-diisopropylethylamine (104 mg, 0.80 mmol). The resulting mixture was stirred for 2 hours at room temperature before the reaction was quenched with ice-water (10 mL). The mixture was extracted with ethyl acetate (3×10 mL) and the combined organic layers were dried over anhydrous sodium sulfate and concentrated under reduced pressure. The residue was purified by prep-TLC with ethyl acetate:petroleum ether=2:1 to afford (R)-benzyl-4-(8-(2-(2-fluoro-5-(trifluoromethyl)benzamido)-3-methylbutanoyl)-3-methyl-2,4-dioxo-1,3,8-triazaspiro[4.5]decan-1-yl)benzoate as a white solid (150 mg, 91%).

LCMS (ESI): m/z=393.4 [M+H]$^+$.

(R)-4-(8-(2-(2-Fluoro-5-(trifluoromethyl)benzamido)-3-methylbutanoyl)-3-methyl-2,4-dioxo-1,3,8-triazaspiro[4.5]decan-1-yl)benzoic Acid

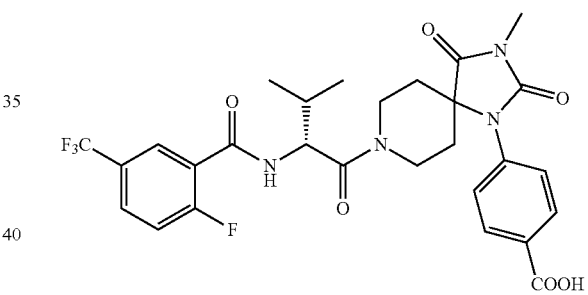

A suspension of (R)-benzyl-4-(8-(2-(2-fluoro-5-(trifluoromethyl)benzamido)-3-methylbutanoyl)-3-methyl-2,4-dioxo-1,3,8-triazaspiro[4.5]decan-1-yl)benzoate (150 mg, 0.22 mmol) and 5% palladium on carbon (10 mg) in methanol (40 mL) was stirred for 30 minutes under a hydrogen atmosphere. The mixture was filtered and the filter cake was washed with methanol (5×10 mL). The filtrate was concentrated under reduced pressure and the residue was purified by prep-HPLC (Gradient: 95% water, 5% acetonitrile, 30-50 min gradient to 25% water, 85% acetonitrile) to afford (R)-4-(8-(2-(2-fluoro-5-(trifluoromethyl)benzamido)-3-methylbutanoyl)-3-methyl-2,4-dioxo-1,3,8-triazaspiro[4.5]decan-1-yl)benzoic acid as a white solid (55.5 mg, 61%).

LCMS (ESI): m/z=593.1 [M+H]$^+$.

$^1$H-NMR (400 MHz, CD$_3$OD): δ=0.80-1.01 (m, 6H), 1.70-1.86 (m, 1H), 1.88-2.24 (m, 4H), 3.10 (s, 3H), 3.47-3.54 (m, 1H), 3.93-3.99 (m, 1H), 4.20-4.31 (m, 1H), 4.43-4.59 (m, 1H), 4.83-4.87 (m, 1H), 7.34-7.46 (m, 3H), 7.85-7.88 (m, 2H), 8.00-8.16 (m, 2H).

Example 224
(R)—N-(1-(1-(4-(2H-Tetrazol-5-yl)phenyl)-3-methyl-2,4-dioxo-1,3,8-triazaspiro[4.5]decan-8-yl)-3-methyl-1-oxobutan-2-yl)-2-fluoro-5-(trifluoromethyl)benzamide
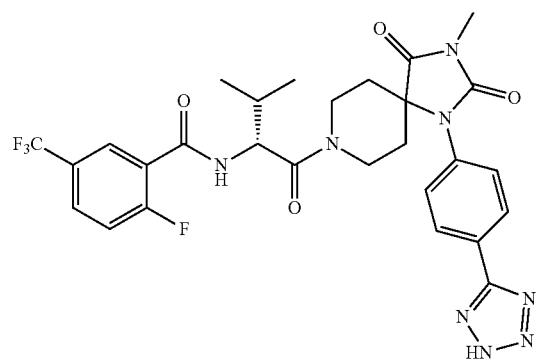 [SMILES: CC(C)[C@@H](NC(=O)c1cc(C(F)(F)F)ccc1F)C(=O)N1CCC2(CC1)C(=O)N(C)C(=O)N2c1ccc(-c2nn[nH]n2)cc1]
Representative Scheme:
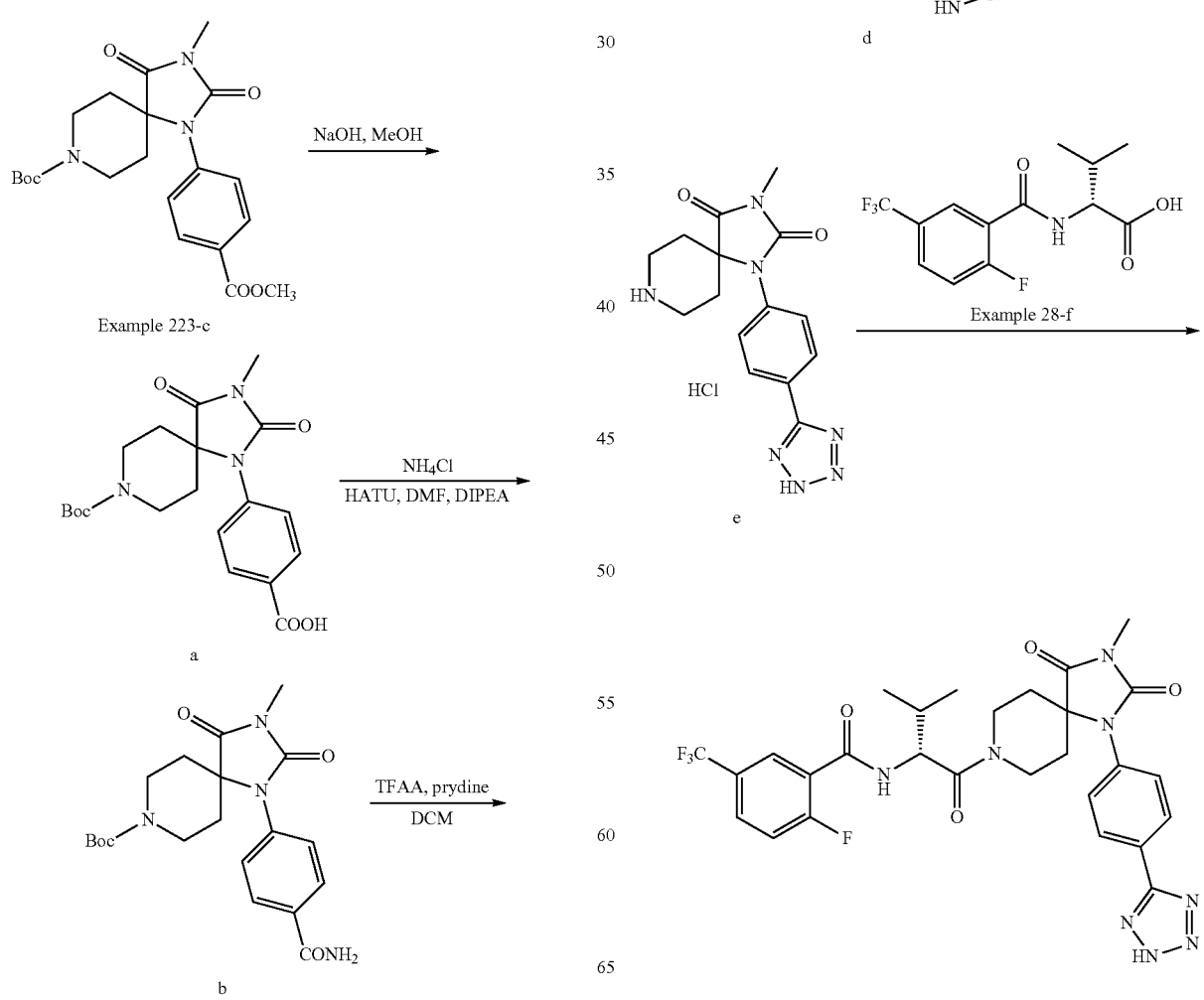

Representative General Procedure

4-(8-(tert-Butoxycarbonyl)-3-methyl-2,4-dioxo-1,3,8-triazaspiro[4.5]decan-1-yl)benzoic Acid

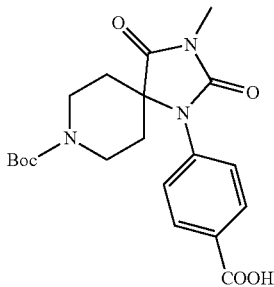 [SMILES: CN1C(=O)N(c2ccc(C(=O)O)cc2)C2(CCN(C(=O)OC(C)(C)C)CC2)C1=O]

To a solution of tert-butyl-1-(4-(methoxycarbonyl)phenyl)-3-methyl-2,4-dioxo-1,3,8-triazaspiro[4.5]decane-8-carboxylate (prepared as described in Example 223-c) (1300 mg, 3.12 mmol) in methanol (25 mL) was added a 15% aqueous sodium hydroxide solution (7 mL). The reaction was heated at reflux for 30 minutes before cooling to room temperature. The pH of the resulting solution was adjusted to 3-4 by addition of 10% aqueous hydrochloric acid solution. The suspension was filtered. The filter cake was washed with water (10 mL) and dried under reduced pressure to afford 4-(8-(tert-butoxycarbonyl)-3-methyl-2,4-dioxo-1,3,8-triazaspiro[4.5]decan-1-yl) benzoic acid as a white solid (1150 mg, 92%).

LCMS (ESI): m/z=404.4 [M+H]$^+$.

tert-Butyl-1-(4-carbamoylphenyl)-3-methyl-2,4-dioxo-1,3,8-triazaspiro[4.5]decane-8-carboxylate

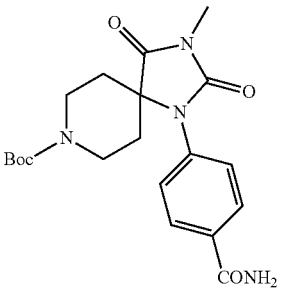 [SMILES: CN1C(=O)N(c2ccc(C(N)=O)cc2)C2(CCN(C(=O)OC(C)(C)C)CC2)C1=O]

To a solution of 4-(8-(tert-butoxycarbonyl)-3-methyl-2,4-dioxo-1,3,8-triazaspiro[4.5]decan-1-yl)benzoic acid (1000 mg 2.48 mmol) in N,N-dimethylformamide (15 mL) was added ammonium chloride (1350 mg, 25.31 mmol), 1-[bis(dimethylamino)methylene]-1H-1,2,3-triazolo[4,5-b]pyridinium-3-oxide hexafluorophosphate (HATU) (2400 mg, 6.33 mmol) and N,N-diisopropylethylamine (2180 mg, 16.87 mmol). The resulting mixture was stirred at room temperature for 24 hours before the reaction was quenched with ice water (15 mL). The organic layer were extracted with ethyl acetate (3×20 mL). The combined organic layers were dried over anhydrous sodium sulfate and concentrated under reduced pressure. The residue was purified by silica gel column chromatography eluting with dichloromethane:methanol=20:1 to afford tert-butyl-1-(4-carbamoylphenyl)-3-methyl-2,4-dioxo-1,3,8-triazaspiro[4.5]decane-8-carboxylate as a white solid (850 mg, 85%).

LCMS (ESI): m/z=403.4 [M+H]$^+$.

tert-Butyl-1-(4-cyanophenyl)-3-methyl-2,4-dioxo-1,3,8-triazaspiro[4.5]decane-8-carboxylate

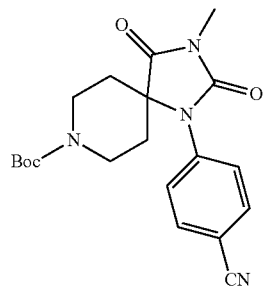 [SMILES: CN1C(=O)N(c2ccc(C#N)cc2)C2(CCN(C(=O)OC(C)(C)C)CC2)C1=O]

To a solution of tert-butyl-1-(4-carbamoylphenyl)-3-methyl-2,4-dioxo-1,3,8-triazaspiro[4.5]decane-8-carboxylate (850 mg 2.11 mmol) in dichloromethane (20 mL) was added pyridine (1500 mg 18.98 mmol) and trifluoroacetic anhydride (2120 mg 10.09 mmol). The resulting mixture was stirred at room temperature for 3 hours before the reaction was quenched with saturated aqueous sodium carbonate solution (20 mL). The mixture was extracted with dichloromethane (3×15 mL). The combined organic layers were dried over anhydrous sodium sulfate and concentrated under reduced pressure. The residue was purified by silica gel column chromatography eluting with ethyl acetate:petroleum ether=1:1 to afford tert-butyl-1-(4-cyanophenyl)-3-methyl-2,4-dioxo-1,3,8-triazaspiro[4.5]decane-8-carboxylate as a brown solid (600 mg, 74%).

LCMS (ESI): m/z=385.4 [M+H]$^+$.

tert-Butyl-1-(4-(2H-tetrazol-5-yl)phenyl)-3-methyl-2,4-dioxo-1,3,8-triazaspiro[4.5]decane-8-carboxylate

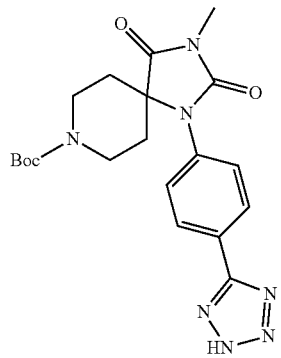 [SMILES: CN1C(=O)N(c2ccc(-c3nn[nH]n3)cc2)C2(CCN(C(=O)OC(C)(C)C)CC2)C1=O]

To a solution of tert-butyl-1-(4-cyanophenyl)-3-methyl-2,4-dioxo-1,3,8-triazaspiro[4.5]decane-8-carboxylate (50 mg 0.13 mmol) in N,N-dimethylformamide (3 mL), was added sodium azide (51 mg 0.078 mmol), ammonium chloride (42 mg 0.78 mmol), copper iodide (10 mg, cat.), and the mixture was heated at reflux for 2 days. After the reaction was quenched with ice water (10 mL), the mixture was extracted with ethyl acetate (3×15 mL). The combined organic layers were dried over anhydrous sodium sulfate and concentrated under reduced pressure. The residue was purified by silica gel column chromatography eluting with dichloromethane:methanol=15:1 to afford tert-butyl-1-(4-(2H-tetrazol-5-yl)phenyl)-3-methyl-2,4-dioxo-1,3,8-triazaspiro[4.5]decane-8-carboxylate as a thick oil (30 mg, 54%).

LCMS (ESI): m/z=428.3 [M+H]$^+$.

$^1$H-NMR (400 MHz, CD$_3$OD): δ=1.38 (s, 9H), 1.76-1.78 (m, 2H), 1.79-1.81 (m, 2H), 2.88 (s, 3H), 3.32-3.54 (m, 2H), 3.98-4.01 (m, 2H), 7.36-7.38 (m, 2H), 8.17-8.19 (m, 2H).

1-(4-(2H-Tetrazol-5-yl)phenyl)-3-methyl-1,3,8-triazaspiro[4.5]decane-2,4-dione hydrochloride

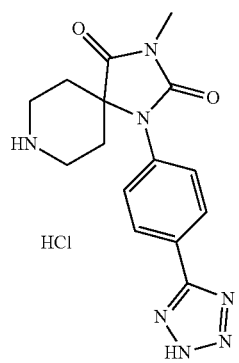 [SMILES: CN1C(=O)N(c2ccc(-c3nn[nH]n3)cc2)C2(CCNCC2)C1=O ; Cl]

A solution of tert-butyl-1-(4-(2H-tetrazol-5-yl)phenyl)-3-methyl-2,4-dioxo-1,3,8-triazaspiro[4.5]decane-8-carboxylate (30 mg, 0.07 mmol) in hydrochloric acid in dioxane (6.0 M, 10 mL) was stirred for 30 minutes. The mixture was concentrated under reduced pressure to afford 1-(4-(2H-tetrazol-5-yl)phenyl)-3-methyl-1,3,8-triazaspiro[4.5]decane-2,4-dione hydrochloride as a white solid (30 mg, crude), which was used directly without any further purification.

LCMS (ESI): m/z=328.3 [M+H]$^+$.

(R)—N-(1-(1-(4-(2H-Tetrazol-5-yl)phenyl)-3-methyl-2,4-dioxo-1,3,8-triazaspiro[4.5]decan-8-yl)-3-methyl-1-oxobutan-2-yl)-2-fluoro-5-(trifluoromethyl)benzamide

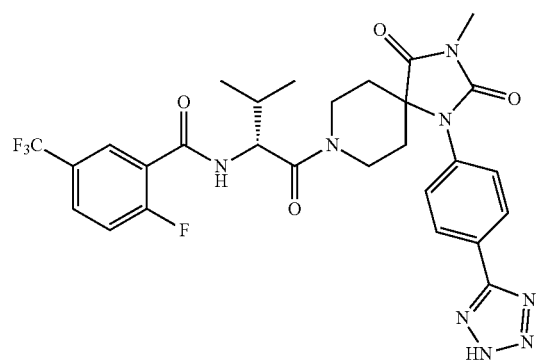 [SMILES: CC(C)[C@@H](NC(=O)c1cc(C(F)(F)F)ccc1F)C(=O)N1CCC2(CC1)C(=O)N(C)C(=O)N2c1ccc(-c2nn[nH]n2)cc1]

To a suspension of 1-(4-(2H-tetrazol-5-yl)phenyl)-3-methyl-1,3,8-triazaspiro[4.5]decane-2,4-dione hydrochloride (30 mg, crude) in dichloromethane (5 mL) was added (R)-2-(2-fluoro-5-(trifluoromethyl)benzamido)-3-methylbutanoic acid (prepared as described in Example 28-f) (22 mg, 0.07 mmol), 1-[bis(dimethylamino)methylene]-1H-1,2,3-triazolo[4,5-b]pyridinium-3-oxide hexafluorophosphate (HATU) (40 mg, 0.11 mmol) and N,N-diisopropylethylamine (28 mg, 0.21 mmol). The resulting mixture was stirred for 2 hours at room temperature before the reaction was quenched with ice-water (10 mL). The mixture was extracted with ethyl acetate (3×10 mL) and the combined organic layers were dried over anhydrous sodium sulfate and concentrated under reduced pressure. The residue was purified by prep-TLC with dichloromethane:methanol=10:1 to afford (R)—N-(1-(1-(4-(2H-tetrazol-5-yl)phenyl)-3-methyl-2,4-dioxo-1,3,8-triazaspiro[4.5]decan-8-yl)-3-methyl-1-oxobutan-2-yl)-2-fluoro-5-(trifluoromethyl)benzamide as a white solid (2.7 mg, 9%).

LCMS (ESI): m/z=617.2 [M+H]$^+$.

$^1$H-NMR (400 MHz, CD$_3$OD): δ=0.78-0.92 (m, 2H), 0.97-1.02 (m, 4H), 1.37-1.41 (m, 1H), 1.75-1.83 (m, 1H), 1.98-2.24 (m, 3H), 3.12 (s, 3H), 3.48-3.55 (m, 2H), 3.94-4.01 (m, 1H), 4.21-4.57 (m, 1H), 4.80-4.84 (m, 1H), 7.22-7.58 (m, 3H), 7.71-8.01 (m, 2H), 8.05-8.20 (m, 2H).

The following 2 compounds were synthesized following the general procedure described above:

Example 225

(R)—N-(1-(1-(4-(2H-Tetrazol-5-yl)phenyl)-3-methyl-2,4-dioxo-1,3,8-triazaspiro[4.5] decan-8-yl)-3-methyl-1-oxobutan-2-yl)-2-fluoro-5-(trifluoromethoxy)benzamide

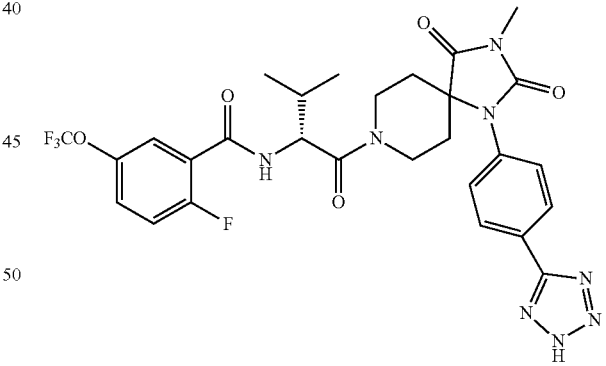

23.6 mg, 19% yield, white solid.

LCMS (ESI): m/z=633.2 [M+H]$^+$.

$^1$H-NMR (400 MHz, CD$_3$OD): δ=0.79-1.00 (m, 6H), 1.75-2.25 (m, 5H), 3.11 (s, 3H), 3.45-3.54 (m, 1H), 3.92-4.03 (m, 1H), 4.21-4.31 (m, 1H), 4.44-4.60 (m, 1H), 4.81-4.87 (m, 1H), 7.14-7.60 (m, 5H), 8.06-8.20 (m, 2H).

Example 226

(R)—N-(1-(1-(4-(2H-Tetrazol-5-yl)phenyl)-3-methyl-2,4-dioxo-1,3,8-triazaspiro[4.5]decan-8-yl)-3-methyl-1-oxobutan-2-yl)-5-(difluoromethoxy)-2-fluorobenzamide

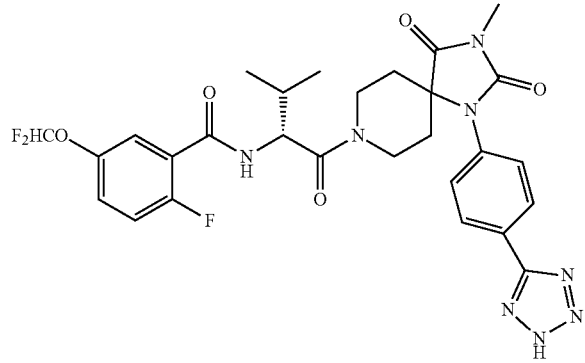 [SMILES: CC(C)[C@@H](NC(=O)c1cc(OC(F)F)ccc1F)C(=O)N1CCC2(CC1)C(=O)N(C)C(=O)N2c1ccc(-c2nn[nH]n2)cc1]

22.4 mg, 20% yield, white solid.

LCMS (ESI): m/z=615.2 [M+H]$^+$.

$^1$H-NMR (400 MHz, CD$_3$OD): δ=0.79-1.01 (m, 6H), 1.71-2.17 (m, 5H), 3.11 (s, 3H), 3.47-3.54 (m, 1H), 3.93-4.00 (m, 1H), 4.20-4.55 (m, 2H), 4.81-4.86 (m, 1H), 6.56-6.93 (m, 1H), 7.03-7.57 (m, 5H), 8.06-8.18 (m, 2H).

Example 227

(R)—N-(1-(1-(4-(2H-Tetrazol-5-yl)phenyl)-3-methyl-4-oxo-1,3,8-triazaspiro[4.5]decan-8-yl)-3-methyl-1-oxobutan-2-yl)-2-fluoro-5-(trifluoromethyl)benzamide

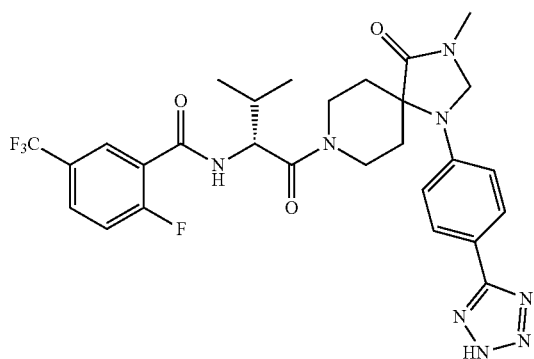

Representative Scheme:

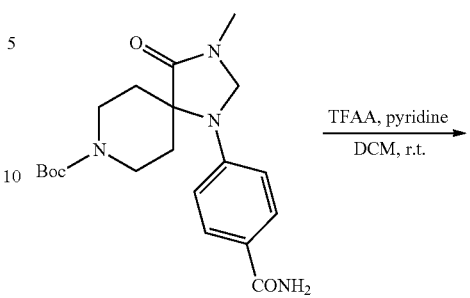

Example 145 or 220

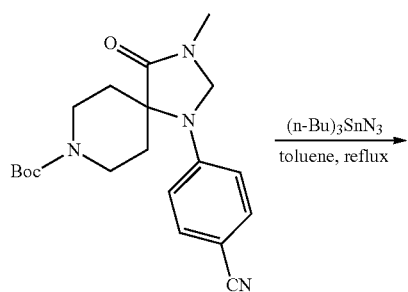

a

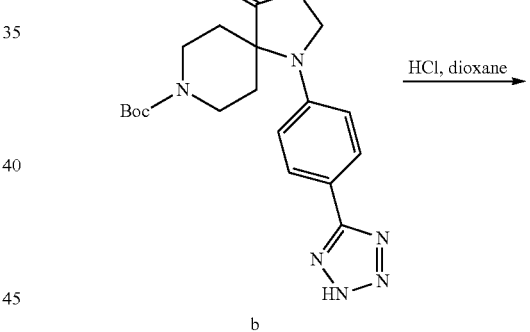

b

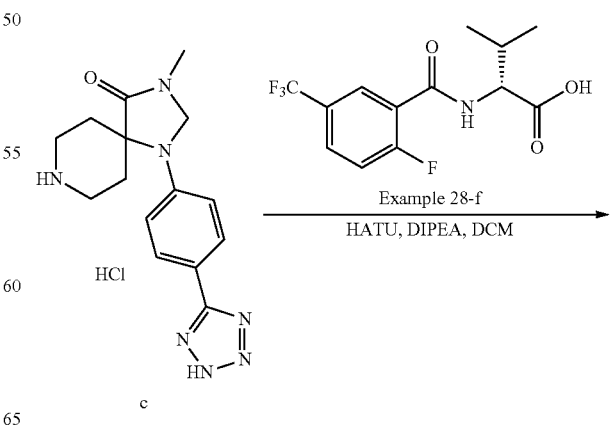

c

-continued

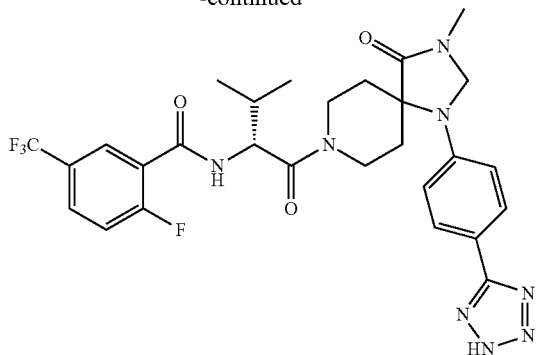

Representative General Procedure tert-Butyl-1-(4-cyanophenyl)-3-methyl-4-oxo-1,3,8-triazaspiro[4.5]decane-8-carboxylate

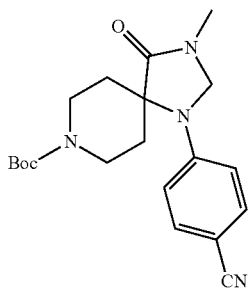 [SMILES: CN1CN(c2ccc(C#N)cc2)C2(CCN(C(=O)OC(C)(C)C)CC2)C1=O]

To a solution of tert-butyl-1-(4-carbamoylphenyl)-3-methyl-4-oxo-1,3,8-triazaspiro[4.5]decane-8-carboxylate (prepared as described in Example 145, or alternatively, as described in Example 220) (320 mg 0.83 mmol) in dichloromethane (50 mL), was added pyridine (652 mg 8.25 mmol), then trifluoroacetic anhydride (866 mg 4.12 mmol). The resulting mixture was stirred at room temperature for 3 hours before the reaction was quenched with a saturated aqueous sodium carbonate solution (15 mL). The mixture was extracted with dichloromethane (3×15 mL). The combined organic layers were dried over anhydrous sodium sulfate and concentrated under reduced pressure. The residue was purified by silica gel column chromatography eluting with ethyl acetate:petroleum ether=1:1 to afford tert-butyl-1-(4-cyanophenyl)-3-methyl-4-oxo-1,3,8-triazaspiro[4.5]decane-8-carboxylate as a thick oil (207 mg, 68%).

LCMS (ESI): m/z=371.4 [M+H]$^+$.

tert-Butyl-1-(4-(2H-tetrazol-5-yl)phenyl)-3-methyl-4-oxo-1,3,8-triazaspiro[4.5]decane-8-carboxylate

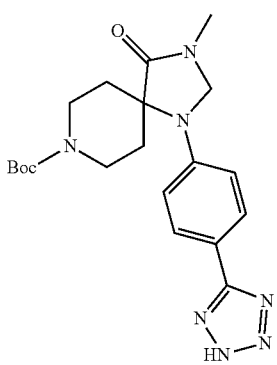 [SMILES: CN1CN(c2ccc(-c3nn[nH]n3)cc2)C2(CCN(C(=O)OC(C)(C)C)CC2)C1=O]

To a solution of tert-butyl-1-(4-cyanophenyl)-3-methyl-4-oxo-1,3,8-triazaspiro[4.5]decane-8-carboxylate (90 mg 0.24 mmol) in toluene (10 mL) was added tributyltin azide (243 mg, 0.73 mmol). The mixture was heated at reflux for 24 hours before the reaction was quenched with ice water (10 mL). The pH of the resulting solution was adjusted to 5-6 by addition of 10% aqueous hydrochloric acid solution. The mixture was extracted with ethyl acetate (3×15 mL). The combined organic layers were dried over anhydrous sodium sulfate and concentrated under reduced pressure. The residue was purified by silica gel column chromatography eluting with dichloromethane:methanol=10:1 to afford tert-butyl-1-(4-(2H-tetrazol-5-yl)phenyl)-3-methyl-4-oxo-1,3,8-triazaspiro[4.5]decane-8-carboxylate (70 mg, 70%).

LCMS (ESI): m/z=414.3 [M+H]$^+$.

$^1$H-NMR (400 MHz, CD$_3$OD): δ=1.54 (s, 9H), 1.65-1.68 (m, 2H), 2.61-2.74 (m, 2H), 3.04 (s, 3H), 3.53-3.73 (m, 2H), 4.04-4.20 (m, 2H), 4.69-4.75 (m, 2H), 6.73-6.76 (m, 2H), 7.95-7.98 (m, 2H).

1-(4-(2H-Tetrazol-5-yl)phenyl)-3-methyl-1,3,8-triazaspiro[4.5]decan-4-one hydrochloride

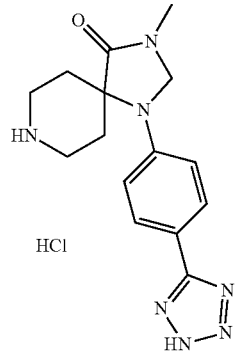 [SMILES: CN1CN(c2ccc(-c3nn[nH]n3)cc2)C2(CCNCC2)C1=O ; Cl]

A solution of tert-butyl-1-(4-(2H-tetrazol-5-yl)phenyl)-3-methyl-4-oxo-1,3,8-triazaspiro[4.5]decane-8-carboxylate (70 mg, 0.17 mmol) in hydrochloric acid in dioxane (6.0 M, 10 mL) was stirred for 30 minutes. The precipitate was collected by filtration and dried under reduced pressure to afford 1-(4-(2H-tetrazol-5-yl)phenyl)-3-methyl-1,3,8-triazaspiro[4.5]decan-4-one hydrochloride as a white solid (58 mg, 98%).

LCMS (ESI): m/z=314.3 [M+H]$^+$.

(R)—N-(1-(1-(4-(2H-Tetrazol-5-yl)phenyl)-3-methyl-4-oxo-1,3,8-triazaspiro[4.5]decan-8-yl)-3-methyl-1-oxobutan-2-yl)-2-fluoro-5-(trifluoromethyl)benzamide

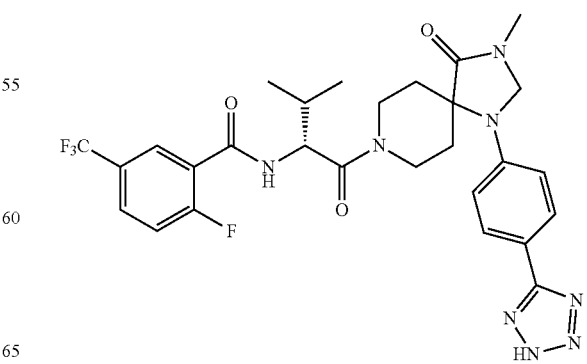

To a suspension of 1-(4-(2H-tetrazol-5-yl)phenyl)-3-methyl-1,3,8-triazaspiro[4.5]decan-4-one hydrochloride (58 mg, 0.16 mmol) in dichloromethane (5 mL) was added (R)-2-(2-fluoro-5-(trifluoromethyl)benzamido)-3-methylbutanoic acid (prepared as described in Example 28-f) (63 mg, 0.20 mmol), 1-[bis(dimethylamino)methylene]-1H-1,2,3-triazolo[4,5-b]pyridinium-3-oxide-hexafluorophosphate (HATU) (97 mg, 0.25 mmol) and N,N-diisopropylethylamine (67 mg, 0.51 mmol). The resulting mixture was stirred for 2 hours at room temperature before the reaction was quenched with ice-water (10 mL). The mixture was extracted with ethyl acetate (3×10 mL) and the combined organic layers were dried over anhydrous sodium sulfate and concentrated under reduced pressure. The residue was purified by prep-TLC with dichloromethane:methanol=10:1 to afford (R)—N-(1-(1-(4-(2H-tetrazol-5-yl)phenyl)-3-methyl-4-oxo-1,3,8-triazaspiro[4.5]decan-8-yl)-3-methyl-1-oxobutan-2-yl)-2-fluoro-5-(trifluoromethyl)benzamide as a white solid (10.5 mg, 11%).

LCMS (ESI): m/z=603.2 [M+H]$^+$.

$^1$H-NMR (400 MHz, CD$_3$OD): δ=1.06-1.33 (m, 6H), 1.73-1.96 (m, 2H), 2.17-2.37 (m, 1H), 2.70-2.81 (m, 1H), 2.90-2.99 (m, 1H), 3.09-3.15 (m, 1H), 3.06 (s, 3H), 3.46-3.65 (m, 1H), 4.02-4.07 (m, 1H), 4.29-4.39 (m, 1H), 4.52-4.64 (m, 1H), 4.99-5.01 (m, 2H), 6.91-6.93 (m, 2H), 7.45-7.50 (m, 1H), 7.68-7.78 (m, 2H), 7.90-8.07 (m, 2H).

Example 228

(R)—N-(1-(1-(1H-Indazol-5-yl)-3-methyl-2,4-dioxo-1,3,8-triazaspiro[4.5]decan-8-yl)-3-methyl-1-oxobutan-2-yl)picolinamide Representative Scheme:

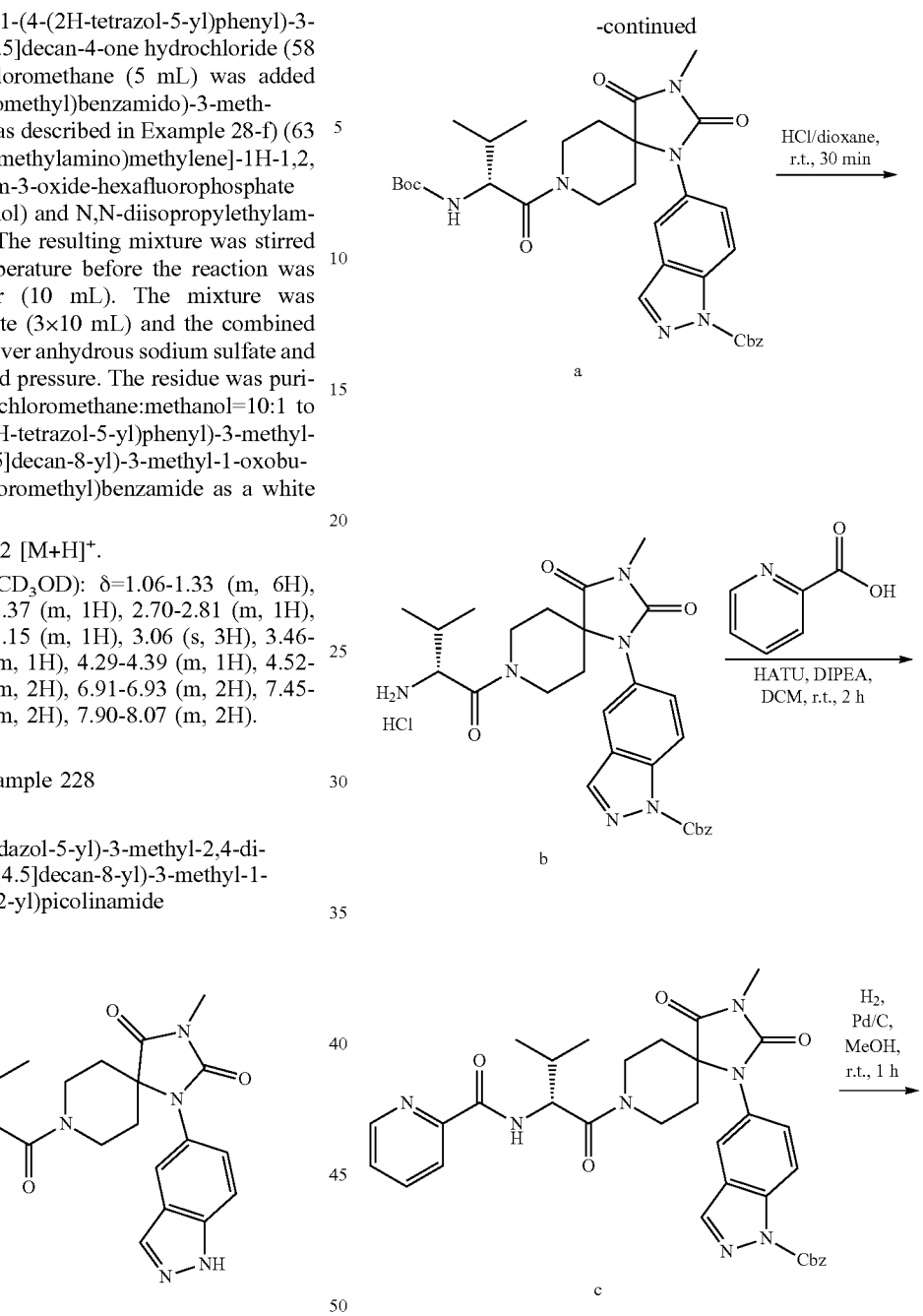

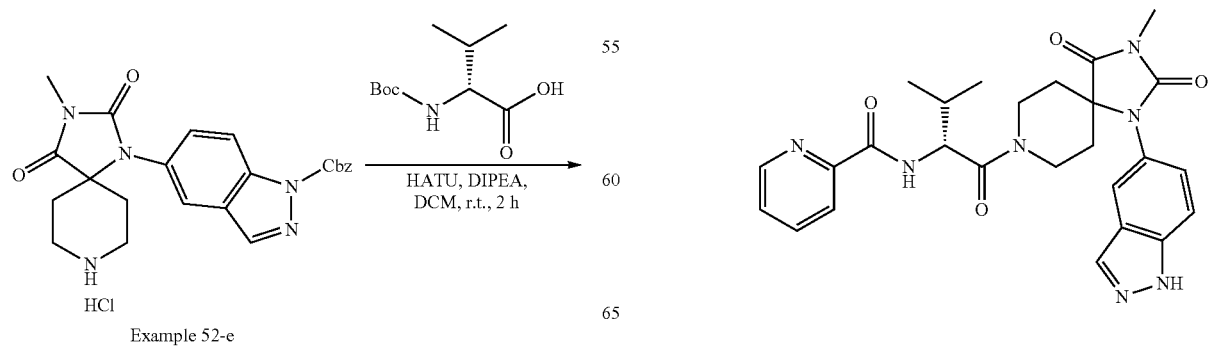

Representative General Procedure (R)-Benzyl-5-(8-(2-(tert-butoxycarbonylamino)-3-methylbutanoyl)-3-methyl-2,4-dioxo-1,3,8-triazaspiro[4.5]decan-1-yl)-1H-indazole-1-carboxylate

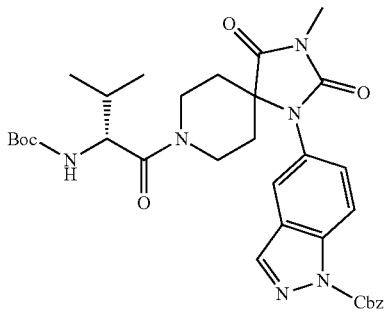 [SMILES: CC(C)[C@@H](NC(=O)OC(C)(C)C)C(=O)N1CCC2(CC1)C(=O)N(C)C(=O)N2c1ccc2c(cnn2C(=O)OCc2ccccc2)c1]

To a suspension of benzyl-5-(3-methyl-2,4-dioxo-1,3,8-triazaspiro[4.5]decan-1-yl)-1H-indazole-1-carboxylate hydrochloride (prepared as described in Example 52-e) (2.80 g, crude) in dichloromethane (100 mL) was added sequentially (R)-2-(tert-butoxycarbonylamino)-3-methylbutanoic acid (1.54 g, 7.10 mmol), 1-[bis(dimethylamino)methylene]-1H-1,2,3-triazolo[4,5-b]pyridinium-3-oxide hexafluorophosphate (HATU) (3.68 g, 9.70 mmol) and N,N-diisopropylethylamine (2.09 g, 16.16 mmol). The resulting mixture was stirred for 2 hours at room temperature before the reaction was quenched with ice-water. The mixture was extracted with dichloromethane (3×50 mL) and the combined organic layers were dried over anhydrous sodium sulfate and concentrated under reduced pressure. The residue was purified by silica gel column chromatography eluting with ethyl acetate:petroleum ether=1:1 to afford (R)-benzyl-5-(8-(2-(tert-butoxycarbonylamino)-3-methylbutanoyl)-3-methyl-2,4-dioxo-1,3,8-triazaspiro[4.5]decan-1-yl)-1H-indazole-1-carboxylate as a white solid (2.20 g, 54%).

LCMS (ESI): m/z=655.2 [M+Na]$^+$.

$^1$H-NMR (300 MHz, CDCl$_3$): δ=0.59-1.35 (m, 15H), 1.67-2.13 (m, 5H), 3.08 (s, 3H), 3.34-3.46 (m, 1H), 3.80-3.88 (m, 1H), 4.09-4.14 (m, 2H), 4.69-4.51 (m, 1H), 5.55 (s, 2H), 6.43-6.62 (m, 1H), 7.38-7.42 (m, 4H), 7.54-7.59 (m, 2H), 7.69-7.79 (m, 1H), 8.18-8.31 (m, 2H).

(R)-Benzyl-5-(8-(2-amino-3-methylbutanoyl)-3-methyl-2,4-dioxo-1,3,8-triazaspiro[4.5]decan-1-yl)-1H-indazole-1-carboxylate hydrochloride

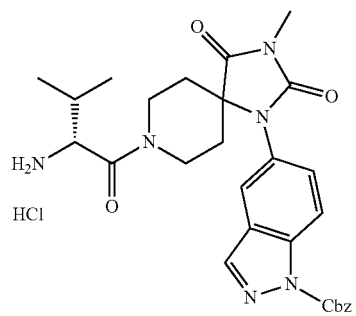 [SMILES: Cl ; CC(C)[C@@H](N)C(=O)N1CCC2(CC1)C(=O)N(C)C(=O)N2c1ccc2c(cnn2C(=O)OCc2ccccc2)c1]

A solution of (R)-benzyl-5-(8-(2-(tert-butoxycarbonylamino)-3-methylbutanoyl)-3-methyl-2,4-dioxo-1,3,8-triazaspiro[4.5]decan-1-yl)-1H-indazole-1-carboxylate (2.20 mg, 3.48 mmol) in hydrochloric acid in dioxane (6.0 M, 10 mL) was stirred for 30 minutes. The precipitate was collected by filtration and dried under reduced pressure to afford (R)-benzyl-5-(8-(2-amino-3-methylbutanoyl)-3-methyl-2,4-dioxo-1,3,8-triazaspiro[4.5]decan-1-yl)-1H-indazole-1-carboxylate hydrochloride as a white solid (2.00 g, crude), which was used directly without any further purification.

LCMS (ESI): m/z=533.2 [M+H]$^+$ (R)-Benzyl-5-(3-methyl-8-(3-methyl-2-(picolinamido)butanoyl)-2,4-dioxo-1,3,8-triazaspiro[4.5]decan-1-yl)-1H-indazole-1-carboxylate

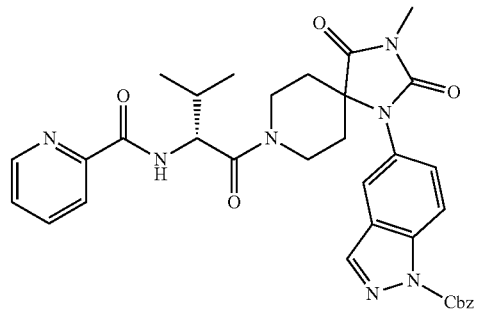 [SMILES: CC(C)[C@@H](NC(=O)c1ccccn1)C(=O)N1CCC2(CC1)C(=O)N(C)C(=O)N2c1ccc2c(cnn2C(=O)OCc2ccccc2)c1]

To a mixture of (R)-benzyl-5-(8-(2-amino-3-methylbutanoyl)-3-methyl-2,4-dioxo-1,3,8-triazaspiro[4.5]decan-1-yl)-1H-indazole-1-carboxylate hydrochloride (100 mg, crude) in dichloromethane (10 mL) was added sequentially picolinic acid (23 mg, 0.19 mmol), 1-[bis(dimethylamino)methylene]-1H-1,2,3-triazolo[4,5-b]pyridinium-3-oxide hexafluorophosphate (HATU) (106 g, 0.28 mmol) and N,N-diisopropylethylamine (61 g, 0.47 mmol). The resulting mixture was stirred for 2 hours at room temperature before the reaction was quenched with ice-water. The mixture was extracted with dichloromethane (3×10 mL) and the combined organic layers were dried over anhydrous sodium sulfate and concentrated under reduced pressure. The residue was purified by prep-TLC with dichloromethane:methanol=15:1 to afford (R)-benzyl-5-(3-methyl-8-(3-methyl-2-(picolinamido)butanoyl)-2,4-dioxo-1,3,8-triazaspiro[4.5]decan-1-yl)-1H-indazole-1-carboxylate as a thick oil (100 mg, 83%).

LCMS (ESI): m/z=638.1 [M+H]$^+$.

(R)—N-(1-(1-(1H-Indazol-5-yl)-3-methyl-2,4-dioxo-1,3,8-triazaspiro[4.5]decan-8-yl)-3-methyl-1-oxobutan-2-yl)picolinamide

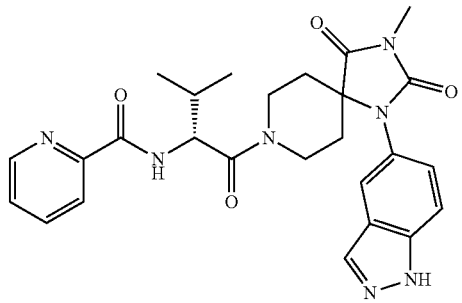 [SMILES: CC(C)[C@@H](NC(=O)c1ccccn1)C(=O)N1CCC2(CC1)C(=O)N(C)C(=O)N2c1ccc2[nH]ncc2c1]

A mixture of (R)-benzyl-5-(3-methyl-8-(3-methyl-2-(picolinamido)butanoyl)-2,4-dioxo-1,3,8-triazaspiro[4.5]decan-1-yl)-1H-indazole-1-carboxylate (100 mg, 0.16 mmol) and 5% palladium on carbon (50 mg) in methanol (10 mL) was stirred for 1 hour under a hydrogen atmosphere. The mixture was filtered and the filter cake was washed with methanol (5×10 mL). The filtrate was concentrated under reduced pressure and the residue was purified by prep-HPLC (Gradient: 95% water, 5% acetonitrile, 30-50 min gradient to 25% water, 85% acetonitrile) to afford (R)—N-(1-(1-(1H-indazol-5-yl)-3-methyl-2,4-dioxo-1,3,8-triazaspiro[4.5]decan-8-yl)-3-methyl-1-oxobutan-2-yl)picolinamide as a white solid (27.6 mg, 29%).

LCMS (ESI): m/z=504.2 [M+H]$^+$.

$^1$H-NMR (400 MHz, CD$_3$OD): δ=0.70-0.94 (m, 6H), 1.71-2.24 (m, 5H), 3.10 (s, 3H), 3.47-3.53 (m, 1H), 3.90-3.98 (m, 1H), 4.13-4.25 (m, 1H), 4.39-4.51 (m, 1H), 4.80-4.82 (m, 1H), 7.12-7.28 (m, 1H), 7.45-8.15 (m, 6H), 8.45-8.62 (m, 1H).

The following 8 compounds were synthesized following the procedure described above:

Example 229

(R)—N-(1-(1-(1H-Indazol-5-yl)-3-methyl-2,4-dioxo-1,3,8-triazaspiro[4.5]decan-8-yl)-3-methyl-1-oxobutan-2-yl)nicotinamide

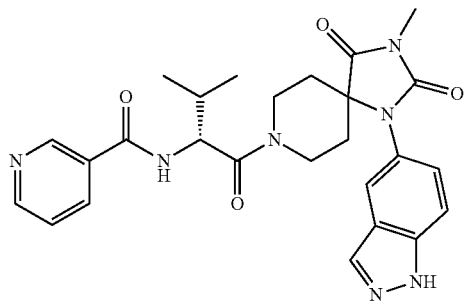 [SMILES: CC(C)[C@@H](NC(=O)c1cccnc1)C(=O)N1CCC2(CC1)C(=O)N(C)C(=O)N2c1ccc2[nH]ncc2c1]

59.8 mg, yield: 63%, white solid.
LCMS (ESI): m/z=504.2 [M+H]$^+$.

$^1$H-NMR (400 MHz, CD$_3$OD): δ=0.63-1.02 (m, 6H), 1.06-1.22 (m, 1H), 1.92-2.28 (m, 4H), 3.11 (s, 3H), 3.47-3.52 (m, 1H), 3.91-3.99 (m, 1H), 4.22-4.51 (m, 2H), 4.69-4.80 (m, 1H), 7.17-7.29 (m, 1H), 7.52-7.78 (m, 3H), 8.05-8.15 (m, 2H), 8.60-9.10 (m, 3H).

Example 230

(R)—N-(1-(1-(1H-Indazol-5-yl)-3-methyl-2,4-dioxo-1,3,8-triazaspiro[4.5]decan-8-yl)-3-methyl-1-oxobutan-2-yl)cyclohexanecarboxamide

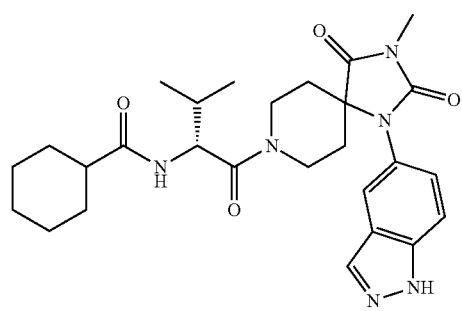 [SMILES: CC(C)[C@@H](NC(=O)C1CCCCC1)C(=O)N1CCC2(CC1)C(=O)N(C)C(=O)N2c1ccc2[nH]ncc2c1]

33.8 mg, yield: 36%, white solid.
LCMS (ESI): m/z=509.2 [M+H]$^+$.

$^1$H-NMR (400 MHz, CD$_3$OD): δ=0.56-0.89 (m, 6H), 1.31-1.41 (m, 7H), 1.54-1.79 (m, 5H), 1.95-2.27 (m, 4H), 3.10 (s, 3H), 3.43-3.54 (m, 1H), 3.86-3.92 (m, 1H), 4.08-4.53 (m, 3H), 7.19-7.26 (m, 1H), 7.62-7.74 (m, 2H), 8.10-8.18 (m, 1H).

Example 231

(R)—N-(1-(1-(1H-Indazol-5-yl)-3-methyl-2,4-dioxo-1,3,8-triazaspiro[4.5]decan-8-yl)-3-methyl-1-oxobutan-2-yl)isonicotinamide

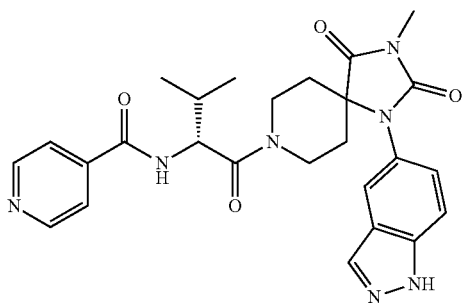

29.8 mg, yield: 31%, yellow solid.
LCMS (ESI): m/z=504.2 [M+H]$^+$.

$^1$H-NMR (400 MHz, CD$_3$OD): δ=0.63-0.98 (m, 6H), 1.72-2.24 (m, 5H), 3.11 (s, 3H), 3.46-3.53 (m, 1H), 3.91-3.97 (m, 1H), 4.22-4.52 (m, 2H), 4.71-4.77 (m, 1H), 7.18-7.29 (m, 1H), 7.53-8.14 (m, 5H), 8.66-8.82 (m, 2H).

Example 232

(R)—N-(1-(1-(1H-Indazol-5-yl)-3-methyl-2,4-dioxo-1,3,8-triazaspiro[4.5]decan-8-yl)-3-methyl-1-oxobutan-2-yl)pivalamide

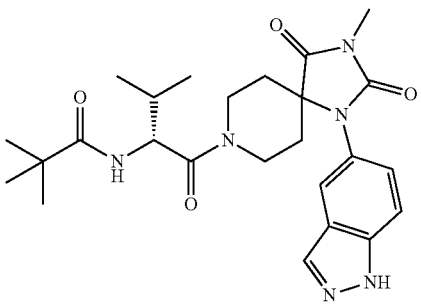 [SMILES: CC(C)[C@@H](NC(=O)C(C)(C)C)C(=O)N1CCC2(CC1)C(=O)N(C)C(=O)N2c1ccc2[nH]ncc2c1]

33.8 mg, yield: 35%, white solid.
LCMS (ESI): m/z=483.2 [M+H]$^+$.

$^1$H-NMR (400 MHz, CD$_3$OD): δ=0.57-0.75 (m, 1H), 0.85-0.88 (m, 10H), 1.18-1.33 (m, 4H), 1.71-2.21 (m, 5H), 3.10 (s, 3H), 3.43-3.49 (m, 1H), 3.80-3.92 (m, 1H), 4.07-4.50 (m, 2H), 4.56-4.59 (m, 1H), 7.09-7.28 (m, 1H), 7.61-7.77 (m, 2H), 8.11-8.14 (m, 1H).

Example 233

(R)—N-(1-(1-(1H-Indazol-5-yl)-3-methyl-2,4-dioxo-1,3,8-triazaspiro[4.5]decan-8-yl)-3-methyl-1-oxobutan-2-yl)benzamide

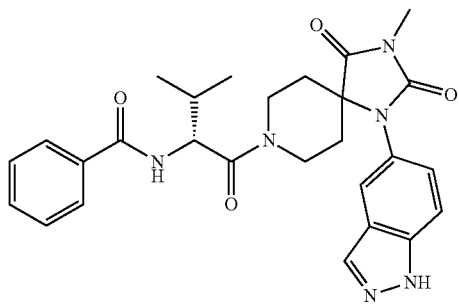 [SMILES: CC(C)[C@@H](NC(=O)c1ccccc1)C(=O)N1CCC2(CC1)C(=O)N(C)C(=O)N2c1ccc2[nH]ncc2c1]

63.6 mg, yield: 67%, white solid.

LCMS (ESI): m/z=503.2 [M+H]$^+$.

$^1$H-NMR (400 MHz, CD$_3$OD): δ=0.61-0.99 (m, 6H), 1.73-2.17 (m, 5H), 3.10 (s, 3H), 3.46-3.52 (m, 1H), 3.90-3.97 (m, 1H), 4.22-4.53 (m, 2H), 4.72-4.74 (m, 1H), 7.13-7.81 (m, 8H), 8.03-8.15 (m, 1H).

Example 234

(R)—N-(1-(1-(1H-Indazol-5-yl)-3-methyl-2,4-dioxo-1,3,8-triazaspiro[4.5]decan-8-yl)-3-methyl-1-oxobutan-2-yl)thiazole-2-carboxamide

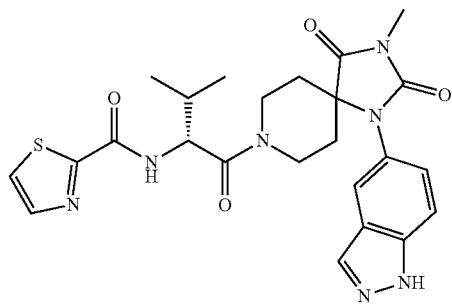 [SMILES: CC(C)[C@@H](NC(=O)c1nccs1)C(=O)N1CCC2(CC1)C(=O)N(C)C(=O)N2c1ccc2[nH]ncc2c1]

31.5 mg, yield: 35%, white solid.

LCMS (ESI): m/z=510.2 [M+H]$^+$.

$^1$H-NMR (400 MHz, CD$_3$OD): δ=0.69-0.98 (m, 6H), 1.70-2.23 (m, 5H), 3.10 (s, 3H), 3.46-3.53 (m, 1H), 3.91-3.98 (m, 1H), 4.12-4.24 (m, 1H), 4.39-4.51 (m, 1H), 4.73-4.78 (m, 1H), 7.14-7.29 (m, 1H), 7.49-7.51 (m, 1H), 7.64-7.67 (m, 1H), 7.76-7.81 (m, 2H), 7.86-7.96 (m, 1H), 8.06-8.15 (m, 1H).

Example 235

(R)—N-(1-(1-(1H-Indazol-5-yl)-3-methyl-2,4-dioxo-1,3,8-triazaspiro[4.5]decan-8-yl)-3-methyl-1-oxobutan-2-yl)-4-(trifluoromethyl)thiazole-2-carboxamide

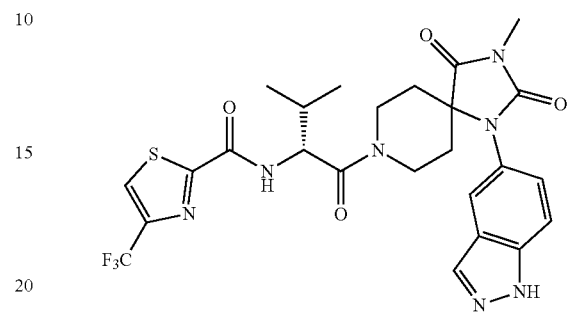

30.5 mg, yield: 34%, white solid.

LCMS (ESI): m/z=578.1 [M+H]$^+$.

$^1$H-NMR (400 MHz, CD$_3$OD): δ=0.69-0.98 (m, 6H), 1.72-2.10 (m, 5H), 3.10 (s, 3H), 3.47-3.53 (m, 1H), 3.89-3.98 (m, 1H), 4.13-4.26 (m, 1H), 4.40-4.52 (m, 1H), 4.73-4.79 (m, 1H), 7.17-7.29 (m, 1H), 7.54-7.77 (m, 2H), 8.06-8.15 (m, 1H), 8.34-8.53 (m, 2H).

Example 236

(R)—N-(1-(1-(1H-Indazol-5-yl)-3-methyl-2,4-dioxo-1,3,8-triazaspiro[4.5]decan-8-yl)-3-methyl-1-oxobutan-2-yl)-2-fluoro-N-methyl-5-(trifluoromethyl)benzamide

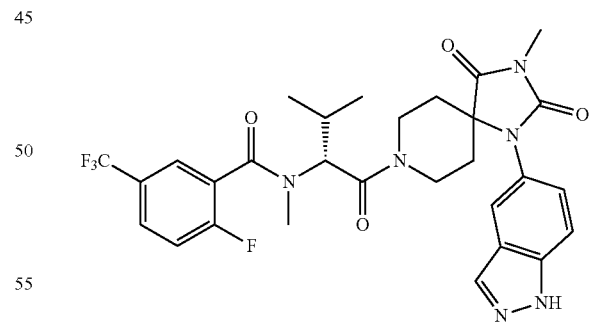

66.1 mg, yield: 67%, white solid.

LCMS (ESI): m/z=603.2 [M+H]$^+$.

$^1$H-NMR (400 MHz, CD$_3$OD): δ=0.57-0.95 (m, 6H), 1.62-1.93 (m, 2H), 2.05-2.40 (m, 3H), 2.50 (s, 2H), 2.80 (s, 1H), 3.11 (s, 3H), 3.49-3.55 (m, 1H), 3.89-3.95 (m, 1H), 4.30-4.55 (m, 2H), 5.11-5.25 (m, 1H), 6.96-8.15 (m, 7H).

Example 237
(R)-4-(3-(2-(Dimethylamino)ethyl)-8-(2-(2-fluoro-5-(trifluoromethyl)benzamido)-3-methylbutanoyl)-2,4-dioxo-1,3,8-triazaspiro[4.5]decan-1-yl)benzoic Acid trifluoroacetic Acid Salt
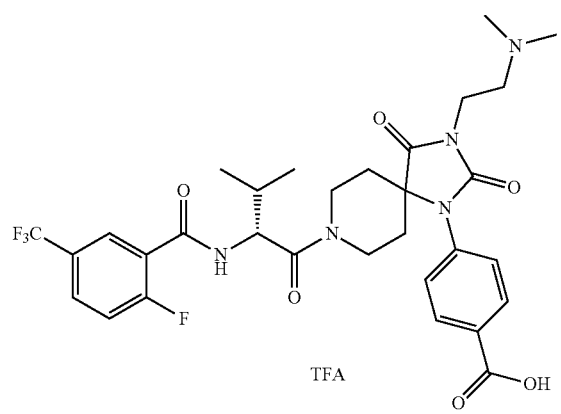 [SMILES: CC(C)[C@@H](NC(=O)c1cc(C(F)(F)F)ccc1F)C(=O)N1CCC2(CC1)C(=O)N(CCN(C)C)C(=O)N2c1ccc(C(=O)O)cc1]
Representative Scheme:
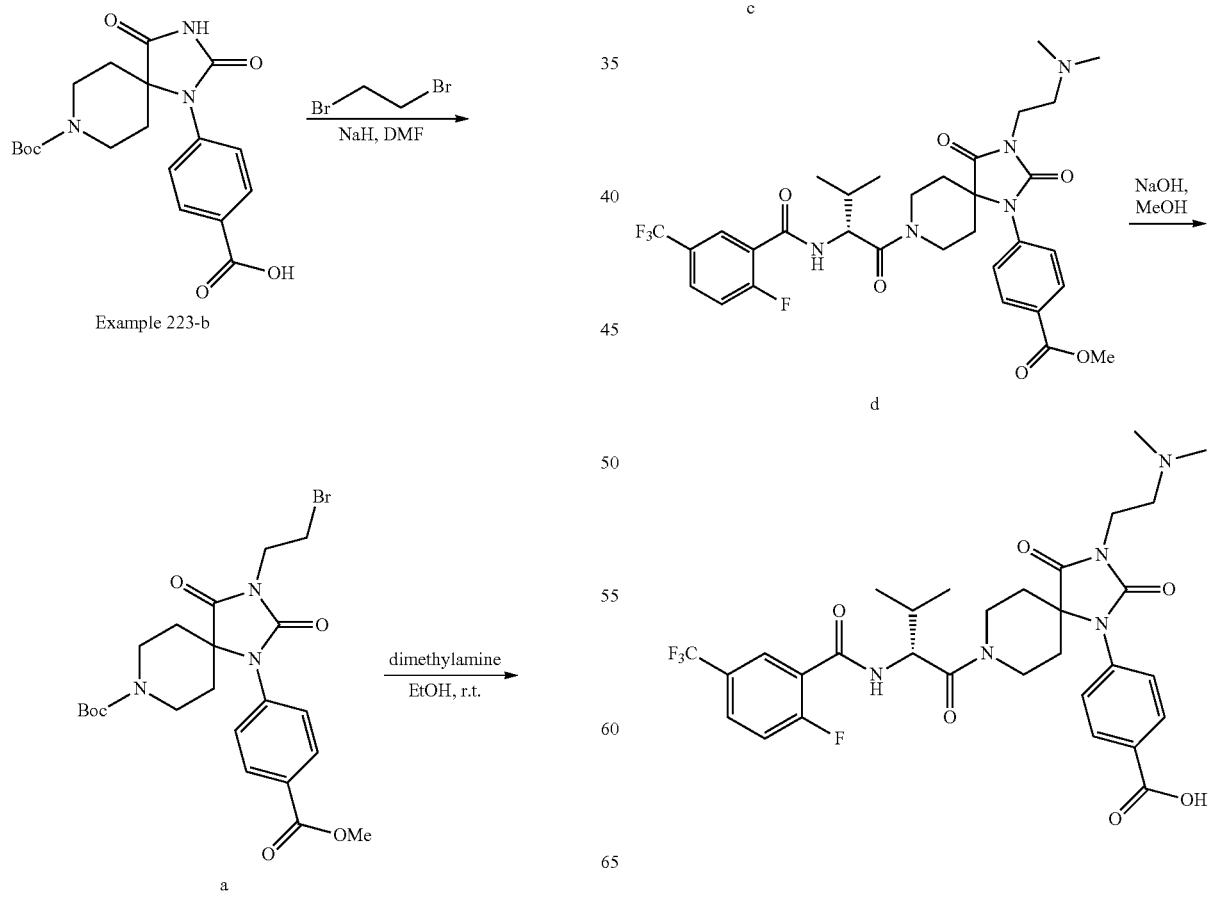
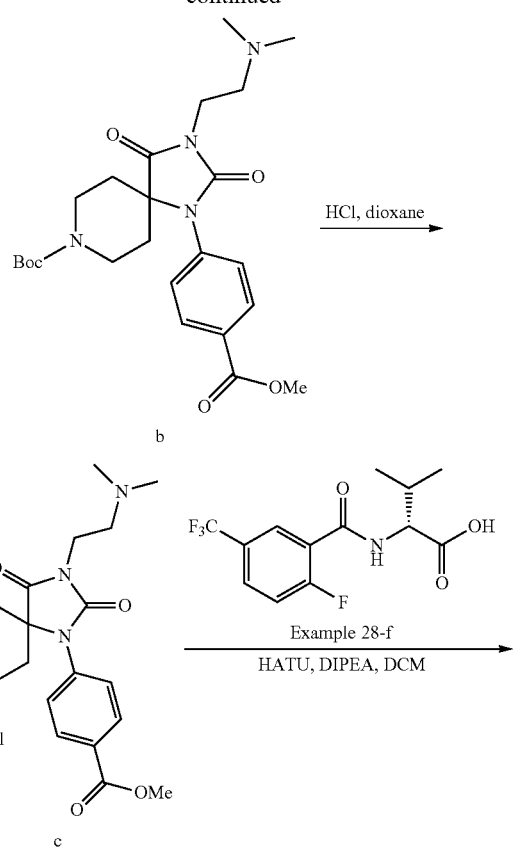

Representative General Procedure tert-Butyl-3-(2-bromoethyl)-1-(4-(methoxycarbonyl) phenyl)-2,4-dioxo-1,3,8-triazaspiro[4.5]decane-8-carboxylate

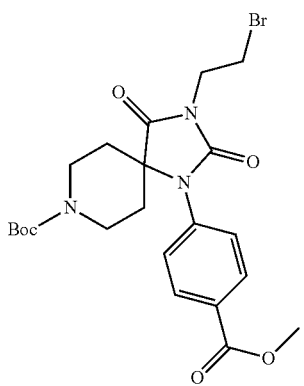 [SMILES: COC(=O)c1ccc(N2C(=O)N(CCBr)C(=O)C23CCN(C(=O)OC(C)(C)C)CC3)cc1]

To a solution of tert-butyl-1-(4-(methoxycarbonyl)phenyl)-2,4-dioxo-1,3,8-triazaspiro[4.5]decane-8-carboxylate (prepared as described in Example 223-b) (600 mg, 1.49 mmol) in N,N-dimethylformamide (10 mL) was added sodium hydride (90 mg, 60% in oil, 2.23 mmol) at 0° C. After stirring for 15 minutes, 1,2-dibromoethane (2800 mg, 14.88 mmol) was added. The resulting mixture was stirred overnight before the reaction was quenched with ice-water (10 mL). The mixture was extracted with ethyl acetate (3×15 mL). The combined organic layers were dried over anhydrous sodium sulfate and concentrated under reduced pressure. The residue was purified by silica gel column chromatography eluting with ethyl acetate:petroleum ether=1:2 to afford tert-butyl-3-(2-bromoethyl)-1-(4-(methoxycarbonyl)phenyl)-2,4-dioxo-1,3,8-triazaspiro[4.5]decane-8-carboxylate as a white solid (480 mg, 65%).

LCMS (ESI): m/z=510.1 [M+H]⁺.

tert-Butyl-3-(2-(dimethylamino)ethyl)-1-(4-(methoxycarbonyl)phenyl)-2,4-dioxo-1,3,8-triazaspiro[4.5]decane-8-carboxylate

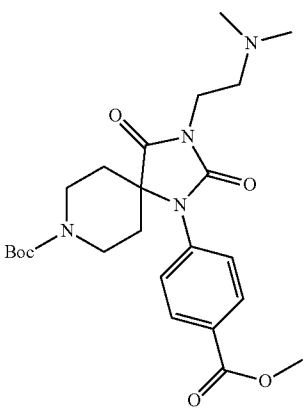 [SMILES: COC(=O)c1ccc(N2C(=O)N(CCN(C)C)C(=O)C23CCN(C(=O)OC(C)(C)C)CC3)cc1]

To a solution of tert-butyl-3-(2-bromoethyl)-1-(4-(methoxycarbonyl)phenyl)-2,4-dioxo-1,3,8-triazaspiro[4.5]decane-8-carboxylate (480 mg, 0.94 mmol) in ethanol (20 mL) was added a 40% aqueous dimethylamine solution (10 mL) and the reaction was stirred overnight. The solvent was removed under reduced pressure and the residue was purified by silica gel column chromatography eluting with dichloromethane:methanol=20:1 to afford tert-butyl-3-(2-(dimethylamino)ethyl)-1-(4-(methoxycarbonyl)phenyl)-2,4-dioxo-1,3,8-triazaspiro[4.5]decane-8-carboxylate as a thick oil (310 mg, 67%).

LCMS (ESI): m/z=475.5 [M+H]⁺.

$^1$H-NMR (400 MHz, CDCl$_3$): δ=1.36 (s, 9H), 1.39-1.45 (m, 2H), 1.65-1.92 (m, 4H), 2.31 (s, 6H), 2.63-2.71 (m, 2H), 3.40-3.58 (m, 2H), 3.88 (s, 3H), 3.90-4.11 (m, 2H), 7.25-7.27 (m, 2H), 8.06-8.09 (m, 2H).

Methyl-4-(3-(2-(dimethylamino)ethyl)-2,4-dioxo-1,3,8-triazaspiro[4.5]decan-1-yl)benzoate hydrochloride

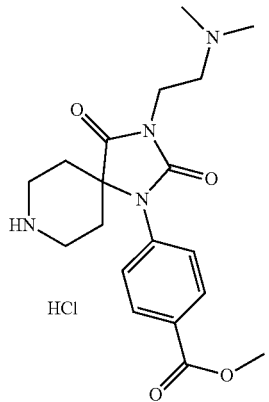 [SMILES: COC(=O)c1ccc(N2C(=O)N(CCN(C)C)C(=O)C23CCNCC3)cc1 ; Cl]

A solution of tert-butyl-3-(2-(dimethylamino)ethyl)-1-(4-(methoxycarbonyl)phenyl)-2,4-dioxo-1,3,8-triazaspiro[4.5] decane-8-carboxylate (310 mg, 0.65 mmol) in hydrochloric acid in dioxane (6.0 M, 10 mL) was stirred for 30 minutes. The precipitate was collected by filtration and dried under reduced pressure to afford methyl-4-(3-(2-(dimethylamino) ethyl)-2,4-dioxo-1,3,8-triazaspiro[4.5]decan-1-yl)benzoate hydrochloride as a white solid (300 mg, crude), which was used directly without any further purification.

LCMS (ESI): m/z=313.4 [M+H]⁺.

(R)-Methyl-4-(3-(2-(dimethylamino)ethyl)-8-(2-(2-fluoro-5-(trifluoromethyl)benzamido)-3-methylbutanoyl)-2,4-dioxo-1,3,8-triazaspiro[4.5]decan-1-yl) benzoate

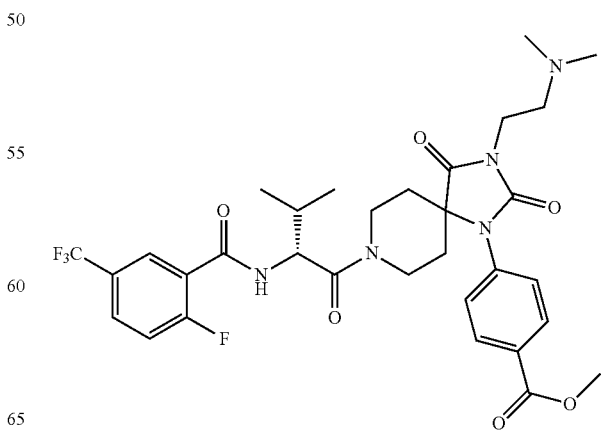

To a mixture of methyl-4-(3-(2-(dimethylamino)ethyl)-2,4-dioxo-1,3,8-triazaspiro[4.5]decan-1-yl)benzoate hydrochloride (300 mg, crude) in dichloromethane (10 mL) was added (R)-2-(2-fluoro-5-(trifluoromethyl)benzamido)-3-methylbutanoic acid (prepared as described in Example 28-f) (201 mg, 0.65 mmol), 1-[bis(dimethylamino)methylene]-1H-1,2,3-triazolo[4,5-b]pyridinium-3-oxide hexafluorophosphate (HATU) (372 mg, 0.98 mmol) and N,N-diisopropylethylamine (295 mg, 2.28 mmol). The resulting mixture was stirred for 2 hours at room temperature before the reaction was quenched with ice-water (10 mL). The mixture was extracted with ethyl acetate (3×10 mL) and the combined organic layers were dried over anhydrous sodium sulfate and concentrated under reduced pressure. The residue was purified by prep-TLC with dichloromethane:methanol=10:1 to afford (R)-methyl-4-(3-(2-(dimethylamino)ethyl)-8-(2-(2-fluoro-5-(trifluoromethyl)benzamido)-3-methylbutanoyl)-2,4-dioxo-1,3,8-triazaspiro[4.5]decan-1-yl)benzoate as a white solid (390 mg, 93%).

LCMS (ESI): m/z=313.4 [M+H]$^+$.

(R)-4-(3-(2-(Dimethylamino)ethyl)-8-(2-(2-fluoro-5-(trifluoromethyl)benzamido)-3-methylbutanoyl)-2,4-dioxo-1,3,8-triazaspiro[4.5]decan-1-yl)benzoic Acid trifluoroacetic Acid Salt

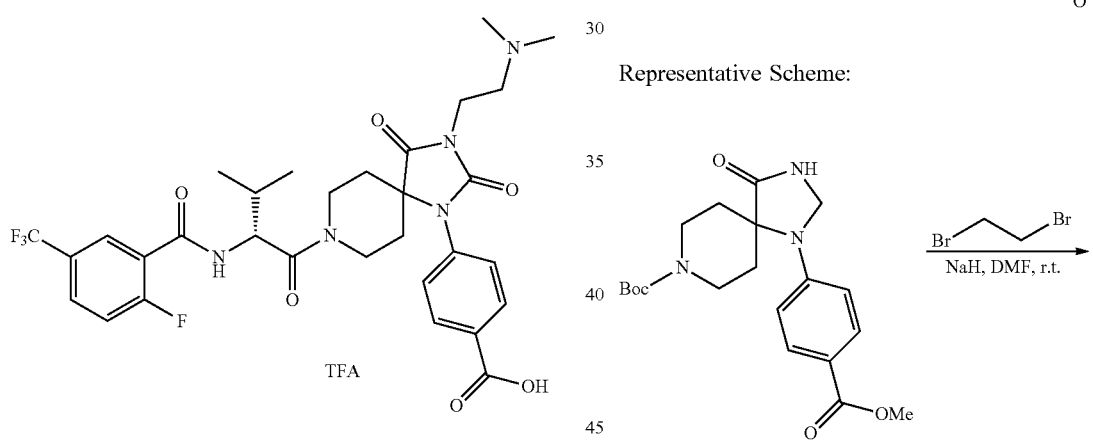

To a solution of (R)-methyl-4-(3-(2-(dimethylamino)ethyl)-8-(2-(2-fluoro-5-(trifluoromethyl) benzamido)-3-methylbutanoyl)-2,4-dioxo-1,3,8-triazaspiro[4.5]decan-1-yl)benzoate (390 mg, 0.59 mmol) in methanol (20 mL) was added a 15% aqueous sodium hydroxide solution (15 mL). The reaction was heated at reflux for 5 minutes before cooling to room temperature. The pH of the resulting solution was adjusted to 5-6 by addition of 10% aqueous hydrochloric acid. The solvent was removed under reduced pressure. To the residue was added Methanol (50 mL), the resulting solid was removed by filtration. The filtrate concentrated under reduced pressure and the residue was purified by prep-HPLC (Gradient: 95% water, 5% acetonitrile, 30-50 min gradient to 25% water, 85% acetonitrile) to afford (R)-4-(3-(2-(dimethylamino)ethyl)-8-(2-(2-fluoro-5-(trifluoromethyl)benzamido)-3-methylbutanoyl)-2,4-dioxo-1,3,8-triazaspiro[4.5]decan-1-yl)benzoic acid trifluoroacetic acid salt as a white solid (16.6 mg, 5%).

LCMS (ESI): m/z=650.2 [M+H]$^+$.

$^1$H-NMR (400 MHz, CD$_3$OD): δ=0.79-1.03 (m, 6H), 1.71-2.34 (m, 5H), 3.04 (s, 6H), 3.47-3.54 (m, 3H), 3.87-4.05 (m, 3H), 4.20-4.37 (m, 1H), 4.41-4.60 (m, 1H), 4.82-4.86 (m, 1H), 7.36-7.48 (m, 3H), 7.85-8.10 (m, 4H).

Example 238

(R)-4-(3-(2-(Dimethylamino)ethyl)-8-(2-(2-fluoro-5-(trifluoromethyl) benzamido)-3-methylbutanoyl)-4-oxo-1,3,8-triazaspiro[4.5]decan-1-yl)benzoic Acid trifluoroacetic Acid Salt

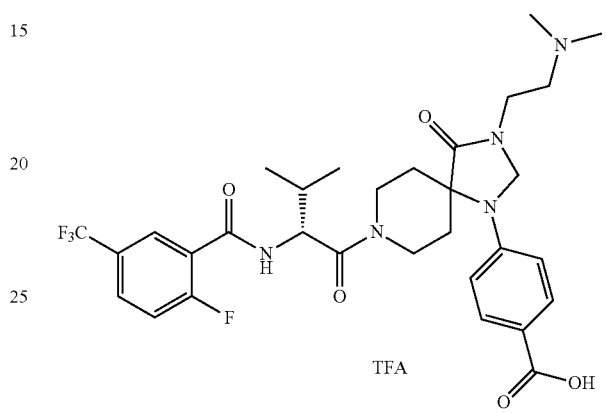

Representative Scheme:

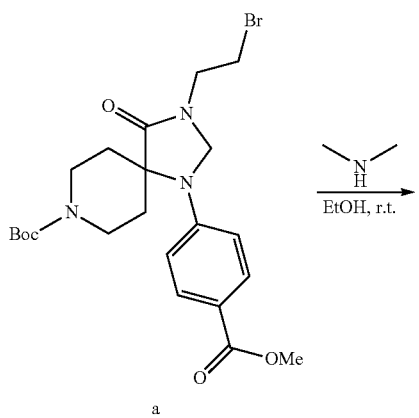

277
-continued

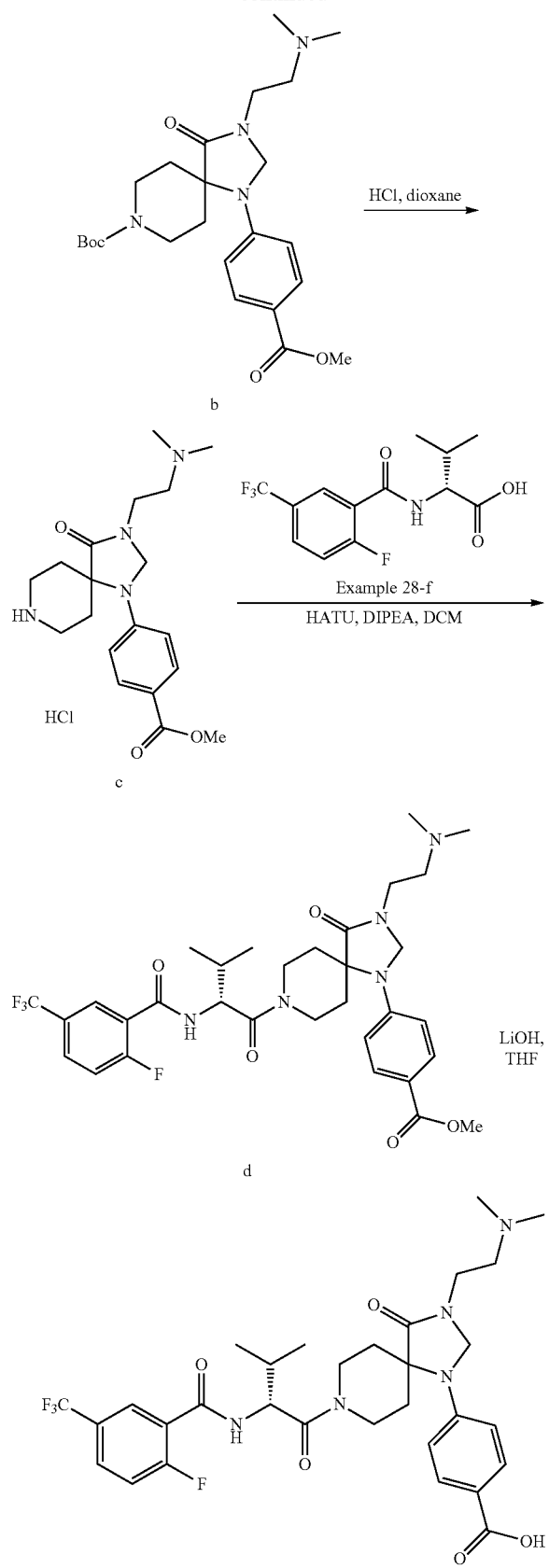

b

Example 28-f
HATU, DIPEA, DCM c

LiOH,
THF d

278

Representative General Procedure tert-Butyl-3-(2-bromoethyl)-1-(4-(methoxycarbonyl)phenyl)-4-oxo-1,3,8-triazaspiro[4.5]decane-8-carboxylate

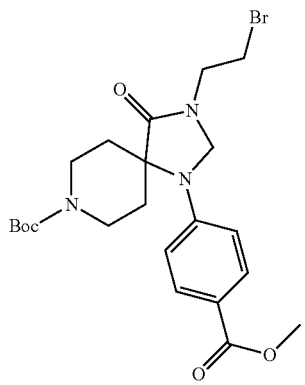 [SMILES: COC(=O)c1ccc(N2CN(CCBr)C(=O)C23CCN(C(=O)OC(C)(C)C)CC3)cc1]

To a solution of tert-butyl-1-(4-(methoxycarbonyl)phenyl)-4-oxo-1,3,8-triazaspiro[4.5]decane-8-carboxylate (prepared as described in Example 149-c) (600 mg, 1.54 mmol) in N,N-dimethylformamide (10 mL) was added sodium hydride (93 mg, 60% in oil, 2.31 mmol) at 0° C. After stirring for 15 minutes, 1,2-dibromoethane (2900 mg, 15.43 mmol) was added. The resulting mixture was stirred overnight before the reaction was quenched with ice-water (10 mL). The mixture was extracted with ethyl acetate (3×15 mL). The combined organic layers were dried over anhydrous sodium sulfate and concentrated under reduced pressure. The residue was purified by silica gel column chromatography eluting with ethyl acetate:petroleum ether=1:1 to afford tert-butyl-3-(2-bromoethyl)-1-(4-(methoxycarbonyl)phenyl)-4-oxo-1,3,8-triazaspiro[4.5]decane-8-carboxylate as a white solid (540 mg, 70%).

LCMS (ESI): m/z=496.1 [M+H]$^+$.

tert-Butyl-3-(2-(dimethylamino)ethyl)-1-(4-(methoxycarbonyl)phenyl)-4-oxo-1,3,8-triazaspiro[4.5]decane-8-carboxylate

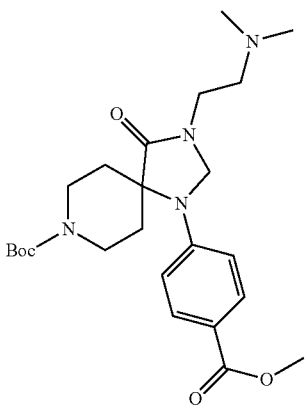 [SMILES: COC(=O)c1ccc(N2CN(CCN(C)C)C(=O)C23CCN(C(=O)OC(C)(C)C)CC3)cc1]

To a solution of tert-butyl-3-(2-bromoethyl)-1-(4-(methoxycarbonyl)phenyl)-4-oxo-1,3,8-triazaspiro[4.5]decane-8-carboxylate (540 mg, 1.09 mmol) in ethanol (20 mL) was added a 40% aqueous dimethylamine solution (10 mL) and the reaction was stirred overnight. The solvent was removed under reduced pressure and the residue was purified by silica gel column chromatography eluting with dichloromethane:methanol=20:1 to afford tert-butyl-3-(2-(dimethylamino)ethyl)-1-(4-(methoxycarbonyl)phenyl)-4-oxo-1,3,8-triazaspiro[4.5]decane-8-carboxylate as a thick oil (340 mg, 69%).

LCMS (ESI): m/z=460.0 [M+H]$^+$.

$^1$H-NMR (300 MHz, CDCl$_3$): δ=1.50 (s, 9H), 1.56-1.61 (m, 2H), 2.23 (s, 6H), 2.48-2.52 (m, 2H), 2.64-2.75 (m, 2H), 2.49-3.52 (m, 4H), 3.85 (s, 3H), 3.96-4.20 (m, 2H), 4.69-4.79 (m, 2H), 6.59-6.62 (m, 2H), 7.82-7.85 (m, 2H).

Methyl-4-(3-(2-(dimethylamino)ethyl)-4-oxo-1,3,8-triazaspiro[4.5]decan-1-yl)benzoate hydrochloride

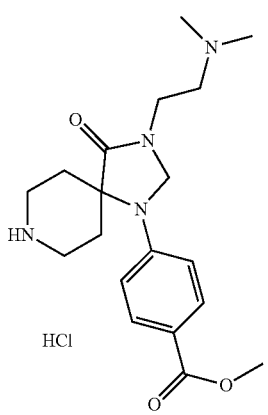 [SMILES: COC(=O)c1ccc(N2CN(CCN(C)C)C(=O)C23CCNCC3)cc1 ; Cl]

A solution of tert-butyl-3-(2-(dimethylamino)ethyl)-1-(4-(methoxycarbonyl)phenyl)-4-oxo-1,3,8-triazaspiro[4.5]decane-8-carboxylate (340 mg, 0.74 mmol) in hydrochloric acid in dioxane (6.0 M, 10 mL) was stirred for 30 minutes. The precipitate was collected by filtration and dried under reduced pressure to afford methyl 4-(3-(2-(dimethylamino)ethyl)-4-oxo-1,3,8-triazaspiro[4.5]decan-1-yl)benzoate hydrochloride as a white solid (300 mg, crude), which was used directly without any further purification.

LCMS (ESI): m/z=396.4 [M+H]$^+$.

(R)-Methyl-4-(3-(2-(dimethylamino)ethyl)-8-(2-(2-fluoro-5-(trifluoromethyl)benzamido)-3-methylbutanoyl)-4-oxo-1,3,8-triazaspiro[4.5]decan-1-yl)benzoate

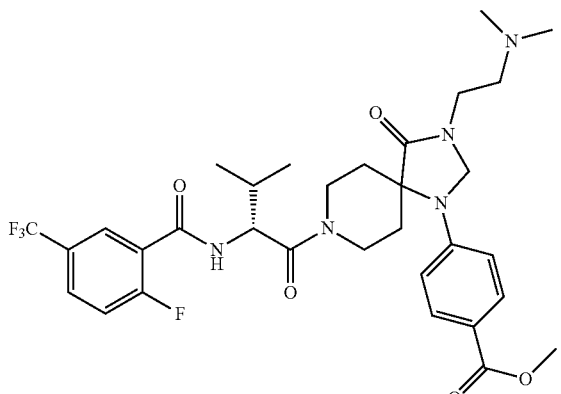

To a suspension of methyl-4-(3-(2-(dimethylamino)ethyl)-4-oxo-1,3,8-triazaspiro[4.5]decan-1-yl)benzoate hydrochloride (300 mg, crude) in dichloromethane (10 mL) was added (R)-2-(2-fluoro-5-(trifluoromethyl)benzamido)-3-methylbutanoic acid (prepared as described in Example 28-f) (227 mg, 0.74 mmol), 1-[bis(dimethylamino)methylene]-1H-1,2,3-triazolo[4,5-b]pyridinium-3-oxide hexafluorophosphate (HATU) (421 mg, 1.11 mmol) and N,N-diisopropylethylamine (333 mg, 2.58 mmol). The resulting mixture was stirred for 2 hours at room temperature before the reaction was quenched with ice-water (10 mL). The mixture was extracted with ethyl acetate (3×10 mL) and the combined organic layers were dried over anhydrous sodium sulfate and concentrated under reduced pressure. The residue was purified by prep-TLC with dichloromethane:methanol=10:1 to afford (R)-methyl-4-(3-(2-(dimethylamino)ethyl)-8-(2-(2-fluoro-5-(trifluoromethyl)benzamido)-3-methylbutanoyl)-4-oxo-1,3,8-triazaspiro[4.5]decan-1-yl)benzoate as a white solid (280 mg, 60%).

LCMS (ESI): m/z=650.0 [M+H]$^+$.

(R)-4-(3-(2-(Dimethylamino)ethyl)-8-(2-(2-fluoro-5-(trifluoromethyl) benzamido)-3-methylbutanoyl)-4-oxo-1,3,8-triazaspiro[4.5]decan-1-yl)benzoic Acid trifluoroacetic Acid Salt

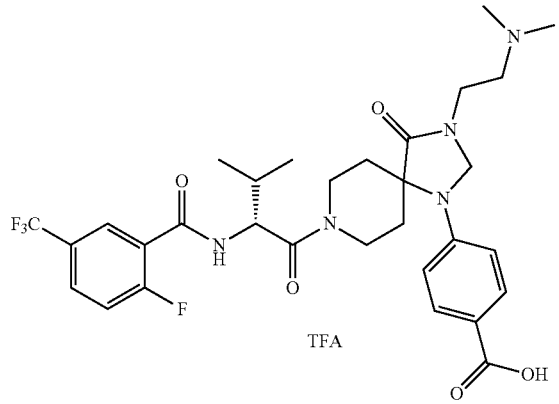 [SMILES: CC(C)[C@@H](NC(=O)c1cc(C(F)(F)F)ccc1F)C(=O)N1CCC2(CC1)C(=O)N(CCN(C)C)CN2c1ccc(C(=O)O)cc1]

To a solution of (R)-methyl-4-(3-(2-(dimethylamino)ethyl)-8-(2-(2-fluoro-5-(trifluoromethyl)benzamido)-3-methylbutanoyl)-4-oxo-1,3,8-triazaspiro[4.5]decan-1-yl)benzoate (280 mg, 0.43 mmol) in tetrahydrofuran (20 mL) was added an aqueous lithium hydroxide solution (2 mL, 1.0 M). The reaction was refluxed for 2 days before cooling to room temperature. The pH of the resulting solution was adjusted to 3-4 by addition of 10% aqueous hydrochloric acid solution. The solvent was removed in reduced pressure. To the residue was added Methanol (50 mL), the resulting solid was removed by filtration. The filtrate was concentrated under reduced pressure and the residue was purified by prep-HPLC (Gradient: 95% water, 5% acetonitrile, 30-50 min gradient to 25% water, 85% acetonitrile) to afford (R)-4-(3-(2-(dimethylamino)ethyl)-8-(2-(2-fluoro-5-(trifluoromethyl)benzamido)-3-methylbutanoyl)-4-oxo-1,3,8-triazaspiro[4.5]decan-1-yl)benzoic acid trifluoroacetic acid salt as a white solid (25.2 mg, 9%).

LCMS (ESI): m/z=636.2 [M+H]$^+$.

$^1$H-NMR (400 MHz, CD$_3$OD): δ=0.91-1.19 (m, 6H), 1.71-2.06 (m, 2H), 2.18-2.35 (m, 1H), 2.79-3.04 (m, 2H), 3.32 (s, 6H), 3.37-3.47 (m, 4H), 3.89-4.12 (m, 3H), 4.31-

4.60 (m, 2H), 4.96-5.09 (m, 2H), 6.77-6.91 (m, 2H), 7.38-7.52 (m, 1H), 7.71-8.04 (m, 4H).
Example 239
(R)-2-Fluoro-N-(3-methyl-1-(3-methyl-2,4-dioxo-1-(pyridin-4-yl)-1,3,8-triazaspiro[4.5]decan-8-yl)-1-oxobutan-2-yl)-5-(trifluoromethyl)benzamide
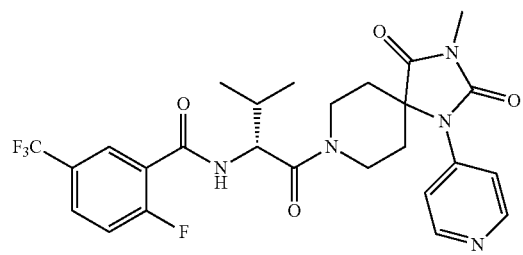 [SMILES: CC(C)[C@@H](NC(=O)c1cc(C(F)(F)F)ccc1F)C(=O)N1CCC2(CC1)C(=O)N(C)C(=O)N2c1ccncc1]
Representative Scheme:
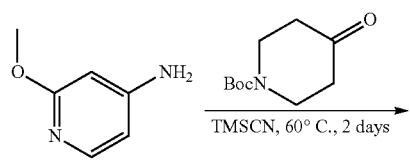
a
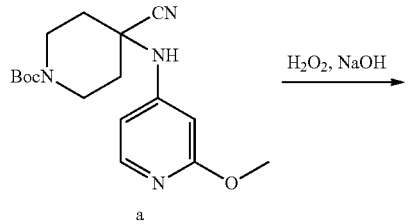
b
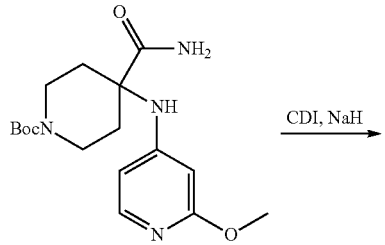
c
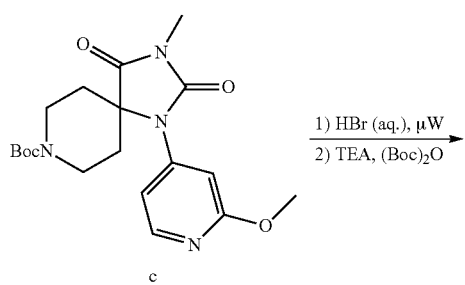
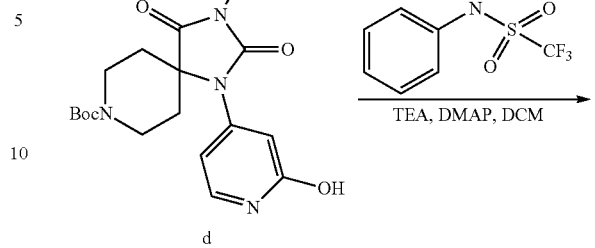
d
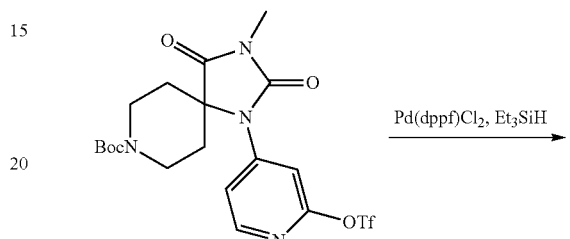
e
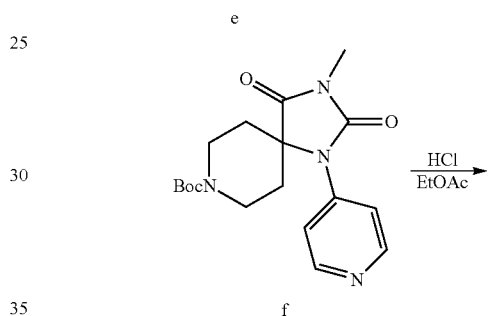
f
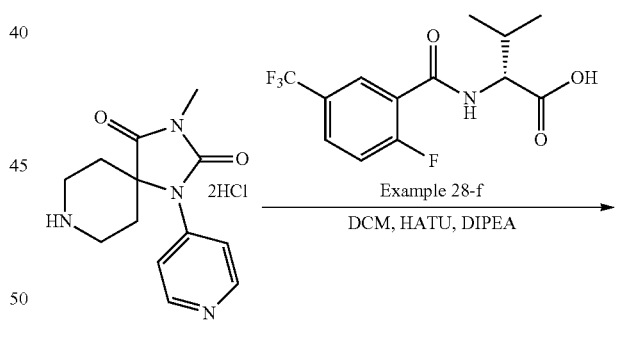
g
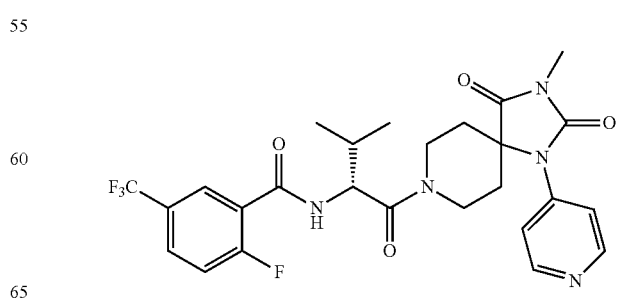

Representative General Procedure tert-Butyl-4-cyano-4-(2-methoxypyridin-4-ylamino)piperidine-1-carboxylate

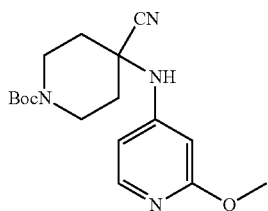 [SMILES: COc1cc(NC2(C#N)CCN(C(=O)OC(C)(C)C)CC2)ccn1]

To a solution of 2-methoxypyridin-4-amine (15 g, 12 mmol) in acetic acid (50 mL) was added tert-butyl-4-oxopiperidine-1-carboxylate (26.6 g, 13 mmol). The resulting mixture was cooled to 0° C. and trimethylsilyl cyanide (17.8 g, 18 mmol) was added. The solution was stirred overnight at room temperature. Saturated aqueous ammonium chloride solution was added (50 mL). The mixture was extracted with ethyl acetate (3×50 mL) and the combined organic layers were dried over anhydrous sodium sulfate and concentrated under reduced pressure. The residue was purified by silica gel column chromatography eluting with dichloromethane:petroleum ether=1:1 to afford tert-butyl-4-cyano-4-(2-methoxypyridin-4-ylamino)piperidine-1-carboxylate as a white solid (15 g, 37%).

LCMS (ESI): m/z=333.1 [M+H]$^+$.

tert-Butyl-4-carbamoyl-4-(2-methoxypyridin-4-ylamino)piperidine-1-carboxylate

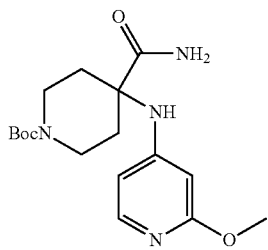 [SMILES: COc1cc(NC2(C(N)=O)CCN(C(=O)OC(C)(C)C)CC2)ccn1]

To a suspension of tert-butyl-4-cyano-4-(2-methoxypyridin-4-ylamino)piperidine-1-carboxylate (2 g, 6.0 mmol) in methanol was added sodium hydroxide (0.48 g, 12 mmol). To the resulting mixture was added dropwise hydrogen peroxide (30%, 20 mL) over 30 minutes. After stirring at room temperature for an additional 1 hour, the reaction was quenched by addition of ice-water (20 mL). The mixture was extracted with ethyl acetate (3×20 mL). The combined organic layer was washed with brine (10 mL) and dried over anhydrous sodium sulfate. The residue was purified by silica gel column chromatography eluting with dichloromethane:methanol=5:1 to afford tert-butyl 4-carbamoyl-4-(2-methoxypyridin-4-ylamino) piperidine-1-carboxylate as a yellow solid (1.9 g, 90%).

LCMS (ESI): m/z=351.2 [M+H]$^+$.

tert-Butyl-1-(2-methoxypyridin-4-yl)-2,4-dioxo-1,3,8-triazaspiro[4.5]decane-8-carboxylate

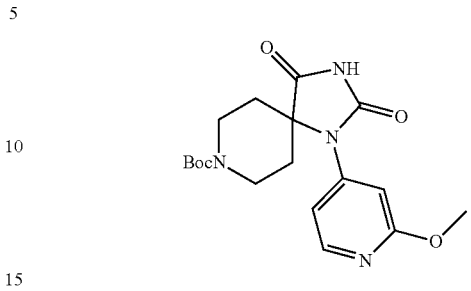

To a solution of tert-butyl-4-carbamoyl-4-(2-methoxypyridin-4-ylamino)piperidine-1-carboxylate (1.9 g, 5.4 mmol) in dimethyl carbonate (20 mL) was added 1,1'-carbonyldiimidazole (2.6 g, 16 mmol) and sodium hydride (0.4 g, 11 mmol). The resulting mixture was heated at 50° C. for 3 hours before the reaction was quenched by addition of ice-water (10 mL). The resulting mixture was extracted with ethyl acetate (3×50 mL). The combined organic layers were washed with brine (10 mL) and dried over anhydrous sodium sulfate. The solvent was removed under reduced pressure to afford tert-butyl-1-(2-methoxypyridin-4-yl)-2,4-dioxo-1,3,8-triazaspiro[4.5] decane-8-carboxylate as a white solid (2 g, crude), which was used directly without any further purification.

LCMS (ESI): m/z=377.1 [M+H]$^+$.

tert-Butyl-1-(2-methoxypyridin-4-yl)-3-methyl-2,4-dioxo-1,3,8-triazaspiro [4.5]decane-8-carboxylate

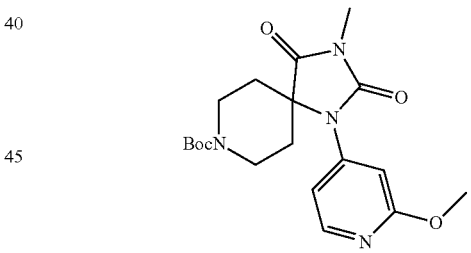

To a solution of tert-butyl-1-(2-methoxypyridin-4-yl)-2,4-dioxo-1,3,8-triazaspiro[4.5] decane-8-carboxylate (2 g, crude) in N,N-dimethylformamide (30 mL) was added sodium hydride (0.426 g, 60% in oil, 10.4 mmol) at 0° C. After stirring for 15 minutes, iodomethane (1130 mg, 7.98 mmol) was added. The resulting mixture was stirred for 15 minutes at room temperature and the reaction was quenched with ice-water (10 mL). The mixture was extracted with ethyl acetate (3×50 mL). The combined organic layers were dried over anhydrous sodium sulfate and concentrated under reduced pressure. The residue was purified by silica gel column chromatography eluting with dichloromethane:methanol=50:1 to afford tert-butyl-1-(2-methoxypyridin-4-yl)-3-methyl-2,4-dioxo-1,3,8-triazaspiro [4.5]decane-8-carboxylate as a yellow solid (2 g, 94% over two steps).

LCMS (ESI): m/z=391.1 [M+H]$^+$.

tert-Butyl-1-(2-hydroxypyridin-4-yl)-3-methyl-2,4-dioxo-1,3,8-triazaspiro[4.5]decane-8-carboxylate

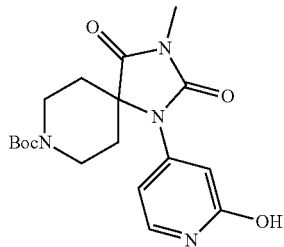 [SMILES: CN1C(=O)N(c2ccnc(O)c2)C2(CCN(C(=O)OC(C)(C)C)CC2)C1=O]

A solution of tert-butyl-1-(2-methoxypyridin-4-yl)-3-methyl-2,4-dioxo-1,3,8-triazaspiro [4.5]decane-8-carboxylate (2 g, 5 mmol) was heated at 130° C. in a microwave reactor for 30 minutes. The solvent was removed under reduced pressure. The residue was dissolved in tetrahydrofuran (20 mL). To the resulting mixture was added aqueous sodium hydroxide (2.0 M, 5.1 mL, 10 mmol) and di-tert-butyl-dicarbonate (1.3 g, 6 mmol). The resulting mixture was stirred for 1 hour before it was poured into ice-water (10 mL). The resulting mixture was extracted with ethyl acetate (3×20 mL). The combined organic layers were dried over anhydrous sodium sulfate and concentrated under reduced pressure. The residue was purified by silica gel column chromatography eluting with ethyl acetate:petroleum ether=4:1 to afford tert-butyl-1-(2-hydroxypyridin-4-yl)-3-methyl-2,4-dioxo-1,3,8-triazaspiro [4.5]decane-8-carboxylate as a white solid (250 mg, 13%).

LCMS (ESI): m/z=377.1 [M+H]$^+$.

tert-Butyl-3-methyl-2,4-dioxo-1-(2-(trifluoromethylsulfonyloxy)pyridin-4-yl)-1,3,8-triazaspiro[4.5]decane-8-carboxylate

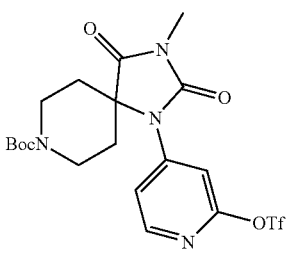 [SMILES: CN1C(=O)N(c2ccnc(OS(=O)(=O)C(F)(F)F)c2)C2(CCN(C(=O)OC(C)(C)C)CC2)C1=O]

To a solution of tert-butyl-1-(2-hydroxypyridin-4-yl)-3-methyl-2,4-dioxo-1,3,8-triazaspiro[4.5]decane-8-carboxylate (200 mg, 0.53 mmol) in dichloromethane (5 mL) was added 1,1,1-trifluoro-N-phenyl-N-(trifluoromethylsulfonyl)methanesulfonamide (228 mg, 0.64 mmol), triethylamine (107 mg, 1.0 mmol) and N,N-dimethylpyridin-4-amine (65 mg, 0.53 mmol) at room temperature. The resulting mixture was stirred for 3 hours before it was diluted with dichloromethane (20 mL). The mixture was washed with brine (20 mL) and dried over anhydrous sodium sulfate. The residue was purified by silica gel column chromatography eluting with ethyl acetate:petroleum ether=3:2 to afford tert-butyl-3-methyl-2,4-dioxo-1-(2-(trifluoromethylsulfonyloxy)pyridin-4-yl)-1,3,8-triazaspiro[4.5]decane-8-carboxylate (250 mg, 92%) as a white solid.

LCMS (ESI): m/z=509.1 [M+H]$^+$.

tert-Butyl-3-methyl-2,4-dioxo-1-(pyridin-4-yl)-1,3,8-triazaspiro[4.5] decane-8-carboxylate

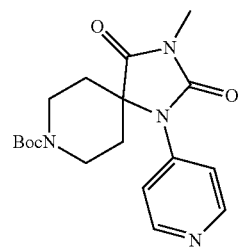 [SMILES: CN1C(=O)N(c2ccncc2)C2(CCN(C(=O)OC(C)(C)C)CC2)C1=O]

To a solution of tert-butyl-3-methyl-2,4-dioxo-1-(2-(trifluoromethylsulfonyloxy)pyridin-4-yl)-1,3,8-triazaspiro[4.5]decane-8-carboxylate (250 mg, 0.49 mmol) in N,N-dimethylformamide (30 mL) was added triethylsilane (114 mg, 0.98 mmol) and 1,1-bis(diphenylphosphino)ferrocene-palladium(I) dichloromethane complex (201 mg, 0.24 mmol). The resulting mixture was stirred under a nitrogen atmosphere for 3 hours. The reaction was quenched by addition of ice-water (20 mL) and the extracted with ethyl acetate (3×20 mL). The combined organic layers were washed with brine (10 mL), dried over anhydrous sodium sulfate and concentrated under reduced pressure. The residue was purified by silica gel column chromatography eluting with ethyl acetate to afford tert-butyl-3-methyl-2,4-dioxo-1-(pyridin-4-yl)-1,3,8-triazaspiro[4.5] decane-8-carboxylate (155 mg, 87%) as a white solid.

LCMS (ESI): m/z=361.2 [M+H]$^+$.

3-Methyl-1-(pyridin-4-yl)-1,3,8-triazaspiro[4.5]decane-2,4-dione hydrochloride

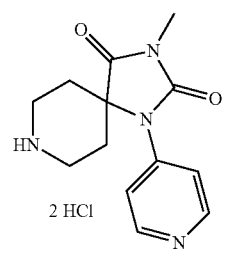

A solution of tert-butyl-3-methyl-2,4-dioxo-1-(pyridin-4-yl)-1,3,8-triazaspiro[4.5] decane-8-carboxylate (155 mg, 0.43 mmol) in hydrochloric acid in dioxane (6.0 M, 20 mL) was stirred for 30 minutes. The precipitate was collected by filtration and dried under reduced pressure to afford 3-methyl-1-(pyridin-4-yl)-1,3,8-triazaspiro[4.5]decane-2,4-dione hydrochloride as a white solid (142 mg, 100%).

LCMS (ESI): m/z=261.1 [M+H]$^+$.

(R)-2-Fluoro-N-(3-methyl-1-(3-methyl-2,4-dioxo-1-(pyridin-4-yl)-1,3,8-triazaspiro[4.5]decan-8-yl)-1-oxobutan-2-yl)-5-(trifluoromethyl)benzamide

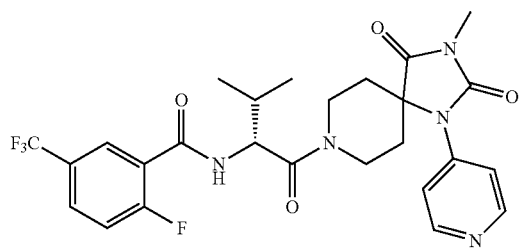 [SMILES: CC(C)[C@@H](NC(=O)c1cc(C(F)(F)F)ccc1F)C(=O)N1CCC2(CC1)C(=O)N(C)C(=O)N2c1ccncc1]

To a mixture of 3-methyl-1-(pyridin-4-yl)-1,3,8-triazaspiro[4.5]decane-2,4-dione hydrochloride (150 mg, 0.45 mmol) in dichloromethane (5 mL) was added sequentially (R)-2-(2-fluoro-5-(trifluoromethyl)benzamido)-3-methylbutanoic acid (prepared as described in Example 28-f) (240 mg, 0.32 mmol), (1-[bis(dimethylamino)methylene]-1H-1,2,3-triazolo[4,5-b]pyridinium-3-oxide hexafluorophosphate (HATU) (443 mg, 1.17 mmol) and N,N-diisopropylethylamine (252 mg, 1.95 mmol). The resulting mixture was stirred for 2 hours at room temperature before the reaction was quenched by addition of with ice-water (5 mL). The mixture was extracted with ethyl acetate (3×10 mL) and the combined organic layers were dried over anhydrous sodium sulfate and concentrated under reduced pressure. The residue was purified by prep-HPLC (acetonitrile and water, acetonitrile from 5% to 80%) to afford (R)-2-fluoro-N-(3-methyl-1-(3-methyl-2,4-dioxo-1-(pyridin-4-yl)-1,3,8-triazaspiro[4.5]decan-8-yl)-1-oxobutan-2-yl)-5-(trifluoromethyl)benzamide as white solid (110 mg, 26%).

LCMS (ESI): m/z=550.1 [M+H]$^+$.

$^1$H-NMR (400 MHz, CDCl$_3$): δ=1.09 (m, 6H), 1.97 (m, 2H), 2.35 (m, 2H), 2.98 (m, 1H), 3.23 (s, 3H), 3.53 (t, J=12.0 Hz, 1H), 4.08 (t, J=12.9 Hz, 1H), 4.29 (m, 1H), 4.83 (m, 2H), 7.34 (m, 2H), 7.86 (m, 1H), 8.27 (m, 2H), 8.68 (m, 2H), 10.84 (s, 1H).

Example 240

(R)-4-(8-(2-(2-Fluoro-5-(trifluoromethyl)benzamido)-3-methylbutanoy)-3-methyl-2,4-dioxo-1,3,8-triazaspiro[4.5]decan-1-yl)pyridine 1-oxide

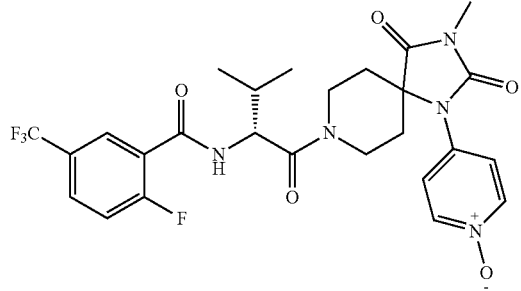

To a solution of (R)-2-fluoro-N-(3-methyl-1-(3-methyl-2,4-dioxo-1-(pyridin-4-yl)-1,3,8-triazaspiro[4.5]decan-8-yl)-1-oxobutan-2-yl)-5-(trifluoromethyl)benzamide (prepared as described in Example 239) (83 mg, 0.15 mmol) in chloroform (5 mL) was added m-chloroperbenzoic acid (53 mg, 0.3 mmol). The resulting mixture was stirred overnight. The solvent was removed under reduced pressure and the residue was purified by prep-HPLC (acetonitrile and water, acetonitrile from 5% to 80%) to afford (R)-4-(8-(2-(2-fluoro-5-(trifluoromethyl)benzamido)-3-methylbutanoyl)-3-methyl-2,4-dioxo-1,3,8-triazaspiro[4.5]decan-1-yl)pyridine 1-oxide as a white solid (70 mg, 82%).

LCMS (ESI): m/z=566.1 [M+H]$^+$.

$^1$H-NMR (400 MHz, CDCl$_3$): δ=1.07-1.10 (m, 6H), 1.89-2.26 (m, 4H), 2.67 (s, 1H), 3.19 (s, 3H), 3.51 (t, J=12.5 Hz, 1H), 4.06-4.20 (m, 2H), 4.75-4.88 (m, 2H), 7.29-7.52 (m, 3H), 7.82 (s, 2H), 8.29-8.40 (m, 3H).

Example 241

(R)-2-Fluoro-N-(1-(1-(4-methoxycyclohexyl)-3-methyl-2,4-dioxo-1,3,8-triazaspiro[4.5]decan-8-yl)-3-methyl-1-oxobutan-2-yl)-5-(trifluoromethyl)benzamide

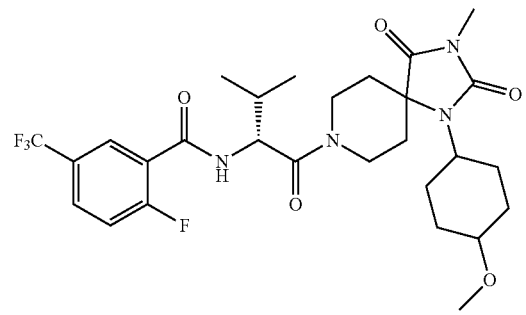 [SMILES: COC1CCC(N2C(=O)N(C)C(=O)C23CCN(C(=O)[C@H](NC(=O)c2cc(C(F)(F)F)ccc2F)C(C)C)CC3)CC1]

Representative Scheme:

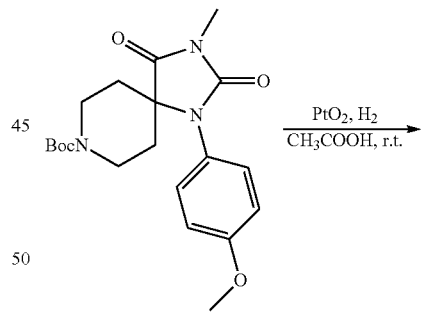

Example 168-d

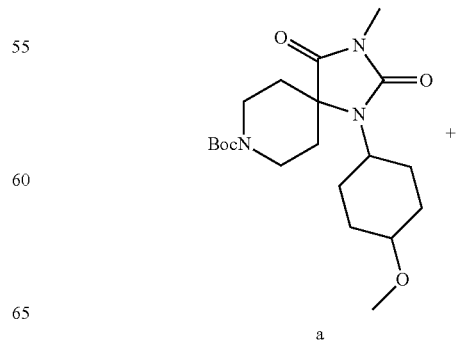

a

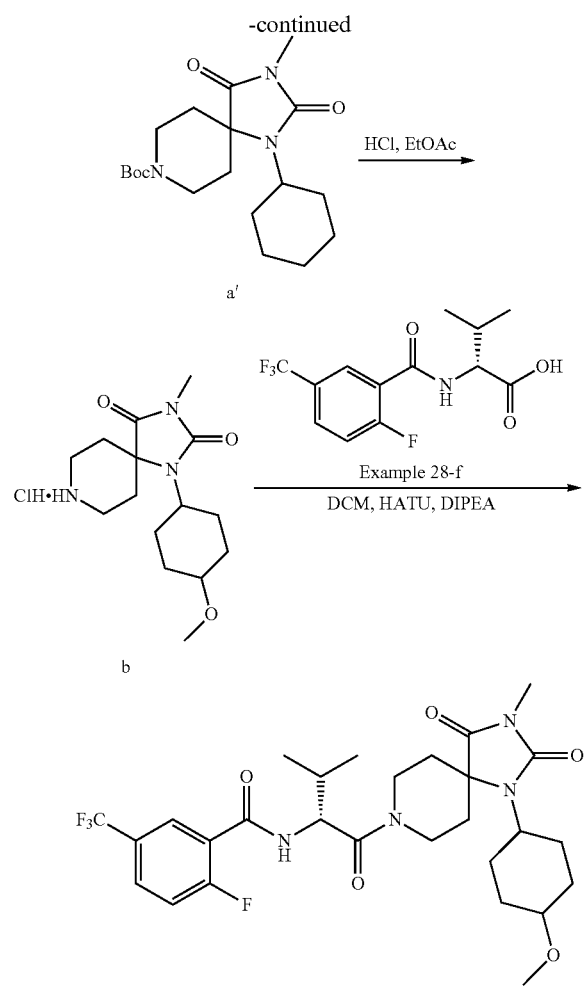

a' b

Representative General Procedure tert-Butyl-1-(4-methoxycyclohexyl)-3-methyl-2,4-dioxo-1,3,8-triazaspiro[4.5] decane-8-carboxylate

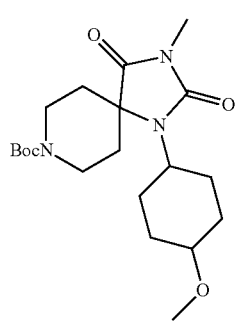

To a solution of tert-butyl-1-(4-methoxyphenyl)-3-methyl-2,4-dioxo-1,3,8-triazaspiro [4.5]decane-8-carboxylate (prepared as described in Example 168-d) (1.2 g, 3.08 mmol) in acetic acid (15 mL) was added platinum dioxide (50 mg, cat.). The mixture was stirred under a hydrogen atmosphere for 4 hours. The catalyst was removed by filtration and the filtrate was concentrated under reduced pressure. The residue was purified by a gel silica column chromatography eluting with petroleum ether:ethyl acetate 5:1 to afford tert-butyl-1-(4-methoxycyclohexyl)-3-methyl-2,4-dioxo-1,3,8-triazaspiro[4.5]decane-8-carboxylate as white solid (250 mg, 20%) and tert-butyl 1-cyclohexyl-3-methyl-2,4-dioxo-1,3,8-triazaspiro[4.5]decane-8-carboxylate (150 mg, 12%) as a white solid.

LCMS (ESI): m/z=396.1 (Example 241-a) and 366.1 (Example 241-a') [M+H]$^+$.

1-(4-Methoxycyclohexyl)-3-methyl-1,3,8-triazaspiro [4.5]decane-2,4-dione hydrochloride)

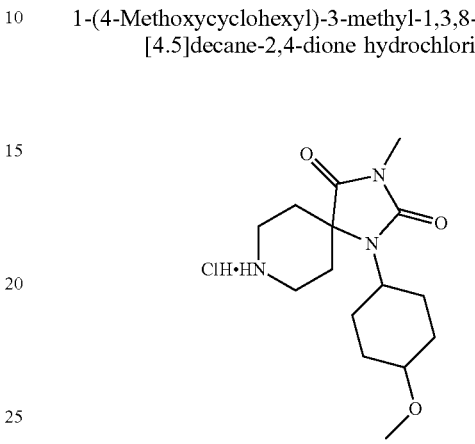

A solution of tert-butyl 1-(4-methoxycyclohexyl)-3-methyl-2,4-dioxo-1,3,8-triazaspiro[4.5]decane-8-carboxylate (250 mg, 0.63 mmol) in hydrochloric acid in dioxane (6.0 M, 20 mL) was stirred for 30 minutes. The precipitate was collected by filtration and dried under reduced pressure to afford 1-(4-methoxycyclohexyl)-3-methyl-1,3,8-triazaspiro[4.5]decane-2,4-dione hydrochloride) as a white solid (170 mg, 85%).

LCMS (ESI): m/z=296.1 [M+H]$^+$.

(R)-2-Fluoro-N-(1-(1-(4-methoxycyclohexyl)-3-methyl-2,4-dioxo-1,3,8-triazaspiro[4.5]decan-8-yl)-3-methyl-1-oxobutan-2-yl)-5-(trifluoromethyl)benzamide

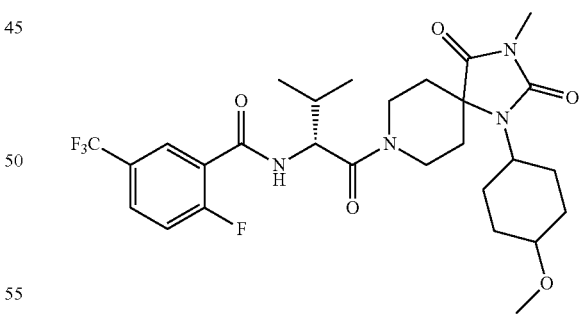

To a mixture of 1-(4-methoxycyclohexyl)-3-methyl-1,3,8-triazaspiro [4.5]decane-2,4-dione hydrochloride) (70 mg, 0.17 mmol) in dichloromethane (5 mL) was added sequentially (R)-2-(2-fluoro-5-(trifluoromethyl)benzamido)-3-methyl-butanoic acid (prepared as described in Example 28-f) (57 mg, 0.19 mmol), (1-[bis(dimethylamino)methylene]-1H-1,2,3-triazolo[4,5-b]pyridinium-3-oxide hexafluorophosphate (HATU) (96 mg, 0.25 mmol) and N,N-diisopropylethylamine (150 mg, 1.164 mmol). The resulting mixture was stirred for 2 hours at room temperature before the reaction was quenched by addition of with ice-water (5 mL). The mixture was extracted with ethyl acetate (3×10 mL) and the combined organic layers were dried over anhydrous sodium sulfate and concentrated under reduced pressure. The residue was purified by prep-TLC with dichloromethane:methanol=15:1 to afford (R)-2-fluoro-N-(1-(1-(4-methoxycyclohexyl)-3-methyl-2,4-dioxo-1,3,8-triazaspiro[4.5]decan-8-yl)-3-methyl-1-oxobutan-2-yl)-5-(trifluoromethyl)benzamide (14.6 mg, 15%) as a white solid.

LCMS (ESI): m/z=585.2 [M+H]⁺.

¹H-NMR (400 MHz, CD₃OD): δ=1.050-1.111 (m, 6H), 1.307-1.439 (m, 5H), 1.713-2.292 (m, 6H), 2.292-2.680 (m, 3H), 2.952 (s, 3H), 3.069-3.204 (m, 1H), 3.321-3.33 (m, 3H), 3.368-3.502 (m, 2H), 3.840-4.016 (m, 1H), 4.211-4.02 (m, 1H), 4.518-4.658 (m, 1H), 7.422-7.535 (m, 1H), 7.861-7.943 (m, 1H), 8.006-8.132 (m, 1H).

Example 242

(R)—N-(1-(1-Cyclohexyl-3-methyl-2,4-dioxo-1,3,8-triazaspiro[4.5] decan-8-yl)-3-methyl-1-oxobutan-2-yl)-2-fluoro-5-(trifluoromethyl)benzamide

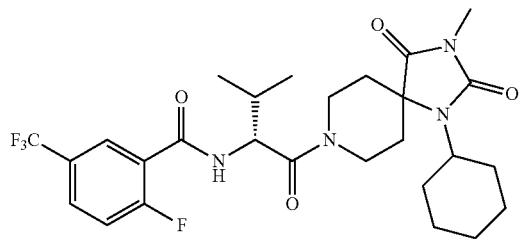 [SMILES: CC(C)[C@@H](NC(=O)c1cc(C(F)(F)F)ccc1F)C(=O)N1CCC2(CC1)C(=O)N(C)C(=O)N2C1CCCCC1]

Representative Scheme:

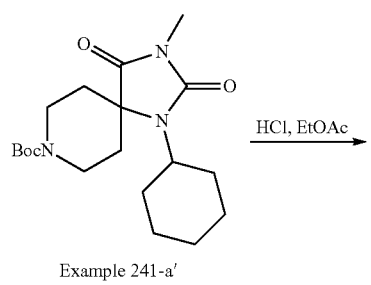

Example 241-a'

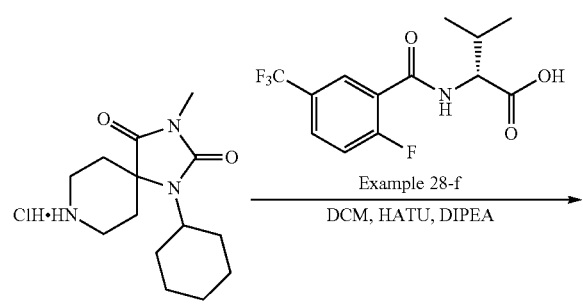

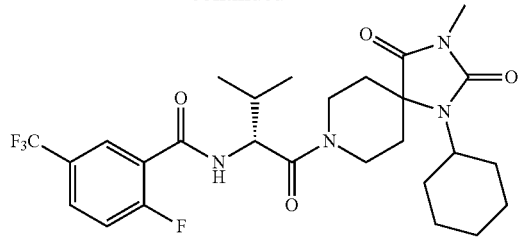

Representative General Procedure

1-Cyclohexyl-3-methyl-1,3,8-triazaspiro[4.5]decane-2,4-dione hydrochloride

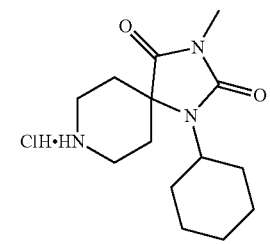

A solution of tert-butyl-1-cyclohexyl-3-methyl-2,4-dioxo-1,3,8-triazaspiro[4.5] decane-8-carboxylate (prepared as described in Example 241) (150 mg, 0.41 mmol) in hydrochloric acid in dioxane (6.0 M, 20 mL) was stirred for 30 minutes. The precipitate was collected by filtration and dried under reduced pressure to afford 1-cyclohexyl-3-methyl-1,3,8-triazaspiro[4.5]decane-2,4-dione hydrochloride (90 mg, 73%) as a white solid.
LCMS (ESI): m/z=266.1 [M+H]⁺.

(R)—N-(1-(1-Cyclohexyl-3-methyl-2,4-dioxo-1,3,8-triazaspiro[4.5] decan-8-yl)-3-methyl-1-oxobutan-2-yl)-2-fluoro-5-(trifluoromethyl)benzamide

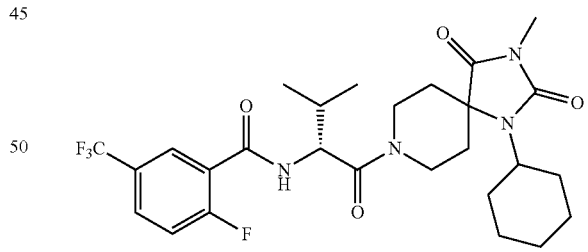

To a mixture of 1-cyclohexyl-3-methyl-1,3,8-triazaspiro[4.5]decane-2,4-dione hydrochloride (90 mg, 0.29 mmol) in dichloromethane (5 mL) was added sequentially (R)-2-(2-fluoro-5-(trifluoromethyl)benzamido)-3-methylbutanoic acid (prepared as described in Example 28-f) (98 mg, 0.32 mmol), (1-[bis(dimethylamino)methylene]-1H-1,2,3-triazolo[4,5-b]pyridinium-3-oxide hexafluorophosphate (HATU) (165 mg, 0.43 mmol) and N,N-diisopropylethylamine (110 mg, 0.89 mmol). The resulting mixture was stirred for 2 hours at room temperature before the reaction was quenched by addition of with ice-water (5 mL). The mixture was extracted with ethyl acetate (3×10 mL) and the combined organic layers were dried over anhydrous sodium sulfate and concentrated under reduced pressure. The residue was purified by prep-TLC with dichloromethane:methanol=15:1 to afford (R)—N-(1-(1-cyclohexyl-3-methyl-2,4-dioxo-1,3,8-triazaspiro[4.5]decan-8-yl)-3-methyl-1-oxobutan-2-yl)-2-fluoro-5-(trifluoromethyl)benzamide as a white solid (34.3 mg, 21%).

LCMS (ESI): m/z=555.2 [M+H]$^+$.

$^1$H-NMR (400 MHz, CDCl3): δ=1.035-1.121 (m, 6H), 1.225-1.279 (m, 3H), 1.514-1.893 (m, 8H), 2.159-2.287 (m, 4H), 2.675-2.902 (m, 1H), 3.013 (s, 3H), 3.384-3.534 (m, 1H), 4.003-4.051 (m, 2H), 4.658-4.688 (m, 1H), 4.929-5.192 (m, 1H), 7.285-7.350 (m, 1H), 7.482-7.509 (m, 1H), 7.785-7.803 (m, 1H), 8.389-8.406 (m, 1H).

Example 243

(R)—N-(3-Methyl-1-(3-methyl-2,4-dioxo-1-(4-methoxy-d$^3$-phenyl)-1,3,8-triazaspiro[4.5]decan-8-yl)-1-oxobutan-2-yl)-3-(trifluoromethyl)-5-fluorobenzamide

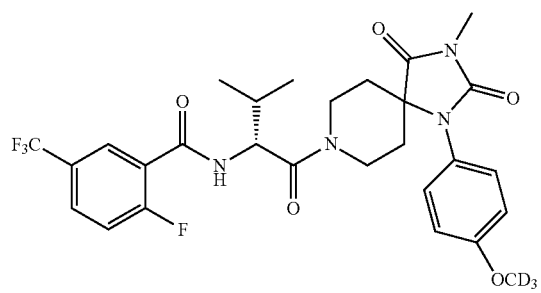

Representative Scheme:

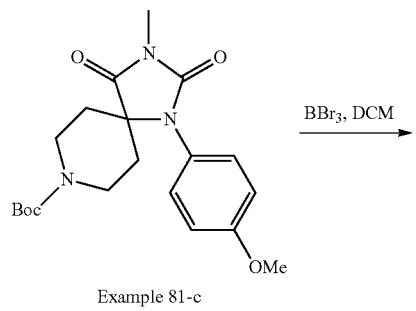

Example 81-c

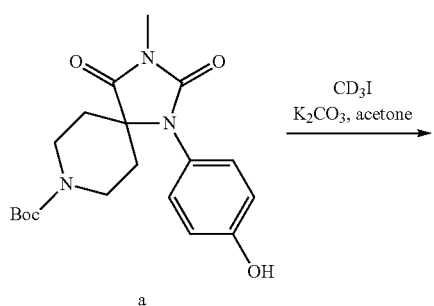

a

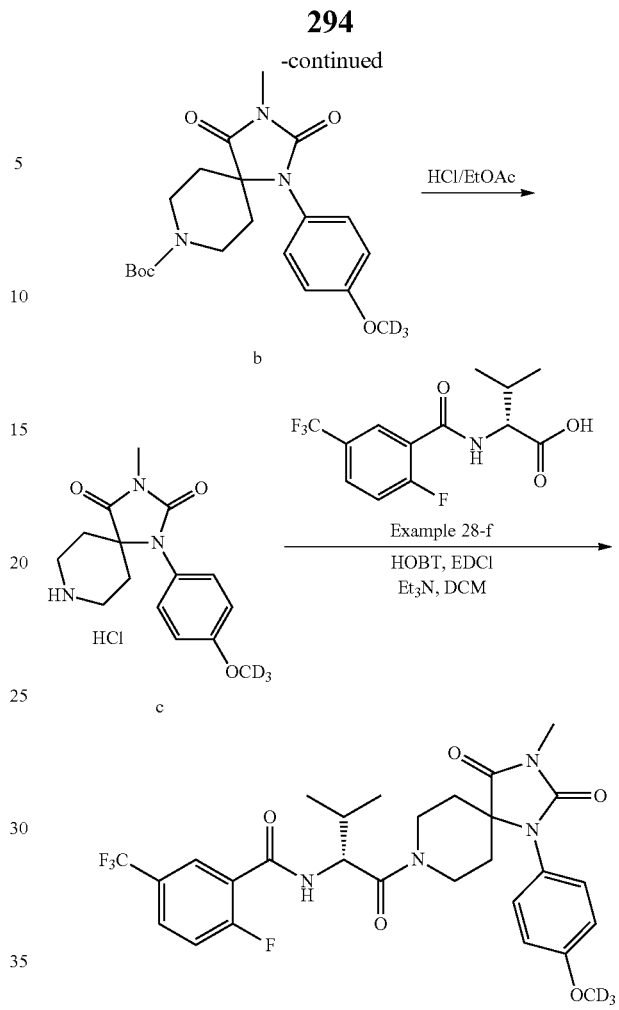

Representative General Procedure tert-Butyl-1-(4-hydroxyphenyl)-3-methyl-2,4-dioxo-1,3,8-triazaspiro[4.5]decane-8-carboxylate

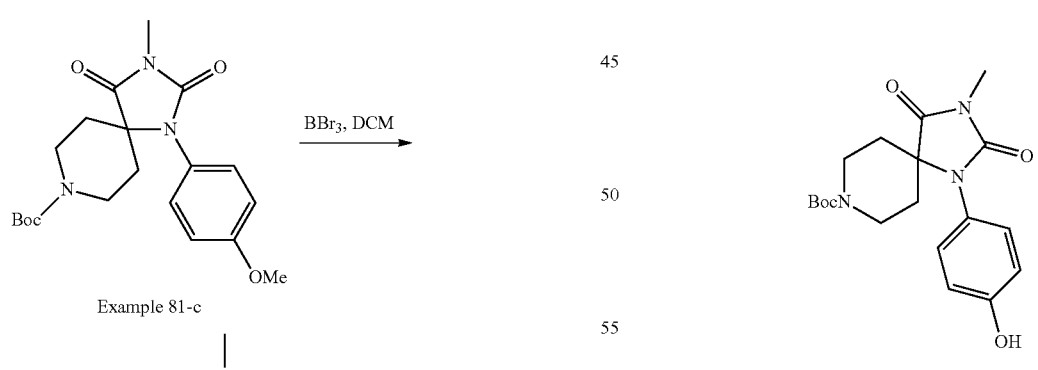

To a solution of tert-butyl-1-(4-methoxyphenyl)-3-methyl-2,4-dioxo-1,3,8-triazaspiro[4.5]decane-8-carboxylate (prepared as described in Example 81-c) (0.6 g, 1.54 mmol) in anhydrous dichloromethane (30 mL) was added boron tribromide (3 mL, 1.0 M in dichloromethane) dropwise at 0° C. Then the solution was stirred at room temperature for 12 hours before the reaction was quenched with water. The aqueous layer was extracted with dichloromethane (30 mL), the combined organic layers were dried over anhydrous sodium sulfate and concentrated under reduced pressure to afford tert-butyl-1-(4-hydroxyphenyl)-3-methyl-2,4-dioxo-1,3,8-triazaspiro[4.5]decane-8-carboxylate as a yellow solid (390 mg, 65%).

LCMS (ESI): m/z=376.2 [M+H]⁺.

tert-Butyl-1-(4-methoxy-d³-phenyl)-3-methyl-2,4-dioxo-1,3,8-triazaspiro[4.5]decane-8-carboxylate

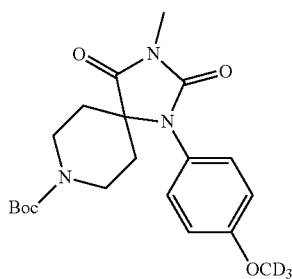

To a solution of tert-butyl-1-(4-hydroxyphenyl)-3-methyl-2,4-dioxo-1,3,8-triazaspiro[4.5]decane-8-carboxylate (0.375 g, 1 mmol) in acetone (30 mL) was added potassium carbonate (0.278 g, 2 mmol) and iodomethane-d³ (0.29 g, 2 mmol), then the resulting mixture was stirred at 60° C. for 6 hours. Then the mixture was concentrated under reduced pressure and the residue was purified by silica gel column chromatography eluting with ethyl acetate:petroleum=1:2 to afford tert-butyl-1-(4-methoxy-d³-phenyl)-3-methyl-2,4-dioxo-1,3,8-triazaspiro[4.5]decane-8-carboxylate as a white solid (210 mg, 54%).

LCMS (ESI): m/z=393.2 [M+H]⁺.

3-Methyl-1-(4-methoxy-d³-phenyl)-1,3,8-triazaspiro[4.5]decane-2,4-dione hydrochloride

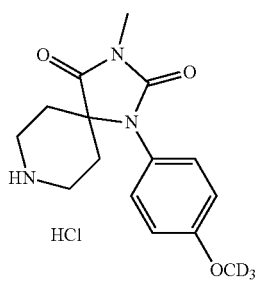

Hydrogen chloride gas was bubbled into a stirring solution of tert-butyl-1-(4-methoxy-d³-phenyl)-3-methyl-2,4-dioxo-1,3,8-triazaspiro[4.5]decane-8-carboxylate (0.21 g, 0.54 mmol) in ethyl acetate (10 mL) for 0.5 hours. Then the mixture was concentrated under reduced pressure to afford 3-methyl-1-(4-methoxy-d³-phenyl)-1,3,8-triazaspiro[4.5]decane-2,4-dione hydrochloride as a white solid (0.17 g, 100%).

LCMS (ESI): m/z=293.2 [M+H]⁺.

(R)—N-(3-Methyl-1-(3-methyl-2,4-dioxo-1-(4-methoxy-d³-phenyl)-1,3,8-triazaspiro[4.5]decan-8-yl)-1-oxobutan-2-yl)-3-(trifluoromethyl)-5-fluorobenzamide

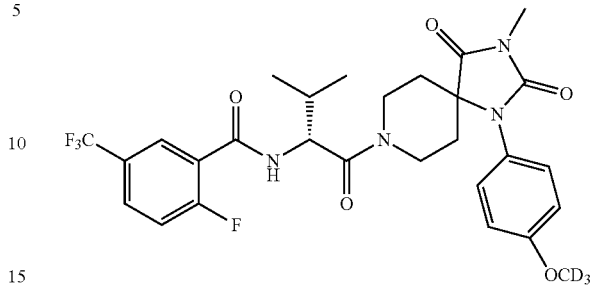

To a solution of 3-methyl-1-(4-methoxy-d³-phenyl)-1,3,8-triazaspiro[4.5]decane-2,4-dione hydrochloride (0.17 g, 0.53 mmol), (R)-2-(2-fluoro-5-(trifluoromethyl)benzamido)-3-methylbutanoic acid (0.196 g, 0.64 mmol) (prepared as described in Example 28-f) and triethylamine (0.16 g, 1.6 mmol) in dichloromethane (20 mL) was added 1-ethyl-3-(3-dimethylaminopropyl)carbodiimide hydrochloride (EDCl) (0.153 g, 0.8 mmol) and 1-hydroxybenzotriazole (HOBT) (0.108 g, 0.8 mmol), then the resulting mixture was stirred at room temperature for 4 hours before the reaction was quenched with water (20 mL). The aqueous layer was extracted with ethyl acetate (3×20 mL), the combined organic layers were dried over anhydrous sodium sulfate and concentrated under reduced pressure. The residue was purified by silica gel column chromatography eluting with dichloromethane:methanol=70:1 to afford (R)—N-(3-methyl-1-(3-methyl-2,4-dioxo-1-(4-methoxy-d³-phenyl)-1,3,8-triazaspiro[4.5]decan-8-yl)-1-oxobutan-2-yl)-3-(trifluoromethyl)-5-fluorobenzamide as a white solid (0.1 g, 33%).

LCMS (ESI): m/z=582.2 [M+H]⁺.

¹H-NMR (400 MHz, CD₃OD): δ=8.05-7.85 (m, 2H), 7.44 (dd, J=20.0, 11.1 Hz, 1H), 7.22 (d, J=8.8 Hz, 1H), 7.13 (d, J=8.8 Hz, 1H), 7.04 (d, J=8.8 Hz, 1H), 6.91 (d, J=8.8 Hz, 1H), 4.85 (s, 1H), 4.45 (dd, J=35.0, 13.1 Hz, 1H), 4.23 (dd, J=30.7, 14.0 Hz, 1H), 3.95 (t, J=13.1 Hz, 1H), 3.49 (dd, J=14.4, 11.6 Hz, 1H), 3.08 (s, 3H), 2.22-1.99 (m, 3H), 1.96-1.81 (m, 1H), 1.71 (td, J=13.1, 4.8 Hz, 1H), 1.05-0.73 (m, 6H).

The following compound was synthesized following the procedure described above:

Example 244

(R)—N-(3-Methyl-1-(3-methyl-2,4-dioxo-1-(4-ethoxyphenyl)-1,3,8-triazaspiro[4.5]decan-8-yl)-1-oxobutan-2-yl)-3-(trifluoromethyl)-5-fluorobenzamide

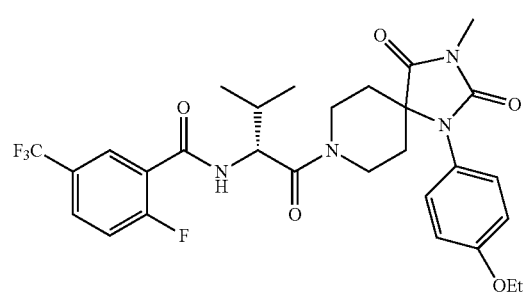 [SMILES: CCOc1ccc(N2C(=O)N(C)C(=O)C23CCN(C(=O)[C@H](NC(=O)c2cc(C(F)(F)F)ccc2F)C(C)C)CC3)cc1]

17 mg, 23% yield, white solid.
LCMS (ESI): m/z=593.2 [M+H]⁺.
¹H-NMR (400 MHz, CD₃OD): δ=8.02-7.90 (m, 2H), 7.47-7.37 (m, 1H), 7.20 (d, J=8.8 Hz, 1H), 7.11 (d, J=8.8 Hz, 1H), 7.03 (d, J=8.8 Hz, 1H), 6.89 (d, J=8.8 Hz, 1H), 4.49 (d, J=13.4 Hz, 1H), 4.27 (d, J=13.9 Hz, 1H), 4.12 (d, J=7.1 Hz, 2H), 4.10-3.90 (m, 3H), 3.49 (t, J=12.8 Hz, 1H), 3.08 (s, 3H), 2.25-2.05 (m, 2H), 1.94 (m, 1H), 1.71 (m, 1H), 1.44-1.30 (m, 4H), 1.27 (dd, J=16.9, 9.8 Hz, 3H), 1.07-0.76 (m, 7H).
Example 245
(R)—N-(1-(1-(Benzo[d]oxazol-5-yl)-3-methyl-2,4-dioxo-1,3,8-triazaspiro[4.5]decan-8-yl)-3-methyl-1-oxobutan-2-yl)-2-fluoro-5-(trifluoromethyl)benzamide
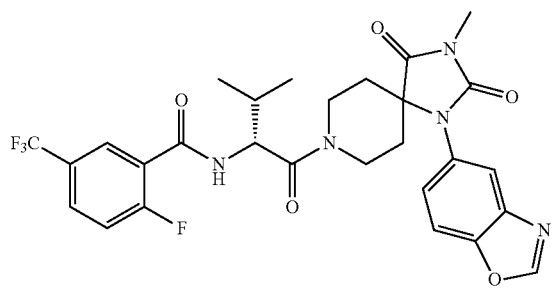 [SMILES: CC(C)[C@@H](NC(=O)c1cc(C(F)(F)F)ccc1F)C(=O)N1CCC2(CC1)C(=O)N(C)C(=O)N2c1ccc2ocnc2c1]
Representative Scheme:
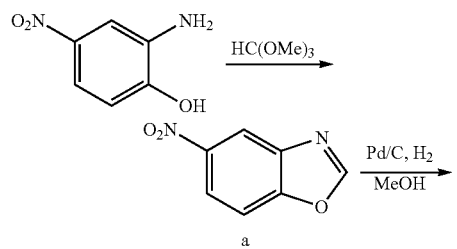
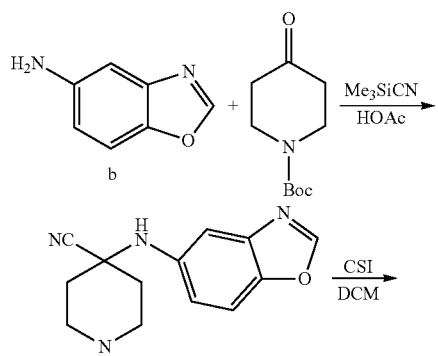
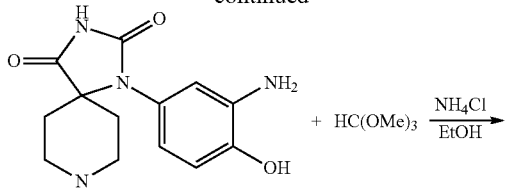
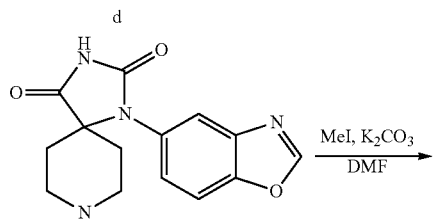
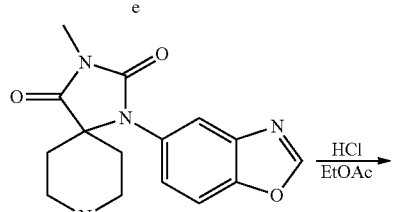
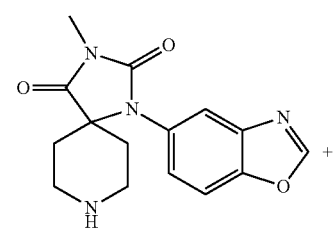
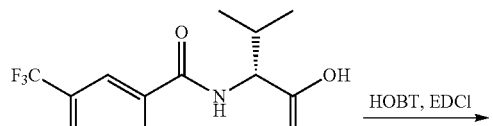
Example 28-f
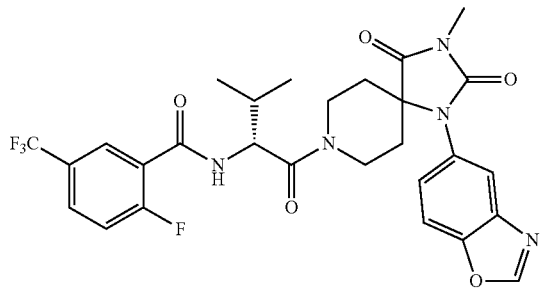

Representative General Procedure

5-Nitrobenzo[d]oxazole

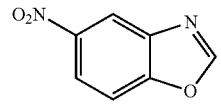

A solution of 2-amino-4-nitrophenol (600 mg, 3.9 mmol) in trimethyl orthoformate (30 mL) was stirred at reflux for 12 hours. The reaction mixture was slowly poured into ice-cold water (100 mL) and extracted with ethyl acetate (100 mL). The organic layer was concentrated under reduced pressure and the residue was purified by silica gel column chromatography eluting with dichloromethane:methanol=30:1 to afford 5-nitrobenzo[d]oxazole as a white solid (530 mg, 83%).

LCMS (ESI): m/z=164.0 [M+H]$^+$.

Benzo[d]oxazol-5-amine

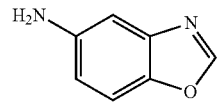 [SMILES: O=[N+]([O-])c1ccc2ocnc2c1]

To a solution of 5-nitrobenzo[d]oxazole (530 mg, 3.23 mmol) in methanol (30 mL) was added palladium on carbon (100 mg, dry, 5%). The mixture was stirred under a hydrogen gas atmosphere at room temperature for 12 hours. The catalyst was removed by filtration and the filtrate was concentrated to dryness under reduced pressure to afford benzo[d]oxazol-5-amine as a yellow solid (430 mg, 100%).

LCMS (ESI): m/z=134.1 [M+H]$^+$.

tert-Butyl-4-(benzo[d]oxazol-5-ylamino)-4-cyanopiperidine-1-carboxylate

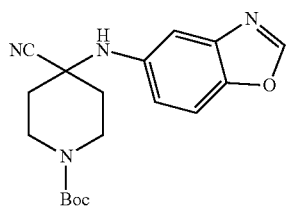 [SMILES: CC(C)(C)OC(=O)N1CCC(C#N)(Nc2ccc3ocnc3c2)CC1]

A mixture of benzo[d]oxazol-5-amine (430 mg, 3.2 mmol) and tert-butyl-4-oxopiperidine-1-carboxylate (637 mg, 3.2 mmol) in acetic acid (10 mL) was stirred at 0° C. for 15 minutes, then trimethylsilyl cyanide (317 mg, 3.2 mmol) was added. The reaction mixture was stirred for 4 hours at room temperature. Then the mixture was slowly poured into concentrated aqueous ammonium hydroxide solution (30 mL) and extracted with ethyl acetate (50 mL). The organic layer was dried over anhydrous sodium sulfate, concentrated under reduced pressure and the residue was purified by silica gel column chromatography eluting with dichloromethane:methanol=40:1 to afford tert-butyl-4-(benzo[d]oxazol-5-ylamino)-4-cyanopiperidine-1-carboxylate as a white solid (500 mg, 46%).

LCMS (ESI): m/z=342.2 [M+H]$^+$.

tert-Butyl-1-(3-amino-4-hydroxyphenyl)-2,4-dioxo-1,3,8-triazaspiro[4.5]decane-8-carboxylate

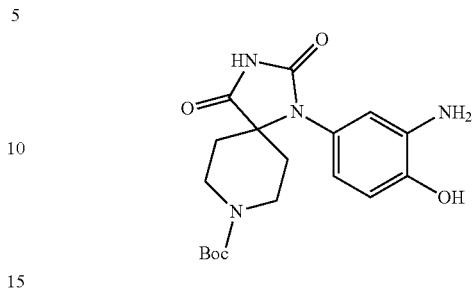

To a solution of tert-butyl-4-(benzo[d]oxazol-5-ylamino)-4-cyanopiperidine-1-carboxylate (500 mg, 1.5 mmol) in dichloromethane (30 mL) was added chlorosulfonyl isocyanate (0.31 mL, 1.65 mmol) dropwise over 15 minutes at 0° C. The mixture was stirred for 1 hour at room temperature and then concentrated under reduced pressure. The residue was dissolved in 1.0 M aqueous hydrochloric acid solution (20 mL) and stirred at reflux for 1 hour. Then the pH of the solution was adjusted to pH 9 by addition of solid potassium carbonate. To the solution was added di-tert-butyl dicarbonate (360 mg, 1.65 mmol) and the reaction mixture was stirred for 12 hours. The mixture was extracted with dichloromethane/methanol=10:1 (60 mL), the organic layer was dried over anhydrous sodium sulfate and concentrated to dryness to afford tert-butyl-1-(3-amino-4-hydroxyphenyl)-2,4-dioxo-1,3,8-triazaspiro[4.5]decane-8-carboxylate as a brownish solid (crude, 500 mg, 88%).

LCMS (ESI): m/z=376.2 [M+H]$^+$.

tert-Butyl-1-(benzo[d]oxazol-5-yl)-2,4-dioxo-1,3,8-triazaspiro[4.5] decane-8-carboxylate

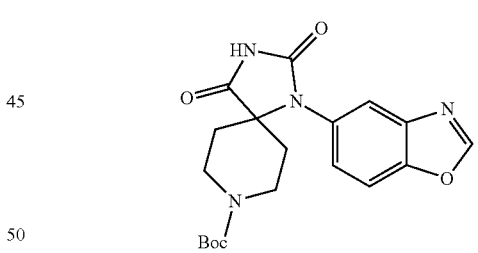

To a solution of tert-butyl-1-(3-amino-4-hydroxyphenyl)-2,4-dioxo-1,3,8-triazaspiro[4.5]decane-8-carboxylate (500 mg, 1.3 mmol) and ammonium chloride (53 mg, 0.15 mmol) in ethanol (30 mL) was added trimethyl orthoformate (5 mL). Then the mixture was stirred for 12 hours at 60° C. The reaction mixture was concentrated under reduced pressure and the residue was purified by silica gel column chromatography eluting with dichloromethane:methanol=20:1 to afford tert-butyl-1-(benzo[d]oxazol-5-yl)-2,4-dioxo-1,3,8-triazaspiro[4.5]decane-8-carboxylate as a white solid (470 mg, 94%).

LCMS (ESI): m/z=386.2 [M+H]$^+$. tert-Butyl-1-(benzo[d]oxazol-5-yl)-3-methyl-2,4-dioxo-1,3,8-triazaspiro[4.5]decane-8-carboxylate

301

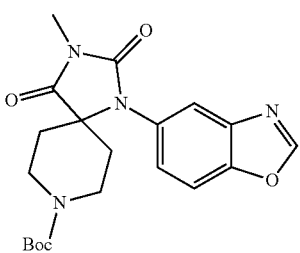 [SMILES: CN1C(=O)N(c2ccc3ocnc3c2)C2(CCN(C(=O)OC(C)(C)C)CC2)C1=O]

To a mixture of tert-butyl-1-(benzo[d]oxazol-5-yl)-2,4-dioxo-1,3,8-triazaspiro[4.5]decane-8-carboxylate (470 mg, 1.2 mmol) and potassium carbonate (337 mg, 2.4 mmol) in N,N-dimethylformamide (10 mL) was added iodomethane (190 mg, 1.34 mmol) and then the mixture was stirred for 1 hour at room temperature. The mixture was concentrated under reduced pressure and the residue was purified by silica gel column chromatography eluting with dichloromethane:methanol=20:1 to afford tert-butyl-1-(benzo[d]oxazol-5-yl)-3-methyl-2,4-dioxo-1,3,8-triazaspiro[4.5]decane-8-carboxylate as a white solid (347 mg, 72%).

LCMS (ESI): m/z=400.2 [M+H]$^+$.

1-(Benzo[d]oxazol-5-yl)-3-methyl-1,3,8-triazaspiro[4.5]decane-2,4-dione hydrochloride

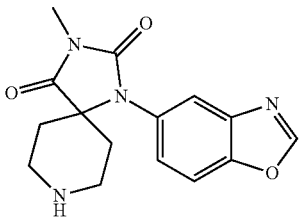 [SMILES: CN1C(=O)N(c2ccc3ocnc3c2)C2(CCNCC2)C1=O]

tert-Butyl-1-(benzo[d]oxazol-5-yl)-3-methyl-2,4-dioxo-1,3,8-triazaspiro[4.5]decane-8-carboxylate (347 mg, 0.87 mmol) was dissolved in a solution of hydrochloric acid in ethyl acetate (2.0 M, 10 mL). The mixture was stirred for 4 hours at room temperature before it was concentrated under reduced pressure to afford crude 1-(benzo[d]oxazol-5-yl)-3-methyl-1,3,8-triazaspiro[4.5]decane-2,4-dione hydrochloride as a white solid (247 mg, 95%), which was used directly in the next step without further purification.

LCMS (ESI): m/z=300.1 [M+H]$^+$.

(R)—N-(1-(1-(Benzo[d]oxazol-5-yl)-3-methyl-2,4-dioxo-1,3,8-triazaspiro[4.5]decan-8-yl)-3-methyl-1-oxobutan-2-yl)-2-fluoro-5-(trifluoromethyl)benzamide

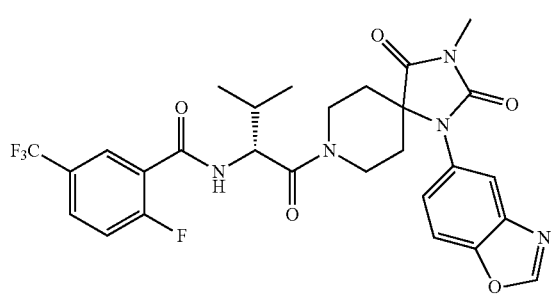 [SMILES: CC(C)[C@@H](NC(=O)c1cc(C(F)(F)F)ccc1F)C(=O)N1CCC2(CC1)C(=O)N(C)C(=O)N2c1ccc2ocnc2c1]

To a mixture of 1-(benzo[d]oxazol-5-yl)-3-methyl-1,3,8-triazaspiro[4.5]decane-2,4-dione hydrochloride (247 mg, 0.82 mmol), (R)-2-(2-fluoro-5-(trifluoromethyl)benzamido)-3-methylbutanoic acid (252 mg, 0.82 mmol) (prepared as described in Example 28-f), 1-ethyl-3-(3-dimethylaminopropyl)carbodiimide hydrochloride (250 mg, 1.3 mmol), and N-hydroxybenzotriazole (176 mg, 1.3 mmol) in dichloromethane (20 mL) was added triethylamine (0.5 mL) at room temperature. The mixture was stirred at room temperature for 5 hours, before it was washed with water (30 mL). The organic layer was concentrated to dryness under reduced pressure and the residue was purified by silica gel column chromatography eluting with dichloromethane:methanol:ammonium hydroxide=20:1:0.1 to afford (R)—N-(1-(1-(benzo[d]oxazol-5-yl)-3-methyl-2,4-dioxo-1,3,8-triazaspiro[4.5]decan-8-yl)-3-methyl-1-oxobutan-2-yl)-2-fluoro-5-(trifluoromethyl)benzamide as a yellow solid (16.6 mg, 3.4%).

LCMS (ESI): m/z=589.2 [M+H]$^+$.

$^1$H-NMR (400 MHz, CD$_3$OD): δ=8.55 (s, 1H), 8.06-7.74 (m, 3H), 7.73-7.66 (m, 1H), 7.43 (dd, J=18.7, 9.0 Hz, 1H), 7.37-7.28 (m, 1H), 4.86-4.78 (m, 1H), 4.58-4.37 (m, 1H), 4.34-4.15 (m, 1H), 3.97 (t, J=12.0 Hz, 1H), 3.51 (t, J=12.0 Hz, 1H), 3.12 (s, 3H), 2.32-1.87 (m, 4H), 1.83-1.67 (m, 1H), 0.99 (t, J=6.2 Hz, 4H), 0.87 (d, J=6.7 Hz, 1H), 0.73 (d, J=6.7 Hz, 1H).

The following compound was synthesized following the procedure described above:

Example 246

(R)—N-(1-(1-(2-Methylbenzo[d]oxazol-5-yl)-3-methyl-2,4-dioxo-1,3,8-triazaspiro[4.5]decan-8-yl)-3-methyl-1-oxobutan-2-yl)-2-fluoro-5-(trifluoromethyl)benzamide

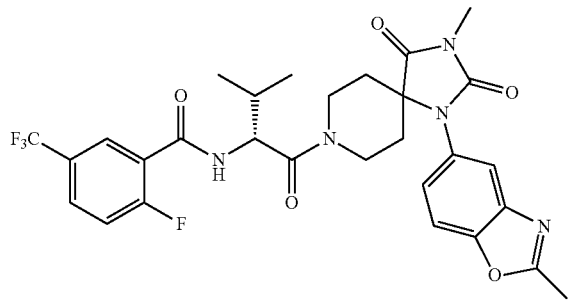 [SMILES: Cc1nc2cc(N3C(=O)N(C)C(=O)C34CCN(C(=O)[C@H](NC(=O)c3cc(C(F)(F)F)ccc3F)C(C)C)CC4)ccc2o1]

40 mg, 36% yield, white solid.

LCMS (ESI): m/z=603.2 [M+H]$^+$.

$^1$H-NMR (400 MHz, CD$_3$OD): δ=7.92-7.82 (m, 1H), 7.74 (dd, J=24.9, 7.4 Hz, 1H), 7.63-7.41 (m, 2H), 7.33 (t, J=9.5 Hz, 1H), 7.22 (dd, J=8.6, 1.9 Hz, 1H), 4.83 (d, J=7.8 Hz, 1H), 4.47 (dd, J=43.4, 13.8 Hz, 1H), 4.24 (dd, J=29.4, 12.7 Hz, 1H), 3.96 (t, J=13.3 Hz, 1H), 3.51 (t, J=13.8 Hz, 1H), 3.11 (s, 3H), 2.66 (d, J=26.8 Hz, 3H), 2.27-2.08 (m, 2H), 2.06-1.96 (m, 1H), 1.80-1.60 (m, 1H), 1.00-0.71 (m, 6H).

Analytical Conditions

Unless otherwise noted, all solvents, chemicals, and reagents were obtained commercially and used without purification. The $^1$H-NMR spectra were obtained in CDCl$_3$, DMSO-d$_6$, CD$_3$OD, or acetone-d$_6$ at 25° C. at 300 MHz or 400 MHz on an OXFORD (Varian) with chemical shift (δ, ppm) reported relative to TMS as an internal standard.

HPLC-MS chromatograms and spectra were obtained with an Agilent 1200-6110 system. Prep-HPLC instruments were Gilson GX-281 (Gilson) and P230 Preparative Gradient System (Gradient: 95% water, 5% acetonitrile, 30-50 min gradient to 25% water, 75% acetonitrile). The microwave instrument was a CEM Discover SP.

Biological Properties

The efficacy of the Examples described herein, as inhibitors of ATX are demonstrated and confirmed by pharmacological in vitro assays. The following assays and their respective methods are carried out with the compounds according to the present invention. Activity possessed by the compounds may be demonstrated in vivo. Those skilled in the art will appreciate that a variety of assay formats may be used to determine the activity of the compounds of this invention.

Autotaxin LPC Cascade Assay:
Assay Buffer:
100 mM Tris-HCl, pH=9
500 mM NaCl
5 mM $MgCl_2$
5 mM $CaCl_2$
0.05% Triton X 100
Reagents:

| Enzyme | Source | Stock conc | Working conc. | Final conc. |
|---|---|---|---|---|
| Autotaxin | X-Chem | 4.6 µM | 20 nM | 5 nM |
| LPC | Sigma L5254 | 8 mM in assay buffer | 400 µM | 100 µM |
| Choline Oxidase | Sigma C5896 | 50 U/mL in water | 0.8 U/mL | 0.1 U/mL |
| HRP | Sigma P8375 | 1000 U/mL in water | 8 U/mL | 1 U/mL |
| Ampliflu Red | Sigma 90101 | 100 mM in DMSO | 400 µM | 50 µM |

HA130 and Test Compounds:

Highest final concentration is 10 M for HA130 (Echelon, B-0701) and 30 M for test compounds. Prepare a 1 mM stock of HA130 and a 3 mM stock of each compound in 100% DMSO. Perform a 1:3 serial dilution in DMSO (transfer 5 l of compound to 10 l of DMSO). Add 240 l of buffer to generate a top working concentration of 40 M (HA130) and 120 M (test compound) in 4% DMSO.

Ampliflu Red—Prepare a stock of 5 mM from 100 mM in 100% DMSO. Further dilute to a working concentration of 400 µM in buffer (8% DMSO).

Together with compound this yields a 2% DMSO final concentration.

Choline Oxidase/HRP—0.8 U/mL CO and 8 U/mL HRP.

Assay Conditions:

Add 5 l of ATX and 5 l of compound in a 384 well plate (Corning 3676). Incubate for 10 mins at RT. Add 5 l of LPC and incubate for 1 hr on the plate shaker. Prepare the CO/HRP and AR immediately prior to use. Add 2.5 l of CO/HRP and follow with 2.5 l AR. Note order of addition, CO/HRP mix before AR. Read fluorescence intensity (ex/em: 530/590 nm) kinetically for 30 min at RT on the Tecan M1000.

TABLE 1

$IC_{50}$ ATX Activity Values For Examples 1-246

| $IC_{50}$ (nM) | Examples |
|---|---|
| ≥1000 | 2, 11, 15, 16, 17, 19, 22, 34, 35, 36, 38, 53, 61, 65, 67, 68, 69, 70, 71, 72, 73, 74, 75, 78, 80, 81, 85, 86, 87, 93, 106, 111, 113, 114, 115, 117, 121, 122, 123, 126, 130, 132, 137, 143, 146, 148, 158, 159, 164, 180, 195, 217, 219, 228, 229, 230, 231, 232, 233, 234, 235, 236, 240, 241. |
| ≥500 ≤1000 | 3, 9, 23, 29, 30, 33, 46, 47, 63, 66, 76, 77, 79, 82, 92, 95, 102, 103, 120, 127, 128, 129, 145, 161, 176, 188, 189. |
| ≥0 ≤500 | 1, 4, 5, 6, 7, 8, 10, 12, 13, 14, 18, 20, 21, 24, 25, 26, 27, 28, 31, 32, 37, 39, 40, 41, 42, 43, 44, 45, 48, 49, 50, 51, 52, 54, 55, 56, 57, 58, 59, 60, 62, 64, 83, 84, 88, 89, 90, 91, 94, 96, 97, 98, 99, 100, 101, 104, 105, 107, 108, 109, 110, 112, 116, 118, 119, 124, 125, 131, 133, 134, 135, 136, 138, 139, 140, 141, 142, 144, 147, 149, 150, 151, 152, 153, 154, 155, 156, 157, 160, 162, 163, 165, 166, 167, 168, 169, 170, 171, 172, 173, 174, 175, 177, 178, 179, 181, 182, 183, 184, 185, 186, 187, 190, 191, 192, 193, 194, 196, 197, 198, 199, 200, 201, 202, 203, 204, 205, 206, 207, 208, 209, 210, 211, 212, 213, 214, 215, 216, 218, 220, 221, 222, 223, 224, 225, 226, 227, 237, 238, 239, 242, 243, 244, 245, 246. |

Further Assays:

An inhibitor of autotaxin is expected to show beneficial effects in human diseases by inhibiting autotaxin in human plasma and tissues as well as in animal models used to recapitulate such human diseases where the disease is caused, mediated and/or propagated by increased LPA levels and/or the activation of ATX. Such diseases which have been reported in the literature include but are not limited to: chronic inflammation, chronic obstructive pulmonary disease (COPD), arthritis, fibrosis, thrombosis, cholestatic pruritus, septic shock, inflammatory bowel disease, asthma, LPS induced lung inflammation, neuropathic pain, atherosclerosis and cardiovascular disease, multiple sclerosis, bone development and cancer. Literature references which describe human diseases where the disease is caused, mediated and/or propagated by increased LPA levels and/or the activation of ATX, autotaxin and LPA and inhibition thereof in in vitro models and animal models used to mimic human diseases caused, mediated and/or propagated by increased LPA levels and/or the activation of ATX include: J Lipid Res. 2014 Mar. 18; 55(7):1192-1214, Cancer Res 2009; 69 (13), 5441; The Journal of Pharmacology and Experimental Therapeutics, 2010, 334 (1), 310; PLOS ONE, 2014, 9 (4), e93230; Biochem. Soc. Trans. 2014, 42, 125; FASEB J. 2014, 28(6), 2655; Arthritis Rheum, 2011, 63(5), 1405; Cell Cycle, 2009, 8 (22), 3695; Mol Carcinog, 2009, 48(9), 801; Clin Cancer Res. 2013 19(23), 6461; Annu Rev Pharmacol Toxicol. 2010, 50, 157; Mol Cancer Ther 208, 7(10), 3352; Front Oncol. 2013, 3, 236; Biomol Ther (Seoul). 2015, 23(1), 1; Osteoarthritis Cartilage 2015, 23(2), 308; Biochim Biophys Acta. 2015, 1851(1), 61; J Lipid Res. 2014, 55(7), 1192; FEBS Lett. 2014, 588(16), 2712; Future Med Chem. 2013, (16), 1935; Biochim Biophys Acta. 2014, 1841(1), 88; Biochim Biophys Acta. 2013, 1831(1), 42; Am J Respir Cell Mol Biol. 2012, 47(5), 563; Am J Respir Cell Mol Biol. 2012, 47(5), 566; Acta Diabetol. 2013, 50(3), 363; Clin Chim Acta. 2012, 413(23-24), 1817; Clin Chim Acta. 2011, 412(13-14), 1201; Life Sci. 2007, 81(12), 1009; Mol Pain 2011, 7, 33; Mol Pain 2010, 6, 78; Biochimie. 2010, 92(6), 698; J Pharmacol Exp Ther. 2010, 333(2), 540; Mol Pain. 2009, 5, 64; Neuroscience 2008, 152(2), 296; Mol Pain 2008, 4, 6; J Neuroimmunol. 2014, 273(1-2), 120; PLoS One. 2013, 8(7), e70941; Nat Rev Rheumatol. 2012, 8(6), 307; J Exp Med. 2012, 209(5), 925; Curr Opin Investig Drugs. 2010, 11(5), 515; Atherosclerosis. 2013, 229(1), 192; J Biol Chem. 2009, 284(11), 7385; Curr Drug Targets 2008, 9(8), 698; Gastroenterology 2010, 139(3), 1008; Lab Invest. 2013, 93(5), 508; J Immunol. 2014, 192(3), 851; Am J Respir Crit Care Med. 2013, 188(8), 889; Am J Respir Crit Care Med. 2013, 188(8), 928; Cell Metab. 2011, 13(5), 592; Exp Cell Res. 2014 Nov. 25. pii: S0014-4827(14)00506-0; Biochem J. 2014, 463(1), 157; Biochim Biophys Acta. 2013, 1831 (1), 74; Hepatology 2012, 56(4), 1391; Biochem Soc Trans. 2012, 40(1), 31; Enzyme Res. 2011, 2011:194857.

Compositions:

The present invention includes pharmaceutical compositions comprising a compound or pharmaceutically acceptable salt thereof of the invention, which is formulated for a desired mode of administration with or without one or more pharmaceutically acceptable and useful carriers.

The compounds can also be included in pharmaceutical compositions in combination with one or more other therapeutically active compounds.

The pharmaceutical compositions of the invention comprise a compound of the invention (or a pharmaceutically acceptable salt thereof) as an active ingredient, optional pharmaceutically acceptable carrier(s) and optionally other therapeutic ingredients or adjuvants. The compositions include compositions suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions can be conveniently presented in unit dosage form and prepared by any of the methods well known in the art of pharmacy.

Compounds of the invention can be combined as the active ingredient in intimate admixture with a pharmaceutical carrier according to conventional pharmaceutical compounding techniques. The carrier can take a wide variety of forms depending on the form of preparation desired for administration, e.g., oral or parenteral (including intravenous). Thus, the pharmaceutical compositions of the invention can be presented as discrete units suitable for oral administration such as capsules, cachets or tablets each containing a predetermined amount of the active ingredient. Further, the compositions can be presented as a powder, as granules, as a solution, as a suspension in an aqueous liquid, as a non-aqueous liquid, as an oil-in-water emulsion, or as a water-in-oil liquid emulsion. In addition to the common dosage forms set out above, the compound represented by Formula I, or a pharmaceutically acceptable salt thereof, can also be administered by controlled release means and/or delivery devices. The compositions can be prepared by any of the methods of pharmacy. In general, such methods include a step of bringing into association the active ingredient with the carrier that constitutes one or more necessary ingredients. In general, the compositions are prepared by uniformly and intimately admixing the active ingredient with liquid carriers or finely divided solid carriers or both. The product can then be conveniently shaped into the desired presentation.

The pharmaceutical carrier employed can be, for example, a solid, liquid, or gas. Examples of solid carriers include lactose, terra alba, sucrose, talc, gelatin, agar, pectin, acacia, magnesium stearate, and stearic acid. Examples of liquid carriers are sugar syrup, peanut oil, olive oil, and water. Examples of gaseous carriers include carbon dioxide and nitrogen.

A tablet containing the composition of this invention can be prepared by compression or molding, optionally with one or more accessory ingredients or adjuvants. Compressed tablets can be prepared by compressing, in a suitable machine, the active ingredient in a free-flowing form such as powder or granules, optionally mixed with a binder, lubricant, inert diluent, surface active or dispersing agent. Molded tablets can be made by molding in a suitable machine, a mixture of the powdered compound moistened with an inert liquid diluent. Each tablet preferably contains from about 0.05 mg to about 5 g of the active ingredient and each cachet or capsule preferably containing from about 0.05 mg to about 5 g of the active ingredient.

A formulation intended for the oral administration to humans may contain from about 0.5 mg to about 5 g of active agent, compounded with an appropriate and convenient amount of carrier material which may vary from about 5 to about 95 percent of the total composition. Unit dosage forms will generally contain between from about 1 mg to about 2 g of the active ingredient, typically 25 mg, 50 mg, 100 mg, 200 mg, 300 mg, 400 mg, 500 mg, 600 mg, 800 mg, or 1000 mg.

Compounds of the invention can be provided for formulation at high purity, for example at least about 90%, 95%, or 98% pure by weight.

Pharmaceutical compositions of the invention suitable for parenteral administration may be prepared as solutions or suspensions of the active compounds in water. A suitable surfactant can be included such as, for example, hydroxypropylcellulose. Dispersions can also be prepared in glycerol, liquid polyethylene glycols, and mixtures thereof in oils. Further, a preservative can be included to prevent the detrimental growth of microorganisms.

Pharmaceutical compositions of the invention suitable for injectable use include sterile aqueous solutions or dispersions. Furthermore, the compositions can be in the form of sterile powders for the extemporaneous preparation of such sterile injectable solutions or dispersions. In all cases, the final injectable form must be sterile and must be effectively fluid for easy syringability. The pharmaceutical compositions must be stable under the conditions of manufacture and storage; thus, preferably should be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), vegetable oils, and suitable mixtures thereof.

Pharmaceutical compositions of the invention can be in a form suitable for topical use such as, for example, an aerosol, cream, ointment, lotion, dusting powder, or the like. Further, the compositions can be in a form suitable for use in transdermal devices. These formulations may be prepared, utilizing a compound represented by Formula I of this invention, or a pharmaceutically acceptable salt thereof, via conventional processing methods. As an example, a cream or ointment is prepared by admixing hydrophilic material and water, together with about 5 wt % to about 10 wt % of the compound, to produce a cream or ointment having a desired consistency.

Pharmaceutical compositions of this invention can be in a form suitable for rectal administration wherein the carrier is a solid. It is preferable that the mixture forms unit dose suppositories. Suitable carriers include cocoa butter and other materials commonly used in the art. The suppositories may be conveniently formed by first admixing the composition with the softened or melted carrier(s) followed by chilling and shaping in molds.

In addition to the aforementioned carrier ingredients, the pharmaceutical formulations described above may include, as appropriate, one or more additional carrier ingredients such as diluents, buffers, flavoring agents, binders, surface-active agents, thickeners, lubricants, preservatives (including anti-oxidants) and the like. Furthermore, other adjuvants can be included to render the formulation isotonic with the blood of the intended recipient.

Compositions containing a compound described by Formula I, or pharmaceutically acceptable salts thereof, may also be prepared in powder or liquid concentrate form.

Uses:

Compounds of the present invention inhibit the activity of ATX in animals, including humans, and are useful in the treatment and/or prevention of various diseases and conditions such as cancer, lymphocyte homing and inflammation, neuropathic pain, fibrotic diseases, thrombosis, and cholestatic pruritus which are caused, mediated and/or propagated by increased LPA levels and/or the activation of ATX. In particular, compounds of the invention, and compositions thereof, are inhibitors of ATX, and are useful in treating conditions modulated, at least in part, by ATX.

In some embodiments, the invention includes a method of treating cancer comprising administering to a mammal in need thereof a therapeutically effective amount of a compound or salt of the invention.

In some embodiments, the invention includes a method of treating a cancer mediated at least in part by ATX comprising administering to a mammal in need thereof a therapeutically effective amount of a compound or salt of Formula I.

In some embodiments, the invention includes a method of treating or a method of manufacturing a medicament for treating a cancer, such as those described herein, which is mediated at least in part by ATX, comprising administering to a mammal in need thereof a therapeutically effective amount of a compound or salt of the invention.

In some embodiments, the invention includes a method of treating lymphocyte homing and inflammation comprising administering to a mammal in need thereof a therapeutically effective amount of a compound or salt of the invention.

In some embodiments, the invention includes a method of treating lymphocyte homing and inflammation mediated at least in part by ATX comprising administering to a mammal in need thereof a therapeutically effective amount of a compound or salt of Formula I.

In some embodiments, the invention includes a method of treating or a method of manufacturing a medicament for treating lymphocyte homing and inflammation, such as those described herein, which is mediated at least in part by ATX, comprising administering to a mammal in need thereof a therapeutically effective amount of a compound or salt of the invention.

In some embodiments, the invention includes a method of treating neuropathic pain comprising administering to a mammal in need thereof a therapeutically effective amount of a compound or salt of the invention.

In some embodiments, the invention includes a method of treating neuropathic pain mediated at least in part by ATX comprising administering to a mammal in need thereof a therapeutically effective amount of a compound or salt of Formula I.

In some embodiments, the invention includes a method of treating or a method of manufacturing a medicament for treating neuropathic pain, such as those described herein, which is mediated at least in part by ATX, comprising administering to a mammal in need thereof a therapeutically effective amount of a compound or salt of the invention.

In some embodiments, the invention includes a method of treating fibrotic diseases comprising administering to a mammal in need thereof a therapeutically effective amount of a compound or salt of the invention.

In some embodiments, the invention includes a method of treating fibrotic diseases mediated at least in part by ATX comprising administering to a mammal in need thereof a therapeutically effective amount of a compound or salt of Formula I.

In some embodiments, the invention includes a method of treating or a method of manufacturing a medicament for treating a fibrotic disease, such as those described herein, which is mediated at least in part by ATX, comprising administering to a mammal in need thereof a therapeutically effective amount of a compound or salt of the invention.

In some embodiments, the invention includes a method of treating thrombosis comprising administering to a mammal in need thereof a therapeutically effective amount of a compound or salt of the invention.

In some embodiments, the invention includes a method of treating thrombosis mediated at least in part by ATX comprising administering to a mammal in need thereof a therapeutically effective amount of a compound or salt of Formula I.

In some embodiments, the invention includes a method of treating or a method of manufacturing a medicament for treating thrombosis, such as those described herein, which is mediated at least in part by ATX, comprising administering to a mammal in need thereof a therapeutically effective amount of a compound or salt of the invention.

In some embodiments, the invention includes a method of treating cholestatic pruritus comprising administering to a mammal in need thereof a therapeutically effective amount of a compound or salt of the invention.

In some embodiments, the invention includes a method of treating cholestatic pruritus mediated at least in part by ATX comprising administering to a mammal in need thereof a therapeutically effective amount of a compound or salt of Formula I.

In some embodiments, the invention includes a method of treating or a method of manufacturing a medicament for cholestatic pruritus, such as those described herein, which is mediated at least in part by ATX, comprising administering to a mammal in need thereof a therapeutically effective amount of a compound or salt of the invention.

The compounds of Formula I of the invention are useful in the treatment of a variety of cancers, including, but not limited to, solid tumors, sarcoma, fibrosarcoma, osteoma, melanoma, retinoblastoma, rhabdomyosarcoma, glioblastoma, neuroblastoma, teratocarcinoma, hematopoietic malignancy, and malignant ascites. More specifically, the cancers include, but not limited to, lung cancer, bladder cancer, pancreatic cancer, kidney cancer, gastric cancer, breast cancer, colon cancer, prostate cancer (including bone metastases), hepatocellular carcinoma, ovarian cancer, esophageal squamous cell carcinoma, melanoma, an anaplastic large cell lymphoma, an inflammatory myofibroblastic tumor, and a glioblastoma.

In some embodiments, the above methods are used to treat one or more of bladder, colorectal, non-small cell lung, breast, or pancreatic cancer. In some embodiments, the above methods are used to treat one or more of ovarian, gastric, head and neck, prostate, hepatocellular, renal, glioma, or sarcoma cancer.

In some embodiments, the invention includes a method, including the above methods, wherein the compound is used to inhibit cellular epithelial to mesenchymal transition (EMT).

In some embodiments, the method further comprises administering at least on additional active agent. In some embodiments, the invention includes a method of treating cancer comprising administering to a mammal in need thereof a therapeutically effective amount of a compound or salt of the invention, wherein at least one additional active anti-cancer agent is used as part of the method.

In some embodiments, the invention includes a method of treating the disease described herein mediated at least in part by ATX comprising administering to a mammal in need thereof a therapeutically effective regimen comprising a compound or salt of Formula I and at least one additional active agent. Generally, dosage levels on the order of from about 0.01 mg/kg to about 150 mg/kg of body weight per day are useful in the treatment of the above-indicated conditions, or alternatively about 0.5 mg to about 7 g per patient per day. For example, inflammation, cancer, psoriasis, allergy/asthma, disease and conditions of the immune system, disease and conditions of the Central Nervous System (CNS), may be effectively treated by the administration of from about 0.01 to 50 mg of the compound per kilogram of body weight per day, or alternatively about 0.5 mg to about 3.5 g per patient per day.

It is understood, however, that the specific dose level for any particular patient will depend upon a variety of factors including the age, body weight, general health, sex, diet, time of administration, route of administration, rate of excretion, drug combination and the severity of the particular disease undergoing therapy.

General Definitions and Abbreviations

Except where otherwise indicated, the following general conventions and definitions apply. Unless otherwise indicated herein, language and terms are to be given their broadest reasonable interpretation as understood by the skilled artisan. Any examples given are nonlimiting.

Any section headings or subheadings herein are for the reader's convenience and/or formal compliance and are non-limiting.

A recitation of a compound herein is open to and embraces any material or composition containing the recited compound (e.g., a composition containing a racemic mixture, tautomers, epimers, stereoisomers, impure mixtures, etc.). In that a salt, solvate, or hydrate, polymorph, or other complex of a compound includes the compound itself, a recitation of a compound embraces materials containing such forms. Isotopically labeled compounds are also encompassed except where specifically excluded. For example, hydrogen is not limited to hydrogen containing zero neutrons. For example, deuterium is referred to herein as "D" and means a hydrogen atom having one neutron.

The term "active agent" of the present invention means a compound of the invention in any salt, polymorph, crystal, solvate, or hydrated form.

The term "pharmaceutically acceptable salt(s)" is known in the art and includes salts of acidic or basic groups which can be present in the compounds and prepared or resulting from pharmaceutically acceptable bases or acids.

The term "substituted" and substitutions contained in formulas herein refer to the replacement of one or more hydrogen radicals in a given structure with a specified radical, or, if not specified, to the replacement with any chemically feasible radical. When more than one position in a given structure can be substituted with more than one substituent selected from specified groups, the substituents can be either the same or different at every position (independently selected) unless otherwise indicated. In some cases, two positions in a given structure can be substituted with one shared substituent. It is understood that chemically impossible or highly unstable configurations are not desired or intended, as the skilled artisan would appreciate.

In descriptions and claims where subject matter (e.g., substitution at a given molecular position) is recited as being selected from a group of possibilities, the recitation is specifically intended to include any subset of the recited group. In the case of multiple variable positions or substituents, any combination of group or variable subsets is also contemplated.

Unless indicated otherwise, a substituent, diradical or other group referred to herein can be bonded through any suitable position to a referenced subject molecule. For example, the term "indolyl" includes 1-indolyl, 2-indolyl, 3-indolyl, etc.

The convention for describing the carbon content of certain moieties is "$(C_{a-b})$" or "$C_a$-$C_b$" meaning that the moiety can contain any number of from "a" to "b" carbon atoms. $C_0$alkyl means a single covalent chemical bond when it is a connecting moiety, and a hydrogen when it is a terminal moiety. Similarly, "x-y" can indicate a moiety containing from x to y atoms, e.g., $_{5-6}$heterocycloalkyl means a heterocycloalkyl having either five or six ring members. "$C_{x-y}$" may be used to define number of carbons in a group. For example, "$C_{0-12}$alkyl" means alkyl having 0-12 carbons, wherein $C_0$alkyl means a single covalent chemical bond when a linking group and means hydrogen when a terminal group.

The term "absent," as used herein to describe a structural variable (e.g., "—R— is absent") means that diradical R has no atoms, and merely represents a bond between other adjoining atoms, unless otherwise indicated.

Unless otherwise indicated (such as by a connecting "-"), the connections of compound name moieties are at the rightmost recited moiety. That is, the substituent name starts with a terminal moiety, continues with any bridging moieties, and ends with the connecting moiety. For example, "heteroarylthio$C_{1-4}$alkyl is a heteroaryl group connected through a thio sulfur to a $C_{1-4}$ alkyl, which alkyl connects to the chemical species bearing the substituent.

The term "aliphatic" means any hydrocarbon moiety, and can contain linear, branched, and cyclic parts, and can be saturated or unsaturated.

The term "alkyl" means any saturated hydrocarbon group that is straight-chain or branched. Examples of alkyl groups include methyl, ethyl, propyl, 2-propyl, n-butyl, iso-butyl, tert-butyl, pentyl, and the like.

The term "alkenyl" means any ethylenically unsaturated straight-chain or branched hydrocarbon group. Representative examples include, but are not limited to, ethenyl, 1-propenyl, 2-propenyl, 1-, 2-, or 3-butenyl, and the like.

The term "alkynyl" means any acetylenically unsaturated straight-chain or branched hydrocarbon group. Representative examples include, but are not limited to, ethynyl, 1-propynyl, 2-propynyl, 1-, 2-, or 3-butynyl, and the like.

The term "alkoxy" means —O-alkyl, —O-alkenyl, or —O-alkynyl. "Haloalkoxy" means an —O— (haloalkyl) group. Representative examples include, but are not limited to, trifluoromethoxy, tribromomethoxy, and the like.

"Haloalkyl" means an alkyl, preferably lower alkyl, that is substituted with one or more same or different halo atoms.

"Hydroxyalkyl" means an alkyl, preferably lower alkyl, that is substituted with one, two, or three hydroxy groups; e.g., hydroxymethyl, 1 or 2-hydroxyethyl, 1,2-, 1,3-, or 2,3-dihydroxypropyl, and the like.

The term "alkanoyl" means —C(O)-alkyl, —C(O)-alkenyl, or —C(O)-alkynyl.

"Alkylthio" means an —S-(alkyl) or an —S-(unsubstituted cycloalkyl) group. Representative examples include, but are not limited to, methylthio, ethylthio, propylthio, butylthio, cyclopropylthio, cyclobutylthio, cyclopentylthio, cyclohexylthio, and the like.

The term "cyclic" means any ring system with or without heteroatoms (N, O, or $S(O)_{0-2}$), and which can be saturated, partially saturated, or unsaturated. Ring systems can be bridged and can include fused rings. The size of ring systems may be described using terminology such as "$_{x-y}$cyclic," which means a cyclic ring system that can have from x to y ring atoms. For example, the term "$_{9-10}$carbocyclic" means a 5,6 or 6,6 fused bicyclic carbocyclic ring system which can be saturated, unsaturated or aromatic. It also means a phenyl fused to one 5 or 6 membered saturated or unsaturated carbocyclic group. Nonlimiting examples of such groups include naphthyl, 1,2,3,4 tetrahydronaphthyl, indenyl, indanyl, and the like.

The term "carbocyclic" means a cyclic ring moiety containing only carbon atoms in the ring(s) without regard to aromaticity. A 3-10 membered carbocyclic means chemically feasible monocyclic and fused bicyclic carbocyclics having from 3 to 10 ring atoms. Similarly, a 4-6 membered carbocyclic means monocyclic carbocyclic ring moieties having 4 to 6 ring carbons, and a 9-10 membered carbocyclic means fused bicyclic carbocyclic ring moieties having 9 to 10 ring carbons.

The term "cycloalkyl" means a non-aromatic 3-12 carbon mono-cyclic, bicyclic, or polycyclic aliphatic ring moiety. Cycloalkyl can be bicycloalkyl, polycycloalkyl, bridged, or spiroalkyl. One or more of the rings may contain one or more double bonds but none of the rings has a completely conjugated pi-electron system. Examples, without limitation, of cycloalkyl groups are cyclopropane, cyclobutane, cyclopentane, cyclopentene, cyclohexane, cyclohexadiene, adamantane, cycloheptane, cycloheptatriene, and the like.

The term "unsaturated carbocyclic" means any cycloalkyl containing at least one double or triple bond. The term "cycloalkenyl" means a cycloalkyl having at least one double bond in the ring moiety.

The terms "bicycloalkyl" and "polycycloalkyl" mean a structure consisting of two or more cycloalkyl moieties that have two or more atoms in common. If the cycloalkyl moieties have exactly two atoms in common they are said to be "fused". Examples include, but are not limited to, bicyclo[3.1.0]hexyl, perhydronaphthyl, and the like. If the cycloalkyl moieties have more than two atoms in common they are said to be "bridged". Examples include, but are not limited to, bicyclo[2.2.1]heptyl ("norbornyl"), bicyclo[2.2.2]octyl, and the like.

The term "spiroalkyl" means a structure consisting of two cycloalkyl moieties that have exactly one atom in common. Examples include, but are not limited to, spiro[4.5]decyl, spiro[2.3]hexyl, and the like.

The term "aromatic" means a planar ring moieties containing 4n+2 pi electrons, wherein n is an integer.

The term "aryl" means aromatic moieties containing only carbon atoms in its ring system. Non-limiting examples include phenyl, naphthyl, and anthracenyl. The terms "arylalkyl" or "arylalkyl" or "aralkyl" refer to any alkyl that forms a bridging portion with a terminal aryl.

"Aralkyl" means alkyl that is substituted with an aryl group as defined above; e.g., —CH$_2$ phenyl, —(CH$_2$)$_2$phenyl, —(CH$_2$)$_3$ phenyl, CH$_3$CH(CH$_3$)CH$_2$phenyl, and the like and derivatives thereof.

The term "heterocyclic" means a cyclic ring moiety containing at least one heteroatom (N, O, or $S(O)_{0-2}$), including heteroaryl, heterocycloalkyl, including unsaturated heterocyclic rings.

The term "heterocycloalkyl" means a non-aromatic monocyclic, bicyclic, or polycyclic heterocyclic ring moiety of 3 to 12 ring atoms containing at least one ring having one or more heteroatoms. The rings may also have one or more double bonds. However, the rings do not have a completely conjugated pi-electron system. Examples, without limitation, of heterocycloalkyl rings include azetidine, oxetane, tetrahydrofuran, tetrahydropyran, oxepane, oxocane, thietane, thiazolidine, oxazolidine, oxazetidine, pyrazolidine, isoxazolidine, isothiazolidine, tetrahydrothiophene, tetrahydrothiopyran, thiepane, thiocane, azetidine, pyrrolidine, piperidine, N-methylpiperidine, azepane, 1,4-diazapane, azocane, [1,3]dioxane, oxazolidine, piperazine, homopiperazine, morpholine, thiomorpholine, 1,2,3,6-tetrahydropyridine and the like. Other examples of heterocycloalkyl rings include the oxidized forms of the sulfur-containing rings. Thus, tetrahydrothiophene-1-oxide, tetrahydrothiophene-1,1-dioxide, thiomorpholine-1-oxide, thiomorpholine-1,1-dioxide, tetrahydrothiopyran-1-oxide, tetrahydrothiopyran-1,1-dioxide, thiazolidine-1-oxide, and thiazolidine-1,1-dioxide are also considered to be heterocycloalkyl rings. The term "heterocycloalkyl" also includes fused ring systems and can include a carbocyclic ring that is partially or fully unsaturated, such as a benzene ring, to form benzofused heterocycloalkyl rings. For example, 3,4-dihydro-1,4-benzodioxine, tetrahydroquinoline, tetrahydroisoquinoline and the like. The term "heterocycloalkyl" also includes heterobicycloalkyl, heteropolycycloalkyl, or heterospiroalkyl, which are bicycloalkyl, polycycloalkyl, or spiroalkyl, in which one or more carbon atom(s) are replaced by one or more heteroatoms selected from O, N, and S. For example, 2-oxa-spiro[3.3]heptane, 2,7-diazaspiro[4.5]decane, 6-oxa-2-thia-spiro[3.4]octane, octahydropyrrolo[1,2-a]pyrazine, 7-azabicyclo[2.2.1]heptane, 2-oxa-bicyclo[2.2.2]octane, and the like, are such heterocycloalkyls.

Examples of saturated heterocyclic groups include, but are not limited to oxiranyl, thiaranyl, aziridinyl, oxetanyl, thiatanyl, azetidinyl, tetrahydrofuranyl, tetrahydrothiophenyl, pyrrolidinyl, tetrahydropyranyl, tetrahydrothiopyranyl, piperidinyl, 1,4-dioxanyl, 1,4-oxathianyl, morpholinyl, 1,4-dithianyl, piperazinyl, 1,4-azathianyl, oxepanyl, thiepanyl, azepanyl, 1,4-dioxepanyl, 1,4-oxathiepanyl, 1,4-oxaazepanyl, 1,4-dithiepanyl, 1,4-thieazepanyl, 1,4-diazepanyl.

Non-aryl heterocyclic groups include saturated and unsaturated systems and can include groups having only 4 atoms in their ring system. The heterocyclic groups include benzo-fused ring systems and ring systems substituted with one or more oxo moieties. Recitation of ring sulfur is understood to include the sulfide, sulfoxide or sulfone where feasible. The heterocyclic groups also include partially unsaturated or fully saturated 4-10 membered ring systems, e.g., single rings of 4 to 8 atoms in size and bicyclic ring systems, including aromatic 6-membered aryl or heteroaryl rings fused to a non-aromatic ring. Also included are 4-6 membered ring systems ("4-6 membered heterocyclic"), which include 5-6 membered heteroaryls, and include groups such as azetidinyl and piperidinyl. Heterocyclics can be heteroatom-attached where such is possible. For instance, a group derived from pyrrole can be pyrrol-1-yl (N-attached) or pyrrol-3-yl (C-attached). Other heterocyclics include imidazo(4,5-b)pyridin-3-yl and benzoimidazol-1-yl.

Examples of heterocyclic groups include pyrrolidinyl, tetrahydrofuranyl, tetrahydrothienyl, tetrahydropyranyl, tetrahydrothiopyranyl, piperidino, morpholino, thiomorpholino, thioxanyl, piperazinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl, 3-azabicyclo[3.1.0]hexanyl, 3-azabicyclo[4.1.0]heptanyl, 3H-indolyl, quinolizinyl, and the like.

The term "unsaturated heterocyclic" means a heterocycloalkyl containing at least one unsaturated bond. The term "heterobicycloalkyl" means a bicycloalkyl structure in which at least one carbon atom is replaced with a heteroatom. The term "heterospiroalkyl" means a spiroalkyl structure in which at least one carbon atom is replaced with a heteroatom.

Examples of partially unsaturated heteroalicyclic groups include, but are not limited to: 3,4-dihydro-2H-pyranyl, 5,6-dihydro-2H-pyranyl, 2H-pyranyl, 1,2,3,4-tetrahydropyridinyl, and 1,2,5,6-tetrahydropyridinyl.

The terms "heteroaryl" or "hetaryl" mean a monocyclic, bicyclic, or polycyclic aromatic heterocyclic ring moiety containing 5-12 atoms. Examples of such heteroaryl rings include, but are not limited to, furyl, thienyl, pyrrolyl, pyrazolyl, imidazolyl, oxazolyl, isoxazolyl, thiazolyl, isothiazolyl, triazolyl, oxadiazolyl, thiadiazolyl, tetrazolyl, pyridyl, pyridazinyl, pyrimidinyl, pyrazinyl, and triazinyl. The terms "heteroaryl" also include heteroaryl rings with fused carbocyclic ring systems that are partially or fully unsaturated, such as a benzene ring, to form a benzofused heteroaryl. For example, benzimidazole, benzoxazole, benzothiazole, benzofuran, quinoline, isoquinoline, quinoxaline, indazole, imidazo[1,2-a]pyridine, 3-methyl-2-oxo-2,3-dihydrobenzo[d]oxazol-5-yl, 2-methyl-2H-indazol-5-yl, 3-methylimidazo[1,5-a]pyridine, 2-methyl-1H-benzo[d]imidazole, 1H-pyrrolo[2,3-b]pyridine, 3,4-Dihydro-2H-benzo[b][1,4]oxazine, 2-oxo-2,3-dihydrobenzo[d]oxazole, 3-oxo-3,4-dihydro-2H-benzo[b][1,4]oxazine, 2,3-Dihydrobenzo[b][1,4]dioxine, 2-methyl-[1,2,4]triazolo[1,5-a]pyridine, and the like. Furthermore, the terms "heteroaryl" include fused 5-6, 5-5, 6-6 ring systems, optionally possessing one nitrogen atom at a ring junction. Examples of such hetaryl rings include, but are not limited to, pyrrolopyrimidinyl, imidazo[1,2-a]pyridinyl, imidazo[2,1-b]thiazolyl, imidazo[4,5-b]pyridine, pyrrolo[2,1-f][1,2,4]triazinyl, and the like. Heteroaryl groups may be attached to other groups through their carbon atoms or the heteroatom(s), if applicable. For example, pyrrole may be connected at the nitrogen atom or at any of the carbon atoms.

Heteroaryls include, e.g., 5 and 6 membered monocyclics such as pyrazinyl and pyridinyl, and 9 and 10 membered fused bicyclic ring moieties, such as quinolinyl. Other examples of heteroaryl include quinolin-4-yl, 7-methoxyquinolin-4-yl, pyridin-4-yl, pyridin-3-yl, and pyridin-2-yl. Other examples of heteroaryl include pyridinyl, imidazolyl, pyrimidinyl, pyrazolyl, triazolyl, pyrazinyl, tetrazolyl, furanyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, thiadiazolyl, furazanyl, benzofurazanyl, benzothiophenyl, benzothiazolyl, benzoxazolyl, quinazolinyl, quinoxalinyl, naphthyridinyl, furopyridinyl, and the like. Examples of 5-6 membered heteroaryls include, thiophenyl, isoxazolyl, 1,2,3-triazolyl, 1,2,3-oxadiazolyl, 1,2,3-thiadiazolyl, 1,2,4-triazolyl, 1,3,4-oxadiazolyl, 1,3,4-thiadiazolyl, 1,2,5-oxadiazolyl, 1,2,5-thiadiazolyl, pyridyl, pyridazinyl, pyrimidinyl, pyrazinyl, 1,2,4 oxadiazolyl, 1,2,5-triazinyl, 1,3,5-triazinyl, 6-oxo-1,6-dihydropyridine, and the like.

"Heteroaralkyl" group means alkyl, preferably lower alkyl, that is substituted with a heteroaryl group; e.g., —CH$_2$pyridinyl, —(CH$_2$)$_2$pyrimidinyl, —(CH$_2$)$_3$imidazolyl, and the like, and derivatives thereof.

A pharmaceutically acceptable heteroaryl is one that is sufficiently stable to be attached to a compound of the invention, formulated into a pharmaceutical composition and subsequently administered to a patient in need thereof.

Examples of monocyclic heteroaryl groups include, but are not limited to: pyrrolyl, furanyl, thiophenyl, pyrazolyl, imidazolyl, isoxazolyl, oxazolyl, isothiazolyl, thiazolyl, 1,2,3-triazolyl, 1,3,4-triazolyl, 1-oxa-2,3-diazolyl, 1-oxa-2,4-diazolyl, 1-oxa-2,5-diazolyl, 1-oxa-3,4-diazolyl, 1-thia-2,3-diazolyl, 1-thia-2,4-diazolyl, 1-thia-2,5-diazolyl, 1-thia-3,4-diazolyl tetrazolyl, pyridinyl, pyridazinyl, pyrimidinyl, pyrazinyl.

Examples of fused ring heteroaryl groups include, but are not limited to: benzoduranyl, benzothiophenyl, indolyl, benzimidazolyl, indazolyl, benzotriazolyl, pyrrolo[2,3-b]pyridinyl, pyrrolo[2,3-c]pyridinyl, pyrrolo[3,2-c]pyridinyl, pyrrolo[3,2-b]pyridinyl, imidazo[4,5-b]pyridinyl, imidazo[4,5-c]pyridinyl, pyrazolo[4,3-d]pyridinyl, pyrazolo[4,3-c]pyridinyl, pyrazolo[3,4-c]pyridinyl, pyrazolo[3,4-b]pyridinyl, isoindolyl, indazolyl, purinyl, indolinyl, imidazo[1,2-a]pyridinyl, imidazo[1,5-a]pyridinyl, pyrazolo[1,5-a]pyridinyl, pyrrolo[1,2-b]pyridazinyl, imidazo[1,2-c]pyrimidinyl, quinolinyl, isoquinolinyl, cinnolinyl, azaquinazoline, quinoxalinyl, phthalazinyl, 1,6-naphthyridinyl, 1,7-naphthyridinyl, 1,8-naphthyridinyl, 1,5-naphthyridinyl, 2,6-naphthyridinyl, 2,7-naphthyridinyl, pyrido[3,2-d]pyrimidinyl, pyrido[4,3-d]pyrimidinyl, pyrido[3,4-d]pyrimidinyl, pyrido[2,3-d]pyrimidinyl, pyrido[2,3-b]pyrazinyl, pyrido[3,4-b]pyrazinyl, pyrimido[5,4-d]pyrimidinyl, pyrimido[2,3-b]pyrazinyl, pyrimido[4,5-d]pyrimidinyl.

"Arylthio" means an —S-aryl or an —S-heteroaryl group, as defined herein. Representative examples include, but are not limited to, phenylthio, pyridinylthio, furanylthio, thienylthio, pyrimidinylthio, and the like and derivatives thereof.

The term "9-10 membered heterocyclic" means a fused 5,6 or 6,6 bicyclic heterocyclic ring moiety, which can be saturated, unsaturated or aromatic. The term "9-10 membered fused bicyclic heterocyclic" also means a phenyl fused to one 5 or 6 membered heterocyclic group. Examples include benzofuranyl, benzothiophenyl, indolyl, benzoxazolyl, 3H-imidazo[4,5-c]pyridin-yl, dihydrophthazinyl, 1H-imidazo[4,5-c]pyridin-1-yl, imidazo[4,5-b]pyridyl, 1,3 benzo[1,3]dioxolyl, 2H-chromanyl, isochromanyl, 5-oxo-2,3 dihydro-5H-[1,3]thiazolo[3,2-a]pyrimidyl, 1,3-benzothiazolyl, 1,4,5,6 tetrahydropyridazyl, 1,2,3,4,7,8hexahydropteridinyl, 2-thioxo-2,3,6,9-tetrahydro-1H-purin-8-yl, 3,7-dihydro-1H-purin-8-yl, 3,4-dihydropyrimidin-1-yl, 2,3- dihydro-1,4-benzodioxinyl, benzo[1,3]dioxolyl, 2H-chromenyl, chromanyl, 3,4-dihydrophthalazinyl, 2,3-dihydro-1H-indolyl, 1,3-dihydro-2H-isoindol-2-yl, 2,4,7-trioxo-1,2,3,4,7,8-hexahydropteridin-yl, thieno[3,2-d]pyrimidinyl, 4-oxo-4,7-dihydro-3H-pyrrolo[2,3-d]pyrimidin-yl, 1,3-dimethyl-6-oxo-2-thioxo-2,3,6,9-tetrahydro-1H-purinyl, 1,2-dihydroisoquinolinyl, 2-oxo-1,3-benzoxazolyl, 2,3-dihydro-5H-1,3-thiazolo-[3,2-a]pyrimidinyl, 5,6,7,8-tetrahydro-quinazolinyl, 4-oxochromanyl, 1,3-benzothiazolyl, benzimidazolyl, benzotriazolyl, purinyl, furylpyridyl, thiophenylpyrimidyl, thiophenylpyridyl, pyrrolylpiridyl, oxazolylpyridyl, thiazolylpiridyl, 3,4-dihydropyrimidin-1-yl imidazolylpyridyl, quinoliyl, isoquinolinyl, quinazolinyl, quinoxalinyl, naphthyridinyl, pyrazolyl[3,4]pyridine, 1,2-dihydroisoquinolinyl, cinnolinyl, 2,3-dihydro-benzo[1,4]dioxin4-yl, 4,5,6,7-tetrahydro-benzo[b]-thiophenyl-2-yl, 1,8-naphthyridinyl, 1,5-napthyridinyl, 1,6-naphthyridinyl, 1,7-napthyridinyl, 3,4-dihydro-2H-1,4-benzothiazine, 4,8-dihydroxy-quinolinyl, 1-oxo-1,2-dihydro-isoquinolinyl, 4-phenyl-[1,2,3]thiadiazolyl, and the like.

The term "aryloxy" means an —O-aryl or an —O-heteroaryl group, as defined herein. Representative examples include, but are not limited to, phenoxy, pyridinyloxy, furanyloxy, thienyloxy, pyrimidinyloxy, pyrazinyloxy, and the like, and derivatives thereof.

The term "oxo" means a compound containing a carbonyl group. One in the art understands that an "oxo" requires a second bond from the atom to which the oxo is attached.

The term "halo" or "halogen" means fluoro, chloro, bromo, or iodo.

"Acyl" means a —C(O)R group, where R can be selected from the nonlimiting group of hydrogen or optionally substituted lower alkyl, trihalomethyl, unsubstituted cycloalkyl, aryl, or other suitable substituent.

"Thioacyl" or "thiocarbonyl" means a —C(S)R" group, with R as defined above.

The term "protecting group" means a suitable chemical group that can be attached to a functional group and removed at a later stage to reveal the intact functional group. Examples of suitable protecting groups for various functional groups are described in T. W. Greene and P. G. M. Wuts, Protective Groups in Organic Synthesis, 2d Ed., John Wiley and Sons (1991 and later editions); L. Fieser and M. Fieser, Fieser and Fieser's Reagents for Organic Synthesis, John Wiley and Sons (1994); and L. Paquette, ed. Encyclopedia of Reagents for Organic Synthesis, John Wiley and Sons (1995). The term "hydroxy protecting group", as used herein, unless otherwise indicated, includes Ac, CBZ, and various hydroxy protecting groups familiar to those skilled in the art including the groups referred to in Greene.

The term "linear structure" means a moiety having substituents that do not cyclize to form a ring system. A representative example includes, but is not limited to, a compound including —$NR^5R^6$ where any atoms of "$R^5$" and any atoms of "$R^6$" do not connect to form a ring.

As used herein, the term "pharmaceutically acceptable salt" means those salts which retain the biological effectiveness and properties of the parent compound and do not present insurmountable safety or toxicity issues.

The term "pharmaceutical composition" means an active compound in any form suitable for effective administration to a subject, e.g., a mixture of the compound and at least one pharmaceutically acceptable carrier.

As used herein, a "physiologically/pharmaceutically acceptable carrier" means a carrier or diluent that does not cause significant irritation to an organism and does not abrogate the biological activity and properties of the administered compound.

A "pharmaceutically acceptable excipient" means an inert substance added to a pharmaceutical composition to further facilitate administration of a compound. Examples, without limitation, of excipients include calcium carbonate, calcium phosphate, various sugars and types of starch, cellulose derivatives, gelatin, vegetable oils and polyethylene glycols.

The term "substituted" and substitutions contained in formulas herein refer to the replacement of one or more hydrogen radicals in a given structure with a specified radical, or, if not specified, to the replacement with any chemically feasible radical. When more than one position in a given structure can be substituted with more than one substituent selected from specified groups, the substituents can be either the same or different at every position (independently selected) unless otherwise indicated. In some cases, two positions in a given structure can be substituted with one shared substituent. It is understood that chemically impossible or highly unstable configurations are not desired or intended, as the skilled artisan would appreciate.

The terms "treat," "treatment," and "treating" means reversing, alleviating, or inhibiting the progress of the disorder or condition to which such term applies, or one or more symptoms of such disorder or condition. "Preventing" means partially or completing treating before the disorder or condition occurs.

"Therapeutically effective amount" means that amount of the compound being administered which will relieve to some extent one or more of the symptoms of the disorder being treated, or result in inhibition of the progress or at least partial reversal of the condition.

NMR Nuclear magnetic resonance
MDP(S) Mass-directed HPLC purification (system)
LC/MS Liquid chromatography mass spectrometry
LDA Lithium diisopropylamide
tert-BuOH tert-Butanol
AcOH Acetic acid
CDI 1,1'-Carbonyldiimidazole
DCE 1,1-Dichloroethane
DCM Dichloromethane
DMF Dimethylformamide
THF Tetrahydrofuran
MeOH Methanol
EtOH Ethanol
EtOAc Ethyl acetate
MeCN Acetonitrile
DMSO Dimethylsulfoxide
Boc tert-Butyloxycarbonyl
DME 1,2-Dimethoxyethane
DMF N,N-Dimethylformamide
DIPEA Diisopropylethylamine
PS-DIEA Polymer-supported diisopropylethylamine
PS-$PPh_3$-Pd Polymer-supported Pd($PPh_3$)$_4$
LAH Lithium aluminum hydride
EDC 1-(3-Dimethylaminopropyl)-3-ethylcarbodiimide
HATU: 1-[bis(dimethylamino)methylene]-1H-1,2,3-triazolo[4,5-b]pyridinium-3-oxide hexafluorophosphate
HOBt 1-Hydroxybenzotnazole
DMAP 4-Dimethylaminopyridine
SEM-Cl 2-(Trimethylsilyl)ethoxymethyl chloride
TBTU O-(Benzotriazol-1-yl)-N,N,N',N'-tetramethyluronium tetrafluoroborate
TEMPO 2,2,6,6-Tetramethylpiperidine-1-oxyl
TFA (A) Trifluoroacetic acid (anhydride)
TLC Thin layer chromatography TMSCN Trimethylsilyl cyanide
Min Minute(s)
NMO N-Methylmorpholine N-oxide
h Hour(s)
d Day(s)
RT, R.T., r.t., r.t or rt Room temperature
$t_R$ Retention time

The invention claimed is:
1. A compound according to Formula I:

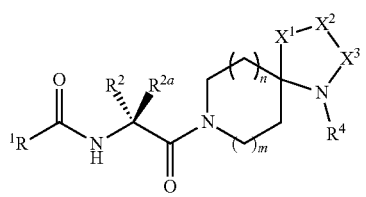

I or a pharmaceutically acceptable salt thereof, wherein:
$X^1$ and $X^2$ are each independently selected from one or more of $C_{1-2}$alkyl, C=O, $NR^3$, or O;
$X^3$ is independently selected from one or more of $C_{1-2}$alkyl, C=O, $NR^3$, O, or $CR^{10}R^{11}$;
m and n are each independently selected from 0, 1 or 2;
$R^1$ is aryl-$C_{3-12}$heterocycloalkyl-, which is optionally substituted with one or more independent $G^1$ substituents;
$R^2$ is selected from $C_{0-12}$alkyl-, $C_{3-12}$cycloalkyl-$C_{0-12}$alkyl-, $C_{3-12}$heterocycloalkyl-$C_{0-12}$alkyl-, heteroaryl-$C_{3-12}$cycloalkyl-, or heteroaryl-$C_{3-12}$heterocycloalkyl-, any of which is optionally substituted with one or more independent $G^2$ substituents;
$R^{2a}$ is selected from $C_{0-12}$alkyl-, $C_{3-12}$cycloalkyl-$C_{0-12}$alkyl-, $C_{3-12}$heterocycloalkyl-$C_{0-12}$alkylheteroaryl-$C_{3-12}$cycloalkyl-, or heteroaryl-$C_{3-12}$heterocycloalkyl-, any of which is optionally substituted with one or more independent $G^{2a}$ substituents;
$R^2$ and $R^{2a}$ are each independently a linear structure, or, $R^2$ and $R^{2a}$ are taken together with the carbon atom to which they are attached to form a 3-12 membered saturated or unsaturated ring, wherein said ring optionally includes one or more additional heteroatoms selected from O, N, or $S(O)_{m1}$;
$R^3$ is selected from $C_{0-12}$alkyl-, $C_{3-12}$cycloalkyl-$C_{0-12}$alkyl-, $C_{3-12}$heterocycloalkyl-$C_{0-12}$alkyl-, aryl-$C_{0-12}$alkyl-, aryl-$C_{3-12}$cycloalkyl-, aryl-$C_{3-12}$heterocycloalkyl-, heteroaryl-$C_{0-12}$alkyl-, heteroaryl-$C_{3-12}$cycloalkyl-, or heteroaryl-$C_{3-12}$heterocycloalkyl-, any of which is optionally substituted with one or more independent $G^3$ substituents;
$R^4$ is selected from $C_{0-12}$alkyl-, $C_{3-12}$cycloalkyl-$C_{0-12}$alkyl-, $C_{3-12}$heterocycloalkyl-$C_{0-12}$alkyl-, aryl-$C_{0-12}$alkyl-, aryl-$C_{3-12}$cycloalkyl-, aryl-$C_{3-12}$heterocycloalkyl-, heteroaryl-$C_{0-12}$alkyl-, heteroaryl-$C_{3-12}$cycloalkyl-, heteroaryl-$C_{3-12}$heterocycloalkyl-, or pyridine-N-oxide, any of which is optionally substituted with one or more independent $G^4$ substituents;
$G^1$, $G^2$, $G^{2a}$, $G^3$, and $G^4$ are each independently selected from one or more of H, D, halo, —CN, —$CD_3$, —$OCD_3$, -oxo-, —$CF_3$, —$OCF_3$, —$OCHF_2$, —$NR^5R^6$, —$NO_2$, —$B(OH)_2$, —$PO(OR^{12})_2$, —$PO(OR^{12})R^{13}$, —$CONR^{12}OH$, —$C_{0-12}$alkyl, —$C_{2-12}$alkenyl, —$C_{2-12}$alkynyl, $C_{3-12}$cycloalkyl-$C_{0-12}$alkyl-, $C_{3-12}$heterocycloalkyl-$C_{0-12}$alkyl-, aryl-$C_{0-12}$alkyl-, heteroaryl-$C_{0-12}$alkyl-, —$OC_{0-12}$alkyl-, —$S(O)_{n1}R^{12}$, —$C(O)R^{12}$,
—$C(O)NR^{12}R^{13}$, —$C(O)$—$C(O)NR^{12}R^{13}$, —$C(O)OR^{12}$, —$C(O)$—$C(O)OR^{12}$, —$OC(O)R^{12}$, —$NR^{12}C(O)R^{13}$, —$NR^{12}C(O)OR^{13}$, —$NR^{12}S(O)_2R^{13}$, —$(CR^{14}R^{15})C(O)R^{13}$, —$(CR^{14}R^{15})C(O)OR^{12}$, —$(CR^{14}R^{15})C(O)NR^{12}R^{13}$, —$(CR^{14}R^{15})_{n1}S(O)_2NR^{12}R^{13}$, —$(CR^{14}R^{15})_{n1}NR^{12}R^{13}$, —$(CR^{14}R^{15})_{n1}OR^{12}$, —$(CR^{14}R^{15})_{n1}S(O)_{n2}R^{12}$, —$NR^{16}C(O)NR^{12}R^{13}$, —$NR^{16}S(O)_2NR^{12}R^{13}$ or —$NR^{16}S(O)NR^{12}R^{13}$, any of which is optionally substituted with one or more independent $Q^1$ substituents;
$Q^1$ is selected from H, D, halo, —CN, —$CD_3$, —$OCD_3$, -oxo-, —$CF_3$, —$OCF_3$, —$OCHF_2$, —$NO_2$, —$B(OH)_2$, —$PO(OR^{17})_2$, —$PO(OR^{17})R^{18}$, $NR^{17}R^{18}$, —$CONR^{17}OH$, $C_{0-12}$alkyl-, —$C_{2-12}$alkenyl, —$C_{2-12}$alkynyl, aryl-$C_{0-12}$alkyl-, heteroaryl-$C_{0-12}$alkyl-, $C_{3-12}$cycloalkyl-$C_{0-12}$alkyl-, $C_{3-12}$heterocycloalkyl-$C_{0-12}$alkyl-, aryl-$C_{0-12}$cycloalkyl-, heteroaryl-$C_{3-12}$cycloalkyl-, $C_{3-12}$heterocycloalkyl-$C_{3-12}$cycloalkyl-, $C_{3-12}$cycloalkyl-$C_{3-12}$cycloalkyl-, $C_{1-12}$alkyl-$C_{3-12}$heterocycloalkyl-, $C_{3-12}$heterocycloalkyl-$C_{3-12}$heterocycloalkyl-, aryl-$C_{3-12}$heterocycloalkyl-, heteroaryl-$C_{3-12}$heterocycloalkyl-, —$OC_{0-12}$alkyl, —$C(O)$—$C(O)NR^{17}R^{18}$, —$C(O)$—$C(O)OR^{17}$, —$OC(O)R^{17}$, —$NR^{17}C(O)R^{18}$, —$NR^{17}S(O)_2R^{18}$, —$(CR^{19}R^{20})_{n3}C(O)R^{17}$, —$(CR^{19}R^{20})_{n3}C(O)OR^{17}$, —$(CR^{19}R^{20})_{n3}C(O)NR^{17}R^{18}$, —$(CR^{19}R^{20})_{n3}S(O)_2NR^{17}R^{18}$, —$(CR^{19}R^{20})_{n3}NR^{17}R^{18}$, —$(CR^{19}R^{20})_{n3}OR^{17}$, —$(CR^{19}R^{20})_{n3}S(O)_{n4}R^{17}$, —$NR^{21}C(O)NR^{17}R^{18}$, —$NR^{21}S(O)_2NR^{17}R^{18}$ or —$NR^{21}S(O)NR^{17}R^{18}$, any of which is optionally substituted with one or more independent $Q^2$ substituents;
$Q^2$ is selected from one or more of H, D, halo, —CN, -oxo-, —$CD_3$, —$OCD_3$, —$CF_3$, —$OCF_3$, —$OCHF_2$, —$NO_2$, —$B(OH)_2$, —$PO(OR^{27})_2$, —$PO(OR^{27})R^{28}$, —$CONR^{27}OH$, —$CONR^{27}R^{28}C_{0-12}$alkyl-, —$C_{2-12}$alkenyl, —$C_{2-12}$alkynyl, —$OC_{0-12}$alkyl, aryl-$C_{0-12}$alkyl-, heteroaryl-$C_{0-12}$alkyl-, $C_{3-12}$cycloalkyl-$C_{0-12}$alkyl-, $C_{3-12}$heterocycloalkyl-$C_{0-12}$alkyl-, aryl-$C_{0-12}$cycloalkyl-, heteroaryl-$C_{3-12}$cycloalkyl-, $C_{3-12}$heterocycloalkyl-$C_{3-12}$cycloalkyl-, $C_{3-12}$cycloalkyl-$C_{3-12}$cycloalkyl-, $C_{1-12}$alkyl-$C_{3-12}$heterocycloalkyl-, $C_{3-12}$heterocycloalkyl-$C_{3-12}$heterocycloalkyl-, aryl-$C_{3-12}$heterocycloalkyl-, heteroaryl-$C_{3-12}$heterocycloalkyl-, —$C(O)$—$C(O)NR^{27}R^{28}$, —$C_{0-12}$alkylC(O)OR^{27}$, —$C(O)$—$C(O)OR^{27}$, —$OC(O)R^{27}$, —$NR^{27}C(O)R^{28}$, —$NR^{27}C(O)OR^{28}$, —$NR^{27}S(O)_2R^{28}$, —$(CR^{29}R^{30})_{n5}C(O)R^{27}$, —$(CR^{29}R^{30})_{n5}C(O)OR^{27}$, —$(CR^{29}R^{30})_{n5}C(O)NR^{27}R^{28}$, —$(CR^{29}R^{30})_{n5}S(O)_2NR^{27}R^{28}$, —$(CR^{29}R^{30})_{n5}NR^{27}R^{28}$, —$(CR^{29}R^{30})_{n5}OR^{27}$, —$(CR^{29}R^{30})_{n5}S(O)_{n6}R^{27}$, —$NR^{30}C(O)NR^{27}R^{28}$, —$NR^{30}S(O)_2NR^{27}R^{28}$ or —$NR^{30}S(O)NR^{27}R^{28}$ substituents, any of which may be optionally substituted;
$R^5$, $R^6$, $R^{10}$, $R^{11}$, $R^{12}$, $R^{13}$, $R^{14}$, $R^{15}$, and $R^{16}$ are each independently selected from one or more of H, $C_{1-6}$alkyl-, $C_{3-8}$cycloalkyl-$C_{0-6}$alkyl-, $C_{3-8}$heterocycloalkyl-$C_{0-6}$alkyl-, aryl-$C_{0-6}$alkyl-, aryl-$C_{3-8}$cycloalkyl-, aryl-$C_{3-8}$heterocycloalkyl-, heteroaryl-$C_{1-6}$alkyl-, heteroaryl-$C_{3-8}$cycloalkyl- or heteroaryl-$C_{3-8}$heterocycloalkyl-, any of which may be optionally substituted;
$R^{17}$, $R^{18}$, $R^{19}$, $R^{20}$, $R^{21}$, $R^{27}$, $R^{28}$, $R^{29}$, and $R^{30}$ are each independently selected from H, $C_{1-6}$alkyl-, $C_{3-8}$cycloalkyl-$C_{0-6}$alkyl-, $C_{3-8}$heterocycloalkyl-$C_{0-6}$alkyl-, aryl-$C_{0-6}$alkyl-, aryl-$C_{3-8}$cycloalkyl-, aryl-$C_{3-8}$heterocycloalkyl-, heteroaryl-$C_{1-6}$alkyl-, heteroaryl-$C_{3-8}$cycloalkyl- or heteroaryl-$C_{3-8}$heterocycloalkyl-, any of which may be optionally substituted;

—$NR^5R^6$ and —$NR^{12}R^{13}$ are each independently a linear structure, or, $R^5$ and $R^6$, or $R^{12}$ and $R^{13}$, respectively, are taken together with the nitrogen atom to which they are attached to form a 3-12 membered saturated or unsaturated ring, wherein said ring optionally includes one or more additional heteroatoms selected from O, N, or $S(O)_{m2}$;

—$CR^{10}R^{11}$ and —$CR^{14}R^{15}$ are each independently a linear structure, or, $R^{10}$ and $R^{11}$, or $R^{14}$ and $R^{15}$ respectively, are taken together with the carbon atom to which they are attached to form a 3-12 membered saturated or unsaturated ring, wherein said ring optionally includes one or more heteroatoms selected from O, N, or $S(O)_{m3}$;

—$CR^{19}R^{20}$ is a linear structure, or, $R^{19}$ and $R^{20}$ are taken together with the carbon atom to which they are attached to form a 3-12 membered saturated or unsaturated ring, wherein said ring optionally includes one or more additional heteroatoms selected from O, N, or $S(O)_{m4}$;

—$NR^{17}R^{18}$ is a linear structure, or, $R^{17}$ and $R^{18}$ are taken together with the nitrogen atom to which they are attached to form a 3-12 membered saturated or unsaturated ring, wherein said ring optionally includes one or more additional heteroatoms selected from O, N, or $S(O)_{m5}$;

—$CR^{29}R^{30}$ is a linear structure, or, $R^{29}$ and $R^{30}$ are taken together with the carbon atom to which they are attached to form a 3-12 membered saturated or unsaturated ring, wherein said ring optionally includes one or more additional heteroatoms selected from O, N, or $S(O)_{m6}$;

—$NR^{27}R^{28}$ is a linear structure, or, $R^{27}$ and $R^{28}$ are taken together with the nitrogen atom to which they are attached to form a 3-12 membered saturated or unsaturated ring, wherein said ring optionally includes one or more additional heteroatoms selected from O, N, or $S(O)_{m7}$;

wherein m1, m2, m3, m4, m5, m6, m7, n1, n2, n3, n4, n5 and n6 are each independently selected from 0, 1 or 2.

2. The compound or salt of claim 1, wherein:
$R^2$ is selected from $C_{0-8}$alkyl-, $C_{3-8}$cycloalkyl-$C_{0-8}$alkyl-, or $C_{3-8}$heterocycloalkyl-$C_{0-8}$alkyl-;
$R^{2a}$ is $C_{0-8}$alkyl-;
$G^2$ is selected from one or more of H, halo, —CN, —$CD_3$, —$OCD_3$, —$CF_3$, —$OCF_3$, —$OCHF_2$, or —$OC_{0-8}$alkyl;
$R^2$ and $R^{2a}$ are each independently a linear structure, or, $R^2$ and $R^{2a}$ are taken together with the carbon atom to which they are attached to form a 3-12 membered saturated or unsaturated ring, wherein said ring optionally includes one or more additional heteroatoms selected from O, or N.

3. The compound or salt of claim 1, wherein $G^2$ is selected from 0 to 3 of H, halo, —CN, —$CD_3$, —$OCD_3$, —$CF_3$, —$OCF_3$, —$OCHF_2$, or —$OC_{0-8}$alkyl.

4. The compound or salt of claim 1, wherein:
$R^3$ is selected from $C_{0-8}$alkyl-, $C_{3-8}$cycloalkyl-$C_{0-8}$alkyl-, or $C_{3-8}$heterocycloalkyl-$C_{0-8}$alkyl-;
$G^3$ is selected from one or more of H, D, halo, —CN, —$CD_3$, —$OCD_3$, -oxo-, —$CF_3$, —$OCF_3$, —$OCHF_2$, —$NR^5R^6$, —$C_{0-8}$alkyl, —$C_{2-8}$alkenyl, —$C_{2-8}$alkynyl, —$OC_{0-8}$alkyl, —$S(O)_{n1}R^{12}$, —$C(O)R^{12}$, —$C(O)NR^{12}R^{13}$, or —$C(O)OR^{12}$.

5. The compound or salt of claim 1, wherein $G^3$ is selected from 0 to 3 of H, D, halo, —CN, —$CD_3$, —$OCD_3$, -oxo-, —$CF_3$, —$OCF_3$, —$OCHF_2$, —$NR^5R^6$, —$C_{0-8}$alkyl, —$C_{2-8}$alkenyl, —$C_{2-8}$alkynyl, —$OC_{0-8}$alkyl, —$S(O)_{n1}R^{12}$, —$C(O)R^{12}$, —$C(O)NR^{12}R^{13}$, or —$C(O)OR^{12}$.

6. The compound or salt of claim 1, wherein:
$R^4$ is selected from $C_{0-8}$alkyl-, $C_{3-8}$cycloalkyl-$C_{3-8}$alkyl-, $C_{3-8}$heterocycloalkyl-$C_{0-8}$alkyl-, aryl-$C_{0-8}$alkyl-, heteroaryl-$C_{0-8}$alkyl-, heteroaryl-$C_{3-8}$cycloalkyl-, heteroaryl-$C_{3-8}$heterocycloalkyl-, or pyridine-N-oxide;
$G^4$ is selected from one or more of H, D, halo, —CN, —$CD_3$, —$OCD_3$, -oxo-, —$CF_3$, —$OCF_3$, —$OCHF_2$, —$NR^5R^6$, —$NO_2$, —$B(OH)_2$, —$CONR^{12}OH$, —$C_{0-8}$alkyl, $C_{3-8}$cycloalkyl-$C_{0-8}$alkyl-, $C_{3-8}$heterocycloalkyl-$C_{0-8}$alkyl-, aryl-$C_{0-8}$alkyl-, heteroaryl-$C_{0-8}$alkyl-, —$OC_{0-8}$alkyl, —$S(O)_{n1}R^{12}$, —$C(O)R^{12}$, —$C(O)NR^{12}R^{13}$, —$C(O)C(O)NR^{12}R^{13}$, —$C(O)OR^{12}$, —$C(O)$—$C(O)OR^{12}$, —$OC(O)R^{12}$, —$NR^{12}C(O)R^{13}$, —$NR^{12}C(O)OR^{13}$, —$(CR^{14}R^{15})C(O)R^{13}$, —$(CR^{14}R^{15})_{n1}S(O)_2NR^{12}R^{13}$, —$(CR^{14}R^{15})_{n1}NR^{12}R^{13}$, —$(CR^{14}R^{15})_{n1}OR^{12}$, —$(CR^{14}R^{15})_{n1}S(O)_{n2}R^{12}$, or —$NR^{16}C(O)NR^{12}R^{13}$.

7. The compound or salt of claim 1, wherein $G^4$ is selected from 0 to 3 of H, D, halo, —CN, —$CD_3$, —$OCD_3$, -oxo-, —$CF_3$, —$OCF_3$, —$OCHF_2$, —$NR^5R^6$, —$NO_2$, —$B(OH)_2$, —$CONR^{12}OH$, —$C_{0-8}$alkyl, $C_{3-8}$cycloalkyl-$C_{0-8}$alkyl-, $C_{3-8}$heterocycloalkyl-$C_{0-8}$alkyl-, aryl-$C_{0-8}$alkyl-, heteroaryl-$C_{0-8}$alkyl-, —$OC_{0-8}$alkyl, —$S(O)_{n1}OR^{12}$, —$C(O)R^{12}$, —$C(O)NR^{12}R^{13}$, —$C(O)$—$C(O)NR^{12}R^{13}$, —$C(O)OR^{12}$, —$C(O)$—$C(O)OR^{12}$, —$OC(O)R^{12}$, —$NR^{12}C(O)R^{13}$, —$NR^{12}C(O)OR^{13}$, —$(CR^{14}R^{15})C(O)R^{13}$, —$(CR^{14}R^{15})_{n1}S(O)_2NR^{12}R^{13}$, —$(CR^{14}R^{15})_{n1}NR^{12}R^{13}$, —$(CR^{14}R^{15})_{n1}OR^{12}$, —$(CR^{14}R^{15})_{n1}S(O)_{n2}R^{12}$, or —$NR^{16}C(O)NR^{12}R^{13}$.

8. The compound or salt of claim 1, wherein:
$Q^1$ is selected from H, D, halo, —CN, —$CD_3$, —$OCD_3$, -oxo-, —$CF_3$, —$OCF_3$, —$OCHF_2$, $NR^{17}R^{18}$, $C_{0-8}$alkyl-, aryl-$C_{0-8}$alkyl-, heteroaryl-$C_{0-8}$alkyl-, $C_{3-8}$cycloalkyl-$C_{0-8}$alkyl-, $C_{3-8}$heterocycloalkyl-$C_{0-8}$alkyl-, aryl-$C_{0-8}$cycloalkyl-, heteroaryl-$C_{3-8}$cycloalkyl-, $C_{3-8}$heterocycloalkyl-$C_{3-8}$cycloalkyl-, $C_{3-8}$cycloalkyl-$C_{3-8}$cycloalkyl-, $C_{1-8}$alkyl-$C_{3-8}$heterocycloalkyl-, $C_{3-8}$heterocycloalkyl-$C_{3-8}$heterocycloalkyl-, aryl-$C_{3-8}$heterocycloalkyl-, heteroaryl-$C_{3-8}$heterocycloalkyl-, —$OC_{0-8}$alkyl, —$C(O)$—$C(O)NR^{17}R^{18}$, —$C(O)$—$C(O)OR^{17}$, —$OC(O)R^{17}$, —$NR^{17}C(O)R^{18}$, —$NR^{17}S(O)_2R^{18}$, —$(CR^{19}R^{20})_{n3}C(O)R^{17}$, —$(CR^{19}R^{20})_{n3}C(O)OR^{17}$, —$(CR^{19}R^{20})_{n3}C(O)NR^{17}R^{18}$, —$(CR^{19}R^{20})_{n3}S(O)_2NR^{17}R^{18}$, —$(CR^{19}R^{20})_{n3}NR^{17}R^{18}$, —$(CR^{19}R^{20})_{n3}OR^{17}$, —$(CR^{19}R^{20})_{n3}S(O)_{n4}R^{17}$, —$NR^{21}C(O)NR^{17}R^{18}$, —$NR^{21}S(O)_2NR^{17}R^{18}$, or —$NR^{21}S(O)NR^{17}R^{18}$.

9. The compound or salt of claim 1, wherein:
$R^2$ is selected from $C_{0-6}$alkyl-, $C_{3-6}$cycloalkyl-$C_{0-6}$alkyl-, or $C_{3-6}$heterocycloalkyl-$C_{0-6}$alkyl-;
$R^{2a}$ is $C_{0-6}$alkyl-;
$G^2$ is selected from one or more of H, halo, —CN, —$CD_3$, —$OCD_3$, —$CF_3$, —$OCF_3$, —$OCHF_2$, or —$OC_{0-6}$alkyl;
$R^2$ and $R^{2a}$ are each independently a linear structure, or, $R^2$ and $R^{2a}$ are taken together with the carbon atom to which they are attached to form a 3-12 membered saturated or unsaturated ring, wherein said ring optionally includes one or more additional heteroatoms selected from O, or N.

10. The compound or salt of claim 1, wherein: $R^2$ and $R^{2a}$ are each independently a linear structure, or, $R^2$ and $R^{2a}$ are taken together with the carbon atom to which they are attached to form a 4-6 membered saturated or unsaturated ring, wherein said ring optionally includes one or more additional heteroatoms selected from O, or N.

11. The compound or salt of claim 1, wherein $G^2$ is selected from 0 to 2 of H, halo, —CN, —CD$_3$, —OCD$_3$, —CF$_3$, —OCF$_3$, —OCHF$_2$, or —OC$_{0-6}$alkyl.

12. The compound or salt of claim 1, wherein:
$R^3$ is selected from C$_{0-6}$alkyl-, C$_{3-6}$cycloalkyl-C$_{0-6}$alkyl-, or C$_{3-6}$heterocycloalkyl-C$_{0-6}$alkyl-;
$G^3$ is selected from one or more of H, D, halo, —CN, —CD$_3$, —OCD$_3$, -oxo-, —CF$_3$, —OCF$_3$, —OCHF$_2$, —NR$^5$R$^6$, —C$_{0-6}$alkyl, —C$_{2-6}$alkenyl, —C$_{2-6}$alkynyl, —OC$_{0-6}$alkyl, —S(O)$_{n1}$R$^{12}$, —C(O)R$^{12}$, —C(O)NR$^{12}$R$^{13}$, or —C(O)OR$^{12}$.

13. The compound or salt of claim 1, wherein $G^3$ is selected from 0 to 2 of H, D, halo, —CN, —CD$_3$, —OCD$_3$, -oxo-, —CF$_3$, —OCF$_3$, —OCHF$_2$, —NR$^5$R$^6$, —C$_{0-6}$alkyl, —C$_{2-6}$alkenyl, —C$_{2-6}$alkynyl, —OC$_{0-6}$alkyl, —S(O)$_{n1}$R$^{12}$, —C(O)R$^{12}$, —C(O)NR$^{12}$R$^{13}$, or —C(O)OR$^{12}$.

14. The compound or salt of claim 1, wherein:
$R^4$ is selected from C$_{0-6}$alkyl-, C$_{3-6}$cycloalkyl-C$_{0-6}$alkyl-, C$_{3-6}$heterocycloalkyl-C$_{0-6}$alkyl-, aryl-C$_{0-6}$alkyl-, heteroaryl-C$_{0-6}$alkyl-, heteroaryl-C$_{3-6}$cycloalkyl-, heteroaryl-C$_{3-6}$heterocycloalkyl-, or pyridine-N-oxide;
$G^4$ is selected from one or more of H, D, halo, —CN, —CD$_3$, —OCD$_3$, -oxo-, —CF$_3$, —OCF$_3$, —OCHF$_2$, —NR$^5$R$^6$, —NO$_2$, —B(OH)$_2$, —CONR$^{12}$OH, —C$_{0-6}$alkyl, C$_{3-6}$cycloalkyl-C$_{0-6}$alkyl-, C$_{3-6}$heterocycloalkyl-C$_{0-6}$alkyl-, aryl-C$_{0-6}$alkyl-, heteroaryl-C$_{0-6}$alkyl-, —OC$_{0-6}$alkyl, —S(O)$_{n1}$R$^{12}$, —C(O)R$^{12}$, —C(O)NR$^{12}$R$^{13}$, —C(O)C(O)NR$^{12}$R$^{13}$, —C(O)OR$^{12}$, —C(O)—C(O)OR$^{12}$, —OC(O)R$^{12}$, —NR$^{12}$C(O)R$^{13}$, —NR$^{12}$C(O)OR$^{13}$, —(CR$^{14}$R$^{15}$)C(O)R$^{13}$, —(CR$^{14}$R$^{15}$)$_{n1}$S(O)$_2$NR$^{12}$R$^{13}$, —(CR$^{14}$R$^{15}$)$_{n1}$NR$^{12}$R$^{13}$, —(CR$^{14}$R$^{15}$)$_{n1}$OR$^{12}$, —(CR$^{14}$R$^{15}$)$_{n1}$S(O)$_{n2}$R$^{12}$, or —NR$^{16}$C(O)NR$^{12}$R$^{13}$.

15. The compound or salt of claim 1, $G^4$ is selected from 0 to 2 of H, D, halo, —CN, —CD$_3$, —OCD$_3$, -oxo-, —CF$_3$, —OCF$_3$, —OCHF$_2$, —NR$^5$R$^6$, —NO$_2$, —B(OH)$_2$, —CONR$^{12}$OH, —C$_{0-6}$alkyl, C$_{3-6}$cycloalkyl-C$_{0-6}$alkyl-, C$_{3-6}$heterocycloalkyl-C$_{0-6}$alkyl-, aryl-C$_{0-6}$alkyl-, heteroaryl-C$_{0-6}$alkyl-, —OC$_{0-6}$alkyl, —S(O)$_{n1}$R$^{12}$, —C(O)R$^{12}$, —C(O)NR$^{12}$R$^{13}$, —C(O)—C(O)NR$^{12}$R$^{13}$, —C(O)OR$^{12}$, —C(O)—C(O)OR$^{12}$, —OC(O)R$^{12}$, —NR$^{12}$C(O)R$^{13}$, —NR$^{12}$C(O)OR$^{13}$, —(CR$^{14}$R$^{15}$)C(O)R$^{13}$, —(CR$^{14}$R$^{15}$)$_{n1}$S(O)$_2$NR$^{12}$R$^{13}$, —(CR$^{14}$R$^{15}$)$_{n1}$NR$^{12}$R$^{13}$, —(CR$^{14}$R$^{15}$)$_{n1}$OR$^{12}$, —(CR$^{14}$R$^{15}$)$_{n1}$S(O)$_{n2}$R$^{12}$, or —NR$^{16}$C(O)NR$^{12}$R$^{13}$.

16. The compound or salt of claim 1, wherein:
$Q^1$ is selected from H, D, halo, —CN, —CD$_3$, —OCD$_3$, -oxo-, —CF$_3$, —OCF$_3$, —OCHF$_2$, NR$^{17}$R$^{18}$, C$_{0-6}$alkyl-, aryl-C$_{0-6}$alkyl-, heteroaryl-C$_{0-6}$alkyl-, C$_{3-6}$cycloalkyl-C$_{0-6}$alkyl-, C$_{3-6}$heterocycloalkyl-C$_{0-6}$alkyl-, aryl-C$_{0-6}$cycloalkyl-, heteroaryl-C$_{3-6}$cycloalkyl-, C$_{3-6}$heterocycloalkyl-C$_{3-6}$cycloalkyl-, C$_{3-6}$cycloalkyl-C$_{3-6}$cycloalkyl-, C$_{1-6}$alkyl-C$_{3-6}$heterocycloalkyl-, C$_{3-6}$heterocycloalkyl-C$_{3-6}$heterocycloalkyl-, aryl-C$_{3-6}$heterocycloalkyl-, heteroaryl-C$_{3-6}$heterocycloalkyl-, —OC$_{0-6}$alkyl, —C(O)—C(O)NR$^{17}$R$^{18}$, —C(O)—C(O)OR$^{17}$, —OC(O)R$^{17}$, —NR$^{17}$C(O)R$^{18}$, —NR$^{17}$S(O)$_2$R$^{18}$, —(CR$^{19}$R$^{20}$)$_{n3}$C(O)R$^{17}$, —(CR$^{19}$R$^{20}$)$_{n3}$C(O)OR$^{17}$, —(CR$^{19}$R$^{20}$)$_{n3}$C(O)NR$^{17}$R$^{18}$, —(CR$^{19}$R$^{20}$)$_{n3}$S(O)$_2$NR$^{17}$R$^{18}$, —(CR$^{19}$R$^{20}$)$_{n3}$NR$^{17}$R$^{18}$, —(CR$^{19}$R$^{20}$)$_{n3}$OR$^{17}$, —(CR$^{19}$R$^{20}$)$_{n3}$S(O)$_{n4}$R$^{17}$, —NR$^{21}$C(O)NR$^{17}$R$^{18}$, —NR$^{21}$S(O)$_2$NR$^{17}$R$^{18}$, or —NR$^{21}$S(O)NR$^{17}$R$^{18}$.

17. The compound or salt of claim 1, wherein:
$R^2$ is selected from methyl, ethyl, propyl, isopropyl, or one of the following groups:

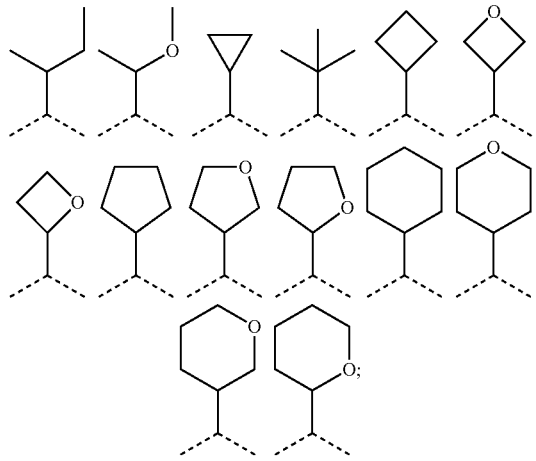

and $R^{2a}$ is selected H, methyl, ethyl, propyl, isopropyl; or $R^2$ and $R^{2a}$ are taken together with the carbon atom to which they are attached to form one of the following groups:

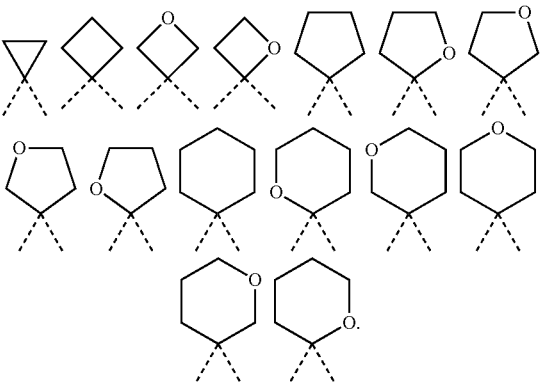

18. The compound or salt of claim 1, wherein:
—NR$^5$R$^6$ and —NR$^{12}$R$^{13}$ are each independently a linear structure, or, $R^5$ and $R^6$, or $R^{12}$ and $R^{13}$, respectively, are taken together with the nitrogen atom to which they are attached to form a 4-8 membered saturated or unsaturated ring, wherein said ring optionally includes one or more additional heteroatoms selected from O, N, or S(O)$_{m2}$;
—CR$^{10}$R$^{11}$ and —CR$^{14}$R$^{15}$ are each independently a linear structure, or, $R^{10}$ and $R^{11}$, or $R^{14}$ and $R^{15}$ respectively, are taken together with the carbon atom to which they are attached to form a 4-8 membered saturated or unsaturated ring, wherein said ring optionally includes one or more heteroatoms selected from O, N, or S(O)$_{m3}$;
—CR$^{19}$R$^{20}$ is a linear structure, or, $R^{19}$ and $R^{20}$ are taken together with the carbon atom to which they are attached to form a 4-8 membered saturated or unsaturated ring, wherein said ring optionally includes one or more additional heteroatoms selected from O, N, or S(O)$_{m4}$;
—NR$^{17}$R$^{18}$ is a linear structure, or, $R^{17}$ and $R^{18}$ are taken together with the nitrogen atom to which they are attached to form a 4-8 membered saturated or unsaturated ring, wherein said ring optionally includes one or more additional heteroatoms selected from O, N, or S(O)$_{m5}$;

—CR$^{29}$R$^{30}$ is a linear structure, or, R$^{29}$ and R$^{30}$ are taken together with the carbon atom to which they are attached to form a 4-8 membered saturated or unsaturated ring, wherein said ring optionally includes one or more additional heteroatoms selected from O, N, or S(O)$_{m6}$;

—NR$^{27}$R$^{28}$ is a linear structure, or, R$^{27}$ and R$^{28}$ are taken together with the nitrogen atom to which they are attached to form a 4-8 membered saturated or unsaturated ring, wherein said ring optionally includes one or more additional heteroatoms selected from O, N, or S(O)$_{m7}$;

wherein m2, m3, m4, m5, m6, and m7 are each independently selected from 0, 1 or 2.

19. The compound or salt of claim 1, which is represented by the Formula Ia:

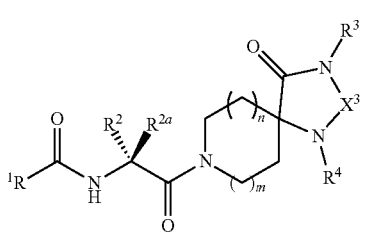

Ia wherein X$^3$ is selected from C=O, or CRo$^{10}$R$^{11}$.

20. The compound of claim 19, wherein R$^{2a}$ is hydrogen.

21. The compound of claim 19, wherein R$^2$ is C$_{1-12}$alkyl-, C$_{3-12}$cycloalkyl-, or C$_{1-12}$heteroalkyl any of which is optionally substituted with one or more independent G$^2$ substituents.

22. The compound of claim 19, wherein R$^3$ is C$_{1-12}$alkyl or C$_{1-12}$heteroalkyl.

23. The compound of claim 19, wherein R$^4$ is C$_{1-12}$alkyl, C$_{3-8}$cycloalkyl, aryl, heteroaryl, aryl-C$_{1-6}$alkyl, heteroaryl-C$_{1-6}$alkyl, or C$_{3-12}$heterocycloalkyl, any of which is optionally substituted with one or more independent Q$^1$ substituents.

24. The compound of claim 19, wherein X$^3$ is C=O.

25. The compound of claim 19, wherein X$^3$ is CR$^{10}$R$^{11}$ wherein R$^{10}$ is hydrogen and R$^{11}$ is hydrogen or methyl.

26. The compound or salt of claim 1, wherein the compounds of Formula I are inhibitors of ATX.

27. A pharmaceutical composition comprising the compound or salt of a compound according to claim 1, formulated with or without one or more pharmaceutical carriers.

28. A method for inhibiting autotaxin (ATX) comprising administering to a subject in need thereof an effective amount of a compound according to claim 1, or a pharmaceutically acceptable salt thereof.

29. The method of claim 28, wherein the compounds binds to and inhibits ATX providing a reduction in LPA levels.

30. The method according to claim 28 comprising administering to the subject one or more additional therapeutically active agents selected from: corticosteroids, immunosuppressants, analgesics, anti-cancer agents, anti-inflammatories, non-steroidal anti-inflammatories, dual cyclooxygenase-1 and -2 inhibitors, cyclooxygenase-2 selective inhibitors, TNFα blockers, kinase inhibitors, chemokine receptor antagonists, bronchodilators, leukotriene receptor antagonists, leukotriene formation inhibitors, prostaglandin receptor antagonists, prostaglandin formation inhibitors, monoacylglycerol kinase inhibitors, phospholipase A1 inhibitors, phospholipase A2 inhibitors, lysophospholipase D (lysoPLD) inhibitors, autotaxin inhibitors, and LPA receptor antagonists.

* * * * *